US008642838B2

(12) United States Patent
Reuzeau

(10) Patent No.: US 8,642,838 B2
(45) Date of Patent: Feb. 4, 2014

(54) PLANTS HAVING ENHANCED YIELD-RELATED TRAITS AND A METHOD FOR MAKING THE SAME

(75) Inventor: Christophe Reuzeau, La Chapelle Gonaguet (FR)

(73) Assignee: BASF Plant Science GmbH, Ludwigshafen (DE)

( * ) Notice: Subject to any disclaimer, the term of this patent is extended or adjusted under 35 U.S.C. 154(b) by 1238 days.

(21) Appl. No.: 12/294,983

(22) PCT Filed: Mar. 30, 2007

(86) PCT No.: PCT/EP2007/053081
§ 371 (c)(1),
(2), (4) Date: Sep. 29, 2008

(87) PCT Pub. No.: WO2007/113237
PCT Pub. Date: Oct. 11, 2007

(65) Prior Publication Data
US 2012/0124702 A1 May 17, 2012

Related U.S. Application Data

(66) Substitute for application No. 60/889,958, filed on Feb. 15, 2007.

(60) Provisional application No. 60/790,151, filed on Apr. 7, 2006, provisional application No. 60/790,116, filed on Apr. 7, 2006, provisional application No. 60/792,225, filed on Apr. 14, 2006, provisional application No. 60/798,602, filed on May 8, 2006, provisional application No. 60/801,687, filed on May 19, 2006.

(30) Foreign Application Priority Data

Mar. 31, 2006 (EP) .................................. 06075822
Mar. 31, 2006 (EP) .................................. 06075823
Apr. 10, 2006 (EP) .................................. 06075918
Apr. 27, 2006 (EP) .................................. 06075957
May 18, 2006 (EP) .................................. 06114140
Jul. 14, 2006 (EP) .................................. 06117235
Jan. 19, 2007 (EP) .................................. 07100833

(51) Int. Cl.
*A01H 1/00* (2006.01)
*A01H 5/00* (2006.01)
*C12N 15/82* (2006.01)
*C12N 15/87* (2006.01)
*C12N 15/00* (2006.01)

(52) U.S. Cl.
USPC ........ 800/290; 800/285; 800/320; 800/320.2; 530/300; 530/350; 435/320.1

(58) Field of Classification Search
None
See application file for complete search history.

(56) References Cited

U.S. PATENT DOCUMENTS

| 6,995,302 B1* | 2/2006 | Kojima et al. ................. 800/298 |
| 2004/0019927 A1 | 1/2004 | Sherman et al. |
| 2004/0034888 A1 | 2/2004 | Liu et al. |
| 2004/0216190 A1 | 10/2004 | Kovalic et al. |

FOREIGN PATENT DOCUMENTS

| EP | 1 033 405 A2 | 9/2000 |
| EP | 1 586 651 A1 | 10/2005 |
| WO | WO-00/36124 A2 | 6/2000 |
| WO | WO-03/002751 A2 | 1/2003 |
| WO | WO-03/013227 A2 | 2/2003 |
| WO | WO-2004/031349 A2 | 4/2004 |
| WO | WO-2005/075655 A2 | 8/2005 |
| WO | WO-2005/085452 A1 | 9/2005 |

OTHER PUBLICATIONS

Chuang et al. (2000) PNAS 97: 4985-4990.*
Kater et al. (2006) J. Exp. Bot. 57: 3433-3444.*
Yamaguchi et al, 2009, Dev. Cell, 17:268-278.*
Ferrandiz et al, 2000, Development, 127:725-734.*
Waterhouse et al, 1998, PNAS, 95:13959-13964.*
Aida, M., et al., "The *Plethora* Genes Mediate Patterning of the *Arabidopsis* Root Stem Cell Niche", Cell, 2004, vol. 119, vol. 109-120.
Chuang, C.-F., et al., "Specific and Heritable Genetic Interference by Double-Stranded RNA in *Arabidopsis thaliana*", PNAS, 2000, vol. 97, No. 9, pp. 4985-4990.
Fitch, W. M., "Homology: A Personal View on Some of the Problems", Trends in Genetics, 2000, vol. 16, No. 5, pp. 227-231.
Kater, M. M., et al., "Functional Conservation of MADS-Box Factors Controlling Floral Organ Identity in Rice and *Arabidopsis*", Journal of Experimental Botany, 2006, vol. 57, No. 13, pp. 3433-3444.
Koonin, E. V., "Orthologs, Paralogs, and Evolutionary Genomics", Annu. Rev. Genet., 2005, vol. 39, pp. 309-338.
Stone, J. M., et al., "*Arabidopsis AtSPL14*, a Plant-Specific SBP-Domain Transcription Factor, Participates in Plant Development and Sensitivity to Fumonisin B1", The Plant Journal, 2005, vol. 41, pp. 744-754.
Unte, U. S., et al., "*SPL8*, an SBP-Box Gene That Affects Pollen Sac Development in *Arabidopsis*", The Plant Cell, 2003, vol. 15, pp. 1009-1019.

(Continued)

*Primary Examiner* — Ashwin Mehta
*Assistant Examiner* — Jason Deveau Rosen
(74) *Attorney, Agent, or Firm* — Novak Druce Connolly Bove + Quigg LLP

(57) ABSTRACT

The present invention relates generally to the field of molecular biology and concerns a method for enhancing yield-related traits in plants, in particular for increasing plant yield and/or early vigor, relative to control plants. More specifically, the present invention concerns a method for enhancing yield-related traits comprising modifying the expression of a nucleic acid encoding a HAL3 polypeptide, MADS15 polypeptide, PLT transcription factor polypeptide, basic/helix-loop-helix (bHLH) transcription factor, or SPL15 transcription factor. The invention also provides constructs useful in the methods of the invention.

28 Claims, 106 Drawing Sheets

(56) References Cited

OTHER PUBLICATIONS

Wright, D. A., et al., "High-Frequency Homologous Recombination in Plants Mediated by Zinc-Finger Nucleases", The Plant Journal, 2005, vol. 44, pp. 693-705.

"Glycine max Protein SEQ ID No. 207507", GeneSeq Database Accession No. AFQ16330, Oct. 18, 2007.

"Glycine max Protein SEQ ID No. 218848", GeneSeq Database Accession No. AFQ27671, Oct. 18, 2007.

Espinosa-Ruiz, A., et al., "*Arabidopsis thaliana* AtHAL3: a flavoprotein related to salt and osmotic tolerance and plant growth", Plant J., 1999, vol. 20, No. 5, pp. 529-539.

"Sequence 7 from Patent WO0036124", EMBL Database, Accession No. AX027396, Sep. 16, 2000.

"*Oryza sativa* Japonica Group cDNA clone:J023010L24, full insert sequence", EMBL Database, Accession No. AK100138, Jul. 19, 2003.

"*Triticum aestivum* clone w11n.pk0039.e3:fis, full insert mRNA sequence", EMBL Database, Accession No. BT009136, Jun. 23, 2003.

"*Zea mays* PCO119881 mRNA sequence", EMBL Database, Accession No. AY105313, May 30, 2002.

"*Picea abies* partial mRNA for putative halotolerance protein HAL3 homolog, (pPA0038 gene)", EMBL Database, Accession No. AJ271130, Jan. 26, 2001.

"BNDH5DCT_UP_001_E10_15DEC2003_072 *Brassica napus* BNDH5DCT *Brassica napus* cDNA 5-, mRNA sequence", EMBL Database, Accession No. CN726994, May 15, 2005.

"*Brassica oleracea* var. alboglabra EST, clone AAFC_WHRI_BoE01a014N23_SP6", EMBL Database, Accession No. AM060322, Aug. 3, 2005.

"KR3B.001J04F.050815T7 KR3B *Nicotiana tabacum* cDNA clone KR3B.001J04, mRNA sequence", EMBL Database, Accession No. DW001590, Dec. 11, 2005.

"EST522101 cTOS *Lycopersicon esculentum* cDNA clone cTOS3N14 5' end, mRNA sequence", EMBL Database, Accession No. BI204061, Jul. 13, 2001.

"EST1076860 Normalized pine embryo library, Lib_D *Pinus taeda* cDNA clone PWABJ77 3' end, mRNA sequence", EMBL Database, Accession No. DR686782, Jul. 14, 2005.

Yi, K., et al., "OsPTF1, a novel transcription factor involved in tolerance to phosphate starvation in rice", Plant Physiol., 2005, vol. 138, No. 4, pp. 2087-2096.

\* cited by examiner

MENGKRDRQDMEVNTTPRKPRVLLAASGSVAAIKFGNLCHCFTEWAEVRAVVTKSS
LHFLDKLSLPQEVTLYTDEDEWSSWNKIGDPVLHIELRRWADVLVIAPLSANTLGK
IAGGLCDNLLTCIIRAWDYTKPLFVAPAMNTLMWNNPFTERHLLSLDELGITLIPP
IKKRLACGDYGNGAMAEPSLIYSTVRLFWESQAHQQTGGTS

```
                                                                                        60
AT_NP_973994          (1)  ------------------MNMEVDTVT-RKPRILLAASGSVASIKFSNLCHCFSEWAE
Translation of Sb_TC94863  (1)  ----------MATSEPVQENLAMDYSQPSKPRVLLAASGSVAAIKFENLCRSFSEWAD
Translation of CDS0218    (1)  ----------MENGKRDRQDMEVNTTP-RKPRVLLAASGSVAAIKFGNLCHCFTEWAE
Translation of Cg_TC38639 (1)  ---------MAYPEPQGADREMVKVNPTP-RKPRVLLAASGSVAAIKFGNLCHCFSEWAE
Translation of HV_TC140402(1)  -----------VKQMATSEPVQQSWELES----SRPVLLAASGSVAAIKFESLCRIFSEWAE
Translation of OS_TC265537(1)  ------------VMTTSESVQETLGLDFPHPSKPRVLLAASGSVAAIKFESLCRSFSEWAE
Translation of Vv_TC40016 (1)  ----------MMMTYAEPLSPEVDAIPVNIAP-RRPRILLAASGSVAAMKFGNLVHSFCEWAE
Translation of Gm_TC228665(1)  ----------VMAGSEPVRAEGETMAVDAAP-RKPRILLAASGSVAAVKFANLCHCFSEWAE
Translation of St_TC115205(1)  ----------------MTSEMEPVQINGAP-RRPRILLAASGSVAAIKFANLCGCFSEWAE
Translation of Zm_TC305749(1)  ----------MATSEPVQESLVVHYSQPSRPVLLAASGSVAAIKFESLCRSFSEWAD
Translation of Pg_TC67564 (1)  MVVLKINTLVQNMDATNSQPDEPGRDANSSQKPRILLAASGSVAAIKFGILAHCLCQWAE 120
AT_NP_973994         (40)  VKAVASKSSLNFVDKPSLPQNVTLYTDEDEWSSWNKIGDPVLHIELRRWADVMIIAPLSA
Translation of Sb_TC94863 (49)  VRAVATASSLHFIDRSSLPSDIVLYTDDDEWSTWKKIGDEVLHIELRKWADIMVIAPLSA
Translation of CDS0218   (48)  VRAVVTKSSLHFLDKLSLPQEVTLYTDEDEWSSWNKIGDPVLHIELRRWADVLVIAPLSA
Translation of Cg_TC38639(51)  VKAVATKASLHFIDRASLPKDLKLYTDEEEWSSWGKIGDSVLHIELRRWADIMVIAPLSA
Translation of HV_TC140402(49) VRAVATKASLHFVDRSSLPSDVVLYTDDDEWSTWTKIGDEVLHIELRKWADIMVIAPLSA
Translation of OS_TC265537(50) VRAVATKASLHFIDRTSLPSNIILYTDDDEWSTWKKIGDEVLHIELRKWADIMVIAPLSA
Translation of Vv_TC40016 (53) VRAVSTSASLHFIDRAALPKDLYLYTDDDEWSSWTKLGDSVLHIELRRWADVMVIAPLSA
Translation of Gm_TC228665(52) VRAVATKPSLHFIDKASLPEDAILYTDNEWSSWKKLGDSVLHIELRRWADIMVIAPLSA
Translation of St_TC115205(45) VKAVATKPSLHFIDKASLPEDAILYTDEEEWSTWKKIGDSVLHIELRRWADIMVIAPLSA
Translation of Zm_TC305749(49) VRAVTTPSLHFVDRSSLPSGIVLYTDDDEWSTWKKIGDEVLHIELRKWADVMVIAPLSA
Translation of Pg_TC67564 (61) VKAVVTKSALHFIDKMSLPANVKLYTDENEWSSWSKIGDTVLHIELRQWADAMVIAPLSA
```

FIGURE 3

```
                                     121                                                                    180
           AT_NP_973994      (100)   NTLAKIAGGICDNLLTCIVRAWDYSKPLFVAPAMNTLMWNNPFTERHLVLLDELGITLIP
Translation of Sb_TC94863    (109)   NTLAKIAGGICDNLLTCIVRAWDYSKPLFVAPAMNTLMWNNPFTERHLQTINQLGILIP
Translation of CDS0218       (108)   NTLGKIAGGICDNLLTCIIRAWDYTKPLFVAPAMNTLMWNNPFTERHLLSLDELGITLIP
Translation of Cg_TC38639    (111)   NTLGKIAGGICDNLLTCVVRAWDYSKPMFVAPAMNTFMWSNPFTEKHLMTIDELGISLIP
Translation of HV_TC140402   (109)   NTLAKIAGGICDNLLTCIIRAWDYKKPIFAAPAMNTFMWNNPFTARHIETMNQLGISLVP
Translation of OS_TC265537   (110)   NTLAKIAGGICDNLLTCIVRAWDYSKPLFVAPAMNTFMWNNPFTSRHLETINLLGISLVP
Translation of Vv_TC40016    (113)   NTLGKIAGGICDNLLTCIVRAWDYSKPMFVAPAMNTFMWTNPFTERHLMTIDELGISLIP
Translation of Gm_TC228665   (112)   NTLGKIAGGICDNLLTCIVRAWDYSKPFFVAPAMNTLMWNNPFTERHFISIDELGISLIP
Translation of St_TC115205   (105)   NTLGKIAGGICDNLLTCIVRAWDYNKPLFVAPAMNTLMWNNPFTERHLMVIDELGISLIP
Translation of Zm_TC305749   (109)   NTLAKIAGGICDNLLTCIVRAWDYSKPLFVAPAMNTLMWNNPFTERHLHTINQLGIALIP
Translation of Pg_TC67564    (121)   NTLAKIAGGICDNLLTCIVRAWDFNKPLFVAPAMNTFMWNNPFTQRHLDSISELGLSLIP 181                                                  237
           AT_NP_973994      (160)   PIKKKLACGDYGNGAMAEPSLIYSTVRLFWESQARKQRDGTS-------------
Translation of Sb_TC94863    (169)   PVTKRLACGDHGNGAMAETSQIYTSVRLAWKTQPHDASSSLVPVSNNRPSSWCLTS
Translation of CDS0218       (168)   PIKKRLACGDYGNGAMAEPSLIYSTVRLFWESQAHQQTGGTS-------------
Translation of Cg_TC38639    (171)   PVSKRLACGDYGNGAMAEPSLIHSTVRLFLESRPQPSD----------------
Translation of HV_TC140402   (169)   PTTKRLACGDYGNGAMAEPSQIHTTVRLACKSQTFGTGISPAHPSSGHPV-----
Translation of OS_TC265537   (170)   PITKRLACGDYGNGAMAEPSVIDSTVRLACKRQPLNTNSSPVVPAGRNLPSS---
Translation of Vv_TC40016    (173)   PVTKRLACGDYGTGAMAEPFLIHSTVRLFLETRAQSSSSNVQ-------------
Translation of Gm_TC228665   (172)   PVTKRLACGDYGNGAMAEPSTIYSTVRLFYESKAQQGRAVVTLR----------
Translation of St_TC115205   (165)   PVSKRLACGDYGNGAMAEPSLIYSTVRLFYESRSQSGGINLA------------
Translation of Zm_TC305749   (169)   PVTKRLACGDYGNGAMAETSQIHTSVRLACKTQPHDASSSLAGPVSNNRPSS---
Translation of Pg_TC67564    (181)   PITKKLACGDYGNGAMAEPSTIDTTLRFSLDPSIV--------------------
```

FIGURE 3 (continued)

SEQ ID NO: 1, AtHAL3a

ATGGAGAATGGGAAAAGAGACAGACAAGACATGGAAGTGAATACCACACCGAGGAAGCCTCGTGTA
CTACTCGCTGCAAGTGGAAGCGTCGCTGCTATCAAATTCGGCAATCTCTGCCATTGCTTCACCGAA
TGGGCAGAAGTCAGAGCCGTCGTTACGAAATCATCTCTACATTTCCTCGATAAACTCTCTCTCCCA
CAAGAAGTGACTCTGTATACTGATGAAGATGAATGGTCTAGCTGGAACAAGATCGGTGATCCTGTC
CTTCACATCGAGCTTAGACGTTGGGCTGATGTTTAGTCATTGCTCCTTTGTCTGCTAACACCTTA
GGCAAGATTGCTGGTGGGCTTTGTGATAATCTTCTGACTTGCATTATACGAGCTTGGGACTATACC
AAACCACTGTTTGTTGCTCCAGCTATGAATACTTTGATGTGGAACAATCCTTTCACTGAAAGGCAT
CTTTTGTCTCTTGATGAACTGGGAATCACACTTATTCCTCCTATCAAGAAGAGACTTGCCTGTGGA
GACTACGGTAATGGAGCTATGGCTGAGCCCTCTCTTATCTATTCCACTGTCAGACTCTTCTGGGAG
TCTCAGGCTCATCAGCAAACCGGTGGAACTAGTTAA

SEQ ID NO: 2, AtHAL3a

MENGKRDRQDMEVNTTPRKPRVLLAASGSVAAIKFGNLCHCFTEWAEVRAVVTKSSLHFLDKLSLP
QEVTLYTDEDEWSSWNKIGDPVLHIELRRWADVLVIAPLSANTLGKIAGGLCDNLLTCIIRAWDYT
KPLFVAPAMNTLMWNNPFTERHLLSLDELGITLIPPIKKRLACGDYGNGAMAEPSLIYSTVRLFWE
SQAHQQTGGTS

SEQ ID NO: 3, forward primer prm00957

AAAAAGCAGGCTCACAATGGAGAATGGGAAAAGAGAC

SEQ ID NO: 4, reverse primer prm00958

AGAAAGCTGGGTTGGTTTTAACTAGTTCCACCG

SEQ ID NO: 5, sequence beta-expansin promoter (Oryza sativa)

AAAACCACCGAGGGACCTGATCTGCACCGGTTTTGATAGTTGAGGGACCCGTTGTGTCTGGTTTTC
CGATCGAGGGACGAAAATCGGATTCGGTGTAAAGTTAAGGGACCTCAGATGAACTTATTCCGGAGC
ATGATTGGGAAGGGAGGACATAAGGCCCATGTCGCATGTGTTTGGACGGTCCAGATCTCCAGATCA
CTCAGCAGGATCGGCCGCGTTCGCGTAGCACCCGCGGTTTGATTCGGCTTCCCGCAAGGCGGCGGC
CGGTGGCCGTGCCGCCGTAGCTTCCGCCGGAAGCGAGCACGCCGCCGCCGCCGACCCGGCTCTGCG
TTTGCACCGCCTTGCACGCGATACATCGGGATAGATAGCTACTACTCTCTCCGTTCACAATGTAA
ATCATTCTACTATTTTCCACATTCATATTGATGTTAATGAATATAGACATATATATCTATTTAGAT
TCATTAACATCAATATGAATGTAGGAAATGCTAGAATGACTTACATTGTGAATTGTGAAATGGACG
AAGTACCTACGATGGATGGATGCAGGATCATGAAAGAATTAATGCAAGATCGTATCTGCCGCATGC
AAAATCTTACTAATTGCGCTGCATATATGCATGACAGCCTGCATGCGGGCGTGTAAGCGTGTTCAT
CCATTAGGAAGTAACCTTGTCATTACTTATACCAGTACTACATACTATATAGTATTGATTTCATGA
GCAAATCTACAAAACTGGAAAGCAATAAGGAATACGGGACTGGAAAAGACTCAACATTAATCACCA
AATATTTCGCCTTCTCCAGCAGAATATATATCTCTCCATCTTGATCACTGTACACACTGACAGTGT
ACGCATAAACGCAGCAGCCAGCTTAACTGTCGTCTCACCGTCGCACACTGGCCTTCCATCTCAGGC
TAGCTTTCTCAGCCACCCATCGTACATGTCAACTCGGCGCGCGCACAGGCACAAATTACGTACAAA
ACGCATGACCAAATCAAAACCACCGGAGAAGAATCGCTCCCGCGCGCGGCGGCGCGCACGTAC
GAATGCACGCACGCACGCCCAACCCCACGACACGATCGCGCGCGACGCCGGCGACACCGGCCATCC
ACCCGCGCCCTCACCTCGCCGACTATAAATACGTAGGCATCTGCTTGATCTTGTCATCCATCTCAC
CACCAAAAAAAAGGAAAAAAAAACAAAACACACCAAGCCAAATAAAAGCGACAA

FIGURE 4

SEQ ID NO: 6, Conserved motif 1

(K/R)PR(V/I)LLAA(S/T)GSVA(A/S)(I/M/V)KF(G/E/A/S)NL(C/V)(H/R/G)(C/S/I)F(T/S)(E/D)WA(E/D)V(R/K)AV(V/A)

SEQ ID NO: 7, conserved motif 2

VLHIELR(R/K/Q)WAD(V/I)(L/M)(V/I)IAPLSANTL(G/A)KIAGG(L/M)CDNLLTC(I/V)(I/V)RAWD(Y/F)(T/S/N/D/K)KP(L/F/M/I)F(V/A)APAMNT(L/F)MW(N/S)NPFT(E/S/Q/A)(R/K)H(L/F/I)($X_1$)($X_2$)(L/I/M)(D/N/S)(E/L/Q)(L/M)G(I/V)(T/S/A/I)L(I/V)PP(I/V/T)(K/T/S)K(R/T/K)LACGD(Y/H)G(N/T)GAM(A/S)E

SEQ ID NO: 8, region of high conservation, present in SEQ ID NO: 2

KPRVLLAASGSVAAIKFGNLCHCFTEWAEVRAVVTKSSLHFLDKLSLPQEVTLYTDEDEWSSWNKI
GDPVLHIELRRWADVLVIAPLSANTLGKIAGGLCDNLLTCIIRAWDYTKPLFVAPAMNTLMWNNPF
TERHLLSLDELGITLIPPIKKRLACGDYGNGAMAEPSLI

SEQ ID NO: 9, AtHAL3b

ATGAATATGGAAGTGGATACAGTAACAAGGAAGCCTCGTATCTTACTAGCTGCAAGTGGAAGTGTG
GCTTCAATTAAGTTCAGTAATCTCTGCCATTGTTTCTCAGAATGGGCTGAAGTCAAAGCCGTCGCT
TCAAAATCATCTCTCAATTTCGTTGATAAACCTTCTCTACCTCAGAATGTGACTCTCTATACAGAT
GAAGATGAATGGTCTAGCTGGAACAAGATTGGTGATCCCGTTCTTCATATCGAGCTCAGACGCTGG
GCTGATGTTATGATCATTGCTCCTTTGTCTGCTAACACATTAGCCAAGATTGCTGGTGGGTTATGT
GATAATCTATTGACATGTATAGTAAGAGCATGGGATTATAGCAAACCGTTGTTTGTTGCACCGGCG
ATGAACACTTTGATGTGGAACAATCCTTTCACAGAACGGCACCTTGTCTTGCTTGATGAACTTGGA
ATCACCCTAATTCCTCCCATCAAGAAGAAACTGGCCTGTGGAGACTACGGTAATGGCGCAATGGCT
GAGCCTTCTCTGATTTATTCCACTGTTAGACTGTTCTGGGAGTCACAAGCTCGTAAACAAAGAGAT
GGAACCAGTTGA

SEQ ID NO: 10, AtHAL3b

MNMEVDTVTRKPRILLAASGSVASIKFSNLCHCFSEWAEVKAVASKSSLNFVDKPSLPQNVTLYTD
EDEWSSWNKIGDPVLHIELRRWADVMIIAPLSANTLAKIAGGLCDNLLTCIVRAWDYSKPLFVAPA
MNTLMWNNPFTERHLVLLDELGITLIPPIKKKLACGDYGNGAMAEPSLIYSTVRLFWESQARKQRD
GTS

SEQ ID NO: 11, AK100138, Oryza sativa (japonica cultivar-group) cDNA clone:J023010L24, full insert sequence

CAACCAAAGTCCAAAGGCTATTCTGAACCGAAGTCCTCCCACACCAAAACTTCGAGGCCCCCGTCG
CGGCACCCTCCTCCGCCGCCGGATCTCCACCGGAGTACGGCGCCGGCCACCCCCTCCTCCCCCGGA
TCTTCACCGCCCCTCAAGTACTGAGGTCATCACTACATCAGAGTCACTACAAGAAACCTTCCCATT
GGATTTCCCTCATCCTAGCAAACCTCGGGTCCTCCTTGCTGCCTCTGGAAGCGTCGCTGCTATAAA
ATTTGAGAGCCTTTGCCGTAGCTTCTCGGAATGGGCAGAAGTCAGAGCCGTCGCCACCAAGGCTTC
ATTACATTTTATTGATAGAACGTCTCTGCCTAGCAATATTATTCTTTACACTGATGATGATGAATG
GTCTACCTGGAAGAAGATAGGGGATGAAGTTTTGCACATTGAACTGCGAAAATGGGCAGATATCAT

FIGURE 4 (continued)

```
GGTGATTGCGCCATTATCAGCTAATACCCTAGCTAAGATTGCTGGTGGTTTATGTGACAACCTCTT
GACATGCATAGTGAGAGCATGGGACTACAGCAAACCACTCTTTGTTGCCCCAGCTATGAACACCTT
CATGTGGAACAACCCGTTCACCAGTCGTCATCTTGAGACAATCAACCTGCTAGGTATATCTTTGGT
CCCTCCCATTACCAAAGGCTGGCCTGTGGTGATTATGGTAATGGTGCAATGGCTGAGCCTTCTGT
GATCGATTCCACCGTCAGGCTTGCTTGCAAGAGACAGCCACTTAATACAAATAGTTCACCTGTGGT
TCCTGCCGGCAGAAACCTCCCATCTAGCTGATGCGGCAACTATTCTGTTCAAGATTAAACTCTGGA
CCTAGTTTTCTATGGTAAAGAGTACTTCGTGTCACAAATGAAATGTTAAGTGATGTCTATGTCGG
CCAACATAGCACCTTTATTGGCCAGTTGTTGTACTACTATTAGTGATATGGTAGGACGTGGAGATT
GGAGAAAGGCTATTGTCCCAGCACTTTAATGTTGCTTTTCCAAATTCTTGTGACATAATGCTAAG
GTGCTGATGAATATGTTCATGTTGTAGCACTATTTTTTCTGCAAATGTTTGCAAAGACTCGTGAT
GGAATC
```

SEQ ID NO: 12, AK100138, Oryza sativa HAL3 protein

```
MTTSESVQETLGLDFPHPSKPRVLLAASGSVAAIKFESLCRSFSEWAEVRAVATKASLHFIDRTSL
PSNIILYTDDDEWSTWKKIGDEVLHIELRKWADIMVIAPLSANTLAKIAGGLCDNLLTCIVRAWDY
SKPLFVAPAMNTFMWNNPFTSRHLETINLLGISLVPPITKRLACGDYGNGAMAEPSVIDSTVRLAC
KRQPLNTNSSPVVPAGRNLPSS
```

SEQ ID NO: 13, BT009136, Triticum aestivum clone w1ln.pk0039.e3:fis, full insert mRNA sequence

```
GCACGAGCAGCCGCGGAGCCGCCAGAGACAGACGCTGCCGCCGTCGGCCGTCCTCCGCCCTCCAGT
TGAGCGGTTCAAGCAGAGCTGATGGCTACATCAGAGCCAGTACAAGAGAGTTTGGTGGTGCACTAC
TCACAACCTAGTAGGCCCCGGGTCCTCCTTGCTGCTTCAGGAAGTGTAGCCGCTATAAAATTTGAG
AGCCTTTGCCGTAGCTTCTCTGAGTGGGCGGATGTCCGAGCTGTGGCCACCACGCCATCCTTGCAC
TTCGTTGATAGATCATCTCTACCAAGTGGCATCGTTCTTTACACTGATGACGATGAATGGTCTACC
TGGAAGAAGATAGGAGATGAAGTCTTACACATCGAGCTGCGGAAATGGGCAGACGTTATGGTGATC
GCTCCATTGTCAGCAAATACCCTGGCTAAGATCGCCGGTGGGTATGCGACAACCTCTTGACCTGC
ATCGTGAGAGCGTGGGACTACAGCAAACCGCTCTTTGTTGCCCCAGCCATGAACACGTTAATGTGG
AACAACCCATTCACGGAGCGGCATCTTCACACAATCAACCAACTGGGCATAGCCTTGATCCCCCCA
GTTACCAAAAGGCTGGCCTGTGGCGATTACGGGAACGGCGCAATGGCCGAAACCTCGCAGATCCAT
ACTTCCGTGAGGCTCGCGTGCAAGACGCAACCGCACGATGCGAGCAGTTCACTCGCGGGTCCTGTC
AGTAATAACCGGCCATCTAGCTGATGCAGCAGTTGGCCACTTGATTGTCAAGCTTAGGAATTTGTT
TTATATGCAGTGTGCATCTGGAGTGTTGTAACAGATTTTTTTCCAACTAGTGTTTGTGTGTATTG
AAATTGGGGGGGAAAGGCTGTTGTCACAGGATAACAATAACTTCCTCCCTGCTCAGTAATTATGAG
TCTATTCAGTTTGTAATTGTCGGTGGGAGTACAATTATGCTACAATATTGTTTGTTTGTGTGTGTG
TGGGAGTTGGGGAGTGCTGCTGCCACAGAGATAGCTTCCTCCCTGCCCAGCCAGTAATGATAGTGA
TTATTCAGTTTGTAGTTGTCAGTGGAAGTGTCCAGCAAACTTTTCTACTACCCTTTGATATTCCTG
GTACAAATGTTGGAACGACTGTCCTAAAAAAAAAAAAAAAAA
```

SEQ ID NO: 14, BT009136, Triticum aestivum HAL3

```
MATSEPVQESLVVHYSQPSRPRVLLAASGSVAAIKFESLCRSFSEWADVRAVATTPSLHFVDRSSL
PSGIVLYTDDDEWSTWKKIGDEVLHIELRKWADVMVIAPLSANTLAKIAGGLCDNLLTCIVRAWDY
SKPLFVAPAMNTLMWNNPFTERHLHTINQLGIALIPPVTKRLACGDYGNGAMAETSQIHTSVRLAC
KTQPHDASSSLACPVSNNRPSS
```

FIGURE 4 (continued)

SEQ ID NO: 15, AY105313, Zea mays PCO119881 mRNA sequence

GCACGAGGTCAGATCGACCTGGACTTTGGCGGCAGCTACTTCTAGAACGCGGCGGCACGGCAGCAA
GCCAGCAAGGAGAACGCGGCGGCACGGGCGTGCTGCTACTTCTGCTTCCTCTCCGACGCTTGCTGT
TGAGCGGTTCAAGCAGAGCTGATGGCTACATCAGAGCCAGTACAAGAGAGTTTGGTGGTGCACTAC
TCACAACCTAGTAGGCCCCGGGTCCTCCTTGCTGCTTCAGGAAGTGTAGCCGCTATAAAATTTGAG
AGCCTTTGCCGTAGCTTCTCTGAGTGGGCGGATGTCCGAGCTGTGGCCACCACGCCATCCTTGCAC
TTCGTTGATAGATCATCTCTACCAAGTGGCATCGTTCTTTACACTGATGACGATGAATGGTCTACC
TGGAAGAAGATAGGAGATGAAGTCTTACACATCGAGCTGCGGAAATGGGCAGACGTTATGGTGATC
GCTCCATTGTCAGCAAATACCCTGGCTAAGATCGCCGGTGGGTTATGCGACAACCTCTTGACCTGC
ATCGTGAGAGCGTGGGACTACAGCAAACCGCTCTTTGTTGCCCCAGCCATGAACACGTTAATGTGG
AACAACCCATTCACGGAGCGGCATCTTCACACAATCAACCAACTGGGCATAGCCTTGATCCCCCCA
GTTACCAAAAGGCTGGCCTGTGGCGATTACGGGAACGGCGCAATGGCCGAAACCTCGCAGATCCAT
ACTTCCGTGAGGCTCGCGTGCAAGACGCAACCGCACGATGCGAGCAGTTCACTCGCGGGTCCTGTC
AGTAATAACCGGCCATCTAGCTGATGCAGCAGTTGGCCACTTGATTGTCAAGCTTAGGAATTTGTT
TTATATGCAGTGTGCATCTGGAGTGTTGTAACAGATTTTTTTCCAACTAGTGTTTGTGTGTATTG
AAATTGGGGGGAAAGGCTGTTGTCACAGGATAACAATAACTTCCTCCCTGCTCAGTAATTATGAG
TCTATTCAGTTTGTAATTGTCGGTGGGAGTACAATTATGCTACAATATTGTTTGTTTGTGTGTGTG
TGGGAGTTGGGGAGTGCTGCTGCCACAGAGATAGCTTCCTCCCTGCCCAGCCAGTAATGATAGTGA
TTATTCAGTTTGTAAAAAAAAAAAAAAAAAAAAAAAAAAAAAAA

SEQ ID NO: 16, AY105313, Zea mays HAL3

MATSEPVQESLVVHYSQPSRPRVLLAASGSVAAIKFESLCRSFSEWADVRAVATTPSLHFVDRSSL
PSGIVLYTDDDEWSTWKKIGDEVLHIELRKWADVMVIAPLSANTLAKIAGGLCDNLLTCIVRAWDY
SKPLFVAPAMNTLMWNNPFTERHLHTINQLGIALIPPVTKRLACGDYGNGAMAETSQIHTSVRLAC
KTQPHDASSSLAGPVSNNRPSS

SEQ ID NO: 17, AJ271130, Picea abies partial mRNA for putative halotolerance protein HAL3 homolog, (pPA0038 gene)

GGACGCGTGGGTACTGTACTGCATATAGAACTCCGGCAATGGGCTGATGCTATGGTGATTGCTCCA
CTATCAGCAAACACGCTTGCTAAGATAGCAGGTGGCCTATGCGACAATCTACTGACTTGCATAATA
CGTGCATGGGACTTTAACAAGCCTCTCTTTGTAGCTCCTGCAATGAATACTTTCATGTGGAACAAC
CCATTTACTCAACGGCATTTGGACTCTATCTCGGAGATGGAGTATCACTTATCCCCCCTATAACA
AAGACGTTAGCTTGTGGTGATTATGGAAATGGTGCAATGTCAGAACCTTCCTCAATAGATACAACT
CTTAGGTTTTCACTCGATCCTTCAATTAAATGAAGTATCTGATCTCCCTTTCTCCAATTCTTGTTA
TGAATCTAACATGCTTAGTACTATGGACTGTGGTATAGACTCAGATTCGTAGCTGGGCTAGACAGC
ATGAACCCAGCTCGTGTGTGGCTATGTTAAGAAATTCTGATGATAAACAATCTCGAACTTATGATT
TATGTAACATTTGTTCCNCCATTCTGGACACTTACAAGAACTGTGTGGATACTCCTGCTTATAAGA
AAATGTGTCAATCTACATTGCATATCATCTAATTTGG

SEQ ID NO: 18, Q9AVS8_PICAB, Putative halotolerance protein HAL3 homolog (Fragment) - Picea abies (Norway spruce) (Picea excelsa).

GRVGTVLHIELRQWADAMVIAPLSANTLAKIAGGLCDNLLTCIIRAWDFNKPLFVAPAMNTFMWNN
PFTQRHLDSISEMGVSLIPPITKTLACGDYGNCAMSEPSSIDTTLRFSLDPSIK

FIGURE 4 (continued)

SEQ ID NO: 19, CN726994 BNDH5DCT_UP_001_E10_15DEC2003_072 Brassica napus BNDH5DCT Brassica napus cDNA 5', mRNA sequence

```
GAGATCTGTAAGGGTTTTCAAAAAGAGCCATGGAGAACGGGAAAAGAGACAGAGAAGACATGGAAG
TGCAGCTCTCCCCTAGAAAGCCCCGCGTACTCCTCGCAGCAACCGGAAGCGTCGCCGCCATCAAAT
TCGGCAACCTCTGCCACTGCTTCACAGAGTGGGCGGAAGTGAGAGCCGTCGTCTCGAAATCGTCTC
TCCACTTCCTCGACAAGCTCTCTCTCCCACAGGAAGTGACTCTCTACACCGACGAAGACGAGTGGT
CGAGCTGGAACAAGATCGGCGATCCCGTGCTTCACATCGAGCTCAGACGCTGGGCTGACGTCATGG
TCATCGCTCCTTTGTCTGCTAACACTTTAGCCAAGATAGCTGGTGGGATGTGTGATAATCTTCTGA
CTTGTATCATAAGAGCTTGGGATTATAGCAAACCGCTTTCGTTGCGCCGGCTATGAATACTTTGA
TGTGGAACAATCCTTTTACGGAGAGGCATCTTTTGTCGCTTGATGAGCTTGGAATCACTCTTATTC
CTCCGATCAAGAAGAGGTTGGCTTGTGGTGACTATGGTAATGGCGCGATGGCTGAGCCGTCTCTTA
TCTATTCCACTGTTAGACTCTTCTGGGAGTCTCAGGCTCATCAGCAAAGTGGTGGAACTAGTTAAT
ACCATGATGGTTTTGCACTTTGCAATGGTTGGTCAGTGTCATAGATTGTTCTGTCTGAAATGCTCG
TCCTTGTATATGTTAAGAACAGCTGTCTGGGTTGATGTCTCTT
```

SEQ ID NO: 20, CN726994 [30 – 656] BNDH5DCT_UP_001_E10_15DEC2003_072 Brassica napus BNDH5DCT Brassica napus cDNA 5', mRNA sequence

```
MENGKRDREDMEVQLSPRKPRVLLAATGSVAAIKFGNLCHCFTEWAEVRAVVSKSSLHFLDKLSLP
QEVTLYTDEDEWSSWNKIGDPVLHIELRRWADVMVIAPLSANTLAKIAGGMCDNLLTCIIRAWDYS
KPLFVAPAMNTLMWNNPFTERHLLSLDELGITLIPPIKKRLACGDYGNGAMAEPSLIYSTVRLFWE
SQAHQQSGGTS
```

SEQ ID NO: 21, AM060322 AAFC_WHRI_BoE01a Brassica oleracea var. alboglabra cDNA clone AAFC_WHRI_BoE01a014N23_SP6, mRNA sequence

```
GACGCGTGGGCGGACGCGTGGGGGGTTTTCAAAAAGAGCCATGGAGAACGGGAAAAGAGACAGAGA
AGACATGGAAGTGCAGCTCTCCCCTAGAAAGCCCCGCGTACTCCTCGCAGCAACCGGAAGCGTCGC
CGCCATCAAATTCGGCAACCTCTGCCACTGCTTCACAGAGTGGGCGGAAGTGAGAGCCGTCGTCTC
GAAATCGTCTCTCCACTTCCTCGACAAGCTCTCTCTCCCACAGGAAGTGACTCTCTACACCGACGA
AGACGAGTGGTCGAGCTGGAACAAGATCGGCGATCCCGTGCTTCACATCGAGCTCAGACGCTGGGC
TGACGTCATGGTCATCGCTCCTTTGTCTGCTAACACTTTAGCCAAGATAGCTGGTGGGATGTGTGA
TAATCTTCTGACTTGTATCATAAGAGCTTGGGATTATAGCAAACCGCTTTCGTTGCGCCGGCTAT
GAATACTTTGATGTGGAACAATCCTTTTACGGAGAGGCATCTTTTGTCGCTTGATGAGCTTGGAAT
CACTCTTATTCCTCCGATCAAGAAGAGGTTGGCTTGTGGTGACTATGGTAATGGCGCGATGGCTGA
GCCGTCTCTTATCTATTCCACTGTTAGNCTCTTCTGGGAGTC
```

SEQ ID NO: 22, AM060322 AAFC_WHRI_BoE01a Brassica oleracea var. alboglabra cDNA clone AAFC_WHRI_BoE01a014N23_SP6, mRNA sequence

```
MENGKRDREDMEVQLSPRKPRVLLAATGSVAAIKFGNLCHCFTEWAEVRAVVSKSSLHFLDKLSLP
QEVTLYTDEDEWSSWNKIGDPVLHIELRRWADVMVIAPLSANTLAKIAGGMCDNLLTCIIRAWDYS
KPLFVAPAMNTLMWNNPFTERHLLSLDELGITLIPPIKKRLACGDYGNGAMAEPSLIYSTVXLFWE
```

FIGURE 4 (continued)

SEQ ID NO: 23, DW001590 KR3B.001J04F.050815T7 KR3B Nicotiana tabacum cDNA clone KR3B.001J04, mRNA sequence

GGAGCTGTGTTGCCGCAGAAGGAGCAAGAATTGTTGGTGCTTCAAGGATAATTGGTGTTGATTTAA
TTCCTAGCAGATTTGATTTAGATTAGGGTAGATATGGAGACTTCAGAGATGGAACCGGTTCAGATT
AACAATGCACCGAGGAGACCTCGCATTCTGCTTGCAGCAAGTGGAAGTGTGGCTGCTATCAAGTTT
GCCAGTCTATGCCGTTCCTTTACTGATTGGGCTGAAGTTAAAGCGGTTGCTACAAAAGCTTCTCTT
CATTTCATAGACAAAGCTTCACTTCCGGAAGATGTCATTCTTTATACTGATGAGGATGAATGGTCA
ACTTGGACGAAGATAGGTGACCGTGTGCTACACATCGAGCTCCGGAGGTGGGCTGATATTATGATT
ATTGCCCCTTTGTCAGCAAATACACTTGGGAAGATTGCTGGTGGACTATGTGATAACTTGTTAACC
TGCATCGTACGAGCATGGGACTACGATAAACCCCTTTTCGTGGCACCAGCAATGAATACATTGATG
TGGAATAATCCATTCACAGAAAAGCACCTTATGGCAATTGATGAGCTTGGGATCTCTCTCATACCA
CCAGTATCAAAGAGACTAGCCTGTGGAGATTACGGGAATGGAGCAATGGCTGAACCGTCTCTGATC
TTCCAAGCTGTAAGACTCTATTATGACGCACAATTACGATCAGGTGGCAGCAACGTGGCGTGATCC
ACAGGTCATGAAATTTCATTCATCGGTTTGTACAAGTGATAGAAGTTGTTGAAATTCAGGACCAGG
AGCCCAGCTGTGTTATTTTTCTCCTAAATTCTTCACCTCCCTAGTATCTTTCTTGTGTCCTAGAGC
TACTTTCAATCAAGGTTCATGTTCATTTTAGTCGATAAAATGAGAATATCACGTAACTGCTGTTAC
TAATGGATGTGATCATGATCATGAACATGAAAAA

SEQ ID NO: 24, KR3B.001J04F.050815T7 KR3B Nicotiana tabacum cDNA clone KR3B.001J04, mRNA sequence (NtHAL3a)

METSEMEPVQINNAPRRPRILLAASGSVAAIKFASLCRSFTDWAEVKAVATKASLHFIDKASLPED
VILYTDEDEWSTWTKIGDRVLHIELRRWADIMIIAPLSANTLGKIAGGLCDNLLTCIVRAWDYDKP
LFVAPAMNTLMWNNPFTEKHLMAIDELGISLIPPVSKRLACGDYGNGAMAEPSLIFQAVRLYYDAQ
LRSGGSNVA

SEQ ID NO: 25, Solanum tuberosum

GAATTGATCGGCGCCGGACTTCGATCACCGTCGGCGTTTCTAAGCCGTCGCCGGAACTAAGCCGGA
GAAAATCTCAATCAAGTGAGCTAAGCACTCGGCGTTTCAACTTCTGGTTATAAATTTATTAAAGCC
TTTGCTCCATTAGGTTAGGTAGATACGGATCCTATGACTTCAGAGATGGAACCAGTTCAGATTAAT
GGTGCACCTAGGAGACCTCGTATTCTGCTGGCAGCAAGTGGAAGTGTGGCTGCAATTAAGTTTGCA
AATCTATGTGGTTGTTTTTCTGAATGGGCAGAAGTTAAAGCAGTTGCAACAAAACCTTCTCTTCAT
TTCATAGACAAAGCTTCACTTCCGGAAGATGCCATTCTATATACTGATGAGGAGGAATGGTCCACT
TGGAAGAAAATTGGTGATAGTGTGCTACACATTGAGCTCCGCAGGTGGGCTGATATTATGGTTATT
GCCCCTTTGTCAGCAAACACACTTGGGAAGATTGCAGGTGGACTATGTGATAACTTGTTAACCTGC
ATCGTACGAGCATGGGACTACAATAAACCCCTTTTGTGGCACCAGCCATGAATACATTGATGTGG
AATAATCCATTCACAGAACGACACCTTATGGTAATTGATGAGCTTGGAATCTCTCTCATACCACCA
CTTTCTAAAAGACTAGCTTGTGCAGATTATGCAAACGGCCTATGGCTGAACCTTCTCTCATCTAC
TCAACTGTAAGACTCTTCTATGAGTCACGGTCACAATCAGGTGGCATCAACTTGGCTTGATCCACG
GATCATTAAATTTTATTCGTCGGTTTGTACAAGTGGTAGAAATTGTTGAAATTCAGGACCTGGAAC
AGTGTTACTTAGCATACACCAGTTGTGTTTATTTTCTCCTTAATTAGTGTCATGTTTGTATCCAA
GAGCTGACTTTCAATCAAGTTTCATGTTCATTGTAGTCTATTGACTCTGAATATTATGCAACTCTA
TATAGTACCCGCTACTAATTATGTAT

FIGURE 4 (continued)

SEQ ID NO: 26, StHAL3

MTSEMEPVQINGAPRRPRILLAASGSVAAIKFANLCGCFSEWAEVKAVATKPSLHFIDKASLPEDA
ILYTDEEEWSTWKKIGDSVLHIELRRWADIMVIAPLSANTLGKIAGGLCDNLLTCIVRAWDYNKPL
FVAPAMNTLMWNNPFTERHLMVIDELGISLIPPVSKRLACGDYGNGAMAEPSLIYSTVRLFYESRS
QSGGINLA

SEQ ID NO: 27, Glycine max

GGTTGAACAGAAGAGATTTAGGCAGCCCGAACCGACGATGTTGTTTTTAACTGACAGCAGCACAAA
GCGAACACTAACACTAACGTGAAACGCGTTGCGTTGTCGGAAAATCACCCTCACCTGATCACTGTG
GAAGTCTCTAGGTGATGGCCGGTTCAGAACCTGTTAGGGCAGAGGGAGAGACTATGGCTGTGGATG
CTGCCCCAAGGAAGCCCCGGATTCTACTTGCTGCTAGTGGGAGTGTTGCTGCTGTCAAATTTGCAA
ATCTTTGTCACTGTTTCTCTGAATGGGCAGATGTAAGAGCAGTTTCCACAAGTGCATCTTTGCATT
TCATTGATAGAGCAGCAATGCCCAAGGATGTAATTCTATACACGGATGACAATGAATGGTCTAGTT
GGAAGAAATTAGGTGATAGCGTGCTTCACATTGAGCTTCGCAAATGGGCTGATATCATGGTCATCG
CTCCATTATCAGCAAACACCCTTGGCAAGATTGCTGGAGGGTTGTGTGACAATCTACTGACATGCA
TCGTTCGAGCCTGGGACTACAGCAAGCCATTCTTTGTTGCACCAGCCATGAACACTTTGATGTGGA
ACAATCCTTTCACTGAGCGGCATTTCATCTCCATTGATGAGCTTGGCATTTCTCTCATCCCGCCTG
TTACAAAGAGGTTAGCTTGTGGGGATTATGGCAATGGTGCCATGGCTGAACCCTCTACCATTTACT
CAACTGTAAGGCTCTTCTATGAGTCAAAGGCTCAGCAAGGTAGAGCTGTGGTAACCTTAAGGTGAA
TGAAGGGGTAGTCCTACGCCCCCATTCATGGTAGTCAATAGCACTCTATAGCAGGATAACGGAGCG
CAGCAGCCCTGAGTTACTATGGAAGTCGAAATCGCTGAGCGATTTTCAATAACCGCTGTAGCGGCT
GCAATAGTGGTCTAAATACAGCTTTTCGGGTGCTACAGCGCAC

SEQ ID NO: 28, GmHAL3

MAGSEPVRAEGETMAVDAAPRKPRILLAASGSVAAVKFANLCHCFSEWADVRAVSTSASLHFIDRA
AMPKDVILYTDDNEWSSWKKLGDSVLHIELRKWADIMVIAPLSANTLGKIAGGLCDNLLTCIVRAW
DYSKPFFVAPAMNTLMWNNPFTERHFISIDELGISLIPPVTKRLACGDYGNGAMAEPSTIYSTVRL
FYESKAQQGRAVVTLR

SEQ ID NO: 29, Vitis vinifera

TTGGGAGAGATGCCACGGCCCTCATTCGCTCTCGATCCCCGACCTCGGCTTCACTCTCTCTAATTT
TCCCGAGCAATTCTCCGAGTTGAGGCTGATTTGAAAGTTAATGATGATGACATATGCAGAACCTTT
GAGTCCAGAAGTTGATGCGATACCAGTCAACATTGCTCCCAGAAGACCCCGGATTCTACTTGCTGC
TAGTGGGAGTGTAGCTGCTATGAAGTTTGGGAATCTCGTCCATTCTTTTTGTGAATGGGCAGAAGT
AAGAGCAGTTGTCACAAAGGCTTCTTTACACTTCATTGATAGAGCAGCACTGCCTAAGGATTTATA
TCTTTACACTGATGATGATGAATGGTCCAGTTGGACAAAATTAGGAGACAGTGTGCTTCACATTGA
GCTCCCGCAGGTCGGCTGATCTCATGGTAATCGCCCCATTATCAGCAAATACACTTGGCAACATTGC
CGGGGGACTGTGTGACAACCTGCTGACATGCATTGTGCGAGCGTGGGACTACAGCAAGCCAATGTT
TGTTGCGCCAGCTATGAACACCTTCATGTGGACCAATCCTTTCACAGAACGCCATCTTATGACAAT
TGATGAACTTGCAATTTCTCTTATTCCACCTGTCACTAAAAGCCTGCTTCCCAGATTATCGGAC
TGGTGCAATGGCTGAACCTTTTCTCATCCACTCAACCGTAAGACTCTTCTTGGAGACACGGGCTCA
ATCAAGTAGCAGTAATGTGCAGTAATTGGGTATGGTTAATCTGTCTGTTGGAGAAGTCACCAGAGA
GTTGGCTGAAATGGCATGTTGGAAATGCTAAACGTAGTTCACTTGGACCGCATTGATTTGTTATG
ACCGTCCATTAAACTTACTACGTCTTGTAGATTGTTGGTATCGGTGGATTTGCATATCCTGTTTCT

FIGURE 4 (continued)

CAATATTTCTAGTAGCGCCTTTTGAATGTTATGTGCCTTGTGTATTAATGGTGAGGGAGAATGTAT
CAGTCTCCTAAATTTCTCAATCTCTGTGTAGACATGCTTGATGATACATTCCTATAAATAGACTCT
GATTTCTGGGC

SEQ ID NO: 30, VvHAL3

MMMTYAEPLSPEVDAIPVNIAPRRPRILLAASGSVAAMKFGNLVHSFCEWAEVRAVVTKASLHFID
RAALPKDLYLYTDDDEWSSWTKLGDSVLHIELRRWADVMVIAPLSANTLGKIAGGLCDNLLTCIVR
AWDYSKPMFVAPAMNTFMWTNPFTERHLMTIDELGISLIPPVTKRLACGDYGTGAMAEPFLIHSTV
RLFLETRAQSSSSNVQ

SEQ ID NO: 31, Hordeum vulgare

CGGCACGAGGCTCCCCAATTCCCTCCGCCCGCGGCGCGCCGCTCCGGGCAGCCTCGGTCGCCGCCG
CCGCCGCCGCTGCCTCCACCTACCGCCGGCCGACGACGCCCTTCGAACCTACCGCCTCCGCCGCCA
TCTTCAACCGCTTATTTGCCTGCGCTCCTACCAGATCGCCTCTGAGTTGAGGGCTCCAAGTGAAGC
AGATGGCTACATCAGAACCGGTACAGCAAAGCTGGGAGCTGGAATCCAGCAGGCCTCGGGTCCTCC
TTGCTGCGTCAGGGAGTGTAGCTGCTATAAAATTCGAGAGCCTCTGCCGTATCTTCTCCGAGTGGG
CGGAAGTCCGAGCTGTGGCGACCAAGTCAGCATTGCACTTTGTTGACAGATCATCTCTGCCAAGCG
ACGTCGTCCTTTACACTGATGATGATGAGTGGTCTACCTGGACAAAGATAGGAGACGAGGTTCTGC
ACATAGAGCTGCGAAAGTGGGCAGACATCATGGTGATCGCCCCTTATCAGCAAACACTCTGGCCA
AGATCGCCGGCGGGTTATGCGACAACCTCCTGACGTGCATTATCCGAGCGTGGGACTACAAGAAGC
CGATCTTCGCCGCGCCAGCCATGAACACCTTCATGTGGAACAACCCATTCACGGCGCGCCACATCG
AGACCATGAACCAACTGGGCATCTCCCTGGTCCCGCCCACCACGAAACGGCTGGCCTGCGGCGACT
ACGGGAACGGCGCGATGGCTGAGCCCTCGCAGATCCACACGACTGTGAGGCTCGCGTGCAAGTCGC
AGACGTTTGGCACGGGCATTTCGCCCGCGCACCCTTCCAGCGGCCACCCCGTCTAGCCGATGCGGT
GATGGTCACTATGTTCAGGTGGTCTAGTACTCGAGGTTTTTCTATGCCGCCCACATCATCAGGGTT
TGAGAAAGTGAAGGGTATCACCAGGTGTTCTGTTCATCGGTGGTGTCTGTATTAACCGAAGTATCG
TACCTGTGGGATATGGATCAGCTTATTTGTTATGTGGTAGTAGACGTTAGGGCGTAGACGTAGAGA
TTGGGGAATTGCTGTTGCTCCAGCC

SEQ ID NO: 32 HvHAL3

MATSEPVQQSWELESSRPRVLLAASGSVAAIKFESLCRIFSEWAEVRAVATKSALHFVDRSSLPSD
VVLYTDDDEWSTWTKIGDEVLHIELRKWADIMVIAPLSANTLAKIAGGLCDNLLTCIIRAWDYKKP
IFAAPAMNTFMWNNPFTARHIETMNQLGISLVPPTTKRLACGDYGNGAMAEPSQIHTTVRLACKSQ
TFGTGISPAHPSSGHPV

SEQ ID NO: 33 Gossypium hirsutum

CCCATTGTCACCTTTAGTGCTGGTGAGCATTTAAGAGAGGGCAGAGCAACGGAGGAAATCCCCTTT
TTTGTGCAGTGGAAGTAAAAATTACCTACCATTAGAAAAGGAGAAGGATTGGTAAAGTATTGCAGC
GCTCCGTAAAGGCATTTTGGTATAGCAAGTAGCAGCAATTCATCAAAAGGCAGCATTTCTTTTTGC
ACCAGGGGCCCTTTAAAAAGCTCAACTCTCGCGCTTCTTTGCGTTTCAAATCTCTCTGCAAGTCGC
AAGGACATCTGAAGCAGAAAGCCCAGATTCCTCTCTAATCTTAGATTCCAGATTTGCATAGGTTAT
GGCGTATCCTGAGCCTCAAGGTGCAGATAGGGAGATGGTTAAGGTCAATCCTACCCCAAGAAAACC
CCGGGTTTTACTCGCTGCCAGTGGAAGTGTAGCTGCCATAAAGTTTGGAATCTCTGCCATTGTTT
CTCTGAATGGGCAGAAGTAAAAGCAGTTGCCACGAAAGCTTCTTTGCATTTCATTGACAGAGCATC

FIGURE 4 (continued)

```
ACTTCCTAAGGATCTAAAGCTTTACACTGATGAGGAGGAATGGTCTAGTTGGGGGAAAATAGGTGA
CAGTGTGCTTCACATTGAGCTTCGTCGATGGGCTGATATTATGGTCATTGCCCCATTGTCAGCAAA
CACACTTGGCAAGATTGCTGGAGGATTATGTGACAATTTGTTAACTTGTGTCGTACGAGCATGGGA
CTACAGCAAGCCAATGTTTGTTGCACCAGCTATGAACACTTTCATGTGGAGCAACCCTTTCACAGA
AAAGCATCTCATGACAATTGATGAGCTTGGTATTTCTCTCATCCCCCCTGTCTCCAAAAGACTAGC
TTGTGGGGACTATGGAAACGGCGCAATGGCAGAACCTTCTCTAATCCACTCGACTGTAAGATTATT
CTTGGAGTCACGACCTCAACCAAGTGACTGAAGATCTATTTATTCGCCATGAATTATAAATACTAT
ATTAGTTGTATGGTAGCCCAGTTGACTCTAGGTTGGGTGTATGTCTATTAGCTGTCTAACAAGCTT
ATTGTACATTTATAGTTGCATTTCCGAGTTTGCTTAACTTTGCATATCATGAGGAGTGGTCTTTGA
ATACTGCTGAAAATTTGATCCTGTAAGCTGATGATACTGATGAGAGTTGGCAG
```

SEQ ID NO: 34, GhHAL3

```
MAYPEPQGADREMVKVNPTPRKPRVLLAASGSVAAIKFGNLCHCFSEWAEVKAVATKASLHFIDRA
SLPKDLKLYTDEEEWSSWGKIGDSVLHIELRRWADIMVIAPLSANTLGKIAGGLCDNLLTCVVRAW
DYSKPMFVAPAMNTFMWSNPFTEKHLMTIDELGISLIPPVSKRLACGDYGNGAMAEPSLIHSTVRL
FLESRPQPSD
```

SEQ ID NO: 35, Sorghum bicolor

```
GCACGAGGGCTCTCTCCGCTCACCTCCACTTCCCCGCCCCCGCCCCGGTCTCCGTCCTTGACACGG
GCGCGCACCCGTCCGCCTCCGACTGACCCGGAGCCGACTCGACCTTGTTCAGGAGGGAGGGAGAGC
CCGAACCGCGGCGGGGCGGGAGGGCTCCTTTTCGTTTGCCCCGCCGGAGGGCCAGCCGCCCCATGG
GCCGGTCGCCTGAGCGCGCTACGTATCAGCTCATCGACCGGCGGAAAGCTGAGCGTTAGCGGAGCT
GATGGCTACATCAGAGCCAGTACAAGAGAATTTGGCGATGGACTACTCACAACCTAGTAAGCCTCG
GGTACTCCTTGCTGCTTCAGGAAGTGTAGCCGCTATAAAATTTGAGAACCTTTGTCGTAGTTTCTC
TGAGTGGGCGGATGTCCGAGCCGTGGCCACCGCATCATCTTTGCACTTTATTGATAGATCATCTCT
TCCAAGTGACATTGTTCTTTACACTGATGATGATGAGTGGTCTACCTGGAAGAAGATAGGAGATGA
AGTTTTACACATTGAGCTGCGTAAATGGGCAGATATTATGGTGATTGCTCCGTTATCAGCAAATAC
CCTGGCTAAGATCGCCGGTGGGTTATGTGACAACCTCTTAACATGCATCGTGAGAGCGTGGGACTA
CAGCAAACCGCTCTTTGTTGCCCCAGCTATGAACACATTAATGTGGAACAACCCATTCACAGAGCG
TCATCTTCAAACGATCAACCAACTGGGCATAATCTTGATCCCCCCAGTTACCAAAAGGTTGGCTTG
TGGCGATCACGGGAATGGTGCAATGGCTGAAACCTCGCAGATCTATACTTCTGTGAGGCTTGCATG
GAAGACGCAACCACATGATGCAAGCAGTTCACTTGTGGTTCCTGTCAGTAATAACCGCCCATCTAG
CTGGTGTTTGACCTCTTAATTAAGAGCTTAGGAATTTGTTTATCTGCAGTGTGCATCTTGATGTT
AGAAATGTTGTACCAATTTTTTTAACCAGTGTTTAGTGTGTATTGTGATGAGAATGTGGGGAAA
GGAAGGTTGTCAGTTGTCACGGTGATAAATTACTGCCAGCTCAGTATCGATAGTGAGGATGAG
```

SEQ ID NO: 36, SbHAL3

```
MATSEPVQENLAMDYSQPSKPRVLLAASGSVAAIKFENLCRSFSEWADVRAVATASSLHFIDRSSL
PSDIVLYTDDDEWSTWKKIGDEVLHIELRKWADIMVIAPLSANTLAKIAGGLCDNLLTCIVRAWDY
SKPLFVAPAMNTLMWNNPFTERHLQTINQLGIILIPPVTKRLACGDHGNGAMAETSQIYTSVRLAW
KTQPHDASSSLVVPVSNNRPSSWCLTS
```

FIGURE 4 (continued)

SEQ ID NO: 37, Lycopersicon esculentum

CTACAATTGATCGGCGCCGGACTTTGATCACCGTCGGCGTTTCTAAGCCGTTGCCGGACTATGCCG
GAGCAAATCTCAATCAAGTGAGCTAACCACTCTGTGTTTCAACTTCTGGTTATAAATTTTTTAAAG
CCTTTGCTCCGTTAGGTTAGGTAGATACGGATCCTATGACTTCAGAGATGGAACCAGTTCAGATTA
ATGGTGCACCTAGGAGACCTCGTATTCTGCTGGCAGCAAGTGGAAGTGTGGCTTCAATTAAGTTTG
CTAATCTATGTCGTTGTTTTCTGAATGGGCAGAAGTTAAAGCAGTTGCAACGAAACCTTCTCTTC
ATTTCATAGACAAAGCTTCGCTTCCGGAAGATGTCATTCTTTATACTGATGAGGAGGAATGGTCCA
CTTGGTGCAGATTGGTGATAGTGTGCTACACATTGAGCTCCGCAGATGGGCTGATATTATGGTTAT
TGCCCCTTTGTCAGCAAACACACTTGGGAAGATTGCAGGTGGACTATGTGATAACTTGTTAACCTG
CATCGTACGAGCATGGGACTACAATAAACCCCTTTTTGTGGCACCAGCCATGAATACATTGATGTG
GAATAATCCATTCACAGAACGACACCTTATGGTAATTGATGAGCTTGGAATCTCTCTCATACCCCC
AGTTTCAAAAAGACTAGCATGTGGAGATTATGGAAATGGCGCTATGGCTGAACCTTCTCTCATTTA
CTCAACTGTAAGACTCTTTTATGAGTCACGGTCACAATCAGGTGGCATCAACTTGGCTTGATTCGC
AGATCATTAAATTTTATTCATCGGTTTGTACAAGTGGTAAAAATTGTTGAAATTCAGGACCTGGAA
CAGTGTTACTTAGCATACACCAGTTGGGTTTATTTTTCTCCTAAATTCTTCACCTCTTTAACTTGT
GTCATGTTTGTATCCAAGCGGTAACTTTCAATCAAGTTTCATGTTCATTGT

SEQ ID NO: 38 tomato HAL3

MTSEMEPVQINGAPRRPRILLAASGSVASIKFANLCRCFSEWAEVKAVATKPSLHFIDKASLPEDV
ILYTDEEXMVHLVQIGDSVLHIELRRWADIMVIAPLSANTLGKIAGGLCDNLLTCIVRAWDYNKPL
FVAPAMNTLMWNNPFTERHLMVIDELGISLIPPVSKRLACGDYGNGAMAEPSLIYSTVRLFYESRS
QSGGINLA

**SEQ ID NO: 39 AtHAL3b long version ,AT_HAL3B TC276427 TC135022
TC164136 TC179155 TC202319 TC237584**

ATGGCGAAAACAGCTCTTACTCCTCCCGCGTCTGGTTCCGAAGTTCCAAGATCCGGTACACCTGGA
GATGCGTCTGGCAACAAACCTCAAACGGATGCCACCGGCGTCTCAGCTACTGATACTGCTTCTCAG
AAACGCGGTCGTGGTCGACCGCCAAAGGCTAAATCTGACTCTTCCCAAATCGGTGCCGTTTCTGCG
AACCCCAGTACTAAACCAAGTGGTCGTCCGAAAAGAAACCTAGCTCACGCTGTTCCTTCTACGTCT
GTGGCGGCGGCTGTGAAGAAACGTGGTAGGGCAAAGAGGTCGACTGTAACGGCGGCTGTGGTTACT
ACTGCTACTGGAGAGGGTTCTAGAAAACGAGGGAGGCAAAGAAAGATGACGTGGCGGCTGCAACT
GTTCCAGCAGAAACTGTGGTGGCTCCAGCTAAGAGACGTGGAAGGAAACCTACTGTCGAAGTAGCT
GCACAGCCTGTGCGCAGGACTAGGAAGGTATTCGGGTTTTCTATGCATGAACAAAAGAGCACTTCA
GTGGCACCGGTAGCTGCAAACGTCGGAGATCTCAAGAAAAGAACCGCACTCTTACAAAAGAAAGTG
AAGGAAGCTGCAGCTAAGTTGAAACAAGCAGTAACAGCAATTGACGAGGTCCAGAAGTTAGCGGAT
GGAATATTGACCAGCGATGACGTCGACTTCTCTGTTTTGTTTCAAACTTAAAGACCCTCGCGGCA
TTTGATTTCGATTTCCGATTAGGGTTCCTCGCAGATCCTCCTTCCTCGGCTATAGAAGAAGATG
AATATGGAAGTGGATACAGTAACAAGGAAGCCTCGTATCTTACTAGCTGCAAGTGGAAGTGTGGCT
TCAATTAAGTTCAGTAATCTCTGCCATTGTTTCTCAGAATGGGCTGAAGTCAAAGCCGTCGCTTCA
AAATCATCTCTCAATTTCGTTGATAAACCTTCTCTACCTCAGAATGTGACTCTCTATACAGATGAA
GATCAATGGTCTAGCTGGAACAACATTGGTGATCCCGTTCTTCATATCGAGCTCACACGCTGGCCT
GATGTTATGATCATTGCTCCTTTGTCTGCTAACACATTAGCCAAGATTGCTGGTGGGTTATGTGAT
AATCTATTGACATGTATAGTAAGAGCATGGGATTATAGCAAACCGTTGTTTGTTGCACCGGCGATG
AACACTTTGATGTGGAACAATCCTTTCACAGAACGGCACCTTGTCTTGCTTGATGAACTTGGAATC

FIGURE 4 (continued)

```
ACCCTAATTCCTCCCATCAAGAAGAAACTGGCCTGTGGAGACTACGGTAATGGCGCAATGGCTGAG
CCTTCTCTGATTTATTCCACTGTTAGACTGTTCTGGGAGTCACAAGCTCGTAAACAAAGAGATGGA
ACCAGTTGA
```

SEQ ID NO: 40 AtHAL3b protein, long version

```
MAKTALTPPASGSEVPRSGTPGDASGNKPQTDATGVSATDTASQKRGRGRPPKAKSDSSQIGAVSA
KASTKPSGRPKRNVAQAVPSTSVAAAVKKRGRAKRSTVTAAVVTTATGEGSRKRGRPKKDDVAAAT
VPAETVVAPAKRRGRKPTVEVAAQPVRRTRKVFGFSMHEQKSTSVAPVAANVGDLKKRTALLQKKV
KEAAAKLKQAVTAIDEVQKLADGILTSDDVDFSVLFSNLKTLAAFDFDFRLGFLADPPSSAIEKKM
NMEVDTVTRKPRILLAASGSVASIKFSNLCHCFSEWAEVKAVASKSSLNFVDKPSLPQNVTLYTDE
DEWSSWNKIGDPVLHIELRRWADVMIIAPLSANTLAKIAGGLCDNLLTCIVRAWDYSKPLFVAPAM
NTLMWNNPFTERHLVLLDELGITLIPPIKKKLACGDYGNGAMAEPSLIYSTVRLFWESQARKQRDG
TS
```

SEQ ID NO: 41, Pinus sp, Pg_TC67564 TC48627

```
ATATTGAAACTCATTTTTAAACACTTATTCTGCACTATAAGAAGCAGCAGGCCCCCAGAAATATGA
GCTTCATACACACAACGGGGGAGTAATCAGCACCATCAAAGGGGGGATTTGCGGCAATTGTGAGAT
CAAGTGGAGGAAGCTGGAATAGATCTAAATCTAGGCCCTTGAGGAGAATGCTCTCCTAATGGTGGT
TTTAAAAATCAATACTCTAGTGCAAAACATGGATGCAACAAATTCTCAACCTGATGAACCTGGAAG
GGATGCTAATTCATCTCAGAAACCACGAATCATTCTAGCAGCCAGCGGGAGTGTGGCAGCAATAAA
ATTTGGAATTCTTGCCCATTGTCTATGTCAATGGGCAGAAGTCAAAGCAGTGGTCACAAAATCTGC
TTTGCATTTCATTGACAAGATGTCTCTTCCGGCTAATGTTAAGCTCTACACTGATGAAAATGAATG
GTCTAGCTGGAGCAAAATAGGTGATACTGTACTGCATATAGAACTCCGGCAATGGGCTGATGCTAT
GGTGATTGCTCCACTCTCAGCAAACACGCTTGCTAAGATAGCAGGTGGCCTATGCGACAATCTACT
TACTTGCATAGTACGTGCATGGGACTTTAACAAGCCTCTCTTTGTAGCTCCTGCAATGAATACTTT
CATGTGGAACAATCCATTTACTCAACGGCATTTGGACTCAATCTCAGAGCTCGGACTATCACTTAT
CCCCCCAATAACAAAGAAGTTAGCTTGTGGTGATTATGGAAATGGTGCAATGGCTGAACCTTCTAC
GATAGATACAACTCTTAGGTTTTCACTTGATCCTTCAATTGTATGAAGTGTCTGATGTCCCGTTCA
ACAATTCTTGTTATGAATCTAACATGCTTAGTACAATGGACTATGGTATAGACCCAGATAGTGTTT
CTTGGTAGCTGGGTTAGACAGCATGAACTCAGCTTGTGTGTGGTGAAGTTAAGTTCTGATGATAAA
CAATCATGAACTTGTGATTTTATGTAACATTTGCTCATTTATTCTGGACACTTACAAGAACTGTGT
GGATACTCCTGCTTATAAGAGAATGTGTCAAACTACTATGCAAATCATCTAATTTGGAACTTGATG
ATGTAAGAGGAGTATGCACTTTATTTTCTTCCCTGTGATAATTATTAATCTCTATGATTG
```

SEQ ID NO: 42, Pinus sp HAL3 Pg_TC67564 TC48627

```
MVVLKINTLVQNMDATNSQPDEPGRDANSSQKPRIILAASGSVAAIKFGILAHCLCQWAEVKAVVT
KSALHFIDKMSLPANVKLYTDENEWSSWSKIGDTVLHIELRQWADAMVIAPLSANTLAKIACGLCD
NLLTCIVRAWDFNKPLFVAPAMNTFMWNNPFTQRHLDSISELGLSLIPPITKKLACGDYGNGAMAE
PSTIDTTLRFSLDPSIV
```

MGRGKVQLKRIENKINRQVTFSKRRNGLLKKAHEISVLCDAEVAAIVFSPKGKLYE
YATDSRMDKILERYERYSYAEKALISAESESEGNWCHEYRKLKAKIETIQKCHKHL
MGEDLESLNLKELQQLEQQLESSLKHIISRKSHLMLESISELQKKERSLQEENKAL
QKELVERQKNVRGQQQVGQWDQTQVQAQAQAQPQAQTSSSSSSMLRDQQALLPPQN
ICYPPVMMGERNDAAAAAAVAAQGQVQLRIGGLPPWMLSHLNA (B)

```
SEQID97    EKQKEKALAHQAHWE---------------------------------QQNQPLQSTNSPPRPFVIAETHPTLN
SEQID99    EKQKIKALAQQAHWE---------------------------------HQNQPAPRG-SPPRPFVIAESHPTLN
SEQID101   GKQKDKAPKQHVQWE---------------------------------KQNQPPPTS-SAPMPFLIGDIHPTPN
SEQID103   EKQKVKALNQQAPWE---------------------------------QQGPPQTSS-SSPTSFLIGDSLPTLN
SEQID44    ERQKNVRGQQQVGQWDQTQVQAQAQ-----------------------AQPQAQTSSSSSMLRDQQALLPP
SEQID95    ERQKNVRGQQQVGQWDQTQVQAQAQ-----------------------AQPQAQTSSSSSMLRDQQALLPP
SEQID93    ERQKNVRGQQQVGQWDQTQVQAQAQ-----------------------AQPQAQTSFFFFMLRDQQALLSP
SEQID87    ERQKAARCQQQEQWDRQTQTQQAQ------------------------NQPQAQTSSSSSFMMRDQQAHAQ
SEQID89    ERQKAARCQQQEQWDRQTQTQQAQ------------------------NQPQAQTSSSSSFMMRDQQAHAQ
SEQID91    ERQKAASRQQQLQQQQQQQMQWEHQAQTQTHTHTQNQPQAQTSSSSSFMMRDQQAHAP
SEQID81    ERQKAVASRQQQQQQQQ-VQWDQTQV----------------------QVQTSSSSSFMMRQDQQGLP
SEQID85    ERQKAVASRQQQQQQQVQWDQQTHA-----------------------QAQTSSSSSSFMMRQDQQGLP
SEQID83    ERQKAAASRQQQQGAVGPADTDPGP-----------------------DKLIIVLLHDEAG---------
SEQID57    EKQ--KACAAQ-----------------------------------QDQTQPQTSSSSSFMRDAPPAAA
SEQID59    EKQ--KAQAAQ-----------------------------------QDQTQPQTSSSSSFMMRDAPPAAT
SEQID61    EKQ--KAHAAQ-----------------------------------QDQTQPQTSSSSSSFMLRDAPPAAN
SEQID63    EKQ--KAHAAQ-----------------------------------QDQTQPQTSSSSSSFMLRDAPPAAN
SEQID53    EKQ--KACAAQ-----------------------------------QDQTQPQTSSSSSFMMRDAPPVAD
SEQID55    EKQ--KACAAQ-----------------------------------QDQTQPQTSSSSSFMMRDAPPVAD
SEQID65    EKQKAHTCQAQ-----------------------------------WEQTQPQTSSSSSFMMGEATPATN
SEQID67    EKQKAHTQQAQ-----------------------------------LEQTQPQTSSSSSFMMGEATPATN
SEQID69    EKQKAQRKQVQ-----------------------------------WGQTQQQTSSSSSCFVIREAAPTTN
SEQID71    EKQKDQRCQVQ-----------------------------------RDQTQQQTSSSTSFMLREAAPTTN
SEQID73    EKQKVQKQQVQ-----------------------------------WDQTQPQTSSSSSFMREALPTTN
SEQID75    EKQKVQKQQVQ-----------------------------------WDQTQPQTSSSSSFMREALPTTN
SEQID77    EKQQVHKRLVQ-----------------------------------WDQTQPQTSSSSSFMMREALPTTN
SEQID79    EKQQVHKRLVQ-----------------------------------WDQTQPQTSSSSSFMMREALPTTN
SEQID107   AKEKAKALVQHAPWE-------------------------------KQNQSQYSSALPPVISDSVPTPT
SEQID105   KRARAKAIEQ..                                  ..QARWKHHNHKQQDNLHNPNIN
```

FIGURE 6 (continued)

```
SEQID97   IG----------------NFQGRTNTVHAEESLQRQMRISSLLPXWMXH-------
SEQID99   IG----------------HFQGRTNAVEAEENQQPXMRICSSLLPPWML-------
SEQID101  IR----------------NFQGRTVADA----------------------------
SEQID103  IG----------------TYQCSGNEHG-EEAAQPQVRIGNSLLPPWMLSHLNG-
SEQID44   QN--ICYPPVMMGERND-------AAAAAVAAQGVQLRIGGLPPWMLSHLNA-
SEQID95   QN--ICYPPVMMGERND-------AAAAAVAAQGQVQLRIGGLPPWMLSHLNA-
SEQID93   QN--ICYPPVMMGQRND-------AAAARRWRPKARCNFRIGGFPPWMLSTFKA-
SEQID87   QN--ICYP_VTMG----------GEAVAAAPG-QQGQLRIGGLPPWMLSHLNA-
SEQID89   QN--ICYPPVTMG----------GEAVAAAPG-QQGQLRIGGLPPWMLSHLNA-
SEQID91   QQNICSYPPVTMG----------GEATAAAAAPEQQAQLRICLPPWMLSHLNA-
SEQID81   PPQNICFPP_SIGERGE-EVAAAAQQQLPPPGQAQPQLRIAGLPPWMLSHLNA-
SEQID85   PPHNICFPP_TMGDRGEELAAAAAAQQQQPLPGQAQPQLRIAGLPPWMLSHLNA-
SEQID83   --------------SAGSAASTKHMLPAADNRRER---------------------
SEQID57   TS----------------IHPAAAGERAGDAAVQPQAPPRTGLPLWMVSHING-
SEQID59   TS----------------IHPAASGERAEDAAVQPQAPPRTGLPLWMVSHING-
SEQID61   TS----------------IHPAAAGERAEDAAVQPQAPPRTGLPPWMVSHING-
SEQID63   TS----------------IHPAATGERAEDAAVQPQAPPRTGLPPWMVSHING-
SEQID53   TS----------------NHPAAAGERAEDVAVQPQVPLRTALPLWMVSHING-
SEQID55   TS----------------NHPAAAGERAEDVAVQPQVPLRTALPLWMVSHING-
SEQID65   CS----------------NPPAAASDRAEDATGQ--PSARTVLPPWMVSHINNG
SEQID67   RS----------------NPPAAASDRAEDATGQ--PPARTVLPPWMVSHLNNG
SEQID69   IS----------------IFPVAAGGRLVEGAAAQP-QARVGLPPWMLSHLSS-
SEQID71   VS----------------IFPVAAGGRVVEGAAAQP-QARVGLPPWMLSHLSC-
SEQID73   IS----------------NYPAAAGERIEDVAAGQPQHVRIGLPPWMLSHING-
SEQID75   IS----------------NYPAAAGERIEDVAAGQPQHERIGLPPWMLSHING-
SEQID77   IS----------------IYAAAAGERAEDAAGQPQ--IHIGLPPWMVSHING-
SEQID79   IS----------------IYAAAAGERAEDAAGQPQ--IHIGLPPWMVSHING-
SEQID107  SR----------------TFQARANEEESPQQPQLRVSNTLLPPWMLSHMNGQ-
SEQID105  IG----------------NYQTRNNEGGVEPATDVQVRVRNLLPFWML-------
```

FIGURE 6 (continued)

SEQ ID NO: 43, OsMADS15 coding sequence

ATGGGGCGGGGGAAGGTGCAGCTGAAGCGGATAGAGAACAAGATCAACAGGCAGGTGACGTTCTCC
AAGAGGAGGAATGGATTGCTGAAGAAGGCGCACGAGATCTCCGTCCTCTGCGACGCCGAGGTCGCC
GCCATCGTCTTCTCCCCCAAGGGCAAGCTCTACGAGTACGCCACTGACTCCAGGATGGACAAAATC
CTTGAACGTTATGAGCGCTATTCATATGCTGAAAAGGCTCTTATTTCAGCTGAATCCGAGAGTGAG
GGAAATTGGTGCCATGAATACAGGAAACTTAAGGCAAAGATTGAGACCATACAAAAATGTCACAAA
CACCTCATGGGAGAGGATCTAGAATCCCTGAATCTCAAAGAACTCCAACAGCTAGAGCAGCAGCTG
GAGAGTTCATTGAAGCACATAATATCAAGAAAGAGCCACCTTATGCTTGAGTCCATTTCCGAGCTG
CAGAAAAAGGAGAGGTCACTGCAGGAGGAGAACAAGGCTCTGCAGAAGGAACTGGTGGAGAGGCAG
AAGAATGTGAGGGGCCAGCAGCAAGTAGGGCAGTGGGACCAAACCCAGGTCCAGGCCCAGGCCCAA
GCCCAACCCCAAGCCCAGACAAGCTCCTCCTCCTCCTCCATGCTGAGGGATCAGCAGGCACTTCTT
CCACCACAAAATATCTGCTACCCGCCGGTGATGATGGGCGAGAGAAATGATGCGGCGGCGGCGGCG
GCGGTGGCGGCGCAGGGCCAGGTGCAACTCCGCATCGGAGGTCTTCCGCCATGGATGCTGAGCCAC
CTCAATGCTTAA

SEQ ID NO: 44, OsMADS15 protein sequence

MGRGKVQLKRIENKINRQVTFSKRRNGLLKKAHEISVLCDAEVAAIVFSPKGKLYEYATDSRMDKI
LERYERYSYAEKALISAESESEGNWCHEYRKLKAKIETIQKCHKHLMGEDLESLNLKELQQLEQQL
ESSLKHIISRKSHLMLESISELQKKERSLQEENKALQKELVERQKNVRGQQQVGQWDQTQVQAQAQ
AQPQAQTSSSSSSMLRDQQALLPPQNICYPPVMMGERNDAAAAAAVAAQGQVQLRIGGLPPWMLSH
LNA

SEQ ID NO: 45

GGGGACAAGTTTGTACAAAAAAGCAGGCTTAAACAATGGGGCGGGGGAAGGT

SEQ ID NO: 46

GGGGACCACTTTGTACAAGAAAGCTGGGTTTGGCCGACGACGACGAC

SEQ ID NO: 47, GOS2 promoter sequence

AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAACAGAGAGATTTTTTTAAAAAATAGAATGAAGATATTCTCAACGTATTGCCAAACATTTAAA
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTATTATTTATCTTTTTCG
ATTAGATCCAACGTACTTACGCACACACTTTCTCCTCATGTCCATGTGTGACTCCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACACAATAGCCATCAAAAGTATCAAACCAACTATTTACGTTTTCACATACAAAAAAAAAAACAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTCCTCCCATCTATAA

FIGURE 8

```
ATTCCTCCCCCCTTTTCCCCTCTCTATATAGGAGGCATCCAAGCCAAGAAGAGGGAGAGCACCAAG
GACACGCGACTAGCAGAAGCCGAGCGACCGCCTTCTTCGATCCATATCTTCCGGTCGAGTTCTTGG
TCGATCTCTTCCCTCCTCCACCTCCTCCTCACAGGGTATGTGCCCTTCGGTTGTTCTTGGATTTAT
TGTTCTAGGTTGTGTAGTACGGGCGTTGATGTTAGGAAAGGGGATCTGTATCTGTGATGATTCCTG
TTCTTGGATTTGGGATAGAGGGGTTCTTGATGTTGCATGTTATCGGTTCGGTTTGATTAGTAGTAT
GGTTTTCAATCGTCTGGAGAGCTCTATGGAAATGAAATGGTTTAGGGTACGGAATCTTGCGATTTT
GTGAGTACCTTTTGTTTGAGGTAAAATCAGAGCACCGGTGATTTGCTTGGTGTAATAAAAGTACG
GTTGTTTGGTCCTCGATTCTGGTAGTGATGCTTCTCGATTTGACGAAGCTATCCTTTGTTTATTCC
CTATTGAACAAAATAATCCAACTTTGAAGACGGTCCCGTTGATGAGATTGAATGATTGATTCTTA
AGCCTGTCCAAAATTTCGCAGCTGGCTTGTTTAGATACAGTAGTCCCCATCACGAAATTCATGGAA
ACAGTTATAATCCTCAGGAACAGGGGATTCCCTGTTCTTCCGATTTGCTTTAGTCCCAGAATTTTT
TTTCCCAAATATCTTAAAAAGTCACTTTCTGGTTCAGTTCAATGAATTGATTGCTACAAATAATGC
TTTTATAGCGTTATCCTAGCTGTAGTTCAGTTAATAGGTAATACCCCTATAGTTTAGTCAGGAGAA
GAACTTATCCGATTTCTGATCTCCATTTTTAATTATATGAAATGAACTGTAGCATAAGCAGTATTC
ATTTGGATTATTTTTTTATTAGCTCTCACCCCTTCATTATTCTGAGCTGAAAGTCTGGCATGAAC
TGTCCTCAATTTTGTTTTCAAATTCACATCGATTATCTATGCATTATCCTCTTGTATCTACCTGTA
GAAGTTTCTTTTTGGTTATTCCTTGACTGCTTGATTACAGAAAGAAATTTATGAAGCTGTAATCGG
GATAGTTATACTGCTTGTTCTTATGATTCATTTCCTTTGTGCAGTTCTTGGTGTAGCTTGCCACTT
TCACCAGCAAAGTTC
```

SEQ ID NO: 48

L(L/V)KKA(H/N)EIS(VI)L(C/Y)DAE(V/I/L)(A/G)(L/A/V)(I/V)(I/V)FS(T/P/A/N)KGKLYE(Y/F)(A/S)(T/S)(D/N/E)S(K/C/R/S)M(D/E)(N/I/R/K)IL(E/D)R

SEQ ID NO: 49

KLK(A/S)(K/R)(V/I)E(A/T/S)(L/I)(Q/N)(K/R/N)(S/C/R)(Q/H)(R/K)HLMGE

SEQ ID NO: 50

Q(P/Q/V/A)QTS(S/F)(S/F)(S/F)(S/F)(S/C/F)(F/M)

SEQ ID NO: 51, first X: any amino acid, preferably L, P or H; second X residue: any amino acid, preferably V or L

(G/A/V/L)(L/P)XWMX(S/H)

SEQ ID NO: 52, Hordeum vulgare subsp. vulgare cultivar Morex VRN-H1 gene, MADS15 complete cds

```
ATGGGGCGCGGGAAGGTGCAGCTGAAGCGGATCGAGAACAAGATCAACCGCCAGGTCACCTTCTCC
AAGCGCCGCTCGGGGCTGCTCAAGAAGGCGCACGAGATCTCCGTGCTCTGCGACGCCGAGGTCGGC
CTCATCATCTTCTCCACCAAGGGAAAGCTCTACGAGTTCTCCACCGAGTCATGTATGGACAAAATT
CTTGAACGGTATGAGCGCTACTCTTATGCAGAAAAGGTTCTCGTTTCAAGTGAATCTGAAATTCAG
GGAAACTGGTGTCACCAATATAGGAAACTGAAGCCCAAGGTTGAGACAATACACAAATGTCAAAAG
CATCTCATGGGAGAGGATCTTGAATCTTTGAATCTCAAGGAGTTGCAGCAACTGGAGCAGCAGCTG
GAAAGCTCACTGAAACATATCAGAGCCAGGAAGAACCAACTTATGCACGAATCCATTTCTGAGCTT
```

FIGURE 8 (continued)

```
CAGAAGAAGGAGAGGTCACTGCAGGAGGAGAATAAAGTTCTCCAGAAGGAACTTGTGGAGAAGCAG
AAGGCCCAGGCGGCGCAGCAAGATCAAACTCAGCCTCAAACCAGCTCTTCTTCTTCTTCCTTCATG
ATGAGGGATGCTCCCCCTGTCGCAGATACCAGCAATCACCCAGCGGCGGCAGGCGAGAGGGCAGAG
GATGTGGCAGTGCAGCCTCAGGTCCCACTCCGGACGGCGCTTCCACTGTGGATGGTGAGCCACATC
AACGGCTGA
```

SEQ ID NO: 53, AAW82995 VRN-H1 [Hordeum vulgare subsp. vulgare]

```
MGRGKVQLKRIENKINRQVTFSKRRSGLLKKAHEISVLCDAEVGLIIFSTKGKLYEFSTESCMDKI
LERYERYSYAEKVLVSSESEIQGNWCHEYRKLKAKVETIQKCQKHLMGEDLESLNLKELQQLEQQL
ESSLKHIRARKNQLMHESISELQKKERSLQEENKVLQKELVEKQKAQAAQQDQTQPQTSSSSSFM
MRDAPPVADTSNHPAAAGERAEDVAVQPQVPLRTALPLWMVSHING
```

SEQ ID NO: 54, AJ249144 Hordeum vulgare mRNA for MADS-box protein 5 (m5 gene) ORF 141-875

```
CTCTCCCCTCCCACTTCACCCAACCACCTGACAGCCATGGCTCCGCCACCTCGCCTCCGCCCGCGC
CTCTGAGAGTAGCCGTCGCGGTCGCTCGCTCGCTCGCTCGCTGCTGCCGGTGTTGGCCCGGTCCTC
GAGCGGAGATGGGGCGCAGGAAGGTGCAGCTGAAGCGGATCGAGAACAAGATCAACCGCCAGGTCA
CCTTCTCCAAGCGCCGCTCGGGGCTGCTCAAGAAGGCGCACGAGATCTCCGTGCTCTACGACGCCG
AGGTCGGCCTCATCATCTTCTCCACCAAGGGAAAGCTCTACGAGTTCTCCACCGAGTCATGTATGG
ACAAAATTCTTGAACGGTATGAGCGCTACTCTTATGCAGAAAAGGTTCTCGTTTCAAGTGAATCTG
AAATTCAGGGAAACTGGTGTCACGAATATAGGAAACTGAAGGCGAAGGTTGAGACAATACAGAAAT
GTCAAAAGCATCTCATGGGAGAGGATCTTGAATCTTTGAATCTCAAGGAGTTGCAGCAACTGGAGC
AGCAGCTGGAAAGCTCACTGAAACATATCAGAGCCAGGAAGAACCAACTTATGCACGAATCCATTT
CTGAGCTTCAGAAGAAGGAGAGGTCACTGCAGGAGGAGAATAAAGTTCTCCAGAAGGAACTTGTGG
AGAAGCAGAAGGCCCAGGCGGCGCAGCAAGATCAAACTCAGCCTCAAACCAGCTCTTCTTCTTCTT
CCTTCATGATGAGGGATGCTCCCCCTGTCGCAGATACCAGCAATCACCCAGCGGCGGCAGGCGAGA
GGGCAGAGGATGTGGCAGTGCAGCCTCAGGTCCCACTCCGGACGGCGCTTCCACTGTGGATGGTGA
GCCACATCAACGGCTGAAGGGCTTCCAGCCCATGTAAGCGTACTATTCAGTACGAGTAACAAGTTG
CAGCGGCCAGCCTGGTGTATCATGCGGTTGCGAACATGCTAACCCCATGGAGGGGAGAGGAAAAGA
AATCAGAGTAAAGCAGCAAGCTGCAGGAATGTGTATATTTCACTTCGTCCACCTCAGTTTCCTTTC
CACCTGGGCTGAGATGGCTGTACGAGTAATCTACCATGTAATTTATATGTAGCATGAGTGACGAAT
TTTCAACTTTCGATGATATCCGTTGCTCCTGGGTGTTGTTTCTGTGAATTAACCTATCGAATATGA
GCGTTGTG
```

SEQ ID NO: 55, CAB97352 MADS-box protein 5 [Hordeum vulgare subsp. vulgare]

```
MGRRKVQLKRIENKINRQVTFSKRRSGLLKKAHEISVLYDAEVGLIIFSTKGKLYEFSTESCMDKI
LERYERYSYAEKVLVSSESEIQGNWCHEYRKLKAKVETIQKCQKHLMGEDLESLNLKELQQLEQQL
ESSLKHIRARKNQLMHESISELQKKERSLQEENKVLQKELVEKQKAQAAQQDQTQPQTSSSSSFM
MRDAPPVADTSNHPAAAGERAEDVAVQPQVPLRTALPLWMVSHING
```

FIGURE 8 (continued)

SEQ ID NO: 56, AB007504 Triticum aestivum TaMADS#11 mRNA for MADS box transcription factor, complete cds

```
GGCACGAGCTCTCTCTCTCTCTCTCTCTCTCTCTCTCTCTCTCCTCGTGCCGAATTCGGCAC
GAGCGGAGATGGGGCGCGGGAAGGTGCAGCTGAAGCGGATCGAGAACAAGATCAACCGGCAGGTGA
CCTTCTCCAAGCGCCGCTCGGGGCTGCTCAAGAAGGCGCACGAGATCTCCGTGCTCTGCGACGCCG
AGGTCGGCCTCATCATCTTCTCCACCAAGGGAAAGCTCTACGAGTTCTCCACCGAGTCATGTATGG
ACAAAATTCTTGAACGGTATGAGCGCTACTCTTATGCAGAAAAGGTTCTCGTTTCAAGTGAATCTG
AAATTCAGGGAAACTGGTGTCACGAATATAGGAAACTGAAGGCGAAGGTTGAGACAATACAGAAAT
GTCAAAAGCATCTGATGGGAGAGGATCTTGAATCTTTGAATCTCAAGGAGTTGCAGCAACTGGAGC
AGCAGCTGGAAAGCTCACTGAAACATATCAGATCCAGGAAGAACCAACTTATGCACGAATCCATTT
CTGAGCTTCAGAAGAAGGAGAGGTCACTGCAGGAGGAGAATAAAGTTCTCCAGAAGGAACTCGTCG
AGAAGCAGAAGGCCCAGGCGGCGCAACAAGATCAGACTCAGCCTCAAACAAGCTCTTCTTCTTCTT
CCTTCATGATGAGGGATGCTCCCCCTGCCGCAGCTACCAGCATTCATCCAGCGGCGGCAGGCGAGA
GGGCAGGGGATGCGGCAGTGCAGCCGCAGGCCCCACCCCGGACGGGGCTTCCACTGTGGATGGTGA
GCCACATCAACGGCTGAAGGGCTTCCAGCCCATATAAGCGTACTATTCAGTAGAGAGTAACAAGTT
GCACCGGCCAGTCTGGTGTATGTTGCGGTTGCTAGCACGCCTGACCCCTTGGAGGGGAAAGGAAAA
GAAATCAGAGTAAAGTAGCAAGCTGCAGCGATGTGTATATTTCACTTTGTCCACCCCAGTTTCCCT
CCCAGCTGGGCTCAATTTACCATGTAATCTATATGTAGCTTGAGTGATGAATTTTCAAGTTTCCAT
GATACCCGTCTCTAGTGGGATGTTGTTTATGTGAATTAACCTATCAAATATGAGCATTGTGTATAT
TGTGATTCTTGAAAATAAATAAATCAGGATCTTTGTCTT
```

SEQ ID NO: 57, BAA33457 MADS box transcription factor [Triticum aestivum]

```
MGRGKVQLKRIENKINRQVTFSKRRSGLLKKAHEISVLCDAEVGLIIFSTKGKLYEFSTESCMDKI
LERYERYSYAEKVLVSSESEIQGNWCHEYRKLKAKVETIQKCQKHLMGEDLESLNLKELQQLEQQL
ESSLKHIRSRKNQLMHESISELQKKERSLQEENKVLQKELVEKQKAQAAQQDQTQPQTSSSSSFM
MRDAPPAAATSIHPAAAGERAGDAAVQPQAPPRTGLPLWMVSHING
```

SEQ ID NO: 58, AY280870 Triticum aestivum MADS-box protein TaVRT-1 mRNA, complete cds ORF 150-884

```
TCCCTCTCCTCCCTCTCTTCCGCCTCACCCAACCACCTGACAGCCATGGCTCCGCCCCCCGCCCC
CGCCTGCGCCTGTCGGAGTAGCCGTCGCGGTCTGCCGGTGTTGGAGGCTTGGGGTGTAGGGTTGGC
CCCGTTCTCCAGCGGAGATGGGGCGCGGGAAGGTGCAGCTGAAGCGGATCGAGAACAAGATCAACC
GGCAGGTGACCTTCTCCAAGCGCCGCTCGGGGCTGCTCAAGAAGGCGCACGAGATCTCCGTGCTCT
GCGACGCCGAGGTCGGCCTCATCATCTTCTCCACCAAGGGAAAGCTCTACGAGTTCTCCACCGAGT
CATGTATGGACAAAATTCTTGAACGGTATGAGCGCTACTCTTATGCAGAAAAGGTTCTCGTTTCAA
GTGAATCTGAAATTCAGGGAAACTGGTGTCACGAATATAGGAAACTGAAGGCGAAGGTTGAGACAA
TACAGAAATGTCAAAAGCATCTGATGGGAGAGGATCTTGAATCTTTGAATCTCAAGGAGTTGCAGC
AACTGGAGCAGCAGCTGGAAAGCTCACTGAAACATATCAGATCCAGGAAGAACCAACTTATGCACG
AATCCATTTCTGAGCTTCAGAAGAAGGAGAGGTCACTGCAGGAGGAGAATAAAGTTCTCCAGAAGG
AACTCGTCGAGAAGCAGAAGGCCCAGGCGGCGCAACAAGATCAGACTCAGCCTCAAACAAGCTCTT
CTTCTTCTTCCTTCATGATGAGGGATGCTCCCCCTGCCGCAACTACCAGCATTCATCCAGCGGCAT
CAGGAGAGAGGGCAGAGGATGCGGCAGTGCAGCCGCAGGCCCCACCCCGGACGGGGCTTCCACTGT
GGATGGTTAGCCACATCAACGGCTGAAGGGCTTCCAGCCCATATAAGCGTACTATTCAGTAGAGAG
TAACAAGTTGCACCGGCCAGCCTGGTGTATGTTGCGGTTGCTAGCATGCCTGACCCCTTGGAGGGG
```

```
AAAGGAAAAGAAATCAGAGTAAAGTAGCAAGCTGCAGTGATGTGTATATTTCACTTTGTCCACCTC
AGTTTCCCTCCCAGCTGGGCTCAATTTACCATGTAATCTATATGTAGCTTGAGTGATGAATTTTCA
AGTTTCCATGATACCCGTCTCGAGCGGGTGTTGTTTATGTGAATTAACCTATCAAATATGAGCATT
GTGTAAAAAAAAAAAAAAAAAA
```

SEQ ID NO: 59, AAP33790 MADS-box protein TaVRT-1 [Triticum aestivum]

```
MGRGKVQLKRIENKINRQVTFSKRRSGLLKKAHEISVLCDAEVGLIIFSTKGKLYEFSTESCMDKI
LERYERYSYAEKVLVSSESEIQGNWCHEYRKLKAKVETIQKCQKHLMGEDLESLNLKELQQLEQQL
ESSLKHIRSRKNQLMHESISELQKKERSLQEENKVLQKELVEKQKAQAAQQDQTQPQTSSSSSSFM
MRDAPPAATTSIHPAASGERAEDAAVQPQAPPRTGLPLWMVSHING
```

SEQ ID NO: 60, Triticum monococcum DV92 chromosome 5AL BAC 231A16, complete sequence

```
ATGGGGCGCGGGAAGGTGCAGCTGAAGCGGATCGAGAACAAGATCAACCGGCAGGTGACCTTCTCC
AAGCGCCGCTCGGGGCTTCTCAAGAAGGCGCACGAGATCTCCGTGCTCTGCGACGCCGAGGTCGGC
CTCATCATCTTCTCCACCAAGGGAAAGCTCTACGAGTTCTCCACCGAGTCATGTATGGACAAAATT
CTTGAACGGTATGAGCGCTATTCTTATGCAGAAAAGGTTCTCGTTTCAAGTGAATCTGAAATTCAG
GGAAACTGGTGTCACGAATATAGGAAACTGAAGGCAAGGTTGAGACAATACAGAAATGTCAAAAA
CATCTCATGGGAGAGGATCTTGAATCTTTGAATCTCAAGGAGTTGCAGCAACTGGAGCAGCAGCTG
GAAAGCTCACTGAAACATATCAGATCCAGGAAGAACCAACTTATGCACGAATCCATTTCTGAGCTG
CAGAAGAAGGAGAGGTCACTGCAGGAGGAGAATAAAGTTCTCCAGAAGGAACTCGTGGAGAAGCAG
AAGGCCCATGCGGCGCAGCAAGATCAAACTCAGCCTCAAACCAGCTCTTCTTCTTCTTCCTTCATG
CTGAGGGATGCTCCCCCTGCCGCAAATACCAGCATTCATCCAGCGGCGGCAGGCGAGAGGGCAGAG
GATGCGGCAGTGCAGCCGCAGGCCCCACCCCGGACGGGGCTTCCACCGTGGATGGTGAGCCACATC
AACGGGTGA
```

SEQ ID NO: 61, AAO72630 MADS box transcription factor AP1 [Triticum monococcum]

```
MGRGKVQLKRIENKINRQVTFSKRRSGLLKKAHEISVLCDAEVGLIIFSTKGKLYEFSTESCMDKI
LERYERYSYAEKVLVSSESEIQGNWCHEYRKLKAKVETIQKCQKHLMGEDLESLNLKELQQLEQQL
ESSLKHIRSRKNQLMHESISELQKKERSLQEENKVLQKELVEKQKAHAAQQDQTQPQTSSSSSSFM
LRDAPPAANTSIHPAAAGERAEDAAVQPQAPPRTGLPPWMVSHING
```

SEQ ID NO: 62, Triticum aestivum cultivar Triple Dirk D line VRN-A1 (VRN-A1) gene, complete cds

```
ATGGGGCGGGGAAGGTGCAGCTGAAGCGGATCGAGAACAAGATCAACCGGCAGGTGACCTTCTCC
AAGCGCCGCTCGGGGCTTCTCAAGAAGGCGCACGAGATCTCCGTGCTCTGCGACGCCGAGGTCGGC
CTCATCATCTTCTCCACCAAGGGAAAGCTCTACGAGTTCTCCACCGAGTCATGTATGGACAAAATT
CTTGAACGGTATGAGCGCTATTCTTATGCAGAAAAGGTTCTCGTTTCAAGTGAATCTGAAATTCAG
GGAAACTGGTGTCACGAATATAGGAAACTGAAGGCAAGGTTGAGACAATACAGAAATGTCAAAAG
CATCTCATGGGAGAGGATCTTGAATCTTTGAATCTCAAGGAGTTGCAGCAACTGGAGCAGCAGCTG
GAAAGCTCACTGAAACATATCAGATCCAGGAAGAACCAACTTATGCACGAATCCATTTCTGAGCTT
CAGAAGAAGGAGAGGTCACTGCAGGAGGAGAATAAAGTTCTCCAGAAGGAACTCGTGGAGAAGCAG
```

FIGURE 8 (continued)

AAGGCCCATGCGGCGCAGCAAGATCAAACTCAGCCTCAAACCAGCTCTTCATCTTCTTCCTTCATG
CTGAGGGATGCTCCCCCTGCCGCAAATACCAGCATTCATCCAGCGGCAACAGGCGAGAGGGCAGAG
GATGCGGCAGTGCAGCCGCAGGCCCCACCCCGGACGGGGCTTCCACCGTGGATGGTGAGCCACATC
AACGGGTGA

SEQ ID NO: 63, AAW73222 VRN-A1 [Triticum aestivum]

MGRGKVQLKRIENKINRQVTFSKRRSGLLKKAHEISVLCDAEVGLIIFSTKGKLYEFSTESCMDKI
LERYERYSYAEKVLVSSESEIQGNWCHEYRKLKAKVETIQKCQKHLMGEDLESLNLKELQQLEQQL
ESSLKHIRSRKNQLMHESISELQKKERSLQEENKVLQKELVEKQKAHAAQQDQTQPQTSSSSSSFM
LRDAPPAANTSIHPAATGERAEDAAVQPQAPPRTGLPPWMVSHING

SEQ ID NO: 64, Lolium perenne MADS1 mRNA, complete cds

ATGGGGCGCGGCAAGGTGCAGCTCAAGCGGATCGAGAACAAGATCAACCGCCAGGTCACCTTCTCC
AAGCGCCGCTCGGGGCTGCTCAAGAAGGCGCACGAGATCTCCGTGCTCTGCGACGCCGAGGTCGGG
CTCATCATCTTCTCCACCAAGGGAAAGCTCTACGAGTTCGCAACCGACTCATGTATGGACAAAATT
CTTGAGCGGTATGAGCGCTACTCCTATGCAGAGAAAGTGCTCATTTCAACCGAATCTGAATTCAG
GGAAACTGGTGTCATGAATATAGGAAACTGAAGGCGAAGGTTGAGACAATACAGAGATGTCAAAAG
CATCTAATGGGAGAGGATCTTGAATCATTGAATCTCAAGGAGTTGCAGCAACTAGAGCAGCAGCTG
GAAAGTTCACTGAAACATATTAGAGCCAGAAAGAACCAGCTTATGCACGAATCCATATCTGAGCTT
CAAAAGAAGGAGAGGTCACTGCAGGAGGAGAATAAAATTCTCCAGAAGGAACTCATAGAAGCAG
AAGGCCCACACGCAGCAAGCGCAGTGGGAGCAAACTCAGCCCCAAACCAGCTCTTCCTCCTCCTCC
TTTATGATGGGGAAGCTACCCCAGCAACAAATTGCAGTAATCCCCCAGCAGCGGCCAGCGACAGA
GCAGAGGATGCGACGGGGCAGCCTTCAGCTCGCACGGTGCTTCCACCATGGATGGTGAGTCACATC
AACAATGGCTGA

SEQ ID NO: 65, AAO45873 MADS1 [Lolium perenne]

MGRGKVQLKRIENKINRQVTFSKRRSGLLKKAHEISVLCDAEVGLIIFSTKGKLYEFATDSCMDKI
LERYERYSYAEKVLISTESEIQGNWCHEYRKLKAKVETIQRCQKHLMGEDLESLNLKELQQLEQQL
ESSLKHIRARKNQLMHESISELQKKERSLQEENKLQKELEKQKAHTQQAQWEQTQPQTSSSSSS
FMMGEATPATNCSNPPAAASDRAEDATGQPSARTVLPPWMVSHINNG

SEQ ID NO: 66, Lolium temulentum MADS-box protein 1 (MADS1) mRNA, complete cds

ATGGGGCGCGGCAAGGTGCAGCTCAAGCGGATCGAGAACAAGATCAACCGCCAGGTCACCTTCTCC
AAGCGCCGCTCAGGCCTGCTCAAGAAGGCGCACGAGATCTCCGTGCTCTGCGACGCAGAGGTCGGG
CTCATCATCTTCTCCACCAAGGGAAAGCTCTACGAGTTCGCCACCGACTCATGTATGGACAAAATT
CTTGAGCGGTATGAGCGCTACTCCTATGCAGAGAAAGTGCTCATTTCAACTGAATCTGAATTCAG
GGAAACTGGTGTCATGAATATAGGAAACTGAAGGCGAAGGTTGAGACAATACAGAGATGTCAAAAG
CATCTAATGGGAGAGGATCTTGAATCATTGAATCTCAAGGAGTTGCAGCAACTAGAGCAGCAGCTG
GAAAGTTCACTGAAACATATTAGATCCAGAAAGAGCCAGCTTATGCACGAATCCATATCTGAGCTT
CAAAAGAAGGAGAGGTCACTGCAAGAGGAGAATAAAATTCTCCAGAAGGAACTCATAGAAGCAG
AAGGCCCACACGCAGCAAGCGCAGTTGGAGCAAACTCAGCCCCAAACCAGCTCTTCCTCCTCCTCC
TTTATGATGGGGAAGCTACCCCAGCAACAAATCGCAGTAATCCCCCAGCAGCGGCCAGCGACAGA
GCAGAGGATGCGACGGGGCAGCCTCCAGCTCGCACGGTGCTTCCACCATGGATGGTGAGTCACCTC
AACAATGGCTGA

FIGURE 8 (continued)

SEQ ID NO: 67, AAD10625 MADS-box protein 1 [Lolium temulentum]

MGRGKVQLKRIENKINRQVTFSKRRSGLLKKAHEISVLCDAEVGLIIFSTKGKLYEFATDSCMDKI
LERYERYSYAEKVLISTESEIQGNWCHEYRKLKAKVETIQRCQKHLMGEDLESLNLKELQQLEQQL
ESSLKHIRSRKSQLMHESISELQKKERSLQEENKILQKELIEKQKAHTQQAQLEQTQPQTSSSSSS
FMMGEATPATNRSNPPAAASDRAEDATGQPPARTVLPPWMVSHLNNG

SEQ ID NO: 68, Zea mays mRNA for putative MADS-domain transcription factor (m15 gene)

ATGGGGCGCGGGAAGGTGCAGCTGAAGCGGATCGAGAACAAGATCAACCGCCAGGTGACCTTCTCC
AAGCGCCGCTCGGGGCTGCTCAAGAAGGCGCACGAGATCTCCGTGCTCTGCGACGCCGAGGTCGCG
CTCATCATCTTCTCCACCAAGGGAAGCTCTACGAGTATTCCACCGATTCATGTATGGACAAAATT
CTTGACCGGTACGAGCGCTACTCCTATGCAGAAAAGGTTCTTATTTCAGCAGAATCTGAAACTCAG
GGCAATTGGTGCCACGAGTATAGAAAACTAAAGGCGAAGGTCGAGACAATACAAAAATGTCAAAAG
CACCTCATGGGAGAGGATCTTGAAACGTTGAATCTCAAAGAGCTTCAGCAACTAGAGCAGCAGCTG
GAGAGTTCACTGAAACATATCAGAACCAGGAAGAACCAACTTATGCTCGAGTCAATTTCGGAGCTC
CAACGGAAGGAGAAGTCGCTGCAGGAGGAGAACAAGGTTCTGCAGAAGGAGCTCGCGGAGAAGCAG
AAAGCCCAGCGGAAGCAAGTGCAATGGGGCCAAACCCAACAGCAGACCAGTTCGTCTTCCTCGTGC
TTCGTGATAAGGGAAGCTGCCCCAACAACAAATATCAGCATTTTTCCTGTGGCAGCAGGCGGGAGG
TTGGTGGAAGGTGCAGCAGCGCAGCCACAGGCTCGCGTTGGACTACCACCATGGATGCTTAGCCAC
CTGAGCAGCTGA

SEQ ID NO: 69, CAD23408 putative MADS-domain transcription factor [Zea mays]

MGRGKVQLKRIENKINRQVTFSKRRSGLLKKAHEISVLCDAEVALIIFSTKGKLYEYSTDSCMDKI
LDRYERYSYAEKVLISAESETQGNWCHEYRKLKAKVETIQKCQKHLMGEDLETLNLKELQQLEQQL
ESSLKHIRTRKNQLMLESISELQRKEKSLQEENKVLQKELAEKQKAQRKQVQWGQTQQQTSSSSSC
FVIREAAPTTNISIFPVAAGGRLVEGAAAQPQARVGLPPWMLSHLSS

SEQ ID NO: 70, Zea mays mRNA for putative MADS-domain transcription factor (m4 gene)

ATGGGGCGCGGGAAGGTGCAGCTGAAGCGGATCGAGAACAAGATCAACCGCCAGGTGACATTCTCC
AAGCGCCGCTCGGGGCTACTCAAGAAGGCGCACGAGATCTCCGTGCTCTGCGACGCCGAGGTCGCG
CTCATCATCTTCTCCACCAAGGGCAAGCTCTACGAGTACTCTACCGATTCATGTATGGACAAAATT
CTTGAACGGTATGAGCGCTACTCCTATGCAGAAAAGGTTCTCATTTCCGCAGAATATGAAACTCAG
GGCAATTGGTGCCATGAATATAGAAAACTAAAGGCGAAGGTCGAGACAATACAGAAATGTCAAAAG
CACCTCATGGGAGAGGATCTTGAAACTTTGAATCTCAAAGAGCTTCAGCAACTAGAGCAGCAGCTG
GAGAGTTCACTGAAACATATCAGAACAAGGAAGAGCCAGCTTATGGTCGAGTCAATTTCAGCGCTC
CAACGGAAGGAGAAGTCACTGCAGGAGGAGAACAAGGTTCTGCAGAAGGAGCTCGCGGAGAAGCAG
AAAGACCAGCGGCAGCAAGTGCAACGGGACCAAACTCAACAGCAGACCAGTTCGTCTTCCACGTCC
TTCATGTTAAGGGAAGCTGCCCCAACAACAAATGTCAGCATCTTCCCTGTGGCAGCAGGCGGGAGG
GTGGTGGAAGGGGCAGCAGCGCAGCCGCAGGCTCGCGTTGGACTGCCACCATGGATGCTTAGCCAT
CTGAGCTGCTGA

FIGURE 8 (continued)

SEQ ID NO: 71, CAD23417 m4 [Zea mays]

MGRGKVQLKRIENKINRQVTFSKRRSGLLKKAHEISVLCDAEVALIIFSTKGKLYEYSTDSCMDKI
LERYERYSYAEKVLISAEYETQGNWCHEYRKLKAKVETIQKCQKHLMGEDLETLNLKELQQLEQQL
ESSLKHIRTRKSQLMVESISALQRKEKSLQEENKVLQKELAEKQKDQRQQVQRDQTQQQTSSSSTS
FMLREAAPTTNVSIFPVAAGGRVVEGAAAQPQARVGLPPWMLSHLSC

SEQ ID NO: 72, Oryza sativa (japonica cultivar-group) MADS-box protein RMADS211 mRNA, complete cds

ATGGGGCGGGGCAAGGTGCAGCTGAAGCGGATCGAGAACAAGATCAACCGGCAGGTGACCTTCTCC
AAGCGCAGGTCGGGGCTGCTCAAGAAGGCGAATGAGATCTCCGTGCTCTGCGACGCCGAGGTCGCG
CTCATCATCTTCTCCACCAAGGGCAAGCTCTACGAGTACGCCACCGACTCATGTATGGACAAAATC
CTTGAACGTTATGAGCGCTACTCCTATGCAGAAAAGGTCCTTATTTCAGCTGAATCTGACACTCAG
GGCAACTGGTGCCACGAATATAGGAAACTGAAGGCTAAGGTTGAGACAATACAGAAATGTCAAAAG
CACCTCATGGGAGAGGATCTTGAATCTTTGAATCTCAAAGAGCTGCAGCAGCTGGAGCAGCAGCTG
GAAAATTCGTTGAAACATATCAGATCCAGAAAGAGCCAACTAATGCTCGAGTCCATTAACGAGCTT
CAACGGAAGGAAAAGTCACTGCAGGAGGAGAATAAGGTCCTACAGAAAGAAAACCCTTGCTCCTTC
CTACAGCTGGTGGAGAAGCAGAAAGTCCAGAAGCAACAAGTGCAATGGGACCAGACACAACCTCAA
ACAAGTTCCTCATCATCCTCCTTCATGATGAGGGAAGCCCTTCCAACAACTAATATCAGTAACTAC
CCTGCAGCAGCTGGCGAAAGGATAGAGGATGTAGCAGCAGGGCAGCCACAGCATGTTCGCATTGGG
CTGCCACCATGGATGCTGAGCCACATCAACGGCTAA

SEQ ID NO: 73, AAS59822 MADS-box protein RMADS211 [Oryza sativa (japonica cultivar-group)]

MGRGKVQLKRIENKINRQVTFSKRRSGLLKKANEISVLCDAEVALIIFSTKGKLYEYATDSCMDKI
LERYERYSYAEKVLISAESDTQGNWCHEYRKLKAKVETIQKCQKHLMGEDLESLNLKELQQLEQQL
ENSLKHIRSRKSQLMLESINELQRKEKSLQEENKVLQKENPCSFLQLVEKQKVQKQQVQWDQTQPQ
TSSSSSSFMMREALPTTNISNYPAAAGERIEDVAAGQPQHVRIGLPPWMLSHING

SEQ ID NO: 74, Oryza sativa MADS14 protein mRNA, complete cds

ATGGGGCGGGGCAAGGTGCAGCTGAAGCGGATCGAGAACAAGATCAACCGGCAGGTGACCTTCTCC
AAGCGCAGGTCAAAACTGCTCAAGAAGGCGAATGAGATCTCCGTGCTCTGCGACGCCGAGGTCGCG
CTCATCATCTTCTCCACCAAGGGCAAGCTCTACGAGTACGCCACCGACTCATGTATGGACAAAATC
CTTGAACGTTATGAGCGCTACTCCTATGCAGAAAAGGTCCTTATTTCAGCTGAATCTGACACTCAG
GGCAACTGGTGCCACGAATATAGGAAACTGAAGGCTAAGGTTGAGACAATACAGAAATGTCAAAAG
CACCTCATGGGAGAGGATCTTGAATCTTTGAATCTCAAAGAGCTGCAGCAGCTGGAGCAGCAGCTG
GAAAATTCGTTGAAACATATCAGATCCAGAAAGAGCCAACTAATGCTCGAGTCCATTAACGAGCTT
CAACGGAAGGAAAAGTCACTGCAGGAGGAGAATAAGGTCCTACAGAAAGAACTGGTGGAGAAGCAG
AAAGTCCAGAAGCAACAAGTGCAATGGGACCAGACACAACCTCAAACAAGTTCCTCATCATCCTCC
TTCATGATGAGGGAAGCCCTTCCAACAACTAATATCAGTAACTACCCTGCAGCAGCTGGCGAAAGG
ATAGAGGATGTAGCAGCAGGGCAGCCACAGCATGAACGCATTGGGCTGCCACCATGGATGCTGAGC
CACATCAACGGCTAA

FIGURE 8 (continued)

SEQ ID NO: 75, AAF19047 MADS14 protein [Oryza sativa]

MGRGKVQLKRIENKINRQVTFSKRRSKLLKKANEISVLCDAEVALIIFSTKGKLYEYATDSCMDKI
LERYERYSYAEKVLISAESDTQGNWCHEYRKLKAKVETIQKCQKHLMGEDLESLNLKELQQLEQQL
ENSLKHIRSRKSQLMLESINELQRKEKSLQEENKVLQKELVEKQKVQKQQVQWDQTQPQTSSSSSS
FMMREALPTTNISNYPAAAGERIEDVAAGQPQHERIGLPPWMLSHING

SEQ ID NO: 76, Dendrocalamus latiflorus MADS-box protein (Mads2) mRNA, complete cds

ATGGGGCGCGGGAAGGTGCAGCTGAAGCGGATCGAGAACAAGATCAACCGGCAAGTGACTTTCTCC
AAGCGCCGGTCGGGGCTGCTCAAGAAGGCGCATGAGATCTCCGTCCTCTGCGACGCCGAGGTCGGC
CTTATCATCTTCTCCACCAAGGGCAAGCTCTACGAGTACGCCACCGACTCATGTATGGACAAAATT
CTTGAACGGTACGAGCGTTACTCCTATGCAGAAAAGGTTCTTATTTCAGCCGAATCTGAAACTCAG
GGCAACTGGTGTCACGAATATAGGAAACTGAAGGCGAAGGTTGAGACGATACAGAAATGTCAAAAG
CACCTCATGGGAGAGGATCCTGAATCTTTGAATCTCAAGGAGCTGCAGCAACTCGAGCAGCAGCTG
GAAAGTTCAGTGAAACATATCAGATCCAGAAAGAGCCAGCTTATGCTCGAGTCCATTTCCGAGCTT
CAAAAGAAGGAGAAGTCACTGCAGGAGGAGAACAAGGTTCTGCAGAAGGAACTCGTGGAGAAGCAG
CAGGTCCATAAACGGTTAGTGCAATGGGACCAAACTCAGCCGCAAACTAGTTCCTCTTCCTCGTCC
TTCATGATGAGGGAAGCTCTCCCAACAACAAATATCAGTATTTACGCTGCGGCAGCCGGCGAGAGG
GCAGAGGACGCAGCAGGGCAGCCTCAGATTCACATTGGGCTGCCGCCATGGATGGTGAGCCACATC
AACGGCTAA

SEQ ID NO: 77, AAR32119 MADS-box protein [Dendrocalamus latiflorus]

MGRGKVQLKRIENKINRQVTFSKRRSGLLKKAHEISVLCDAEVGLIIFSTKGKLYEYATDSCMDKI
LERYERYSYAEKVLISAESETQGNWCHEYRKLKAKVETIQKCQKHLMGEDPESLNLKELQQLEQQL
ESSVKHIRSRKSQLMLESLSELQKKEKSLQEENKVLQKELVEKQQVHKRLVQWDQTQPQTSSSSSS
FMMREALPTTNISIYAAAAGERAEDAAGQPQIHIGLPPWMVSHING

SEQ ID NO: 78, Dendrocalamus latiflorus MADS-box protein (Mads1) mRNA, complete cds

ATGGGGCGCGGGAAGGTGCAGCTGAAGCGGATCGAGAACAAGATCAACCGGCAAGTGACTTTCTCC
AAGCGCCGGTCGGGGCTGCTCAAGAAGGCGCATGAGATCTCCGTCCTCTGCGACGCCGAGGTCGGC
CTTATCATCTTCTCCACCAAGGGCAAGCTCTACGAGTACGCCACCGACTCATGTATGGACAAAATT
CTTGAACGGTACGAGCGTTACTCCTATGCAGAAAAGGTTCTTATTTCAGCCGAATCTGAAACTCAG
GGCAACTGGTGTCACGAATATAGGAAACTGAAGGCGAAGGTTGAGACGATACAGAAATGTCAAAAG
CACCTCATGGGAGAGGATCTTGAATCTTTGAATCTCAAGGAGCTGCAGCAACTCGAGCAGCAGCTG
GAAAGTTCAGTGAAACATATCAGATCCAGAAAGAGCCAGCTTATGCTCGAGTCCATTTCCGAGCTT
CAAAAGAAGGAGAAGTCACTGCAGGAGGAGAACAAGGTTCTGCAGAAGGAACTCGTGGAGAAGCAG
CAGGTCCATAAACGGTTAGTGCAATGGGACCAAACTCAGCCGCAAACTAGTTCCTCTTCCTCGTCC
TTCATGATGAGGGAAGCTCTCCCAACAACAAATATCAGTATTTACGCTGCGGCAGCCGGCGAGAGG
GCAGAGGACGCAGCAGGGCAGCCTCAGATTCACATTGGGCTGCCGCCATGGATGGTGAGCCACATC
AACGGCTAA

FIGURE 8 (continued)

SEQ ID NO: 79, AAR32118 MADS-box protein [Dendrocalamus latiflorus]

MGRGKVQLKRIENKINRQVTFSKRRSGLLKKAHEISVLCDAEVGLIIFSTKGKLYEYATDSCMDKI
LERYERYSYAEKVLISAESETQGNWCHEYRKLKAKVETIQKCQKHLMGEDLESLNLKELQQLEQQL
ESSVKHIRSRKSQLMLESISELQKKEKSLQEENKVLQKELVEKQQVHKRLVQWDQTQPQTSSSSSS
FMMREALPTTNISIYAAAAGERAEDAAGQPQIHIGLPPWMVSHING

SEQ ID NO: 80, Zea mays MADS box protein 3 (mads3) mRNA, complete cds

ATGGGGCGCGGCAAGGTGCAGCTGAAGCGGATAGAGAACAAGATAAACCGGCAGGTGACCTTCTCC
AAGCGCCGGAACGGGCTGCTGAAGAAGGCGCACGAGATCTCCGTCCTCTGCGACGCCGAGGTCGCC
GTCATCGTCTTCTCCCCCAAGGGCAAGCTCTACGAGTACGCCTCCGACTCCCGCATGGACAAAATT
CTAGAACGTTATGAGCGATATTCCTATGCTGAAAAGGCTCTTATTTCAGCTGAATCTGAAAGTGAG
GGAAATTGGTGCCACGAATACAGGAAACTGAAGGCCAAAATTGAGACCATACAAAGATGCCACAAG
CACCTGATGGGAGAGGATCTAGAGTCTTTGAATCCAAAAGAGCTCCAACAACTAGAGCAGCAGCTG
GAGAGCTCACTGAAGCACATCAGATCAAGAAAGAGCCACCTTATGGCCGAGTCAATTTCTGAGCTA
CAGAAGAAGGAGAGGTCACTGCAGGAGGAGAACAAGATTCTACAGAAGGAACTTTCAGAGAGGCAG
AAGGCGGTCGCTAGCCGGCAGCAGCAGCAGCAGCAGGTGCAGTGGGACCAGCAGACACAGGTCCAG
GTCCAGACAAGCTCATCGTCTTCTTCCTTCATGATGAGGCAGGATCAGCAGGGACTGCCACCTCCA
CAAAACATCTGCTTCCCGCCGTTGAGCATCGGAGAGAGAGGCGAAGAGGTGGCTGCGGCGGCGCAG
CAGCAGCTGCCTCCTCCGGGGCAGGCGCAACCACAGCTCCGCATCGCAGGTCTGCCGCCATGGATG
CTGAGCCACCTCAATGCATAA

SEQ ID NO: 81, AAG43200 MADS box protein 3 [Zea mays]

MGRGKVQLKRIENKINRQVTFSKRRNGLLKKAHEISVLCDAEVAVIVFSPKGKLYEYASDSRMDKI
LERYERYSYAEKALISAESESEGNWCHEYRKLKAKIETIQRCHKHLMGEDLESLNPKELQQLEQQL
ESSLKHIRSRKSHLMAESISELQKKERSLQEENKILQKELSERQKAVASRQQQQQQVQWDQQTQVQ
VQTSSSSSSFMMRQDQQGLPPPQNICFPPLSIGERGEEVAAAAQQQLPPPGQAQPQLRIAGLPPWM
LSHLNA

SEQ ID NO: 82, Sorghum bicolor putative MADS box protein (SbMADS2) mRNA, partial cds

GCAAGGTGCAGCTCAAGCGGATAGAGAACAAGATAAACCGGCAGGTGACCTTCTCCAAGCGCCGCA
ACGGGCTGCTCAAGAAGGCGCACGAGATCTCCGTCCTCTGCGACGCCGAGGTCGCCGTCATCGTCT
TCTCCCCCAAGGGCAAGCTCTATGAGTACGCCACCGACTCCCGCATGGACAAAATTCTCGAACGTT
ATGAGCGATATTCCTATGCTGAAAAGGCTCTTATTTCAGCTGAATCTGAAAGTGAGGGAAACTGGT
GCCACGAATACAGGAAACTGAAGGCCAAAATTGAGACCATTCAAAAATGCCACAAGCACCTGATGG
GAGAGGATCTAGAGTCTTTGAATCCCAAAGAGCTCCAACAACTAGAGCAGCAGCTGGAGAGCTCAC
TGAAGCACATCAGATCAAGAAAGAGCCACCTTATGGCTGAGTCTATTTCTGAACTACAGAAGAAGG
AGAGGTCACTGCAGGAGGAGAACAAGGCTCTACAGAAGGAACTTGCGGAGAGGCAGAAGGCGGCCG
CGAGCAGGCAGCAGCAGCAAGGTGCAGTGGGACCAGCAGACACAGACCCAGGCCCAGACAAGCTCA
TCATCGTCCTCCTTCATGATGAGGCAGGATCAGCAGGGTCTGCCGCCTCCACAAAACATATGCTTC
CCGCCGCTGATAATCGGAGAGAGAGGTGA

FIGURE 8 (continued)

SEQ ID NO: 83, AAB50181 MADS box protein

KVQLKRIENKINRQVTFSKRRNGLLKKAHEISVLCDAEVAVIVFSPKGKLYEYATDSRMDKILERY
ERYSYAEKALISAESESEGNWCHEYRKLKAKIETIQKCHKHLMGEDLESLNPKELQQLEQQLESSL
KHIRSRKSHLMAESISELQKKERSLQEENKALQKELAERQKAAASRQQQQGAVGPADTDPGPDKLI
IVLLHDEAGSAGSAASTKHMLPAADNRRER

SEQ ID NO: 84, Zea mays MADS-box protein (ZAP1) mRNA, complete cds

ATGGGGCGCGGCAAGGTACAGCTGAAGCGGATAGAGAACAAGATAAACCGGCAGGTGACCTTCTCC
AAGCGCCGGAACGGCCTGCTCAAGAAGGCGCACGAGATCTCCGTCCTCTGCGATGCCGAGGTCGCC
GTCATCGTCTTCTCCCCCAAGGGCAAGCTCTACGAGTACGCCACCGACTCCCGCATGGACAAAATT
CTTGAACGCTATGAGCGATATTCCTATGCTGAAAAGGCTCTTATTTCAGCTGAATCTGAAAGTGAG
GGAAATTGGTGCCACGAATACAGGAAACTGAAGGCCAAAATTGAGACCATACAAAAATGCCACAAG
CACCTGATGGGAGAGGATCTAGAGTCTTTGAATCCCAAAGAGCTCCAGCAACTAGAGCAGCAGCTG
GATAGCTCACTGAAGCACATCAGATCAAGGAAGAGCCACCTTATGGCCGAGTCTATTTCTGAGCTA
CAGAAGAAGGAGAGGTCACTGCAGGAGGAGAACAAGGCTCTGCAGAAGGAACTTGCGGAGAGGCAG
AAGGCCGTCGCGAGCCGGCAGCAGCAGCAACAGCAGCAGGTGCAGTGGGACCAGCAGACACATGCC
CAGGCCCAGACAAGCTCATCATCGTCCTCCTTCATGATGAGGCAGGATCAGCAGGGACTGCCGCCT
CCACACAACATCTGCTTCCCGCCGTTGACAATGGGAGATAGAGGTGAAGAGCTGGCTGCGGCGGCG
GCGGCGCAGCAGCAGCAGCCACTGCCGGGGCAGGCGCAACCGCAGCTCCGCATCGCAGGTCTGCCA
CCATGGATGCTGAGCCACCTCAATGCATAA

SEQ ID NO: 85, AAB00081 Zea mays MADS box protein

MGRGKVQLKRIENKINRQVTFSKRRNGLLKKAHEISVLCDAEVAVIVFSPKGKLYEYATDSRMDKI
LERYERYSYAEKALISAESESEGNWCHEYRKLKAKIETIQKCHKHLMGEDLESLNPKELQQLEQQL
DSSLKHIRSRKSHLMAESISELQKKERSLQEENKALQKELAERQKAVASRQQQQQQQVQWDQQTHA
QAQTSSSSSSFMMRQDQQGLPPPHNICFPPLTMGDRGEELAAAAAAQQQQPLPGQAQPQLRIAGLP
PWMLSHLNA

SEQ ID NO: 86, Lolium temulentum MADS-box protein 2 (MADS2) mRNA, alternatively spliced product, complete cds

ATGGGTCGCGGCAAGGTGCAGCTGAAGCGGATAGAGAACAAGATAAACCGTCAGGTGACATTCTCC
AAGCGCCGCAACGGGCTACTCAAGAAGGCGCACGAGATCTCCGTCCTCTGCGACGCCGAGGTCGCC
GTCGTCGTCTTCTCCCCGAAAGGGAAGCTCTATGAGTACGCCACTGACTCCAGCATGGACAAAATT
CTTGAACGTTATGAACGCTACTCTTATGCTGAAAAGGCTTTGATTTCAGCTGAATCTGAAAGTGAG
GGAAATTGGTGCCATGAATACAGGAAGCTGAAGGCAAAGATTGAGACTATACAAAAATGTCACAAG
CACCTCATGGGGGAGGATCTGGAGTGTCTAAACCTGAAAGAGCTCCAACAACTAGAGCAGCAGCTG
GAGAGTTCATTGAAGCACATCAGATCGAGAAAGAGCCACCTTATGATGGAGTCCATTTCTGAGCTA
CAGAAGAAGGAGCGGTCACTCCAGGAGGAGAACAAGGCTCTACAGAAGGAACTGGTGGAGAGGCAG
AAGGCGGCCAGGCAGCAGCAGCAAGAGCAGTGGACCGTCAGACCCAAACACAACAAGCCCAAAAC
CAACCTCAGGCCCAGACGAGCTCATCATCTTCCTCCTTCATGATGAGGGATCAGCAGGCCCATGCT
CAACAAAACATCTGTTACCCGCTGGTGACAATGGGTGGAGAGGCTGTGGCCGCGGCGCCAGGGCAG
CAGGGGCAGCTTCGCATCGGAGGCCTGCCACCATGGATGCTGAGCCACCTCAACGCTTGA

FIGURE 8 (continued)

SEQ ID NO: 87, AAD10626 MADS-box protein 2 [Lolium temulentum]

MGRGKVQLKRIENKINRQVTFSKRRNGLLKKAHEISVLCDAEVAVVVFSPKGKLYEYATDSSMDKI
LERYERYSYAEKALISAESESEGNWCHEYRKLKAKIETIQKCHKHLMGEDLECLNLKELQQLEQQL
ESSLKHIRSRKSHLMMESISELQKKERSLQEENKALQKELVERQKAARQQQQEQWDRQTQTQQAQN
QPQAQTSSSSSFMMRDQQAHAQQNICYPLVTMGGEAVAAAPGQQGQLRIGGLPPWMLSHLNA

SEQ ID NO: 88, Lolium perenne MADS2 mRNA, complete cds

ATGGGTCGCGGCAAGGTGCAGCTGAAGCGGATAGAGAACAAGATAAACCGTCAGGTGACCTTCTCC
AAGCGCCGCAACGGGCTACTCAAGAAGGCGCACGAGATCTCCGTCCTCTGCGACGCCGAGGTCGCC
GTCGTCGTCTTCTCCCCGAAAGGGAAGCTCTATGAGTACGCCACTGACTCCAGCATGGACAAAATT
CTTGAACGTTATGAACGCTACTCTTATGCTGAAAAGGCTTTGATTTCAGCTGAATCTGAAAGTGAG
GGAAATTGGTGCCATGAATACAGGAAACTGAAGGCGAAGATTGAGACTATACAAAAATGTCACAAG
CACCTCATGGGGGAGGATCTGGAGTGTCTAAACCTGAAAGAGCTCCAACAACTAGAGCAGCAGCTG
GAGAGTTCATTGAAGCACATCAGATCGAGAAGAGCCACCTTATGATGGAGTCCATTTCTGAGCTA
CAGAAGAAGGAGCGGTCACTCCAGGAGGAGAACAAGGCTCTACAGAAGGAACTGGTGGAGAGGCAG
AAGGCGGCCAGGCAGCAGCAGCAAGAGCAGTGGGACCGTCAGACCCAAACACAACAAGCCCAAAAC
CAACCTCAGGCCCAGACGAGCTCATCATCTTCCTCCTTCATGATGAGGGATCAGCAGGCCCATGCT
CAACAAAACATCTGTTACCCGCCGGTGACAATGGGTGGAGAGGCTGTGGCCGCGGCGCCAGGGCAG
CAGGGGCAGCTTCGCATCGGAGGCCTGCCACCATGGATGCTGAGCCACCTCAACGCTTGA

SEQ ID NO: 89, AAO45874 MADS2 [Lolium perenne]

MGRGKVQLKRIENKINRQVTFSKRRNGLLKKAHEISVLCDAEVAVVVFSPKGKLYEYATDSSMDKI
LERYERYSYAEKALISAESESEGNWCHEYRKLKAKIETIQKCHKHLMGEDLECLNLKELQQLEQQL
ESSLKHIRSRKSHLMMESISELQKKERSLQEENKALQKELVERQKAARQQQQEQWDRQTQTQQAQN
QPQAQTSSSSSFMMRDQQAHAQQNICYPPVTMGGEAVAAAPGQQGQLRIGGLPPWMLSHLNA

SEQ ID NO: 90, Hordeum vulgare mRNA for MADS-box protein 8 (m8 gene)

ATGGGTCGCGGTAAGGTGCAGCTGAAGCGGATAGAGAACAAGATAAATCGGCAGGTGACCTTCTCC
AAGCGCCGCAACGGGCTCCTGAAGAAGGCGCACGAGATCTCCGTCCTCTGTGACGCAGAGGTCGCC
GTCATCGTCTTCTCCCCCAAAGGCAAGCTCTATGAGTACGCCACCGACTCCAGCATGGACAAAATT
CTTGAACGTTATGAGCGCTACTCTTATGCTGAAAAGGCTCTTATTCAGCTGAATCTGAAAGTGAG
GGGAATTGGTGTCATGAATACAGGAAACTTAAGGCGAAGATTGAGACCATACAGAAGTGTCACAAG
CACCTCATGGGAGAGGATCTGGATTCTCTGAACCTCAAAGAACTCCAACAACTGGAGCAGCAGCTG
GAGAGTTCATTGAAGCACATCAGATCGAGAAGAGCCATCTTATGATGGAGTCCATTTCTGAGCTA
CAGAAGAAGGAGAGGTCACTGCAGGAGGAGAACAAGGCCCTACAGAAGGAACTGGTGGAGAGGCAG
AAGGCGGCCAGCAGGCAGCAGCAGCTGCAGCAGCAGCAACAACAACAACAAATGCAATGGGAGCAC
CAAGCCCAGACCCAAACCCATACCCATACTCAAAACCAGCCCCAAGCCCAGACTAGCTCATCATCT
TCCTCTTTCATGATGAGGGATCAGCAGGCCCATGCCCCTCAACAGAACATTTGTAGCTACCCACCG
GTGACGATGGGTGGGGAGGCGACGGCGGCGGCGGCGGCGCCGGAGCAGCAGGCTCAGCTTCGCATA
TGCCTACCGCCATGGATGCTGAGCCACCTCAACGCTTGA

FIGURE 8 (continued)

SEQ ID NO: 91, CAB97354 MADS-box protein 8 [Hordeum vulgare subsp. vulgare]

MGRGKVQLKRIENKINRQVTFSKRRNGLLKKAHEISVLCDAEVAVIVFSPKGKLYEYATDSSMDKI
LERYERYSYAEKALISAESESEGNWCHEYRKLKAKIETIQKCHKHLMGEDLDSLNLKELQQLEQQL
ESSLKHIRSRKSHLMMESISELQKKERSLQEENKALQKELVERQKAASRQQQLQQQQQQQMQWEH
QAQTQTHTHTQNQPQAQTSSSSSSFMMRDQQAHAPQQNICSYPPVTMGGEATAAAAAPEQQAQLRI
CLPPWMLSHLNA

SEQ ID NO: 92, Oryza sativa MADS-box protein FDRMADS3 mRNA, complete cds

ATGGGGCGGGGGAAGGTGCAGCTGAAGCGGATAGAGAACTCGATGAACCGGCAGGTGACGTTCTCC
AAGAGGAGGAATGGATTGCTGAAGAAGGCGCACGAGATCTCCGTCCTCTGCGACGCCGAGGTCGCC
GCCATCGTCTTCTCCCCCAAGGGCAAGCTCTACGAGTACGCCACTGACTCCAGGATGGACAAAATC
CTTGAACGTTATGAGCGCTATTCATATGCTGAAAAGGCTCTTATTTCAGCTGAATCTGAGAGTGAG
GGAAATTGGTGCCATGAATACAGGAAGCTTAAGGCAAAGATTGAGACCATACAAAAATGTCACAAA
CACCTCATGGGAGAGGATCTAGAATCCCTGAATCTCAAAGAACTCCAACAGCTAGAGCAGCAGCTG
GAGAGTTCATTGAAGCACATAAGATCAAGAAAGAGCCACCTTATGCTTGAGTCCATTTCCGAGCTG
CAGAAAAAGGAGAGGTCACTGCAGGAGGAGAACAAGGCTCTGCAGAAGGAACTGGTGGAGAGGCAG
AAGAATGTGAGGGGCCAGCAGCAAGTAGGGCAGTGGGACCAAACCCAGGTCCAGGCCCAGGCCCAA
GCCCAACCCCAAGCCCAGACAAGCTTCTTCTTCTTCATGCTGAGGGATCAGCAGGCACTTCTT
TCACCACAAAATATCTGCTACCCGCCGGTGATGATGGGCCAGAGAAATGATGCGGCGGCGCGGCGG
CGGTGGCGGCCCAAGGCCAGGTGCAACTTCCGCATTGGAGGCTTTCCGCCATGGATGCTGAGCACC
TTCAAGGCTTAA

SEQ ID NO: 93, AAL09473 MADS-box protein FDRMADS3 [Oryza sativa]

MGRGKVQLKRIENSMNRQVTFSKRRNGLLKKAHEISVLCDAEVAAIVFSPKGKLYEYATDSRMDKI
LERYERYSYAEKALISAESESEGNWCHEYRKLKAKIETIQKCHKHLMGEDLESLNLKELQQLEQQL
ESSLKHIRSRKSHLMLESISELQKKERSLQEENKALQKELVERQKNVRGQQQVGQWDQTQVQAQAQ
AQPQAQTSFFFFFMLRDQQALLSPQNICYPPVMMGQRNDAAARRRWRPKARCNFRIGGFPPWMLST
FKA

SEQ ID NO: 94, Oryza sativa MADS15 protein mRNA, complete cds

ATGGGGCGGGGGAAGGTGCAGCTGAAGCGGATAGAGAACAAGATCAACAGGCAGGTGACGTTCTCC
AAGAGGAGGAATGGATTGCTGAAGAAGGCGCACGAGATCTCCGTCCTCTGCGACGCCGAGGTCGCC
GCCATCGTCTTCTCCCCCAAGGGCAAGCTCTACGAGTACGCCACTGACTCCAGGATGGACAAAATC
CTTGAACGTTATGAGCGCTATTCATATGCTGAAAAGGCTCTTATTTCAGCTGAATCCGAGAGTGAG
GGAAATTGGTGCCATGAATACAGGAAACTTAAGGCAAAGATTGAGACCATACAAAAATGTCACAAA
CACCTCATGGGAGAGGATCATGAATCCCTGAATCTCAAAGAACTCCAACAGCTAGAGCAGCAGCTG
GAGAGTTCATTGAAGCACATAATATCAAGAAAGAGCCACCTTATGCTTGAGTCCATTTCCGACCTG
CAGAAAAAGGAGAGGTCACTGCAGGAGGAGAACAAGGCTCTGCAGAAGGAACTGGTGGAGAGGCAG
AAGAATGTGAGGGGCCAGCAGCAAGTAGGGCAGTGGGACCAAACCCAGGTCCAGGCCCAGGCCCAA
GCCCAACCCCAAGCCCAGACAAGCTCCTCCTCCTCCATGCTGAGGGATCAGCAGGCACTTCTT
CCACCACAAAATATCTGCTACCCGCCGGTGATGATGGGCGAGAGAAATGATGCGGCGGCGGCGGCG
GCGGTGGCGGCGCAGGGCCAGGTGCAACTCCGCATCGGAGGTCTTCCGCCATGGATGCTGAGCCAC
CTCAATGCTTAA

FIGURE 8 (continued)

SEQ ID NO: 95, AAF19048 MADS15 protein [Oryza sativa]

MGRGKVQLKRIENKINRQVTFSKRRNGLLKKAHEISVLCDAEVAAIVFSPKGKLYEYATDSRMDKI
LERYERYSYAEKALISAESESEGNWCHEYRKLKAKIETIQKCHKHLMGEDHESLNLKELQQLEQQL
ESSLKHIISRKSHLMLESISELQKKERSLQEENKALQKELVERQKNVRGQQQVGQWDQTQVQAQAQ
AQPQAQTSSSSSSMLRDQQALLPPQNICYPPVMMGERNDAAAAAAVAAQGQVQLRIGGLPPWMLSH
LNA

SEQ ID NO: 96, Tradescantia virginiana FRUITFULL-like MADS-box (TvFL2) mRNA, partial cds

GGGCTGGTGAAGAAGGCTCATGAGATCTCDATKYTRTGTGATGCYGAGGTTGCGCTTATTATTTTC
TCTACTAAAGGCAAACTATACGAGTATGCCACTGATTCCAAAATGGAAAATATCCTTGAACGCTAT
GAACGTTACTCATATGCTGAGAAGGCTTTAACTTCATCAGATCCTGAATTACAGGGAAATTGGTGC
CAAGAGTATGTTAAACTTAAGGCTAAGGTTGAGGCCTTACATAAAAGCCAAAGGCATCTTATGGGA
GAGCAACTAGAAGCGTTGGATCTCAAAGAATTGCAGCAACTAGAGCATCAACTTGAAGGTTCTTTG
AGGCTTGTCAGGTCAAGAAAGACTCAAATGATGTTGGACTCCATTTCCGAACTTCAGAGGAAGGAA
AAGTCTCTGGAAGAGCAAAACAAGAACCTAGAGAAGGAGATTTTGGAGAAGCAGAAAGAAAAGGCT
CTGGCACACCAAGCTCACTGGGAACAGCAGAATCAGCCACTACAAAGCACTAATTCGCCTCCAAGG
CCCTTCGTGATTGCAGAAACTCATCCAACACTAAACATTGGAAATTTCCAAGGTAGAACAAATACC
GTCCATGCAGAAGAAAGTCTGCAGCGTCAGATGAGGATCAGCAGCAGCCTACTGCCMYCMTGGATG
MTTCACMA

SEQ ID NO: 97, AAP83415 FRUITFULL-like MADS-box [Tradescantia virginiana]

GLVKKAHEISXLCDAEVALIIFSTKGKLYEYATDSKMENILERYERYSYAEKALTSSDPELQGNWC
QEYVKLKAKVEALHKSQRHLMGEQLEALDLKELQQLEHQLEGSLRLVRSRKTQMMLDSISELQRKE
KSLEEQNKNLEKEILEKQKEKALAHQAHWEQQNQPLQSTNSPPRPFVIAETHPTLNIGNFQGRTNT
VHAEESLQRQMRISSSLLPXWMXH

SEQ ID NO: 98, AY306190 Tradescantia virginiana FRUITFULL-like MADS-box (TvFL1) mRNA, partial cds

GTGCAGCTGAAACGGATGGAGAACAAGATTAACAGGCAGGTGACGTTTTCTAAACGTCGAGGAGGG
CTGCTGAAGAAAGCTCATGAGATCTCTATTCTATGTGATGCTGAGATTGCTCTTATTATTTCTCT
ACTAAAGGGAAGCTCTATGAGTATGCCACCAATTCCAAAATGGACAATATTCTTGAACGCTATGAG
CGTTACTCATATGCTGAAAGGCTCTAACTTCATCAGATCCTGATATACAGGGAAATTGGTGCCAA
GAGTATGCTAAACTTAAGTCTAAGGTTGAGGCTTTATGTAAAAGCCAAAGGCATCTTATGGGAGAG
CAGCTTGAAACATTGAATCTCAAGAATTGCAGCAACTAGAGCAACAGCTCGAAGGTTCTCTAAAG
CATGTCAGGTCAAGAAAGACTCAAGTTATGCTGGACTCTATTTCTGAACTTCAGAGGAAGGAAAAG
TCACTAGAGGAGCAAAACAAGAACCTAGAGAAGGAGATTTTGGAGAAGCAGAAAATCAAGGCTCTT
GCACAGCAGGCTCACTGGGAACACCAGAATCAACCAGCACCAAGGGGTTCACCTCCTAGGCCATTT
GTGATTGCAGAGTCTCATCCGACACTAAATATTGGACATTCCAAGGCAGGACAAATGCAGTCGAA
GCAGAAGAAAATCAGCAGCCTCAKATGAGAATTTGCAGTAGCCTCCTGCCCCCTGGATGCTT

FIGURE 8 (continued)

SEQ ID NO: 99, AAP83414 FRUITFULL-like MADS-box [Tradescantia virginiana]

VQLKRMENKINRQVTFSKRRGGLLKKAHEISILCDAEIALIIFSTKGKLYEYATNSKMDNILERYE
RYSYAEKALTSSDPDIQGNWCQEYAKLKSKVEALCKSQRHLMGEQLETLNLKELQQLEQQLEGSLK
HVRSRKTQVMLDSISELQRKEKSLEEQNKNLEKEILEKQKIKALAQQAHWEHQNQPAPRGSPPRPF
VIAESIIPTLNIGIIFQGRTNAVEAEENQQPXMRICSSLLPPWML

SEQ ID NO: 100, AY306192 Tradescantia virginiana FRUITFULL-like MADS-box (TvFL3) mRNA, partial cds

GGGCTKGTGAAGAAAGCTCATGAGATCTCGGTACTTTGTGATGCTGAGCTTGCTCTTATTATCTTC
TCTCCCAAAGGCAAGCTCTATGAGTATGCCACCGATTCCAAAATGGAAATTATTCTTGAACGCTAT
GAACGTTACACCTACGCTGAAAAAGCTTTAATTGCATCAGATCCTGATGTACAGGGAAACTGGTGT
CATGAGTACATTAAGCTTAAAGCTAAATTTGAGGCCTTGAATAAAAGCCAGAGGCATCTTATGGGA
GAACAACTAGATACGTTGAACCAAAAGGAATTGCTGCAACTAGAGACTAAGCTTGAAGGTTCTCTG
AAAAACGTCAGGTCAAGAAAGACTCAACTTATGTTGGATTCCATTTCTGAGCTTCAAGAAAAGGGA
AAGTCACTCCAGGAGCAAAACACCTGCCTAGAAAAGGAGATTTTGGGAAAACAGAAAGACAAGGCT
CCCAAACAGCATGTTCAGTGGGAAAAACAGAATCAACCACCACCTACCTCTTCTGCGCCAATGCCA
TTCCTCATTGGTGATATTCACCCAACCCCTAATATCAGAAATTTCCAAGGCAGAACAGTAGCTGAT
GCAGA

SEQ ID NO: 101, AAP83416 FRUITFULL-like MADS-box [Tradescantia virginiana]

GLVKKAHEISVLCDAELALIIFSPKGKLYEYATDSKMEIILERYERYTYAEKALIASDPDVQGNWC
HEYIKLKAKFEALNKSQRHLMGEQLDTLNQKELLQLETKLEGSLKNVRSRKTQLMLDSISELQEKG
KSLQEQNTCLEKEILGKQKDKAPKQHVQWEKQNQPPPTSSAPMPFLIGDIHPTPNIRNFQGRTVAD
A

SEQ ID NO: 102, Elaeis guineensis MADS box transcription factor (SQUA1) mRNA, complete cds

ATGGGGAGAGGGAGGGTGCAGCTGAGGCGGATCGAGAACAAGATAAACCGGCAGGTGACGTTCTCG
AAGCGCCGGTCGGGGCTCCTGAAGAAAGCCCACGAGATCTCCGTCCTCTGCGACGCCGAGGTCGCC
CTCATCATCTTCTCGACCAAGGGCAAGCTCTACGAGTACGCCACCGACTCCTGCATGGAAAGGATT
CTTGAACGCTATGAACGTTACACCTATGCAGAAAAAGCACTAATTTCATCTGGACCCGAATTGCAG
GGTAACTGGTGCCATGAATTTGGCAAACTCAAAGCTAAGGTTGAGGCTTTACAAAAAAGCCAAAGG
CATCTCATGGGTGAGCAACTTGAGCCCTTGAATCTCAAAGAACTCCAGCAACTAGAGCAACAGCTT
GAAAGTTCTTTAAAGCATATAAGAACCAGAAAGTGCCAACTCATGTTTGAATCCATCTCTGAGCTT
CAAAAAAGGAAAAGTCACTGCAGGAGCAGAACAAGATGCTGGAGAAGGAGCTCATGGAGAAGCAG
AAGGTGAAGGCACTAAACCAGCAGGCACCTTGGGAGCAGCAAGGCCCGCCGCAGACAAGCTCATCA
TCCCCAACCTCCTTCCTGATCGGACACTCTCTCCCCACCCTGAATATTGGGACATACCAATGTAGC
GGAAATGAACATGGGGAGGAAGCAGCACAACCCCAGGTTCGTATAGGAAACAGCCTGTTACCACCT
TGGATGCTTAGCCACTTGAACGGGTAG

FIGURE 8 (continued)

SEQ ID NO: 103, AAQ03221 MADS box transcription factor [Elaeis guineensis]

MGRGRVQLRRIENKINRQVTFSKRRSGLLKKAHEISVLCDAEVALIIFSTKGKLYEYATDSCMERI
LERYERYTYAEKALISSGPELQGNWCHEFGKLKAKVEALQKSQRHLMGEQLEPLNLKELQQLEQQL
ESSLKHIRTRKCQLMFESISELQKKEKSLQEQNKMLEKELMEKQKVKALNQQAPWEQQGPPQTSSS
SPTSFLIGDSLPTLNIGTYQCSGNEIIGEEAAQPQVRIGNSLLPPWMLSIILNG

SEQ ID NO: 104, Allium sp. AL-2003 FRUITFULL-like MADS-box (AlFL) mRNA, partial cds

GTGCAATTGAAGAGGATGGAAAACAAGATTAATAGACAAGTGACCTTCTCAAAAAGAAGAAATGGT
TTGTTGAAGAAAGCTCATGAGATTTCWGTGCTTTGTGATGCAGAAGTTGCACTTATTGTTTTCTCT
GCTAAAGGAAAACTCTATGAATATTCAACTGATTCAAGTATGGAAAAAATTCTGGAGAGGTATGAA
CGTTATTGCTTTGCGGAGAAATCATCAACAATGAGTGACATTGACTCCCAGGAGGATTGGAGCCTT
GAATATCACAAACTGAAGGCTAAGGTTGAGAGTTTAAACAACAGGCAAAGGCATCTTATGGGAGAG
CAACTTGAATCTCTGAGTCTTCGAGAAATTGGACAGCTTGAGCAACAACTTGAGAATTCTCTCAAA
ACTGTTCGGACGCGCAAGAGCCAAGAATTGTTAAGTTCTATTTCAGAGCTTCAGGACAAGGAGAAA
ACTTTGCGAGATGAGAACAAAGCTTTAGAAAATGAGCTTATGAAAAGGGCCAGGGCAAAAGCTATT
CTGGAACAACAAGCACGATGGAAGCATCATAATCATAAACAACAGGATAATCTTCATAATCCAAAT
ATCAACATTGGAAATTACCAAACAAGGAACAATGAGGGAGGAGTTGAGCCAGCAACGGATGTTCAA
GTACGTGTTGTTAGAAATTTGTTGCCCCACTGGATGCTT

SEQ ID NO: 105, AAP83362 FRUITFULL-like MADS-box [Allium sp. AL-2003]

VQLKRMENKINRQVTFSKRRNGLLKKAHEISVLCDAEVALIVFSAKGKLYEYSTDSSMEKILERYE
RYCFAEKSSTMSDIDSQEDWSLEYHKLKAKVESLNNRQRHLMGEQLESLSLREIGQLEQQLENSLK
TVRTRKSQELLSSISELQDKEKTLRDENKALENELMKRARAKAILEQQARWKHHNHKQQDNLHNPN
INIGNYQTRNNEGGVEPATDVQVRVVRNLLPHWML

SEQ ID NO: 106, Dendrobium grex Madame Thong-IN MADS box protein DOMADS2 mRNA, complete cds

ATGGGTCGTGGCAGGGTGCAGCTGAAGCGAATCGAGAATAAAATAAACCGGCAGGTGACGTTCTCG
AAGCGGAGATCTGGTTTGCTTAAGAAGGCGCACGAGATCTCCGTGCTCTGTGACGCTGAAGTTGCT
CTGATCGTTTTTTCCAATAAGGGAAAGCTTATGAGTATTCCACCGATTCCAGCATGGAGAAAATT
CTTGAACGGTATGAGCGTTATTCATATGCTGAAAGAGCATTATTTTCCAATGAGGCCAACCCCCAG
GCTGATTGGCGCCTTGAATATAATAAACTGAAGGCAAGGGTTGAAAGCTTACAGAAGAGCCAAAGG
CACCTTATGGGGGAGCAACTTGACTCCTTGAGCATTAAAGAACTCCAACGTCTAGAGCAACAGCTT
GAAAGTTCCTTGAAGTTTATACGATCCAGAAAGACACAGCTCATACTACATTCAATTTCCGAGCTA
CAAAAGATGGAAAAAATATTGCTGGAGCAAAACAAGACCTTAGAGAAGGAGATTATAGCTAAAGAG
AAAGCCAAAGCTTTGGTGCAGCATGCCCCATGGGAGAAGCAAAACCAGTCCAATATAGCTCTGCA
CTCCCGCCTGTGATTTCGGATTCTGTCCCAACTCCACCAGCAGAACGTTTCAAGCCAGAGCCAAT
GAAGAAGAATCACCTCAGCCACAGTTAAGAGTAAGCAACACTCTGCTGCCCCATGGATGCTCAGT
CATATGAATGGACAATAA

SEQ ID NO: 107, AAF13261 MADS box protein DOMADS2 [Dendrobium grex Madame Thong-In]

MGRGRVQLKRIENKINRQVTFSKRRSGLLKKAHEISVLCDAEVALIVFSNKGKLYEYSTDSSMEKI
LERYERYSYAERALFSNEANPQADWRLEYNKLKARVESLQKSQRHLMGEQLDSLSIKELQRLEQQL
ESSLKFIRSRKTQLILHSISELQKMEKILLEQNKTLEKEIIAKEKAKALVQHAPWEKQNQSQYSSA
LPPVISDSVPTPTSRTFQARANEEESPQPQLRVSNTLLPPWMLSHMNGQ

SEQ ID NO: 108, Oryza sativa GOS2 promoter variant

AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAAGAGAGAGATTTTTTTAAAAAAATAGAATGAAGATATTCTGAACGTATTGGCAAAGATTTAAA
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTTATTATTTATCTTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAAGAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTTCTCCCATCTATAA
ATTCCTCCCCCTTTTCCCCTCTCTATATAGGAGGCATCCAAGCCAAGAAGAGGGAGAGCACCAAG
GACACGCGACTAGCAGAAGCCGAGCGACCGCCTTCTCGATCCATATCTTCCGGTCGAGTTCTTGGT
CGATCTCTTCCCTCCTCCACCTCCTCCTCACAGGGTATGTGCCTCCCTTCGGTTGTTCTTGGATTT
ATTGTTCTAGGTTGTGTAGTACGGGCGTTGATGTTAGGAAAGGGGATCTGTATCTGTGATGATTCC
TGTTCTTGGATTTGGGATAGAGGGGTTCTTGATGTTGCATGTTATCGGTTCGGTTTGATTAGTAGT
ATGGTTTTCAATCGTCTGGAGAGCTCTATGGAAATGAAATGGTTTAGGGATCGGAATCTTGCGATT
TTGTGAGTACCTTTTGTTTGAGGTAAAATCAGAGCACCGGTGATTTTGCTTGGTGTAATAAAGTAC
GGTTGTTTGGTCCTCGATTCTGGTAGTGATGCTTCTCGATTTGACGAAGCTATCCTTTGTTTATTC
CCTATTGAACAAAAATAATCCAACTTTGAAGACGGTCCCGTTGATGAGATTGAATGATTGATTCTT
AAGCCTGTCCAAAATTTCGCAGCTGGCTTGTTTAGATACAGTAGTCCCCATCACGAAATTCATGGA
AACAGTTATAATCCTCAGGAACAGGGGATTCCCTGTTCTTCCGATTTGCTTTAGTCCCAGAATTTT
TTTTCCCAAATATCTTAAAAAGTCACTTTCTGGTTCAGTTCAATGAATTGATTGCTACAAATAATG
CTTTTATAGCGTTATCCTAGCTGTAGTTCAGTTAATAGGTAATACCCCTATAGTTTAGTCAGGAGA
AGAACTTATCCGATTTCTGATCTCCATTTTAATTATATGAAATGAACTGTAGCATAAGCAGTATT
CATTTGGATTATTTTTTTATTAGCTCTCACCCCTTCATTATTCTGAGCTGAAAGTCTGGCATGAA
CTGTCCTCAATTTGTTTTCAAATTCACATCGATTATCTATGCATTATCCTCTTGTATCTACCTGT
AGAAGTTTCTTTTTGGTTATTCCTTGACTGCTTGATTACAGAAAGAAATTTATGAAGCTGTAATCG
GGATAGTTATACTGCTTGTTCTTATGATTCATTTCCTTTGTGCAGTTCTTGGTGTAGCTTGCCACT
TTCACCAGCAAAGTTC

FIGURE 8 (continued)

SEQ ID NO: 109, OsMADS15 coding sequence
ATGGGGCGGGGGAAGGTGCAGCTGAAGCGGATAGAGAACAAGATCAACAGGCAGGTGACGTTCTCC
AAGAGGAGGAATGGATTGCTGAAGAAGGCGCACGAGATCTCCGTCCTCTGCGACGCCGAGGTCGCC
GCCATCGTCTTCTCCCCCAAGGGCAAGCTCTACGAGTACGCCACTGACTCCAGGATGGACAAAATC
CTTGAACGTTATGAGCGCTATTCATATGCTGAAAAGGCTCTTATTTCAGCTGAATCCGAGAGTGAG
GGAAATTGGTGCCATGAATACAGGAAACTTAAGGCAAAGATTGAGACCATACAAAAATGTCACAAA
CACCTCATGGGAGAGGATCTAGAATCCCTGAATCTCAAGAACTCCAACAGCTAGAGCAGCAGCTG
GAGAGTTCATTGAAGCACATAATATCAAGAAAGAGCCACCTTATGCTTGAGTCCATTTCCGAGCTG
CAGAAAAAGGAGAGGTCACTGCAGGAGGAGAACAAGGCTCTGCAGAAGGAACTGGTGGAGAGGCAG
AAGAATGTGAGGGGCCAGCAGCAAGTAGGGCAGTGGGACCAAACCCAGGTCCAGGCCCAGGCCCAA
GCCCAACCCCAAGCCCAGACAAGCTCCTCCTCCTCCTCCATGCTGAGGGATCAGCAGGCACTTCTT
CCACCACAAAATATCTGCTACCCGCCGGTGATGATGGGCGAGAGAAATGATGCGGCGGCGGCGGCG
GCGGTGGCGGCGCAGGGCCAGGTGCAACTCCGCATCGGAGGTCTTCCGCCATGGATGCTGAGCCAC
CTCAATGCTTAA

SEQ ID NO: 110, OsMADS15 protein sequence
MGRGKVQLKRIENKINRQVTFSKRRNGLLKKAHEISVLCDAEVAAIVFSPKGKLYEYATDSRMDKI
LERYERYSYAEKALISAESESEGNWCHEYRKLKAKIETIQKCHKHLMGEDLESLNLKELQQLEQQL
ESSLKHIISRKSHLMLESISELQKKERSLQEENKALQKELVERQKNVRGQQQVGQWDQTQVQAQAQ
AQPQAQTSSSSSSMLRDQQALLPPQNICYPPVMMGERNDAAAAAAVAAQGQVQLRIGGLPPWMLSH
LNA

SEQ ID NO: 111
GGGGACAAGTTTGTACAAAAAAGCAGGCTTAAACAATGGGGCGGGGGAAGGT

SEQ ID NO: 112
GGGGACCACTTTGTACAAGAAAGCTGGGTTTGGCCGACGACGACGAC

SEQ ID NO: 113, GOS2 promoter sequence
AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAGAGTCGCTACACTAGTTTCGTTTTCCTTAGTAATTAAGT
GGGAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAAGAGAGAGATTTTTTTAAAAAAATAGAATGAAGATATTCTGAACGTATTGGCAAAGATTTAAA
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTATTATTTATCTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAAGAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTCCTCCCATCTATAA
ATTCCTCCCCCTTTTCCCTCTCTATATAGGAGGCATCCAAGCCAAGAAGAGGGAGAGCACCAAG
GACACGCGACTAGCAGAAGCCGAGCGACCGCCTTCTTCGATCCATATCTTCCGGTCGAGTTCTTGG
TCGATCTCTTCCCTCCTCCACCTCCTCCTCACAGGGTATGTGCCCTTCGGTTGTTCTTGGATTTAT
TGTTCTAGGTTGTGTAGTACGGGCGTTGATGTTAGGAAGGGGATCTGTATCTGTGATGATTCCTG

FIGURE 11

```
TTCTTGGATTTGGGATAGAGGGGTTCTTGATGTTGCATGTTATCGGTTCGGTTTGATTAGTAGTAT
GGTTTTCAATCGTCTGGAGAGCTCTATGGAAATGAAATGGTTTAGGGTACGGAATCTTGCGATTTT
GTGAGTACCTTTTGTTTGAGGTAAAATCAGAGCACCGGTGATTTTGCTTGGTGTAATAAAAGTACG
GTTGTTTGGTCCTCGATTCTGGTAGTGATGCTTCTCGATTTGACGAAGCTATCCTTTGTTTATTCC
CTATTGAACAAAAATAATCCAACTTTGAAGACGGTCCCGTTGATGAGATTGAATGATTGATTCTTA
AGCCTGTCCAAAATTTCGCAGCTGGCTTGTTTAGATACAGTAGTCCCCATCACGAAATTCATGGAA
ACAGTTATAATCCTCAGGAACAGGGGATTCCCTGTTCTTCCGATTTGCTTTAGTCCCAGAATTTTT
TTTCCCAAATATCTTAAAAAGTCACTTTCTGGTTCAGTTCAATGAATTGATTGCTACAAATAATGC
TTTTATAGCGTTATCCTAGCTGTAGTTCAGTTAATAGGTAATACCCCTATAGTTTAGTCAGGAGAA
GAACTTATCCGATTTCTGATCTCCATTTTAATTATATGAAATGAACTGTAGCATAAGCAGTATTC
ATTTGGATTATTTTTTTATTAGCTCTCACCCCTTCATTATTCTGAGCTGAAAGTCTGGCATGAAC
TGTCCTCAATTTTGTTTTCAAATTCACATCGATTATCTATGCATTATCCTCTTGTATCTACCTGTA
GAAGTTTCTTTTTGGTTATTCCTTGACTGCTTGATTACAGAAAGAAATTTATGAAGCTGTAATCGG
GATAGTTATACTGCTTGTTCTTATGATTCATTTCCTTTGTGCAGTTCTTGGTGTAGCTTGCCACTT
TCACCAGCAAAGTTC
```

SEQ ID NO: 114
L(L/V)KKA(H/N)EIS(VI)L(C/Y)DAE(V/I/L)(A/G)(L/A/V)(I/V)(I/V)FS(T/P/A/N)KGKLYE(Y/F)(A/S)(T/S)(D/N/E)S(K/C/R/S)M(D/E)(N/I/R/K)IL(E/D)R

SEQ ID NO: 115
KLK(A/S)(K/R)(V/I)E(A/T/S)(L/I)(Q/N)(K/R/N)(S/C/R)(Q/H)(R/K)HLMGE

SEQ ID NO: 116
Q(P/Q/V/A)QTS(S/F)(S/F)(S/F)(S/F)(S/C/F)(F/M)

SEQ ID NO: 117, first X: any amino acid, preferably L, P or H; second X residue: any amino acid, preferably V or L
(G/A/V/L)(L/P)XWMX(S/H)

SEQ ID NO: 118, Hordeum vulgare subsp. vulgare cultivar Morex VRN-H1 gene, MADS15 complete cds
```
ATGGGCGCGGGAAGGTGCAGCTGAAGCGGATCGAGAACAAGATCAACCGCCAGGTCACCTTCTCC
AAGCGCCGCTCGGGGCTGCTCAAGAAGGCGCACGAGATCTCCGTGCTCTGCGACGCCGAGGTCGGC
CTCATCATCTTCTCCACCAAGGGAAAGCTCTACGAGTTCTCCACCGAGTCATGTATGGACAAAATT
CTTGAACGGTATGAGCGCTACTCTTATGCAGAAAAGGTTCTCGTTTCAAGTGAATCTGAAATTCAG
GGAAACTGGTGTCACGAATATAGGAAACTGAAGGCGAAGGTTGAGACAATACAGAAATGTCAAAAG
CATCTCATGGGAGAGGATCTTGAATCTTTGAATCTCAAGGAGTTGCAGCAACTGGAGCAGCAGCTG
GAAAGCTCACTGAAACATATCAGAGCCAGGAAGAACCAACTTATGCACGAATCCATTTCTGAGCTT
CAGAAGAAGGAGAGGTCACTGCAGGAGGAGAATAAAGTTCTCCAGAAGGAACTTGTGGAGAAGCAG
AAGGCCCAGGCGGCGCAGCAAGATCAAACTCAGCCTCAAACCAGCTCTTCTTCTTCTTCCTTCATG
ATGAGGGATGCTCCCCCTGTCGCAGATACCAGCAATCACCCAGCGGCGGCAGGCGAGAGGGCAGAG
GATGTGGCAGTGCAGCCTCAGGTCCCACTCCGGACGGCGCTTCCACTGTGGATGGTGAGCCACATC
AACGGCTGA
```

FIGURE 11 (continued)

SEQ ID NO: 119, AAW82995 VRN-H1 [Hordeum vulgare subsp. vulgare]
MGRGKVQLKRIENKINRQVTFSKRRSGLLKKAHEISVLCDAEVGLIIFSTKGKLYEFSTESCMDKI
LERYERYSYAEKVLVSSESEIQGNWCHEYRKLKAKVETIQKCQKHLMGEDLESLNLKELQQLEQQL
ESSLKHIRARKNQLMHESISELQKKERSLQEENKVLQKELVEKQKAQAAQQDQTQPQTSSSSSSFM
MRDAPPVADTSNHPAAAGERAEDVAVQPQVPLRTALPLWMVSHING

SEQ ID NO: 120, AJ249144 Hordeum vulgare mRNA for MADS-box protein 5 (m5 gene) ORF 141-875
CTCTCCCCTCCCACTTCACCCAACCACCTGACAGCCATGGCTCCGCCACCTCGCCTCCGCCCGCGC
CTCTGAGAGTAGCCGTCGCGGTCGCTCGCTCGCTCGCTGCTGCCGGTGTTGGCCCGGTCCTC
GAGCGGAGATGGGGCGCAGGAAGGTGCAGCTGAAGCGGATCGAGAACAAGATCAACCGCCAGGTCA
CCTTCTCCAAGCGCCGCTCGGGGCTGCTCAAGAAGGCGCACGAGATCTCCGTGCTCTACGACGCCG
AGGTCGGCCTCATCATCTTCTCCACCAAGGGAAAGCTCTACGAGTTCTCCACCGAGTCATGTATGG
ACAAAATTCTTGAACGGTATGAGCGCTACTCTTATGCAGAAAAGGTTCTCGTTTCAAGTGAATCTG
AAATTCAGGGAAACTGGTGTCACGAATATAGGAAACTGAAGGCGAAGGTTGAGACAATACAGAAAT
GTCAAAAGCATCTCATGGGAGAGGATCTTGAATCTTTGAATCTCAAGGAGTTGCAGCAACTGGAGC
AGCAGCTGGAAAGCTCACTGAAACATATCAGAGCCAGGAAGAACCAACTTATGCACGAATCCATTT
CTGAGCTTCAGAAGAAGGAGAGGTCACTGCAGGAGGAGAATAAAGTTCTCCAGAAGGAACTTGTGG
AGAAGCAGAAGGCCCAGGCGGCGCAGCAAGATCAAACTCAGCCTCAAACCAGCTCTTCTTCTTCTT
CCTTCATGATGAGGGATGCTCCCCCTGTCGCAGATACCAGCAATCACCCAGCGGCGGCAGGCGAGA
GGGCAGAGGATGTGGCAGTGCAGCCTCAGGTCCCACTCCGGACGGCGCTTCCACTGTGGATGGTGA
GCCACATCAACGGCTGAAGGGCTTCCAGCCCATGTAAGCGTACTATTCAGTACGAGTAACAAGTTG
CAGCGGCCAGCCTGGTGTATCATGCGGTTGCGAACATGCTAACCCCATGGAGGGGAGAGGAAAAGA
AATCAGAGTAAAGCAGCAAGCTGCAGGAATGTGTATATTTCACTTCGTCCACCTCAGTTTCCTTTC
CACCTGGGCTGAGATGGCTGTACGAGTAATCTACCATGTAATTTATATGTAGCATGAGTGACGAAT
TTTCAACTTTCGATGATATCCGTTGCTCCTGGGTGTTGTTTCTGTGAATTAACCTATCGAATATGA
GCGTTGTG

SEQ ID NO: 121, CAB97352 MADS-box protein 5 [Hordeum vulgare subsp. vulgare]
MGRRKVQLKRIENKINRQVTFSKRRSGLLKKAHEISVLYDAEVGLIIFSTKGKLYEFSTESCMDKI
LERYERYSYAEKVLVSSESEIQGNWCHEYRKLKAKVETIQKCQKHLMGEDLESLNLKELQQLEQQL
ESSLKHIRARKNQLMHESISELQKKERSLQEENKVLQKELVEKQKAQAAQQDQTQPQTSSSSSSFM
MRDAPPVADTSNHPAAAGERAEDVAVQPQVPLRTALPLWMVSHING

SEQ ID NO: 122, AB007504 Triticum aestivum TaMADS#11 mRNA for MADS box transcription factor, complete cds
GGCACGAGCTCTCTCTCTCTCTCTCTCTCTCTCTCTCTCTCCTCGTGCCGAATTCGGCAC
GAGCGGAGATGGGGCGCGGGAAGGTGCAGCTGAAGCGGATCGAGAACAAGATCAACCGGCAGGTGA
CCTTCTCCAAGCGCCGCTCGGGGCTGCTCAAGAAGGCGCACGAGATCTCCGTGCTCTGCGACGCCG
AGGTCGGCCTCATCATCTTCTCCACCAAGGGAAAGCTCTACGAGTTCTCCACCGAGTCATGTATGG
ACAAAATTCTTGAACGGTATGAGCGCTACTCTTATGCAGAAAAGGTTCTCGTTTCAAGTGAATCTG
AAATTCAGGGAAACTGCTGTCACGAATATACGAAACTGAAGGCGAAGCTTCAGACAATACACAAAT
GTCAAAAGCATCTGATGGGAGAGGATCTTGAATCTTTGAATCTCAAGGAGTTGCAGCAACTGGAGC
AGCAGCTGGAAAGCTCACTGAAACATATCAGATCCAGGAAGAACCAACTTATGCACGAATCCATTT
CTGAGCTTCAGAAGAAGGAGAGGTCACTGCAGGAGGAGAATAAAGTTCTCCAGAAGGAACTCGTCG
AGAAGCAGAAGGCCCAGGCGGCGCAACAAGATCAGACTCAGCCTCAAACAAGCTCTTCTTCTTCTT
CCTTCATGATGAGGGATGCTCCCCCTGCCGCAGCTACCAGCATTCATCCAGCGGCGGCAGGCGAGA FIGURE 11 (continued)

```
GGGCAGGGGATGCGGCAGTGCAGCCGCAGGCCCCACCCCGGACGGGGCTTCCACTGTGGATGGTGA
GCCACATCAACGGCTGAAGGGCTTCCAGCCCATATAAGCGTACTATTCAGTAGAGAGTAACAAGTT
GCACCGGCCAGTCTGGTGTATGTTGCGGTTGCTAGCACGCCTGACCCCTTGGAGGGGAAAGGAAAA
GAAATCAGAGTAAAGTAGCAAGCTGCAGCGATGTGTATATTTCACTTTGTCCACCCCAGTTTCCCT
CCCAGCTGGGCTCAATTTACCATGTAATCTATATGTAGCTTGAGTGATGAATTTTCAAGTTTCCAT
GATACCCGTCTCTAGTGGGATGTTGTTTATGTGAATTAACCTATCAAATATGAGCATTGTGTATAT
TGTGATTCTTGAAAATAAATAAATCAGGATCTTTGTCTT
```

SEQ ID NO: 123, BAA33457 MADS box transcription factor [Triticum aestivum]
```
MGRGKVQLKRIENKINRQVTFSKRRSGLLKKAHEISVLCDAEVGLIIFSTKGKLYEFSTESCMDKI
LERYERYSYAEKVLVSSESEIQGNWCHEYRKLKAKVETIQKCQKHLMGEDLESLNLKELQQLEQQL
ESSLKHIRSRKNQLMHESISELQKKERSLQEENKVLQKELVEKQKAQAAQQDQTQPQTSSSSSFM
MRDAPPAAATSIHPAAAGERAGDAAVQPQAPPRTGLPLWMVSHING
```

SEQ ID NO: 124, AY280870 Triticum aestivum MADS-box protein TaVRT-1 mRNA, complete cds ORF 150-884
```
TCCCTCTCCTCCCTCTCTTCCGCCTCACCCAACCACCTGACAGCCATGGCTCCGCCCCCCGCCCC
CGCCTGCGCCTGTCGGAGTAGCCGTCGCGGTCTGCCGGTGTTGGAGGCTTGGGGTGTAGGGTTGGC
CCCGTTCTCCAGCGGAGATGGGCGCGGGAAGGTGCAGCTGAAGCGGATCGAGAACAAGATCAACC
GGCAGGTGACCTTCTCCAAGCGCCGCTCGGGGCTGCTCAAGAAGGCGCACGAGATCTCCGTGCTCT
GCGACGCCGAGGTCGGCCTCATCATCTTCTCCACCAAGGGAAAGCTCTACGAGTTCTCCACCGAGT
CATGTATGGACAAAATTCTTGAACGGTATGAGCGCTACTCTTATGCAGAAAAGGTTCTCGTTTCAA
GTGAATCTGAAATTCAGGGAAACTGGTGTCACGAATATAGGAAACTGAAGGCGAAGGTTGAGACAA
TACAGAAATGTCAAAAGCATCTGATGGGAGAGGATCTTGAATCTTTGAATCTCAAGGAGTTGCAGC
AACTGGAGCAGCAGCTGGAAAGCTCACTGAAACATATCAGATCCAGGAAGAACCAACTTATGCACG
AATCCATTTCTGAGCTTCAGAAGAAGGAGAGGTCACTGCAGGAGGAGAATAAAGTTCTCCAGAAGG
AACTCGTCGAGAAGCAGAAGGCCCAGGCGGCGCAACAAGATCAGACTCAGCCTCAAACAAGCTCTT
CTTCTTCTTCCTTCATGATGAGGGATGCTCCCCCTGCCGCAACTACCAGCATTCATCCAGCGGCAT
CAGGAGAGAGGGCAGAGGATGCGGCAGTGCAGCCGCAGGCCCCACCCCGGACGGGGCTTCCACTGT
GGATGGTTAGCCACATCAACGGCTGAAGGGCTTCCAGCCCATATAAGCGTACTATTCAGTAGAGAG
TAACAAGTTGCACCGGCCAGCCTGGTGTATGTTGCGGTTGCTAGCATGCCTGACCCCTTGGAGGGG
AAAGGAAAAGAAATCAGAGTAAAGTAGCAAGCTGCAGTGATGTGTATATTTCACTTTGTCCACCTC
AGTTTCCCTCCCAGCTGGGCTCAATTTACCATGTAATCTATATGTAGCTTGAGTGATGAATTTTCA
AGTTTCCATGATACCCGTCTCGAGCGGGTGTTGTTTATGTGAATTAACCTATCAAATATGAGCATT
GTGTAAAAAAAAAAAAAAAAA
```

SEQ ID NO: 125, AAP33790 MADS-box protein TaVRT-1 [Triticum aestivum]
```
MGRGKVQLKRIENKINRQVTFSKRRSGLLKKAHEISVLCDAEVGLIIFSTKGKLYEFSTESCMDKI
LERYERYSYAEKVLVSSESEIQGNWCHEYRKLKAKVETIQKCQKHLMGEDLESLNLKELQQLEQQL
ESSLKHIRSRKNQLMHESISELQKKERSLQEENKVLQKELVEKQKAQAAQQDQTQPQTSSSSSFM
MRDAPPAATTSIHPAASGERAEDAAVQPQAPPRTGLPLWMVSHING
```

SEQ ID NO: 126, Triticum monococcum DV92 chromosome 5AL BAC 231A16, complete sequence
```
ATGGGCGCGGGAAGGTGCAGCTGAAGCGGATCGAGAACAAGATCAACCGGCAGGTGACCTTCTCC
AAGCGCCGCTCGGGGCTTCTCAAGAAGGCGCACGAGATCTCCGTGCTCTGCGACGCCGAGGTCGGC
CTCATCATCTTCTCCACCAAGGGAAAGCTCTACGAGTTCTCCACCGAGTCATGTATGGACAAAATT
```

FIGURE 11 (continued)

```
CTTGAACGGTATGAGCGCTATTCTTATGCAGAAAAGGTTCTCGTTTCAAGTGAATCTGAAATTCAG
GGAAACTGGTGTCACGAATATAGGAAACTGAAGGCGAAGGTTGAGACAATACAGAAATGTCAAAAA
CATCTCATGGGAGAGGATCTTGAATCTTTGAATCTCAAGGAGTTGCAGCAACTGGAGCAGCAGCTG
GAAAGCTCACTGAAACATATCAGATCCAGGAAGAACCAACTTATGCACGAATCCATTTCTGAGCTG
CAGAAGAAGGAGAGGTCACTGCAGGAGGAGAATAAAGTTCTCCAGAAGGAACTCGTGGAGAAGCAG
AAGGCCCATGCGGCGCAGCAAGATCAAACTCAGCCTCAAACCAGCTCTTCTTCTTCTTCCTTCATG
CTGAGGGATGCTCCCCCTGCCGCAAATACCAGCATTCATCCAGCGGCGGCAGGCGAGAGGGCAGAG
GATGCGGCAGTGCAGCCGCAGGCCCCACCCCGGACGGGGCTTCCACCGTGGATGGTGAGCCACATC
AACGGGTGA
```

SEQ ID NO: 127, AAO72630 MADS box transcription factor AP1 [Triticum monococcum]
```
MGRGKVQLKRIENKINRQVTFSKRRSGLLKKAHEISVLCDAEVGLIIFSTKGKLYEFSTESCMDKI
LERYERYSYAEKVLVSSESEIQGNWCHEYRKLKAKVETIQKCQKHLMGEDLESLNLKELQQLEQQL
ESSLKHIRSRKNQLMHESISELQKKERSLQEENKVLQKELVEKQKAHAAQQDQTQPQTSSSSSSFM
LRDAPPAANTSIHPAAAGERAEDAAVQPQAPPRTGLPPWMVSHING
```

SEQ ID NO: 128, Triticum aestivum cultivar Triple Dirk D line VRN-A1 (VRN-A1) gene, complete cds
```
ATGGGCGGGGGAAGGTGCAGCTGAAGCGGATCGAGAACAAGATCAACCGGCAGGTGACCTTCTCC
AAGCGCCGCTCGGGGCTTCTCAAGAAGGCGCACGAGATCTCCGTGCTCTGCGACGCCGAGGTCGGC
CTCATCATCTTCTCCACCAAGGGAAAGCTCTACGAGTTCTCCACCGAGTCATGTATGGACAAAATT
CTTGAACGGTATGAGCGCTATTCTTATGCAGAAAAGGTTCTCGTTTCAAGTGAATCTGAAATTCAG
GGAAACTGGTGTCACGAATATAGGAAACTGAAGGCGAAGGTTGAGACAATACAGAAATGTCAAAAG
CATCTCATGGGAGAGGATCTTGAATCTTTGAATCTCAAGGAGTTGCAGCAACTGGAGCAGCAGCTG
GAAAGCTCACTGAAACATATCAGATCCAGGAAGAACCAACTTATGCACGAATCCATTTCTGAGCTT
CAGAAGAAGGAGAGGTCACTGCAGGAGGAGAATAAAGTTCTCCAGAAGGAACTCGTGGAGAAGCAG
AAGGCCCATGCGGCGCAGCAAGATCAAACTCAGCCTCAAACCAGCTCTTCATCTTCTTCCTTCATG
CTGAGGGATGCTCCCCCTGCCGCAAATACCAGCATTCATCCAGCGGCAACAGGCGAGAGGGCAGAG
GATGCGGCAGTGCAGCCGCAGGCCCCACCCCGGACGGGGCTTCCACCGTGGATGGTGAGCCACATC
AACGGGTGA
```

SEQ ID NO: 129, AAW73222 VRN-A1 [Triticum aestivum]
```
MGRGKVQLKRIENKINRQVTFSKRRSGLLKKAHEISVLCDAEVGLIIFSTKGKLYEFSTESCMDKI
LERYERYSYAEKVLVSSESEIQGNWCHEYRKLKAKVETIQKCQKHLMGEDLESLNLKELQQLEQQL
ESSLKHIRSRKNQLMHESISELQKKERSLQEENKVLQKELVEKQKAHAAQQDQTQPQTSSSSSSFM
LRDAPPAANTSIHPAATGERAEDAAVQPQAPPRTGLPPWMVSHING
```

SEQ ID NO: 130, Lolium perenne MADS1 mRNA, complete cds
```
ATGCGCGCGCGCAAGCTCCACCTCAAGCGGATCGAGAACAAGATCAACCGCCAGGTCACCTTCTCC
AAGCGCCGCTCGGGGCTGCTCAAGAAGGCGCACGAGATCTCCGTGCTCTGCGACGCCGAGGTCGGG
CTCATCATCTTCTCCACCAAGGGAAAGCTCTACGAGTTCGCAACCGACTCATGTATGGACAAAATT
CTTCACCGGTATGAGCGCTACTCCTATCCACACAAAGTGCTCATTTCAACCGAATCTGAAATTCAG
GGAAACTGGTGTCATGAATATAGGAAACTGAAGGCGAAGGTTGAGACAATACAGAGATGTCAAAAG
CATCTAATGGGAGAGGATCTTGAATCATTGAATCTCAAGGAGTTGCAGCAACTAGAGCAGCAGCTG
GAAAGTTCACTGAAACATATTACAGCCAGAAACAACCAGCTTATCCACCAATCCATATCTGAGCTT
CAAAAGAAGGAGAGGTCACTGCAGGAGGAGAATAAAATTCTCCAGAAGGAACTCATAGAGAAGCAG
AAGGCCCACACGCAGCAAGCGCAGTGGGAGCAAACTCAGCCCCAAACCAGCTCTTCCTCCTCCTCC
```

FIGURE 11 (continued)

TTTATGATGGGGGAAGCTACCCCAGCAACAAATTGCAGTAATCCCCCAGCAGCGGCCAGCGACAGA
GCAGAGGATGCGACGGGGCAGCCTTCAGCTCGCACGGTGCTTCCACCATGGATGGTGAGTCACATC
AACAATGGCTGA

SEQ ID NO: 131, AAO45873 MADS1 [Lolium perenne]
MGRGKVQLKRIENKINRQVTFSKRRSGLLKKAHEISVLCDAEVGLIIFSTKGKLYEFATDSCMDKI
LERYERYSYAEKVLISTESEIQGNWCHEYRKLKAKVETIQRCQKHLMGEDLESLNLKELQQLEQQL
ESSLKHIRARKNQLMHESISELQKKERSLQEENKILQKELIEKQKAHTQQAQWEQTQPQTSSSSSS
FMMGEATPATNCSNPPAAASDRAEDATGQPSARTVLPPWMVSHINNG

SEQ ID NO: 132, Lolium temulentum MADS-box protein 1 (MADS1) mRNA, complete cds
ATGGGGCGCGGCAAGGTGCAGCTCAAGCGGATCGAGAACAAGATCAACCGCCAGGTCACCTTCTCC
AAGCGCCGCTCAGGCCTGCTCAAGAAGGCGCACGAGATCTCCGTGCTCTGCGACGCAGAGGTCGGG
CTCATCATCTTCTCCACCAAGGGAAAGCTCTACGAGTTCGCCACCGACTCATGTATGGACAAAATT
CTTGAGCGGTATGAGCGCTACTCCTATGCAGAGAAAGTGCTCATTTCAACTGAATCTGAAATTCAG
GGAAACTGGTGTCATGAATATAGGAAACTGAAGGCGAAGGTTGAGACAATACAGAGATGTCAAAAG
CATCTAATGGGAGAGGATCTTGAATCATTGAATCTCAAGGAGTTGCAGCAACTAGAGCAGCAGCTG
GAAAGTTCACTGAAACATATTAGATCCAGAAAGAGCCAGCTTATGCACGAATCCATATCTGAGCTT
CAAAAGAAGGAGAGGTCACTGCAAGAGGAGAATAAAATTCTCCAGAAGGAACTCATAGAAGCAG
AAGGCCCACACGCAGCAAGCGCAGTTGGAGCAAACTCAGCCCCAAACCAGCTCTTCCTCCTCCTCC
TTTATGATGGGGGAAGCTACCCCAGCAACAAATCGCAGTAATCCCCCAGCAGCGGCCAGCGACAGA
GCAGAGGATGCGACGGGGCAGCCTCCAGCTCGCACGGTGCTTCCACCATGGATGGTGAGTCACCTC
AACAATGGCTGA

SEQ ID NO: 133, AAD10625 MADS-box protein 1 [Lolium temulentum]
MGRGKVQLKRIENKINRQVTFSKRRSGLLKKAHEISVLCDAEVGLIIFSTKGKLYEFATDSCMDKI
LERYERYSYAEKVLISTESEIQGNWCHEYRKLKAKVETIQRCQKHLMGEDLESLNLKELQQLEQQL
ESSLKHIRSRKSQLMHESLSELQKKERSLQEENKILQKELIEKQKAHTQQAQLEQTQPQTSSSSSS
FMMGEATPATNRSNPPAAASDRAEDATGQPPARTVLPPWMVSHLNNG

SEQ ID NO: 134, Zea mays mRNA for putative MADS-domain transcription factor (m15 gene)
ATGGGGCGCGGAAGGTGCAGCTGAAGCGGATCGAGAACAAGATCAACCGCCAGGTGACCTTCTCC
AAGCGCCGCTCGGGGCTGCTCAAGAAGGCGCACGAGATCTCCGTGCTCTGCGACGCCGAGGTCGCG
CTCATCATCTTCTCCACCAAAGGGAAGCTCTACGAGTATTCCACCGATTCATGTATGGACAAAATT
CTTGACCGGTACGAGCGCTACTCCTATGCAGAAAAGGTTCTTATTTCAGCAGAATCTGAAACTCAG
GGCAATTGGTGCCACGAGTATAGAAAACTAAGGCGAAGGTCGAGACAATACAAAATGTCAAAAG
CACCTCATGGGAGAGGATCTTGAAACGTTGAATCTCAAAGAGCTTCAGCAACTAGAGCAGCAGCTG
GAGACTTCACTCAAACATATCAGAACCAGGAAGAACCAACTTATGCTCCACTCAATTTCGGACCTC
CAACGGAAGGAGAAGTCGCTGCAGGAGGAGAACAAGGTTCTGCAGAAGGAGCTCGCGGAGAAGCAG
AAAGCCCAGCGGAAGCAAGTGCAATGGGCCAAACCCAACAGCAGACCAGTTCGTCTTCCTCGTGC
TTCGTGATAAGCGAAGCTGCCCCAACAACAAATATCAGCATTTTCCTGTCGGCAGCAGGCGGCAGCC
TTGGTGGAAGGTGCAGCAGCGCAGCCACAGGCTCGCGTTGGACTACCACCATGGATGCTTAGCCAC
CTGAGCAGCTGA SEQ ID NO: 135, CAD23408 putative MADS-domain transcription factor [Zea mays]
MGRGKVQLKRIENKINRQVTFSKRRSGLLKKAHEISVLCDAEVALIIFSTKGKLYEYSTDSCMDKI
LDRYERYSYAEKVLISAESETQGNWCHEYRKLKAKVETIQKCQKHLMGEDLETLNLKELQQLEQQL
ESSLKHIRTRKNQLMLESISELQRKEKSLQEENKVLQKELAEKQKAQRKQVQWGQTQQQTSSSSSC
FVIREAAPTTNISIFPVAAGGRLVEGAAAQPQARVGLPPWMLSHLSS SEQ ID NO: 136, Zea mays mRNA for putative MADS-domain transcription factor (m4 gene)
ATGGGGCGCGGGAAGGTGCAGCTGAAGCGGATCGAGAACAAGATCAACCGCCAGGTGACATTCTCC
AAGCGCCGCTCGGGGCTACTCAAGAAGGCGCACGAGATCTCCGTGCTCTGCGACGCCGAGGTCGCG
CTCATCATCTTCTCCACCAAGGGCAAGCTCTACGAGTACTCTACCGATTCATGTATGGACAAAATT
CTTGAACGGTATGAGCGCTACTCCTATGCAGAAAAGGTTCTCATTTCCGCAGAATATGAAACTCAG
GGCAATTGGTGCCATGAATATAGAAAACTAAAGGCGAAGGTCGAGACAATACAGAAATGTCAAAAG
CACCTCATGGGAGAGGATCTTGAAACTTTGAATCTCAAAGAGCTTCAGCAACTAGAGCAGCAGCTG
GAGAGTTCACTGAAACATATCAGAACAAGGAAGAGCCAGCTTATGGTCGAGTCAATTTCAGCGCTC
CAACGGAAGGAGAAGTCACTGCAGGAGGAGAACAAGGTTCTGCAGAAGGAGCTCGCGGAGAAGCAG
AAAGACCAGCGGCAGCAAGTGCAACGGGACCAAACTCAACAGCAGACCAGTTCGTCTTCCACGTCC
TTCATGTTAAGGGAAGCTGCCCCAACAACAAATGTCAGCATCTTCCCTGTGGCAGCAGGCGGGAGG
GTGGTGGAAGGGCAGCAGCGCAGCCGCAGGCTCGCGTTGGACTGCCACCATGGATGCTTAGCCAT
CTGAGCTGCTGA SEQ ID NO: 137, CAD23417 m4 [Zea mays]
MGRGKVQLKRIENKINRQVTFSKRRSGLLKKAHEISVLCDAEVALIIFSTKGKLYEYSTDSCMDKI
LERYERYSYAEKVLISAEYETQGNWCHEYRKLKAKVETIQKCQKHLMGEDLETLNLKELQQLEQQL
ESSLKHIRTRKSQLMVESISALQRKEKSLQEENKVLQKELAEKQKDQRQQVQRDQTQQQTSSSSTS
FMLREAAPTTNVSIFPVAAGGRVVEGAAAQPQARVGLPPWMLSHLSC SEQ ID NO: 138, Oryza sativa (japonica cultivar-group) MADS-box protein RMADS211 mRNA, complete cds
ATGGGGCGGGGCAAGGTGCAGCTGAAGCGGATCGAGAACAAGATCAACCGGCAGGTGACCTTCTCC
AAGCCCAGGTCGGGGCTGCTCAACAACGCCAATCACATCTCCGTGCTCTGCGACGCCGAGGTCGCC
CTCATCATCTTCTCCACCAAGGGCAAGCTCTACGAGTACGCCACCGACTCATGTATGGACAAAATC
CTTGAACGTTATGAGCGCTACTCCTATGCAGAAAAGGTCCTTATTTCAGCTGAATCTGACACTCAG
GGCAACTGGTGCCACGAATATAGGAAACTGAAGGCTAAGGTTGAGACAATACAGAAATGTCAAAAG
CACCTCATGGGAGAGGATCTTGAATCTTTGAATCTCAAAGAGCTGCAGCAGCTGGAGCAGCAGCTG
GAAAATTCGTTGAAACATATCAGATCCAGAAAGAGCCAACTAATGCTCGAGTCCATTAACGAGCTT
CAACGGAAGGAAAAGTCACTGCAGGAGGAGAATAAGGTCCTACAGAAAGAAAACCCTTGCTCCTTC
CTACAGCTGGTGGAGAAGCAGAAAGTCCAGAAGCAACAAGTGCAATGGGACCAGACACAACCTCAA
ACAAGTTCCTCATCATCCTCCTTCATGATGAGGGAAGCCCTTCCAACAACTAATATCAGTAACTAC
CCTGCAGCAGCTGGCGAAAGGATAGAGGATGTAGCAGCAGGGCAGCCACAGCATGTTCGCATTGGG
CTGCCACCATGGATGCTGAGCCACATCAACGGCTAA SEQ ID NO: 139, AAS59822 MADS-box protein RMADS211 [Oryza sativa (japonica cultivar-group)]
MGRGKVQLKRIENKINRQVTFSKRRSGLLKKANEISVLCDAEVALIIFSTKGKLYEYATDSCMDKI
LERYERYSYAEKVLISAESDTQGNWCHEYRKLKAKVETIQKCQKHLMGEDLESLNLKELQQLEQQL
ENSLKHIRSRKSQLMLESINELQRKEKSLQEENKVLQKENPCSFLQLVEKQKVQKQQVQWDQTQPQ
TSSSSSFMMREALPTTNISNYPAAAGERIEDVAAGQPQHVRIGLPPWMLSHING

FIGURE 11 (continued)

SEQ ID NO: 140, Oryza sativa MADS14 protein mRNA, complete cds
ATGGGGCGGGGCAAGGTGCAGCTGAAGCGGATCGAGAACAAGATCAACCGGCAGGTGACCTTCTCC
AAGCGCAGGTCAAAACTGCTCAAGAAGGCGAATGAGATCTCCGTGCTCTGCGACGCCGAGGTCGCG
CTCATCATCTTCTCCACCAAGGGCAAGCTCTACGAGTACGCCACCGACTCATGTATGGACAAAATC
CTTGAACGTTATGAGCGCTACTCCTATGCAGAAAAGGTCCTTATTTCAGCTGAATCTGACACTCAG
GGCAACTGGTGCCACGAATATAGGAAACTGAAGGCTAAGGTTGAGACAATACAGAAATGTCAAAAG
CACCTCATGGGAGAGGATCTTGAATCTTTGAATCTCAAAGAGCTGCAGCAGCTGGAGCAGCAGCTG
GAAAATTCGTTGAAACATATCAGATCCAGAAAGAGCCAACTAATGCTCGAGTCCATTAACGAGCTT
CAACGGAAGGAAAAGTCACTGCAGGAGGAGAATAAGGTCCTACAGAAAGAACTGGTGGAGAAGCAG
AAAGTCCAGAAGCAACAAGTGCAATGGGACCAGACACAACCTCAAACAAGTTCCTCATCATCCTCC
TTCATGATGAGGGAAGCCCTTCCAACAACTAATATCAGTAACTACCCTGCAGCAGCTGGCGAAAGG
ATAGAGGATGTAGCAGCAGGGCAGCCACAGCATGAACGCATTGGGCTGCCACCATGGATGCTGAGC
CACATCAACGGCTAA

SEQ ID NO: 141, AAF19047 MADS14 protein [Oryza sativa]
MGRGKVQLKRIENKINRQVTFSKRRSKLLKKANEISVLCDAEVALIIFSTKGKLYEYATDSCMDKI
LERYERYSYAEKVLISAESDTQGNWCHEYRKLKAKVETIQKCQKHLMGEDLESLNLKELQQLEQQL
ENSLKHIRSRKSQLMLESINELQRKEKSLQEENKVLQKELVEKQKVQKQQVQWDQTQPQTSSSSSS
FMMREALPTTNISNYPAAAGERIEDVAAGQPQHERIGLPPWMLSHING

SEQ ID NO: 142, Dendrocalamus latiflorus MADS-box protein (Mads2) mRNA, complete cds
ATGGGGCGCGGGAAGGTGCAGCTGAAGCGGATCGAGAACAAGATCAACCGGCAAGTGACTTTCTCC
AAGCGCCGGTCGGGGCTGCTCAAGAAGGCGCATGAGATCTCCGTCCTCTGCGACGCCGAGGTCGGC
CTTATCATCTTCTCCACCAAGGGCAAGCTCTACGAGTACGCCACCGACTCATGTATGGACAAAATT
CTTGAACGGTACGAGCGTTACTCCTATGCAGAAAAGGTTCTTATTTCAGCCGAATCTGAAACTCAG
GGCAACTGGTGTCACGAATATAGGAAACTGAAGGCGAAGGTTGAGACGATACAGAAATGTCAAAAG
CACCTCATGGGAGAGGATCCTGAATCTTTGAATCTCAAGGAGCTGCAGCAACTCGAGCAGCAGCTG
GAAAGTTCAGTGAAACATATCAGATCCAGAAAGAGCCAGCTTATGCTCGAGTCCATTTCCGAGCTT
CAAAAGAAGGAGAAGTCACTGCAGGAGGAGAACAAGGTTCTGCAGAAGGAACTCGTGGAGAAGCAG
CAGGTCCATAAACGGTTAGTGCAATGGGACCAAACTCAGCCGCAAACTAGTTCCTCTTCCTCGTCC
TTCATGATGAGGGAAGCTCTCCCAACAACAAATATCAGTATTTACGCTGCGGCAGCCGGCGAGAGG
GCAGAGGACGCAGCAGGGCAGCCTCAGATTCACATTGGGCTGCCGCCATGGATGGTGAGCCACATC
AACGGCTAA

SEQ ID NO: 143, AAR32119 MADS-box protein [Dendrocalamus latiflorus]
MGRGKVQLKRIENKINRQVTFSKRRSGLLKKAHEISVLCDAEVGLIIFSTKGKLYEYATDSCMDKI
LERYERYSYAEKVLISAESETQGNWCHEYRKLKAKVETIQKCQKHLMGEDPESLNLKELQQLEQQL
ESSVKHIRSRKSQLMLESISELQKKEKSLQEENKVLQKELVEKQQVHKRLVQWDQTQPQTSSSSSS
FMMREALPTTNISIYAAAAGERAEDAACQPQIHIGLPPWMVSHING

SEQ ID NO: 144, Dendrocalamus latiflorus MADS-box protein (Mads1) mRNA, complete cds
ATGGGGCGCGGGAAGGTGCAGCTGAAGCGGATCGAGAACAAGATCAACCGGCAAGTGACTTTCTCC
AAGCGCCGGTCGGGGCTGCTCAAGAAGGCGCATGAGATCTCCGTCCTCTGCGACGCCGAGGTCGGC
CTTATCATCTTCTCCACCAAGGGCAAGCTCTACGAGTACGCCACCGACTCATGTATGGACAAAATT
CTTGAACGGTACGAGCGTTACTCCTATGCAGAAAAGGTTCTTATTTCAGCCGAATCTGAAACTCAG
GGCAACTGGTGTCACGAATATAGGAAACTGAAGGCGAAGGTTGAGACGATACAGAAATGTCAAAAG CACCTCATGGGAGAGGATCTTGAATCTTTGAATCTCAAGGAGCTGCAGCAACTCGAGCAGCAGCTG
GAAAGTTCAGTGAAACATATCAGATCCAGAAAGAGCCAGCTTATGCTCGAGTCCATTTCCGAGCTT
CAAAAGAAGGAGAAGTCACTGCAGGAGGAGAACAAGGTTCTGCAGAAGGAACTCGTGGAGAAGCAG
CAGGTCCATAAACGGTTAGTGCAATGGGACCAAACTCAGCCGCAAACTAGTTCCTCTTCCTCGTCC
TTCATGATGAGGGAAGCTCTCCCAACAACAAATATCAGTATTTACGCTGCGGCAGCCGGCGAGAGG
GCAGAGGACGCAGCAGGGCAGCCTCAGATTCACATTGGGCTGCCGCCATGGATGGTGAGCCACATC
AACGGCTAA

SEQ ID NO: 145, AAR32118 MADS-box protein [Dendrocalamus latiflorus]
MGRGKVQLKRIENKINRQVTFSKRRSGLLKKAHEISVLCDAEVGLIIFSTKGKLYEYATDSCMDKI
LERYERYSYAEKVLISAESETQGNWCHEYRKLKAKVETIQKCQKHLMGEDLESLNLKELQQLEQQL
ESSVKHIRSRKSQLMLESISELQKKEKSLQEENKVLQKELVEKQQVHKRLVQWDQTQPQTSSSSSS
FMMREALPTTNISIYAAAAGERAEDAAGQPQIHIGLPPWMVSHING

SEQ ID NO: 146, Zea mays MADS box protein 3 (mads3) mRNA, complete cds
ATGGGCCGCGCCAACGTGCAGCTGAACCGGATAGAGAACAAGATAAACCGGCAGGTGACCTTCTCC
AAGCGCCGGAACGGGCTGCTGAAGAAGGCGCACGAGATCTCCGTCCTCTGCGACGCCGAGGTCGCC
GTCATCGTCTTCTCCCCCAAGGGCAAGCTCTACGAGTACGCCTCCGACTCCCGCATGGACAAAATT
CTAGAACGTTATGAGCGATATTCCTATGCTGAAAAGGCTCTTATTTCAGCTGAATCTGAAAGTGAG
GGAAATTGGTGCCACGAATACAGGAAACTGAAGGCCAAAATTGAGACCATACAAAGATGCCACAAG
CACCTGATGGGAGAGGATCTAGAGTCTTTGAATCCAAAAGAGCTCCAACAACTAGAGCAGCAGCTG
GAGAGCTCACTGAAGCACATCAGATCAAGAAAGAGCCACCTTATGGCCGAGTCAATTTCTGAGCTA
CAGAAGAAGGAGAGGGTCACTGCAGGAGGAGAACAAGATTCTACAGAAGGAACTTTCAGAGAGGCAG
AAGGCGGTCGCTAGCCGGCAGCAGCAGCAGCAGCAGGTGCAGTGGGACCAGCAGACACAGGTCCAG
GTCCAGACAAGCTCATCGTCTTCTTCCTTCATGATGAGGCAGGATCAGCAGGGACTGCCACCTCCA
CAAAACATCTGCTTCCCGCCGTTGAGCATCGGAGAGAGAGGCGAAGAGGTGGCTGCGGCGGCGCAG
CAGCAGCTGCCTCCTCCGGGGCAGGCGCAACCACAGCTCCGCATCGCAGGTCTGCCGCCATGGATG
CTGAGCCACCTCAATGCATAA

SEQ ID NO: 147, AAG43200 MADS box protein 3 [Zea mays]
MGRGKVQLKRIENKINRQVTFSKRRNGLLKKAHEISVLCDAEVAVIVFSPKGKLYEYASDSRMDKI
LERYERYSYAEKALISAESESEGNWCHEYRKLKAKIETIQRCHKHLMGEDLESLNPKELQQLEQQL
ESSLKHIRSRKSHLMAESISELQKKERSLQEENKILQKELSERQKAVASRQQQQQQVQWDQQTQVQ
VQTSSSSSSFMMRDQQGLPPPQNICFPPLSIGERGEEVAAAAQQQLPPPGQAQPQLRIAGLPPWM
LSHLNA

SEQ ID NO: 148, Sorghum bicolor putative MADS box protein (SbMADS2) mRNA, partial cds
GCAAGGTGCAGCTCAAGCGGATAGAGAACAAGATAAACCGGCAGGTGACCTTCTCCAAGCGCCGCA
ACGGGCTGCTCAAGAAGGCGCACGAGATCTCCGTCCTCTGCGACGCCGAGGTCGCCGTCATCGTCT
TCTCCCCCAAGGGCAAGCTCTATGAGTACGCCACCGACTCCCGCATGGACAAAATTCTCGAACGTT
ATGAGCGATATTCCTATGCTGAAAAGGCTCTTATTTCAGCTGAATCTGAAAGTGAGGGAAACTGGT
GCCACGAATACAGGAAACTGAAGGCCAAAATTGAGACCATTCAAAAATGCCACAAGCACCTGATGG
GAGAGGATCTAGAGTCTTTGAATCCAAAAGAGCTCCAACAACTAGAGCAGCAGCTGGAGAGCTCAC
TGAAGCACATCAGATCAAGAAAGAGCCACCTTATGGCTGAGTCTATTTCTGAACTACAGAAGAAGG
AGAGGTCACTGCAGGAGGAGAACAAGGCTCTACAGAAGGAACTTGCGGAGAGGCAGAAGGCGGCCG
CGAGCAGGCAGCAGCAGCAAGGTGCAGTGGGACCAGCAGACACAGACCCAGGCCCAGACAAGCTCA
TCATCGTCCTCCTTCATGATGAGGCAGGATCAGCAGGGTCTGCCGCCTCCACAAAACATATGCTTC
CCGCCGCTGATAATCGGAGAGAGAGGTGA FIGURE 11 (continued)

SEQ ID NO: 149, AAB50181 MADS box protein
KVQLKRIENKINRQVTFSKRRNGLLKKAHEISVLCDAEVAVIVFSPKGKLYEYATDSRMDKILERY
ERYSYAEKALISAESESEGNWCHEYRKLKAKIETIQKCHKHLMGEDLESLNPKELQQLEQQLESSL
KHIRSRKSHLMAESISELQKKERSLQEENKALQKELAERQKAAASRQQQQGAVGPADTDPGPDKLI
IVLLHDEAGSAGSAASTKHMLPAADNRRER

SEQ ID NO: 150, Zea mays MADS-box protein (ZAP1) mRNA, complete cds
ATGGGGCGCGGCAAGGTACAGCTGAAGCGGATAGAGAACAAGATAAACCGGCAGGTGACCTTCTCC
AAGCGCCGGAACGGCCTGCTCAAGAAGGCGCACGAGATCTCCGTCCTCTGCGATGCCGAGGTCGCC
GTCATCGTCTTCTCCCCAAGGGCAAGCTCTACGAGTACGCCACCGACTCCCGCATGGACAAAATT
CTTGAACGCTATGAGCGATATTCCTATGCTGAAAAGGCTCTTATTTCAGCTGAATCTGAAAGTGAG
GGAAATTGGTGCCACGAATACAGGAAACTGAAGGCCAAAATTGAGACCATACAAAAATGCCACAAG
CACCTGATGGGAGAGGATCTAGAGTCTTTGAATCCCAAAGAGCTCCAGCAACTAGAGCAGCAGCTG
GATAGCTCACTGAAGCACATCAGATCAAGGAAGAGCCACCTTATGGCCGAGTCTATTTCTGAGCTA
CAGAAGAAGGAGAGGTCACTGCAGGAGGAGAACAAGGCTCTGCAGAAGGAACTTGCGGAGAGGCAG
AAGGCCGTCGCGAGCCGGCAGCAGCAGCAACAGCAGCAGGTGCAGTGGGACCAGCAGACACATGCC
CAGGCCCAGACAAGCTCATCATCGTCCTCCTTCATGATGAGGCAGGATCAGCAGGGACTGCCGCCT
CCACACAACATCTGCTTCCCGCCGTTGACAATGGGAGATAGAGGTGAAGAGCTGGCTGCGGCGGCG
GCGGCGCAGCAGCAGCAGCCACTGCCGGGGCAGGCGCAACCGCAGCTCCGCATCGCAGGTCTGCCA
CCATGGATGCTGAGCCACCTCAATGCATAA

SEQ ID NO: 151, AAB00081 Zea mays MADS box protein
MGRGKVQLKRIENKINRQVTFSKRRNGLLKKAHEISVLCDAEVAVIVFSPKGKLYEYATDSRMDKI
LERYERYSYAEKALISAESESEGNWCHEYRKLKAKIETIQKCHKHLMGEDLESLNPKELQQLEQQL
DSSLKHIRSRKSHLMAESISELQKKERSLQEENKALQKELAERQKAVASRQQQQQQQVQWDQQTHA
QAQTSSSSSSFMMRQDQQGLPPPHNICFPPLTMGDRGEELAAAAAAQQQQPLPGQAQPQLRIAGLP
PWMLSHLNA

SEQ ID NO: 152, Lolium temulentum MADS-box protein 2 (MADS2) mRNA, alternatively spliced product, complete cds
ATGGGTCGCGGCAAGGTGCAGCTGAAGCGGATAGAGAACAAGATAAACCGTCAGGTGACATTCTCC
AAGCGCCGCAACGGGCTACTCAAGAAGGCGCACGAGATCTCCGTCCTCTGCGACGCCGAGGTCGCC
GTCGTCGTCTTCTCCCCGAAAGGGAAGCTCTATGAGTACGCCACTGACTCCAGCATGGACAAAATT
CTTGAACGTTATGAACGCTACTCTTATGCTGAAAAGGCTTTGATTTCAGCTGAATCTGAAAGTGAG
GGAAATTGGTGCCATGAATACAGGAAGCTGAAGGCGAAGATTGAGACTATACAAAAATGTCACAAG
CACCTCATGGGGGAGGATCTGGAGTGTCTAAACCTGAAAGAGCTCCAACAACTAGAGCAGCAGCTG
GAGAGTTCATTGAAGCACATCAGATCGAGAAAGAGCCACCTTATGATGGAGTCCATTTCTGAGCTA
CAGAAGAAGGAGCGGTCACTCCAGGAGGAGAACAAGGCTCTACAGAAGGAACTGGTGGAGAGGCAG
AAGGCGGCCAGGCAGCAGCAGCAAGAGCAGTGGGACCGTCAGACCCAAACACAACAAGCCCAAAAC
CAACCTCAGGCCCAGACGAGCTCATCATCTTCCTCCTTCATGATGAGGGATCAGCAGGCCCATGCT
CAACAAAACATCTGTTACCCGCTGGTGACAATGGGTGGAGAGGCTGTGGCCGCGGCGCCAGGGCAG
CAGGGGCAGCTTCGCATCGGAGGCCTGCCACCATGGATGCTGAGCCACCTCAACGCTTGA

SEQ ID NO: 153, AAD10626 MADS-box protein 2 [Lolium temulentum]
MGRGKVQLKRIENKINRQVTFSKRRNGLLKKAHEISVLCDAEVAVVVFSPKGKLYEYATDSSMDKI
LERYERYSYAEKALISAESESEGNWCHEYRKLKAKIETIQKCHKHLMGEDLECLNLKELQQLEQQL
ESSLKHIRSRKSHLMMESISELQKKERSLQEENKALQKELVERQKAARQQQQEQWDRQTQTQQAQN
QPQAQTSSSSSFMMRDQQAHAQQNICYPLVTMGGEAVAAAPGQQGQLRIGGLPPWMLSHLNA

FIGURE 11 (continued)

SEQ ID NO: 154, Lolium perenne MADS2 mRNA, complete cds
ATGGGTCGCGGCAAGGTGCAGCTGAAGCGGATAGAGAACAAGATAAACCGTCAGGTGACCTTCTCC
AAGCGCCGCAACGGGCTACTCAAGAAGGCGCACGAGATCTCCGTCCTCTGCGACGCCGAGGTCGCC
GTCGTCGTCTTCTCCCCGAAAGGGAAGCTCTATGAGTACGCCACTGACTCCAGCATGGACAAAATT
CTTGAACGTTATGAACGCTACTCTTATGCTGAAAAGGCTTTGATTTCAGCTGAATCTGAAAGTGAG
GGAAATTGGTGCCATGAATACAGGAAACTGAAGGCGAAGATTGAGACTATACAAAAATGTCACAAG
CACCTCATGGGGGAGGATCTGGAGTGTCTAAACCTGAAAGAGCTCCAACAACTAGAGCAGCAGCTG
GAGAGTTCATTGAAGCACATCAGATCGAGAAAGAGCCACCTTATGATGGAGTCCATTTCTGAGCTA
CAGAAGAAGGAGCGGTCACTCCAGGAGGAGAACAAGGCTCTACAGAAGGAACTGGTGGAGAGGCAG
AAGGCGGCCAGGCAGCAGCAGCAAGAGCAGTGGGACCGTCAGACCCAAACACAACAAGCCCAAAAC
CAACCTCAGGCCCAGACGAGCTCATCATCTTCCTCCTTCATGATGAGGGATCAGCAGGCCCATGCT
CAACAAAACATCTGTTACCCGCCGGTGACAATGGGTGGAGAGGCTGTGGCCGCGGCGCCAGGGCAG
CAGGGGCAGCTTCGCATCGGAGGCCTGCCACCATGGATGCTGAGCCACCTCAACGCTTGA

SEQ ID NO: 155, AAO45874 MADS2 [Lolium perenne]
MGRGKVQLKRIENKINRQVTFSKRRNGLLKKAHEISVLCDAEVAVVVFSPKGKLYEYATDSSMDKI
LERYERYSYAEKALISAESESEGNWCHEYRKLKAKIETIQKCHKHLMGEDLECLNLKELQQLEQQL
ESSLKHIRSRKSHLMMESISELQKKERSLQEENKALQKELVERQKAARQQQEQWDRQTQTQQAQN
QPQAQTSSSSSFMMRDQQAHAQQNICYPPVTMGGEAVAAAPGQQGQLRIGGLPPWMLSHLNA

SEQ ID NO: 156, Hordeum vulgare mRNA for MADS-box protein 8 (m8 gene)
ATGGGTCGCGGTAAGGTGCAGCTGAAGCGGATAGAGAACAAGATAAATCGGCAGGTGACCTTCTCC
AAGCGCCGCAACGGGCTCCTGAAGAAGGCGCACGAGATCTCCGTCCTCTGTGACGCAGAGGTCGCC
GTCATCGTCTTCTCCCCCAAAGGCAAGCTCTATGAGTACGCCACCGACTCCAGCATGGACAAAATT
CTTGAACGTTATGAGCGCTACTCTTATGCTGAAAAGGCTCTTATTTCAGCTGAATCTGAAAGTGAG
GGGAATTGGTGTCATGAATACAGGAAACTTAAGGCGAAGATTGAGACCATACAGAAGTGTCACAAG
CACCTCATGGGAGAGGATCTGGATTCTCTGAACCTCAAAGAACTCCAACAACTGGAGCAGCAGCTG
GAGAGTTCATTGAAGCACATCAGATCGAGAAAGAGCCATCTTATGATGGAGTCCATTTCTGAGCTA
CAGAAGAAGGAGAGGTCACTGCAGGAGGAGAACAAGGCCCTACAGAAGGAACTGGTGGAGAGGCAG
AAGGCGGCCAGCAGGCAGCAGCAGCTGCAGCAGCAGCAACAACAACAAATGCAATGGGAGCAC
CAAGCCCAGACCCAAACCCATACCCATACTCAAAACCAGCCCCAAGCCCAGACTAGCTCATCATCT
TCCTCTTTCATGATGAGGGATCAGCAGGCCCATGCCCCTCAACAGAACATTTGTAGCTACCCACCG
GTGACGATGGGTGGGGAGGCGACGGCGGCGGCGGCGCCGGAGCAGCAGGCTCAGCTTCGCATA
TGCCTACCGCCATGGATGCTGAGCCACCTCAACGCTTGA

SEQ ID NO: 157, CAB97354 MADS-box protein 8 [Hordeum vulgare subsp. vulgare]
MGRGKVQLKRIENKINRQVTFSKRRNGLLKKAHEISVLCDAEVAVIVFSPKGKLYEYATDSSMDKI
LERYERYSYAEKALISAESESEGNWCHEYRKLKAKIETIQKCHKHLMGEDLDSLNLKELQQLEQQL
ESSLKHIRSRKSHLMMESISELQKKERSLQEENKALQKELVERQKAASRQQQLQQQQQQQMQWEH
QAQTQTHTHTQNQPQAQTSSSSSSFMMRDQQAHAPQQNICSYPPVTMGGEATAAAAAPEQQAQLRI
CLPPWMLSHLNA

SEQ ID NO: 158, Oryza sativa MADS-box protein FDRMADS3 mRNA, complete cds
ATGGGGCGGGGAAGGTGCAGCTGAAGCGGATAGAGAACTCGATGAACCGGCAGGTGACGTTCTCC
AAGAGGAGGAATGGATTGCTGAAGAAGGCGCACGAGATCTCCGTCCTCTGCGACGCCGAGGTCGCC
GCCATCGTCTTCTCCCCCAAGGGCAAGCTCTACGAGTACGCCACTGACTCCAGGATGGACAAAATC

FIGURE 11 (continued)

```
CTTGAACGTTATGAGCGCTATTCATATGCTGAAAAGGCTCTTATTTCAGCTGAATCTGAGAGTGAG
GGAAATTGGTGCCATGAATACAGGAAGCTTAAGGCAAAGATTGAGACCATACAAAAATGTCACAAA
CACCTCATGGGAGAGGATCTAGAATCCCTGAATCTCAAAGAACTCCAACAGCTAGAGCAGCAGCTG
GAGAGTTCATTGAAGCACATAAGATCAAGAAAGAGCCACCTTATGCTTGAGTCCATTTCCGAGCTG
CAGAAAAGGAGAGGTCACTGCAGGAGGAGAACAAGGCTCTGCAGAAGGAACTGGTGGAGAGGCAG
AAGAATGTGAGGGCCAGCAGCAAGTAGGGCAGTGGGACCAAACCCAGGTCCAGGCCCAGGCCCAA
GCCCAACCCCAAGCCCAGACAAGCTTCTTCTTCTTCTTCATGCTGAGGGATCAGCAGGCACTTCTT
TCACCACAAAATATCTGCTACCCGCCGGTGATGATGGGCCAGAGAAATGATGCGGCGGCGCGGCGG
CGGTGGCGGCCCAAGGCCAGGTGCAACTTCCGCATTGGAGGCTTTCCGCCATGGATGCTGAGCACC
TTCAAGGCTTAA
```

SEQ ID NO: 159, AAL09473 MADS-box protein FDRMADS3 [Oryza sativa]
```
MGRGKVQLKRIENSMNRQVTFSKRRNGLLKKAHEISVLCDAEVAAIVFSPKGKLYEYATDSRMDKI
LERYERYSYAEKALISAESESEGNWCHEYRKLKAKIETIQKCHKHLMGEDLESLNLKELQQLEQQL
ESSLKHIRSRKSHLMLESISELQKKERSLQEENKALQKELVERQKNVRGQQQVGQWDQTQVQAQAQ
AQPQAQTSFFFFFMLRDQQALLSPQNICYPPVMMGQRNDAAARRRWRPKARCNFRIGGFPPWMLST
FKA
```

SEQ ID NO: 160, Oryza sativa MADS15 protein mRNA, complete cds
```
ATGGGGCGGGGAAGGTGCAGCTGAAGCGGATAGAGAACAAGATCAACAGGCAGGTGACGTTCTCC
AAGAGGAGGAATGGATTGCTGAAGAAGGCGCACGAGATCTCCGTCCTCTGCGACGCCGAGGTCGCC
GCCATCGTCTTCTCCCCCAAGGGCAAGCTCTACGAGTACGCCACTGACTCCAGGATGGACAAAATC
CTTGAACGTTATGAGCGCTATTCATATGCTGAAAAGGCTCTTATTTCAGCTGAATCCGAGAGTGAG
GGAAATTGGTGCCATGAATACAGGAAACTTAAGGCAAAGATTGAGACCATACAAAAATGTCACAAA
CACCTCATGGGAGAGGATCATGAATCCCTGAATCTCAAAGAACTCCAACAGCTAGAGCAGCAGCTG
GAGAGTTCATTGAAGCACATAATATCAAGAAAGAGCCACCTTATGCTTGAGTCCATTTCCGAGCTG
CAGAAAAGGAGAGGTCACTGCAGGAGGAGAACAAGGCTCTGCAGAAGGAACTGGTGGAGAGGCAG
AAGAATGTGAGGGCCAGCAGCAAGTAGGGCAGTGGGACCAAACCCAGGTCCAGGCCCAGGCCCAA
GCCCAACCCCAAGCCCAGACAAGCTCCTCCTCCTCCATGCTGAGGGATCAGCAGGCACTTCTT
CCACCACAAAATATCTGCTACCCGCCGGTGATGATGGGCGAGAGAAATGATGCGGCGGCGGCGGCG
GCGGTGGCGGCGCAGGGCCAGGTGCAACTCCGCATCGGAGGTCTTCCGCCATGGATGCTGAGCCAC
CTCAATGCTTAA
```

SEQ ID NO: 161, AAF19048 MADS15 protein [Oryza sativa]
```
MGRGKVQLKRIENKINRQVTFSKRRNGLLKKAHEISVLCDAEVAAIVFSPKGKLYEYATDSRMDKI
LERYERYSYAEKALISAESESEGNWCHEYRKLKAKIETIQKCHKHLMGEDHESLNLKELQQLEQQL
ESSLKHIISRKSHLMLESISELQKKERSLQEENKALQKELVERQKNVRGQQQVGQWDQTQVQAQAQ
AQPQAQTSSSSSSMLRDQQALLPPQNICYPPVMMGRNDAAAAAVAAQGQVQLRIGGLPPWMLSH
LNA
```

SEQ ID NO: 162, Tradescantia virginiana FRUITFULL-like MADS-box (TvFL2) mRNA, partial cds
```
GGGCTGGTGAAGAAGGCTCATGAGATCTCDATKYTRTGTGATGCYGAGGTTGCGCTTATTATTTTC
TCTACTAAAGGCAAACTATACGAGTATGCCACTGATTCCAAAATGGAAATATCCTTGAACGCTAT
GAACGTTACTCATATGCTGAGAAGGCTTTAACTTCATCAGATCCTGAATTACAGGGAAATTGGTGC
CAAGAGTATGTTAAACTTAAGGCTAAGGTTGAGGCCTTACATAAAGCCAAAGGCATCTTATGGGA
GAGCAACTAGAAGCGTTGGATCTCAAAGAATTGCAGCAACTAGAGCATCAACTTGAAGGTTCTTTG
AGGCTTGTCAGGTCAAGAAAGACTCAAATGATGTTGGACTCCATTTCCGAACTTCAGAGGAAGGAA
```

FIGURE 11 (continued)

```
AAGTCTCTGGAAGAGCAAAACAAGAACCTAGAGAAGGAGATTTTGGAGAAGCAGAAAGAAAAGGCT
CTGGCACACCAAGCTCACTGGGAACAGCAGAATCAGCCACTACAAAGCACTAATTCGCCTCCAAGG
CCCTTCGTGATTGCAGAAACTCATCCAACACTAAACATTGGAAATTTCCAAGGTAGAACAAATACC
GTCCATGCAGAAGAAAGTCTGCAGCGTCAGATGAGGATCAGCAGCAGCCTACTGCCMYCMTGGATG
MTTCACMA
```

SEQ ID NO: 163, AAP83415 FRUITFULL-like MADS-box [Tradescantia virginiana]
```
GLVKKAHEISXLCDAEVALIIFSTKGKLYEYATDSKMENILERYERYSYAEKALTSSDPELQGNWC
QEYVKLKAKVEALHKSQRHLMGEQLEALDLKELQQLEHQLEGSLRLVRSRKTQMMLDSISELQRKE
KSLEEQNKNLEKEILEKQKEKALAHQAHWEQQNQPLQSTNSPPRPFVIAETHPTLNIGNFQGRTNT
VHAEESLQRQMRISSSLLPXWMXH
```

SEQ ID NO: 164, AY306190 Tradescantia virginiana FRUITFULL-like MADS-box (TvFL1) mRNA, partial cds
```
GTGCAGCTGAAACGGATGGAGAACAAGATTAACAGGCAGGTGACGTTTTCTAAACGTCGAGGAGGG
CTGCTGAAGAAAGCTCATGAGATCTCTATTCTATGTGATGCTGAGATTGCTCTTATTATTTTCTCT
ACTAAAGGGAAGCTCTATGAGTATGCCACCAATTCCAAAATGGACAATATTCTTGAACGCTATGAG
CGTTACTCATATGCTGAAAAGGCTCTAACTTCATCAGATCCTGATATACAGGGAAATTGGTGCCAA
GAGTATGCTAAACTTAAGTCTAAGGTTGAGGCTTTATGTAAAAGCCAAAGGCATCTTATGGGAGAG
CAGCTTGAAACATTGAATCTCAAAGAATTGCAGCAACTAGAGCAACAGCTCGAAGGTTCTCTAAAG
CATGTCAGGTCAAGAAAGACTCAAGTTATGCTGGACTCTATTTCTGAACTTCAGGAGGAAGGAAAG
TCACTAGAGGAGCAAAACAAGAACCTAGAGAAGGAGATTTTGGAGAAGCAGAAAATCAAGGCTCTT
GCACAGCAGGCTCACTGGGAACACCAGAATCAACCAGCACCAAGGGGTTCACCTCCTAGGCCATTT
GTGATTGCAGAGTCTCATCCGACACTAAATATTGGACATTTCCAAGGCAGGACAAATGCAGTCGAA
GCAGAAGAAAATCAGCAGCCTCAKATGAGAATTTGCAGTAGCCTCCTGCCCCCCTGGATGCTT
```

SEQ ID NO: 165, AAP83414 FRUITFULL-like MADS-box [Tradescantia virginiana]
```
VQLKRMENKINRQVTFSKRRGGLLKKAHEISILCDAEIALIIFSTKGKLYEYATNSKMDNILERYE
RYSYAEKALTSSDPDIQGNWCQEYAKLKSKVEALCKSQRHLMGEQLETLNLKELQQLEQQLEGSLK
HVRSRKTQVMLDSISELQRKEKSLEEQNKNLEKEILEKQKIKALAQQAHWEHQNQPAPRGSPPRPF
VIAESHPTLNIGHFQGRTNAVEAEENQQPXMRICSSLLPPWML
```

SEQ ID NO: 166, AY306192 Tradescantia virginiana FRUITFULL-like MADS-box (TvFL3) mRNA, partial cds
```
GGGCTKGTGAAGAAAGCTCATGAGATCTCGGTACTTTGTGATGCTGAGCTTGCTCTTATTATCTTC
TCTCCCAAAGGCAAGCTCTATGAGTATGCCACCGATTCCAAAATGGAAATTATTCTTGAACGCTAT
GAACGTTACACCTACGCTGAAAAAGCTTTAATTGCATCAGATCCTGATGTACAGGGAAACTGGTGT
CATGAGTACATTAAGCTTAAAGCTAAATTTGAGGCCTTGAATAAAAGCCAGAGGCATCTTATGGGA
GAACAACTAGATACGTTGAACCAAAAGGAATTGCTGCAACTAGAGACTAAGCTTGAAGGTTCTCTG
AAAAACGTCAGGTCAAGAAAGACTCAACTTATGTTGGATTCCATTTCTGAGCTTCAAGAAAAGGGA
AAGTCACTCCAGGAGCAAAACACCTGCCTAGAAAAGGAGATTTGGGAAAACAGAAAGACAAGGCT
CCCAAACAGCATGTTCAGTGGGAAAAACAGAATCAACCACCACCTACCTCTTCTGCGCCAATGCCA
TTCCTCATTGGTGATATTCACCCAACCCCTAATATCAGAAATTTCCAAGGCAGAACAGTAGCTGAT
GCAGA
```

FIGURE 11 (continued)

SEQ ID NO: 167, AAP83416 FRUITFULL-like MADS-box [Tradescantia virginiana]
GLVKKAHEISVLCDAELALIIFSPKGKLYEYATDSKMEIILERYERYTYAEKALIASDPDVQGNWC
HEYIKLKAKFEALNKSQRHLMGEQLDTLNQKELLQLETKLEGSLKNVRSRKTQLMLDSISELQEKG
KSLQEQNTCLEKEILGKQKDKAPKQHVQWEKQNQPPPTSSAPMPFLIGDIHPTPNIRNFQGRTVAD
A

SEQ ID NO: 168, Elaeis guineensis MADS box transcription factor (SQUA1) mRNA, complete cds
ATGGGGAGAGGGAGGGTGCAGCTGAGGCGGATCGAGAACAAGATAAACCGGCAGGTGACGTTCTCG
AAGCGCCGGTCGGGGCTCCTGAAGAAAGCCCACGAGATCTCCGTCCTCTGCGACGCCGAGGTCGCC
CTCATCATCTTCTCGACCAAGGGCAAGCTCTACGAGTACGCCACCGACTCCTGCATGGAAAGGATT
CTTGAACGCTATGAACGTTACACCTATGCAGAAAAAGCACTAATTTCATCTGGACCCGAATTGCAG
GGTAACTGGTGCCATGAATTTGGCAAACTCAAAGCTAAGGTTGAGGCTTTACAAAAAAGCCAAAGG
CATCTCATGGGTGAGCAACTTGAGCCCTTGAATCTCAAAGAACTCCAGCAACTAGAGCAACAGCTT
GAAAGTTCTTTAAAGCATATAAGAACCAGAAAGTGCCAACTCATGTTTGAATCCATCTCTGAGCTT
CAAAAAAGGAAAAGTCACTGCAGGAGCAGAACAAGATGCTGGAGAAGGAGCTCATGGAGAAGCAG
AAGGTGAAGGCACTAAACCAGCAGGCACCTTGGGAGCAGCAAGGCCCGCCGCAGACAAGCTCATCA
TCCCCAACCTCCTTCCTGATCGGAGACTCTCTCCCCACCCTGAATATTGGGACATACCAATGTAGC
GGAAATGAACATGGGGAGGAAGCAGCACAACCCCAGGTTCGTATAGGAAACAGCCTGTTACCACCT
TGGATGCTTAGCCACTTGAACGGGTAG

SEQ ID NO: 169, AAQ03221 MADS box transcription factor [Elaeis guineensis]
MGRGRVQLRRIENKINRQVTFSKRRSGLLKKAHEISVLCDAEVALIIFSTKGKLYEYATDSCMERI
LERYERYTYAEKALISSGPELQGNWCHEFGKLKAKVEALQKSQRHLMGEQLEPLNLKELQQLEQQL
ESSLKHIRTRKCQLMFESISELQKKEKSLQEQNKMLEKELMEKQKVKALNQQAPWEQQGPPQTSSS
SPTSFLIGDSLPTLNIGTYQCSGNEHGEEAAQPQVRIGNSLLPPWMLSHLNG

SEQ ID NO: 170, Allium sp. AL-2003 FRUITFULL-like MADS-box (AlFL) mRNA, partial cds
GTGCAATTGAAGAGGATGGAAAACAAGATTAATAGACAAGTGACCTTCTCAAAAAGAAGAAATGGT
TTGTTGAAGAAAGCTCATGAGATTTCWGTGCTTTGTGATGCAGAAGTTGCACTTATTGTTTTCTCT
GCTAAAGGAAAACTCTATGAATATTCAACTGATTCAAGTATGGAAAAAATTCTGGAGAGGTATGAA
CGTTATTGCTTTGCGGAGAAATCATCAACAATGAGTGACATTGACTCCCAGGAGGATTGGAGCCTT
GAATATCACAAACTGAAGGCTAAGGTTGAGAGTTTAAACAACAGGCAAAGGCATCTTATGGGAGAG
CAACTTGAATCTCTGAGTCTTCGAGAAATTGGACAGCTTGAGCAACAACTTGAGAATTCTCTCAAA
ACTGTTCGGACGCGCAAGAGCCAAGAATTGTTAAGTTCTATTTCAGAGCTTCAGGACAAGGAGAAA
ACTTTGCGAGATGAGAACAAAGCTTTAGAAAATGAGCTTATGAAAAGGGCCAGGGCAAAAGCTATT
CTGGAACAACAAGCACGATGGAAGCATCATAATCATAAACAACAGGATAATCTTCATAATCCAAAT
ATCAACATTGGAAATTACCAAACAAGGAACAATGAGGGAGGAGTTGAGCCAGCAACGGATGTTCAA
GTACGTGTTGTTAGAAATTTGTTGCCCCACTGGATGCTT

SEQ ID NO: 171, AAP83362 FRUITFULL-like MADS-box [Allium sp. AL-2003]
VQLKRMENKINRQVTFSKRRNGLLKKAHEISVLCDAEVALIVFSAKGKLYEYSTDSSMEKILERYE
RYCFAEKSSTMSDIDSQEDWSLEYHKLKAKVESLNNRQRHLMGEQLESLSLREIGQLEQQLENSLK
TVRTRKSQELLSSISELQDKEKTLRDENKALENELMKRARAKAILEQQARWKHHNHKQQDNLHNPN
INIGNYQTRNNEGGVEPATDVQVRVVRNLLPHWML

FIGURE 11 (continued)

SEQ ID NO: 172, Dendrobium grex Madame Thong-IN MADS box protein DOMADS2 mRNA, complete cds
ATGGGTCGTGGCAGGGTGCAGCTGAAGCGAATCGAGAATAAAATAAACCGGCAGGTGACGTTCTCG
AAGCGGAGATCTGGTTTGCTTAAGAAGGCGCACGAGATCTCCGTGCTCTGTGACGCTGAAGTTGCT
CTGATCGTTTTTTCCAATAAGGGAAAGCTTTATGAGTATTCCACCGATTCCAGCATGGAGAAAATT
CTTGAACGGTATGAGCGTTATTCATATGCTGAAAGAGCATTATTTTCCAATGAGGCCAACCCCCAG
GCTGATTGGCGCCTTGAATATAATAAACTGAAGGCAAGGGTTGAAAGCTTACAGAAGAGCCAAAGG
CACCTTATGGGGAGCAACTTGACTCCTTGAGCATTAAAGAACTCCAACGTCTAGAGCAACAGCTT
GAAAGTTCCTTGAAGTTTATACGATCCAGAAAGACACAGCTCATACTACATTCAATTTCCGAGCTA
CAAAAGATGGAAAAAATATTGCTGGAGCAAAACAAGACCTTAGAGAAGGAGATTATAGCTAAAGAG
AAAGCCAAAGCTTTGGTGCAGCATGCCCCATGGGAGAAGCAAAACCAGTCCCAATATAGCTCTGCA
CTCCCGCCTGTGATTTCGGATTCTGTCCCAACTCCCACCAGCAGAACGTTTCAAGCCAGAGCCAAT
GAAGAAGAATCACCTCAGCCACAGTTAAGAGTAAGCAACACTCTGCTGCCCCCATGGATGCTCAGT
CATATGAATGGACAATAA

SEQ ID NO: 173, AAF13261 MADS box protein DOMADS2 [Dendrobium grex Madame Thong-In]
MGRGRVQLKRIENKINRQVTFSKRRSGLLKKAHEISVLCDAEVALIVFSNKGKLYEYSTDSSMEKI
LERYERYSYAERALFSNEANPQADWRLEYNKLKARVESLQKSQRHLMGEQLDSLSIKELQRLEQQL
ESSLKFIRSRKTQLILHSISELQKMEKILLEQNKTLEKEIIAKEKAKALVQHAPWEKQNQSQYSSA
LPPVISDSVPTPTSRTFQARANEEESPQPQLRVSNTLLPPWMLSHMNGQ

SEQ ID NO: 174, Oryza sativa GOS2 promoter variant
AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAAGAGAGAGATTTTTTTAAAAAAATAGAATGAAGATATTCTGAACGTATTGGCAAAGATTTAAA
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTATTATTTATCTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAAGAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTTCTCCCATCTATAA
ATTCCTCCCCCTTTTCCCCTCTCTATATAGGAGGCATCCAAGCCAAGAAGAGGGAGAGCACCAAG
GACACGCGACTAGCAGAAGCCGAGCGACCGCCTTCTCGATCCATATCTTCCGGTCGAGTTCTTGGT
CGATCTCTTCCCTCCTCCACCTCCTCCTCACAGGGTATGTGCCTCCCTTCGGTTGTTCTTGGATTT
ATTGTTCTAGGTTGTGTAGTACGGGCGTTGATGTTAGGAAAGGGGATCTGTATCTGTGATGATTCC
TGTTCTTGGATTTGGGATAGAGGGGTTCTTGATGTTGCATGTTATCGGTTCGGTTTGATTAGTAGT
ATGGTTTTCAATCGTCTGGAGAGCTCTATGGAAATGAAATGGTTTAGGGATCGGAATCTTGCGATT
TTGTGAGTACCTTTTGTTTGAGGTAAAATCAGAGCACCGGTGATTTGCTTGGTGTAATAAAGTAC
GGTTGTTTGGTCCTCGATTCTGGTAGTGATGCTTCTCGATTTGACGAAGCTATCCTTTGTTTATTC
CCTATTGAACAAAATAATCCAACTTTGAAGACGGTCCCGTTGATGAGATTGAATGATTGATTCTT
AAGCCTGTCCAAAATTTCGCAGCTGGCTTGTTTAGATACAGTAGTCCCCATCACGAAATTCATGGA

```
AACAGTTATAATCCTCAGGAACAGGGGATTCCCTGTTCTTCCGATTTGCTTTAGTCCCAGAATTTT
TTTTCCCAAATATCTTAAAAAGTCACTTTCTGGTTCAGTTCAATGAATTGATTGCTACAAATAATG
CTTTTATAGCGTTATCCTAGCTGTAGTTCAGTTAATAGGTAATACCCCTATAGTTTAGTCAGGAGA
AGAACTTATCCGATTTCTGATCTCCATTTTAATTATATGAAATGAACTGTAGCATAAGCAGTATT
CATTTGGATTATTTTTTTATTAGCTCTCACCCCTTCATTATTCTGAGCTGAAAGTCTGGCATGAA
CTGTCCTCAATTTTGTTTTCAAATTCACATCGATTATCTATGCATTATCCTCTTGTATCTACCTGT
AGAAGTTTCTTTTGGTTATTCCTTGACTGCTTGATTACAGAAAGAAATTTATGAAGCTGTAATCG
GGATAGTTATACTGCTTGTTCTTATGATTCATTTCCTTTGTGCAGTTCTTGGTGTAGCTTGCCACT
TTCACCAGCAAAGTTC
```

FIGURE 11 (continued)

According to Kim *et al.*, (2006), Mol Biol Evol 23(1): 107-120

40 seeds from a control plant 40 seeds from a transgenic plant

SEQ ID NO: 175, Arabidopsis thaliana Arath_PLT1 nucleic acid sequence related to NM 112975
ATGAATTCTAACAACTGGCTTGGCTTTCCTCTTTCACCGAACAACTCTTCTTTGCCTCCTCATGAA
TACAACCTTGGCTTGGTCAGCGACCATATGGACAACCCTTTTCAAACACAAGAGTGGAATATGATC
AATCCACACGGTGGAGGAGGAGATGAAGGAGGAGAGGTTCCAAAAGTGGCCGATTTTCTCGGTGTG
AGCAAACCGGACGAAAACCAATCCAACCACCTAGTGCTTTACAACGACTCAGACTACTACTTCCAT
ACCAATAGCTTGATGCCTAGCGTCCAATCAAACGATGTCGTTGTAGCAGCTTGTGACTCCAATACT
CCTAACAACAGTAGCTATCATGAGCTTCAAGAGAGTGCTCACAATCTACAGTCACTTACTTTGTCC
ATGGGGACCACCGCTGGTAATAATGTTGTAGACAAAGCTTCACCATCCGAGACCACCGGGGATAAC
GCTAGCGGTGGAGCACTAGCCGTTGTTGAGACGGCCACGCCAAGACGTGCATTGGACACTTTCGGA
CAACGAACCTCGATCTATCGTGGTGTCACAAGACATCGATGGACTGGTCGATATGAGGCTCATCTA
TGGGATAATAGTTGTAGAAGGGAAGGCCAGTCTAGGAAAGGAAGACAAGTTTACTTGGGTGGATAT
GATAAAGAAGATAAAGCAGCAAGATCATATGATCTAGCTGCACTTAAGTACTGGGGTCCCTCAACT
ACTACTAATTTCCCCATTACAAACTACGAGAAAGAAGTAGAGGAAATGAAGCACATGACGAGGCAA
GAGTTCGTGGCTGCCATTAGAAGGAAAAGTAGTGGATTTTCGAGAGGCGCTTCGATGTATCGAGGA
GTTACAAGGCACCACCAACATGGAAGATGGCAAGCAAGGATCGGCCGAGTCGCCGGGAACAAAGAC
CTCTACTTGGGAACTTTTAGCACTGAGGAAGAAGCAGCAGAAGCTTACGATATAGCTGCAATAAAG
TTTAGAGGACTTAATGCAGTGACCAACTTCGAGATCAACCGGTACGACGTGAAAGCCATTCTAGAG
AGTAGCACTCTTCCCATCGGAGGAGGCGCAGCTAAACGGCTCAAAGAAGCTCAAGCTCTTGAGTCT
TCAAGGAAACGCGAGGCGGAGATGATAGCCCTTGGTTCAAGTTTCCAGTACGGTGGTGGCTCGAGC
ACAGGCTCTGGCTCCACCTCATCAAGACTTCAGCTTCAACCTTACCCTCTAAGCATTCAACAACCA
TTAGAGCCTTTTCTATCTCTTCAGAACAATGACATCTCTCATTACAACAACAACAATGCTCACGAT
TCCTCCTCTTTTAATCACCATAGCTATATCCAGACACAACTTCATCTCCACCAACAGACCAACAAT
TACTTGCAGCAACAGTCGAGCCAGAACTCTCAGCAGCTCTACAATGCGTATCTTCATAGCAATCCG
GCTCTGCTTCATGGACTTGTCTCTACCTCTATCGTTGACAACAATAATAACAATGGAGGCTCTAGT
GGGAGCTACAACACTGCAGCATTTCTTGGGAACCACGGTATTGGTATTGGGTCCAGCTCGACTGTT
GGATCGACCGAGGAGTTTCCAACCGTTAAAACAGATTACGATATGCCTTCCAGTGATGGAACCGGA
GGGTATAGTGGTTGGACCAGTGAGTCTGTTCAGGGGTCAAACCCTGGTGGTGTTTTCACTATGTGG
AATGAGTAA SEQ ID NO: 176, Arabidopsis thaliana Arath_PLT1 deduced polypeptide
MNSNNWLGFPLSPNNSSLPPHEYNLGLVSDHMDNPFQTQEWNMINPHGGGDEGGEVPKVADFLGV
SKPDENQSNHLVAYNDSDYYFHTNSLMPSVQSNDVVVAACDSNTPNNSSYHELQESAHNLQSLTLS
MGTTAGNNVVDKASPSETTGDNASGGALAVVETATPRRALDTFGQRTSIYRGVTRHRWTGRYEAHL
WDNSCRREGQSRKGRQVYLGGYDKEDKAARSYDLAALKYWGPSTTTNFPITNYEKEVEEMKHMTRQ
EFVAAIRRKSSGFSRGASMYRGVTRHHQHGRWQARIGRVAGNKDLYLGTFSTEEEAAEAYDIAAIK
FRGLNAVTNFEINRYDVKAILESSTLPIGGGAAKRLKEAQALESSRKREAEMIALGSSFQYGGGSS
TGSGSTSSRLQLQPYPLSIQQPLEPFLSLQNNDISHYNNNNAHDSSSFNHHSYIQTQLHLHQQTNN
YLQQQSSQNSQQLYNAYLHSNPALLHGLVSTSIVDNNNNNGGSSGSYNTAAFLGNHGIGIGSSSTV
GSTEEFPTVKTDYDMPSSDGTGGYSGWTSESVQGSNPGGVFTMWNE SEQ ID NO: 177, Arabidopsis thaliana Arath_PLT2 nucleic acid sequence related to NM_103997
ATGAATTCTAACAACTGGCTCGCGTTCCCTCTATCACCAACTCACTCTTCTTTGCCGCCTCACATT
CACTCTTCACAAAATTCTCATTTCAATCTAGGTTTGGTCAACGACAATATCGACAACCCTTTTCAA
AACCAAGGATGGAATATGATCAATCCACATGGTGGAGGCGGCGAAGGTGGAGAGGTTCCAAAAGTG
GCTGATTTCTTAGGAGTGAGCAAATCGGGGGATCATCACACCGATCACAACCTCGTACCTTATAAC
GACATTCATCAAACCAACGCCTCCGACTACTACTTTCAAACCAATAGCTTGTTACCTACAGTCGTC

FIGURE 17

```
ACTTGTGCCTCTAATGCTCCTAATAATTATGAGCTTCAAGAGAGTGCACACAATTTGCAATCTCTC
ACTCTCTCTATGGGAAGTACTGGAGCTGCCGCTGCAGAAGTCGCCACTGTGAAAGCCTCGCCGGCT
GAGACTAGTGCCGATAATAGTAGCAGCACTACCAACACAAGCGGAGGAGCCATCGTTGAGGCTACA
CCGAGACGGACTTTGGAAACTTTTGGACAACGAACCTCTATCTATCGTGGAGTTACAAGACATAGA
TGGACCGGTAGATATGAAGCTCATCTTTGGGATAATAGCTGTAGAAGAGAAGGACAATCAAGGAAA
GGAAGACAAGTCTACTTAGGTGGGTATGACAAAGAAGAGAAAGCAGCCAGAGCATATGATCTAGCT
GCACTTAAATATTGGGGTCCCTCTACTACTACCAACTTTCCGATAACTAACTACGAAGGAAGTA
GAGGAGATGAAAAACATGACGAGACAAGAGTTTGTGGCTTCTATAAGAAGGAAGAGTAGCGGATTC
TCGCGTGGTGCATCCATGTATCGTGGAGTAACAAGGCATCATCAACATGGAAGATGGCAAGCAAGG
ATCGGCCGAGTTGCTGGAAACAAAGATCTCTACTTGGGAACATTCAGCACGGAGGAAGAAGCAGCA
GAAGCTTATGACATAGCTGCGATAAAGTTTCGAGGTCTAAACGCGGTTACAAACTTTGAGATAAAT
CGGTATGATGTGAAAGCCATCCTGGAGAGCAACACACTTCCTATAGGAGGTGGTGCGGCTAAACGG
CTCAAAGAAGCTCAAGCTCTAGAATCATCAAGAAAACGAGAGGAAATGATAGCCCTCGGATCAAAT
TTCCATCAATATGGTGCAGCGAGCGGCTCGAGCTCTGTTGCTTCCAGCTCTAGGCTTCAGCTTCAA
CCTTACCCTCTAAGCATTCAACAACCTTTTGAGCATCTTCATCATCATCAGCCTTTACTTACTCTA
CAGAACAACAACGATATCTCTCAGTATCATGATTCCTTTAGTTACATTCAGACGCAGCTTCATCTT
CACCAACAACAAACCAACAATTACTTGCAGTCTTCTAGTCACACTTCACAGCTCTACAATGCTTAT
CTTCAGAGTAACCCTGGTCTGCTTCATGGATTTGTCTCTGATAATAACAACACTTCAGGGTTTCTT
GGAAACAATGGGATTGGTATTGGGTCAAGCTCTACCGTTGGATCATCGGCTGAGGAAGAGTTTCCA
GCCGTGAAAGTCGATTACGATATGCCTCCTTCCGGTGGAGCTACAGGGTATGGAGGATGGAATAGT
GGAGAGTCTGCTCAAGGATCGAATCCAGGAGGTGTTTTCACGATGTGGAATGAATAA
```

SEQ ID NO: 178, Arabidopsis thaliana Arath_PLT2 deduced polypeptide sequence

```
MNSNNWLAFPLSPTHSSLPPHIHSSQNSHFNLGLVNDNIDNPFQNQGWNMINPHGGGGEGGEVPKV
ADFLGVSKSGDHHTDHNLVPYNDIHQTNASDYYFQTNSLLPTVVTCASNAPNNYELQESAHNLQSL
TLSMGSTGAAAAEVATVKASPAETSADNSSSTTNTSGGAIVEATPRRTLETFGQRTSIYRGVTRHR
WTGRYEAHLWDNSCRREGQSRKGRQVYLGGYDKEEKAARAYDLAALKYWGPSTTTNFPITNYEKEV
EEMKNMTRQEFVASIRRKSSGFSRGASMYRGVTRHHQHGRWQARIGRVAGNKDLYLGTFSTEEEAA
EAYDIAAIKFRGLNAVTNFEINRYDVKAILESNTLPIGGGAAKRLKEAQALESSRKREEMIALGSN
FHQYGAASGSSSVASSSRLQLQPYPLSIQQPFEHLHHHQPLLTLQNNNDISQYHDSFSYIQTQLHL
HQQQTNNYLQSSSHTSQLYNAYLQSNPGLLHGFVSDNNNTSGFLGNNGIGIGSSSTVGSSAEEEFP
AVKVDYDMPPSGGATGYGGWNSGESAQGSNPGGVFTMWNE
```

SEQ ID NO: 179, Glycine max Glyma_PLT nucleic acid sequence compiled from EST's BU964973.1, CA783156.1, BM309051.1, BM309377.1

```
ATGAACAACAACTGGCTTTCGTTCCCTCTTTCTCCTACTCATTCTTCCTTACCAGCTCATGATCTT
CAAGCAACTCAATATCATCAATTTTCCCTTGGGTTAGTGAACGAGAACATGGATAACCCTTTCCAA
AATCATGATTGGAATCTGATTAACACCCATAGTAGCAACGAAATTCCAAAAGTGGCTGATTTCTA
GGAGTCACCAACTCTGAAAATCAGTCAGACCTTGCAGCCTTAAACGAATTCATTCAAATGATTCA
GATTATCTGTTCACAAACAACAGTCTGGTGCCTATGCAAAACCCTGTGTTGGACACACCTAGCAAT
GAGTATCAAGAAATGCTAATAGTAATTTGCAATCATTGACATTATCCATGGGAAGTGGTAAGGAT
TCAACATGTGAAACCAGTGGTGAAAATAGCACAAACACTACTGTTGAAGTTGCACCTAGAAGAACT
TTGGATACATTCGGGCAGAGAACATCCATATATCGTGGAGTAACTCGACATAGATGGACTGGAAGG
TATGAAGCTCATCTTTGGGATAATAGCTGTAGAAGGGAAGGCCAATCAAGAAAAGGACGCCAAGTT
TATTTGGGTGGATATGATAAAGAAGAGAAAGCAGCTAGAGCTTATGATTTAGCTGCACTGAAGTAC
TGGGGGACATCCACCACTACCAACTTTCCAATTAGCAACTATGAGAAGGAATTGGATGAAATGAAA
CACATGACGAGACAAGAATTTGTTGCCGCCATTAGAAGGAAAGCAGTGGTTTCTCCAGGGGTGCA
```

FIGURE 17 (continued)

```
TCAATGTATCGTGGAGTTACAAGGCATCACCAACACGGAAGATGGCAAGCAAGGATTGGCAGAGTT
GCAGGAAACAAAGATCTTTACTTGGGAACTTTCAGTACTGAGGAAGAGGCTGCAGAAGCATACGAC
ATAGCAGCGATAAAGTTCAGAGGTCTCAACGCTGTCACAAACTTTGACATGAGCCGCTACGACGTG
AAAGCCATTCTTGAAAGCAACACTCTCCCAATAGGAGGAGGCGCTGCAAAGCGTCTGAAAGAAGCT
CAAGCTCTAGAATCTTCGAGAAAACGCGAAGAGATGATTGCACTAGGCTCATCTTCCACGTTCCAA
TACGGAACCTCAGCAAGCTCTTCTAGGCTTCACGCTTACCCTCTAATGCAGCACCACCACCAGTTC
GAGCAACCTCAACCTCTGCTAACTCTTCAAAACCACGACATAAGTTCTTCTCACTTCTCTCACCAG
CAAGACCCTTTGCATCATCAGGGTTACATCCAAACGCAGCTTCAGTTGCACCAGCAGAGTGGCGCT
TCTTCTTATAGCTTTCAGAATAATGCTCAGTTCTACAATGGTTACCTTCAGAACCACCCTGCATTG
CTTCAGGGAATGATGAACATGGGGTCTTCTTCTTCCTCATCTGTGTTGGAGAATAATAATAGT
AACAATAATAATAATGTTGGTGGGTTTGTGGGAAGTGGGTTTGGTATGGCTTCGAATGCAACG
GCGGGGAACACGGTGGGGACAGCGGAGGAGTTAGGGCTGGTGAAGGTGGACTATGACATGCCGGCT
GGAGGTTACGGTGGCTGGTCGGCGGCGGACTCCATGCAGACGTCAAATGGTGGGGTGTTCACAATG
TGGAATGATTAA

SEQ ID NO: 180, Glycine max Glyma_PLT deduced polypeptide sequence
MNNNWLSFPLSPTHSSLPAHDLQATQYHQFSLGLVNENMDNPFQNHDWNLINTHSSNEIPKVADFL
GVSKSENQSDLAALNEIHSNDSDYLFTNNSLVPMQNPVLDTPSNEYQENANSNLQSLTLSMGSGKD
STCETSGENSTNTTVEVAPRRTLDTFGQRTSIYRGVTRHRWTGRYEAHLWDNSCRREGQSRKGRQV
YLGGYDKEEKAARAYDLAALKYWGTSTTTNFPISNYEKELDEMKHMTRQEFVAAIRRKSSGFSRGA
SMYRGVTRHHQHGRWQARIGRVAGNKDLYLGTFSTEEEAAEAYDIAAIKFRGLNAVTNFDMSRYDV
KAILESNTLPIGGGAAKRLKEAQALESSRKREEMIALGSSSTFQYGTSASSSRLHAYPLMQHHHQF
EQPQPLLTLQNHDISSSHFSHQQDPLHHQGYIQTQLQLHQQSGASSYSFQNNAQFYNGYLQNHPAL
LQGMMNMGSSSSSSSVLENNNSNNNNNNVGGFVGSGFGMASNATAGNTVGTAEELGLVKVDYDMPA
GGYGGWSAADSMQTSNGGVFTMWND SEQ ID NO: 181, Glycine max Glyma_PLT2 nucleic acid sequence
compiled from EST's BU926204.1, BU547204.1, CA783156.1, BU927164.1
ATGAACAACAACTGGCTTTCGTTCCCTCTTTCTCCTACTCATTCTTCCTTACCAGCTCATGATCTT
CAAGCAACTCAATATCATCAATTTTCCCTTGGGTTAGTGAACGAGAACATGGATAACCCTTTCCAA
AATCATGATTGGAATCTGATTAACACCCATAGTAGCAACGAAATTCCAAAAGTGGCTGATTTTCTA
GGAGTGAGCAAGTCTGAAAATCAGTCAGACCTTGCAGCCTTAAACGAATTCATTCAAATGATTCA
GATTATCTGTTCACAAACAACAGTCTGGTGCCTATGCAAAACCCTGTGTTGGACACACCTAGCAAT
GAGTATCAAGAAAATGCTAATAGTAATTTGCAATCATTGACATTATCCATGGGAAGTGGTAAGGAT
TCAACATGTGAAACCAGTGGTGAAAATAGCACAAACACTACTGTTGAAGTTGCACCTAGAAGAACT
TTGGATACATTCGGGCAGAGAACATCCATATATCGTGGAGTAACTCGACATAGATGGACTGGAAGG
TATGAAGCTCATCTTTGGGATAATAGCTGTAGAAGGGAAGGCCAATCAAGAAAAGGACGCCAAGTT
TATTTGGGTGGATATGATAAGAAGAGAAAGCAGCTAGGGCTTATGATTTAGCTGCACTGAAGTAC
TGGGGGACATCCACCACTACCAACTTTCCAATTAGTAACTATGAGAAGGAATTGGATGAAATGAAA
CACATGACGCGACAAGAATTTGTTGCTGCCATTAGAAGGAAAAGCAGTGGTTTCTCCAGGGGTGCA
TCAATGTATCGTGGAGTTACAAGGCATCACCAACACGGAAGATGGCAAGCAAGAATTGGCAGAGTT
GCAGGAAACAAAGATCTTTACTTGGGAACTTTCAGTACTGAAGAAGAGGCTGCTGAAGCATACGAC
ATAGCTGCGATAAAGTTCAGAGGTCTCAACCCTGTCACAAACTTTGACATCAGCCCGCTACGACGTG
AAAGCCATCCTTGAAAGCAACACTCTCCCAATAGGAGGAGGAGCTGCAAAGCGTCTGAAAGAAGCT
CAAGCTCTAGAATCTTCGAGAAAGCGCGAAGAGATGATTGCACTAGGATCATCCACATTCCAATAT
GGAACCACAAGCTCTAATTCTAGGCTACATGCTTACCCTCTAATGCAGCACCACCACCAGTTTGAA
CAACCTCAACCTCTGCTAACTTTGCAAAACCATGATATCAGTTCTCACTTCTCTCACCAGCAAGAC
CCTTTGCATCAGGGTTACATCCAAACGCAGCTTCAGTTGCACCAGCAGCAGAGTGGTGGTTCTTCT
```

```
TCTTATAGCTTTCAGAATAATAATATAAATAATGCTCAGTTCTATAATGGTTATAATCTTCAGAAC
CACCCTGCATTGCTTCAGGGAATGATTAACATGGGGTCTTCATCTTCTTCATCTGTGTTGGAGAAT
AATAATAGTACCAATAATAATGTTGGTGGGTTTGTGGGAAGTGGGTTTGGTATGGCTTCTAATGCA
ACGTCGGGGAACACGGTGGGGACGGCGGAGGAGCTAGGGCTGGTGAAGGTGGACTATGACATGCCG
ACTGGTGGTTACGGTGGATGGTCGGCGGCGGCGGCGGCGGAGTCCATGCAGACGTCGAATAGTGGG
GTGTTCACAATGTGGAATGACTGA
```

SEQ ID NO: 182, Glycine max Glyma_PLT2 deduced polypeptide sequence
```
MNNNWLSFPLSPTHSSLPAHDLQATQYHQFSLGLVNENMDNPFQNHDWNLINTHSSNEIPKVADFL
GVSKSENQSDLAALNEIHSNDSDYLFTNNSLVPMQNPVLDTPSNEYQENANSNLQSLTLSMGSGKD
STCETSGENSTNTTVEVAPRRTLDTFGQRTSIYRGVTRHRWTGRYEAHLWDNSCRREGQSRKGRQV
YLGGYDKEEKAARAYDLAALKYWGTSTTTNFPISNYEKELDEMKHMTRQEFVAAIRRKSSGFSRGA
SMYRGVTRHHQHGRWQARIGRVAGNKDLYLGTFSTEEEAAEAYDIAAIKFRGLNAVTNFDMSRYDV
KAILESNTLPIGGGAAKRLKEAQALESSRKREEMIALGSSTFQYGTTSSNSRLHAYPLMQHHHQFE
QPQPLLTLQNHDISSHFSHQQDPLHQGYIQTQLQLHQQQSGGSSSYSFQNNNINNAQFYNGYNLQN
HPALLQGMINMGSSSSSSVLENNNSTNNNVGGFVGSGFGMASNATSGNTVGTAEELGLVKVDYDMP
TGGYGGWSAAAAAESMQTSNSGVFTMWND
```

SEQ ID NO: 183, Medicago truncatula Medtr_PLT nucleic acid sequence AC144930.20
```
ATGAACAATAACTGGCTTTCATTCCCTCTCTCACCTTCTCATTCTTCCTTACCTTCTAATGATCTT
CAAGCAACTCAATATCATCACTTTCCTCTTGGATTAGTCAATGACAACATGGAAAACCCTTTCCAA
AATCATGATTGGAATCTGATGAACACACACAACAGCAATGAAGTTCCAAAGGTTGCGGATTTTCTC
GGTGTATGCAAGTCTGAAAATCACTCAGATCTTGCTACACCGAACGAAATTCAATCTAATGATTCA
GATTATCTGTTTACAAATAACAATACTCTCATGCCAATGCAAAACCAAATGGTTACAACATGCACC
AATGAGTATCAAGAAAAGGCTAGTAATAGTAATTTGCAGTCTTTGACATTATCCATGGGAAGTGGT
AAAGATTCAACATGTGAAACTAGTGGTGAAAATAGTACAAACACTGTTGAAGTTGCTGTTCCTAAA
AGAACTTCAGAGACATTTGGACAAAGAACTTCGATATATCGCGGTGTAACAAAACATAGATGGACT
GGAAGGTATGAAGCTCACCTTTGGGATAACAGCTGTAGAAGGGAAGGTCAGTCGAGAAAAGGCCGC
CAAGGTGGATATGATAAAGAAGAGAAAGCTGCTAGGTCTTATGATTTAGCTGCACTTAAGTACTGG
GGGACATCCACCACTACCAACTTTCCAGTTAGCAACTATGAGAAGGAAATAGATGAAATGAAGCAC
ATGACAAGACAAGAATTTGTTGCCTCTATTAGAAGGAAAAGCAGCGGTTTCTCTAGGGGTGCATCA
ATGTACCGTGGAGTTACAAGGCATCACCAACATGGAAGATGGCAAGCAAGGATTGGCAGAGTTGCA
GGAAATAAAGATCTATACTTGGGAACTTTCAGCACTGAAGAAGAGGCTGCAGAAGCATACGACATA
GCAGCAATAAAATTCAGAGGACTCAACGCTGTAACAAACTTTGACATGACTCGTTACGACGTGAAA
GCCATTCTCGAAAGCAACACACTGCCAATTGGAGGAGGAGCTGCAAAAAGACTAAAAGAAGCACAA
GCTCTAGAAACTTCGAGAAAACGCGAAGAAATGCTTGCACTTAACTCATCATCTTTCCAATATGGA
ACATCAAGCTCTAGTAACACTAGACTCCAACCCTACCCTCTCATGCAATATCATCACCAATTTGAA
CAACCTCAACCATTGCTAACATTACAAAACAACCATGAAAGCTTGAATTCTCAACAATTCTCTCAA
CACCAAGGTGGTGGTTATTTCCAAACACAGCTTGAGTTGTGTCAACAACAAAACCAACAACCATCT
CAGAATAGTAACATAGGTTCATTCTACAATGGTTATTATCAGAATCATCCTGGTTTGTTTCAGATG
AATAATATAGGATCTTCTTCTTCATCTTCGGTGATGGGAAATAATGGTGGTGGTTCTAGTGGGATT
TATAGTAATAGTGGAGGGTTAATTAGTAATAATGCTGTTGAGGAATTTGTGCCGGTTAAGGTTGAT
TATGACATGCAAGGTGATGGAAGTGGTTTTGGCGGCTGGTCGGCGGCAGGAGAGAACATGCAGACT
GCTGATTTGTTTACAATGTGGAATGACTATGAGACAAGAGAGAATTAG
```

FIGURE 17 (continued)

SEQ ID NO: 184, Medicago truncatula Medtr_PLT deduced polypeptide sequence
MNNNWLSFPLSPTHSSLPAHDLQATQYHQFSLGLVNENMDNPFQNHDWNLINTHSSNEIPKVADFL
GVSKSENQSDLAALNEIHSNDSDYLFTNNSLVPMQNPVLDTPSNEYQENANSNLQSLTLSMGSGKD
STCETSGENSTNTTVEVAPRRTLDTFGQRTSIYRGVTRHRWTGRYEAHLWDNSCRREGQSRKGRQV
YLGGYDKEEKAARAYDLAALKYWGTSTTTNFPISNYEKELDEMKHMTRQEFVAAIRRKSSGFSRGA
SMYRGVTRHHQHGRWQARIGRVAGNKDLYLGTFSTEEEAAEAYDIAAIKFRGLNAVTNFDMSRYDV
KAILESNTLPIGGGAAKRLKEAQALESSRKREEMIALGSSTFQYGTTSSNSRLHAYPLMQHHHQFE
QPQPLLTLQNHDISSHFSHQQDPLHQGYIQTQLQLHQQQSGGSSSYSFQNNNINNAQFYNGYNLQN
HPALLQGMINMGSSSSSVLENNNSTNNNVGGFVGSGFGMASNATSGNTVGTAEELGLVKVDYDMP
TGGYGGWSAAAAAESMQTSNSGVFTMWND SEQ ID NO: 185, Oryza sativa Orysa_PLT nucleic acid sequence NM_190301
ATGGCCACCATGAACAACTGGCTGGCCTTCTCCCTCTCCCCGCAGGATCAGCTCCCGCCGTCTCAG
ACCAACTCCACTCTCATCTCCGCCGCCGCCACCACCACCACCGCCGGCGACTCCTCCACCGGCGAC
GTCTGCTTCAACATCCCCCAAGATTGGAGCATGAGGGGATCGGAGCTCTCGGCGCTCGTCGCCGAG
CCGAAGCTGGAGGACTTCCTCGGCGGCATCTCCTTCTCGGAGCAGCAGCATCATCACGGCGGCAAG
GGCGGCGTGATCCCGAGCAGCGCCGCCGCTTGCTACGCGAGCTCCGGCAGCAGCGTCGGCTACCTG
TACCCTCCTCCAAGCTCATCCTCGCTCCAGTTCGCCGACTCCGTCATGGTGGCCACCTCCTCGCCC
GTCGTCGCCCACGACGGCGTCAGCGGCGGCGGCATGGTGAGCGCCGCCGCCGCCGCGGCGGCCAGT
GGCAACGGCGGCATTGGCCTGTCCATGATCAAGAACTGGCTCCGGAGCCAGCCGGCGCCGCAGCCG
GCGCAGGCGCTGTCTCTGTCCATGAACATGGCGGGGACGACGACGGCGCAGGGCGGCGGCGCCATG
GCGCTCCTCGCCGGCGCAGGGGAGCGAGGCCGGACGACGCCCGCGTCAGAGAGCCTGTCCACGTCG
GCGCACGGAGCGACGACGGCGACGATGGCTGGTGGTCGCAAGGAGATTAACGAGGAAGGCAGCGGC
AGCGCCGGCGCCGTGGTTGCCGTCGGCTCGGAGTCAGGCGGCAGCGGCGCCGTGGTGGAGGCCGGC
GCGGCGGCGGCGGCGGCGAGGAAGTCCGTCGACACGTTCGGCCAGAGAACATCGATCTACCGCGGC
GTGACAAGGCATAGATGGACAGGGAGGTATGAGGCTCATCTTTGGGACAACAGCTGCAGAAGAGAG
GGCCAAACTCGCAAGGGTCGTCAAGGTGGTTATGACAAAGAGGAAAAAGCTGCTAGAGCTTATGAT
TTGGCTGCTCTCAAATACTGGGGCCCGACGACGACGACAAATTTTCCGGTAAATAACTATGAAAAG
GAGCTGGAGGAGATGAAGCACATGACAAGGCAGGAGTTCGTAGCCTCTTTGAGAAGGAAGAGCAGT
GGTTTCTCCAGAGGTGCATCCATTTACCGTGGAGTAACTAGGCATCACCAGCATGGGAGATGGCAA
GCAAGGATAGGAAGAGTTGCAGGGAACAAGGACCTCTACTTGGGCACCTTCAGCACGCAGGAGGAG
GCGGCGGAGGCGTACGACATCGCGGCGATCAAGTTCCGGGGGCTCAACGCCGTCACCAACTTCGAC
ATGAGCCGCTACGACGTCAAGAGCATCCTCGACAGCGCTGCCCTCCCCGTCGGCACCGCCGCCAAG
CGCCTCAAGGACGCCGAGGCCGCCGCCGCCTACGACGTCGGCCGCATCGCCTCGCACCTCGGCGGC
GACGGCGCCTACGCCGCGCATTACGGCCACCACCACCACTCGGCCGCCGCCGCCTGGCCGACCATC
GCGTTCCAGGCGGCGGCGGCGCCGCCGCCGCACGCCGCCGGGCTTTACCACCCGTACGCGCAGCCG
CTGCGTGGGTGGTGCAAGCAGGAGCAGGACCACGCCGTGATCGCGGCGGCGCACAGCCTGCAGGAT
CTCCACCACCTCAACCTCGGCGCCGCCGCCGCCGCGCATGACTTCTTCTCGCAGGCGATGCAGCAG
CAGCACGGCCTCGGCAGCATCGACAACGCGTCGCTCGAGCACAGCACCGGCTCCAACTCCGTCGTC
TACAACGGCGACAATGGCGGCGGAGGCGGCGGCTACATCATGGCGCCGATGAGCGCCGTGTCGGCC
ACGGCCACCGCGGTGGCGAGCAGCCACGATCACGGCGGCGACGGCGGGAAGCAGGTGCAGATGGGG
TACGACAGCTACCTCGTCGGCGCAGACGCCTACGGCGGCGGCGGCGCCGGGAGGATGCCATCCTGG
GCGATGACGCCGGCGTCGGCGCCGGCCGCCACGAGCAGCAGCGACATGACCGGAGTCTGCCATGGC
GCACAGCTCTTCAGCGTCTGGAACGACACATAA FIGURE 17 (continued)

SEQ ID NO: 186, Oryza sativa Orysa_PLT deduced polypeptide sequence
MATMNNWLAFSLSPQDQLPPSQTNSTLISAAATTTTAGDSSTGDVCFNIPQDWSMRGSELSALVAE
PKLEDFLGGISFSEQQHHHGGKGGVIPSSAAACYASSGSSVGYLYPPPSSSSLQFADSVMVATSSP
VVAHDGVSGGGMVSAAAAAAASGNGGIGLSMIKNWLRSQPAPQPAQALSLSMNMAGTTTAQGGGAM
ALLAGAGERGRTTPASESLSTSAHGATTATMAGGRKEINEEGSGSAGAVVAVGSESGGSGAVVEAG
AAAAAARKSVDTFGQRTSIYRGVTRHRWTGRYEAHLWDNSCRREGQTRKGRQGGYDKEEKAARAYD
LAALKYWGPTTTTNFPVNNYEKELEEMKHMTRQEFVASLRRKSSGFSRGASIYRGVTRHHQHGRWQ
ARIGRVAGNKDLYLGTFSTQEEAAEAYDIAAIKFRGLNAVTNFDMSRYDVKSILDSAALPVGTAAK
RLKDAEAAAAYDVGRIASHLGGDGAYAAHYGHHHHSAAAAWPTIAFQAAAAPPPHAAGLYHPYAQP
LRGWCKQEQDHAVIAAAHSLQDLHHLNLGAAAAAHDFFSQAMQQQHGLGSIDNASLEHSTGSNSVV
YNGDNGGGGGGYIMAPMSAVSATATAVASSHDHGGDGGKQVQMGYDSYLVGADAYGGGGAGRMPSW
AMTPASAPAATSSSDMTGVCHGAQLFSVWNDT

SEQ ID NO: 187, Zea mays Zeama_PLT nucleic acid sequence CS155772.1
ATGGCCACTGTGAACAACTGGCTCGCTTTCTCCCTCTCCCCGCAGGAGCTGCCGCCCTCCCAGACG
ACGGACTCCACACTCATCTCGGCCGCCACCGCCGACCATGTCTCCGGCGATGTCTGCTTCAACATC
CCCCAAGATTGGAGCATGAGGGGATCAGAGCTTTCGGCGCTCGTCGCGGAGCCGAAGCTGGAGGAC
TTCCTCGGCGGCATCTCCTTCTCCGAGCAGCATCACAAGGCCAACTGCAACATGATACCCAGCACT
AGCAGCACAGTTTGCTACGCGAGCTCAGGTGCTAGCACCGGCTACCATCACCAGCTGTACCACCAG
CCCACCAGCTCAGCGCTCCACTTCGCGGACTCCGTAATGGTGGCCTCCTCGGCCGGTGTCCACGAC
GGCGGTGCCATGCTCAGCGCGGCCGCCGCTAACGGTGTCGCTGGCGCTGCCAGTGCCAACGGCGGC
GGCATCGGGCTGTCCATGATTAAGAACTGGCTGCGGAGCCAACCGGCGCCCATGCAGCCGAGGGTG
GCGGCGGCTGAGGGCGCGCAGGGGCTCTCTTTGTCCATGAACATGGCGGGGACGACCCAAGGCGCT
GCTGGCATGCCACTTCTCGCTGGAGAGCGCGCACGGGCGCCCGAGAGTGTATCGACGTCAGCACAG
GGTGGAGCCGTCGTCGTCACGGCGCCGAAGGAGGATAGCGGTGGCAGCGGTGTTGCCGGCGCTCTA
GTAGCCGTGAGCACGGACACGGGTGGCAGCGGCGGCGTCGGCTGACAACACGGCAAGGAAGACG
GTGGACACGTTCGGGCAGCGCACGTCGATTTACCGTGGCGTGACAAGGCATAGATGGACTGGGAGA
TATGAGGCACATCTTTGGGATAACAGTTGCAGAAGGGAAGGGCAAACTCGTAAGGGTCGTCAAGTC
TATTTAGGTGGCTATGATAAAGAGGAGAAAGCTGCTAGGGCTTATGATCTTGCTGCTCTGAAGTAC
TGGGGTGCCACAACAACAACAAATTTTCCAGTGAGTAACTACGAAAAGGAGCTCGAGGACATGAAG
CACATGACAAGGCAGGAGTTTGTAGCGTCTCTGAGAAGGAAGAGCAGTGGTTTCTCCAGAGGTGCA
TCCATTTACAGGGGAGTGACTAGGCATCACCAACATGGAAGATGGCAAGCACGGATTGGACGAGTT
GCAGGGAACAAGGATCTTTACTTGGGCACCTTCAGCACCCAGGAGGAGGCAGCGGAGGCGTACGAC
ATCGCGGCGATCAAGTTCCGCGGCCTCAACGCCGTCACCAACTTCGACATGAGCCGCTACGACGTG
AAGAGCATCCTGGACAGCAGCGCCCTCCCCATCGGCAGCGCCGCCAAGCGCCTCAAGGAGGCCGAG
GCCGCAGCGTCCGCGCAGCACCACCACGCCGGCGTGGTGAGCTACGACGTCGGCCGCATCGCCTCG
CAGCTCGGCGACGGCGGAGCCCTGGCGGCGGCGTACGGCGCGCACTACCACGGCGCCGCCTGGCCG
ACCATCGCGTTCCAGCCGGGCGCCGCCAGCACAGGCCTGTACCACCCGTACGCGCAGCAGCCAATG
CGCGGCGGCGGGTGGTGCAAGCAGGAGCAGGACCACGCGGTGATCGCGGCCGCGCACAGCCTGCAG
GACCTCCACCACCTGAACCTGGGCGCGGCCGGCGCGCACGACTTTTCTCGGCAGGGCAGCAGGCC
GCCGCCCCTGCCGATCCACGGCCTCGGTAGCATCGACACTCCGTCCTCGAGCACAGCACCCGCTCC
AACTCCGTCGTCTACAACGGCGGGGTCGGCGACAGCAACGGCGCCAGCGCCGTCGGCGGCAGTGGC
GGTGGCTACATGATGCCGATGAGCGCTGCCGGAGCAACCACTACATCGGCAATGGTGAGCCACGAG
CAGGTGCATGCACGGGCCTACGACGAAGCCAAGCAGGCTGCTCAGATGGGGTACGAGAGCTACCTG
GTGAACGCGGAGAACAATGGTGGCGGAAGGATGTCTGCATGGGGACTGTCGTGTCTGCAGCCGCG
GCGGCAGCAGCAAGCAGCAACGACAACATGGCCGCCGACGTCGGCCATGGCGGCGCGCAGCTCTTC
ACTGTCTCCAACGACACTTAA FIGURE 17 (continued)

SEQ ID NO: 188, Zea mays Zeama_PLT deduced polypeptide sequence
MATVNNWLAFSLSPQELPPSQTTDSTLISAATADHVSGDVCFNIPQDWSMRGSELSALVAEPKLED
FLGGISFSEQHHKANCNMIPSTSSTVCYASSGASTGYHHQLYHQPTSSALHFADSVMVASSAGVHD
GGAMLSAAAANGVAGAASANGGGIGLSMIKNWLRSQPAPMQPRVAAAEGAQGLSLSMNMAGTTQGA
AGMPLLAGERARAPESVSTSAQGGAVVVTAPKEDSGGSGVAGALVAVSTDTGGSGGASADNTARKT
VDTFGQRTSIYRGVTRHRWTGRYEAHLWDNSCRREGQTRKGRQVYLGGYDKEEKAARAYDLAALKY
WGATTTTNFPVSNYEKELEDMKHMTRQEFVASLRRKSSGFSRGASIYRGVTRHHQHGRWQARIGRV
AGNKDLYLGTFSTQEEAAEAYDIAAIKFRGLNAVTNFDMSRYDVKSILDSSALPIGSAAKRLKEAE
AAASAQHHHAGVVSYDVGRIASQLGDGGALAAAYGAHYGAAWPTIAFQPGAASTGLYHPYAQQPM
RGGGWCKQEQDHAVIAAAHSLQDLHHLNLGAAGAHDFFSAGQQAAAAAMHGLGSIDSASLEHSTGS
NSVVYNGGVGDSNGASAVGGSGGGYMMPMSAAGATTTSAMVSHEQVHARAYDEAKQAAQMGYESYL
VNAENNGGGRMSAWGTVVSAAAAAAASSNDNMAADVGHGGAQLFSVWNDT

SEQ ID NO: 189, Lotus corniculatus Lotco_PLT partial nucleic acid sequence AP007400
AGATCTCTCTCTGCAGTGCACAATCCAGTGGTAAGCACATGTAGTAATGGTAATGAGTCTCAAGAA
AATGGTAATGGTAATTTGCAATCGTTGACATTATCCATGGGAAGTGGTAAGGATTCAACATGTGAA
ACCAGTGGTGACACTAGTACCAACACTATCGAAGCTGTGCCTAGAAGAACCTTGGAGACATTTGGG
CAAAGAACATCTATATATCGAGGTGTAACAAGACATAGATGGACCGGAAGGTATGAAGCTCACCTT
TGGGACAATAGCTGTAGAAGGGAAGGACAGTCAAGGAAAGGTCGCCAAGGTGGATATGATAAAGAA
GACAAAGCAGCTAGGGCCTATGATTTAGCTGCCCTTAAGTACTGGGGACATCCACTACTACCAAC
TTTCCGGTTAGCAACTATGAGAAGGAAGTGGATGACATGAAGCATATGACAAGACAAGAATTTGTG
GCTTCCATTAGAAGGAAAAGCAGTGGTTTCTCGAGGGGTGCTTCAATGTATCGTGGAGTTACAAGG
CATCATCAACATGGGAGGTGGCAAGCAAGGATTGGAAGAGTTGCAGGAAACAAAGATCTTTACTTG
GGAACTTTCGGTACTGAGGAAGAGGCGGCAGAAGCTTACGACATAGCTGCGATAAAGTTCAGAGGC
CTTAACGCCATCACCAACTTTGACATGAACCGTTACGATGTGAAAGCCATTCTAGAGAGCAACACC
CTCCCAATCGGAGGAGGAGCTTCAAAAAGGCTAAAAGAAACTCAAGCTCTGGAATCTTCAAGAAAA
CGTGAAGATCAGATGATTGCACTCGGCTCAACATTTCATCAATACGGAATTGCAACCCCATCAAGC
TCTACAAGGCCACAACCTTACCCGCTAAACCTAATGCATCATCACAATCAGTTTGAACAACAGCCT
CAACCATTTCTAACCTTACAAAACCATGACATTAATTCTCAATACTCCATCATCAGCAGGACCCT
TCGTTTCAGCAGAGTTACATTCAAACACAGCTTCAGTTGCAGTTGAATCAACACGGTGGTGGTGGT
TCTAGTTATGCTCAAGAAACAGCTCCTCATCAGAACAGTGAGTTCTATAATGGTGGAAATTATTAC
CTTCAGAACCTTCAGGGAATGATGATGAACAATAGTATGGGGTCTTGTTCTTCATCGTCTGTGTTG
GAGAATGATCATAATGCTGCTGCTGGTGGGCTTCTTTTGTGGGTCCCGCAGCGGAGGAACTTGGG
TTGGTTAAGGTTGATTATGACATGGATGCTGCTGCTGGCGGTGGTTATGGTGGTTGGTCAGCGGCG
GAGTCCATGCACACGTCGGCGGCTGGTGGTTTGTTTACTATGTGGAATGAGTGA

SEQ ID NO: 190, Lotus corniculatus Lotco_PLT partial deduced polypeptide sequence
RSLSAVHNPVVSTCSNCNESQENCNCNLQSLTLSMCSCKDSTCETSCDTSTNTIEAVPRRTLETFC
QRTSIYRGVTRHRWTGRYEAHLWDNSCRREGQSRKGRQGGYDKEDKAARAYDLAALKYWGTSTTN
FPVSNYEKEVDDMKHMTRQEFVASIRRKSSGFSRGASMYRGVTRHHQHGRWQARIGRVAGNKDLYL
GTFCTEEEAAEAYDIAAIKFRCLNAITNFDMNRYDVKAILESNTLPICGCASKRLKETQALESSRK
REDQMIALGSTFHQYGIATPSSSTRPQPYPLNLMHHHNQFEQQPQPFLTLQNHDINSQYSHHQQDP
SFQQSYIQTQLQLQLNQHGGGGSSYAQETAPHQNSEFYNGGNYYLQNLQGMMMNNSMGSCSSSSVL
ENDHNAAAGGASFVGPAAEELGLVKVDYDMDAAAGGGYGGWSAAESMHTSAAGGLFTMWNE FIGURE 17 (continued)

SEQ ID NO: 191, AP2 domain of Arath_PLT1 and Arath_PLT2
PRR(A/T)L(D/E)TFGQRTSIYRGVTRHRWTGRYEAHLWDNSCRREGQSRKGRQVYLGGYDKE(D
/E)KAAR(S/A)YDLAALKYWGPSTTTNFPITNYEKEVEEMK(H/N)MTRQEFVA(A/S)IRRKSS
GFSRGASMYRGVTRHHQHGRWQARIGRVAGNKDLYLGTFSTEEEAAEAYDIAAIKFRGLNAVTNFE
INRYDVKAILES(S/N)TLPIGGGAAKRLKEA

SEQ ID NO: 192, motif 1
PK(V/L)(A/E)DFLG

SEQ ID NO: 193, motif 2, less degenerated
(V/L)F(T/S)(M/V)WN(D/E)

SEQ ID NO: 194 Oryza sativa Gos2 promoter
AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAAGAGAGAGATTTTTTTAAAAAAATAGAATGAAGATATTCTGAACGTATTGGCAAAGATTTAAA
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTATTATTTATCTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAAGAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTCCTCCCATCTATAA
ATTCCTCCCCCCTTTTCCCCTCTCTATATAGGAGGCATCCAAGCCAAGAAGAGGGAGAGCACCAAG
GACACGCGACTAGCAGAAGCCGAGCGACCGCCTCTTCGATCCATATCTTCCGGTCGAGTTCTTGG
TCGATCTCTTCCCTCCTCCACCTCCTCCTCACAGGGTATGTGCCCTTCGGTTGTTCTTGGATTTAT
TGTTCTAGGTTGTGTAGTACGGGCGTTGATGTTAGGAAAGGGGATCTGTATCTGTGATGATTCCTG
TTCTTGGATTTGGGATAGAGGGGTTCTTGATGTTGCATGTTATCGGTTCGGTTTGATTAGTAGTAT
GGTTTTCAATCGTCTGGAGAGCTCTATGGAAATGAAATGGTTTAGGGTACGGAATCTTGCGATTTT
GTGAGTACCTTTTGTTTGAGGTAAAATCAGAGCACCGGTGATTTTGCTTGGTGTAATAAAAGTACG
GTTGTTTGGTCCTCGATTCTGGTAGTGATGCTTCTCGATTTGACGAAGCTATCCTTTGTTTATTCC
CTATTGAACAAAAATAATCCAACTTTGAAGACGGTCCCGTTGATGAGATTGAATGATTGATTCTTA
AGCCTGTCCAAAATTTCGCAGCTGGCTTGTTTAGATACAGTAGTCCCCATCACGAAATTCATGGAA
ACAGTTATAATCCTCAGGAACAGGGGATTCCCTGTTCTTCCGATTTGCTTAGTCCCAGAATTTTT
TTTCCCAAATATCTTAAAAAGTCACTTTCTGGTTCAGTTCAATGAATTGATTGCTACAAATAATGC
TTTTATAGCGTTATCCTAGCTGTAGTTCAGTTAATAGGTAATACCCCTATAGTTTAGTCAGGAGAA
GAACTTATCCGATTTCTGATCTCCATTTTAATTATATGAAATGAACTGTAGCATAAGCAGTATTC
ATTTGGATTATTTTTTTATTAGCTCTCACCCCTTCATTATTCTGAGCTGAAAGTCTGGCATGAAC
TGTCCTCAATTTTGTTTTCAAATTCACATCGATTATCTATGCATTATCCTCTTGTATCTACCTGTA
GAAGTTTCTTTTTGGTTATTCCTTGACTGCTTGATTACAGAAAGAAATTTATGAAGCTGTAATCGG
GATAGTTATACTGCTTGTTCTTATGATTCATTTCCTTTGTGCAGTTCTTGGTGTAGCTTGCCACTT
TCACCAGCAAAGTTC

FIGURE 17 (continued)

SEQ ID NO: 195, prm08180
GGGGACAAGTTTGTACAAAAAAGCAGGCTTAAACAATGATCAATCCACACGGTG

SEQ ID NO: 196, prm08181
GGGGACCACTTTGTACAAGAAAGCTGGGTTCCTTGTTTACTCATTCCACA

SEQ ID NO: 197, prm08182
GGGGACAAGTTTGTACAAAAAAGCAGGCTTAAACAATGAATTCTAACAACTGGCTC

SEQ ID NO: 198, prm08183
GGGGACCACTTTGTACAAGAAAGCTGGGTTCATCTTTTATTCATTCCACA

SEQ ID NO: 199, Populus tremuloides PLT I nucleic acid sequence
ATGAATTCTAACAACTGGCTTTCATTTCCTCTTTCTCCTACTCATCCTTCCTTGCCTGCTCATCTA
CATGCATCCCACCCTCATCAATTCTCTCTAGGGTTAGTCAATGATAATATGGAAAACCCATTTCAA
ACTCAAGAGTGGAGTCTTCTTAACACTCATCAAGGCAACAATGAAGTGCCAAAGGTTGCAGACTTT
CTTGGTGTGAGCAAATCTGAGAATCAATCAGATCTTGTAGCCTTCAATGAAATTCAAGCTAATGAA
TCTGACTATCTCTTTTCAAACAATAGTCTAGTACCAGTCCAAAATGCTGTTGTAGGCGCCAATAAT
ACCTTTGAGTTTCAAGAAAATGCTAGCAATTTGCAGTCATTAACATTGTCTATGGGCAGTGCTAGT
GGTAAAGGTTCTACATGTGAACCCAGTGGGGATAATAGCACTAATACTGTTGAAGCTGCTGCACCA
AGAAGAACTTTGGATACATTTGGGCAAAGAACATCCATATATCGTGGTGTAACAAGGCATCGATGG
ACAGGAAGGTATGAAGCTCATTTATGGGATAATAGTTGCAGAAGAGAAGGTCAATCTAGGAAAGGA
AGACAGGGTGGCTATGACAAAGAAGAAAAGGCAGCTAGGGCTTATGATCTTGCTGCACTTAAGTAC
TGGGGAACATCCACCACTACCAATTTTCCAATCAGCAACTACGAGAAAGAAATAGAGGAAATGAAG
CACATGACCAGGCAAGAATTTGTGGCCTCCATTAGAAGGAAGAGTAGTGGCTTCTCTAGGGGTGCA
TCCATGTATCGTGGAGTTACAAGGCATCACCAGCATGGTAGATGGCAAGCAAGGATAGGCAGAGTT
GCAGGAAACAAAGATCTCTACTTGGGAACTTTTAGCACTGAGGAGGAGGCTGCAGAAGCTTATGAC
ATAGCAGCAATAAAGTTTAGAGGGCTTAATGCAGTGACTAACTTTGACATGAATCGATATGATGTG
AAGAGCATTCTTGAAAGCAATACTTTGCCAATTGGAGGAGGGGCAGCCAAACGGCTAAAGGAGGCT
CAAGCAATTGAATCATCACGAAAAAGAGAAGAAATGATTGCTCTTGGCTCAAGTTTTCCATATGGA
TCAACTTCAAGCTCTAGCAGGCTACAAGCTTACCCTCTAATGCAGACACCATTTGAGCAACCTCAA
CCTTTACTTACTCTACAAAATCAAGACATTTCTCAGTACACTCAGGATTCCTCATCATTCCACCAA
AATTTCCTTCAAACACAGCTTCATTTGCACCAGCAATCTACAGGGTCTAATTTCCTGCATAACCAA
TCAAACCAAAACCCTCAATATTACAATAGTTATATCCAAAACAATCCAGCTTTACTTCATGGATTG
TGGAACATGGGTTCTTCATCATCTGTAATGGAGAATAATGGAAGTTCTAGTGGGAGCTATAGTACT
GGAGGTTATCTGGGAAATGGGCTGGGAATGGCTTCCAATTCAACAGGGTCTAATGCAGTAGGATCA
GCCGAGGAACTTGCACTTGTCAAAGTTGATTATGATATGCCTTCTAGTGGCTATGGAAGCTGGTCT
GGGGACTCAGTCCAGGGATCCAATCCAGGTGTTTTCACTATGTGGAATGAGTGA

SEQ ID NO: 200, Populus tremuloides PLT I polypeptide sequence
MNSNNWLSFPLSPTHPSLPAHLHASHPHQFSLGLVNDNMENPFQTQEWSLLNTHQGNNEVPKVADF
LGVSKSENQSDLVAFNEIQANESDYLFSNNSLVPVQNAVVGANNTFEFQENASNLQSLTLSMGSAS
GKGSTCEPSGDNSTNTVEAAAPRRTLDTFGQRTSIYRGVTRHRWTGRYEAHLWDNSCRREGQSRKG
RQGGYDKEEKAARAYDLAALKYWGTSTTNFPISNYEKEIEEMKHMTRQEFVASIRRKSSGFSRGA
SMYRGVTRHHQHGRWQARIGRVAGNKDLYLGTFSTEEEAAEAYDIAAIKFRGLNAVTNFDMNRYDV
KSILESNTLPIGGAAKRLKEAQAIESSRKREEMIALCSSFPYGSTSSSSRLQAYPLMQTPFEQPQ
PLLTLQNQDISQYTQDSSFHQNFLQTQLHLHQQSTGSNFLHNQSNQNPQYYNSYIQNNPALLHGL
WNMGSSSSVMENNGSSSGSYSTGGYLGNGLMASNSTGSNAVGSAEELALVKVDYDMPSSGYGSWS
GDSVQGSNPGVFTMWNE

FIGURE 17 (continued)

SEQ ID NO: 201, Populus tremuloides PLT II nucleic acid sequence
ATGTTTTTTTTTTGTTTCCTTTAGAGTGGAGTCTTCTTAACACTCAAGGCAACAATGAAGTGCCA
AAGGTTGCAGATTTTCTTGGTGTAAGTAAATCTGAGAATCAATCAGATCTCGTAGCCTTCAATGAA
ATTCAAGCCAGTGATTCTGAGTATCTCTTTTCAAGCAATAGTCTGTTGCCGGTCCAAAATGCTGTG
GTAGCCGCCAGTACTAACTACGAATTTCAAGAAAATCCTAGCAATTTGCAGTCATTAACATTGTCT
ATGGGCAGTGCTAGTGGTAAGGGTTCTAAATGTGAAACCAGTGGTGATAATAGTACTAATTCTGTC
GAAGCTGCTGCTCCAAGAAGGACTTTGGATACATTTGGTCAAAGAACATCCATCTATCGTGGTGTA
ACAAGGCATCGATGGACAGGAAGGTATGAAGCTCATTTATGGGATAATAGTTGCAGAAGAGAAGGT
CAATCCAGGAAAGGAAGACAAGGTGGCTATGACAAAGAAGACAAGGCTGCTAGGGCTTATGATCTT
GCTGCACTTAAGTACTGGGGAACATCGACCACTACCAATTTTCCTATCAGCAACTATGAGAAAGAA
CTAGAGGACATGAAGAACATGACCAGACAAGAATTTGTGGCCTCCATTAGAAGGAAGAGTAGTGGC
TTCTCTAGGGGTGCATCCATGTATCGTGGAGTCACAAGGCATCACCAACATGGAAGATGGCAAGCA
AGAATTGGTAGAGTTGCAGGAAACAAAGATCTCTACTTGGGAACTTTTAGCACTGAGGAGGAGGCT
GCAGAAGCTTATGACATAGCAGCAATAAAGTTTAGAGGGCTTAATGCAGTGACTAATTTTGACATG
AATCGATATGATGTGAAAAGCATTCTTGAGAGCAATAGTTTGCCAATTGGAGGAGGGGCAGCCAAA
AGGCTAAAGGAGGCTCAAGCAATCGAATCGTCACAAAAACGAGAAGAAATGATTGCTCTTGGATCA
AGTTATCCATATGGATCAACTTCAAGCTCTAGTCGACAACAAGCTTACTCTCTAATGCAGAAACCA
TTTGAGCAACCTCAACCTTTACTTACTCTACAAAATCAAGACATTTCTCAGTACACTCAAGATTCT
TCATTTCAGCAAAATTACCTTCAAACACAGCTTCATTTGCACCAGCTATCTGCAGGGTCTAATTTC
CTGCATAATAACCAATCAAGCCAAAATCCTCAGTATTACAACAGCTATATCCAAAACAATCCCACT
TTGCTTCATGGATTGTGGAACATGGGTTCTTCATCATCTCTAATGGAGAATAATGGCAGTTCTAGT
GGGAGTTATAGTACTGTCGGTTATCTGGGAAATGGGTTGGGAATGGCTACCAATTCAACAGGGTCT
AATGCAGTAGCTGAGGAACTTCCACTTGTTAAGATAGATTATGATATGCCTTCTGGTGGCTATGGA
AGTTGGTCTGGGGAATCAGTTCAGGGATCCAACCCAGGTGTTTTTACAATGTGGAATGAGTGA

SEQ ID NO: 202, Populus tremuloides PLT II polypeptide sequence
MFFFLFPLEWSLLNTQGNNEVPKVADFLGVSKSENQSDLVAFNEIQASDSEYLFSSNSLLPVQNAV
VAASTNYEFQENPSNLQSLTLSMGSASGKGSKCETSGDNSTNSVEAAAPRRTLDTFGQRTSIYRGV
TRHRWTGRYEAHLWDNSCRREGQSRKGRQGGYDKEDKAARAYDLAALKYWGTSTTTNFPISNYEKE
LEDMKNMTRQEFVASIRRKSSGFSRGASMYRGVTRHHQHGRWQARIGRVAGNKDLYLGTFSTEEEA
AEAYDIAAIKFRGLNAVTNFDMNRYDVKSILESNSLPIGGGAAKRLKEAQAIESSQKREEMIALGS
SYPYGSTSSSSRQQAYSLMQKPFEQPQPLLTLQNQDISQYTQDSSFQQNYLQTQLHLHQLSAGSNF
LHNNQSSQNPQYYNSYIQNNPTLLHGLWNMGSSSSLMENNGSSSGSYSTVGYLGNGLGMATNSTGS
NAVAEELPLVKIDYDMPSGGYGSWSGESVQGSNPGVFTMWNE

SEQ ID NO: 203, Vitis vinifera PLT partial nucleic acid sequence
TCTTGATAAATCCCAAAACTGACTGTGTAGGTACTGAGGAGGAAGCTGCAGAAGCCTATGATATTG
CAGCAATAAAGTTCAGAGGCCTTAATGCAGTGACCAACTTTGACATGAATCGATACGATGTGAAGA
GCATTCTTGAAAGCAACACTCTTCCGATAGGTGGGGAGCGGCCAAGCGGCTAAAGGAGGCTCAAG
CAATTGAATCATCAAGAAAACGGGAAGAAATGATAGCCCTAGGTTCAAGTTTCCAATATGGGAGCT
CGAGCTCTAGCAGGTTACAGACATATCCTCTAATGCAGCAGCAGTTTGAGCAACCTCAGCCTTTAC
TAACATTACAGAACCAAGAACCATTACTAACTTTGCAAAACCCTGAAATTTCTCAGTACCCCCAAG
ACTCCCAGTTTCACCAAAACTACATCCAAACTCAGTTGCAGTTGCACCAGCAATCTGGGTCGTACC
TGAACCATTCAAGCCAAAGTCCTCAGTTCTACAACAGTTACCTCCACAACAACCCGGCTCTTCTTC
ATGGGCTGATGAGTATGGCTCTTCTTCATCTGTCATGGAGAATAATGGGAGTTCTAGTGGGAGTT
ACAATGGAGGMTACTTCAATAATGGACTTGGGGTTGCTTCGAATTCTACGGTGGCTAGTGCAGTAG
GATCAGCAGAGGAGCTTCCCCTCATCAAGGTTGATTACGATATGCCGGCCGCAGGCTATGGCAGCT
GGTCAGGTGACTCAGTTCAGGGACAGAATGCTGGAGTTTTTACAATGTGGAATGACTGA FIGURE 17 (continued)

SEQ ID NO: 204, Vitis vinifera PLT partial translated polypeptide sequence
LINPKTDCVGTEEEAAEAYDIAAIKFRGLNAVTNFDMNRYDVKSILESNTLPIGGGAAKRLKEAQA
IESSRKREEMIALGSSFQYGSSSSSRLQTYPLMQQQFEQPQPLLTLQNQEPLLTLQNPEISQYPQD
SQFHQNYIQTQLQLHQQSGSYLNHSSQSPQFYNSYLHNNPALLHGLMSMGSSSSVMENNGSSSGSY
NGGYFNNGLGVASNSTVASAVGSAEELPLIKVDYDMPAAGYGSWSGDSVQGQNAGVFTMWND

SEQ ID NO: 205, Brassica napus PLT partial nucleic acid sequence
GGAACATCGGCCGAGGAAGAGTTTCCCACGGTTAAAGTTGATTACGATATGCCTCCTTTAGGTGGA
GCCACAGGGTGTGAACGATGGACTAATGGAGAGAATGGTCAGGGGTCAAATCCAGGAGGTGTCTTC
ACAATGTGGAATGAATAA

SEQ ID NO: 206, Brassica napus PLT partial translated polypeptide sequence
GTSAEEEFPTVKVDYDMPPLGGATGCERWTNGENGQGSNPGGVFTMWNE

SEQ ID NO: 207, Phaseolus coccineus PLT partial nucleic acid sequence
TCGAATGCATCGTCGGGTAATGCGGTGGGCACGGCGGAGGAACTTGGATTGGTGAAAGTTGACTAT
GACATGCCGGCCGGAGGTTACGGTGGTTGGTCGGCGGCGGCGGCGGAATCCATGCAGACGTCAAAT
GGTGGGGTGTTCACAATGTGGAATGAGTGA

SEQ ID NO: 208, Phaseolus coccineus PLT partial translated polypeptide sequence
SNASSGNAVGTAEELGLVKVDYDMPAGGYGGWSAAAAESMQTSNGGVFTMWNE

SEQ ID NO: 209, Motif 2
(V/L)FX(M/V)WN(D/E)

SEQ ID NO: 210, variant GOS2 promoter
AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATCG
AGGTAGCCATAATTGTCATCAAACTCTTCTTGAATAAAAAAATCTTTCTAGCTGAACTCAATGGGT
AAAGAGAGAGATTTTTTTTAAAAAAATAGAATGAAGATATTCTGAACGTATTGGCAAAGATTTAAA
CATATAATTATATAATTTATAGTTTGTGCATTCGTCATATCGCACATCATTAAGGACATGTCTTA
CTCCATCCCAATTTTTATTTAGTAATTAAAGACAATTGACTTATTTTATTATTTATCTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAAGAATT
TTCCTCGTCCGCGACCGCCAATCTCCCATATTGGGCACACAGCCAACAACAGAGTCGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTTCTCCCATCTATAA
ATTCCTCCCCCCTTTTCCCCTCTCTATATAGGAGGCATCCAAGCCAAGAAGAGGGAGAGCACCAAG
GACACGCGACTAGCAGAAGCCGAGCGACCGCCTTCTCGATCCATATCTTCCGGTCGAGTTCTTGGT
CGATCTCTTCCCTCCTCCACCTCCTCCTCACAGGGTATGTGCCTCCCTTCGGTTGTTCTTGGATTT

FIGURE 17 (continued)

```
ATTGTTCTAGGTTGTGTAGTACGGGCGTTGATGTTAGGAAAGGGGATCTGTATCTGTGATGATTCC
TGTTCTTGGATTTGGGATAGAGGGGTTCTTGATGTTGCATGTTATCGGTTCGGTTTGATTAGTAGT
ATGGTTTTCAATCGTCTGGAGAGCTCTATGGAAATGAAATGGTTTAGGGATCGGAATCTTGCGATT
TTGTGAGTACCTTTTGTTTGAGGTAAAATCAGAGCACCGGTGATTTTGCTTGGTGTAATAAAGTAC
GGTTGTTTGGTCCTCGATTCTGGTAGTGATGCTTCTCGATTTGACGAAGCTATCCTTTGTTTATTC
CCTATTGAACAAAAATAATCCAACTTTGAAGACGGTCCCGTTGATGAGATTGAATGATTGATTCTT
AAGCCTGTCCAAAATTTCGCAGCTGGCTTGTTTAGATACAGTAGTCCCCATCACGAAATTCATGGA
AACAGTTATAATCCTCAGGAACAGGGGATTCCCTGTTCTTCCGATTTGCTTTAGTCCCAGAATTTT
TTTTCCCAAATATCTTAAAAAGTCACTTTCTGGTTCAGTTCAATGAATTGATTGCTACAAATAATG
CTTTTATAGCGTTATCCTAGCTGTAGTTCAGTTAATAGGTAATACCCCTATAGTTTAGTCAGGAGA
AGAACTTATCCGATTTCTGATCTCCATTTTAATTATATGAAATGAACTGTAGCATAAGCAGTATT
CATTTGGATTATTTTTTTATTAGCTCTCACCCCTTCATTATTCTGAGCTGAAAGTCTGGCATGAA
CTGTCCTCAATTTGTTTTCAAATTCACATCGATTATCTATGCATTATCCTCTTGTATCTACCTGT
AGAAGTTTCTTTTTGGTTATTCCTTGACTGCTTGATTACAGAAAGAAATTTATGAAGCTGTAATCG
GGATAGTTATACTGCTTGTTCTTATGATTCATTTCCTTTGTGCAGTTCTTGGTGTAGCTTGCCACT
TTCACCAGCAAAGTTC
```

SEQ ID NO: 211, MT promoter sequence (PRO0126)
```
CTTGTTGTTGATCTGTGCCCCCAAGAAGAATAACACTCTACTCTTACTTGTTGGAAAAAAATAGTA
TTAGCAACCACGCATATGCAAATTTTAATGCAGTAATAATAAGAGATGGATCGATCGTTTCCAGC
TCTTGTATATGTGACTGGCCCTGCTTTATGTGTGTAGTGTTAATTTCAGCTTAGCAGTACGTGAT
TAGTGATGGACAATAATTGTCGCAGACGTATCTATCAATTGCTCCTGTTGTGTGATGCTTTAACTG
TTGGAATCAAAGTTGCGTTGCCTTTGTTGTTATGAGGAGGAATATATATGTTGGGGCAGGAAAAGA
ATGGAGGAGAGATCGTTCTCCATATCCTTATCATCGGCCTCGTCACTGCTCGCAGTTTAACTTTTT
GGTGATGCGAGCGATGGTCAGCCATATATATACTCCCATGCTGCATGCTAGTAATCAATATACGCC
TTGTAAAAGTAAACGATCGTCTAGTAATTGCAATATCATAGGGGTAGCCATTGACAGAGATCTACA
TAGATAGAGGGGAACAAGAATTGACACTCCACAGATGCTCCACTCATTCACCTTTACTAATTTAT
ATCTTTTGATGTTTGATCGATCGATCGATCCGTCCGTCGGTGTCTCGACGAATAAAAACTGCAAAT
CGAACTGTATGTATATAATATAGCGTCGTAAATTAAATTAAATTAAATCGAACTGAATACTACATG
TCGAAGCAAGAATTAGTTCAACTAAAAGATTTAGTTTTTCCGGTTGCAATATCTGTGAAATTAATT
GAAGAAATTAAGAAGAAAACTGGAGAGATATATATATGGATGAGACAAAATGAGATAAGACGCATG
ATGGTCCCTCGGATGATGTCGTCCGTTCCTTATTTCCATTCATGGCAGCTGCTATCGCTATCTAG
TGCGCGCGGCATCTCCAATCCCATCCATTCTAGTGGTCGATCTAGCTACTACTGAGTATTGTTTTT
TCTTCTTTTTACTACTGTTGATTATTCTGCAACTGCAGTTAGATGCTTGCTACTCCTACATCGATC
TCTCTCGCGCGGGCGTATGCATTGCATTCACTACTGATGATCCGTGGGTGTAGTGTGGGTGGCTAT
AAATAGGGCAGGGTGCGGTTGCCATTGCTCCTCAGGCCAGCAACTGAGAAGCTCCATACAAGTAAG
CAGCAGCTAGTTGCCGACAAGGCCAGAGAAGGAAGAAGAAGCTCTCATCATCATCAC
```

```
                        201                                                                                   300
SEQ ID NO: 229  (163)   IKLHEVITIHEEE-GAEIINANHSVAGQKMFYTIHSRAS-------SSRIGIDVPRVSERLRALLQLYSHENQAPSCMHNNQVLRYNDGANATPPKELV
SEQ ID NO: 225  (130)   FMFCEIIRVLTEELGAEITHAGYSIVDDAVFHTLHCKVE-------EHDY-GARSQIPERLEKIVNSVH--------------------------------
SEQ ID NO: 213  (152)   GASFHRAVRAVEDA-GGQVQNAHFSVAGAKAVTIHAMIG-------DG--YGGIERVVQRLKEAIRSN--------------------------------
SEQ ID NO: 221  (117)   -VMLHKLVSVFEEE-GAQVMSANLQNLNDRTFYTIIAQA-------IICRIGIDPSRIEERLRDIIS--------------------------------
SEQ ID NO: 223   (58)   -VMLHELVSIFEEE-GAQVMSANLQNLNDRTTYTIIAQA-------IISRIGIDPSRIEERVRKIIHGYIYFEA--------------------------
SEQ ID NO: 227   (83)   -FLFSETFRVLHEE-GVDIVNASYKVNEDSVFHSIHCQVG------EF--GNEAARISERLKKFMQDY--------------------------------
SEQ ID NO: 219  (117)   -VMLHELVSIFEEE-GAQVMSANLQNLNDRTTYTIIAQVPHPHAYAIISRIGIDPSRIEERVRKIIHGYIYFEA--------------------------
SEQ ID NO: 215  (175)   -VKFHDVITVLEEE-GADIISANFSLAAHNFYTIYSRAF-------SSRIGIEASRISERLRALV---------------------------------
SEQ ID NO: 217  (165)   -VRLHEVIGVLEEE-GAEVVNASFSVVGDKIFYTLHSQAL------CSRIGLDASRVSHRLRNLLLQY--------------------------------
Consensus       (201)   VMLHELISVLEEE GAEVM ANFSVL DK FYTIHAQA        SRIGID SRI ERLR II    Y 301                          340
SEQ ID NO: 229  (254)   GNNDIGGTNKVANHECESWVEQDQVMWSSLLASISPELLE
SEQ ID NO: 225  (191)   ----------------------------------------
SEQ ID NO: 213  (211)   ----------------------------------------
SEQ ID NO: 221  (175)   ----------------------------------------
SEQ ID NO: 223  (123)   ----------------------------------------
SEQ ID NO: 227  (141)   ----------------------------------------
SEQ ID NO: 219  (189)   ----------------------------------------
SEQ ID NO: 215  (232)   ----------------------------------------
SEQ ID NO: 217  (225)   ----------------------------------------
Consensus       (301)
```

FIGURE 18 (continued)

| Global similarity and identity over the full length of the polypeptide | 1 | 2 | 3 | 4 | 5 | 6 | 7 | 8 | 9 |
|---|---|---|---|---|---|---|---|---|---|
| 1. SEQ ID NO: 221 |      | 51.4 | 77.1 | 25.3 | 26.8 | 20.3 | 25   | 29.9 | 22.1 |
| 2. SEQ ID NO: 223 | 57.5 |      | 64.9 | 16.7 | 17.9 | 24.3 | 14.7 | 18.9 | 15.6 |
| 3. SEQ ID NO: 219 | 83   | 64.9 |      | 23.6 | 26.3 | 20.7 | 23.2 | 28.6 | 20.9 |
| 4. SEQ ID NO: 215 | 45   | 30.3 | 42   |      | 38.1 | 18.4 | 29.3 | 23.7 | 34.4 |
| 5. SEQ ID NO: 217 | 47.3 | 32.6 | 47.3 | 60.2 |      | 19.2 | 27.8 | 27.5 | 29.2 |
| 6. SEQ ID NO: 227 | 40.8 | 42.9 | 39.4 | 33.8 | 35.3 |      | 17.1 | 33.2 | 13   |
| 7. SEQ ID NO: 213 | 39   | 23.8 | 36.2 | 44.2 | 46   | 31.9 |      | 29   | 18.7 |
| 8. SEQ ID NO: 225 | 45.8 | 31.6 | 50   | 42   | 45.1 | 50   | 45.7 |      | 20.4 |
| 9. SEQ ID NO: 229 | 36.9 | 25.9 | 34.8 | 46.1 | 42.7 | 24.2 | 30.7 | 35.5 |      |

FIGURE 19 A

| Similairyt/identity over the bHLH domain | 1 | 2 | 3 | 4 | 5 | 6 |
|---|---|---|---|---|---|---|
| 1. SEQ ID NO: 229 |      | 64.4 | 44.4 | 26.6 | 33.9 | 42.9 |
| 2. SEQ ID NO: 215 | 74.6 |      | 45.8 | 34.2 | 28.8 | 42.4 |
| 3. SEQ ID NO: 217 | 55.6 | 62.5 |      | 30.4 | 27.8 | 38.9 |
| 4. SEQ ID NO: 213 | 39.2 | 41.8 | 44.3 |      | 25.3 | 32.9 |
| 5. SEQ ID NO: 219 | 48.2 | 45.8 | 41.7 | 35.4 |      | 41.5 |
| 6. SEQ ID NO: 225 | 62.5 | 55.9 | 54.2 | 43   | 60.4 |      |

FIGURE 19 B

SEQ ID NO: 212 - CDS3159 - DNA sequence
ATGAAGAGCAGGAAGAACAGCACGACGAGCACAAAAGCAGCAGGCAGCTGCCACACCAGCAGCAGC
GGAGGAGGAGGAGGCGGCGGCAACTGCTATAGCAGCAGCAGTAGCAAGATGGAGCGCAAGGATGTG
GAGAAGAATCGGCGCCTCCACATGAAGGGTCTCTGCCTCAAGCTCTCCTCCCTCATCCCCGCCGCC
GCTCCCCGCCGCCATCACCACCACTACTCCACCTCCTCCTCCTCATCGCCGCCCTCCTCCACCAAG
GAGGCTGTGACGCAGCTGGATCACCTGGAGCAGGCGGCGGCGTACATCAAGCAGCTCAAGGGGAGG
ATCGACGAGCTGAAGAAGAGGAAGCAGCAGGCGGCGGCACTCACCACCAGCACCAGCAATGGCGGC
GGCGGCGGGATGCCGGTGGTGGAGGTGCGGTGCCAGGATGGGACGCTGGACGTGGTGGTGGTGAGC
GAGGCGATCAGGGAGGAGAGGGAGAGGGCGGTGCGGCTGCACGAGGTGATCGGCGTGCTGGAGGAA
GAAGGCGCGGAGGTGGTGAACGCCAGCTTCTCCGTCGTCGGCGACAAGATCTTCTACACTCTCCAC
TCCCAGGCGCTCTGCTCCAGGATCGGCCTCGACGCCTCCAGGGTCTCCCACAGGCTGCGCAACCTC
CTCCTCCAATATTAA

SEQ ID NO: 213 - CDS3159 - protein sequence
MKSRKNSTTSTKAAGSCHTSSSGGGGGGGNCYSSSSSKMERKDVEKNRRLHMKGLCLKLSSLIPAA
APRRHHHHYSTSSSSSPPSSTKEAVTQLDHLEQAAAYIKQLKGRIDELKKRKQQAAALTTSTSNGG
GGGMPVVEVRCQDGTLDVVVVSEAIREERERAVRLHEVIGVLEEEGAEVVNASFSVVGDKIFYTLH
SQALCSRIGLDASRVSHRLRNLLLQY

SEQ ID NO: 214 - DNA of Os_NP_908393.1
ATGGATCAGGAGAAGGCGGACGGCGGCGGCAGGAGGAGGAGGAGCAGGGCGACGAGTAGCAGCGGC
AGCGGCGCGAGCAGCACGGCGGCGGCGGCGGCGGAGAGGAAGGAGATGGAGCGCAGGAGGCGG
CAGGACATGAAGGGCCTCTGCGTCAAGCTCGCCTCTCTCATCCCCAAAGAACACTGCTCCATGTCC
AAGATGCAGGCGGCGTCTAGGACCCAGCTGGGCAGCCTGGACGAAGCGGCGGCCTACATCAAGAAG
CTCAAGGAAAGGGTGGACGAGCTGCACCACAAGAGGAGCATGATGAGTATCACATCATCGCGCTGC
CGCTCAGGAGGAGGAGGAGGACCAGCTGCTGCTGCTGGCCAGTCGACGAGCGGCGGCGGCGGCGGG
GAAGAAGAAGAAGAAGATATGACGAGGACGACGGCGGCGGCGGCGGTGGTGGAGGTGCGGCAGCAC
GTGCAGGAGGGGTCGCTGATCAGCTTGGACGTGGTGCTGATCTGCAGCGCAGCGAGGCCGGTCAAG
TTCCACGACGTCATCACCGTCCTCGAGGAAGAAGGCGCCGACATCATCTCCGCCAACTTCTCCCTC
GCCGCCCACAATTTCTACTACACCATCTACTCCAGGGCCTTTAGCTCAAGAATTGGCATAGAGGCT
TCGAGGATTTCTGAGAGACTACGGGCATTGGTATGA

SEQ ID NO: 215 - Os_NP_908393.1
MDQEKADGGGRRRRSRATSSSGSGASSTAAAAAAERKEMERRRRQDMKGLCVKLASLIPKEHCSMS
KMQAASRTQLGSLDEAAAYIKKLKERVDELHHKRSMMSITSSRCRSGGGGGPAAAAGQSTSGGGGG
EEEEEDMTRTTAAAAVVEVRQHVQEGSLISLDVVLICSAARPVKFHDVITVLEEEGADIISANFSL
AAHNFYYTIYSRAFSSRIGIEASRISERLRALV

SEQ ID NO: 216 - Os_XM_464787.1
ATGGAGATCCCGCCGCCGTCAGCTGGTGGCGGAGGCGGCGGCGGCAAGCCCGACCGGAAGACGACG
GAGCGCATCCGCCGCGAGCAGATGAACAAGCTCTACTCCCACCTCGACTCCCTCGTCCGCTCCGCT
CCCCCCACAGTTAATTCCATTCCTTCACATTCAAATTCAAATTCAAAATACCATCAAAGAAAATTA
CGGATTCTCGGTGGGGCGGCGGCGGCGACGACGAGGCCGGACGGTTGGGGGTGGCGGCGGAGTAC
ATAAGGCAGACGCAGGAGAGGGTGGACATGCTGAGGGAGAAGAAGGGGAGCTCACCGGCGGCGGC
GGCGGCGGCTCCTCGTCGTCGTCCGGCGCCGGGGCGGCCACGGCCGCCGCGCCGGAGGTGGAGGTG
CAGCACCTGGGGTCCGGCCTGCACGCCATCCTCTTCACCGGCGCCGCCCACCGACGCGCCTCC
TTCCACGCCGTCCGCGTCGAGGACGCCGGCGGCCAGGTGCAGAACGCGCACTTCTCCGTC
GCCGGCGCCAAGGCCGTCTACACCATCCACGCCATGATTGGAGATGGATATGGAGGCATTGAGAGG
GTGGTGCAGAGATTAAAGGAAGCAATACGGAGCAACTAA

FIGURE 21

SEQ ID NO: 217 - Os_XP_464787.1
MEIPPPSAGGGGGGGKPDRKTTERIRREQMNKLYSHLDSLVRSAPPTVNSIPSHSNSNSKYHQRKL
RILGGAAAATTRPDRLGVAAEYIRQTQERVDMLREKKRELTGGGGGGSSSSSGAGAATAAAPEVEV
QHLGSGLHAILFTGAPPTDGASFHRAVRAVEDAGGQVQNAHFSVAGAKAVYTIHAMIGDYGGIER
VVQRLKEAIRSN

SEQ ID NO: 218 - At1g10585 DNA
ATGGGGAGAGCAAGAGAAATAGGAGAAGGAAACTCATCGTCGTTAAGGGAACAACGAAACCTCAGA
GAGAAGGATCGAAGGATGCGCATGAAACATCTCTTCTCTATACTTTCTTCTCATGTTTCTCCCACT
CGCAAGTTACCAGTGCCTCACCTTATAGATCAAGCGACATCATACATGATCCAATTGAAAGAGAAT
GTAAATTATTTGAAAGAGAAGAAAAGGACATTGTTACAAGGAGAACTCGGGAATCTCTACGAAGGG
TCGTTTCTTCTACCCAAACTCAGTATTCGTTCGCGGGATTCGACCATAGAAATGAATCTGATCATG
GATCTAAACATGAAAAGAGTAATGTTACACGAGCTTGTGAGTATTTTGAAGAAGAAGGAGCTCAA
GTAATGAGTGCTAATCTTCAGAACTTGAATGATAGGACCACTTACACAATCATAGCCCAGGCTATC
ATTAGTCGGATTGGCATTGATCCATCAAGGATAGAAGAGAGTACGGAAAATCATCTATGGATAT
ATATATTTTGAAGCATGA

SEQ ID NO: 219 - At1g10585
MGRAREIGEGNSSSLREQRNLREKDRRMRMKHLFSILSSHVSPTRKLPVPHLIDQATSYM
IQLKENVNYLKEKKRTLLQGELGNLYEGSFLLPKLSIRSRDSTIEMNLIMDLNMKRVMLH
ELVSIFEEEGAQVMSANLQNLNDRTTYTIIAQVPHPHAYAIISRIGIDPSRIEERVRKII
YGYIYFEA

SEQ ID NO: 220 - At1g10585 variant 2 (AC007067.4) DNA
ATGGAAAGAGCGAGAGAAATAGGAGAAGGAAGCGCATCGTCATTACGGGAACAACGAAACCTCAGA
GAGAAAGAACGACGAATGCGCATGAAACATCTCTTCTCCATACTCTCTTCTCATGTTTCTCCCACT
CGTAGGTTGCCAGTGCCTCAACTTATAGATCAAGCGGTATCATACATGATCCAACTGAAAGAGAAG
GTAAACTATTTGAATGAGATGAAAAGGAGAATGTTAGGAGGAGAAGTCAAAAATCGCTCTGAAGGG
TCGTCTCTTCTGCCAAAACTCAGTATTCGTTCACTGGATTCGATCATAGAAATGAATCTGGTTATG
GATCTAAACATGAAAGGAGTAATGTTACACAAGCTTGTGAGTGTTTTGAAGAAGAAGGAGCTCAA
GTGATGAGTGCTAATCTTCAGAACTTGAATGATAGGACCTTTTATACAATCATAGCCCAGGCTATC
ATATGTCGGATCGGGATTGATCCATCAAGGATAGAAGAGAGATTAAGGGATATAATCTCATGA

SEQ ID NO: 221 - At1g10585 variant 2
MERAREIGEGSASSLREQRNLREKERRMRMKHLFSILSSHVSPTRRLPVPQLIDQAVSYMIQLKEK
VNYLNEMKRRMLGGEVKNRSEGSSLLPKLSIRSLDSIIEMNLVMDLNMKGVMLHKLVSVFEEEGAQ
VMSANLQNLNDRTFYTIIAQAIICRIGIDPSRIEERLRDIIS

SEQ ID NO: 222 - At1g10585 variant 3 (AY050959.1) DNA
ATGATCCAATTGAAAGAGAATGTAAATTATTTGAAAGAGAAGAAAAGGACATTGTTACAAGGAGAA
CTCGGGAATCTCTACGAAGGGTCGTTTCTTCTACCCAAACTCAGTATTCGTTCGCGGGATTCGACC
ATAGAAATGAATCTGATCATGGATCTAAACATGAAAAGAGTAATGTTACACGAGCTTGTGAGTATT
TTTGAAGAAGAAGGAGCTCAAGTAATGAGTGCTAATCTTCAGAACTTGAATGATAGGACCACTTAC
ACAATCATAGCCCAGGCTATCATTAGTCGGATTGGCATTGATCCATCAAGGATAGAAGAGAGTA
CGGAAAATCATCTATGGATATATATATTTTGAAGCATGA

SEQ ID NO: 223 - At1g10585 variant 3
MIQLKENVNYLKEKKRTLLQGELGNLYEGSFLLPKLSIRSRDSTIEMNLIMDLNMKRVMLHELVSI
FEEEGAQVMSANLQNLNDRTTYTIIAQAIISRIGIDPSRIEERVRKIIYGYIYFEA

FIGURE 21 (continued)

SEQ ID NO: 224 - At4g20970 DNA
ATGGAGCCGAGCCATTCAAACACAGGTCAATCAAGATCTGTAGATCGCAAAACGGTTGAGAAAAAT
AGAAGGATGCAAATGAAGTCTCTCTACTCAGAACTCATCTCTCTTCTTCCTCATCATTCTTCTACG
GAGCCTTTAACACTACCTGATCAGCTAGATGAAGCTGCAAACTACATCAAGAAGCTACAAGTGAAC
GTGGAGAAAAAGAGAGAAAGGAAAAGGAACCTCGTTGCGACTACAACTTTGGAGAAACTGAATTCC
GTCGGATCTTCATCGGTTTCGTCGAGCGTCGATGTCTCCGTGCCAAGAAAGCTGCCAAAAATCGAG
ATTCAAGAAACTGGTTCCATTTTTTCACATCTTTCTTGTGACAAGCTTGGAACACAAGTTTATGTTT
TGTGAGATCATTCGTGTTCTCACCGAGGAATTAGGAGCTGAGATCACTCATGCTGGATACTCCATT
GTTGATGATGCTGTCTTCCACACCCTTCACTGCAAGGTGGAAGAACACGATTATGGAGCTAGGAGT
CAAATTCCTGAAAGACTGGAGAAGATTGTGAACAGTGTTCACTAA

SEQ ID NO: 225 - At4g20970
MEPSHSNTGQSRSVDRKTVEKNRRMQMKSLYSELISLLPHHSSTEPLTLPDQLDEAANYIKKLQVN
VEKKRERKRNLVATTTLEKLNSVGSSSVSSSVDVSVPRKLPKIEIQETGSIFHIFLVTSLEHKFMF
CEIIRVLTEELGAEITHAGYSIVDDAVFHTLHCKVEEHDYGARSQIPERLEKIVNSVH

SEQ ID NO: 226 - DNA sequence of Mt_ABD32361.1
ATGACATCTCTAACAAAGGAGGCGATTTCAGTGCCGGATCAGCTAAAGGAAGCAACAAACTACATA
AAGAAATTGCAGATCAACCTGGAGAAAATGAAGGAAAAGAAGAATTTTCTACTAGGAATTCAAAGG
CCAAATGTGAATTTGAATAGAAACCAGAAGATGGGATTAAAGTCTCCAAAAATTAAGATACAACAA
ATTGGTTTAGTCTTAGAGGTTGTTCTAATAACTGGATTGGAGTCTCAGTTTTTGTTCAGCGAAACC
TTTCGAGTTCTTCATGAAGAAGGAGTTGATATTGTTAATGCTAGTTATAAGGTCAATGAAGATTCT
GTTTTCCATTCAATACACTGCCAGGTAGGAGAATTTGGCAATGAAGCTGCAAGAATATCTGAGAGA
TTGAAGAAGTTTATGCAAGACTATTAG

SEQ ID NO: 227 - Mt_ABD32361.1
MTSLTKEAISVPDQLKEATNYIKKLQINLEKMKEKKNFLLGIQRPNVNLNRNQKMGLKSPKIKIQQ
IGLVLEVVLITGLESQFLFSETFRVLHEEGVDIVNASYKVNEDSVFHSIHCQVGEFGNEAARISER
LKKFMQDY

SEQ ID NO: 228 - DNA sequence of Hv-TC140459
ATGAATGCCTGCGCTCTGAACTCGATGGAGCCGGTGAAGGCGAAGCCGGCGAGGGGCGGGAAGAGG
AGCAGGGAGAGCGGCGGCACGGCGGTGGTGCTGCTGGAGAAGAAGGAGTCGGAGAAGGAGAGGAGG
AAGCGCATGAAGGCGCTCTGCGAGAAGCTCGCATCCCTCATCCCAAGGGAACACTGCTGCTCCACC
ACTGATACAATGACCCAGCTAGGCAGCCTGGATGTGGGGCATCGTATATCAAGAAGCTGAAGGAG
AGGGTCGATGAGCTACAACGTAGGATGACCTCTGCGCAGACCTTGGATACCTTCAGAGGAGACACT
AGCATCCCAACGCCCACTACCACCACTACCACGAAAAGCGTTGTAGGGTCGCTGGAAGAAGAGAAA
GCTCGGGAGGCATCGGCACCCGTATTGCAGGTGCGGCAACACGACGATTCAAGCATGGAGGTGAGA
TTGATATGCTGCATGAAGAGGCCGATCAAGCTCCATGAGGTGATCACCATCCATGAGGAAGAAGGT
GCTGAGATCATCAACGCCAATCACTCTGTTGCTGGCCAAAAAATGTTCTACACTATACACTCTCGG
GCCTCTAGCTCGAGAATTGGCATAGATGTTCCAAGGGTTTCTGAACGACTGCGAGCATTGCTCCAA
CTTTATTCGCATGAAAATCAGGCACCGTCGTGCATGCACAACAATCAAGTCCTCAGGTACAATGAT
GGGGCCAACGCGACTCCTCCCAAGGAGCTCGTCGGCAACAATGATATAGGTGGAACCAACAAGGTG
GCAAACCACGAGTCTCACTCTTGGTTGAGCAACACCAAGTCATCTCCACTTCCCTGCTTGCGTCA
ATATCACCAGAGTTGCTCGAGTAG

SEQ ID NO: 229 - Hv-TC140459
MNACALNSMEPVKAKPARGGKRSRESGGTAVVLLEKKESEKERRKRMKALCEKLASLIPREHCCST
TDTMTQLGSLDVGASYIKKLKERVDELQRRMTSAQTLDTFRGDTSIPTPTTTTTKSVVGSLEEEK

FIGURE 21 (continued)

AREASAPVLQVRQHDDSSMEVRLICCMKRPIKLHEVITIHEEEGAEIINANHSVAGQKMFYTIHSR
ASSSRIGIDVPRVSERLRALLQLYSHENQAPSCMHNNQVLRYNDGANATPPKELVGNNDIGGTNKV
ANHECESWVEQDQVMWSSLLASISPELLE

SEQ ID NO: 230 - Oryza sativa Gos2 promoter
AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAATCTTTCTAGCTGAACTCAATGGGT
AAAGAGAGAGATTTTTTTAAAAAAATAGAATGAAGATATTCTGAACGTATTGGCAAAGATTTAAA
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTATTATTTATCTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAGAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTCCTCCCATCTATAA
ATTCCTCCCCCTTTTCCCCTCTCTATATAGGAGGCATCCAAGCCAAGAAGAGGGAGAGCACCAAG
GACACGCGACTAGCAGAAGCCGAGCGACCGCCTTCTTCGATCCATATCTTCCGGTCGAGTTCTTGG
TCGATCTCTTCCCTCCTCCACCTCCTCCTCACAGGGTATGTGCCCTTCGGTTGTTCTTGGATTTAT
TGTTCTAGGTTGTGTAGTACGGGCGTTGATGTTAGGAAAGGGGATCTGTATCTGTGATGATTCCTG
TTCTTGGATTTGGGATAGAGGGGTTCTTGATGTTGCATGTTATCGGTTCGGTTGATTAGTAGTAT
GGTTTTCAATCGTCTGGAGAGCTCTATGGAAATGAAATGGTTTAGGGTACGGAATCTTGCGATTTT
GTGAGTACCTTTGTTTGAGGTAAAATCAGAGCACCGGTGATTTGCTTGGTGTAATAAAAGTACG
GTTGTTTGGTCCTCGATTCTGGTAGTGATGCTTCTCGATTTGACGAAGCTATCCTTTGTTTATTCC
CTATTGAACAAAATAATCCAACTTTGAAGACGGTCCCGTTGATGAGATTGAATGATTGATTCTTA
AGCCTGTCCAAAATTTCGCAGCTGGCTTGTTTAGATACAGTAGTCCCCATCACGAAATTCATGGAA
ACAGTTATAATCCTCAGGAACAGGGGATTCCCTGTTCTTCCGATTTGCTTAGTCCCAGAATTTTT
TTTCCCAAATATCTTAAAAAGTCACTTTCTGGTTCAGTTCAATGAATTGATTGCTACAAATAATGC
TTTTATAGCGTTATCCTAGCTGTAGTTCAGTTAATAGGTAATACCCCTATAGTTTAGTCAGGAGAA
GAACTTATCCGATTTCTGATCTCCATTTTAATTATATGAAATGAACTGTAGCATAAGCAGTATTC
ATTTGGATTATTTTTTTATTAGCTCTCACCCCTTCATTATTCTGAGCTGAAAGTCTGGCATGAAC
TGTCCTCAATTTTGTTTTCAAATTCACATCGATTATCTATGCATTATCCTCTTGTATCTACCTGTA
GAAGTTTCTTTTTGGTTATTCCTTGACTGCTTGATTACAGAAAGAAATTTATGAAGCTGTAATCGG
GATAGTTATACTGCTTGTTCTTATGATTCATTTCCTTTGTGCAGTTCTTGGTGTAGCTTGCCACTT
TCACCAGCAAAGTTC

SEQ ID NO: 231 - sense primer: prm06808
GGGGACAAGTTTGTACAAAAAAGCAGGCTTAAACAATGAAGAGCAGGAAGAACAGC

SEQ ID NO: 232 - antisense primer: prm06809
GGGGACCACTTTGTACAAGAAAGCTGGGTGCAGAGTGAAAGAGTGGTGTG

SEQ ID NO: 233 - Oryza sativa GOS2 promoter variant
AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAGAGTCGCTACACTAGTTTCGTTTTCCTTAGTAATTAAGT FIGURE 21 (continued)

```
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAAGAGAGAGATTTTTTTAAAAAAATAGAATGAAGATATTCTGAACGTATTGGCAAAGATTTAAA
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTATTATTTATCTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAAGAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTTCTCCCATCTATAA
ATTCCTCCCCCCTTTTCCCCTCTCTATATAGGAGGCATCCAAGCCAAGAAGAGGGAGAGCACCAAG
GACACGCGACTAGCAGAAGCCGAGCGACCGCCTTCTCGATCCATATCTTCCGGTCGAGTTCTTGGT
CGATCTCTTCCCTCCTCCACCTCCTCCTCACAGGGTATGTGCCTCCCTTCGGTTGTTCTTGGATTT
ATTGTTCTAGGTTGTGTAGTACGGGCGTTGATGTTAGGAAAGGGGATCTGTATCTGTGATGATTCC
TGTTCTTGGATTTGGGATAGAGGGGTTCTTGATGTTGCATGTTATCGGTTCGGTTTGATTAGTAGT
ATGGTTTTCAATCGTCTGGAGAGCTCTATGGAAATGAAATGGTTTAGGGATCGGAATCTTGCGATT
TTGTGAGTACCTTTTGTTTGAGGTAAAATCAGAGCACCGGTGATTTGCTTGGTGTAATAAAGTAC
GGTTGTTTGGTCCTCGATTCTGGTAGTGATGCTTCTCGATTTGACGAAGCTATCCTTTGTTTATTC
CCTATTGAACAAAAATAATCCAACTTTGAAGACGGTCCCGTTGATGAGATTGAATGATTGATTCTT
AAGCCTGTCCAAAATTTCGCAGCTGGCTTGTTTAGATACAGTAGTCCCCATCACGAAATTCATGGA
AACAGTTATAATCCTCAGGAACAGGGGATTCCCTGTTCTTCCGATTTGCTTTAGTCCCAGAATTTT
TTTTCCCAAATATCTTAAAAAGTCACTTTCTGGTTCAGTTCAATGAATTGATTGCTACAAATAATG
CTTTTATAGCGTTATCCTAGCTGTAGTTCAGTTAATAGGTAATACCCCTATAGTTTAGTCAGGAGA
AGAACTTATCCGATTTCTGATCTCCATTTTTAATTATATGAAATGAACTGTAGCATAAGCAGTATT
CATTTGGATTATTTTTTTATTAGCTCTCACCCCTTCATTATTCTGAGCTGAAAGTCTGGCATGAA
CTGTCCTCAATTTTGTTTTCAAATTCACATCGATTATCTATGCATTATCCTCTTGTATCTACCTGT
AGAAGTTTCTTTTTGGTTATTCCTTGACTGCTTGATTACAGAAAGAAATTTATGAAGCTGTAATCG
GGATAGTTATACTGCTTGTTCTTATGATTCATTTCCTTTGTGCAGTTCTTGGTGTAGCTTGCCACT
TTCACCAGCAAAGTTC
```

SEQ ID NO: 296 Zea mays bHLH 300926
```
ATGCACAACTGCAAAGAAACCAGCAAGAATGCGCCGGCGGTTTATAGTTCCCCGCTACTGCACCGC
TCTCTGCTGCAGGCTGCAGCTTTGACTACCAACTCATACAGTACTAGTACTATACTAGAGTACTAC
TACGCCATTAGCACGGTGGTTGCANTAGGCCGTGGTCTGGAGGTCTCTCTCAGCTCAGACGAGGAT
CGTCGGAGCAAGCAGCAGCGCGTGCAGCCTCTGGGAGACCCTGGCGGCGTCGACGCCGATCCTGGG
GCTGAGCGCCTGCGAGTGGACGGTGTAGAATATCTTGTCCCGATGACGGAGAAGCTGGCGCTGAC
CACCTCGGCGCCCTCCTGCTCCAGCACGGTGATGACCTCGTGCAGCTTGAAGGGCCTGGCGGCCTC
GCTGATGAGCACCACGTCCAGCGTCCGTCCTGGCACCGCACCTCGATGACCGGCATGCGCACGCC
TCCGCCCCCGCCGGTGGACCCGGCCCCCGCCGTTGCAGCCTCCGTCCCCGCCCGCCGCCGTTCCA
GCAGCCCGCCTTCCGCTGCTTCAGCGCCTCGATCCGCTCCTTGAGCTGCTTGATGTACGCCGCCGC
GCTGTCCAGCTGGTCCAGCTGCGTCACCGCGTCCTGCTTGTTGCCGGGATTGGAGGACACCGCCGC
CGACGCGGCGTCGGAGAGGAGGGAGGCGTGCGTGGCGGCGGCGGCGGCGGGAGGGATGAGGGA
GGAGAGCTTGAGGCAGAGGCCCTTCATGTGCAGCCTCCGGTTCTTCTCCACGTCCTTCCTCTCCAG
CTTGCACCCCCGCCGCTGCTGTGCGCGTTCCTCTCCCCGCGGCGCAGGCGCCCGAGCTGCCCCC
GCTGCTCTGCCTCCGGCTCTTCATCTCGATCGACCNGACCGGTCTGCAGATCTCTCCTTGGCTGTT
CTCGTCGCTGCTCCTGCCGGGCGTGAAGCNGCGCAGCCTTTGGTTGGGACTTGGGAGGGACAAGTT
GCAACAGCACCCACGGGCCACGGCACGGAGGGGCGAAAGGCAAGGAGGCCAGGACAAGACGAGAG
```

```
AAATACAGGCCGGGGGAGATGGCTCCGTGGCGCGTACGTGTGTCTACCTGCATGTTGGTTGATCCG
ATTGCATCTGCTGTAACCATATATTAA
```

SEQ ID NO: 297 Zea mays bHLH 300926
```
MHNCKETSKNAPAVYSSPLLHRSLLQAAALTTNSYSTSTILEYYYAISTVVAXGRGLEVSLSSDED
RRSKQQRVQPLGDPGGVDADPGAERLRVDGVEYLVPDDGEAGADHLGALLLQHGDDLVQLEGPGGL
ADEHHVQRPVLAPHLDDRHAHASAAAGGPGRRRCSLRGRAAAVAAARLPLLQRLDPLLELLDVRRR
AVQLVQLRHRVLLVAGIGGHRRRRGVGEEGGVRGGGGGGGRDEGGELEAEALHVQPPVLHVLPLQ
LAPPAAAVRVPLPRGAGARAAPAALPPALHLDRPDRSADLSLAVLVAAPAGREAAQPLVGTWEGQV
ATAPTGHGTEGAKGKEARTRREKYRPGEMAPWRVRVSTCMLVDPIASAVTIY
```

SEQ ID NO: 298 Zea mays bHLH 303926
```
ATGGAGATGAGAGCGAAGAAGAGCAGCAGAAGCAGCACGAGCAACACCAGCGGCAGCACGACGACC
ACGGCGGTGGAGAGGAAGGAGATCGAGAGGAGGAGGAGGCAGCAGATGAAGAGCCTCTGCGCCAAG
CTCGCCTCCCTCATCCCGAAAGAACACTACTCCTCCAAGGATGCTATGACCCAGCTGGGTAGCCTA
GACGAGGCAGCCACGTACATAAAGAGACTCAAGGAGAGGGTGGAGGAGCTGCGGCACAAGAGCGCC
TCTGCACGGCTCTTGGCCGCTGGCAGTGGCACGAGACGAGGCGGAGGAGGAGGAGGCGCCTCCACA
TCGTCGGCAGCGACGACCACGGCGAGCGGTGGCGCAGGATCATCTGAAGAAGCCGGCCGGCGGGAG
GACGACATGCCGCCGGCGGTGGTAGAGGTTCGGCAGCACAATGACGGGTCAAGCCTGGACGTGGTG
CTCATCAGCAGCGCGGCGCGACCCTTCAAGCTGCACGAGGTGGTCACCGTGCTGGAGGAAGAAGGC
GCCGAGACCGACAACGCCAACCTCTCCGTCGCCGGCACCAAAATCTTCTACACCATCCACTGCAAG
GCCTTTTGCCCAAGAATCGGTATAGATGTTTCAAGAGTTTCTGAAAGATTAAGAGCATTGGGATGA
```

SEQ ID NO:299 Zea mays bHLH 303926
```
MEMRAKKSSRSSTSNTSGSTTTTAVERKEIERRRQQMKSLCAKLASLIPKEHYSSKDAMTQLGSL
DEAATYIKRLKERVEELRHKSASARLLAAGSGTRRGGGGGASTSSAATTTASGGAGSSEEAGRRE
DDMPPAVVEVRQHNDGSSLDVVLISSAARPFKLHEVVTVLEEEGAETDNANLSVAGTKIFYTIHCK
AFCPRIGIDVSRVSERLRALG
```

SEQ ID NO: 300 Glycine max bHLH 5303275
```
ATGGGTCAACAACAACAGGGAAGTCAACCTTCTCCAACCAAAGTCGAAAGAAAGATTGTAGAGAAA
AACAGGAGAAGCCAGATGAAGAACCTCTATTCCGAACTCAACTCTCTTCCCTACCCGTAATCCC
AAGGAAGCGATGTCACTGCCTGATCAAATAGATGAAGCAATCAACTATATCAAAAGCCTAGAGACA
AAAGTGAAGCTGGAGCAGGAGAAGAAAGAAAGGTTAAAGGAAAGGAAGAGAACTCGTGGTGGCTGT
TCGAGTTCTTCTGAAGCACAAGGAAGCCTGAAATCGCCAAATATCCAGATTCACGAAACGGGAAAT
TTGCTTGAAGTCATTCTAACATGTGGGGTCGATAGCCAGTTCATGTTCTGTGAAATTATTCGAATT
TTGCATGAAGAGAACGTCGAGGTCATCAATGCCAATTCTTCAATGGTCGGAGATTTAGTGATTCAT
GTTGTGCACGGGGAGGTTGAGCCATCTATCTATCAATTCGGAGCGACCAAAGTGAGTGAGAAGCTG
AAATGGTTTATGAACGGATCCTTCAGTGATGTGGAAATGGAGCCTGAATTAATGTGGAATTTTAAA
ATTGATGCTACTGAGCCGTGGGGCTTCTAGATGATCTTACACTGGACAATGTCTTACCACCAAAT
ACTTTGTAA
```

SEQ ID NO: 301 Glycine max bHLH 5303275
```
MGQQQQGSQPSPTKVERKIVEKNRRSQMKNLYSELNSLLPTRNPKEAMSLPDQIDEAINYIKSLET
KVKLEQEKKERLKERKRTGGCSSSSEAQGSLKSPNIQIHETGNLLEVILTCGVDSQFMFCEIIRI
LHEENVEVINANSSMVCDLVIHVVHGEVEPSIYQFGATKVSEKLKWFMNCSFSDVEMEPELMWNFK
IDATEPWGLLDDLTLDNVLPPNTL
```

```
                         211                                                                          280
Arath_SPL15    (157) AAMIKSVLG----DPTAWSTARSVMQR-PGPWQINPVRET-HPHMNVLSHGSS-----------------
 Arath_SPL9    (173) AGMNGSFLGN   QETGWPSSRTEDTR VMRRPVSSP        SWQINPMNVFSCGSVG         G
   Goshi_SPL   (190) FIVDFSAYPRI-SGRDAWPAARSI-EC-ITGNRS-TATGS-SFSHPRQNNSSKPP--------HDHFLQG-
   Vitvi_SPL   (184) FLMDFAAYPRH-PERDTWPTTRAS-DR-VPCNGT-TAMGR-FLPHPWQSNSENP----------LFLQG-
   Aqufo_SPL   (181) FLMDFTAYPRL-AGRDAWQTVKAG-NW-ADGNQTS-PIKK-LLPHQWQGNSENPPPIVYSQAPHPYLQG-
   Crysa_SPL   (202) FTLDFSYPRVPSSVRNAWPAICPC-DRLSCCLQWHRNVAP-HCHSSAVACYCANTYS---------CQCS
   Zeama_SPL   (183) FMLDFSYPRVSSAMRGGFPAVRAGGERVPGGIQWQAGLDP-RHHQGAVAGYGAHYGSE--------GGSS
   Medtr_SPL   (169) FLMEFASNPKH-SIRN-----------SPGNQ-----TT-AIGWPWPGNTESPS--------SNLFIQG-
   Nicbe_SPL   (181) FLVDFTAYPNL-TGGA-WPNTRSS-DR-GWDNQST-ASGK-LLQSHWLNSSENPT--------SDLVLQG-
   Scltu_SPL   (178) FLVDFSSHQNV-NDSS-WPNTRAS-EC-GWDHQS---SGK-FLQRPWLNSENAA--------SELVLQG-
   Maldo_SPL   (180) FLMDFTAYPRF-SGRDTW-TTRTS-ER-APVNQNANDAGK-FIQQPWQSNSDIST-------SGFYIQG-
   Lacsa_SPL   (174) FLMDFSSCSR---GRIQWPGTRAA-PPPRAAIDLPIAGEK-FPPIPWQSNIDNPP---------P--YVP
   Iponi_SPL   (157) FVMDFASYP--------YPCGKGS-----WRPSTN-CVGN-FLQQPWQRNSEDPP--------PKLIILGS
 Zeama_SPL II  (163) FLLDFSYPRVPSSVRDAWPGICHGGDRMIGTVQWHGHQEPPHPHRSAAAGYGNHAAYN-------CHGGL
 Crysa_SPL II  (174) FVVDFSYPRVPSSVRDAWPAICPS-DRMSCSICWQCG-HELHPHRSAVACYSDHHAFS--------SHCC Consensus    (211) FLMDFSA     S R AWP  RA  DR    Q              W ANSE              LQG
```

```
                                                      MOTIF 2
                         281                                                                          350
Arath_SPL15    (204)     SFTTCPEMIN     NNST    DSSCALSLLSN  YPIHQQ    QLQTPTN     TWRPSS
 Arath_SPL9    (223) ---GGTSFSSPEIMDTKLESYKGIG---DSNCALSLLSN HQPHDN-----NNNNNNNNNNNNNTWRASS
   Goshi_SPL   (247) -SPCCTSFSSTC--ISPCECFTCSC---DSSCALSLLSN--QPWC------SRNQALN----------F
   Vitvi_SPL   (238) -SAGGTSFHGPG--TPSGECFTGAS---DSSCALSILSN--QPWS------SRNRASG----------L
   Aqufo_SPL   (245) -VASCSIFSSTR--IPSAECFAGVS---DSSCALSLLSN--QPWN------PRNQTSD----------
   Crysa_SPL   (261) SSSGPPVFAGPN--LPPGGCLAGVGAAT DSSCALSLLST--QPWDTTTHSAAASHNQAAAM------S
   Zeama_SPL   (244) SSARPPVFPGPE--LPPGGCLAGV--PA DSSCALSLLST--QPWD---AAHSHSHSHAA--------P
   Medtr_SPL   (212) SVGGTSFPGAR  HPPEETYTGVT    DSNCALSLLSN  QTWG    SQNTEPS          P
   Nicbe_SPL   (237) -SVARGANYSGPGIIPSGNCFSGVS---DSNGALSILSN--EPWG------SRNQSSS----------L
   Scltu_SPL   (232) -SATRTSYPS----VPSCDYFPCVS---DSSCALSILSN--RSWG------SRNRSPS----------L
   Maldo_SPL   (237) -SAGGTSYPGPG--IPPGECVTVVT---DSSCALSLLSN--QPWG------SRNRVLG----------A
   Lacsa_SPL   (228) ---------PCCCFNCVHE-DSTRALSILSN  HSSG      SRNQSLS                
   Iponi_SPL   (205) DAAARATYPS-----PCGEYFNGVS---DSTRALSILSN NQPWG------SRNQCPSG---------L
 Zeama_SPL II  (226) VAGGAPMLSSAAFELPPGGCVAGVA--A DSSCALSLLST--QPWDTT----SHDHRSP---------AM
 Crysa_SPL II  (234) SAAGAPMIHIPAFELTSGGCIAGVAT   DSSCALSLLST   QPWDTTQSTSSHNRSPP      MS Consensus    (281) SAGGT F     IP GECF GVS     DSSCALSLLSN  QPW       SRN miR156 peptide target sequence                        CALSLLS
```

```
                         351                                                                          420
Arath_SPL15    (249) GFDSMISFSDK--VTMAQPPPISTHQPPISTHQQYISQTWEVIAG---EKSNSHYMSPVSQISEPADFQI
 Arath_SPL9    (282) GFGPMT-------VTMAQPP-------PAPSQHQYLNPPWVFKDN---DNDMSPVLN-LGRYTEPDNCQI
   Goshi_SPL   (292) SVNGVISTEG   SSAAQPTT    IIGAVVNPYSNASLDFNGS DTVRSSIIKMLPIILDLGQIPDPVN
   Vitvi_SPL   (283) GANSFMNPEG---ASMAQPTA----PHSAAINHFPSTSWDFKGN-EGSSSSQEMPPPDIGLGQISQPIN-
   Aqufo_SPL   (290) EVNNIVNGEG---VSMARSIA-----PHSAVVTNFTNNTWNFKGNSEVSGSSHELPRQVS------QPVT-
   Crysa_SPL   (319) TITSFDGNPV---APSAMAG------SYMAPSPWTG--SRGHEGGG---RSVAHQLPHEVSIDEVHPGPS-
   Zeama_SPL   (295) TAGFDCGSPV---APSLMAAS-----SYIAPSPWTETDSWGHECG---RSVPQLPPDDVPLGEVHSGSSS
   Medtr_SPL   (257) GLNNMLNFNG---TPMTQLG---------------TSSHGVAMH-QIPNN-YEVVPDIGRGHILHPIG-
   Nicbe_SPL   (284) GVNGLVNTDG---GHTVHPSG-----SHAAPVNHYSGPTWGFKGN-FASSSSHATPPDI GTGHTSCHAV-
   Scltu_SPL   (275) GVNSQVHTDG---VHTTQPSG-----SHGAPTNHFSSPSI SFKGN-FASSSSHEMPPPDI GTGCMLQASD-
   Maldo_SPL   (282) GMNSLMNTCG---VPVAQPVP-----HSATSNHFPTTSWGFKGN-ENGSSSHGMLPDIGLGQISQPIS-
   Lacsa_SPL   (260) -HFYYTNPFA---GAYVHQLH-----QPTTGTGAGFGTMVEVTAT---GWVYFTHDAHT GTGHVPQS-G-
   Iponi_SPL   (251) GVNSLINTDG---TLAVHPSG-----SHAAVINEFSSSPWGFKGN-QATTSSDKIILPDS--------
 Zeama_SPL II  (278) PAAGAFDGTPV  APSVMASS              YAASSSAWTGSRDPAADGARNAQRLDDALHLVHPGSA
 Crysa_SPL II  (290) STASAFGGGNNPVSPSVMASN------YMAASPGWNSSSRGHDGA---RNVHLPPPHGVVLNEVPPG-SV Consensus    (351) G N LI  G           P         H  A    F  S SW F G     SS   M    DLGLG I
```

FIGURE 24 (continued)

SEQ ID NO: 234, Arabidopsis thaliana Arath_SPL15 (At3g57920) nucleic acid sequence NM_115654.1
ATGGAGTTGTTAATGTGTTCGGGTCAGGCCGAGTCAGGTGGTTCCTCTTCCACCGAGTCTTCTTCA
CTCAGTGGTGGACTCAGGTTTGGTCAGAAGATCTACTTCGAGGATGGATCCGGATCCAGAAGCAAG
AACCGGGTCAATACCGTTCGTAAGTCGTCTACCACGGCGAGGTGCCAAGTGGAAGGTTGTAGAATG
GATCTAAGCAATGTTAAAGCTTATTACTCGAGACACAAAGTTTGTTGCATTCACTCTAAATCATCT
AAAGTCATTGTCTCTGGTCTTCATCAAAGGTTTTGTCAACAATGTAGCAGGTTTCACCAGCTTTCT
GAGTTTGACTTGGAGAAAAGAAGTTGTCGCAGAAGACTCGCTTGTCATAACGAACGACGAAGAAAA
CCACAACCCACAACGGCTCTTTTCACTTCTCATTACTCTCGAATCGCTCCATCTCTTTACGGAAAC
CCCAATGCTGCAATGATTAAAAGCGTTTTGGGAGATCCTACTGCGTGGTCAACCGCAAGATCAGTG
ATGCAGCGGCCTGGACCGTGGCAGATTAATCCAGTTAGGGAAACCCATCCACACATGAATGTTTTA
TCACATGGAAGCTCAAGCTTTACTACATGTCCAGAGATGATAAACAACAATAGCACAGATTCAAGC
TGTGCTCTCTCTCTTCTGTCAAACTCATACCCAATTCATCAGCAGCAACTTCAGACACCAACAAAT
ACATGGCGACCATCTTCTGGTTTCGACTCGATGATCTCATTCTCCGATAAGGTTACAATGGCTCAG
CCACCGCCCATTTCAACCCATCAGCCGCCCATCTCAACACATCAGCAGTACCTCAGCCAAACTTGG
GAAGTCATCGCGGGCGAAAAGAGCAATTCACATTATATGTCTCCTGTGAGTCAAATCTCGGAGCCA
GCAGATTTCCAGATAAGCAATGGCACCACAATGGGTGGATTTGAGCTGTATCTTCATCAGCAGGTT
CTGAAGCAATACATGGAACCCGAGAACACAAGAGCTTATGACTCCTCCTCAACATTTCAATTGG
TCTCTTTGA

SEQ ID NO: 235, Arabidopsis thaliana Arath_SPL15 deduced polypeptide sequence
MELLMCSGQAESGGSSSTESSSLSGGLRFGQKIYFEDGSGSRSKNRVNTVRKSSTTARCQVEGCRM
DLSNVKAYYSRHKVCCIHSKSSKVIVSGLHQRFCQQCSRFHQLSEFDLEKRSCRRRLACHNERRRK
PQPTTALFTSHYSRIAPSLYGNPNAAMIKSVLGDPTAWSTARSVMQRPGPWQINPVRETHPHMNVL
SHGSSSFTTCPEMINNNSTDSSCALSLLSNSYPIHQQQLQTPTNTWRPSSGFDSMISFSDKVTMAQ
PPPISTHQPPISTHQQYLSQTWEVIAGEKSNSHYMSPVSQISEPADFQISNGTTMGGFELYLHQQV
LKQYMEPENTRAYDSSPQHFNWSL

SEQ ID NO: 236, Arabidopsis thaliana Arath_SPL9 (At2g42200) nucleic acid sequence AY150378
ATGGACATGGGTTCCAACTCCGGTCCGGGTCATGGTCCGCGTCAGGCAGAGTCGGGTGGTTCCTCC
ACTGAGTCATCCTCTTTCAGTGGAGGGCTCATGTTTGGCCAGAAGATCTACTTCGAGGACGGTGGT
GGTGGATCCGGGTCTTCTTCCTCAGGTGGTCGTTCAAACAGACGTGTCCGTGGAGGCGGGTCGGGT
CAGTCGGGTCAGATACCAAGGTGCCAAGTGGAAGGTTGTGGGATGGATCTAACCAATGCAAAAGGT
TATTACTCGAGACACCGAGTTTGTGGAGTGCACTCTAAAACACCTAAAGTCACTGTGGCTGGTATC
GAACAGAGGTTTTGTCAACAGTGCAGCAGGTTTCATCGACTTCCGGAATTTGACCTAGAGAAAAGG
AGTTGCCGCAGGAGACTCGCTGGTCATAATGAGCGACGAAGGAAGCCACAGCCTGCGTCTCTCTCT
GTGTTAGCTTCTCGTTACGGGAGGATCGCACCTTCGCTTTACGAAAATGGTGATGCTGGAATGAAT
GGAAGCTTTCTTGGGAACCAAGAGATAGGATGGCCAAGTTCAAGAACATTGGATACAAGAGTGATG
AGGCGGCCAGTGTCGTCACCGTCATGGCAGATCAATCCAATGAATGTATTTAGTCAAGGTTCAGTT
GGTGGAGGAGGGACAAGCTTCTCATCTCCAGAGATTATGGACACTAAACTAGAGAGCTACAAGGGA
ATTGGCGACTCAAACTGTGCTCTCTCTTCTGTCAAATCCACATCAACCACATGACAACAACAAC
AACAACAACAACAACAACAACAACAACAATACATGGCGAGCTTCTTCAGGTTTTGGCCCGATG
ACGGTTACAATGGCTCAACCACCACCTGCACCTAGCCAGCATCAGTATCTGAACCCGCCTTGGGTA
TTCAAGGACAATGATAATGATATGTCTCCTGTTTTGAATTTAGGTCGATACACCGAGCCAGATAAT
TGTCAGATAAGTAGTGGCACGGCAATGGGTGAGTTCGAGTTATCTGATCACCATCATCAAAGTAGG
AGACAGTACATGGAAGATGAGAACACAAGGGCTTATGACTCTTCTTCACCATACCAACTGGTCC
CTCTGA

FIGURE 26

SEQ ID NO: 237, Arabidopsis thaliana Arath_SPL9 deduced
polypeptide sequence
MEMGSNSGPGHGPGQAESGGSSTESSSFSGGLMFGQKIYFEDGGGGSGSSSSGGRSNRRVRGGGSG
QSGQIPRCQVEGCGMDLTNAKGYYSRHRVCGVHSKTPKVTVAGIEQRFCQQCSRFHQLPEFDLEKR
SCRRRLAGHNERRRKPQPASLSVLASRYGRIAPSLYENGDAGMNGSFLGNQEIGWPSSRTLDTRVM
RRPVSSPSWQINPMNVFSQGSVGGGGTSFSSPEIMDTKLESYKGIGDSNCALSLLSNPHQPHDNNN
NNNNNNNNNNNTWRASSGFGPMTVTMAQPPPAPSQHQYLNPPWVFKDNDNDMSPVLNLGRYTEPDN
CQISSGTAMGEFELSDHHHQSRRQYMEDENTRAYDSSSHHTNWSL SEQ ID NO: 238, Aquilegia formosa x Aquilegia pubescens SPL
nucleic acid sequence contig of DR915312 DR949057.1
ATGGAAATGGGTTCCAGCTCTTTCGCTGGTGGTGGGGGTAAGGGTGCTTCTGGTTCATCTGATTCT
TCACTGAATGGTTTGAAATTTGGGAAGAAAATCTACTTTGAAGATGTGGGTATTGGAGTTTTAGGC
AAGTCAAGTGTTGGGTCTCCGTCAATTTTGGTTTCTGAAGCTCGGTTGCCACCGGCTTCGTCGGTG
AAGAAGGGTAGAGGGGTTTTGCAAGGACAACCACCTAGATGTTCTGTTGAAGGTTGTAAGCTTGAT
CTTACTGATGCTAAGCCTTATTACTCAAGGCACAAAGTCTGTGGTATGCACTCTAAATCTCCTAAA
GTAATTGTTGGTGGTTTGGAGCAGAGGTTTTGCCAGCAGTGTAGCAGATTTCATCTACTCTGTGAA
TTTGACCAAGGCAAGCGAAGCTGTCGTAGACGTCTAGCTGGCCACAATGAGCGTCGAAGAAAACCA
CAACCTGGATCAATATTTTCACCGCGCTATGGTCGTGTGTCACCATCTTTCCAAGAAAATAGCACC
AGAGGAGGAGGTTTTCTAATGGACTTCACAGCGTACCCAAGGCTGGCAGGAAGGGATGCATGGCAA
ACAGTAAAAGCCGGCAATTGGGCAGATGGAAACCAAACCTCTCCTATTAAGAAGCTTCTCCCACAT
CAATGGCAAGGCAATTCAGAGAATCCTCCTCCTATTGTCTATTCTCAGGCACCTCACCCGTATCTG
CAAGGTGTGGCTAGTGGATCAATTTTTTCCAGTACAAGAATACCTTCAGCCGAGTGTTTTGCTGGT
GTCTCTGACTCCAGCTGTGCTCTCTCTCTTCTGTCAAATCAACCATGGAACCCCAGAAACCAGACT
TCCGATTTGGAGGTGAATAACATAGTGAACGGTGAAGGGGTATCCATGGCAAGATCTATAGCACCT
CATAGTGCTGTAGTCACCAACTTCACGAACAACACATGGAATTTTAAGGGCAACAGTGAAGTTAGT
GGCAGTTCCCATGAAATTCCACGTCAGGTGTCGCAGCCAGTCACCAATCATTTCTCCAGTGAGCTC
GATCTAGCTCAGCAGGGGAACAGGCAGTACATGGAGATCCGGCATTCAAGGGATTTTGGTTCTTCC
ACTCACCAGATGCACTGGTCTCTTTGA SEQ ID NO: 239, Aquilegia formosa x Aquilegia pubescens SPL
deduced polypeptide sequence
MEMGSSSFAGGGGKGASGSSDSSLNGLKFGKKIYFEDVGIGVLGKSSVGSPSILVSEARLPPASSV
KKGRGVLQGQPPRCSVEGCKLDLTDAKPYYSRHKVCGMHSKSPKVIVGGLEQRFCQQCSRFHLLCE
FDQGKRSCRRRLAGHNERRRKPQPGSIFSPRYGRVSPSFQENSTRGGGFLMDFTAYPRLAGRDAWQ
TVKAGNWADGNQTSPIKKLLPHQWQGNSENPPPIVYSQAPHPYLQGVASGSIFSSTRIPSAECFAG
VSDSSCALSLLSNQPWNPRNQTSDLEVNNIVNGEGVSMARSIAPHSAVVTNFTNNTWNFKGNSEVS
GSSHEIPRQVSQPVTNHFSSELDLAQQGNRQYMEIRHSRDFGSSTHQMHWSL SEQ ID NO: 240, Gossypium hirsutum SPL nucleic acid sequence
DT566400
ATGGAAATGGGTTCGGGCTCTTTGACTGAGTCGGGCGGTTCTCCCACCAACTCTTCCGCCGAGTCA
CTCAACGGCTTGAAGTTCGGTAAAAAGATCTACTTTGAGGATACAGCCGCTGTCGCCGCCGCCGCT
GGTGGTAAAAGTGTTGGTGGTGGTGCAAACATAGGGACTCCATCCAAGTCCGGTCCAGCATCTTCA
AGCTTAGCCGGGTCGTGTAGGAAAGCCAGGGTTGATGGAATGGCGCAAGGGGTTCTGCCTTCTAGG
TGTCAAGTAGAAGGGTGTAAAGTGGATCTAGTGATGCTAAGGCTTACTATTCAAGGCATAAGGTT
TGTTGTATGCACTCTAAGTCATCTAAAGTCATTGTTGCTGGTCTCGAGCAAAGATTTGTCAGCAG
TGTAGCAGATTTCATCAGCTTTCTGAATTTGACAAAGGGAAACGGAGTTGTCGTAGACGGCTTGCA FIGURE 26 (continued)

```
GGTCACAATGAGCGACGCAGGAAACCACCACCTGGATCATTATTTTCCTCTCCTTATGGCCGGCTT
TCTTCCTCTATTATTGAAAATGGCAGTAGAGGTGGAAGCTTTATAGTGGATTTCTCAGCATACCCA
AGGCTTTCAGGAAGGGATGCATGGCCAGCAGCTCGATCGTTAGAATGCATAACTGGAAATCGAAGC
ACAGCCACTGGAAGCTCATTTTCACATCCACGGCAAAACAACTCCAGCAAACCTCCTCATGACCAT
TTCTTGCAAGGTTCACCATGTGGGACTAGTTTCTCCAGCACTGGAATTTCTCCAGGAGAATGCTTC
ACAGGGTCTGGTGACTCAAGCTGTGCTCTCTCTTCTGTCAAATCAACCGTGGGGCTCCAGGAAC
CAGGCTTTGAATTTTTCTGTAAATGGCGTGATAAGTACTGAAGGGTCCTCTGCGGCACAACCAACA
ACGCTTCATGGTGCAGTTGTGAACCCTTATTCAAATGCCTCTTTGGATTTCAATGGCAGTGACACT
GTTCGCAGTTCTCACAAGATGCTGCCACACCTAGATTTGGGTCAAATCCCAGACCCTGTTAACTGT
CAATTCTCTAGTGACCTTGAGTTGTCTCAACAAAGCTGGAGGTCATATATCGAACATGAGCAGTCC
GGGGCAGCCTATGACGACTCCATGCAGCATATCCACTGGACGCTCTAA
```

SEQ ID NO: 241, Gossypium hirsutum SPL deduced polypeptide sequence
```
MEMGSGSLTESGGSPTNSSAESLNGLKFGKKIYFEDTAAVAAAAGGKSVGGGANIGTPSKSGPASS
SLAGSCRKARVDGMAQGVLPSRCQVEGCKVDLSDAKAYYSRHKVCCMHSKSSKVIVAGLEQRFCQQ
CSRFHQLSEFDKGKRSCRRRLAGHNERRRKPPPGSLFSSPYGRLSSSIIENGSRGGSFIVDFSAYP
RLSGRDAWPAARSLECITGNRSTATGSSFSHPRQNNSSKPPHDHFLQGSPCGTSFSSTGISPGECF
TGSGDSSCALSLLSNQPWGSRNQALNFSVNGVISTEGSSAAQPTTLHGAVVNPYSNASLDFNGSDT
VRSSHKMLPHLDLGQIPDPVNCQFSSDLELSQQSWRSYIEHEQSGAAYDDSMQHIHWTL
```

SEQ ID NO: 242, Ipomoea nil SPL nucleic acid sequence contig of BJ576204.1 BJ556115 BJ567301
```
ATGGAACTGGGTTCTTCTTCTTCTTCTACCTCTACCTCCGCCGACTCCTCATCCGACGGCTTGAAG
TTCGGCAAAAAGTCTACTTTGAAGATGCGGGTGGTGGGAGTGGTGGGTCGTCGCTGCCGGCCAAG
AGAGGGAGGAGCGCGGTGGCGCAAGGCGGACAGCCACCCAGGTGCCAGGTGGAAGGGTGCAAGGCA
GATCTGAGTGAATTTAAGGCTTATTACTCAAAGCATAAAGTTTGTGGTATGCACTCCAAGTCTCCT
AAGGTCATTGTTTCTGGGCTTGAACAGAGATTCTGCCAGCAGTGCAGCAGGTTTCATCAATTGAGT
GAATTTGATCAAGTAAAAAGGAGCTGCCGTAGGCGTTTGGCTGGTCATAATGAGCGTCGTAGGAAG
CCCCCACTTGGATCCATATTGTCCACACATTATGGGACTCTTTCTTCTTCAATGTTTGGAAACAAT
GGCCACTTTGTGATGGATTTCGCCTCATACCCATATCCGGGTGGTAAGGGCTCATGCGGCCAAGT
ACCAATGGCGTGGGGAACTTTCTTCAACAACCATGGCAGAGAAACTCTGAAGATCCCCCACCCAAG
CTTCTTTTGCTAGGTTCGGATGCTGCTGCTAGGGCTACTTATCCCAGTCCTTGTGGAGAATACTTC
AATGGGGTCTCGGATTCCACCCGTGCTCTCTCTCTTCTGTCAAACTCAAATCAGCCCTGGGGCTCG
AGAAACCAACAACCCTCTGGTCTCGGGGTTAATAGCTTACTTAACACTGATGGAACGCTTGCTGTT
CATCCATCCGGTTCCCATGCTGCCGTTATCAATGAATTTTCTTCAAGTCCATGGGGTTTTAAAGGC
AATCAAGCCACTACCAGCTCAGATAAGATCCTTCCTGATAGTCACTATTCTGGTGAGCTCGAGATG
ATGGCTCATCAACAAACTGGACGAGCATACATGGGAATGGAGTACTCGACGGGTTATGATTCTTCT
GTCCAGAATGTGCACTGGACTCTCTGA
```

SEQ ID NO: 243, Ipomoea nil SPL deduced polypeptide sequence
```
MELGSSSSTSTSADSSSDGLKFGKKVYFEDAGGGSGGSSLPAKRGRSAVAQGGQPPRCQVEGCKA
DLSEFKAYYSKHKVCGMHSKSPKVIVSGLEQRFCQQCSRFHQLSEFDQVKRSCRRRLAGHNERRRK
PPLGSILSTHYGTLSSSMFGNNGHFVMDFASYPYPGGKGSWRPSTNGVGNFLQQPWQRNSEDPPPK
LLLLGSDAAARATYPSPCGEYFNGVSDSTRALSLLSNSNQPWGSRNQQPSGLGVNSLLNTDGTLAV
HPSCSHAAVINEFSSSPWGFKGNQATTSSDKILPDSHYSGELEMMAHQQTGRAYMGMEYSTGYDSS
VQNVHWTL
```

FIGURE 26 (continued)

SEQ ID NO: 244, Lactuca sativa SPL nucleic acid sequence contig of DY966949 DW119178
ATGGAGATGGGTGGTTCGAGTGGTTCTTCGGAGTCGCAACTGCTCAAAATTGGTTTGCAATTCGGG
AAAGAAATCTATTTTGAGGATGTGGGAGTTGGAGCTCAGGTTAAATCCGATGATGGGTTGTCTCCG
GCGAGCGGCGGCGATGCTGCTGGAGGGCCGCAGAAGAAAGGGAGAACTGCTGGTGGGGTGGTGAGT
GGTTTTGGACAACAGCAACCACCGAGGTGTCAGGTGGAAGGTTGTAATCTGGATCTGAGTGATGCT
AAAAGTTACTATTCAAGGCACAAAGTTTGTGGTGCTCATTCGAAAACGGCTAAGGTCATTGTTAAT
GGCCTTGAACAGAGATTCTGCCAACAGTGCAGCAGGTTCCATCAACTACCAGAGTTTGACCAGGGA
AAAAGAAGCTGCAGGAGACGATTGGCTGGGCACAATGAACGTAGAAGAAAGCCATCTCTGCTATCC
ACTCGCTATGGAACTGTCTCCTCCTCAATCTTTGAAAACAATGGGAATTCTGGAGGCTTTCTAATG
GACTTTTCGTCATGCTCAAGAGGAAGGATTCAGTGGCCAGGAACAAGGGCGGCACCACCGCCTCGA
GCCGCCATCGACCTCCCAATTGCCGGAGAAAAGTTCCCACCGCTTCCATGGCAAAGCAACCTGGAT
AATCCACCTCCTTATGTTCCACCAGGAGGGTGTTTTAATGGAGTCCATGAGGACTCCAACTGTGCT
CTCTCTCTTCTGTCAAATCACTCATCTGGCTCAAGGAACCAATCCCTGAGCCATGAGTACTATATC
AACCCTCAAGCTGGTGCATATGTGCACCAGCTTCATCAACAACAACCCCAACCGCAGCTGGGTTC
GGAACCATGGTTGAGGTCACCGCCACTCGCTGGGTATACGACACCCATCATGCCCATTTGGGTTTG
GGTCACGTCCCACAGTCTGGTGGTGGCTACTCTGGTGAGGTTGGACTTGGTCCACATGGTGGGGGA
AGGCGATATGACTCATCTGTTGACCACATTGACTGGTCACTTTGA

SEQ ID NO: 245, Lactuca sativa SPL deduced polypeptide sequence
MEMGGSSGSSESQLLKIGLQFGKEIYFEDVGVGAQVKSDDGLSPASGGDAAGGPQKKGRTAGGVVS
GFGQQQPPRCQVEGCNLDLSDAKSYYSRHKVCGAHSKTAKVIVNGLEQRFCQQCSRFHQLPEFDQG
KRSCRRRLAGHNERRRKPSLLSTRYGTVSSSIFENNGNSGGFLMDFSSCSRGRIQWPGTRAAPPPR
AAIDLPIAGEKFPPLPWQSNLDNPPPYVPPGGCFNGVHEDSNCALSLLSNHSSGSRNQSLSHEYYI
NPEAGAYVHQLHQPTTGTGAGFGTMVEVTATGWVYETHDAHLGLGHVPQSGGGYSGEVGLGPHGGG
RRYDSSVDHIDWSL

SEQ ID NO: 246, Malus domestica SPL nucleic acid sequence contig of CN891102.1, CO868185.1, CV523507
ATGGAAATGGGCTCGAGTTCTAAGACCGAGTCAGCGAGCTCTTCCTCCTCTTCGCCGCCCAACTCC
TCCGCTGAGTCACTCAACGGCTTGAAATTCGGCCGGAAAATCTACTTTGAGGATGGGGGTTTTGGA
GCTCTGCACAAATCATCATGCGGGTCTGCTGCTGGGTCTTCCTCCGCCGGGGCTACGCCGCCAAAG
AAGCAAAGGGGCGGCGGAAATTTGGGTCAGCCGCCGCGGTGTCAGGTGGAGGGCTGCGAGGTAGAT
CTGAGTGGTGCCAAAGCTTACTATTCCAGGCACAAAGTCTGTGGCTTGCACTCTAAAACTCCCACT
GTCATTGTTGCTGGTCTTGAACAGAGGTTTTGCCAACAGTGTAGCAGGTTTCATTTACTTCCTGAA
TTTGATCAAGGAAAACGTAGTTGTCGTAGACGCTTGGCTGGGCATAATGAGCGTCGTAGAAAACCA
CCTCCAGGATCCATACTGTCTACGCGTGGCAGACTTTCTTCGTCTCTCTACGAAAACAGCAGCAGA
ATTGGAAGCTTTCTGATGGACTTCACTGCATACCCAAGGTTTTCTGGGAGGGATACATGGACAACA
AGAACCTCTGAGCGAGCACCTGTTAATCAAAATGCCAATGACGCAGGGAAGTTTCTACAACAGCCG
TGGCAGAGCAACTCTGATATTTCTACATCCGGCTTTTACCTACAAGGTTCAGCAGGCGGGACTAGT
TATCCTGGTCCTGGAATTCCTCCAGGAGAATGTGTCACAGTAGTCACTGACTCAAGCTGTGCTCTC
TCTCTTCTGTCAAATCAGCCATGGGCTCTCGAAACCGAGTATTGGTGCTGGGATGAATTCCTTG
ATGAACACTCAAGGGGTACCTGTGGCTCAACCAGTCCTCATTCTGCAACCTCCAATCACTTTCCG
ACCACTTCGTGGGGTTTCAAAGGAAATGAAAATGGTAGCAGCTCACACGGGATGCTTCCAGATCTG
GGTCTCGGTCAAATCTCGCAGCCGCTTAGCAGTCAGTACTCTGGTGTGCTGGAGCTGTCTCAACAG
GGTAGGAGGCAGCAACACATGGAACTCGGACACACCAGGGGCTATGACTCCACCAGTCAGCAGATG
CACTGGTCACTTTAA

SEQ ID NO: 247, Malus domestica SPL deduced polypeptide sequence
MEMGSSSKTESASSSSSPPNSSAESLNGLKFGRKIYFEDGGFGALHKSSCGSAAGSSSAGATPPK
KQRGGGNLGQPPRCQVEGCEVDLSGAKAYYSRHKVCGLHSKTPTVIVAGLEQRFCQQCSRFHLLPE
FDQGKRSCRRRLAGIINERRRKPPPGSILSTRGRLSSSLYENSSRIGSFLMDFTAYPRFSGRDTWTT
RTSERAPVNQNANDAGKFLQQPWQSNSDISTSGFYLQGSAGGTSYPGPGIPPGECVTVVTDSSCAL
SLLSNQPWGSRNRVLGAGMNSLMNTQGVPVAQPVPHSATSNHFPTTSWGFKGNENGSSSHGMLPDL
GLGQISQPLSSQYSGVLELSQQGRRQQHMELGHTRGYDSTSQQMHWSL

SEQ ID NO: 248, Medicago trunculata SPL nucleic acid spliced from AC170989.2
ATGGATTCAGGAGGCAACTCTTCTTCAGAAGAGTCCTCACTTAATGGCTTGAAATTTGGCCAACGA
ATCTATTTCGAAGATACAGCTCTTACTGCTGCTTCTGCTGCTGCTAGTACTACCATTGCTGCT
GGTTCTCCTTCTTCTTCTGGTTCAAAGAAAGGAAGAGGTGGGTCAGTTCAACATTCTCAACCACCT
AGGTGTCAAGTTGAAGGATGTAAACTAGATCTGACTGATGCTAAAGCTTACTATTCTAGACACAAA
GTTTGTAGCATGCACTCTAAATCCCCTACTGTTACTGTTTCTGGTCTTCAACAAAGGTTTTGTCAA
CAATGTAGCAGATTTCATCAGCTTGCTGAGTTTGATCAAGGAAAAAGAAGTTGTCGGAGACGACTA
GCTGGTCATAATGAGCGTCGCAGAAAGCCCCCACCCAGCTCTCTCTTAACCTCACGTTTTGCCAGG
CTTTCTTCGTCTGTTTTTGGTAACAGCGACAGAGGTGGCAGCTTTTTGATGGAATTTGCTTCAAAT
CCGAAACATAGTCTGAGGAATTCACCCGGAAATCAAACCACAGCAATCGGTTGGCCTTGGCCGGGG
AACACGGAGTCGCCATCTAGCAACCTTTTCTTGCAAGGTTCGGTGGGTGGGACAAGCTTCCCTGGT
GCCAGGCATCCTCCCGAGGAAACTTACACTGGAGTCACAGATTCAAACTGTGCTCTCTCTCTTCTG
TCAAATCAAACATGGGGTTCTCAAAACACAGAACCAAGTCCTGGATTGAATAACATGCTGAATTTC
AACGGGACACCCATGACACAACTTGGTACATCTTCTCATGGTGTAGCCATGCATCAAATTCCAAAC
AATTACGAGGTTGTCCCTGATCTTGGTCGGGGTCACATTTTGCATCCTCTTGGTAGCCAACACTCT
GGCGAGCTTGATCTGTTGCAGCAGGGAAGGAGGCATTATATGGATGTAGAACATTCCAGGGCCTAT
GAATCTTCTCAGTGGTCACTGTAA

SEQ ID NO: 249, Medicago trunculata SPL deduced polypeptide sequence
MDSGGNSSSEESSLNGLKFGQRIYFEDTALTAASAAAASTTIAAGSPSSSGSKKGRGGSVQHSQPP
RCQVEGCKLDLTDAKAYYSRHKVCSMHSKSPTVTVSGLQQRFCQQCSRFHQLAEFDQGKRSCRRRL
AGHNERRRKPPPSSLLTSRFARLSSSVFGNSDRGGSFLMEFASNPKHSLRNSPGNQTTAIGWPWPG
NTESPSSNLFLQGSVGGTSFPGARHPPEETYTGVTDSNCALSLLSNQTWGSQNTEPSPGLNNMLNF
NGTPMTQLGTSSHGVAMHQIPNNYEVVPDLGRGHILHPLGSQHSGELDLLQQGRRHYMDVEHSRAY
ESSQWSL

SEQ ID NO: 250, Nicotiana bentamiana SPL nucleic acid sequence contig of CK284078.1, CK294165
ATGGAACTTCTGGCTTCTGCTTCTTCTTCTACTTCTACTAATTCTACTTCCCCTGACTCTCCTCCC
AACACTTTAAAATTTGGTCAAAAAATCTACTTTGAGCATGTTGGACTTCAGCACCTCAAATCAGCA
ACTGGGTCGTCGTCGTCATCGCCGCCGGTCATCGGAACTCCGGCGCCGGCGATGTCCAAGAAGGA
AGAGGGGGTGGTGTAGTTCAAGGTCGGCAACCACCTAGGTGTCAAGTTGAAGGGTGTGAAGCAGAT
CTGAGTGATGTTAAGGCTTACTATTCAAGGCACAAAGTCTGTGCTACACATTCTAAGTCCTGTG
GTCATTGTTGCTGGTCTTGAACAAAGATTTGTCAACAGTGTAGCAGGTTTCATCGGTTGCCAGAA
TTTGACCAAGGGAAACGCAGTTGCCGCAGGCGCCTAGCAGGCCATAATGAGCGTCGGAGGAAACCT
CCACCTGGATCTCTTTTGTCTAATCGCTATGGAAGTCTTTCTTCATCAATTTGAAAACAATGGC
AGATCTGGAAGTTTTCTGGTTGACTTCACTGCATATCCGAATCTCACTGGAGGTGCATGGCCAAAT
ACTAGATCATCTGATCGAGGATGGGATAATCAATCCACTGCGTCAGGGAAGCTTCTCCAAAGTCAT
TGGCTGAACAGTTCTGAAAATCCGACATCCGACCTTGTTCTGCAAGGTTCAGTTGCTAGGGGTGCC

FIGURE 26 (continued)

```
AATTATTCTGGTCCTGGTATTATTCCTTCCGGAAACTGCTTCTCTGGAGTCTCAGATTCCAATGGT
GCTCTCTCTCTTCTGTCAAATGAGCCATGGGGCTCGAGGAACCAATCCTCTAGCCTCGGGGTTAAC
GGCTTGGTCAACACTGATGGCGGACATACCGTTCACCCATCGGGTTCCCATGCTGCTCCTGTCAAT
CACTACTCAGGCCCTCTATGGGGATTTAAAGGAAATGAAGCTAGTAGCAGTTCACATGCAATACCT
CCTGATCTCGGGCTGGGTCACATTTCTCAACATGCTGTCAATCAGTACTCTGGTGAGCCTGGGATG
GCTCAGCACAGTGGAAGACAGTACATGGGACTGGAGCATTCAAAGGGTTATAATTCTTCTGTTCAG
AATGTGCACTGGACACTTTGA
```

SEQ ID NO: 251, Nicotiana bentamiana SPL deduced polypeptide sequence
```
MELLASASSSTSTNSTSPDSPPNTLKFGQKIYFEHVGLQHLKSATGSSSSSPPVIGTPAPAMSKKG
RGGGVVQGRQPPRCQVEGCEADLSDVKAYYSRHKVCATHSKSPVVIVAGLEQRFCQQCSRFHRLPE
FDQGKRSCRRRLAGHNERRRKPPPGSLLSNRYGSLSSSIFENNGRSGSFLVDFTAYPNLTGGAWPN
TRSSDRGWDNQSTASGKLLQSHWLNSSENPTSDLVLQGSVARGANYSGPGIIPSGNCFSGVSDSNG
ALSLLSNEPWGSRNQSSSLGVNGLVNTDGGHTVHPSGSHAAPVNHYSGPLWGFKGNEASSSSHAIP
PDLCLCHISQHAVNQYSCEPCMAQHSCRQYMCLEHSKCYNSSVQNVHWTL
```

SEQ ID NO: 252, Oryza sativa SPL nucleic acid sequence XM_483285
```
ATGGAGATGGCCAGTGGAGGAGGCGCCGCCGCCGCCGGCGGCGGAGTAGGCGGCAGCGGCGGC
GGTGGTGGTGGAGGGGACGAGCACCGCCAGCTGCACGGTCTCAAGTTCGGCAAGAAGATCTACTTC
GAGGACGCCGCCGCGGCAGCAGGCGGCGGCGGCACTGGCAGTGGCAGTGGCAGCGCGAGCGCCGCG
CCGCCGTCCTCGTCTTCCAAGGCGGCGGGTGGTGCACCCGGCGGAGCGGCAACAACAAGGGCAAC
GGCGTGGCCGCGGCGGCGCCACCGCCGCCGCCGCCGCCGCGGTGCCAGGTGGAGGGGTGCGGC
GCGGATCTGAGCGGGATCAAGAACTACTACTGCCGCCACAAGGTGTGCTTCATGCATTCCAAGGCT
CCCCGCGTCGTCGTCGCCGGCCTCGAGCAGCGCTTCTGCCAGCAGTGCAGCAGGTTCCACCTGCTG
CCTGAATTTGACCAAGGAAAACGCAGCTGCCGCAGACGCCTTGCAGGTCATAATGAGCGCCGGAGG
AGGCCGCAAACCCCTTTGGCATCACGCTACGGTCGACTAGCTGCATCTGTTGGTGAGCATCGCAGG
TTCAGAAGCTTTACGTTGGATTTCTCCTACCCAAGGGTTCCAAGCAGCGTAAGGAATGCATGGCCA
GCAATTCAACCAGGCGATCGGATCTCCGGTGGTATCCAGTGGCACAGGAACGTAGCTCCTCATGGT
CACTCTAGTGCAGTGGCGGGATATGGTGCCAACACATACAGCGGCCAAGGTAGCTCTTCTTCAGGG
CCACCGGTGTTCGCTGGCCCAAATCTCCCTCCAGGTGGATGTCTCGCAGGGGTCGGTGCCGCCACC
GACTCGAGCTGTGCTCTCTCTTCTGTCAACCCAGCCATGGATACTACTACCCACAGTGCCGCT
GCCAGCCACAACCAGGCTGCAGCCATGTCCACTACCACCAGCTTTGATGGCAATCCTGTGGCACCC
TCCGCCATGGCGGGTAGCTACATGGCACCAAGCCCTGGACAGGTTCTCGGGGCCATGAGGGTGGT
GGTCGGAGCGTGGCGCACCAGCTACCACATGAAGTCTCACTTGATGAGGTGCACCCTGGTCCTAGC
CATCATGCCCACTTCTCCGGTGAGCTTGAGCTTGCTCTGCAGGGGAACGGTCCAGCCCCAGCACCA
CGCATCGATCCTGGGTCCGGCAGCACCTTCGACCAAACCAGCAACACGATGGATTGGTCTCTGTAG
```

SEQ ID NO: 253, Oryza sativa SPL deduced polypeptide sequence
```
MEMASGGGAAAAAGGGVGGSGGGGGGDEHRQLHGLKFGKKIYFEDAAAAAGGGGTGSGSGSASAA
PPSSSSKAAGGGRGGGGKNKGKGVAAAAPPPPPPPPPRCQVEGCGADLSGIKNYYCRHKVCFMHSKA
PRVVVAGLEQRFCQQCSRFHLLPEFDQGKRSCRRRLAGHNERRRRPQTPLASRYGRLAASVGEHRR
FRSFTLDFSYPRVPSSVRNAWPAIQPGDRISGGIQWHRNVAPHGHSSAVAGYGANTYSGQGSSSSG
PPVFAGPNLPPGGCLAGVGAATDSSCALSLLSTQPWDTTTHSAAASHNQAAAMSTTTSFDGNPVAP
SAMAGSYMAPSPWTGSRGHEGGGRSVAHQLPHEVSLDEVHPGPSHHAHFSGELELALQGNGPAPAP
RIDPGSGSTFDQTSNTMDWSL
```

FIGURE 26 (continued)

SEQ ID NO: 254, Oryza sativa SPL II nucleic acid sequence spliced from AC108762
ATGGCGACCGGCGGCAGCGGCGGCGGCGGCGGAGGTGGAGGTGGTGGTGACGATGTCCACGGGCTC
AAGTTCGGCAAGAAGATCTACTTCGAGCAGGACGCGGCGGCGTCGGCGTCGGCGGCGGCGGTGGAG
TCGTCGTCGACGTCGTCGGGCGGAGGCGGCAAGAAGGGGAAGGGCGTGGCGGCGGCGGCGGCGCCC
CCGCCGCCGCTGCCGCCGAGGTGCCAGGTGGAGGGTTGCGGCGTGGATCTGAGCGGCGTCAAGCCG
TACTACTGCCGCCACAAGGTGTGCTACATGCACGCCAAGGAGCCCATCGTCGTCGTCGCCGGCCTC
GAGCAGCGCTTCTGCCAACAGTGCAGCAGGTTCCACCAATTACCTGAATTTGATCAAGAAAAAAA
AGCTGCCGCAGACGCCTTGCAGGTCACAATGAACGCCGGAGGAAGCCGACACCTGGACCTCTTTCT
TCTCGCTATGGCCGGCTTGCTGCATCCTTTCATGAAGAGCCAGGCAGGTCCAGAAGCTTTGTGGTA
GATTTCTCATACCCAAGGGTTCCAAGCAGTGTGAGGGATGCGTGGCCTGCTATTCAGCCCAGCGAT
CGCATGTCCGGTTCAATCCAGTGGCAAGGGGCCATGAACTCCATCCTCACCGCAGCGCAGTTGCG
GGATACAGTGATCACCATGCGTTCAGCAGCCATGGTGGCTCAGCGGCTGGGGCACCAATGCTCCAC
CACCCAGCCTTTGAGCTCACCTCAGGTGGATGTCTCGCGGGAGTCGCCACCGACTCCAGCTGTGCT
CTCTCTCTTCTGTCAACTCAGCCATGGGATACTACCCAAAGCACCAGCAGCCACAACCGGTCCCCG
CCAATGTCGTCAACGGCCAGCGCCTTCGGAGGCGGCAACAACCCGGTGTCGCCCTCGGTCATGGCA
AGCAACTACATGGCGGCGAGCCCCGGCTGGAACAGCTCCAGCCGGGGCCATGACGGCGCCAGGAAC
GTGCACCTGCCGCCACCGCACGGGGTTGTGCTGAACGAGGTCCCTCCGGGCTCTGTCCACCACGGC
CATTTCTCCGGCGAGCTCGAGCTCGCACTGCAGGGAGGTGCCCCGTCCAACCGGCCGGAAGCCGAG
CATGGCTCCGGCAGCGGCGCCTTCAGCCACTCCACCAATGCCATGAACTGGTCTCTGTAG

SEQ ID NO: 255, Oryza sativa SPLII deduced polypeptide sequence
MATGGSGGGGGGGGGDDVHGLKFGKKIYFEQDAAASASAAAVESSSTSSGGGGKKGKGVAAAAAP
PPPLPPRCQVEGCGVDLSGVKPYYCRHKVCYMHAKEPIVVVAGLEQRFCQQCSRFHQLPEFDQEKK
SCRRRLAGHNERRRKPTPGPLSSRYGRLAASFHEEPGRSRSFVVDFSYPRVPSSVRDAWPAIQPSD
RMSGSIQWQGGHELHPHRSAVAGYSDHHAFSSHGGSAAGAPMLHHPAFELTSGGCLAGVATDSSCA
LSLLSTQPWDTTQSTSSHNRSPPMSSTASAFGGGNNPVSPSVMASNYMAASPGWNSSSRGHDGARN
VHLPPPHGVVLNEVPPGSVHHGHFSGELELALQGGAPSNRPEAEHGSGSGAFSHSTNAMNWSL

SEQ ID NO: 256, Solanum tuberosum SPL nucleic acid sequence contig of CK246692.1, CK254420.1
ATGGAACTGGGTTCAGTTTCTTCTTCTGGTAATTCAAGCTCATCTGATTCTTTGAATGGTTTGAAG
TTTGGTAAGAAAATCTACTTTGAAATGTGGGTGTTGGAGTTCAGGTCAAGAATGGAAGTGGGTCG
TCGCCGGTGACCGGAGATGGGAACATGCCACCGGCTCCGGCGACGACTAAGAGGGGGAGGGTGGG
TTGGTGCAGGGTGGTCATCCACCTAGGTGTCAAGTTGAAGGTTGTCAGGCAGATCTGAGTGATGCT
AAGGCTTACTATTCAAGGCATAAAGTTTGTGGTATGCACTCTAAGTCTCCTACTGTTGTTGTTGCT
GGTCTTGAACAGAGGTTTTGCCAACAGTGTAGCAGGTTCCATCAATTAACTGAATTCGACCAGGGG
AAAAGGAGTTGCCGCAGGAGACTGGCATGCATAATGAGCGTCGTAGGAAGCCTCCATCTGGATCT
CTTTTCTCTACACACTACGGGAATCTTTCTTCATCAATATTGAAAATAATAGCAGCAGATCCGGA
AGCTTTCTGGTCGACTTCAGCTCACACCAAAATGTCAATGATAGTTCATGGCCAAATACTCGAGCA
TCTGAACAAGGATGGATCATCAATCATCAGGGAAGTTCCTTCAACGTCCTTGGCTGAATAACTCT
GAAAATGCTGCCAGTGAGCTTGTTTGCAAGGTTCAGCTACCAGGACCAGTTATCCTAGTGTTCCT
TCTGGAGACTATTTTCCTGGAGTCTCAGATTCAAGTGGTGCTCTCTCTTCTGTCAAATCGGTCC
TGGGGATCAAGGAATCGATCTCCAAGTCTTGGGGTTAACAGCCAAGTTCACATTGATGGGGTACAC
ACCATTCAACCTTCAGGTTCTCATGGTGCACCTACCAATCACTTCTCAAGCCCTTCATTGAGTTTT
AAAGGAAATGAAGCTAGCAGCAGTTCACATGAGATGCCTCCTGATCTCGGTTTGGGTCAAATGTTA
CAAGCTTCTGATAATCCATACTGTGGCGAGCTTGGGATGGCTCAGCATGGTGATGGACGACAATAC
ATGGAACTGGACCAGTCCAAGGGTTATCATCCTTCTGTTCAGAATGTGCACTGGACTCTTTGA FIGURE 26 (continued)

SEQ ID NO: 257, Solanum tuberosum SPL deduced polypeptide sequence
MELGSVSSSGNSSSSDSLNGLKFGKKIYFGNVGVGVQVKNGSGSSPVTGDGNMPPAPATTKRGRGG
LVQGGHPPRCQVEGCQADLSDAKAYYSRHKVCGMHSKSPTVVVAGLEQRFCQQCSRFHQLTEFDQG
KRSCRRRLACHNERRRKPPSGSLFSTHYGNLSSSIFENNSSRSGSFLVDFSSHQNVNDSSWPNTRA
SEQGWDHQSSGKFLQRPWLNNSENAASELVLQGSATRTSYPSVPSGDYFPGVSDSSGALSLLSNRS
WGSRNRSPSLGVNSQVHIDGVHTIQPSGSHGAPTNHFSSPSLSFKGNEASSSSHEMPPDLGLGQML
QASDNPYCGELGMAQHGDGRQYMELDQSKGYHPSVQNVHWTL

SEQ ID NO: 258, Vitis vinifera SPL nucleic acid sequence contig of CV098277, CV092812.1
ATGGAAAGGGGTTCGAGCTCTTTGACCGTTTCCAGCTCTTCGGCCAACTCGTCTGAGTCGCTCAAC
GGGTTGAAATTTGGGCAGAAGATATATTTTGAAGATTTGGGCGTTGGAGCTCCGGCCAAATCGGGA
ACCGGCTCCTCCTCCTCCTCCTCTGCCGCCGGCTCCGGTGGTCGCCCACCTCCGGCGCCGCCAAAG
AAGGTAAGAGGTAGTGGGGTTGTTCAGGGAGGCCAACCACCGAGGTGTCAAGTTGAAGGGTGTAAA
CTAGATCTGAGTGATGCCAAAGCTTACTATTCAAGGCATAAAGTGTGTGGTATGCATTCGAAGTCT
CCAACGGTCATTGTTGCGGGCCTTGAGCAGAGGTTTTGCCAGCAGTGTAGCAGATTTCATCAGCTT
GCCGAATTTGACCAAGGAAAACGAAGTTGTCGTAGGCGCCTGGCTGGTCATAATGAGCGTCGCAGG
AAGCCACCACCTGGATCTTTATTGTCCTCACGCTATGGGCGACTTTCTTCATCCATTTTTGAAAAC
AGCAGCAGGGTGGGAGGAGGCTTTCTGATGGACTTTGCTGCATACCCAAGGCATCCCGAGAGGGAT
ACTTGGCCAACTACAAGAGCATCTGATCGGGTACCTGGAAATCAAACCACTGCGATGGGAAGGTTT
CTTCCACATCCATGCAGAGCAACTCTGAGAATCCTCTCTTTCTGCAAGGTTCAGCCGGCGGGACC
AGCTTTCATGGTCCTGGAATTCCTTCAGGAGAATGTTTCACAGGGGCCTCCGACTCAAGCTGTGCT
CTCTCTCTTCTGTCAAATCAGCCATGGAGCTCCAGGAATCGAGCATCTGGTCTTGGAGCAAACAGC
TTCATGAATCCTGAAGGGGCATCCATGGCGCAACCCACAGCTCCTCATAGTGCAGCTATCAATCAC
TTCCCAAGCACCTCGTGGGATTTCAAGGGCAATGAAGGTAGTAGCAGTTCGCAGGAGATGCCACCT
GATCTTGGTCTTGGTCAAATTTCACAGCCTATTAATAGCCAGTTCTCAGGTGGGGCGAGTTGCCC
CAACAGAGTGGAAGGCAATACATGGAACTCGAGCACTCCAGGGCTTATGACACTTCCACTCAGCAG
ATGCACTGGTCACTTTAG

SEQ ID NO: 259, Vitis vinifera SPL deduced polypeptide sequence
MERGSSSLTVSSSSANSSESLNGLKFGQKIYFEDLGVGAPAKSGTGSSSSSAAGSGGRPPPAPPK
KVRGSGVVQGGQPPRCQVEGCKLDLSDAKAYYSRHKVCGMHSKSPTVIVAGLEQRFCQQCSRFHQL
AEFDQGKRSCRRRLAGHNERRRKPPPGSLLSSRYGRLSSSIFENSSRVGGGFLMDFAAYPRHPERD
TWPTTRASDRVPGNQTTAMGRFLPHPWQSNSENPLFLQGSAGGTSFHGPGIPSGECFTGASDSSCA
LSLLSNQPWSSRNRASGLGANSFMNPEGASMAQPTAPHSAAINHFPSTSWDFKGNEGSSSSQEMPP
DLGLGQISQPINSQFSGGGELPQQSGRQYMELEHSRAYDTSTQQMHWSL

SEQ ID NO: 260, Zea mays SPL nucleic acid sequence contig of EB160653, DY235599, DV029129
ATGGAGTCCGGCGGTGGCGGGGACGACCAGCTGCACGGCCTCAAGTTCGGCAAGAAGATCTACTTC
GAGGACGCCGCCGGCTCCAGCAGCGGCAGCAGCAGCGGCGGTGGCAGCGCGCCCGCGCCTCCAGCG
ACGCAGCAGCCGTCGCCGCCGGCCGCTTCGCCTAGGGCCCCGGCCGGCGGCGGCAGGAGGGGCAGG
GCCGCGGCCGGCGGCGCGGGCCCCTCGACGGCGCCCGCGCCCGCGCGCTGCCAGGTCGACGGCTGC
AACGTTGACCTCACCGACGTCAAGCCCGCCTACTACTGCCGCCACAAGGTGTGCAAAATGCACTCC
AAGGAGCCCCGCGTCCTCGTCAACGGCCTCGAGCAGCGCTTCTGCCAGCAGTGCAGCAGGTTCCAC
CAGCTGCCTGAATTCGACCAGCTAAAGAAGAGCTGCCGCAAACGCCTCGCAGGCCACAACGAGCGC
CGGAGGAGGCCGCCGCCTGGACCCCTTGCGTCACGATACGGCCGTCACGCTGCGTCGCTCGGCGAG
CCCGGCAGGCTCAGAAGCTTCATGCTGGATTTCTCGTACCCGAGGGTCTCAAGCGCCATGAGGGGT FIGURE 26 (continued)

```
GGGTTTCCCGCGGTGAGGGCCGGTGGTGAAAGGGTGCCTGGCGGGATCCAGTGGCAAGCGGGCTTG
GATCCTCGTCACCACCAAGGCGCGGTCGCGGGATACGGCGCCCACTATGGGAGCGAGGGTGGTAGC
TCGTCGTCGGCGAGGCCGCCGGTGTTCCCTGGCCCGGAGCTGCCCCCAGGTGGATGCCTTGCAGGA
GTCCCCGCGGACTCCAGCTGTGCTCTCTCTCTTCTGTCAACTCAGCCATGGGATGCTGCCCACAGC
CACAGCCACAGCCACGCTGCGCCAACAGCGGGTTTCGACGGCGGCAGCCCTGTGGCGCCCTCCCTC
ATGGCGGCGAGTAGCTACATCGCGCCGAGCCCCTGGACCGAGACCGACTCCTGGGGCCACGAAGGC
GGGCGGAGCGTGCCTCAGCTGCCACCTGACGACGTCCCCCTCGGCGAGGTGCACTCCGGCTCGAGC
AGCCACCACGGCCAGTTCTCAGGTGAGCTCGAGCTCGCCCTGCAGGGAAACAGGCCAGCGCCAGGG
TCGGCGGCACCGCCAGCGCCGCGCAATAATCAGGGCTCCGCGGGCACGTTCGACCAGGCTGGCAAC
ACGATGGACTGGTCGCTCTAG
```

SEQ ID NO: 261, Zea mays SPL deduced polypeptide sequence
```
MESGGGGDDQLHGLKFGKKIYFEDAAGSSSGSSSGGGSAPAPPATQQPSPPAASPRAPAGGGRRGR
AAAGGAGPSTAPAPARCQVDGCNVDLTDVKPAYYCRHKVCKMHSKEPRVLVNGLEQRFCQQCSRFH
QLPEFDQLKKSCRKRLAGHNERRRRPPPGPLASRYGRHAASLGEPGRLRSFMLDFSYPRVSSAMRG
GFPAVRAGGERVPGGIQWQAGLDPRHHQGAVAGYGAHYGSEGGSSSSARPPVFPGPELPPGGCLAG
VPADSSCALSLLSTQPWDAAHSHSHSHAAPTAGFDGGSPVAPSLMAASSYIAPSPWTETDSWGHEG
GRSVPQLPPDDVPLGEVHSGSSSHHGQFSGELELALQGNRPAPGSAAPPAPRNNQGSAGTFDQAGN
TMDWSL
```

SEQ ID NO: 262, Zea mays SPL II nucleic acid sequence contig of AJ011619, DV033513.1, DY532686.1
```
ATGGCGACCGGCGGCGGCAGCAGCAGGAGCGACGACGTGCGCGGGCTCAAGTTTGGCAAGAAGATC
TACTTCGAGCAGGACGGCGGGAGCGGGAGCGGGGCGGGGGCGGTGGGCGGCAGGAAGGGGAAGGGC
GTGGCCACCGGTGGCGCGAGGCCGGCGTCCGCCGCCTCCGCAGCCCAGCCGCCGAGGTGCCAGGTG
GACGGGTGCGGCGTGGATCTGAGCGCCGTCAAGCAGTACTACTGCCGGCACAAGGTGTGCAACATG
CACTCCAAGGAGCCGCGCGTCTTCGTCGCCGGCATCGAGCAGCGCTTCTGCCAACAGTGCAGCAGG
TTCCACCAGCTACATGAATTTGACCAAGGGAAACGTAGCTGCCGCCGCCGCCTCATCGGTCACAAC
GAGCGCCGGAGGAAGCCACCACCTGGACCTCTCACTTCACGATATGGCCGGCTCGCTGCATCACTT
CAAGAGCCTGGCAGGTTCAGAAGCTTCCTGCTCGACTTCTCGTACCCAAGGGTTCCAAGCAGCGTG
AGGGATGCGTGGCCAGGAATCCAGCACGGTGGCGACAGGATGCTGGGCACCGTCCAGTGGCATGGG
CACCAAGAACCTCCTCACCCACACCGCAGTGCAGCTGCTGGCTATGGCAACCATGCTGCATACAAC
TGCCATGGCGGCTTGGTAGCAGGCGGGGCCCCAATGCTCTCCTCTGCCGCCTTTGAGCTCCCGCCT
GGCGGATGTGTCGCGGGAGTTGCCGCCGACTCCAGCTGTGCTCTCTCTCTTCTGTCAACTCAGCCA
TGGGACACGACCTCCCACGACCACCGGTCCCCAGCAATGCCCGCGGCCGGCGCCTTCGACGGCACC
CCGGTGGCGCCGTCCGTCATGGCGAGCAGCTACGCGGCGTCGAGCGCCTGGACGGGCTCGCGGGAC
CCCGCTGCCGACGGCGCCAGGAACGCGCAGCGTCTCGACGATGCTCTGCACCTGGTCCACCCAGGC
TCCGCGGCGGTCCACTTCTCCGGCGAGCTCGAGCTCGCCCTGCAGGGAAGCGGCGGGCCGCCACAC
CTGCCGCGCGTCGACCATGGCGGCTCCGGCGGCGGCACCTTCAACCATTCCACCACCAGCGCGATG
AACTGGTCCCTGTAG
```

SEQ ID NO: 263, Zea mays SPL II deduced polypeptide sequence
```
MATGGGSSRSDDVRGLKFGKKIYFEQDGGSGSGAGAVGGRKGKGVATGGARPASAASAAQPPRCQV
DGCGVDLSAVKQYYCRHKVCNMHSKEPRVFVAGIEQRFCQQCSRFHQLHEFDQGKRSCRRRLIGHN
ERRRKPPPGPLTSRYGRLAASLQEPGRFRSFLLDFSYPRVPSSVRDAWPGIQHGGDRMLGTVQWHG
HQEPPHPHRSAAAGYGNHAAYNCHGGLVAGGAPMLSSAAFELPPGGCVAGVAADSSCALSLLSTQP
WDTTSHDHRSPAMPAAGAFDGTPVAPSVMASSYAASSAWTGSRDPAADGARNAQRLDDALHLVHPG
SAAVHFSGELELALQGSGGPPHLPRVDHGGSGGGTFNHSTTSAMNWSL
```

FIGURE 26 (continued)

SEQ ID NO: 264, Sorghum propinquum SPL partial nucleic acid sequence BF422188
ATGGAGTCCGGTGGCGCCAGTGGCGGCGGCGGCGGGGACGACCAGCTGCACGGCCTCAAGTTCGGC
AAGAAGATCTACTTCGAGGACGCCGCCGCGGTCGGCTCCAGCAGCGGTGGCGGTGGCGGTGGCAGT
GGCAGTGCTAGCGCGACCCCCGCGCCTCCAGCGACGCAGCAGCCGTCCCCGCCGCAGGCCGCTTCG
CCCAGGGCAGCCAGCGGCGGCGGCGGCAGGAGGGGCAGGGCCGCGGGCGGCCCCTCCCCGGCGCCC
GCGCCCGCGCGCTGCCAGGTCGACGGCTGCAACGTGGACCTCACCGACGTCAAGCCCTACTACTGC
CGCCACAAGGTCTGCAAAATGCACTCCAAGGAGCCCCGCGTCGTCGTCAACGGCCTCGAGCAGCGC
TTCTGCC

SEQ ID NO: 265, Sorghum propinquum partial SPL deduced polypeptide sequence
MESGGASGGGGGDDQLHGLKFGKKIYFEDAAAVGSSSGGGGGSGSASATPAPPATQQPSPPQAAS
PRAASGGGGRRGRAAGGPSPAPAPARCQVDGCNVDLTDVKPYYCRHKVCKMHSKEPRVVVNGLEQR
FC

SEQ ID NO: 266, Allium cepa SPL partial nucleic acid sequence CF444518.1
ATGGAAATGGGTTCGAGCTCTGAGCCAATTTCTGACTCTCTCGATGGGCTCACATTCGGCGAAAAA
ATTTACTTTGAAGATTCCACTACCAGTACTGCAAGTACTACTAGCAATACAATTGCTGCTCCTCCC
AAAAAGGGAAAATCTTTAGCTTCTTCGTCCACTAATATCAACTCTAATCAGCAACAAATAAGCATA
CCTAGATGCCAGGTTGAAGGATGCAAAGTTGATTTGACTGGAGCTAAAGCCTATTACTGCAGGCAT
AAGGTTTGCGGAGTTCATTCAAAATCACCAAAAGTTGTGGTTGCTGGAATTGAACAGAGGTTTTGT
CAGCAGTGCAGCAGGTTCCACCAGTTGCAAGAATTTGACCAAGGAAAAAGAAGCTGCCGCAGACGC
CTAGCTGGACACAATGAGCGTCGTAGAAAGCCGCCTCCAGGCCCTTCCCGTTATGGAAGGATGTCA
TCATCTGTCTATGATGGCAGTAACAGATTCAGAGGATTCCTGATGGACTTCAGTTACCCGAGGCCC
ATACAGCCTCCTCCAGGAGATCATCTATGGCCTAGACTGTCCAACATTCCATCATACCCAGCAAAC
CCAAACACTGCATCTAACATTCATGTTGCTCAACCGTACATGCATGCAATGAATCACTACAGTTCC
GAGCTTCCACACAGGAATACATGGTCTGGCGTCTGCGACTTGAGCTGTGCTCTCTCTTCTGTCA
CTCAAC

SEQ ID NO: 267, Allium cepa partial SPL deduced polypeptide sequence
MEMGSSSEPISDSLDGLTFGEKIYFEDSTTSTASTTSNTIAAPPKKGKSLASSSTNINSNQQQISI
PRCQVEGCKVDLTGAKAYYCRHKVCGVHSKSPKVVVAGIEQRFCQQCSRFHQLQEFDQGKRSCRRR
LAGHNERRRKPPPGPSRYGRMSSSVYDGSNRFRGFLMDFSYPRPIQPPPGDHLWPRLSNIPSYPAN
PNTASNIHVAQPYMHAMNHYSSELPHRNTWSGVCDLSCALSLLSLN

SEQ ID NO: 268, Antirrhinum majus SPL partial nucleic acid sequence AMA011623
TCAGCTGCTGGTGGAGCAGAGGAATCTCTCAATGGGTTGAAGTTTGGCAAGAAAATATACTTTGAG
GAGGCTAAGGCAAAGAAAGGGAAGAGTACCGGTGGGGTGGTTAGGTGCCAGGTGGAGGGGTGTGAG
GTAGATCTGAGTGATGCTAAGGCTTACTATTTGAGACACAAAGTTTGTAGTATGCATTCAAAGTCT
CCAAAGGTCATTGTTGCTGGAATAGAACAAAGGTTTTGCCAGCAGTGCAGCAGGTTCCATCAATTG
CCTGAATTTGACCAAGGAAAACGGAGTTGCCGCAGACGCCTTGCAGGCCACAACGAACGTCGGAGG
AAGCCATCTCCAGGATCTATGATGTCTCCTTACTATGGAAGTCTTTCTCCAACCTTATTTGATAAC
CAAAATAGAACTGGAGGCTTTTGATGGACTTCAGCACTTACCCAAATCTCGCTGGGAAAGATTCA
TGGCCAAATACAATACCCGAACGAGGATTGGGAGGTCCAGCAAGTCCATGGCAGAGCGACATGCAA FIGURE 26 (continued)

```
AATCCTGTACCTGAGTTTTTGCGAGGTACAACAAATAGGCCAAGTTTTTCTGGTCTTGGAGTATCT
TCCGAAGAATGTTTTAGCGGAGTCTCTAATTCCAGCACTGCTCTCTCTCTTCTGTCAAATCAGTCC
TGGGGCTCCAGAAACTCGAACAATTTTCTTGGTACCAATGGAAACGGGCCAACCATAGTTCAGCCG
TCTATTAACCCTGGTGCCACAATTGGACAGTTTACCTGTCCCTCTTGGGGTTTTGGAGGCAACCCA
GCTGATAACACCTCCCATGATATGCCTCCCAATCTGAATTTAGGACAATTTTCTCACTCCAGTAAC
AGTCACTATACTGGAGAGCCTGGGGTAGTCCAACTGAGCCACGGACAATTCCAGGACCTCGATCAC
TCAAGAGGCTATGATTCTTCCGTTCAGGACATGCATTGGTCACTT
```

SEQ ID NO: 269, Antirrhinum majus partial SPL deduced polypeptide sequence
```
SAAGGAEESLNGLKFGKKIYFEEAKAKKGKSTGGVVRCQVEGCEVDLSDAKAYYLRHKVCSMHSKS
PKVIVAGIEQRFCQQCSRFHQLPEFDQGKRSCRRRLAGHNERRRKPSPGSMMSPYYGSLSPTLFDN
QNRTGGFLMDFSTYPNLAGKDSWPNTIPERGLGGPASPWQSDMQNPVPEFLRGTTNRPSFSGLGVS
SEECFSGVSNSSTALSLLSNQSWGSRNSNNFLGTNGNGPTIVQPSINPGATIGQFTCPSWGFGGNP
ADNTSHDMPPNLNLGQFSHSSNSHYTGEPGVVQLSHGQFQDLDHSRGYDSSVQDMHWSL
```

SEQ ID NO: 270, Brassica napus SPL partial nucleic acid sequence CX189447
```
GACTTGGAGAAAAGAAGTTGTAGAAGACGTCTAGCTTGTCATAACGAAAGAAGAAGAAAGCCCCAA
GCAACAACAGCAGCTCTTTTGGCTTCTGGTTACTCTAGAATCGCTCCATCTCTTTACGGAAGCGTT
TTGGGAGATCCTACAACGTGGTCAACCGCAAGATCTGTGATGGGACGGTCCGCACCGTGGGATAGC
CATCAACTGATGAACGTTTTGTCACAGGGAAGTTCAAGGTTTAGTATAACATACCCAGAGATGGTG
AACAATAATAGCACAGACTCAAGCTGTGCTCTCTCTTCTGTCAAACTCAAACACAACTCAGCAG
CAGCAGCAGACATCAACCAATGCTTACTTGATGGACGCAGAAAGGGTTACAATGGCTAAGTCACCG
CCTGTTTCAGTACACAATCAGTACTCGAAACAAACCTGGGAGTTCATGTCAGGCAAAAGAGCAAT
TGGCCTTGTGTGTCGTCCCCTGTTTGGGACTGAGACAAATCTCTGAGCCAGATGATGACCTCCAG
TTCCTGATGAGCAATGGCACCACAATGGGTGGATTCGAGCTGAACCTACAGCAGGAGCAGGTTCTG
AGGCAATACTCTTCTACTCAAAATTTTACTTGGCCTCTT
```

SEQ ID NO: 271, Brassica napus partial SPL deduced polypeptide sequence
```
DLEKRSCRRRLACHNERRRKPQATTAALLASGYSRIAPSLYGSVLGDPTTWSTARSVMGRSAPWDS
HQLMNVLSQGSSRFSITYPEMVNNNSTDSSCALSLLSNSNTTQQQQQTSTNAYLMDAERVTMAKSP
PVSVHNQYSKQTWEFMSGEKSNWPCVSSPVLGLRQISEPDDDLQFLMSNGTTMGGFELNLQQEQVL
RQYSSTQNFTWPL
```

SEQ ID NO: 272, Saccharum officinarum SPL partial nucleic acid sequence contig of CA113070, CA254724
```
CTCGTCGTCAACGGCCTCGAGCAGCGCTTCTGCCAGCAGTGCAGCAGGTTCCACCAGCTGCCTGAA
TTTGACCAACTAAAGAAAAGCTGCCGCAGACGTCTTGCAGGCCACAATGAACGCCGGAGGAGGCCA
CCTCCTGGACCTCTTGCATCACGATATGGTCGCCTTGCTGCATCATTTGGTGAGCCCGGCAGGTTC
CGAAGCTTTATGTTGGATTTCTCATACCCAAGGGTTCCAGGCACCATGAGGGATGGGTTTCCGGCA
GTTCGACCTGGCGAAAGGGTGCCTGGTAGTATCCAGTGGCAAGCGGGCTTAGATCCTCATCATCAT
CAAAGCGCGGTCGCAGGATACGGTGCCCACTCATATGGGAGCCAGGGTAGCTCGTCGTCGTCAAGG
CCACCGGTGTTCCCTGGTCCAGAGCTCCCCCAGGTGGATGTCTTGCAGGAGTCCCTCGGACTCT
AGCTGTGCTCTCTCTCTTCTGTCAACTCAGCCATGGGATACTACCCACAGCGCCGGCCACAGCCAT
GCTGGATCAATGCCTGCAACAGCAGGTTTTGACGGCAACCCTGTGGCACCCTCCCTCATGGCGAGT
```

FIGURE 26 (continued)

```
AGCTACATTGCGCCAAGCCCCTGGACTGACTCCCGGGGCCATGAAGGCGGGCGGAACGTGCCTCAG
TTGCCACCTGACGTCCCCCTCAGCGAGGTGCACTCTGGCTCAAGCAGCCATCACGGCCAGTTCTCA
GGTGAGCTCGAGCTTGCCCTGCAGGGAAACAGGCCAGCACCAGGGTCAGCGCCAGCGCCGCGCAAT
GATCAGGGCTCCACGGGCACGTTCGACCAGTCCGGCAACACAATGGACTGGTCGCTCTAG
```

SEQ ID NO: 273, Saccharum officinarum partial SPL deduced polypeptide sequence

```
LVVNGLEQRFCQQCSRFHQLPEFDQLKKSCRRRLAGHNERRRRPPPGPLASRYGRLAASFGEPGRF
RSFMLDFSYPRVPGTMRDGFPAVRPGERVPGSIQWQAGLDPHHHQSAVAGYGAHSYGSQGSSSSSR
PPVFPGPELPPGGCLAGVPSDSSCALSLLSTQPWDTTHSAGHSHAGSMPATAGFDGNPVAPSLMAS
SYIAPSPWTDSRGHEGGRNVPQLPPDVPLSEVHSGSSSHHGQFSGELELALQGNRPAPGSAPAPRN
DQGSTGTFDQSGNTMDWSL
```

SEQ ID NO: 274, Festuca arundinacea SPL partial nucleic acid sequence DT706587.1
```
GGCACGAGGGTGGATCTGAGCGGCTCCAAGACCTACTACTGCCGCCACAAGGTCTGCTCCATGCAC
TCCAAGGCGCCCCGCGTCGTCGTCGCCGGCCTCGAGCAGCGCTTCTGCCAGCAGTGCAGCAGGTTC
CACCAGTTGCCTGAATTTGACAATGGAAAACGCAGCTGCCGCAGACGTCTCGCAGGTCACAATGAA
CGCCGTAGGAAGCCGCCTCCTGGCCCTCTGGCGTCACGCTATGGCCGACTCGCTGCATCCTTTGAA
GAACCGGGCAGGTACAGAAGCTTTCTGTTAGATTTCTCCTACCCAAGGGTTCCGAGCAGCGTGCGG
GATGCTTGGCCTGCAGTTCGACCAGGCTACCGTATGCCCAGTGAAATCCAGTGGCAAGGGAACCTA
GACCTGCGTCCTCACACGGGTTATGGCCCACATGCATA
TGGCAGCCACGGCTTCCCCGGTCCAGAGCTCCCTCCAGGCGGGTGTCTCACAGGGGTCGCCACCGA
CTCCAGCTGTGCTCTCTCTCTTCTGTCAACTCAGCCATGGGATACCACCACCCACGGTGCCAGCCA
CGACCATCGGTCTGCGGCCATGTCCGCGGCCGCGGGCTTCGACGGCAGCCCTGCGGCAGTGTCACC
CTCCATCATGGCGAG
```

SEQ ID NO: 275, Festuca arundinacea partial SPL deduced polypeptide sequence
```
gtrvdlsgsktyycrhkvcsmhskaprvvvagleqrfcqqcsrfhqlpefdngkrscrrrlaghne
rrrkpppgplasrygrlaasfeepgryrsflldfsyprvpssvrdawpavrpgyrmpseiqwqgnl
dlrphtgygphaygshgfpgpelppggcltgvatdsscalsllstqpwdttthgashdhrsaamsa
aagfdgspaavspsima
```

SEQ ID NO: 276, Motif 1
(G/T)L(K/R/M/Q)FG(K/Q/R)(K/R/E)(I/V)YF(E/G)

SEQ ID NO: 277, SPL DNA-binding domain (DBD) of Arath_SPL15 transcription factor
```
TARCQVEGCRMDLSNVKAYYSRHKVCCIHSKSSKVIVSGLHQRFCQQCSRFHQLSEFDLEKRSCRR
RLACHNERRRKP
```

SEQ ID NO: 278, Motif 2
DS(S/N/T)(C/G/R)ALSLLS(N/T)

FIGURE 26 (continued)

SEQ ID NO: 279, Oryza sativa HMG promoter
CATGCGGCTAATGTAGATGCTCACTGCGCTAGTAGTAAGGTACTCCAGTACATTATGGAATATACA
AAGCTGTAATACTCGTATCAGCAAGAGAGAGGCACACAAGTTGTAGCAGTAGCACAGGATTAGAAA
AACGGGACGACAAATAGTAATGGAAAAACAAAAAAAAACAAGGAAACACATGGCAATATAAATGGA
GAAATCACAAGAGGAACAGAATCCGGGCAATACGCTGCGAAAGTACTCGTACGTAAAAAAAAGAGG
CGCATTCATGTGTGGACAGCGTGCAGCAGAAGCAGGGATTTGAAACCACTCAAATCCACCACTGCA
AACCTTCAAACGAGGCCATGGTTTGAAGCATAGAAAGCACAGGTAAGAAGCACAACGCCCTCGCTC
TCCACCCTCCCACCCAATCGCGACGCACCTCGCGGATCGGTGACGTGGCCTCGCCCCCCAAAATA
TCCCGCGGCGTGAACCTCACACCCCGGCCCACCCACCTGTCACGTTGGCACATGTTGCTTATGCT
TCCCGGCCGCACCAAAATATCAACGCGGCGCGGCCCAAAATTTCCAAAATCCCGCCCAAGCCCCTG
GCGCGTGCCGCTCTTCCACCCAGGTCCCTCTCGTAATCCATAATGGCGTGTGTACCCTCGGCTGGT
TGTACGTGGGCGGGTTACCCTGGGGGTGTGGGTGGATGACGGGTGGGCCGGAGGAGGTCCGGCCC
CGCGCGTCATCGCGGGGCGGGGTGTAGCGGGTGCGAAAAGGAGGCGATCGGTACGAAAATTCAAAT
TAGGAGGTGGGGGCGGGGCCCTTGGAGAATAAGCGGAATCGCAGATATGCCCCTGACTTGGCTTG
GCTCCTCTTCTTCTTATCCCTTGTCCTCGCAACCCCGCTTCCTTCTCCTCTCCTCTTCTCTTCT
CTTCTCTGGTGGTGTGGGTGTGTCCCTGTCTCCCCTCTCCTTCCTCCTCTCCTTTCCCCTCCTCTC
TTCCCCCCTCTCACAAGAGAGAGAGCGCCAGACTCTCCCCAGGTGAGGTGAGACCAGTCTTTTTGC
TCGATTCGACGCGCCTTTCACGCCGCCTCGCGCGGATCTGACCGCTTCCCTCGCCCTTCTCGCAGG
ATTCAGCC

SEQ ID NO: 280, primer prm07277
GGGGACAAGTTTGTACAAAAAAGCAGGCTTAAACAATGGAGTTGTTAATGTGTTCG

SEQ ID NO: 281, primer prm07278
GGGGACCACTTTGTACAAGAAAGCTGGGTTGATGAAGATCTTAAAAGGTGA

SEQ ID NO: 282, Brassica rapa SPL nucleic acid sequence
ATGGATAGGGGTTCCAACTCGGGTCTTGGTCTTGGTCCAGGCCAGACAGAGTCGGGTGGTTCATCC
ACTGAGTCATCCTCTTTAAGTGGAGGGCTCATGTTTGGCCAGAGGATCTACTTCGAGGACGCTGGA
GGTGGAACCGGGTCTTCTTCCTCCGGCGGGTCAAACAGAAGGGTACGTGGAAGCGGGTCGGGTCCT
TCGGGTCAGATACCAAGGTGTCAAGTGGAAGGTTGTGGAATGGATCTAACCAATGCAAAGGGTTAT
TACACGAGGCATAGAGTTTGTGGAATGCACTCTAAAACACCAAAAGTCATTGTCGCTGGTATAGAA
CAAAGGTTTTGTCAACAGTGCAGCAGGTTTCATCAGCTTCCGGAATTTGACCTAGAGAAAGGAGT
TGCCGTAGGAGACTCGCTGGTCATAATGAGAGACGAAGGAAGCCACAGCCTGCGTCTCTATCTGTG
TTGTCTTCTCGTTATGGGAGGATCACTCCTTCTCTATACGGAAATGGTGAAACTACAATGAATGGG
AGCTTTCTTGGTTCCCAAGAAATGGGTTGGAATAGTGCAAGAACGTTGGATACAAGAGTGATGAGA
CGGCCACCGTCGTGGCAGATCAATCCTATGAATGTGTTTAGTCATGGATCAGTAAGTGGAGGAGGA
GGAGGAGGGATAAGCTTCTCATCTCCAGAGATTATGGACACTAAACCAGAGAGCTACAAGGGAATT
GGCAGCGACTCAAACTGTGCTCTCTCTCTTCTGTCAAACCCACATCAGCCACATGACAACAACAAC
AGCAACAACACATGGAGAACTTCTTCGGGTTTTGGTCCGATGACGGTTACAATGGCTCAGCCACCA
CCTGCACCTAGCCAGCAGCATCAGTATCTGAACCCGCCTTGGGTATTCAAGGACGATGATAATAGC
TGTCCGAATGATATGTCTCCTGTTTTGAATCTTGGTCGGTTCACCGAGACAGAGATAAGCGGTGGA
ACGACTTTGGGTGAGTTCGAGTTATCTGACCATCATCATCAGAATAGGAGGCAGTACATGGAAAGT
GAGAACACAAGGGCTTATGGCTCTTCTTCACACCATAACAACTGGTCTCTCTGA FIGURE 26 (continued)

SEQ ID NO: 283, Brassica rapa SPL translated polypeptide sequence
MDRGSNSGLGLGPGQTESGGSSTESSSLSGGLMFGQRIYFEDAGGGTGSSSSGGSNRRVRGSGSGP
SGQIPRCQVEGCGMDLTNAKGYYTRHRVCGMHSKTPKVIVAGIEQRFCQQCSRFHQLPEFDLEKRS
CRRRLAGHNERRRKPQPASLSVLSSRYGRITPSLYGNGETTMNGSFLGSQEMGWNSARTLDTRVMR
RPPSWQINPMNVFSHGSVSGGGGGGISFSSPEIMDTKPESYKGIGSDSNCALSLLSNPHQPHDNNN
SNNTWRTSSGFGPMTVTMAQPPPAPSQQHQYLNPPWVFKDDDNSCPNDMSPVLNLGRFTETETSGG
TTLGEFELSDHHHQNRRQYMESENTRAYGSSSHHNNWSL

SEQ ID NO: 284, Glycine max SPL nucleic acid sequence
ATGGCTTCAGACGCCAAACTCTCCTCTTCTGAGTCCCTCAACGGTTTGAAATTCGGCCAAAAAATC
TATTTTGAGGATGTTGGTCTTGCTACTCCAGCCACCTCTCTTACTTCTTCTTCTTCTTCTTCT
GCTGCTACTGTTACTTCTTCTTCTTCTTCAAGGAAAGGAAGAGGTGGGTCTGTTCAACCAGCTCAA
CCTCCCAGGTGTCAAGTTGAAGGGTGCAAAGTAGATCTGAGTGATGCAAAAGCTTACTATTCTAGA
CACAAGGTCTGTGGCATGCACTCTAAATCCCCTTCAGTCATTGTTGCTGGTCTTCAACAAAGGTTT
TGTCAACAGTGTAGCAGGTTTCATCAGCTTCCTGAGTTTGATCAAGGAAAAAGAAGTTGCCGTAGG
CGACTAGCTGGCCATAATGAACGTCGGAGAAAGCCCCCAACAAGCTCCCTCTTAACCTCTCGCTAT
GCCAGACTTTCTTCGTCTGCTTTTGATAATAGTGGCAGAGGTAGCAACTTTCTGATGGAATTGACT
TCATACCCAAAGCTTAGTCTGAGAAATTCACTTCCAACTCCTAGATCATCTGAGCTAGCTCCTGGA
AATCAAACCTCCACACTTAGCTGGAATGGCAACTCAGAGACATCATCTGACCTTTTCTTGCAAGGT
TCGGTGGGTGGGACAAGCTTCGCCAGCCCGGGACATCCTCCAGGGGAAAGTTACATTGGGGTCACC
GACACGAGCTGTGCTCTCTCTTCTGTCAAATCAAACATGGGGTTCTAGAAACACAGCACCAAGT
CTTGGGTTGAGTAACATGATAAATTTCAACGGGACACCCTTGACACAACTTGCTGCATCATCTCAT
GGTGCATCAATCCATCAACTTCCAAATACCTCGTGGTTTTTCAAGGGCATTGATTCTGGTAACTGT
TCGCCCGAGGTGGTCCCTGATCTAGGTCTCGGTCAGATTTCACAGCCTCTCAATAGCCAACTTCAT
GGTGAGCTGGACCTGTCCCAACAGGGCAGGAGGCATTATATGGATCTAGAACAGTCCAGGGCATAT
GAATCTGCTCATTGGTCACTTTAA

SEQ ID NO: 285, Glycine max SPL nucleic acid sequence
MASDAKLSSSESLNGLKFGQKIYFEDVGLATPATSLTSSSSSSSAATVTSSSSSRKGRGGSVQPAQ
PPRCQVEGCKVDLSDAKAYYSRHKVCGMHSKSPSVIVAGLQQRFCQQCSRFHQLPEFDQGKRSCRR
RLAGHNERRRKPPTSSLLTSRYARLSSSAFDNSGRGSNFLMELTSYPKLSLRNSLPTPRSSELAPG
NQTSTLSWNGNSFTSSDLFLQGSVGGTSFASPGHPPGFSYIGVTDTSCALSLLSNQTWGSRNTAPS
LGLSNMINFNGTPLTQLAASSHGASIHQLPNTSWFFKGIDSGNCSPEVVPDLGLGQISQPLNSQLH
GELDLSQQGRRHYMDLEQSRAYESAHWSL

SEQ ID NO: 286 Populus tremuloides SPL nucleic acid sequence
ATGGAAATGGATTCAGGCTCCCTAACCGAGTCAGCTACTTCCAATGCAACTTCTCCGCCAGCTGAG
TCTGTTAATGGATTGAAATTTGGTAAGAAGATTTACTTTGAGGATCACGTGGGGGTCGGTGCTCCG
GCTAAGAGCGGAACTGGGTCATCCTCATCCGGTTCCGGGTCAGGGTCATCTAGGAAGGCTCAAGGT
GCACAGCACCACCAGCCACCAAGCTGTCAACTTGAAGCGTCCAAACTAGATCTGAGTGATGCTAAG
ACTTACTATTCAAGGCACAAAGTTTGTAGTATGCACTCCAAGTCTCCTAGAGTTATTGTTGCTGGT
TTGGTGCAAAGATTTTGCCAGCAATGTAGCAGATTTCATCTACTTCCTGAATTTGACCAAGGAAAA
CCAAGTTGCCGCACGCGCCTAGCTGGCCATAATGACCCACGGAGGAACCACCATCTGGATCCGTG
TTGTCCGCTCGCCATGGCCGATTCTCTCCCTCTTTGTTTGATAATAGCAGCAGAGCTGGAGGCCTT
CTTGTGGACTTTAGTGCATATCCAAGGCATACTGGGAGAGATGGATGGCCTGCAGCAAGGTCTTCT
GAGCTTACCCCCGCGAATCATACTGCTGCCACAGGAACGTCTATATCTCATATGTGGCAGATAACC
TCCCAGAATCCTCCATCCAACCTTTGCTTGCAAGGCTCAACTGGCGGACTGGCCTTTCAGTTCA
GGAATTCCTCCGGGAGAATGCTTCACAGGAGTTGCTGTTTCAGACTCGAGCTGTGCTCTCTCTCTT FIGURE 26 (continued)

```
CTGTCAAATCAACCATGGGGCTCCACAAACCGAGCATCAAGTCTTGCGGTGAATGACTTGTTTAGT
GCCGAAGAGGCACCCGTGGTTCAATCAACAGCTCACCATGGTGCGGCTGTCAATCAGTATCCAATC
CCTTGGAGCTTCAAGAGCAATGAAGGAAGTAACAGTTCACATGAGATGTGCCCTGATCTAGGTCTG
GGTCAAATTTCAATGCCTCTCAACAGTCAACTTGCTGGTCAGCTCGAGCAGTCTCAACAGAATAGG
AGGCAATACATGGACCTCGAGCATTCCAGGGCTTATGACTCTTCAACCCAGCACATCCACTGGTCA
CTTTAA
```

SEQ ID NO: 287, Populus tremuloides SPL translated polypeptide sequence
```
MEMDSGSLTESATSNATSPPAESVNGLKFGKKIYFEDHVGVGAPAKSGTGSSSSGSGSGSSRKAQG
GQHQQPPRCQVEGCKVDLSDAKTYYSRHKVCSMHSKSPRVIVAGLVQRFCQQCSRFHLLPEFDQGK
RSCRRRLAGHNERRRKPPSGSVLSARHGRFSPSLFDNSSRAGGLLVDFSAYPRHTGRDGWPAARSS
ELTPGNDTAATGRSISHMWQISSQNPPSNLCLQGSTGGTGLFSSGIPPGECFTGVAVSDSSCALSL
LSNQPWGSTNRASSLAVNDLFSAEEAPVVQSTAHHGAAVNQYPIPWSFKSNEGSNSSHEMCPDLGL
GQISMPLNSQLAGQLEQSQQNRRQYMDLEHSRAYDSSTQHIHWSL
```

SEQ ID NO: 288, Citrus clementina SPL partial nucleic acid sequence DY293795
```
ATGGAACTGGGTTCAGACTATTTGGCTGAATCAGGTGGTGGCTCCGGCTCCGGCTCAGGCTCCGGC
TTATCATCCGCTGAGCCATCACTTAATGGTTTGAAGTTTGGCAAAAAAATCTATTTTGAGGATGTC
GGTACTGCCGGAGCTCCATTTCCAGGATCTGGGTCATCATCTGGGTCCGGGTCAGGGTCAGGTTCA
GGGTCAGGGAGGAAGGTGAGGGGTGTTGGCGGTGGTATGGTTACTAGTGGGCAGCAGCCACCAAGG
TGCCAAGTGGAGGGTGTAAAGTTGATCTGAGTGATGCCAAAGCTTACTATTCAAGGCACAAAGTT
TGTGGCATGCATTCAAAGTCTCCTGTTGTCACTGTTGCCGGCCTTGAGCAGAGGTTTTGCCAGCAA
TGTAGCAGATTTCATCAGCTTCCGGAGTTTGACCAAGGAAAACGAAGTTGCCGCAGGCGCCTGGCA
GGCCATAATGAGCGCCGGAGGAAGCCAACTTCTGGACCATTTTGGGCACTCGTTATGGCAGGCTC
TCTTCCTCTGTCATTGAGAACAGCAGCCAAGGTGGAGGATTTCTGATCGACTTCAGTGCATATCAG
ATGGTTGGTGGGAGGGATGGATGGCCAGTGACAAGTGTCTCCAAGCAGGTATCTGGAAATCAAACC
ACTGTCACAGCAAGGCATCTTCCTCAGCCACTATGGCAAAACCACTCTCAGGATCCTCCACCTGAT
CGTTACCTTCAGTGTTCAACAGCTGGGACTGGTTTCTCTGGTCCTGGAATTCCTTGTGGAGGATGC
TTCACAGGAGTTGCTGACTCAAACTGTGCTCTCTCTCTTCTGTCAAATCAACCATGGGGCTCTAAG
AACCCGACACCGGGTCATGGAGTGGGTGACTTAATGCATGCCCATACCAAATCCGTCACTCAACCA
GTATCGCCCCATGGAGCAGCTATTAATCAATATCCAAACATGTCATGGGGGTTCAAGGGCAATGC
AACCTGGTAGCAGTTCCACACCAAATGGCCCCCCAAATGGGGTTTGGGTTCAACATTCCGGCCCAT
TAA
```

SEQ ID NO: 289, Citrus clementina SPL partial translated polypeptide sequence partial
```
MELGSDYLAESGGGSGSGSGSGLSSAEPSLNGLKFGKKIYFEDVGTAGAPFPGSGSSSGSGSGSGS
GSGRKVRGVGGGMVTSGQQPPRCQVEGCKVDLSDAKAYYSRHKVCGMHSKSPVVTVAGLEQRFCQQ
CSRFHQLPEFDQGKRSCRRRLAGHNERRRKPTSGPFLGTRYGRLSSSVIENSSQGGGFLIDFSAYQ
MVGGRDGWPVTSVSKQVSGNQTTVTARHLPQPLWQNHSQDPPPDRYLQCSTAGTGFSGPGIPCGGC
FTGVADSNCALSLLSNQPWGSKNPTPGHGVGDLMHAHTKSVTQPVSPHGAAINQYPNMSWGVQGQC
NLVAVPHQMAPQMGFGFNIPAH
```

FIGURE 26 (continued)

SEQ ID NO: 290, Beta vulgaris SPL partial nucleic acid sequence
ATGGATACGGGTTCAAATTATCCGACCGTTAAGGGGTCATCATCAACCTCTTCATCATCTGGGTTG
TCGGATTCTTTAAATGGGCTGAAATTTGGGCAAAAAATATACTTTGAAGATGTGGGTGGTGTTGGA
ACTTCCGGCAAGTCTTCCGTCGCCGGAAGTGGTGGTGCTCCGGCGAAAAGGGCCGGAAAAGGGGTG
GTGCAAAGTGGGCAACCACCAAGGTGTCAAGTAGAAGGGTGTAAGATAGATCTTAGTGATGCTAAA
ACTTATTATTCTAGGCATAAAGTTTGTGGTATGCACTCTAAATCTTCTGTTGTTATTGTTGCTGGT
CTTGAGCAACGTTTTTGCCAGCAGTGCAGCAGATTTCATCGGCTTCCTGAGTTTGACCAAGGGAAA
CGAAGTTGTCGCAGACGCCTTGCTGGTCATAATGAGCGTCGAAGAAAACCACCACCTGGGTCTTTG
TTATCATCACGTTTGGGACGTCTCTCTTCATCCCTTTTTGGTGATAACACCGGCGGAAGTGGTGGA
TTCTTATTGGACTTCTCTTCGTATCCACGGCATTCTG

SEQ ID NO: 291, Beta vulgaris SPL partial translated polypeptide sequence
MDTGSNYPTVKGSSSTSSSSGLSDSLNGLKFGQKIYFEDVGGVGTSGKSSVAGSGGAPAKRAGKGV
VQSGQPPRCQVEGCKIDLSDAKTYYSRHKVCGMHSKSSVVIVAGLEQRFCQQCSRFHRLPEFDQGK
RSCRRRLAGHNERRRKPPPGSLLSSRLGRLSSSLFGDNTGGSGGFLLDFSSYPRHS

SEQ ID NO: 292, Hevea brasiliensis SPL partial nucleic acid sequence
ATGGAAATGGGTTCGGGCTCTTTGACAGAGTCAGGTACCTCCAACGCCACTTCTCCACCTGCTGAG
TCAATAAATGGGTTGAAATTTGGCCAAAAAATCTATTTTGAGAATGCGGGGGCTAAGACTCCGGCC
AAATCTGCACCCGGGTCTTCATCTTCCGGGTCCGGGGCCCCGTCCAGGAAGGTTCACGGTGGGCAG
CAGCAGCAGCCACCCAGGTGTCAAGTTGAGGGATGTAAAGTGGATCTGAGTGATGCTAAGGCTTAT
TATTCGAGGCACAAAGTTTGTGGTATGCACTCTAAGTCTCCTAAGGTCATTGTTGCTGGTTTGGAG
CAAAGATTTTGCCAGCAGTGTAGTAGATTTCATCAGCTTCCTGAATTTGACCAAGGAAAACGAAGT
TGCCGCAGACGCCTAGCTGGTCATAATGAACGGCGGAGGAAGCCACCAACTGGATCAGTGCTGTCA
TCTCGCTATAACAGACTTTTTTCAACAATTTTTGATAACAGCAGCCGAGCTGGGGGCATTCTTGTG
GATTTCAG

SEQ ID NO: 293, Hevea brasiliensis SPL partial nucleic acid sequence
MEMGSGSLTESGTSNATSPPAESINGLKFGQKIYFENAGAKTPAKSAPGSSSSGSGAPSRKVHGGQ
QQQPPRCQVEGCKVDLSDAKAYYSRHKVCGMHSKSPKVIVAGLEQRFCQQCSRFHQLPEFDQGKRS
CRRRLAGHNERRRKPPTGSVLSSRYNRLFSTIFDNSSRAGGILVD

SEQ ID NO: 294, Oryza sativa HMGB promoter variant
CATGCGGCTAATGTAGATGCTCACTGCGCTAGTAGTAAGGTACTCCAGTACATTATGGAATATACA
AAGCTGTAATACTCGTATCAGCAAGAGAGAGGCACACAAGTTGTAGCAGTAGCACAGGATTAGAAA
AACGGGACGACAAATAGTAATGGAAAAACAAAAAAAAACAAGGAAACACATGGCAATATAAATGGA
GAAATCACAAGAGGAACAGAATCCGGGCAATACGCTGCGAAAGTACTCGTACGTAAAAAAAAGAGG
CGCATTCATGTGTGGACAGCGTGCAGCAGAAGCAGGGATTTGAAACCACTCAAATCCACCACTGCA
AACCTTCAAACGAGGCCATGGTTTGAAGCATAGAAAGCACAGGTAAGAAGCACAACGCCCTCGCTC
TCCACCCTCCCACCCAATCGCCACGCACCTCGCGGATCGGTGACCTGCCCTCCCCCCCAAAAATA
TCCCGCGGCGTGAAGCTGACACCCCGGGCCCACCCACCTGTCACGTTGGCACATGTTGGTTATGGT
TCCCGGCCGCACCAAAATATCAACGCGGCGCGGCCCAAAATTTCCAAAATCCCGCCCAAGCCCCTG
GCCCCGTGCCGCTCTTCCACCCAGGTCCCTCTCCTAATCCATAATCGCCTGTGTACCCTCCGCTCGT
TGTACGTGGGCGGGTTACCCTGGGGGTGTGGGTGGATGACGGGTGGGCCCGGAGGAGGTCCGGCCC
CGCGCGTCATCGCGGGGCGGGGTGTAGCGGGTGCGAAAAGGAGGCGATCGGTACGAAAATTCAAAT

FIGURE 26 (continued)

```
TAGGAGGTGGGGGGCGGGGCCCTTGGAGAATAAGCGGAATCGCAGATATGCCCCTGACTTGGCTTG
GCTCCTCTTCTTCTTATCCCTTGTCCTCGCAACCCCGCTTCCTTCTCTCCTCTCCTCTTCTCTTCT
CTTCTCTGGTGGTGTGGGTGTGTCCCTGTCTCCCCTCTCCTTCCTCCTCTCCTTTCCCCTCCTCTC
TTCCCCCCTCTCACAAGAGAGAGAGCGCCAGACTCTCCCCAGGTGAGGTGAGACCAGTCTTTTTGC
TCGATTCGACGCGCCTTTCACGCCGCCTCGCGCGGATCTGACCGCTTCCCTCGGCCTTCTCGCAGG
ATTCAGCC
```

SEQ ID NO: 295, Oryza sativa GOS2 promoter
```
AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAAGAGAGAGATTTTTTTTAAAAAAATAGAATGAAGATATTCTGAACGTATTGGCAAAGATTTAAA
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTTATTATTTATCTTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAAGAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTTCTCCCATCTATAA
ATTCCTCCCCCCTTTTCCCCTCTCTATATAGGAGGCATCCAAGCCAAGAAGAGGGAGAGCACCAAG
GACACGCGACTAGCAGAAGCCGAGCGACCGCCTTCTCGATCCATATCTTCCGGTCGAGTTCTTGGT
CGATCTCTTCCCTCCTCCACCTCCTCCTCACAGGTATGTGCCTCCCTTCGGTTGTTCTTGGATTT
ATTGTTCTAGGTTGTGTAGTACGGGCGTTGATGTTAGGAAAGGGGATCTGTATCTGTGATGATTCC
TGTTCTTGGATTTGGGATAGAGGGGTTCTTGATGTTGCATGTTATCGGTCGGTTTGATTAGTAGT
ATGGTTTTCAATCGTCTGGAGAGCTCTATGGAAATGAAATGGTTTAGGGATCGGAATCTTGCGATT
TTGTGAGTACCTTTTGTTTGAGGTAAAATCAGAGCACCGGTGATTTTGCTTGGTGTAATAAAGTAC
GGTTGTTTGGTCCTCGATTCTGGTAGTGATGCTTCTCGATTTGACGAAGCTATCCTTTGTTTATTC
CCTATTGAACAAAAATAATCCAACTTTGAAGACGGTCCCGTTGATGAGATTGAATGATTGATTCTT
AAGCCTGTCCAAAATTTCGCAGCTGGCTTGTTTAGATACAGTAGTCCCCATCACGAAATTCATGGA
AACAGTTATAATCCTCAGGAACAGGGGATTCCCTGTTCTTCCGATTTGCTTTAGTCCCAGAATTTT
TTTTCCCAAATATCTTAAAAAGTCACTTTCTGGTTCAGTTCAATGAATTGATTGCTACAAATAATG
CTTTTATAGCGTTATCCTAGCTGTAGTTCAGTTAATAGGTAATACCCCTATAGTTTAGTCAGGAGA
AGAACTTATCCGATTTCTGATCTCCATTTTAATTATATGAAATGAACTGTAGCATAAGCAGTATT
CATTTGGATTATTTTTTTATTAGCTCTCACCCCTTCATTATTCTGAGCTGAAAGTCTGGCATGAA
CTGTCCTCAATTTTGTTTCAAATTCACATCGATTATCTATGCATTATCCTCTTGTATCTACCTGT
AGAAGTTTCTTTTTGGTTATTCCTTGACTGCTTGATTACAGAAAGAAATTTATGAAGCTGTAATCG
GGATAGTTATACTGCTTGTTCTTATGATTCATTTCCTTTGTGCAGTTCTTGGTGTAGCTTGCCACT
TTCACCAGCAAAGTTC
```

PLANTS HAVING ENHANCED YIELD-RELATED TRAITS AND A METHOD FOR MAKING THE SAME

RELATED APPLICATIONS

This application is a national stage application (under 35 U.S.C. 371) of PCT/EP2007/053081, filed Mar. 30, 2007, which claims benefit of European applications 06075822.4, filed Mar. 31, 2006; 06075823.2, filed Mar. 31, 2006; 06075918.0, filed Apr. 10, 2006; 06075957.8, filed Apr. 27, 2006; 06114140.4, filed May 18, 2006; 06117235.9, filed Jul. 14, 2006 and 07100833.8, filed Jan. 19, 2007 and U.S. Provisional applications 60/790,151, filed Apr. 7, 2006; 60/790, 116, filed Apr. 7, 2006; 60/792,225, filed Apr. 14, 2006; 60/798,602, filed May 8, 2006; 60/801,687filed May 19, 2006 and 60/889,958, filed Feb. 15, 2007.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Revised_Sequence_Listing__13987__00095. The size of the text file is 523 KB, and the text file was created on Mar. 21, 2011.

The present invention relates generally to the field of molecular biology and concerns a method for improving various plant growth characteristics by modulating expression in a plant of a nucleic acid encoding a GRP (Growth-Related Protein). The present invention also concerns plants having modulated expression of a nucleic acid encoding a GRP, which plants have improved growth characteristics relative to corresponding wild type plants or other control plants. The invention also provides constructs useful in the methods of the invention.

The ever-increasing world population and the dwindling supply of arable land available for agriculture fuels research towards increasing the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

A trait of particular economic interest is increased yield. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance and early vigour may also be important factors in determining yield. Optimizing the above-mentioned factors may therefore contribute to increasing crop yield.

Seed yield is a particularly important trait, since the seeds of many plants are important for human and animal nutrition. Crops such as corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain.

Another important trait for many crops is early vigour. Improving early vigour is an important objective of modern rice breeding programs in both temperate and tropical rice cultivars. Long roots are important for proper soil anchorage in water-seeded rice. Where rice is sown directly into flooded fields, and where plants must emerge rapidly through water, longer shoots are associated with vigour. Where drill-seeding is practiced, longer mesocotyls and coleoptiles are important for good seedling emergence. The ability to engineer early vigour into plants would be of great importance in agriculture. For example, poor early vigor has been a limitation to the introduction of maize (Zea mays L.) hybrids based on Corn Belt germplasm in the European Atlantic.

A further important trait is that of improved abiotic stress tolerance. Abiotic stress is a primary cause of crop loss worldwide, reducing average yields for most major crop plants by more than 50% (Wang et al., Planta (2003) 218: 1-14). Abiotic stresses may be caused by drought, salinity, extremes of temperature, chemical toxicity and oxidative stress. The ability to improve plant tolerance to abiotic stress would be of great economic advantage to farmers worldwide and would allow for the cultivation of crops during adverse conditions and in territories where cultivation of crops may not otherwise be possible.

Crop yield may therefore be increased by optimising one of the above-mentioned factors.

Depending on the end use, the modification of certain yield traits may be favoured over others. For example for applications such as forage or wood production, or bio-fuel resource, an increase in the vegetative parts of a plant may be desirable, and for applications such as flour, starch or oil production, an increase in seed parameters may be particularly desirable. Even amongst the seed parameters, some may be favoured over others, depending on the application. Various mechanisms may contribute to increasing seed yield, whether that is in the form of increased seed size or increased seed number.

One approach to increasing yield (seed yield and/or biomass) in plants may be through modification of the inherent growth mechanisms of a plant, such as the cell cycle or various signalling pathways involved in plant growth or in defense mechanisms.

It has now been found that various growth characteristics may be improved in plants by modulating expression in a plant of a nucleic acid encoding a GRP (Growth-Related Protein) in a plant. The GRP may be one of the following: a MADS-box transcription factor (OsMADS15), a PLT transcription factor, a bHLH transcription factor, an SPL15 transcription factor, and a halotolerance protein (HAL3).

BACKGROUND

Halotolerance Proteins

Many enzymatic processes in a cell require the involvement of Coenzyme A (CoA or CoASH). Coenzyme A (CoASH) itself is a highly polar molecule, consisting of adenosine 3',5'-diphosphate linked to 4-phosphopantethenic acid (Vitamin B5) and thence to β-mercaptoethylamine. The free SH group may be esterified, depending on the process in which CoA is involved. The pathway of CoA synthesis has been elucidated in bacteria, animals and plants. In plants, the conversion of the CoA precursor 4'-phosphopantothenoyl-cysteine (PPC) into 4'-phosphopantetheine is catalysed by the flavoprotein 4'-phosphopantothenoyl-cysteine decarboxylase (PPCDC or HAL3, Kupke et al. J. Biol. Chem. 276, 19190-19196, 2001). The gene encoding HAL3 proteins may be part of a small gene family: the *Arabidopsis* genome comprises two isoforms (AtHAL3a and AtHAL3b; Espinoza-Ruiz et al. Plant J. 20, 529-539, 1999), in tobacco 3 HAL3 genes are present (Yonamine et al. J. Exp. Bot. 55, 387-395, 2004), though in rice HAL3 is a single copy gene. It is suggested that AtHAL3 and other HAL3 proteins function as a trimer, with each monomer having a flavin mononucleotide (FMN) bound (Albert et al. Structure 8, 961-969, 2000). The FMN cofactor is postulated to play a role in the redox reaction generating 4'-phosphopantetheine.

The molecular function of HAL3 proteins is not fully elucidated yet. The HAL3 proteins show homology to the yeast SIS2 protein, which is involved in halotolerance (Ferrando et al., Mol. Cell. Biol. 15, 5470-5481). Plants or plant cells ectopically expressing HAL3 show improved salt, osmotic or lithium stress tolerance (Espinoza-Ruiz et al., 1999; Yonamine et al., 2004). Tobacco HAL3a overexpression in BY2 cells reportedly caused an increase in intracellular proline content, which may contribute to the salt tolerant phenotype (Yonamine et al., 2004). Furthermore, *Arabidopsis* plants overexpressing AtHAL3a displayed a faster growth rate than the wild type plants (Espinoza-Ruiz et al., 1999). The AtHAL3b protein was shown to interact with the cell cycle protein CDKB1;1 (WO 00/36124), therefore it was postulated that AtHAL3b is useful for conferring salt stress tolerance to plants and for increasing the growth rate of plants under salt stress conditions Surprisingly, it has now been found that preferentially increasing expression of a nucleic acid encoding a HAL3 polypeptide in expanding tissues gives plants having increased yield relative to control plants, which yield increase is at least 10% compared to the control plants.

Transcription Factors

Transcription factors are usually defined as proteins that bind to a cis-regulatory element (eg. an enhancer, a TATA box) and that, in association with RNA polymerase, are capable of activating and/or repressing transcription. The *Arabidopsis* genome codes for at least 1533 transcriptional regulators, which account for ~5.9% of its estimated total number of genes (Riechmann et al., 2000 (Science Vol. 290, 2105-2109)).

MADS15

The MADS-box genes constitute a large gene family of eukaryotic transcriptional regulators involved in diverse aspects of yeast, plant and animal development. MADS-box genes encode a strongly conserved MADS domain responsible for DNA binding to specific boxes in the regulatory region of their target genes. The gene family can be divided into two main lineages, type I and type II. Type II genes are also named MIKC-type proteins, referring to the four functional domains they possess (FIG. 5, (Jack, Plant Mol. Biol. 46, 515-520, 2001)):

- MADS for DNA binding, about 60 amino acids (highly conserved) located at the N-terminal end of the protein;
- I for intervening domain (less conserved), involved in the selective formation of MADS dimer;
- K for keratin domain (well conserved) responsible for dimerisation;
- C for C-terminal region (variable in sequence and length) involved in transcriptional activation, or in the formation of a multimeric transcription factor complex.

Over 100 MADS-box genes have been identified in *Arabidopsis*, and have been phylogenetically classified into 12 clades, each clade having specific deviations from the MADS consensus (Thiessen et al. J. Mol. Evol. 43, 484-516, 1996). OsMADS15 belongs to the SQUA clade (for SQUAMOSA, from *Antirrhinum majus*). Genes of the SQUA clade are classified as A function organ identity genes with reference to the ABC floral organ identity specification model, proposed by Coen and Meyerowitz in 1991 (Nature 353, 31-7). Besides OsMADS15, rice OsMADS14, OsMADS18, and OsMADS20 are also part of the SQUA clade.

The SQUA clade in dicotyledonous plants (dicots) is subdivided into two subgroups, the AP1 and the FUL subclades (in which OsMADS15 clusters). These subclades diverge essentially with respect to the specific amino acid motifs located at the C-terminus of their respective proteins (Litt and Irish, Genetics 165, 821-833, 2003). In addition to the presence of a specific AP1 amino acid motif, the dicot AP1 clade related proteins usually comprise a farnesylation motif at their C-terminus (this motif is CAAX, where C is cysteine, A is usually an aliphatic amino acid, and X is methionine, glutamine, serine, cysteine or alanine). In monocotyledonous plants (monocots), the SQUA clade proteins are also subdivided into two main groups, which may be distinguished based on conserved C-terminal motifs located within the last 15 amino acids of the proteins: LPPWMLS (for example OsMADS15, SEQ ID NO: 117) and LPPWMLR (for example OsMADS18). In contrast to dicot sequences of the SQUA clade, monocot sequences of the SQUA clade do not possess a farnesylation motif at their C-terminus.

OsMADS15 was postulated to function in a complex with other proteins to control organ formation. However, so far no mutants with a visible phenotype have been identified; no experimental data have been presented relating to ectopic expression or down-regulated expression of OsMADS15, except for the data presented in WO 01/14559 (EP1209232, U.S. Pat. No. 6,995,302). In this disclosure, transgenic *Fagopyrum esculentum* plants expressing OsMADS15 in sense direction showed increased branching, whereas transgenics expressing the antisense construct had decreased growth and suppressed branching. *Kalanchoë daigremontiana* transformed with the sense construct had leaf development around the roots, which was taken as an indication of increased branching. The authors stated that no changes were observed in terms of flower development and structure of these flowers. The orthologue of OsMADS15 in *Arabidopsis* is APETALA1 (AP1). Ectopic expression of AP1 results in a decrease of flowering time, and AP1 mutants exhibit delayed flowering and have abnormal flowers.

PLT

The AP2 (apetala2)/ERF (ethylene-responsive responsive element-binding factor) family comprises transcription factors with at least one highly conserved DNA binding domain, the AP2 domain. The AP2 domain was originally described in APETALA2 (AP2), an *Arabidopsis* protein involved in developmental programs such as meristem identity regulation and floral organ specification (Jofuku et al., (1994) Plant Cell 6, 1211-1225). AP2/ERF proteins are divided into subfamilies based on whether they contain one (ERF subfamily) or two (AP2 subfamily) DNA binding domains (FIG. 12). More than 140 AP2/ERF genes have been identified in the *Arabidopsis thaliana* genome (Reichmann et al. (2000) Science 290: 2105-2110), amongst which up to 18 belong to the AP2 subfamily (Kim et al. (2006) Mol Bio Evol 23(1): 107-120).

Two *Arabidopsis* AP2 subfamily transcription factor polypeptides, encoded by the Plethora 1 (PLT1) and Plethora 2 (PLT2) genes, collectively called PLT genes, have been shown to be required for stem cell specification and maintenance specifically in the root meristem. In RT-PCR analysis, PLT transcripts were mainly detected in roots, indicating that PLT expression is strongly associated with root identity. Ectopic PLT expression in the *Arabidopsis* embryo induces homeotic transformation of apical domains into root stem cells, roots, or hypocotyls (Aida et al (2004) Cell 119:109-120).

US patent application 2004/0045049 and international patent application WO03/013227 provide the nucleic acid sequence encoding the *Arabidopsis* PLT1 transcription factor (referred to in the applications as G1793). Overexpression of G1793 (using the CaMV 35S promoter) in *Arabidopsis* was reported to produce alterations in cotyledon morphology, a mild reduction in overall plant size and thin inflorescences (possibly with abnormal flowers) compared to wild type controls. G1793 overexpressors produced more seed oil than control plants. Nucleic acid sequences encoding potential *Glycine max*, *Oryza sativa* and *Zea mays* orthologs are provided.

International patent application WO 03/002751 provides for a *Glycine max* nucleic acid sequence encoding a PLT polypeptide, with sequence similarity to a corn nucleic acid sequence identified by gene profiling (by DNA microarray).

International patent application WO 05/075655 provides for *Oryza sativa* and *Zea mays* nucleic acid sequences with sequence similarity to the *Arabidopsis* PLT genes.

bHLH

The basic/helix-loop-helix (bHLH) proteins are a superfamily of transcription factors that bind as dimers to specific DNA target sites and that have been well characterized in non-plant eukaryotes as important regulatory components in diverse biological processes. The distinguishing characteristic of the bHLH family is a bipartite domain consisting of approximately 60 amino acids. This bipartite domain is comprised of a DNA-binding basic region, which binds to a consensus hexanucleotide E-box and two α-helices separated by a variable loop region. The two α-helices promote dimerization, allowing the formation of homo- and heterodimers between different family members. While the bHLH domain is evolutionarily conserved, there is little sequence similarity between clades beyond the domain.

Bailey et al., 2003 (The Plant Cell, Vol. 15, 2497-2501) report the total number of detected bHLH genes in *Arabidopsis thaliana* to be 162, making bHLH genes one of the largest families of transcription factors in *Arabidopsis*; the rice genome reportedly contains 131 bHLH genes (Buck and Atchley, 2003 (J. Mol. Evol. 56:742-750)). Heim et al., 2003 (Mol. Biol. Evol. 20(5):735-747) identified 12 subfamilies of bHLH genes from *Arabidopsis thaliana* based on structural similarities.

The bHLH proteins from plants that have been characterized have been reported to function in anthocyanin biosynthesis, phytochrome signaling, globulin expression, fruit dehiscence, carpel and epidermal development (Buck and Atchley, 2003).

SPL

The Squamosa promoter binding protein-like (SPL) transcription factor polypeptides are structurally diverse proteins that share a highly conserved DNA binding domain (DBD) of about 80 amino acid residues in length (Klein et al. (1996) Mol Gen Genet 259: 7-16; Cardon et al. (1999) Gene 237: 91-104). The SPL transcription factor DNA consensus sequence binding site in the promoter of target genes is 5'-TNCGTACAA-3' where N represents any base. Within the SPL DBD are ten conserved cysteine (Cys) or histidine (His) residues (see FIG. 23) of which eight are zinc coordinating residues binding two zinc ions necessary for the formation of SPL specific zinc finger tertiary structure (Yamasaki et al. (2004) J Mol Biol 337: 49-63). A second conserved feature within the SPL DBD is a bipartite nuclear localisation signal. Outside of the DBD, a micro RNA (miRNA) target motif (miR156) is found in most of the nucleic acid sequences encoding SPL transcription factor polypeptides (either in the coding region, or the 3' UTR) across the plant kingdom (Rhoades et al. (2002) Cell 110: 513-520). miRNAs control SPL gene expression post-transcriptionally by targeting SPL encoding mRNAs for degradation or by translational repression.

Riechmann et al. (Science 290: 2105-2109, 2000) report 16 SPL transcription factor polypeptides in *Arabidopsis thaliana*, with little sequence similarity between themselves (apart from the abovementioned features), the size of the deduced SPL polypeptide ranging from 131 to 927 amino acids. Nevertheless, pairs of SPL transcription factor polypeptides sharing higher sequence homology were detected within the SPL family of this plant (Cardon et al. (1999)).

The SPL transcription factor polypeptides (only found in plants) characterized to date have been shown to function in plant development, in particular in flower development. Transgenic plants overexpressing an SPL3 transcription factor polypeptide were reported to flower earlier (Cardon et al. (1997) Plant J 12: 367-377).

In European patent application EP1033405, the nucleic acid and deduced polypeptide sequences of the SPL15 transcription factor polypeptide are presented.

In international patent application WO03013227, a nucleic acid sequence (and deduced polypeptide sequence; internal reference G2346) is presented that encodes part of the SPL15 transcription factor polypeptide however 38 amino acids from the C-terminal end of the SPL15 transcription factor. Transgenic *Arabidopsis thaliana* plants constitutively overexpressing the modified SPL15 transcription factor (or G2346) polypeptide have slightly enlarged cotyledons. At later stages of development, the same plants are reported to show no consistent differences from control plants.

SUMMARY OF THE INVENTION

Surprisingly, it has now been found that preferentially increasing expression of a nucleic acid encoding a HAL3 polypeptide in expanding tissues gives plants having enhanced yield-related traits, in particular increased early vigour and increased seed yield relative to control plants, which seed yield increase is at least 10% compared to the control plants.

According to another embodiment of present invention, there is provided a method for enhancing yield-related traits, in particular for increasing early vigour of a plant and increasing seed yield of a plant, relative to control plants, comprising preferentially increasing expression of a nucleic acid encoding a HAL3 polypeptide in expanding tissues of a plant.

Surprisingly, it has now been found that modulating expression of a nucleic acid encoding a MADS15 polypeptide gives plants having enhanced yield-related traits, in particular increased yield relative to control plants.

According one embodiment, there is provided a method for increasing plant yield relative to control plants, comprising increasing expression of a nucleic acid encoding a MADS15 polypeptide in a plant. The increased yield comprised increased vegetative biomass but not increased seed yield.

According to another embodiment, the present invention provides methods for increasing yield of a plant relative to control plants, comprising decreasing the level and/or activity of an endogenous MADS15 polypeptide. The increased yield comprised higher seed yield, but did not comprise increased vegetative biomass.

Surprisingly, it has now been found that increasing expression of a nucleic acid encoding a PLT transcription factor polypeptide gives plants having enhanced yield related traits, in particular increased yield relative to control plants.

According to a further embodiment, there is provided a method for increasing plant yield relative to control plants, comprising increasing expression in a plant of a nucleic acid encoding a PLT transcription factor polypeptide.

Surprisingly, it has now been found that modulating expression in a plant of a nucleic acid encoding a particular class of bHLH transcription factor gives plants having enhanced yield-related traits relative to control plants. The particular class of bHLH transcription factor suitable for enhancing yield-related traits in plants is described in detail below.

According to a further embodiment, the present invention provides a method for enhancing yield-related traits in plants relative to control plants, comprising modulating expression in a plant of a nucleic acid encoding a particular class of bHLH transcription factor.

Surprisingly, it has now been found that increasing expression in a plant of a nucleic acid encoding an SPL15 transcription factor polypeptide gives plants having enhanced yield related traits, in particular increased yield relative to control plants.

According to a further embodiment, the invention provides a method for increasing yield in plants relative to control plants, comprising increasing expression in a plant of a nucleic acid encoding an SPL15 transcription factor polypeptide.

Definitions

Polypeptide(s)/Protein(s)

The terms "polypeptide" and "protein" are used interchangeably herein and refer to amino acids in a polymeric form of any length.

Polynucleotide(s)/Nucleic Acid(s)/Nucleic Acid Sequence(s)/Nucleotide Sequence(s)

The terms "polynucleotide(s)", "nucleic acid sequence(s)", "nucleotide sequence(s)", "nucleic acid(s)" are used interchangeably herein and refer to nucleotides, either ribonucleotides or deoxyribonucleotides or a combination of both, in a polymeric form of any length.

Control Plant(s)

The choice of suitable control plants is a routine part of an experimental setup and may include corresponding wild type plants or corresponding plants without the gene of interest. The control plant is typically of the same plant species or even of the same variety as the plant to be assessed. The control plant may also be a nullizygote of the plant to be assessed. A "control plant" as used herein refers not only to whole plants, but also to plant parts, including seeds and seed parts.

Homoloque(s)

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company and Table 1 below).

TABLE 1

Examples of conserved amino acid substitutions

| Residue | Conservative Substitutions | Residue | Conservative Substitutions |
|---|---|---|---|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu, Val | | |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Derivatives

"Derivatives" include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein.

Orthologue(s)/Paralogue(s)

Orthologues and paralogues encompass evolutionary concepts used to describe the ancestral relationships of genes. Paralogues are genes within the same species that have originated through duplication of an ancestral gene and orthologues are genes from different organisms that have originated through speciation.

Domain

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

Motif/Consensus Sequence/Signature

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Hybridisation

The term "hybridisation" as defined herein is a process wherein substantially homologous complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. High stringency hybridisation conditions are typically used for isolating hybridising sequences that have high sequence similarity to the target nucleic acid sequence. However, nucleic acids may deviate in sequence and still encode a substantially identical polypeptide, due to the degeneracy of the genetic code. Therefore medium stringency hybridisation conditions may sometimes be needed to identify such nucleic acid molecules.

The $T_m$ is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the $T_m$ decreases about 1° C. per % base mismatch. The $T_m$ may be calculated using the following equations, depending on the types of hybrids:

1) DNA-DNA hybrids (Meinkoth and Wahl, Anal. Biochem., 138: 267-284, 1984):

$$T_m = 81.5°\text{C.} + 16.6 \times \log_{10}[\text{Na}^+]^a + 0.41 \times \%[G/C^b] - 500 \times [L^c]^{-1} - 0.61 \times \% \text{ formamide}$$

2) DNA-RNA or RNA-RNA hybrids:

$$T_m = 79.8 + 18.5(\log_{10}[\text{Na}^+]^a) + 0.58(\%G/C^b) + 11.8 \,(\%G/C^b)^2 - 820/L^c$$

3) oligo-DNA or oligo-RNA$^d$ hybrids:
For <20 nucleotides: $T_m = 22\,(I_n)$
For 20-35 nucleotides: $T_m = 22 + 1.46\,(I_n)$ $^a$ or for other monovalent cation, but only accurate in the 0.01-0.4 M range.
$^b$ only accurate for % GC in the 30% to 75% range.
$^c$ L=length of duplex in base pairs.
$^d$ Oligo, oligonucleotide; $I_n$, effective length of primer=2× (no. of G/C)+(no. of A/T).

Non-specific binding may be controlled using any one of a number of known techniques such as, for example, blocking the membrane with protein containing solutions, additions of heterologous RNA, DNA, and SDS to the hybridisation buffer, and treatment with Rnase. For non-homologous probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid. When nucleic acids of known sequence are hybridised, the hybrid length may be determined by aligning the sequences and identifying the conserved regions described herein. 1×SSC is 0.15M NaCl and 15 mM sodium citrate; the hybridisation solution and wash solutions may additionally include 5×Denhardt's reagent, 0.5-1.0% SDS, 100 µg/ml denatured, fragmented salmon sperm DNA, 0.5% sodium pyrophosphate.

For the purposes of defining the level of stringency, reference can be made to Sambrook et al. (2001) Molecular Cloning: a laboratory manual, 3rd Edition Cold Spring Harbor Laboratory Press, CSH, New York or to Current Protocols in Molecular Biology, John Wiley & Sons, N.Y. (1989 and yearly updates).

Splice Variant

The term "splice variant" as used herein encompasses variants of a nucleic acid sequence in which selected introns and/or exons have been excised, replaced, displaced or added, or in which introns have been shortened or lengthened. Such variants will be ones in which the biological activity of the protein is substantially retained; this may be achieved by selectively retaining functional segments of the protein. Such splice variants may be found in nature or may be manmade. Methods for predicting and isolating such splice variants are well known in the art (see for example Foissac and Schiex, BMC Bioinformatics. 2005; 6: 25).

Allelic Variant

Alleles or allelic variants are alternative forms of a given gene, located at the same chromosomal position. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

Gene Shuffling/Directed Evolution

Gene shuffling or directed evolution consists of iterations of DNA shuffling followed by appropriate screening and/or selection to generate variants of nucleic acids or portions thereof encoding proteins having a modified biological activity (Castle et al., (2004) Science 304(5674): 1151-4; U.S. Pat. Nos. 5,811,238 and 6,395,547).

Regulatory Element/Control Sequence/Promoter

The terms "regulatory element", "control sequence" and "promoter" are all used interchangeably herein and are to be taken in a broad context to refer to regulatory nucleic acid sequences capable of effecting expression of the sequences to which they are ligated. The term "promoter" typically refers to a nucleic acid control sequence located upstream from the transcriptional start of a gene and which is involved in recognising and binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid molecule in a cell, tissue or organ.

A "plant promoter" comprises regulatory elements, which mediate the expression of a coding sequence segment in plant cells. Accordingly, a plant promoter need not be of plant origin, but may originate from viruses or micro-organisms, for example from viruses which attack plant cells. The "plant promoter" can also originate from a plant cell, e.g. from the plant which is transformed with the nucleic acid sequence to be expressed in the inventive process and described herein. This also applies to other "plant" regulatory signals, such as "plant" terminators. The promoters upstream of the nucleotide sequences useful in the methods of the present invention can be modified by one or more nucleotide substitution(s), insertion(s) and/or deletion(s) without interfering with the functionality or activity of either the promoters, the open reading frame (ORF) or the 3'-regulatory region such as terminators or other 3' regulatory regions which are located away from the ORF. It is furthermore possible that the activity of the promoters is increased by modification of their sequence, or that they are replaced completely by more active promoters, even promoters from heterologous organisms. For expression in plants, the nucleic acid molecule must, as described above, be linked operably to or comprise a suitable promoter which expresses the gene at the right point in time and with the required spatial expression pattern.

For the identification of functionally equivalent promoters, the promoter strength and/or expression pattern of a candidate promoter may be analysed for example by operably linking the promoter to a reporter gene and assaying the expression level and pattern of the reporter gene in various tissues of the plant. Suitable well-known reporter genes include for example beta-glucuronidase or beta galactosidase. The promoter activity is assayed by measuring the enzymatic activity of the beta-glucuronidase or beta-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid used in the methods of the present invention, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6:

986-994). Generally by "weak promoter" is intended a promoter that drives expression of a coding sequence at a low level. By "low level" is intended at levels of about $1/10,000$ transcripts to about $1/100,000$ transcripts, to about $1/500,0000$ transcripts per cell. Conversely, a "strong promoter" drives expression of a coding sequence at high level, or at about $1/10$ transcripts to about $1/100$ transcripts to about $1/1,000$ transcripts per cell.

Operably Linked

The term "operably linked" as used herein refers to a functional linkage between the promoter sequence and the gene of interest, such that the promoter sequence is able to initiate transcription of the gene of interest.

Constitutive Promoter

A "constitutive promoter" refers to a promoter that is transcriptionally active during most, but not necessarily all, phases of growth and development and under most environmental conditions, in at least one cell, tissue or organ. Table 2 below gives examples of constitutive promoters.

TABLE 2

Examples of constitutive promoters

| Gene Source | Reference |
| --- | --- |
| Actin | McElroy et al, Plant Cell, 2: 163-171, 1990 |
| HMGB | WO 2004/070039 |
| CAMV 35S | Odell et al, Nature, 313: 810-812, 1985 |
| CaMV 19S | Nilsson et al., Physiol. Plant. 100: 456-462, 1997 |
| GOS2 | de Pater et al, Plant J Nov; 2(6): 837-44, 1992, WO 2004/065596 |
| Ubiquitin | Christensen et al, Plant Mol. Biol. 18: 675-689, 1992 |
| Rice cyclophilin | Buchholz et al, Plant Mol Biol. 25(5): 837-43, 1994 |
| Maize H3 histone | Lepetit et al, Mol. Gen. Genet. 231: 276-285, 1992 |
| Alfalfa H3 histone | Wu et al. Plant Mol. Biol. 11: 641-649, 1988 |
| Actin 2 | An et al, Plant J. 10(1); 107-121, 1996 |
| 34S FMV | Sanger et al., Plant. Mol. Biol., 14, 1990: 433-443 |
| Rubisco small subunit | U.S. Pat. No. 4,962,028 |
| OCS | Leisner (1988) Proc Natl Acad Sci USA 85(5): 2553 |
| SAD1 | Jain et al., Crop Science, 39 (6), 1999: 1696 |
| SAD2 | Jain et al., Crop Science, 39 (6), 1999: 1696 |
| nos | Shaw et al. (1984) Nucleic Acids Res. 12(20): 7831-7846 |
| V-ATPase | WO 01/14572 |
| Super promoter | WO 95/14098 |
| G-box proteins | WO 94/12015 |

Ubiquitous Promoter

A ubiquitous promoter is active in substantially all tissues or cells of an organism.

Developmentally-Regulated Promoter

A developmentally-regulated promoter is active during certain developmental stages or in parts of the plant that undergo developmental changes.

Inducible Promoter

An inducible promoter has induced or increased transcription initiation in response to a chemical (for a review see Gatz 1997, Annu. Rev. Plant Physiol. Plant Mol. Biol., 48:89-108), environmental or physical stimulus, or may be "stress-inducible", i.e. activated when a plant is exposed to various stress conditions, or a "pathogen-inducible" i.e. activated when a plant is exposed to exposure to various pathogens.

Organ-Specific/Tissue-Specific Promoter

An organ-specific or tissue-specific promoter is one that is capable of preferentially initiating transcription in certain organs or tissues, such as the leaves, roots, seed tissue etc. For example, a "root-specific promoter" is a promoter that is transcriptionally active predominantly in plant roots, substantially to the exclusion of any other parts of a plant, whilst still allowing for any leaky expression in these other plant parts. Promoters able to initiate transcription in certain cells only are referred to herein as "cell-specific".

A green tissue-specific promoter as defined herein is a promoter that is transcriptionally active predominantly in green tissue, substantially to the exclusion of any other parts of a plant, whilst still allowing for any leaky expression in these other plant parts.

Examples of green tissue-specific promoters which may be used to perform the methods of the invention are shown in Table 3 below.

TABLE 3

Examples of green tissue-specific promoters

| Gene | Expression | Reference |
| --- | --- | --- |
| Maize Orthophosphate dikinase | Leaf specific | Fukayama et al., 2001 |
| Maize Phosphoenolpyruvate carboxylase | Leaf specific | Kausch et al., 2001 |
| Rice Phosphoenolpyruvate carboxylase | Leaf specific | Liu et al., 2003 |
| Rice small subunit Rubisco | Leaf specific | Nomura et al., 2000 |
| rice beta expansin EXBP9 | Shoot specific | WO 2004/070039 |
| Pigeonpea small subunit Rubisco | Leaf specific | Panguluri et al., 2005 |
| Pea RBCS3A | Leaf specific | |

Another example of a tissue-specific promoter is a meristem-specific promoter, which is transcriptionally active predominantly in meristematic tissue, substantially to the exclusion of any other parts of a plant, whilst still allowing for any leaky expression in these other plant parts Terminator The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

Modulation

The term "modulation" means in relation to expression or gene expression, a process in which the expression level is changed by said gene expression in comparison to the control plant, preferably the expression level is increased. The original, unmodulated expression may be of any kind of expression of a structural RNA (rRNA, tRNA) or mRNA with subsequent translation. The term "modulating the activity" shall mean any change of the expression of the inventive nucleic acid sequences or encoded proteins, which leads to increased yield and/or increased growth of the plants.

Increased Expression/Overexpression

The term "increased expression" or "overexpression" as used herein means any form of expression that is additional to the original wild-type expression level.

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., PCT/US93/03868), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

Endogenous Gene

Reference herein to an "endogenous" gene not only refers to the gene in question as found in a plant in its natural form (i.e., without there being any human intervention), but also refers to that same gene (or a substantially homologous nucleic acid/gene) in an isolated form subsequently (re)introduced into a plant (a transgene). For example, a transgenic plant containing such a transgene may encounter a substantial reduction of the transgene expression and/or substantial reduction of expression of the endogenous gene.

Decreased Expression

Reference herein to "reduction or substantial elimination" is taken to mean a decrease in endogenous gene expression and/or polypeptide levels and/or polypeptide activity relative to control plants. The reduction or substantial elimination is in increasing order of preference at least 10%, 20%, 30%, 40% or 50%, 60%, 70%, 80%, 85%, 90%, or 95%, 96%, 97%, 98%, 99% or more reduced compared to that of control plants.

For the reduction or substantial elimination of expression an endogenous gene in a plant, a sufficient length of substantially contiguous nucleotides of a nucleic acid sequence is required. In order to perform gene silencing, this may be as little as 20, 19, 18, 17, 16, 15, 14, 13, 12, 11, 10 or fewer nucleotides, alternatively this may be as much as the entire gene (including the 5' and/or 3' UTR, either in part or in whole). The stretch of substantially contiguous nucleotides may be derived from the nucleic acid encoding the protein of interest (target gene), or from any nucleic acid capable of encoding an orthologue, paralogue or homologue of the protein of interest. Preferably, the stretch of substantially contiguous nucleotides is capable of forming hydrogen bonds with the target gene (either sense or antisense strand), more preferably, the stretch of substantially contiguous nucleotides has, in increasing order of preference, 50%, 60%, 70%, 80%, 85%, 90%, 95%, 96%, 97%, 98%, 99%, 100% sequence identity to the target gene (either sense or antisense strand). A nucleic acid sequence encoding a (functional) polypeptide is not a requirement for the various methods discussed herein for the reduction or substantial elimination of expression of an endogenous gene.

This reduction or substantial elimination of expression may be achieved using routine tools and techniques. A preferred method for the reduction or substantial elimination of endogenous gene expression is by introducing and expressing in a plant a genetic construct into which the nucleic acid (in this case a stretch of substantially contiguous nucleotides derived from the gene of interest, or from any nucleic acid capable of encoding an orthologue, paralogue or homologue of any one of the protein of interest) is cloned as an inverted repeat (in part or completely), separated by a spacer (non-coding DNA).

In such a preferred method, expression of the endogenous gene is reduced or substantially eliminated through RNA-mediated silencing using an inverted repeat of a nucleic acid or a part thereof (in this case a stretch of substantially contiguous nucleotides derived from the gene of interest, or from any nucleic acid capable of encoding an orthologue, paralogue or homologue of the protein of interest), preferably capable of forming a hairpin structure. The inverted repeat is cloned in an expression vector comprising control sequences. A non-coding DNA nucleic acid sequence (a spacer, for example a matrix attachment region fragment (MAR), an intron, a polylinker, etc.) is located between the two inverted nucleic acids forming the inverted repeat. After transcription of the inverted repeat, a chimeric RNA with a self-complementary structure is formed (partial or complete). This double-stranded RNA structure is referred to as the hairpin RNA (hpRNA). The hpRNA is processed by the plant into siRNAs that are incorporated into an RNA-induced silencing complex (RISC). The RISC further cleaves the mRNA transcripts, thereby substantially reducing the number of mRNA transcripts to be translated into polypeptides. For further general details see for example, Grierson et al. (1998) WO 98/53083; Waterhouse et al. (1999) WO 99/53050).

Performance of the methods of the invention does not rely on introducing and expressing in a plant a genetic construct into which the nucleic acid is cloned as an inverted repeat, but any one or more of several well-known "gene silencing" methods may be used to achieve the same effects.

One such method for the reduction of endogenous gene expression is RNA-mediated silencing of gene expression (downregulation). Silencing in this case is triggered in a plant by a double stranded RNA sequence (dsRNA) that is substantially similar to the target endogenous gene. This dsRNA is further processed by the plant into about 20 to about 26 nucleotides called short interfering RNAs (siRNAs). The siRNAs are incorporated into an RNA-induced silencing complex (RISC) that cleaves the mRNA transcript of the endogenous target gene, thereby substantially reducing the number of mRNA transcripts to be translated into a polypeptide. Preferably, the double stranded RNA sequence corresponds to a target gene.

Another example of an RNA silencing method involves the introduction of nucleic acid sequences or parts thereof (in this case a stretch of substantially contiguous nucleotides derived from the gene of interest, or from any nucleic acid capable of encoding an orthologue, paralogue or homologue of the protein of interest) in a sense orientation into a plant. "Sense orientation" refers to a DNA sequence that is homologous to an mRNA transcript thereof. Introduced into a plant would therefore be at least one copy of the nucleic acid sequence. The additional nucleic acid sequence will reduce expression of the endogenous gene, giving rise to a phenomenon known as co-suppression. The reduction of gene expression will be more pronounced if several additional copies of a nucleic acid sequence are introduced into the plant, as there is a positive correlation between high transcript levels and the triggering of co-suppression.

Another example of an RNA silencing method involves the use of antisense nucleic acid sequences. An "antisense" nucleic acid sequence comprises a nucleotide sequence that is complementary to a "sense" nucleic acid sequence encoding a protein, i.e. complementary to the coding strand of a double-stranded cDNA molecule or complementary to an mRNA transcript sequence. The antisense nucleic acid sequence is preferably complementary to the endogenous gene to be silenced. The complementarity may be located in the "coding region" and/or in the "non-coding region" of a gene. The term "coding region" refers to a region of the nucleotide sequence comprising codons that are translated into amino acid residues. The term "non-coding region" refers to 5' and 3' sequences that flank the coding region that are transcribed but not translated into amino acids (also referred to as 5' and 3' untranslated regions).

Antisense nucleic acid sequences can be designed according to the rules of Watson and Crick base pairing. The antisense nucleic acid sequence may be complementary to the entire nucleic acid sequence (in this case a stretch of substantially contiguous nucleotides derived from the gene of interest, or from any nucleic acid capable of encoding an orthologue, paralogue or homologue of the protein of interest), but may also be an oligonucleotide that is antisense to only a part of the nucleic acid sequence (including the mRNA 5' and 3' UTR). For example, the antisense oligonucleotide sequence may be complementary to the region surrounding the translation start site of an mRNA transcript encoding a polypeptide. The length of a suitable antisense oligonucleotide sequence is known in the art and may start from about 50, 45, 40, 35, 30, 25, 20, 15 or 10 nucleotides in length or less. An antisense nucleic acid sequence according to the invention may be constructed using chemical synthesis and enzymatic ligation reactions using methods known in the art. For example, an antisense nucleic acid sequence (e.g., an antisense oligonucleotide sequence) may be chemically synthesized using naturally occurring nucleotides or variously modified nucleotides designed to increase the biological stability of the molecules or to increase the physical stability of the duplex formed between the antisense and sense nucleic acid sequences, e.g., phosphorothioate derivatives and acridine substituted nucleotides may be used. Examples of modified nucleotides that may be used to generate the antisense nucleic acid sequences are well known in the art. Known nucleotide modifications include methylation, cyclization and 'caps' and substitution of one or more of the naturally occurring nucleotides with an analogue such as inosine. Other modifications of nucleotides are well known in the art.

The antisense nucleic acid sequence can be produced biologically using an expression vector into which a nucleic acid sequence has been subcloned in an antisense orientation (i.e., RNA transcribed from the inserted nucleic acid will be of an antisense orientation to a target nucleic acid of interest). Preferably, production of antisense nucleic acid sequences in plants occurs by means of a stably integrated nucleic acid construct comprising a promoter, an operably linked antisense oligonucleotide, and a terminator.

The nucleic acid molecules used for silencing in the methods of the invention (whether introduced into a plant or generated in situ) hybridize with or bind to mRNA transcripts and/or genomic DNA encoding a polypeptide to thereby inhibit expression of the protein, e.g., by inhibiting transcription and/or translation. The hybridization can be by conventional nucleotide complementarity to form a stable duplex, or, for example, in the case of an antisense nucleic acid sequence which binds to DNA duplexes, through specific interactions in the major groove of the double helix. Antisense nucleic acid sequences may be introduced into a plant by transformation or direct injection at a specific tissue site. Alternatively, antisense nucleic acid sequences can be modified to target selected cells and then administered systemically. For example, for systemic administration, antisense nucleic acid sequences can be modified such that they specifically bind to receptors or antigens expressed on a selected cell surface, e.g., by linking the antisense nucleic acid sequence to peptides or antibodies which bind to cell surface receptors or antigens. The antisense nucleic acid sequences can also be delivered to cells using the vectors described herein.

According to a further aspect, the antisense nucleic acid sequence is an a-anomeric nucleic acid sequence. An a-anomeric nucleic acid sequence forms specific double-stranded hybrids with complementary RNA in which, contrary to the usual b-units, the strands run parallel to each other (Gaultier et al. (1987) Nucl Ac Res 15: 6625-6641). The antisense nucleic acid sequence may also comprise a 2'-o-methylribonucleotide (Inoue et al. (1987) Nucl Ac Res 15, 6131-6148) or a chimeric RNA-DNA analogue (Inoue et al. (1987) FEBS Lett. 215, 327-330).

The reduction or substantial elimination of endogenous gene expression may also be performed using ribozymes. Ribozymes are catalytic RNA molecules with ribonuclease activity that are capable of cleaving a single-stranded nucleic acid sequence, such as an mRNA, to which they have a complementary region. Thus, ribozymes (e.g., hammerhead ribozymes (described in Haselhoff and Gerlach (1988) Nature 334, 585-591) can be used to catalytically cleave mRNA transcripts encoding a polypeptide, thereby substantially reducing the number of mRNA transcripts to be translated into a polypeptide. A ribozyme having specificity for a nucleic acid sequence can be designed (see for example: Cech et al. U.S. Pat. No. 4,987,071; and Cech et al. U.S. Pat. No. 5,116,742). Alternatively, mRNA transcripts corresponding to a nucleic acid sequence can be used to select a catalytic RNA having a specific ribonuclease activity from a pool of RNA molecules (Bartel and Szostak (1993) Science 261, 1411-1418). The use of ribozymes for gene silencing in plants is known in the art (e.g., Atkins et al. (1994) WO 94/00012; Lenne et al. (1995) WO 95/03404; Lutziger et al. (2000) WO 00/00619; Prinsen et al. (1997) WO 97/13865 and Scott et al. (1997) WO 97/38116).

Gene silencing may also be achieved by insertion mutagenesis (for example, T-DNA insertion or transposon insertion) or by strategies as described by, among others, Angell and Baulcombe ((1999) Plant J 20(3): 357-62), (Amplicon VIGS WO 98/36083), or Baulcombe (WO 99/15682).

Gene silencing may also occur if there is a mutation on an endogenous gene and/or a mutation on an isolated gene/nucleic acid subsequently introduced into a plant. The reduction or substantial elimination may be caused by a non-functional polypeptide. For example, a polypeptide may bind to various interacting proteins; one or more mutation(s) and/or truncation(s) may therefore provide for a polypeptide that is still able to bind interacting proteins (such as receptor proteins) but that cannot exhibit its normal function (such as signalling ligand).

A further approach to gene silencing is by targeting nucleic acid sequences complementary to the regulatory region of the gene (e.g., the promoter and/or enhancers) to form triple helical structures that prevent transcription of the gene in target cells. See Helene, C., Anticancer Drug Res. 6, 569-84, 1991; Helene et al., Ann. N.Y. Acad. Sci. 660, 27-36 1992; and Maher, L. J. Bioassays 14, 807-15, 1992.

Other methods, such as the use of antibodies directed to an endogenous polypeptide for inhibiting its function in planta, or interference in the signalling pathway in which a polypeptide is involved, will be well known to the skilled man. In particular, it can be envisaged that manmade molecules may be useful for inhibiting the biological function of a target polypeptide, or for interfering with the signalling pathway in which the target polypeptide is involved.

Alternatively, a screening program may be set up to identify in a plant population natural variants of a gene, which variants encode polypeptides with reduced activity. Such natural variants may also be used for example, to perform homologous recombination.

Artificial and/or natural microRNAs (miRNAs) may be used to knock out gene expression and/or mRNA translation. Endogenous miRNAs are single stranded small RNAs of typically 19-24 nucleotides long. They function primarily to regulate gene expression and/or mRNA translation. Most plant microRNAs (miRNAs) have perfect or near-perfect complementarity with their target sequences. However, there are natural targets with up to five mismatches. They are processed from longer non-coding RNAs with characteristic fold-back structures by double-strand specific RNases of the Dicer family. Upon processing, they are incorporated in the RNA-induced silencing complex (RISC) by binding to its main component, an Argonaute protein. MiRNAs serve as the specificity components of RISC, since they base-pair to target nucleic acids, mostly mRNAs, in the cytoplasm. Subsequent regulatory events include target mRNA cleavage and destruction and/or translational inhibition. Effects of miRNA overexpression are thus often reflected in decreased mRNA levels of target genes.

Artificial microRNAs (amiRNAs), which are typically 21 nucleotides in length, can be genetically engineered specifically to negatively regulate gene expression of single or multiple genes of interest. Determinants of plant microRNA target selection are well known in the art. Empirical parameters for target recognition have been defined and can be used to aid in the design of specific amiRNAs, Schwab R, 2005. Convenient tools for design and generation of amiRNAs and their precursors are also available to the public, Schwab et al., 2006.

For optimal performance, the gene silencing techniques used for reducing expression in a plant of an endogenous gene requires the use of nucleic acid sequences from monocotyledonous plants for transformation of monocotyledonous plants, and from dicotyledonous plants for transformation of dicotyledonous plants. Preferably, a nucleic acid sequence from any given plant species is introduced into that same species. For example, a nucleic acid sequence from rice is transformed into a rice plant. However, it is not an absolute requirement that the nucleic acid sequence to be introduced originates from the same plant species as the plant in which it will be introduced. It is sufficient that there is substantial homology between the endogenous target gene and the nucleic acid to be introduced.

Described above are examples of various methods for the reduction or substantial elimination of expression in a plant of an endogenous gene. A person skilled in the art would readily be able to adapt the aforementioned methods for silencing so as to achieve reduction of expression of an endogenous gene in a whole plant or in parts thereof through the use of an appropriate promoter, for example.

Selectable Marker (Gene)/Reporter Gene

"Selectable marker", "selectable marker gene" or "reporter gene" includes any gene that confers a phenotype on a cell in which it is expressed to facilitate the identification and/or selection of cells that are transfected or transformed with a nucleic acid construct of the invention. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilisation of xylose, or antinutritive markers such as the resistance to 2-deoxyglucose). Expression of visual marker genes results in the formation of colour (for example β-glucuronidase, GUS or β-galactosidase with its coloured substrates, for example X-Gal), luminescence (such as the luciferin/luceferase system) or fluorescence (Green Fluorescent Protein, GFP, and derivatives thereof). This list represents only a small number of possible markers. The skilled worker is familiar with such markers. Different markers are preferred, depending on the organism and the selection method.

It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acids have been introduced successfully, the process according to the invention for introducing the nucleic acids advantageously employs techniques which enable the removal or excision of these marker genes. One such a method is what is known as co-transformation. The co-transformation method employs two vectors simultaneously for the transformation, one vector bearing the nucleic acid according to the invention and a second bearing the marker gene(s). A large proportion of transformants receives or, in the case of plants, comprises (up to 40% or more of the transformants), both vectors. In case of transformation with *Agrobacteria*, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible. Naturally, these methods can also be applied to microorganisms such as yeast, fungi or bacteria.

Transgenic/Transgene/Recombinant

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or
(b) genetic control sequence(s) which is operably linked with the nucleic acid sequence according to the invention, for example a promoter, or
(c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acids used in the method of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein.

Transformation

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein TM et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the *agrobacteria* to act on plant seeds or to inoculate the plant meristem with *agrobacteria*. It has proved particularly expedient in accordance with the invention to allow a suspension of transformed *agrobacteria* to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). *Agrobacteria* transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F.F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with *agrobacteria* and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed *agrobacteria*, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J and Bent, A F (1998). The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3): 425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229).

T-DNA Activation Tagging

T-DNA activation tagging (Hayashi et al. Science (1992) 1350-1353), involves insertion of T-DNA, usually containing a promoter (may also be a translation enhancer or an intron), in the genomic region of the gene of interest or 10 kb up- or downstream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to modified expression of genes near the inserted T-DNA. The resulting transgenic plants show dominant phenotypes due to modified expression of genes close to the introduced promoter.

Tilling

TILLING (Targeted Induced Local Lesions In Genomes) is a mutagenesis technology useful to generate and/or identify nucleic acids encoding proteins with modified expression and/or activity. TILLING also allows selection of plants carrying such mutant variants. These mutant variants may exhibit modified expression, either in strength or in location or in timing (if the mutations affect the promoter for example). These mutant variants may exhibit higher activity than that exhibited by the gene in its natural form. TILLING combines high-density mutagenesis with high-throughput screening methods. The steps typically followed in TILLING are: (a) EMS mutagenesis (Redei G P and Koncz C (1992) In Methods in *Arabidopsis* Research, Koncz C, Chua N H, Schell J, eds. Singapore, World Scientific Publishing Co, pp. 16-82; Feldmann et al., (1994) In Meyerowitz E M, Somerville C R, eds, *Arabidopsis*. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum et al., (2000) Nat Biotechnol 18: 455-457; reviewed by Stemple (2004) Nat Rev Genet 5(2): 145-50).

Homologous Recombination

Homologous recombination allows introduction in a genome of a selected nucleic acid at a defined selected position. Homologous recombination is a standard technology used routinely in biological sciences for lower organisms such as yeast or the moss *Physcomitrella*. Methods for performing homologous recombination in plants have been described not only for model plants (Offring a et al. (1990) EMBO J 9(10): 3077-84) but also for crop plants, for example rice (Terada et al. (2002) Nat Biotech 20(10): 1030-4; Iida and Terada (2004) Curr Opin Biotech 15(2): 132-8).

Yield

The term "yield" in general means a measurable produce of economic value, typically related to a specified crop, to an area, and to a period of time. Individual plant parts directly contribute to yield based on their number, size and/or weight, or the actual yield is the yield per acre for a crop and year, which is determined by dividing total production (includes both harvested and appraised production) by planted acres.

Early Vigour

Early vigour (active healthy well-balanced growth especially during early stages of plant growth) may result from increased plant fitness due to, for example, the plants being better adapted to their environment (i.e. optimizing the use of energy resources and partitioning between shoot and root). Plants having early vigour also show increased seedling survival and a better establishment of the crop, which often results in highly uniform fields (with the crop growing in uniform manner, i.e. with the majority of plants reaching the various stages of development at substantially the same time), and often better and higher yield. Therefore, early vigour may be determined by measuring various factors, such as thousand kernel weight, percentage germination, percentage emergence, seedling growth, seedling height, root length, root and shoot biomass and many more.

Increase/Improve/Enhance

The terms "increase", "improve" or "enhance" are interchangeable and shall mean in the sense of the application at least a 5%, 6%, 7%, 8%, 9% or 10%, preferably at least 15% or 20%, more preferably 25%, 30%, 35% or 40% more yield and/or growth in comparison to control plants as defined herein.

Seed Yield

Increased seed yield may manifest itself as one or more of the following: a) an increase in seed biomass (total seed weight) which may be on an individual seed basis and/or per plant and/or per hectare or acre; b) increased number of flowers per plant; c) increased number of (filled) seeds; d) increased seed filling rate (which is expressed as the ratio between the number of filled seeds divided by the total number of seeds); e) increased harvest index, which is expressed as a ratio of the yield of harvestable parts, such as seeds, divided by the total biomass; and f) increased thousand kernel weight (TKW), which is extrapolated from the number of filled seeds counted and their total weight. An increased TKW may result from an increased seed size and/or seed weight, and may also result from an increase in embryo and/or endosperm size.

An increase in seed yield may also be manifested as an increase in seed size and/or seed volume. Furthermore, an increase in seed yield may also manifest itself as an increase in seed area and/or seed length and/or seed width and/or seed perimeter. Increased yield may also result in modified architecture, or may occur because of modified architecture.

Plant

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana*, *Agropyron* spp., *Agrostis stolonifera*, *Allium* spp., *Amaranthus* spp., *Ammophila arenaria*, *Ananas comosus*, *Annona* spp., *Apium graveolens*, *Arachis* spp., *Artocarpus* spp., *Asparagus officinalis*, *Avena* spp. (e.g. *Avena sativa*, *Avena fatua*, *Avena byzantina*, *Avena fatua* var. *sativa*, *Avena hybrida*), *Averrhoa carambola*, *Bambusa* sp., *Benincasa hispida*, *Bertholletia excelsea*, *Beta vulgaris*, *Brassica* spp. (e.g. *Brassica napus*, *Brassica rapa* ssp. [canola, oilseed rape, turnip rape]), *Cadaba farinosa*, *Camellia sinensis*, *Canna indica*, *Cannabis sativa*, *Capsicum* spp., *Carex elata*, *Carica papaya*, *Carissa macrocarpa*, *Carya* spp., *Carthamus tinctorius*, *Castanea* spp., *Ceiba pentandra*, *Cichorium endivia*, *Cinnamomum* spp., *Citrullus lanatus*, *Citrus* spp., *Cocos* spp., *Coffea* spp., *Colocasia esculenta*, *Cola* spp., *Corchorus* sp., *Coriandrum sativum*, *Corylus* spp., *Crataegus* spp., *Crocus sativus*, *Cucurbita* spp., *Cucumis* spp., *Cynara* spp., *Daucus carota*, *Desmodium* spp., *Dimocarpus longan*, *Dioscorea* spp., *Diospyros* spp., *Echinochloa* spp., *Elaeis* (e.g. *Elaeis guineensis*, *Elaeis oleifera*), *Eleusine coracana*, *Erianthus* sp., *Eriobotrya japonica*, *Eucalyptus* sp., *Eugenia uniflora*, *Fagopyrum* spp., *Fagus* spp., *Festuca arundinacea*, *Ficus carica*, *Fortunella* spp., *Fragaria* spp., *Ginkgo biloba*, *Glycine* spp. (e.g. *Glycine max*, *Soja hispida* or *Soja max*), *Gossypium hirsutum*, *Helianthus* spp. (e.g. *Helianthus annuus*), *Hemerocallis fulva*, *Hibiscus* spp., *Hordeum* spp. (e.g. *Hordeum vulgare*), *Ipomoea batatas*, *Juglans* spp., *Lactuca sativa*, *Lathyrus* spp., *Lens culinaris*, *Linum usitatissimum*, *Litchi chinensis*, *Lotus* spp., *Luffa acutangula*, *Lupinus* spp., *Luzula sylvatica*, *Lycopersicon* spp. (e.g. *Lycopersicon esculentum*, *Lycopersicon lycopersicum*, *Lycopersicon pyriforme*), *Macrotyloma* spp., *Malus* spp., *Malpighia emarginata*, *Mammea americana*, *Mangifera indica*, *Manihot* spp., *Manilkara zapota*, *Medicago sativa*, *Melilotus* spp., *Mentha* spp., *Miscanthus sinensis*, *Momordica* spp., *Morus nigra*, *Musa* spp., *Nicotiana* spp., *Olea* spp., *Opuntia* spp., *Ornithopus* spp., *Oryza* spp. (e.g. *Oryza sativa*, *Oryza latifolia*), *Panicum miliaceum*, *Panicum virgatum*, *Passiflora edulis*, *Pastinaca sativa*, *Pennisetum* sp., *Persea* spp., *Petroselinum crispum*, *Phalaris arundinacea*, *Phaseolus* spp., *Phleum pratense*, *Phoenix* spp., *Phragmites australis*, *Physalis* spp., *Pinus* spp., *Pistacia vera*, *Pisum* spp., *Poa* spp., *Populus* spp., *Prosopis* spp., *Prunus* spp., *Psidium* spp., *Punica granatum*, *Pyrus communis*, *Quercus* spp., *Raphanus sativus*, *Rheum rhabarbarum*, *Ribes* spp., *Ricinus communis*, *Rubus* spp., *Saccharum* spp., *Salix* sp., *Sambucus* spp., *Secale cereale*, *Sesamum* spp., *Sinapis* sp., *Solanum* spp. (e.g. *Solanum tuberosum*, *Solanum integrifolium* or *Solanum lycopersicum*), *Sorghum bicolor*, *Spinacia* spp., *Syzygium* spp., *Tagetes* spp., *Tamarindus indica*, *Theobroma cacao*, *Trifolium* spp., *Triticosecale rimpaui*, *Triticum* spp. (e.g. *Triticum aestivum*, *Triticum durum*, *Triticum turgidum*, *Triticum hybernum*, *Triticum macha*, *Triticum* sativum or *Triticum vulgare*), *Tropaeolum minus*, *Tropaeolum majus*, *Vaccinium* spp., *Vicia* spp., *Vigna* spp., *Viola odorata*, *Vitis* spp., *Zea mays*, *Zizania palustris*, *Ziziphus* spp., amongst others.

DETAILED DESCRIPTION OF THE INVENTION

Detailed Description for HAL3

According to a first embodiment of the present invention, there is provided a method for increasing plant yield relative to control plants, comprising preferentially increasing expression of a nucleic acid encoding a HAL3 polypeptide in expanding tissues of a plant.

Any reference hereinafter to a "protein useful in the methods of the invention" is taken to mean a HAL3 polypeptide as defined herein. Any reference hereinafter to a "nucleic acid useful in the methods of the invention" is taken to mean a nucleic acid capable of encoding such an HAL3 polypeptide. The nucleic acid to be introduced into a plant (and therefore useful in performing the methods of the invention) is any nucleic acid encoding the type of protein which will now be described, hereafter also named "HAL3 nucleic acid" or "HAL3 gene".

A "reference", "reference plant", "control", "control plant", "wild type" or "wild type plant" is in particular a cell, a tissue, an organ, a plant, or a part thereof, which was not produced according to the method of the invention. Accordingly, the terms "wild type", "control" or "reference" are exchangeable and can be a cell or a part of the plant such as an organelle or tissue, or a plant, which was not modified or treated according to the herein described method according to the invention. Accordingly, the cell or a part of the plant such as an organelle or a plant used as wild type, control or reference corresponds to the cell, plant or part thereof as much as possible and is in any other property but in the result of the process of the invention as identical to the subject matter of the invention as possible. Thus, the wild type, control or reference is treated identically or as identical as possible, saying that only conditions or properties might be different which do not influence the quality of the tested property. That means in other words that the wild type denotes (1) a plant, which carries the unaltered or not modulated form of a gene or allele or (2) the starting material/plant from which the plants produced by the process or method of the invention are derived.

Preferably, any comparison between the wild type plants and the plants produced by the method of the invention is carried out under analogous conditions. The term "analogous conditions" means that all conditions such as, for example, culture or growing conditions, assay conditions (such as buffer composition, temperature, substrates, pathogen strain, concentrations and the like) are kept identical between the experiments to be compared.

The "reference", "control", or "wild type" is preferably a subject, e.g. an organelle, a cell, a tissue, a plant, which was not modulated, modified or treated according to the herein described process of the invention and is in any other property as similar to the subject matter of the invention as possible. The reference, control or wild type is in its genome, transcriptome, proteome or metabolome as similar as possible to the subject of the present invention. Preferably, the term "reference-" "control-" or "wild type-"-organelle, -cell, -tissue or plant, relates to an organelle, cell, tissue or plant, which is nearly genetically identical to the organelle, cell, tissue or plant, of the present invention or a part thereof preferably 95%, more preferred are 98%, even more preferred are 99.00%, in particular 99.10%, 99.30%, 99.50%, 99.70%, 99.90%, 99.99%, 99, 999% or more. Most preferable the "reference", "control", or "wild type" is preferably a subject, e.g. an organelle, a cell, a tissue, a plant, which is genetically identical to the plant, cell organelle used according to the method of the invention except that nucleic acid molecules or the gene product encoded by them are changed, modulated or modified according to the inventive method.

In case, a control, reference or wild type differing from the subject of the present invention only by not being subject of the method of the invention can not be provided, a control, reference or wild type can be a plant in which the cause for the modulation of the activity conferring the increase of the metabolites as described under examples.

The increase referred to the activity of the polypeptide amounts in a cell, a tissue, a organelle, an organ or an organism or a part thereof preferably to at least 5%, preferably to at least 10% or at to least 15%, especially preferably to at least 20%, 25%, 30% or more, very especially preferably are to at least 40%, 50% or 60%, most preferably are to at least 70% or more in comparison to the control, reference or wild type.

The term "increased yield" is taken to mean an increase in biomass (weight) of one or more parts of a plant, which may include aboveground (harvestable) parts and/or (harvestable) parts below ground. Preferably, the increase in yield is at least 10% over the yield of corresponding wild type plants.

In particular, such harvestable parts are seeds, and performance of the methods of the invention results in plants having increased seed yield relative to the seed yield of control plants.

The term "expression" or "gene expression" means the appearance of a phenotypic trait as a consequence of the transcription of a specific gene or specific genes. The term "expression" or "gene expression" in particular means the transcription of a gene or genes into structural RNA (rRNA, tRNA) or mRNA with subsequent translation of the latter into a protein. The process includes transcription of DNA, processing of the resulting mRNA product and its translation into an active protein.

Performance of the methods of the invention gives plants having enhanced yield-related traits. In particular performance of the methods of the invention gives plants having increased yield, especially increased seed yield relative to control plants. The terms "yield" and "seed yield" are described in more detail in the "definitions" section herein.

Reference herein to enhanced yield-related traits is taken to mean an increase in biomass (weight) of one or more parts of a plant, which may include aboveground (harvestable) parts and/or (harvestable) parts below ground. In particular, such harvestable parts are seeds, and performance of the methods of the invention results in plants having increased seed yield relative to the seed yield of suitable control plants.

Taking corn as an example, a yield increase may be manifested as one or more of the following: increase in the number of plants per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

According to a preferred feature of the present invention, performance of the methods of the invention gives plants having increased seed yield relative to control plants. Therefore according to the present invention, there is provided a method for increasing seed yield in plants relative to the seed yield of control plants, the method comprising preferentially increasing expression of a nucleic acid encoding a HAL3 polypeptide in shoot tissues, preferably in expanding tissues of a plant shoot.

Since the transgenic plants according to the present invention have increased yield, it is likely that these plants exhibit an increased growth rate (during at least part of their life cycle), relative to the growth rate of control plants at a corresponding stage in their life cycle.

The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, greenness index, flowering time and speed of seed maturation. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of corn plants followed by, for example, the sowing and optional harvesting of soybean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

According to a preferred feature of the present invention, performance of the methods of the invention gives plants having an increased growth rate relative to control plants. Therefore, according to the present invention, there is provided a method for increasing the growth rate of plants, which method comprises modulating expression, preferably increasing expression, in a plant of a nucleic acid encoding a HAL3 polypeptide as defined herein.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi and insects.

In particular, the methods of the present invention may be performed under non-stress conditions or under conditions of mild drought to give plants having increased yield relative to control plants. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signaling pathways and cellular responses, such as the production of stress proteins, up-regulation of anti-oxidants, accumulation of compatible solutes and growth arrest. The term "non-stress" conditions as used herein are those environmental conditions that allow optimal growth of plants. Persons skilled in the art are aware of normal soil conditions and climatic conditions for a given location.

Performance of the methods of the invention gives plants grown under non-stress conditions or under mild drought conditions increased yield relative to suitable control plants grown under comparable conditions. Therefore, according to the present invention, there is provided a method for increasing yield in plants grown under non-stress conditions or under mild drought conditions, which method comprises increasing expression in a plant of a nucleic acid encoding a HAL3 polypeptide.

Performance of the methods of the invention gives plants grown under conditions of nutrient deficiency, particularly under conditions of nitrogen deficiency, increased yield relative to control plants grown under comparable conditions. Therefore, according to the present invention, there is provided a method for increasing yield in plants grown under conditions of nutrient deficiency, which method comprises increasing expression in a plant of a nucleic acid encoding a HAL3 polypeptide. Nutrient deficiency may result from a lack or excess of nutrients such as nitrogen, phosphates and other phosphorous-containing compounds, potassium, calcium, cadmium, magnesium, manganese, iron and boron, amongst others.

According to a second preferred feature of the invention, performance of the methods of the invention gives plants having increased plant vigour relative to control plants, particularly during the early stages of plant development (typically three, four weeks post germination in the case of rice and maize, but this will vary from species to species) leading to early vigour. Therefore, according to the present invention, there is provided a method for increasing the plant early vigour, which method comprises modulating, preferably increasing expression in a plant of a nucleic acid encoding a HAL3 polypeptide. Preferably the increase in seedling vigour is achieved by expressing the nucleic acid encoding the HAL3 polypeptide under the control of a shoot specific promoter. There is also provided a method for producing plants having early vigour relative to control plants, which method comprises modulating, preferably increasing, expression in a plant of a nucleic acid encoding a HAL3 polypeptide.

Early vigour may also result from increased plant fitness due to, for example, the plants being better adapted to their environment (i.e. optimizing the use of energy resources and partitioning between shoot and root). Plants having early vigour also show increased seedling survival and a better establishment of the crop, which often results in highly uniform fields (with the crop growing in uniform manner, i.e. with the majority of plants reaching the various stages of development at substantially the same time), and often better and higher yield. Therefore, early vigour may be determined by measuring various factors, such as thousand kernel weight, percentage germination, percentage emergence, seedling growth, seedling height, root length, root and shoot biomass and many more.

The methods of the invention are advantageously applicable to any plant.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs. According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, triticale, sorghum and oats.

Other advantageous plants are selected from the group consisting of Asteraceae such as the genera *Helianthus, Tagetes* e.g. the species *Helianthus annus* [sunflower], *Tagetes lucida, Tagetes erecta* or *Tagetes tenuifolia* [Marigold], Brassicaceae such as the genera *Brassica, Arabadopsis* e.g. the species *Brassica napus, Brassica rapa* ssp. [canola, oilseed rape, turnip rape] or *Arabidopsis thaliana*. Fabaceae such as the genera *Glycine* e.g. the species *Glycine max, Soja hispida* or *Soja max* [soybean]. Linaceae such as the genera *Linum* e.g. the species *Linum usitatissimum*, [flax, linseed]; Poaceae such as the genera *Hordeum, Secale, Avena, Sorghum, Oryza, Zea, Triticum* e.g. the species *Hordeum vulgare* [barley]; *Secale cereale* [rye], *Avena sativa, Avena fatua, Avena byzantina, Avena fatua* var. *sativa, Avena hybrida* [oat], *Sorghum bicolor* [Sorghum, millet], *Oryza sativa, Oryza latifolia* [rice], *Zea mays* [corn, maize] *Triticum aestivum, Triticum durum, Triticum turgidum, Triticum hybernum, Triticum macha, Triticum sativum* or *Triticum vulgare* [wheat, bread wheat, common wheat]; Solanaceae such as the genera *Solanum, Lycopersicon* e.g. the species *Solanum tuberosum* [potato], *Lycopersicon esculentum, Lycopersicon lycopersicum, Lycopersicon pyriforme, Solanum integrifolium* or *Solanum lycopersicum* [tomato].

The term "HAL3 polypeptide" as defined herein refers to a flavoprotein belonging to the superfamily HFCD (Homo-oligomeric Flavin containing Cys Decarboxylases; Kupke J. Biol. Chem. 276, 27597-27604, 2001). These proteins share a flavin-binding motif, conserved active-site residues and are trimeric or dodecameric enzymes. HAL3 proteins preferably comprise from N-terminus to C-terminus (i) a substrate binding helix, (ii) an insertion His motif, (iii) a PXMNXXMW motif and (iv) a substrate recognition clamp (FIG. 1). These four domains are predicted to be involved in substrate binding, the insertion His motif comprises a conserved His residue that is involved in the active site whereas the sequence in the substrate recognition clamp may be somewhat variable in sequence and length (Blaesse et al., EMBO J. 19, 6299-6310, 2000). The structural features (i) to (iv) are also described in Kupke et al. (2001), which disclosure is incorporated herein by reference. Typically, HAL3 polypeptides are capable of binding of FMN cofactors.

```
Typically the substrate binding helix is comprised in sequence motif 1
with the following consensus sequence (SEQ ID NO: 6):
(K/R) PR (V/I) (I/L) LAA (S/T) GSVA (A/S) (I/M/V) KF (G/E/A/S) (N/S/I) L (C/V/A)
(H/R/G) (C/S/I) (F/L) (T/S/C) (E/D/Q) WA (E/D) V (R/K) AV (V/A/S).

The insertion His motif, the PXMNXXMW motif and the substrate recognition
clamp are part of sequence motif 2 with the following consensus sequence
(SEQ ID NO: 7):
VLHIELR (R/K/Q) WAD (V/I/A) (L/M) (V/I) IAPLSANTL (G/A) KIAGG (L/M) CDNLLTC
(I/V) (I/V) RAWD (Y/F) (T/S/N/D/K) KP (L/F/M/I) F (V/A) APAMNT (L/F) MW
(N/S/T) NPFT (E/S/Q/A) (R/K) H (L/F/I) (X₁) (X₂) (L/I/M) (D/N/S) (E/L/Q)
(L/M) G (I/V/L) (T/S/A/I) L (I/V) PP (I/V/T) (K/T/S) K (R/T/K) LACGD (Y/H)
G (N/T) GAM (A/S) E
wherein X₁ may be any amino acid, preferably X₁ is one of L, V, E, H, D,
M, I or Q and wherein X₂ may be any amino acid, preferably X₂ is one of
S, L, T, A, or V.
```

These motifs form part of a larger conserved region in the protein, as an example, the conserved region of *Arabidopsis* HAL3a is given as SEQ ID NO: 8. HAL3 polypeptides useful in the methods of the present invention have in increasing order of preference at least 65%, 70%, 75%, 80%, 85%, 90% or 95% sequence identity to the conserved region represented by SEQ ID NO: 8.

The conserved region in HAL3 proteins, as exemplified in SEQ ID NO: 8 and comprising the above described features (i) to (iv), encompasses a Flavoprotein domain which may be identified using specialised databases e.g. SMART (Schultz et al. (1998) Proc. Natl. Acad. Sci. USA 95, 5857-5864;

Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAIPress, Menlo Park; Hulo et al., Nucl. Acids. Res. 32:D134-D137, (2004)) or Pfam (Bateman et al., Nucleic Acids Research 30(1): 276-280 (2002)). This FMN-binding domain (Pfam entry PF02441, InterPro entry IPR003382) is typically found in flavoprotein enzymes. The terms "domain" and "motif" are defined in the definitions section above.

The conserved region in SEQ ID NO: 2, as represented by SEQ ID NO: 8, may also in other HAL3 proteins be identified, using methods for the alignment of sequences for comparison as described hereinabove. In some instances, the default parameters may be adjusted to modify the stringency of the search. For example using BLAST, the statistical significance threshold (called "expect" value) for reporting matches against database sequences may be increased to show less stringent matches. This way, short nearly exact matches may be identified, including the conserved motifs 1 and 2 (SEQ ID NO: 6 and 7), or matches with one or more conservative change at any position.

HAL3 polypeptides (at least in their native form) and their homologues typically catalyse the decarboxylation of 4'-phosphopantothenoylcysteine to 4'-phosphopantetheine, a step in coenzyme A biosynthesis, which reaction may be tested in a biochemical assay; alternatively, HAL3 activity may be assayed by a complementation test with a dfp mutant E. coli strain (Kupke et al 2001; Yonamine et al 2004). The enzyme is also able to decarboxylate pantothenoylcysteine to pantothenoylcysteamine. Furthermore, the protein is involved in conferring salt and osmotic stress tolerance to plants, which feature may be useful in a bioassay for HAL3.

SEQ ID NO: 2 (encoded by SEQ ID NO: 1) is an example of a HAL3 polypeptide comprising from N-terminus to C-terminus features (i) a substrate binding helix, (ii) an insertion His motif, (iii) a PXMNXXMW motif and (iv) a substrate recognition clamp; and having in increasing order of preference at least 65%, 70%, 75%, 80%, 85%, 90% or 95% sequence identity to the conserved region represented by SEQ ID NO: 8. Further examples of HAL3 polypeptides comprising features (i) to (iv) are given in Table A in the examples section below:

Homologues of a HAL3 polypeptide may also be used to perform the methods of invention. Homologues (or homologous proteins) may readily be identified using routine techniques well known in the art, such as by sequence alignment. Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the alignment of two complete sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information. Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art.

The sequence identity values may be determined over the entire conserved domain (as indicated above) or over the full length nucleic acid or amino acid sequence using the programs mentioned above using the default parameters.

Homologues also include orthologues and paralogues. Orthologues and paralogues may easily be found by performing a so-called reciprocal blast search. This may be done by a first BLAST involving submitting a query sequence (for example, SEQ ID NO: 1 or SEQ ID NO: 2) for a BLAST search against any sequence database, such as the publicly available NCBI database. BLASTN or TBLASTX (using standard default values) may be used when starting from a nucleotide sequence and BLASTP or TBLASTN (using standard default values) may be used when starting from a protein sequence. The BLAST results may optionally be filtered. The full-length sequences of either the filtered results or non-filtered results are then submitted to a second BLAST search (BLAST back) against sequences from the organism from which the query sequence is derived (where the query sequence is SEQ ID NO: 1 or SEQ ID NO: 2 the second BLAST would therefore be against Arabidopsis sequences). The results of the first and second BLAST searches are then compared. A paralogue is identified if a high-ranking hit from the first BLAST is from the same species as from which the query sequence is derived; an orthologue is identified if a high-ranking hit is not from the same species as from which the query sequence is derived. Preferred orthologues are orthologues of AtHAL3a (SEQ ID NO: 2), AtHAL3b (SEQ ID NO: 10) or of the long form of AtHAL3b (SEQ ID NO: 40). High-ranking hits are those having a low E-value. The lower the E-value, the more significant the score (or in other words the lower the chance that the hit was found by chance). Computation of the E-value is well known in the art. In the case of large families, ClustalW may be used, followed by a neighbour joining tree, to help visualize clustering of related genes and to identify orthologues and paralogues. In addition to E-values, comparisons are also scored by percentage identity. Percentage identity refers to the number of identical nucleotides (or amino acids) between the two compared nucleic acid (or polypeptide) sequences over a particular length. Preferably, HAL3 polypeptide homologues have in increasing order of preference at least 60%, 70%, 80%, 85%, 90%, 95%, 96%, 97%, 98% or 99% or more sequence identity or similarity (functional identity) to an unmodified HAL3 polypeptide as represented by SEQ ID NO: 2. Preferably, HAL3 polypeptide homologues are as represented by the sequences referred to in Table A.

The HAL3 polypeptide useful in the methods of the present invention may be a derivative of SEQ ID NO: 2. "Derivatives" include peptides, oligopeptides, polypeptides which may, compared to the amino acid sequence of the naturally-occurring form of the protein, such as the one presented in SEQ ID NO: 2, comprise substitutions of amino acids with non-naturally occurring amino acid residues, or additions of non-naturally occurring amino acid residues. Derivatives of the proteins as represented by the sequences listed in Table A are further examples which may be suitable for use in the methods of the invention Examples of nucleic acids encoding HAL3 polypeptides include but are not limited to those represented by the sequences listed in Table A. Variants of nucleic acids encoding HAL3 polypeptides may be suitable for use in the methods of the invention. Suitable variants include portions of nucleic acids encoding HAL3 polypeptides and/or nucleic acids capable of hybridising with nucleic acids/genes encoding HAL3 polypeptides. Further variants include splice variants and allelic variants of nucleic acids encoding HAL3 polypeptides.

The term "portion" as defined herein refers to a piece of DNA encoding a polypeptide comprising from N-terminus to C-terminus features (i) a substrate binding helix, (ii) an insertion His motif, (iii) a PXMNXXMW motif and (iv) a substrate recognition clamp; and having in increasing order of preference at least 65%, 70%, 75%, 80%, 85%, 90% or 95% sequence identity to the conserved region represented by SEQ ID NO: 8.

A portion may be prepared, for example, by making one or more deletions to a nucleic acid encoding a HAL3 polypeptide. The portions may be used in isolated form or they may be fused to other coding (or non coding) sequences in order to, for example, produce a protein that combines several activities. When fused to other coding sequences, the resulting polypeptide produced upon translation may be bigger than that predicted for the HAL3 portion. Preferably, the portion codes for a polypeptide with substantially the same biological activity as the HAL3 polypeptide of SEQ ID NO: 2. The portion is typically at least 50, 100, 150 or 200 nucleotides in length, preferably at least 250, 300, 350 or 400 nucleotides in length, more preferably at least 450, 500, 550, 600 or 650 nucleotides in length.

Preferably, the portion is a portion of a nucleic acid as represented by the sequences listed in Table A. Most preferably the portion is a portion of a nucleic acid as represented by SEQ ID NO: 1.

The terms "fragment", "fragment of a sequence" or "part of a sequence" "portion" or "portion thereof" mean a truncated sequence of the original sequence referred to. The truncated sequence (nucleic acid or protein sequence) can vary widely in length; the minimum size being a sequence of sufficient size to provide a sequence with at least a comparable function and/or activity of the original sequence referred to or hybidizing with the nucleic acid molecule of the invention or used in the process of the invention under stringent conditions, while the maximum size is not critical. In some applications, the maximum size usually is not substantially greater than that required to provide the desired activity and/or function(s) of the original sequence. A comparable function means at least 40%, 45% or 50%, preferably at least 60%, 70%, 80% or 90% or more of the original sequence.

Another variant of a nucleic acid encoding a HAL3 polypeptide, useful in the methods of the present invention, is a nucleic acid capable of hybridising under reduced stringency conditions, preferably under stringent conditions, with a probe derived from the nucleic acid as defined hereinbefore, which hybridising sequence encodes a polypeptide comprising from N-terminus to C-terminus features (i) a substrate binding helix, (ii) an insertion His motif, (iii) a PXMNXXMW motif and (iv) a substrate recognition clamp; and has in increasing order of preference at least 65%, 70%, 75%, 80%, 85%, 90% or 95% sequence identity to the conserved region represented by SEQ ID NO: 8.

Preferably, the hybridising sequence is one that is capable of hybridising to a nucleic acid as represented by (or to probes derived from) the sequences listed in Table A, or to a portion of any of these sequences (the target sequence). Most preferably the hybridising sequence is capable of hybridising to SEQ ID NO: 1 (or to probes derived therefrom). Probes are generally less than 700 bp or 600 bp in length, preferably less than 500, 400 bp, 300 bp 200 bp or 100 bp in length. Commonly, probe lengths for DNA-DNA hybridisations such as Southern blotting, vary between 100 and 500 bp, whereas the hybridising region in probes for DNA-DNA hybridisations such as in PCR amplification generally are shorter than 50 but longer than 10 nucleotides, preferably they are 15, 20, 25, 30, 35, 40, 45 or 50 bp in length.

The HAL3 polypeptide may be encoded by a splice variant. The term "splice variant" as used herein encompasses variants of a nucleic acid sequence in which selected introns and/or exons have been excised, replaced, displaced or added, or in which introns have been shortened or lengthened. Such variants will be ones in which the substantial biological activity of the protein is retained, which may be achieved by selectively retaining functional segments of the protein. Such splice variants may be found in nature or may be manmade. Methods for making such splice variants are well known in the art.

Preferred splice variants are splice variants of the nucleic acid encoding a HAL3 polypeptide comprising from N-terminus to C-terminus (i) a substrate binding helix, (ii) an insertion His motif, (iii) a PXMNXXMW motif and (iv) a substrate recognition clamp; and having in increasing order of preference at least 65%, 70%, 75%, 80%, 85%, 90% or 95% sequence identity to the conserved region represented by SEQ ID NO: 8.

Further preferred splice variants of nucleic acids encoding HAL3 polypeptides comprising features as defined hereinabove are splice variants of a nucleic acid as represented by any one of the sequences listed in Table A. Most preferred is a splice variant of a nucleic acid sequence as represented by SEQ ID NO: 1.

The HAL3 polypeptide may also be encoded by an allelic variant of a nucleic acid encoding a polypeptide comprising from N-terminus to C-terminus (i) a substrate binding helix, (ii) an insertion His motif, (iii) a PXMNXXMW motif and (iv) a substrate recognition clamp; and having in increasing order of preference at least 65%, 70%, 75%, 80%, 85%, 90% or 95% sequence identity to the conserved region represented by SEQ ID NO: 8.

Preferred allelic variants of nucleic acids encoding HAL3 polypeptides comprising features as defined hereinabove are allelic variants of a nucleic acid as represented by any one of the sequences listed in Table A. Most preferred is an allelic variant of a nucleic acid sequence as represented by SEQ ID NO: 1.

Directed evolution (or gene shuffling) may also be used to generate variants of nucleic acids encoding HAL3 polypeptides. Site-directed mutagenesis may be used to generate variants of nucleic acids encoding HAL3 polypeptides. Several methods are available to achieve site-directed mutagenesis, the most common being PCR based methods (Current Protocols in Molecular Biology. Wiley Eds.).

Nucleic acids encoding HAL3 polypeptides may be derived from any natural or artificial source. The nucleic acid may be modified from its native form in composition and/or genomic environment through deliberate human manipulation. Preferably the HAL3 nucleic acid is from a plant, further preferably from a dicotyledonous plant, more preferably from the family Brassicaceae, most preferably the nucleic acid is from *Arabidopsis thaliana*.

The increased expression of a nucleic acid encoding a HAL3 polypeptide, preferentially in shoots of a plant, may be performed by introducing a genetic modification (preferably in the locus of a HAL3 gene). The locus of a gene as defined herein is taken to mean a genomic region, which includes the gene of interest and 10 KB up- or downstream of the coding region.

The genetic modification may be introduced, for example, by any one (or more) of the following methods: T-DNA activation, TILLING and homologous recombination (as described in the definitions section) or by introducing and increasing expression a nucleic acid encoding a HAL3 polypeptide preferentially in expanding tissues of a plant. Following introduction of the genetic modification, there follows an optional step of selecting for increased expression of a nucleic acid encoding a HAL3 factor polypeptide preferentially in expanding tissues, which increased expression gives plants having increased yield.

T-DNA activation tagging results in transgenic plants that show dominant phenotypes due to modified expression of genes close to the introduced promoter. The promoter to be introduced may be any promoter capable of increasing expression of the nucleic acid encoding a HAL3 polypeptide preferentially in expanding tissues of a plant.

A genetic modification may also be introduced in the locus of a gene encoding a HAL3 polypeptide using the technique of TILLING (Targeted Induced Local Lesions In Genomes). Plants carrying such mutant variants have increased expression of a nucleic acid encoding a HAL3 polypeptide preferentially in expanding plant tissues.

T-DNA activation and TILLING are examples of technologies that enable the generation of genetic modifications comprising preferentially increasing expression of a nucleic acid encoding a HAL3 polypeptide in expanding tissues of plants.

The effects of the invention may also be reproduced using homologous recombination. The nucleic acid to be targeted is preferably the region controlling the natural expression of a nucleic acid encoding a HAL3 polypeptide in a plant. A weak promoter specific for expression in shoots is introduced into this region, replacing it partly or substantially all of it.

A preferred method for introducing a genetic modification (which in this case need not be in the locus of a HAL3 gene) is to introduce and express preferentially in the shoot of a plant a nucleic acid encoding a HAL3 polypeptide, as defined hereinabove. The nucleic acid to be introduced into a plant may be a full-length nucleic acid or may be a portion or a hybridising sequence or another nucleic acid variant as hereinbefore defined.

The methods of the invention rely on preferentially increased expression of a nucleic acid encoding a HAL3 polypeptide in shoot tissue of a plant, preferably in the cell expansion zone of vegetative shoots.

The invention also provides genetic constructs and vectors to facilitate introduction and/or preferential expression of the nucleic acid sequences useful in the methods according to the invention, in shoots, preferably in expanding tissues of a plant shoots.

Therefore, there is provided a gene construct comprising:
(i) a nucleic acid encoding a HAL3 polypeptide as defined hereinabove;
(ii) one or more control sequences, of which at least one is a shoot-specific promoter, operably linked to the nucleic acid of (i).

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells. The invention therefore provides use of a gene construct as defined hereinabove in the methods of the invention.

Plants are transformed with a vector comprising the sequence of interest (i.e., a nucleic acid encoding a HAL3 polypeptide). The skilled artisan is well aware of the genetic elements that must be present on the vector in order to successfully transform, select and propagate host cells containing the sequence of interest. The sequence of interest is operably linked to one or more control sequences (at least to a promoter).

Suitable promoters, which are functional in plants, are generally known. They may take the form of constitutive or inducible promoters. Suitable promoters can enable the development- and/or tissue-specific expression in multicelled eukaryotes; thus, leaf-, root-, flower-, seed-, stomata-, tuber- or fruit-specific promoters may advantageously be used in plants.

Different plant promoters usable in plants are promoters such as, for example, the USP, the LegB4-, the DC3 promoter or the ubiquitin promoter from parsley.

For expression in plants, the nucleic acid molecule must, as described above, be linked operably to or comprise a suitable promoter which expresses the gene at the right point in time and in a cell- or tissue-specific manner. Usable promoters are constitutive promoters (Benfey et al., EMBO J. 8 (1989) 2195-2202), such as those which originate from plant viruses, such as 35S CAMV (Franck et al., Cell 21 (1980) 285-294), 19S CaMV (see also U.S. Pat. No. 5,352,605 and WO 84/02913), 34S FMV (Sanger et al., Plant. Mol. Biol., 14, 1990: 433-443), the parsley ubiquitin promoter, or plant promoters such as the Rubisco small subunit promoter described in U.S. Pat. No. 4,962,028 or the plant promoters PRP1 [Ward et al., Plant. Mol. Biol. 22 (1993)], SSU, PGEL1, OCS [Leisner (1988) Proc Natl Acad Sci USA 85(5): 2553-2557], lib4, usp, mas [Comai (1990) Plant Mol Biol 15 (3):373-381], STLS1, ScBV (Schenk (1999) Plant Mol Biol 39(6):1221-1230), B33, SAD1 or SAD2 (flax promoters, Jain et al., Crop Science, 39 (6), 1999: 1696-1701) or nos [Shaw et al. (1984) Nucleic Acids Res. 12(20):7831-7846]. Further examples of constitutive plant promoters are the sugarbeet V-ATPase promoters (WO 01/14572). Examples of synthetic constitutive promoters are the Super promoter (WO 95/14098) and promoters derived from G-boxes (WO 94/12015). If appropriate, chemical inducible promoters may furthermore also be used, compare EP-A 388186, EP-A 335528, WO 97/06268. Stable, constitutive expression of the proteins according to the invention a plant can be advantageous. However, inducible expression of the polypeptide of the invention is advantageous, if a late expression before the harvest is of advantage, as metabolic manipulation may lead to plant growth retardation.

The expression of plant genes can also be facilitated via a chemical inducible promoter (for a review, see Gatz 1997, Annu. Rev. Plant Physiol. Plant Mol. Biol., 48:89-108). Chemically inducible promoters are particularly suitable when it is desired to express the gene in a time-specific manner. Examples of such promoters are a salicylic acid inducible promoter (WO 95/19443), and abscisic acid-inducible promoter (EP 335 528), a tetracyclin-inducible promoter (Gatz et al. (1992) Plant J. 2, 397-404), a cyclohexanol- or ethanol-inducible promoter (WO 93/21334) or others as described herein.

Other suitable promoters are those which react to biotic or abiotic stress conditions, for example the pathogen-induced PRP1 gene promoter (Ward et al., Plant. Mol. Biol. 22 (1993) 361-366), the tomato heat-inducible hsp80 promoter (U.S. Pat. No. 5,187,267), the potato chill-inducible alpha-amylase promoter (WO 96/12814) or the wound-inducible pinII promoter (EP-A-0 375 091) or others as described herein.

Preferred promoters are in particular those which bring gene expression in tissues and organs, in seed cells, such as endosperm cells and cells of the developing embryo. Suitable promoters are the oilseed rape napin gene promoter (U.S. Pat. No. 5,608,152), the *Vicia faba* USP promoter (Baeumlein et al., Mol Gen Genet, 1991, 225 (3): 459-67), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980), the bean arc5 promoter, the carrot DcG3 promoter, or the Legumin B4 promoter (LeB4; Baeumlein et al., 1992, Plant Journal, 2 (2): 233-9), and promoters which bring about the seed-specific expression in monocotyledonous plants such as maize, barley, wheat, rye, rice and the like. Advantageous seed-specific promoters are the sucrose binding protein promoter (WO 00/26388), the phaseolin promoter and the napin promoter. Suitable promoters which must be considered are the barley Ipt2 or Ipt1 gene promoter (WO 95/15389 and WO 95/23230), and the promoters described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene and the rye secalin gene). Further suitable promoters are Amy32b, Amy 6-6 and Aleurain [U.S. Pat. No. 5,677,474], Bce4 (oilseed rape) [U.S. Pat. No. 5,530,149], glycinin (soya) [EP 571 741], phosphoenolpyruvate carboxylase (soya) [JP 06/62870], ADR12-2 (soya) [WO 98/08962], isocitrate lyase (oilseed rape) [U.S. Pat. No. 5,689,040] or α-amylase (barley) [EP 781 849]. Other promoters which are available for the expression of genes in plants are leaf-specific promoters such as those described in DE-A 19644478 or light-regulated promoters such as, for example, the pea petE promoter.

Further suitable plant promoters are the cytosolic FBPase promoter or the potato ST-LSI promoter (Stockhaus et al., EMBO J. 8, 1989, 2445), the *Glycine max* phosphoribosylpyrophosphate amidotransferase promoter (GenBank Accession No. U87999) or the node-specific promoter described in EP-A-0 249 676.

In a preferred embodiment, the nucleic acid sequence encoding a HAL3 polypeptide is operably linked to a shoot a shoot specific promoter. A shoot-specific promoter refers to any promoter able to drive expression of the gene of interest in vegetative plant shoot tissues. Preferably, the shoot specific promoter is able to preferentially drive expression of the gene of interest in expanding tissues of vegetative shoots, that is in the cell expansion zone of vegetative shoots. Reference herein to "preferentially" driving expression in the shoot is taken to mean driving expression of any sequence operably linked thereto in the cell expansion zone of vegetative shoots substantially to the exclusion of driving expression elsewhere in the plant, apart from any residual expression due to leaky promoter expression. The shoot-specific promoter may be either a natural or a synthetic promoter.

Preferably, the shoot-specific promoter is a promoter isolated from a beta-expansin gene, such as a rice beta expansin EXBP9 promoter (WO 2004/070039), as represented by SEQ ID NO: 5 or a promoter of similar strength and/or a promoter with a similar expression pattern as the rice beta expansin promoter (i.e. a functionally equivalent promoter).

It should be clear that the applicability of the present invention is not restricted to the nucleic acid encoding a HAL3 polypeptide represented by SEQ ID NO: 1, nor is the applicability of the invention restricted to expression of a nucleic acid encoding a HAL3 polypeptide when driven by a beta expansin promoter.

Optionally, one or more terminator sequences (also a control sequence) may be used in the construct introduced into a plant. Additional regulatory elements may include transcriptional as well as translational enhancers. Those skilled in the art will be aware of terminator and enhancer sequences that may be suitable for use in performing the invention. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

Other control sequences (besides promoter, enhancer, silencer, intron sequences, 3'UTR and/or 5'UTR regions) may be protein and/or RNA stabilizing elements.

For the detection and/or selection of the successful transfer of the nucleic acid sequences as depicted in the sequence protocol and used in the process of the invention, it is advantageous to use marker genes (=reporter genes). These marker genes enable the identification of a successful transfer of the nucleic acid molecules via a series of different principles, for example via visual identification with the aid of fluorescence, luminescence or in the wavelength range of light which is discernible for the human eye, by a resistance to herbicides or antibiotics, via what are known as nutritive markers (auxotrophism markers) or antinutritive markers, via enzyme assays or via phytohormones. Examples of such markers which may be mentioned are GFP (=green fluorescent protein); the luciferin/luceferase system, the β-galactosidase with its colored substrates, for example X-Gal, the herbicide resistances to, for example, imidazolinone, glyphosate, phosphinothricin or sulfonylurea, the antibiotic resistances to, for example, bleomycin, hygromycin, streptomycin, kanamycin, tetracyclin, chloramphenicol, ampicillin, gentamycin, geneticin (G418), spectinomycin or blasticidin, to mention only a few, nutritive markers such as the utilization of mannose or xylose, or antinutritive markers such as the resistance to 2-deoxyglucose. This list is a small number of possible markers. The skilled worker is very familiar with such markers. Different markers are preferred, depending on the organism and the selection method.

The present invention also encompasses plants obtainable by the methods according to the present invention. The present invention therefore provides plants, plant parts or plant cells thereof obtainable by the method according to the present invention, which plants or parts or cells thereof comprise a nucleic acid transgene encoding a HAL3 polypeptide under the control of a shoot-specific promoter.

The invention also provides a method for the production of transgenic plants having increased yield relative to control plants, comprising introduction and preferential expression of a nucleic acid encoding a HAL3 polypeptide in the shoot of a plant.

Host plants for the nucleic acids or the vector used in the method according to the invention, the expression cassette or construct or vector are, in principle, advantageously all plants, which are capable of synthesizing the polypeptides used in the inventive method.

More specifically, the present invention provides a method for the production of transgenic plants having increased yield which method comprises:

(i) introducing and preferentially expressing a nucleic acid encoding a HAL3 polypeptide in the shoot of a plant; and (ii) cultivating the plant cell under conditions promoting plant growth and development.

The nucleic acid may be introduced directly into a plant cell or into the plant itself (including introduction into a tissue, organ or any other part of a plant). According to a preferred feature of the present invention, the nucleic acid is preferably introduced into a plant by transformation.

The transfer of foreign genes into the genome of a plant is called transformation. In doing this the methods described for the transformation and regeneration of plants from plant tissues or plant cells are utilized for transient or stable transformation. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Further advantageous transformation methods, in particular for plants, are known to the skilled worker and are described herein below.

Generally after transformation, plant cells or cell groupings are selected for the presence of one or more markers which are encoded by plant-expressible genes co-transferred with the gene of interest, following which the transformed material is regenerated into a whole plant.

As mentioned *Agrobacteria* transformed with an expression vector according to the invention may also be used in the manner known per se for the transformation of plants such as experimental plants like *Arabidopsis* or crop plants, such as, for example, cereals, maize, oats, rye, barley, wheat, soya, rice, cotton, sugarbeet, canola, sunflower, flax, hemp, potato, tobacco, tomato, carrot, bell peppers, oilseed rape, tapioca, cassava, arrow root, tagetes, alfalfa, lettuce and the various tree, nut, and grapevine species, in particular oil-containing crop plants such as soya, peanut, castor-oil plant, sunflower, maize, cotton, flax, oilseed rape, coconut, oil palm, safflower (*Carthamus tinctorius*) or cocoa beans, for example by bathing scarified leaves or leaf segments in an agrobacterial solution and subsequently growing them in suitable media.

In addition to the transformation of somatic cells, which then has to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with *agrobacteria* and seeds are obtained from the developing plants of which a certain proportion is transformed and thus transgenic [Feldman, K A and Marks M D (1987). Mol Gen Genet. 208:274-289; Feldmann K (1992). In: C Koncz, N-H Chua and J Shell, eds, Methods in *Arabidopsis* Research. Word Scientific, Singapore, pp. 274-289]. Alternative methods are based on the repeated removal of the influorescences and incubation of the excision site in the center of the rosette with transformed *agrobacteria*, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J and Bent, A F (1998). The Plant J. 16, 735-743]. A certain proportion of transgenic seeds are harvested in both cases, and these seeds can be distinguished from nontransgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process, which has been schematically displayed in Klaus et al., 2004 [ Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview can be taken from Bock (2001) Transgenic plastids in basic research and plant biotechnology. J Mol Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient cointegrated maker gene (Klaus et al., 2004, Nature Biotechnology 22(2), 225-229).

The genetically modified plant cells can be regenerated via all methods with which the skilled worker is familiar. Suitable methods can be found in the abovementioned publications by S. D. Kung and R. Wu, Potrykus or Höfgen and Willmitzer.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, or quantitative PCR, all techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid encoding a HAL3 polypeptide. Preferred host cells according to the invention are plant cells.

The invention also extends to harvestable parts of a plant such as, but not limited to seeds, leaves, fruits, flowers, stems, rhizomes, tubers and bulbs. The invention furthermore relates to products derived, preferably directly derived, from a harvestable part of such a plant, such as dry pellets or powders, oil, fat and fatty acids, starch or proteins.

The present invention also encompasses use of nucleic acids encoding HAL3 polypeptides and use of HAL3 polypeptides in increasing plant yield as defined hereinabove in the methods of the invention.

Nucleic acids encoding HAL3 polypeptides, or HAL3 polypeptides, may find use in breeding programmes in which a DNA marker is identified which may be genetically linked to a HAL3 gene. The nucleic acids/genes, or the HAL3 polypeptides may be used to define a molecular marker. This DNA or protein marker may then be used in breeding programmes to select plants having increased yield as defined hereinabove in the methods of the invention.

Allelic variants of a HAL3 nucleic acid/gene may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give increased yield. Selection is typically carried out by monitoring growth performance of plants containing different allelic variants of the sequence in question. Growth performance may be monitored in a greenhouse or in the field. Further optional steps include crossing plants in which the superior allelic variant was identified with another plant. This could be used, for example, to make a combination of interesting phenotypic features.

A nucleic acid encoding a HAL3 polypeptide may also be used as probes for genetically and physically mapping the genes that they are a part of, and as markers for traits linked to those genes. Such information may be useful in plant breeding in order to develop lines with desired phenotypes. Such use of HAL3 nucleic acids requires only a nucleic acid sequence of at least 15 nucleotides in length. The HAL3 nucleic acids may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the HAL3 nucleic acids. The resulting banding patterns may then be subjected to genetic analyses using computer programs such as MapMaker (Lander et al. (1987) Genomics 1: 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the HAL3 nucleic acid in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridisation (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acids. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having increased yield, as described hereinbefore. This increased yield may also be combined with other economically advantageous traits, such as further yield-enhancing traits, tolerance to other abiotic and biotic stresses, traits modifying various architectural features and/or biochemical and/or physiological features.

Detailed Description for MADS15 up

Surprisingly, it has now been found that modulating expression in a plant of a nucleic acid encoding a MADS15 polypeptide gives plants having enhanced yield-related traits relative to control plants. The particular class of MADS15 polypeptides suitable for enhancing yield-related traits in plants is described in detail below.

The present invention provides a method for enhancing yield-related traits in plants relative to control plants, comprising modulating expression in a plant of a nucleic acid encoding a MADS15 polypeptide.

Any reference hereinafter to a "protein useful in the methods of the invention" is taken to mean a MADS15 polypeptide as defined herein. Any reference hereinafter to a "nucleic acid useful in the methods of the invention" is taken to mean a nucleic acid capable of encoding such a MADS15 polypeptide.

A preferred method for modulating (preferably, increasing) expression of a nucleic acid encoding a protein useful in the methods of the invention is by introducing and expressing in a plant a nucleic acid encoding a protein useful in the methods of the invention as defined below.

The nucleic acid to be introduced into a plant (and therefore useful in performing the methods of the invention) is any nucleic acid encoding the type of protein which will now be described, hereafter also named "MADS15 nucleic acid" or "MADS15 gene".

The term "MADS15 polypeptide" as defined herein refers to a protein that falls in the group of FUL-like MADS box proteins as delineated by Adam et al. (J. Mol. Evol. 62, 15-31). FUL-like MADS box proteins are part of the SQUA-MOSA subfamily and have the typical MIKC$^c$ architecture: a MADS domain (M) at the N-terminus, followed by an intervening domain (I) involved in dimerisation, a highly conserved keratin domain (K) and a variable domain (C) at the C-terminus, which is responsible for binding of interacting proteins or transcriptional activation (De Bodt et al. Trends in Plant Science 8, 475-483).

Plant MADS15 polypeptides may also be identified by the presence of certain conserved motifs. The presence of these conserved motifs may be identified using methods for the alignment of sequences for comparison as described hereinabove. In some instances, the default parameters may be adjusted to modify the stringency of the search. For example using BLAST, the statistical significance threshold (called "expect" value) for reporting matches against database sequences may be increased to show less stringent matches. This way, short nearly exact matches may be identified. Upon identification of a MADS15 polypeptide by the presence of these motifs, a person skilled in the art may easily derive the corresponding nucleic acid encoding the polypeptide comprising the relevant motifs, and use a sufficient length of contiguous nucleotides of the same to perform any one or more of the gene silencing methods described above (for the reduction or substantial elimination of an endogenous MADS15 gene expression).

Typically, the presence of at least one of the motifs 1 to 4 should be sufficient to identify any query sequence as a MADS15, however, the presence of at least motifs 1 and 2 is preferred. The consensus sequence provided is based on the monocot sequences given in the sequence listing. A person skilled in the art would be well aware that the consensus sequence may vary somewhat if further or different sequences (for example from dicotyledonous plants) were used for comparison.

```
Motif 1, located in the MADS domain (SEQ ID NO: 48):
L (L/V) KKA (H/N) EIS (VI) L (C/Y) DAE (V/I/L) (A/G) (L/A/V) (I/V) (I /V)
 FS
(T/P/A/N) KGKLYE (Y/F) (A/S) (T/S) (D/N/E) S (K/C/R/S) M (D/E) (N/I/R/K) IL
(E/D) R.

Preferably, this conserved sequence motif 1 has the sequence:
LLKKAHEISVLCDAEVA (L/V) I (I/V) FS (T/P) KGKLYEYATDS (C/R) M (D/E) (R/K)
ILER, most preferably the conserved sequence motif 1 has the sequence:
LLKKAHEISVLCDAEVAAIVFSPKGKLYEYATDSRMDKILER Motif 2, located in the K domain (SEQ ID NO: 49):
KLK (A/S) (K/R) (V/I ) E (A/T/S) (L/I) (Q/N) (K/R/N) (S/C/R) (Q/H) (R/K)
HLMGE Preferably, this conserved sequence motif 2 has the sequence:
KLKAK (V/I) E (A/T) (L/I) QK (S/C) (Q/H) (R/K) HLMGE More preferably, this conserved sequence motif 2 has the sequence:
KLKAKIETIQKCHKHLMGE
```

Optionally, the MADS15 polypeptide or its homologue may comprise in the C domain motif 3 and/or motif 4:

```
motif 3 (SEQ ID NO: 50):
Q (P/Q/V/A) QTS (S/F) (S/F) (S/F) (S/F)
(S/C/F) (F/M)
```

```
motif 4 (SEQ ID NO: 51):
(G/A/V/L) (L/P) XWMX (S/H)
``` wherein the first X residue in motif 4 may be any amino acid, but preferably L, P or H; and wherein the second X residue may be any amino acid, but preferably V or L.

Alternatively, the C-domain (starting behind the keratin domain, i.e. at R175 in SEQ ID NO: 44) may be characterised by the increased occurrence of glutamine (normally 3.93%, here at least 8.77% with a maximum of 26.73%), in addition, the content in alanine, proline, and/or serine may also be increased (above 7.8%, 4.85% and 6.89% respectively).

Alternatively formulated, a preferred MADS15 protein useful in the methods of the present invention comprises at least an N-terminal MADS domain corresponding to the SMART domain SM00432 (Pfam PF00319) followed by a Keratin domain corresponding to the K-box region defined in Pfam as PF01486, more preferably, the MADS15 protein has in its MADS domain the conserved signature of SEQ ID NO: 48 and in its K-domain the conserved signature of SEQ ID NO: 49, most preferably, the MADS15 protein has the sequence given in SEQ ID NO: 44.

Examples of proteins useful in the methods of the invention and nucleic acids encoding the same are given below in table D of Example 8.

Also useful in the methods of the invention are homologues of any one of the amino acid sequences given in table D.

Also useful in the methods of the invention are derivatives of any one of the polypeptides given in table D or orthologues or paralogues of any of the aforementioned SEQ ID NOs. A preferred derivative is a derivative of SEQ ID NO: 44. Derivatives of the polypeptides given in table D are further examples which may be suitable for use in the methods of the invention. Derivatives useful in the methods of the present invention preferably have similar biological and functional activity as the unmodified protein from which they are derived.

The invention is illustrated by transforming plants with the *Oryza sativa* nucleic acid sequence represented by SEQ ID NO: 43, encoding the polypeptide sequence of SEQ ID NO: 44, however performance of the invention is not restricted to these sequences. The methods of the invention may advantageously be performed using any nucleic acid encoding a protein useful in the methods of the invention as defined herein, including orthologues and paralogues, such as any of the nucleic acid sequences given in table D. The amino acid sequences given in table D may be considered to be orthologues and paralogues of the MADS15 polypeptide represented by SEQ ID NO: 44.

Orthologues and paralogues may easily be found by performing a so-called reciprocal blast search. Typically, this involves a first BLAST involving BLASTing a query sequence (for example using any of the sequences listed in table D) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 43 or SEQ ID NO: 44, the second BLAST would therefore be against Oryza sativa sequences). The results of the first and second BLASTs are then compared. A paralogue is identified if a high-ranking hit from the first blast is from the same species as from which the query sequence is derived, a BLAST back then ideally results in the query sequence as highest hit; an orthologue is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbour joining tree, to help visualize clustering of related genes and to identify orthologues and paralogues.

Table D gives examples of orthologues and paralogues of the MADS15 protein represented by SEQ ID NO 44. Further orthologues and paralogues may readily be identified using the BLAST procedure described above.

The proteins of the invention are identifiable by the presence of the conserved MADS and/or keratin domain(s) (shown in FIG. 5). Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244, InterPro (Mulder et al., (2003) Nucl. Acids. Res. 31, 315-318, Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAIPress, Menlo Park; Hulo et al., Nucl. Acids. Res. 32:D134-D137, (2004), or Pfam (Bateman et al., Nucleic Acids Research 30(1): 276-280 (2002). A set of tools for in silico analysis of protein sequences is available on the ExPASY proteomics server (hosted by the Swiss Institute of Bioinformatics (Gasteiger et al., ExPASy: the proteomics server for in-depth protein knowledge and analysis, Nucleic Acids Res. 31:3784-3788 (2003)).

Domains may also be identified using routine techniques, such as by sequence alignment. Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art. Furthermore, instead of using full-length sequences for the identification of homologues, specific domains (such as the MADS or keratin domain, or one of the motifs defined above) may be used as well. The sequence identity values, which are indicated below in Example 10 as a percentage were determined over the entire nucleic acid or amino acid sequence, and/or over selected domains or conserved motif(s), using the programs mentioned above using the default parameters.

Furthermore, a MADS15 protein may also be identifiable by its ability or inability to bind DNA and to interact with other proteins. DNA-binding activity and protein-protein interactions may readily be determined in vitro or in vivo using techniques well known in the art. Examples of in vitro assays for DNA binding activity include: gel retardation analysis using known MADS-box DNA binding domains (West et al. (1998) Nucl Acid Res 26(23): 5277-87), or yeast one-hybrid assays. An example of an in vitro assay for protein-protein interactions is the yeast two-hybrid analysis (Fields and Song (1989) Nature 340:245-6). Proteins known to interact with OsMADS15 include other MADS proteins (such as those involved in the flowering signalling complex), receptor like kinases such a Clavata1 and Clavata2, Erecta, BRI1 or RSK. Further details are provided in Example 13.

Nucleic acids encoding proteins useful in the methods of the invention need not be full-length nucleic acids, since performance of the methods of the invention does not rely on the use of full-length nucleic acid sequences. Examples of nucleic acids suitable for use in performing the methods of the invention include the nucleic acid sequences given in table D, but are not limited to those sequences. Nucleic acid variants may also be useful in practising the methods of the invention. Examples of such nucleic acid variants include portions of nucleic acids encoding a protein useful in the methods of the invention, nucleic acids hybridising to nucleic acids encoding a protein useful in the methods of the invention, splice variants of nucleic acids encoding a protein useful in the methods of the invention, allelic variants of nucleic acids encoding a protein useful in the methods of the invention and variants of nucleic acids encoding a protein useful in the methods of the invention that are obtained by gene shuffling. The terms portion, hybridising sequence, splice variant, allelic variant and gene shuffling will now be described.

According to the present invention, there is provided a method for enhancing yield-related traits in plants, comprising introducing and expressing in a plant a portion of any one of the nucleic acid sequences given in table D, or a portion of a nucleic acid encoding an orthologue, paralogue or homologue of any of the amino acid sequences given in table D.

Portions useful in the methods of the invention, encode a polypeptide falling within the definition of a nucleic acid encoding a protein useful in the methods of the invention as defined herein and having substantially the same biological activity as the amino acid sequences given in table D. Preferably, the portion is a portion of any one of the nucleic acids given in table D. The portion is typically at least 400 consecutive nucleotides in length, preferably at least 600 consecutive nucleotides in length, more preferably at least 700 consecutive nucleotides in length and most preferably at least 800 consecutive nucleotides in length, the consecutive nucleotides being of any one of the nucleic acid sequences given in table D. Most preferably the portion is a portion of the nucleic acid of SEQ ID NO: 43. Preferably, the portion encodes an amino acid sequence comprising (any one or more of) the MADS and keratin domain as defined herein.

A portion of a nucleic acid encoding a MADS15 protein as defined herein may be prepared, for example, by making one or more deletions to the nucleic acid. The portions may be used in isolated form or they may be fused to other coding (or non coding) sequences in order to, for example, produce a protein that combines several activities. When fused to other coding sequences, the resultant polypeptide produced upon translation may be bigger than that predicted for the MADS15 protein portion.

Another nucleic acid variant useful in the methods of the invention is a nucleic acid capable of hybridising, under reduced stringency conditions, preferably under stringent conditions, with a nucleic acid encoding a MADS15 protein as defined herein, or with a portion as defined herein.

Hybridising sequences useful in the methods of the invention, encode a polypeptide having a MADS and/or keratin domain (see the alignment of FIG. 6) and having substantially the same biological activity as the MADS15 protein represented by any of the amino acid sequences given in table D. The hybridising sequence is typically at least 400 consecutive nucleotides in length, preferably at least 600 consecutive nucleotides in length, more preferably at least 700 consecutive nucleotides in length and most preferably at least 800 consecutive nucleotides in length, the consecutive nucleotides being of any one of the nucleic acid sequences given in table D. Preferably, the hybridising sequence is one that is capable of hybridising to any of the nucleic acids given in table D, or to a portion of any of these sequences, a portion being as defined above. Most preferably, the hybridising sequence is capable of hybridising to a nucleic acid as represented by SEQ ID NO: 43 or to a portion thereof. Preferably, the hybridising sequence encodes an amino acid sequence comprising any one or more of the motifs or domains as defined herein.

According to the present invention, there is provided a method for enhancing yield-related traits in plants, comprising introducing and expressing in a plant a nucleic acid capable of hybridizing to any one of the nucleic acids given in table D, or comprising introducing and expressing in a plant a nucleic acid capable of hybridising to a nucleic acid encoding an orthologue, paralogue or homologue of any of the nucleic acid sequences given in table D.

Another nucleic acid variant useful in the methods of the invention is a splice variant encoding a MADS15 protein as defined hereinabove.

According to the present invention, there is provided a method for enhancing yield-related traits in plants, comprising introducing and expressing in a plant a splice variant of any one of the nucleic acid sequences given in table D, or a splice variant of a nucleic acid encoding an orthologue, paralogue or homologue of any of the amino acid sequences given in table D.

Preferred splice variants are splice variants of a nucleic acid represented by SEQ ID NO: 43 or a splice variant of a nucleic acid encoding an orthologue or paralogue of SEQ ID NO: 44. Preferably, the amino acid sequence encoded by the splice variant comprises any one or more of the motifs or domains as defined herein.

Another nucleic acid variant useful in performing the methods of the invention is an allelic variant of a nucleic acid encoding a MADS15 protein as defined hereinabove. The allelic variants useful in the methods of the present invention have substantially the same biological activity as the MADS15 protein of SEQ ID NO: 44.

According to the present invention, there is provided a method for enhancing yield-related traits in plants, comprising introducing and expressing in a plant an allelic variant of any one of the nucleic acids given in table D, or comprising introducing and expressing in a plant an allelic variant of a nucleic acid encoding an orthologue, paralogue or homologue of any of the amino acid sequences given in table D.

Preferably, the allelic variant is an allelic variant of SEQ ID NO: 43 or an allelic variant of a nucleic acid encoding an orthologue or paralogue of SEQ ID NO: 44. Preferably, the amino acid sequence encoded by the allelic variant comprises any one or more of the motifs or domains as defined herein.

A further nucleic acid variant useful in the methods of the invention is a nucleic acid variant obtained by gene shuffling. Gene shuffling or directed evolution may also be used to generate variants of nucleic acids encoding MADS15 proteins as defined above.

According to the present invention, there is provided a method for enhancing yield-related traits in plants, comprising introducing and expressing in a plant a variant of any one of the nucleic acid sequences given in table D, or comprising introducing and expressing in a plant a variant of a nucleic acid encoding an orthologue, paralogue or homologue of any of the amino acid sequences given in table D, which variant nucleic acid is obtained by gene shuffling.

Preferably, the variant nucleic acid obtained by gene shuffling encodes an amino acid sequence comprising any one or more of the motifs or domains as defined herein.

Furthermore, nucleic acid variants may also be obtained by site-directed mutagenesis. Several methods are available to achieve site-directed mutagenesis, the most common being PCR based methods (Current Protocols in Molecular Biology. Wiley Eds.).

Nucleic acids encoding MADS15 proteins may be derived from any natural or artificial source. The nucleic acid may be modified from its native form in composition and/or genomic environment through deliberate human manipulation. Preferably the MADS15-encoding nucleic acid is from a plant, further preferably from a monocotyledonous plant, more preferably from the Poaceae family, most preferably the nucleic acid is from *Oryza sativa*.

Any reference herein to a MADS15 protein is therefore taken to mean a MADS15 protein as defined above. Any nucleic acid encoding such a MADS15 protein is suitable for use in performing the methods of the invention.

The present invention also encompasses plants or parts thereof (including seeds) obtainable by the methods according to the present invention. The plants or parts thereof comprise a nucleic acid transgene encoding a MADS15 protein as defined above.

The invention also provides genetic constructs and vectors to facilitate introduction and/or expression of the nucleic acid sequences useful in the methods according to the invention, in a plant. The gene constructs may be inserted into vectors, which may be commercially available, suitable for transforming into plants and suitable for expression of the gene of interest in the transformed cells. The invention also provides use of a gene construct as defined herein in the methods of the invention.

More specifically, the present invention provides a construct comprising
(a) nucleic acid encoding MADS15 protein as defined above;
(b) one or more control sequences capable of driving expression of the nucleic acid sequence of (a); and optionally
(c) a transcription termination sequence.

Plants are transformed with a vector comprising the sequence of interest (i.e., a nucleic acid encoding a MADS15 polypeptide as defined herein. The skilled artisan is well aware of the genetic elements that must be present on the vector in order to successfully transform, select and propagate host cells containing the sequence of interest. The sequence of interest is operably linked to one or more control sequences (at least to a promoter).

Advantageously, any type of promoter may be used to drive expression of the nucleic acid sequence.

The promoter may be a constitutive promoter; alternatively, the promoter may be an inducible promoter, i.e. having induced or increased transcription initiation in response to a chemical or a stress-inducible promoter, or a pathogen-induced promoter.

Additionally or alternatively, the promoter may be an organ-specific or tissue-specific promoter, or the promoter may be a ubiquitous promoter, or the promoter may be developmentally regulated. Furthermore, the promoter may be organ-specific or tissue-specific or cell-specific.

Preferably, the MADS15 nucleic acid or variant thereof is operably linked to a constitutive promoter. A preferred constitutive promoter is one that is also substantially ubiquitously expressed. Further preferably the promoter is derived from a plant, more preferably a monocotyledonous plant. Most preferred is use of a GOS2 promoter (for example from rice, SEQ ID NO: 47 or SEQ ID NO: 108). It should be clear that the applicability of the present invention is not restricted to the MADS15 nucleic acid represented by SEQ ID NO: 43, nor is the applicability of the invention restricted to expression of a MADS15 nucleic acid when driven by a GOS2 promoter. Examples of other constitutive promoters or functionally equivalent promoters which may also be used to drive expression of a MADS15 nucleic acid are shown in the definitions section.

Optionally, one or more terminator sequences may be used in the construct introduced into a plant. Additional regulatory elements may include transcriptional as well as translational enhancers. Those skilled in the art will be aware of terminator and enhancer sequences that may be suitable for use in performing the invention. Such sequences would be known or may readily be obtained by a person skilled in the art.

An intron sequence may also be added to the 5' untranslated region (UTR) or in the coding sequence to increase the amount of the mature message that accumulates in the cytosol.

Other control sequences (besides promoter, enhancer, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection of the successful transfer of the nucleic acid sequences as used in the methods of the invention and/or selection of transgenic plants comprising these nucleic acids, it is advantageous to use marker genes (or reporter genes). Therefore, the genetic construct may optionally comprise a selectable marker gene.

The invention also provides a method for the production of transgenic plants having enhanced yield-related traits relative to control plants, comprising introduction and expression in a plant of any nucleic acid encoding a MADS15 protein as defined hereinabove.

More specifically, the present invention provides a method for the production of transgenic plants having increased yield, which method comprises:
(i) introducing and expressing in a plant or plant cell a MADS15 nucleic acid or variant thereof; and
(ii) cultivating the plant cell under conditions promoting plant growth and development.

The nucleic acid may be introduced directly into a plant cell or into the plant itself (including introduction into a tissue, organ or any other part of a plant). According to a preferred feature of the present invention, the nucleic acid is preferably introduced into a plant by transformation.

The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid encoding a MADS15 protein as defined hereinabove. Preferred host cells according to the invention are plant cells.

Host plants for the nucleic acids or the vector used in the method according to the invention, the expression cassette or construct or vector are, in principle, advantageously all plants, which are capable of synthesizing the polypeptides used in the inventive method.

The invention also extends to harvestable parts of a plant such as, but not limited to seeds, leaves, fruits, flowers, stems, rhizomes, roots, tubers and bulbs. The invention furthermore relates to products derived, preferably directly derived, from a harvestable part of such a plant, such as dry pellets or powders, oil, fat and fatty acids, starch or proteins.

According to a preferred feature of the invention, the modulated expression is increased expression.

As mentioned above, a preferred method for modulating (preferably, increasing) expression of a nucleic acid encoding a MADS15 protein is by introducing and expressing in a plant a nucleic acid encoding a MADS15 protein; however the effects of performing the method, i.e. enhancing yield-related traits may also be achieved using other well known techniques. A description of some of these techniques will now follow.

One such technique is T-DNA activation tagging. The resulting transgenic plants show dominant phenotypes due to modified expression of genes close to the introduced promoter.

The effects of the invention may also be reproduced using the technique of TILLING (Targeted Induced Local Lesions In Genomes), or by homologous recombination.

Reference herein to enhanced yield-related traits is taken to mean an increase in biomass (weight) of one or more parts of a plant, which may include aboveground (harvestable) parts and/or (harvestable) parts below ground.

Taking corn as an example, a yield increase may be manifested as one or more of the following: increase in the number of plants established per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

In a particular embodiment, such harvestable parts are roots, and performance of the methods of the invention results in plants having increased root growth relative to the root growth of suitable control plants. Root development is an essential determinant of plant growth and crop yield since the root is the main channel to extract nutrients from the environment.

Increased root yield may for example manifest itself as one of more of the following: a) increased amount of root biomass (whereby a discrimination between thick roots and thin roots may be made by defining a certain threshold), b) increased average root diameter, c) increased total root biomass, and d) increased root biomass/shoot biomass ratio. For the purpose of this invention, it should be understood that the term 'root growth' encompasses all aspects of growth of the different parts that make up the root system at different stages of its development, both in monocotyledonous and dicotyledonous plants. It is to be understood that enhanced growth of the root can result from enhanced growth of one or more of its parts including the primary root, lateral roots, adventitious roots, etc. all of which fall within the scope of this invention.

Since the transgenic plants according to the present invention have increased yield, it is likely that these plants exhibit an increased growth rate (during at least part of their life cycle), relative to the growth rate of control plants at a corresponding stage in their life cycle. The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, greenness index, flowering time and speed of seed maturation. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of corn plants followed by, for example, the sowing and optional harvesting of soy bean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

According to a preferred feature of the present invention, performance of the methods of the invention gives plants having an increased growth rate relative to control plants. Therefore, according to the present invention, there is provided a method for increasing the growth rate of plants, which method comprises modulating expression, preferably increasing expression, in a plant of a nucleic acid encoding a MADS15 protein as defined herein.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi and insects.

In particular, the methods of the present invention may be performed under non-stress conditions or under conditions of mild drought to give plants having increased yield relative to control plants. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signaling pathways and cellular responses, such as the production of stress proteins, up-regulation of anti-oxidants, accumulation of compatible solutes and growth arrest. The term "non-stress" conditions as used herein are those environmental conditions that allow optimal growth of plants. Persons skilled in the art are aware of normal soil conditions and climatic conditions for a given location.

Performance of the methods of the invention gives plants grown under non-stress conditions or under mild drought conditions increased yield relative to control plants grown under comparable conditions. Therefore, according to the present invention, there is provided a method for increasing yield in plants grown under non-stress conditions or under mild drought conditions, which method comprises increasing expression in a plant of a nucleic acid encoding a MADS15 polypeptide.

Performance of the methods of the invention gives plants grown under conditions of nutrient deficiency, particularly under conditions of nitrogen deficiency, increased yield relative to control plants grown under comparable conditions. Therefore, according to the present invention, there is provided a method for increasing yield in plants grown under conditions of nutrient deficiency, which method comprises increasing expression in a plant of a nucleic acid encoding a MADS15 polypeptide. Nutrient deficiency may result from a lack or excess of nutrients such as nitrogen, phosphates and other phosphorous-containing compounds, potassium, calcium, cadmium, magnesium, manganese, iron and boron, amongst others.

In a preferred embodiment of the invention, the increase in yield and/or growth rate occurs according to the methods of the present invention under non-stress conditions.

The methods of the invention are advantageously applicable to any plant.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs. According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, triticale, sorghum and oats.

The present invention also encompasses use of nucleic acids encoding the MADS15 protein described herein and use of these MADS15 proteins in enhancing yield-related traits in plants.

Nucleic acids encoding the MADS15 protein described herein, or the MADS15 proteins themselves, may find use in breeding programmes in which a DNA marker is identified which may be genetically linked to a MADS15-encoding gene. The nucleic acids/genes, or the MADS15 proteins themselves may be used to define a molecular marker. This DNA or protein marker may then be used in breeding programmes to select plants having enhanced yield-related traits as defined hereinabove in the methods of the invention.

Allelic variants of a MADS15 protein-encoding nucleic acid/gene may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give increased yield. Selection is typically carried out by monitoring growth performance of plants containing different allelic variants of the sequence in question. Growth performance may be monitored in a greenhouse or in the field. Further optional steps include crossing plants in which the superior allelic variant was identified with another plant. This could be used, for example, to make a combination of interesting phenotypic features.

Nucleic acids encoding MADS15 proteins may also be used as probes for genetically and physically mapping the genes that they are a part of, and as markers for traits linked to those genes. Such information may be useful in plant breeding in order to develop lines with desired phenotypes. Such use of MADS15 protein-encoding nucleic acids requires only a nucleic acid sequence of at least 15 nucleotides in length. The MADS15 protein-encoding nucleic acids may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the MADS15 protein-encoding nucleic acids. The resulting banding patterns may then be subjected to genetic analyses using computer programs such as MapMaker (Lander et al. (1987) Genomics 1: 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the MADS15 protein-encoding nucleic acid in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridisation (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acids. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having enhanced yield-related traits, as described hereinbefore. These traits may also be combined with other economically advantageous traits, such as further yield-enhancing traits, tolerance to other abiotic and biotic stresses, traits modifying various architectural features and/or biochemical and/or physiological features.

Detailed Description of MADS15 Down

It has now surprisingly been found that decreasing the level and/or activity of an endogenous MADS15 polypeptide gives plants having enhanced yield-related traits, in particular increased yield relative, to corresponding wild type plants. The present invention therefore provides methods for enhancing yield related traits, particularly for increasing yield of a plant relative to control plants, comprising decreasing the level and/or activity of an endogenous MADS15 polypeptide. Reference herein to "control plants" is taken to mean corresponding wild type plants in which there is no reduction in activity of the endogenous MADS15 polypeptide.

Advantageously, performance of the methods according to the present invention results in plants having increased yield, particularly increased seed yield and/or increased biomass, relative to corresponding wild type plants.

The term "increased yield" as defined herein is taken to mean an increase in biomass (weight) of one or more parts of a plant, which may include aboveground (harvestable) parts and/or (harvestable) parts below ground.

In particular, such harvestable parts include vegetative biomass and/or seeds, and performance of the methods of the invention results in plants having increased yield (in vegetative biomass and/or seed) relative to the yield of control plants.

Taking corn as an example, a yield increase may be manifested as one or more of the following: increase in the number of plants per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

The increase in seed yield may also be manifested as an increase in seed size and/or seed volume. This may increase the amount, or change the composition of, substances in the seed, such as oils, proteins and carbohydrates.

According to a preferred feature, performance of the methods of the invention result in plants having increased yield, particularly increased biomass and/or seed yield. Therefore, according to the present invention, there is provided a method for increasing plant yield, which method comprises decreasing the level of activity of a MADS15 polypeptide or a homologue thereof, preferably by downregulating expression of a MADS15 gene or a homologue thereof.

Since the transgenic plants according to the present invention have increased yield, it is likely that these plants exhibit an increased growth rate (during at least part of their life cycle), relative to the growth rate of corresponding wild type plants at a corresponding stage in their life cycle. The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, flowering time and speed of seed maturation. An increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of corn plants followed by, for example, the sowing and optional harvesting of soy bean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

Performance of the methods of the invention gives plants having an increased growth rate. Therefore, according to the present invention, there is provided a method for increasing the growth rate of plants relative to control plants, which method comprises preferentially reducing the expression level and/or activity of an endogenous MADS15 gene in a plant.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi and insects.

In particular, the methods of the present invention may be performed under non-stress conditions or under conditions of mild drought to give plants having increased yield relative to control plants. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signaling pathways and cellular responses, such as the production of stress proteins, up-regulation of anti-oxidants, accumulation of compatible solutes and growth arrest. The term "non-stress" conditions as used herein are those environmental conditions that allow optimal growth of plants. Persons skilled in the art are aware of normal soil conditions and climatic conditions for a given location.

Performance of the methods of the invention gives plants grown under non-stress conditions or under mild drought conditions increased yield relative to control plants grown under comparable conditions. Therefore, according to the present invention, there is provided a method for increasing yield in plants grown under non-stress conditions or under mild drought conditions, which method comprises reducing expression of an endogenous MADS15 gene in a plant.

Performance of the methods of the invention gives plants grown under conditions of nutrient deficiency, particularly under conditions of nitrogen deficiency, increased yield relative to control plants grown under comparable conditions. Therefore, according to the present invention, there is provided a method for increasing yield in plants grown under conditions of nutrient deficiency, which method comprises decreasing expression in a plant of a nucleic acid encoding a MADS15 polypeptide. Nutrient deficiency may result from a lack or excess of nutrients such as nitrogen, phosphates and other phosphorous-containing compounds, potassium, calcium, cadmium, magnesium, manganese, iron and boron, amongst others.

In a preferred embodiment of the invention, the increase in yield and/or growth rate occurs according to the methods of the present invention under non-stress conditions.

The methods of the invention are advantageously applicable to any plant.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs. According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, triticale, sorghum and oats.

Reference herein to a "decrease" in level of an endogenous MADS15 protein in a plant is taken to mean a reduction in protein concentration or substantial elimination of an endogenous MADS15 protein relative to endogenous MADS15 protein levels found in corresponding wild type plants. This reduction or substantial elimination may result in reduced or substantially abolished MADS15 protein activity in a plant.

Reference herein to a "decrease" in activity of an endogenous MADS15 protein in a plant is taken to mean a reduction in MADS15 protein activity or substantial elimination of activity of an endogenous MADS15 protein relative to endogenous MADS15 protein activity levels found wild type plants.

Preferably, the reduction in endogenous MADS15 protein level and/or activity is obtained by downregulating the expression of the endogenous MADS15 gene.

Reference herein to an "endogenous" MADS15 gene not only refers to MADS15 genes as found in a plant in its natural form (i.e., without there being any human intervention), but also refers to isolated MADS15 genes subsequently introduced into a plant. For example, a transgenic plant containing a MADS15 transgene may encounter a reduction or substantial elimination of the MADS15 transgene expression and/or reduced or substantial elimination of expression of an endogenous MADS15 gene.

This reduction (or substantial elimination) of endogenous MADS15 gene expression may be achieved using any one or more of several well-known gene silencing methods. "Gene silencing" or "downregulation" of expression, as used herein, refers to a reduction or the substantial elimination of MADS15 gene expression and/or MADS15 polypeptide levels and/or MADS15 polypeptide activity.

One such method for reduction or substantial elimination of endogenous MADS15 gene expression is RNA-mediated downregulation of gene expression (RNA silencing). Silencing in this case is triggered in a plant by a double stranded RNA molecule (dsRNA) that is substantially homologous to a target MADS15 gene. This dsRNA is further processed by the plant into about 21 to about 26 nucleotides called short interfering RNAs (siRNAs). The siRNAs are incorporated into an RNA-induced silencing complex (RISC) that cleaves the mRNA of a MADS15 target gene, thereby reducing or substantially eliminating the number of MADS15 mRNAs to be translated into a MADS15 protein.

One example of an RNA silencing method involves the introduction of coding sequences or parts thereof in a sense orientation into a plant. The additional gene, or part thereof, will silence an endogenous MADS15 gene, giving rise to a phenomenon known as co-suppression. The reduction of MADS15 gene expression will be more pronounced if several additional copies are introduced into the plant, as there is a positive correlation between high transcript levels and the triggering of co-suppression.

Another example of an RNA silencing method involves the use of antisense MADS15 nucleic acid sequences.

The antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection). Preferably, production of antisense nucleic acids in plants occurs by means of a stably integrated transgene comprising a promoter operative for constitutive expression in plants, an antisense oligonucleotide, and a terminator.

A preferred method for reduction or substantial elimination of endogenous MADS15 gene expression via RNA silencing is by using an expression vector into which a MADS15 gene or fragment thereof has been cloned as an inverted repeat (in part or completely), separated by a spacer (non-coding DNA).

In still another embodiment, the reduction or substantial elimination of endogenous MADS15 expression may be obtained by using ribozymes. For example, a derivative of a Tetrahymena L-19 IVS RNA can be constructed in which the nucleotide sequence of the active site is complementary to the nucleotide sequence to be cleaved in an MADS15-encoding mRNA.

Gene silencing may also be achieved by insertion mutagenesis or if there is a mutation on the endogenous MADS15 gene and/or a mutation on an isolated MADS15 gene subsequently introduced into a plant. The reduction or substantial elimination of MADS15 protein activity may be caused by a non-functional MADS15. For example, MADS15 binds to various interacting proteins; one or more mutation(s) and/or truncation(s) within the MADS box of a MADS15 may therefore provide for a MADS15 protein that is still able to bind interacting proteins but that cannot exhibit its normal function as transcription factor.

A further approach to gene silencing is by targeting nucleotide sequences complementary to the regulatory region of the MADS15 gene (e.g., the MADS15 promoter and/or enhancers) to form triple helical structures that prevent transcription of the MADS15 gene in target cells.

Still another approach to gene silencing is described by Hiratsu et al. (Plant J. 34, 733-739, 2003). This method does not depend on sequence homology to the targeted gene but involves the use of a repression sequence domain in transcriptional gene fusions, and has been used to modify traits of agronomic interest (Fujita et al., Plant Cell 17, 3470-3488, 2005 and Mitsuda at al., Plant Cell 17, 2993-3006, 2005). Typically, a nucleotide chimeric fusion is made between a gene encoding a protein capable of positively influencing the expression of the targeted gene (such as a transcription activator), and a nucleotide fragment encoding a repression domain. Upon expression of the chimeric gene fusion, the expression of the targeted gene is repressed, usually in a dominant negative fashion. Repression domains are well known in the art, for example the EAR motif present in some AP2 and Zinc finger transcription factor. Methods based on repression domains are well suited to overcome gene redundancy for the targeted gene in the plant species of choice.

Described above are examples of various methods for gene silencing (for the reduction or substantial elimination of endogenous MADS15 gene expression. The methods of the invention rely on the reduction of expression of an endogenous MADS15 gene in a plant. A person skilled in the art would readily be able to adapt the aforementioned methods for silencing so as to achieve gene silencing in a whole plant or in parts thereof through the use of an appropriate promoter, for example.

It should be noted that the essence of the present invention resides in the advantageous and surprising results found upon reduction or substantial elimination of endogenous MADS15 gene expression in a plant, and is not limited to any particular method for such reduction or substantial elimination of endogenous MADS15 protein activity. The activity of a MADS15 polypeptide may also be decreased or eliminated by introducing a genetic modification (preferably in the locus of a MADS15 gene). The locus of a gene as defined herein is taken to mean a genomic region, which includes the gene of interest and 10 kb up- or down stream of the coding region.

The genetic modification may be introduced, for example, by any one (or more) of the following methods: T-DNA inactivation, TILLING, site-directed mutagenesis, directed evolution, homologous recombination. Following introduction of the genetic modification, there follows a step of selecting for decreased activity of a MADS15 polypeptide, which decrease in activity gives plants having increased yield.

T-DNA inactivation tagging involves insertion of a T-DNA, in the genomic region of the gene of interest or 10 kb up- or downstream of the coding region of a gene in a configuration such that the T-DNA inhibits expression of the targeted gene. Typically, regulation of expression of the targeted gene by its natural promoter is disrupted. The T-DNA is randomly inserted into the plant genome, for example, through *Agrobacterium* infection and leads to down-regulated expression of genes near the inserted T-DNA. The resulting transgenic plants show phenotypes due to inhibited expression of genes close to the introduced T-DNA.

A genetic modification may also be introduced in the locus of a MADS15 gene using the technique of TILLING (Targeted Induced Local Lesions In Genomes).

Site-directed mutagenesis and random mutagenesis may be used to generate variants of MADS15 nucleic acids. Several methods are available to achieve site-directed mutagenesis, the most common being PCR based methods (current protocols in molecular biology. Wiley Eds.).

Directed evolution may also be used to generate variants of MADS15 nucleic acids. This consists of iterations of DNA shuffling followed by appropriate screening and/or selection to generate variants of MADS15 nucleic acids or variants thereof encoding MADS15 polypeptides having a modified (here decreased or abolished) biological activity (Castle et al., (2004) Science 304(5674): 1151-4; U.S. Pat. Nos. 5,811,238 and 6,395,547).

T-DNA activation, TILLING, site-directed mutagenesis and directed evolution are examples of technologies that enable the generation of novel alleles and MADS15 variants.

The effects of the invention may also be reproduced using homologous recombination. The nucleic acid to be targeted may be an allele encoding an inactive protein or a protein with decreased activity, used to replace the endogenous gene or may be introduced in addition to the endogenous gene, and needs to be targeted to the locus of the MADS15 gene.

Other methods, such as the use of antibodies directed to the endogenous MADS15 for inhibiting its function in planta, or interference in the signalling pathway in which MADS15 is involved, will be well known to the skilled man. Alternatively, a screening program may be set up to identify natural variants of a MADS15 gene, which variants have reduced MADS15 activity, or no MADS15 activity at all. Such natural variants may also be used in the methods of the present invention.

For optimal performance, the gene silencing techniques used for the reduction or substantial elimination of endogenous MADS15 gene expression requires the use of MADS15 nucleic acid sequences from monocotyledonous plants for transformation into monocotyledonous plants. Preferably, a MADS15 nucleic acid from any given plant species is introduced into that same species. For example, a MADS15 nucleic acid from rice (be it a full length MADS15 sequence or a fragment) is transformed into a rice plant. The MADS15 nucleic acid need not be introduced into the same plant variety.

Reference herein to a "MADS15 gene" or a "MADS15 nucleic acid" is taken to mean a polymeric form of a deoxyribonucleotide or a ribonucleotide polymer of any length, either double- or single-stranded, or analogues thereof, that have the essential characteristic of a natural ribonucleotide in that they can hybridise to nucleic acids in a manner similar to naturally occurring polynucleotides. A "MADS15 gene" or a "MADS15 nucleic acid" refers to a sufficient length of substantially contiguous nucleotides of a MADS15-encoding gene to perform gene silencing; this may be as little as 20 or fewer nucleotides. A gene encoding a (functional) protein is not a requirement for the various methods discussed above for the reduction or substantial elimination of expression of an endogenous MADS15 gene.

The methods of the invention may be performed using a sufficient length of substantially contiguous nucleotides of a MADS15 gene/nucleic acid, which may consist of 20 or fewer nucleotides, which may be from any part of the MADS15 gene/nucleic acid, such as the 5' end of the coding region that is well conserved amongst the MADS15 gene family, or encoding one of the conserved motifs described below.

MADS15 genes are well known in the art and useful in the methods of the invention are substantially contiguous nucleotides of the plant MADS15 genes/nucleic acid described in Moon et al. (Plant Physiol. 120, 1193-1204, 1999).

Other MADS15 gene/nucleic acid sequences may also be used in the methods of the invention, and may readily be identified by a person skilled in the art. MADS15 polypeptides may be identified by the presence of one or more of several well-known features (see below). Upon identification of a MADS15 polypeptide, a person skilled in the art could easily derive, using routine techniques, the corresponding encoding nucleic acid sequence and use a sufficient length of contiguous nucleotides of the same to perform any one or more of the gene silencing methods described above.

The term "MADS15 polypeptide or homologue thereof" as defined herein refers to a protein that falls in the group of FUL-like MADS box proteins as delineated by Adam et al. (J. Mol. Evol. 62, 15-31). FUL-like MADS box proteins are part of the SQUAMOSA subfamily and have the typical MIKC$^c$ architecture: a MADS domain (M) at the N-terminus, followed by an intervening domain (I) involved in dimerisation, a highly conserved keratin domain (K) and a variable domain (C) at the C-terminus, which is responsible for binding of interacting proteins or transcriptional activation (De Bodt et al. Trends in Plant Science 8, 475-483).

Plant MADS15 polypeptides may also be identified by the presence of certain conserved motifs. The presence of these conserved motifs may be identified using methods for the alignment of sequences for comparison as described hereinabove. In some instances, the default parameters may be adjusted to modify the stringency of the search. For example using BLAST, the statistical significance threshold (called "expect" value) for reporting matches against database sequences may be increased to show less stringent matches. This way, short nearly exact matches may be identified. Upon identification of a MADS15 polypeptide by the presence of these motifs, a person skilled in the art may easily derive the corresponding nucleic acid encoding the polypeptide comprising the relevant motifs, and use a sufficient length of contiguous nucleotides of the same to perform any one or more of the gene silencing methods described above (for the reduction or substantial elimination of an endogenous MADS15 gene expression).

Typically, the presence of at least one of the motifs 1 to 4 should be sufficient to identify any query sequence as a MADS15, however the presence of at least motifs 1 and 2 is preferred. The consensus sequence provided is based on the monocot sequences given in the sequence listing. A person skilled in the art would be well aware that the consensus sequence may vary somewhat if further or different sequences (for example from dicot sequences) were used for comparison.

```
Motif 1, located in the MADS domain (SEQ ID NO: 114):
L (L/V) KKA (H/N) EIS (VI) L (C/Y) DAE (V/I/L) (A/G) (L/A/V) (I/V) (I/V) FS
(T/P/A/N) KGKLYE (Y/F) (A/S) (T/S) (D/N/E) S (K/C/R/S) M (D/E) (N/I/R/K) IL
(E/D) R.

Preferably, this conserved sequence motif 1 has the sequence:
LLKKAHEISVLCDAEVA (L/A/V) I (I/V) FS (T/P) KGKLYEYATDS (C/R) M (D/E) (R/K)
ILER, most preferably the conserved sequence motif 1 has the sequence:
LLKKAHEISVLCDAEVAAIVFSPKGKLYEYATDSRMDKILER Motif 2, located in the K domain (SEQ ID NO: 115):
KLK (A/S) (K/R) (V/I) E (A/T/S) (L/I) (Q/N) (K/R/N) (S/C/R) (Q/H) (R/K)
HLMGE Preferably, this conserved sequence motif 2 has the sequence:
KLKAK (V/I) E (A/T) (L/I) QK (S/C) (Q/H) (R/K) HLMGE More preferably, this conserved sequence motif 2 has the sequence:
KLKAKIETIQKCHKHLMGE
```

Optionally, the MADS15 polypeptide or its homologue may comprise in the C domain motif 3 and/or motif 4:

```
motif 3 (SEQ ID NO: 116):
Q (P/Q/V/A) QTS (S/F) (S/F) (S/F) (S/F)
(S/C/F) (F/M)

motif 4 (SEQ ID NO: 117):
(G/A/V/L) (L/P) XWMX (S/H)
``` wherein the first X residue in motif 4 may be any amino acid, but preferably L, P or H; and wherein the second X residue may be any amino acid, but preferably V or L.

Alternatively, the C-domain (starting behind the keratin domain, i.e. at R175 in SEQ ID NO: 110) may be characterised by the increased occurrence of glutamine (normally 3.93%, here at least 8.77% with a maximum of 26.73%), in addition, the content in alanine, proline, and/or serine may also be increased (above 7.8%, 4.85% and 6.89% respectively).

Alternatively formulated, a preferred MADS15 protein useful in the methods of the present invention comprises at least an N-terminal MADS domain corresponding to the SMART domain SM00432 (Pfam PF00319) followed by a Keratin domain corresponding to the K-box region defined in Pfam as PF01486, more preferably, the MADS15 protein has in its MADS domain the conserved signature of SEQ ID NO: 114 and in its K-domain the conserved signature of SEQ ID NO: 115, most preferably, the MADS15 protein has the sequence given in SEQ ID NO: 110.

Homologues, as defined above, may readily be identified using routine techniques well known in the art, such as by sequence alignment; homologues of OsMADS15 may have been named differently in various plant species, therefore the gene/protein names should not be used for identifying orthologues or paralogues. Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the alignment of two complete sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information. Homologous sequences may readily be identified using, for example, the ClustalW multiple sequence alignment algorithm (version 1.83), with the default pairwise alignment parameters, and a scoring method in percentage. Minor manual editing may be performed to optimise alignment between conserved motifs (see below), as would be apparent to a person skilled in the art.

The various structural domains in a MADS15 protein may be identified using specialised databases e.g. SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318;), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAIPress, Menlo Park; Hulo et al., Nucl. Acids. Res. 32:D134-D137, (2004)) or Pfam (Bateman et al., Nucleic Acids Research 30(1): 276-280 (2002)).

Furthermore, a MADS15 protein may also be identifiable by its ability to bind DNA and to interact with other proteins. DNA-binding activity and protein-protein interactions may readily be determined in vitro or in vivo using techniques well known in the art. Examples of in vitro assays for DNA binding activity include: gel retardation analysis using known MADS-box DNA binding domains (West et al. (1998) Nucl Acid Res 26(23): 5277-87), or yeast one-hybrid assays. An example of an in vitro assay for protein-protein interactions is the yeast two-hybrid analysis (Fields and Song (1989) Nature 340:245-6). Proteins known to interact with OsMADS15 include other MADS proteins (such as those involved in the flowering signalling complex), receptor like kinases such a Clavata1 and Clavata2, Erecta, BRI1 or RSK.

Therefore upon identification of a MADS15 polypeptide using one or several of the features described above, a person skilled in the art may easily derive the corresponding nucleic acid encoding the polypeptide, and use a sufficient length of substantially contiguous nucleotides of the same to perform any one or more of the gene silencing methods described above (for the reduction or substantial elimination of an endogenous MADS15 gene expression).

Preferred for use in the methods of the invention is a sufficient length of substantially contiguous nucleotides of SEQ ID NO: 109 (OsMADS15), or the use of a sufficient length of substantially contiguous nucleotides of a nucleic acid sequence encoding an orthologue or paralogue of OsMADS15 (SEQ ID NO: 109). Examples of such orthologues and paralogues of OsMADS15 are provided in Table D below. Close homologues of OsMADS15 are the proteins represented by SEQ ID NO: 147, 149, 151, 153, 155, 157, 159, 161, 163, 165, 167, 169, 171 and 173.

Orthologues in, for example, monocot plant species may easily be found by performing a so-called reciprocal blast search. This may be done by a first blast involving blasting a query sequence (for example, SEQ ID NO: 109 or SEQ ID NO: 110) against any sequence database, such as the publicly available NCBI database. BLASTN or TBLASTX (using standard default values) may be used when starting from a nucleotide sequence and BLASTP or TBLASTN (using standard default values) may be used when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 109 or SEQ ID NO: 110 the second blast would therefore be against rice sequences). The results of the first and second BLASTs are then compared. A paralogue is identified if a high-ranking hit from the first blast is from the same species as from which the query sequence is derived; an orthologue is identified if a high-ranking hit is not from the same species as from which the query sequence is derived. High-ranking hits are those having a low E-value. The lower the E-value, the more significant the score (or in other words the lower the chance that the hit was found by chance). Computation of the E-value is well known in the art. In the case of large families, ClustalW may be used, followed by a neighbour joining tree, to help visualize clustering of related genes and to identify orthologues and paralogues.

The source of the substantially contiguous nucleotides of a MADS15 gene/nucleic acid may be any plant source or artificial source. For optimal performance, the gene silencing techniques used for the reduction or substantial elimination of endogenous MADS15 gene expression requires the use of MADS15 sequences from monocotyledonous plants for transformation into monocotyledonous plants. Preferably, MADS15 sequences from the family Poaceae are transformed into plants of the family Poaceae. Further preferably, a MADS15 nucleic acid from rice (be it a full length MADS15 sequence or a fragment) is transformed into a rice plant. The MADS15 nucleic acid need not be introduced into the same plant variety. Most preferably, the MADS15 nucleic acid from rice is a sufficient length of substantially contiguous nucleotides of SEQ ID NO: 109 (OsMADS15) or a sufficient length of substantially contiguous nucleotides of a nucleic acid sequence encoding an orthologue or paralogue of OsMADS15 (SEQ ID NO: 110). As mentioned above, a person skilled in the art would be well aware of what would constitute a sufficient length of substantially contiguous nucleotides to perform any of the gene silencing methods defined hereinabove, this may be as little as 20 or fewer substantially contiguous nucleotides in some cases.

The invention also provides genetic constructs and vectors to facilitate introduction and/or expression of the nucleotide sequences useful in the methods according to the invention.

Therefore, there is provided a gene construct comprising one or more control sequences capable of driving expression of a sense and/or antisense MADS15 nucleic acid sequence in a plant so as to silence an endogenous MADS15 gene in the plant; and optionally a transcription termination sequence. Preferably, the control sequence is a constitutive and ubiquitous promoter.

A preferred construct for gene silencing is one comprising an inverted repeat of a MADS15 gene or fragment thereof, preferably capable of forming a hairpin structure, which inverted repeat is under the control of a constitutive promoter.

Therefore, the invention provides a construct comprising:
 (a) a MADS15 nucleic acid capable of forming a hairpin structure;
 (b) one or more control sequences capable of driving expression of the nucleic acid sequence of (a); and optionally
 (c) a transcription termination sequence.

Constructs useful in the methods according to the present invention may be created using recombinant DNA technology well known to persons skilled in the art. The gene constructs may be inserted into vectors, which may be commercially available, suitable for transforming into plants and suitable for expression of the gene of interest in the transformed cells. The invention therefore provides use of a gene construct as defined hereinabove in the methods of the invention.

The sequence of interest is operably linked to one or more control sequences (at least to a promoter) capable of increasing expression in a plant.

Advantageously, any type of promoter may be used to drive expression of the nucleic acid sequence. The promoter may be an inducible promoter, i.e. having induced or increased transcription initiation in response to a developmental, chemical, environmental or physical stimulus. Additionally or alternatively, the promoter may be a tissue-preferred or cell-preferred promoter, i.e. one that is capable of preferentially initiating transcription in certain tissues, such as the leaves, roots, seed tissue etc, or even in specific cells. Promoters able to initiate transcription in certain tissues or cells only are referred to herein as "tissue-specific", respectively "cell-specific".

Preferably, the MADS15 nucleic acid or functional variant thereof is operably linked to a constitutive promoter. Preferably the promoter is a ubiquitous promoter and is expressed predominantly throughout the plant. Preferably, the constitutive promoter capable of preferentially expressing the nucleic acid throughout the plant has a comparable expression profile to a GOS2 promoter. More preferably, the constitutive promoter has the same expression profile as the rice GOS2 promoter, most preferably, the promoter capable of preferentially expressing the nucleic acid throughout the plant is the GOS2 promoter from rice (SEQ ID NO: 113 or SEQ ID NO: 174). It should be clear that the applicability of the present invention is not restricted to the MADS15 nucleic acid represented by SEQ ID NO: 109, nor is the applicability of the invention restricted to expression of a MADS15 nucleic acid when driven by a GOS2 promoter. An alternative constitutive promoter that is useful in the methods of the present invention is the high mobility group protein promoter (PRO0170, SEQ ID NO: 40 in WO2004070039). Examples of other constitutive promoters that may also be used to drive expression of a MADS15 nucleic acid are shown in the definitions section.

Optionally, one or more terminator sequences may also be used in the construct introduced into a plant. Additional regulatory elements may include transcriptional as well as translational enhancers. Those skilled in the art will be aware of terminator and enhancer sequences that may be suitable for use in performing the invention. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1. The genetic construct may optionally comprise a selectable marker gene.

The present invention also encompasses plants including plant parts obtainable by the methods according to the present invention having increased yield relative to control plants and which have reduced or substantially eliminated expression of an endogenous MADS15 gene.

The invention furthermore provides a method for the production of transgenic plants having increased yield relative to control plants, which transgenic plants have reduced or substantially eliminated expression of an endogenous MADS15 gene.

More specifically, the present invention provides a method for the production of transgenic plants having increased seed yield which method comprises:
introducing and expressing in a plant, plant part or plant cell a gene construct comprising one or more control sequences capable of preferentially driving expression of an inverted repeat MADS15 nucleic acid sequence in a plant so as to silence an endogenous MADS15 gene in the plant; and
cultivating the plant, plant part or plant cell under conditions promoting plant growth and development.

Preferably, the construct introduced into a plant is one comprising an inverted repeat (in part or complete) of a MADS15 gene or fragment thereof, preferably capable of forming a hairpin structure.

According to a preferred feature of the present invention, the construct is introduced into a plant by transformation.

Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, or quantitative PCR, all techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also extends to harvestable parts of a plant such as seeds and products derived, preferably directly derived, from a harvestable part of such a plant, such as dry pellets or powders, oil, fat and fatty acids, starch or proteins.

The present invention also encompasses use of MADS15 nucleic acids for the reduction or substantial elimination of endogenous MADS15 gene expression in a plant for increasing plant seed yield as defined hereinabove.

Nucleic acids encoding the MADS15 protein described herein, or the MADS15 proteins themselves, may find use in breeding programmes in which a DNA marker is identified which may be genetically linked to a MADS15-encoding gene. The nucleic acids/genes, or the MADS15 proteins themselves may be used to define a molecular marker. This DNA or protein marker may then be used in breeding programmes to select plants having enhanced yield-related traits as defined hereinabove in the methods of the invention.

Allelic variants of a MADS15 protein-encoding nucleic acid/gene may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give increased yield. Selection is typically carried out by monitoring growth performance of plants containing different allelic variants of the sequence in question. Growth performance may be monitored in a greenhouse or in the field. Further optional steps include crossing plants in which the superior allelic variant was identified with another plant. This could be used, for example, to make a combination of interesting phenotypic features.

Nucleic acids encoding MADS15 proteins may also be used as probes for genetically and physically mapping the genes that they are a part of, and as markers for traits linked to those genes. Such information may be useful in plant breeding in order to develop lines with desired phenotypes. Such use of MADS15 protein-encoding nucleic acids requires only a nucleic acid sequence of at least 15 nucleotides in length. The MADS15 protein-encoding nucleic acids may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the MADS15 protein-encoding nucleic acids. The resulting banding patterns may then be subjected to genetic analyses using computer programs such as MapMaker (Lander et al. (1987) Genomics 1: 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the MADS15 protein-encoding nucleic acid in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridisation (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acids. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having enhanced yield-related traits, as described hereinbefore. These traits may also be combined with other economically advantageous traits, such as further yield-enhancing traits, tolerance to other abiotic and biotic stresses, traits modifying various architectural features and/or biochemical and/or physiological features.

Detailed Description of PLT

Surprisingly, it has now been found that increasing expression of a nucleic acid encoding a PLT transcription factor polypeptide gives plants having enhanced yield-related traits, in particular increased yield relative to control plants.

According to the present invention, there is provided a method for increasing plant yield relative to control plants, comprising increasing expression in a plant of a nucleic acid encoding a PLT transcription factor polypeptide.

The term "increased yield" as defined herein is taken to mean an increase in biomass (weight) of one or more parts of a plant, which may include aboveground (harvestable) parts and/or (harvestable) parts below ground.

In particular, such harvestable parts are seeds, and performance of the methods of the invention results in plants having increased seed yield relative to the seed yield of control plants.

Taking corn as an example, a yield increase may be manifested as one or more of the following: increase in the number of plants per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

According to a preferred feature of the present invention, performance of the methods of the invention gives plants having increased seed yield relative to control plants. Therefore according to the present invention, there is provided a method for increasing seed yield in plants relative to the seed yield of control plants, the method comprising increasing expression in a plant of a nucleic acid encoding a PLT transcription factor polypeptide.

Since the transgenic plants according to the present invention have increased yield, it is likely that these plants exhibit an increased growth rate (during at least part of their life cycle), relative to the growth rate of corresponding wild type plants at a corresponding stage in their life cycle. The increased growth rate may be specific to one or more parts of a plant (including seeds), or may be throughout substantially the whole plant. A plant having an increased growth rate may even exhibit early flowering. The increase in growth rate may take place at one or more stages in the life cycle of a plant or during substantially the whole plant life cycle. Increased growth rate during the early stages in the life cycle of a plant may reflect enhanced vigour (increased seedling vigor at emergence). The increase in growth rate may alter the harvest cycle of a plant allowing plants to be sown later and/or harvested sooner than would otherwise be possible. If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of corn plants followed by, for example, the sowing and optional harvesting of soy bean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

Performance of the methods of the invention gives plants having an increased growth rate. Therefore, according to the present invention, there is provided a method for increasing the growth rate of plants, which method comprises increasing expression in a plant of a nucleic acid encoding a PLT transcription factor polypeptide.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi and insects.

In particular, the methods of the present invention may be performed under non-stress conditions or under conditions of mild drought to give plants having increased yield relative to control plants. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signaling pathways and cellular responses, such as the production of stress proteins, up-regulation of anti-oxidants, accumulation of compatible solutes and growth arrest. The term "non-stress" conditions as used herein are those environmental conditions that allow optimal growth of plants. Persons skilled in the art are aware of normal soil conditions and climatic conditions for a given location.

Performance of the methods of the invention gives plants grown under non-stress conditions or under mild drought conditions enhanced yield-related traits relative to control plants grown under comparable conditions. Therefore, according to the present invention, there is provided a method for enhancing yield-related traits, in particular for increasing yield, in plants grown under non-stress conditions or under mild drought conditions, which method comprises increasing expression in a plant of a nucleic acid encoding a PLT transcription factor polypeptide.

The methods of the invention are advantageously applicable to any plant.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs. According to a preferred embodiment of the present invention, the plant is a crop plant. Examples of crop plants include soybean, sunflower, canola, alfalfa, rapeseed, cotton, tomato, potato and tobacco. Examples of typical crop plants grown for oil production include soybean, sunflower, cotton, canola, peanuts or palm. Examples of typical crop plants grown for starch production include rice, wheat, barley, corn or potato. Further preferably, the plant is a monocotyledonous plant. Examples of monocotyledonous plants include sugarcane. More preferably the plant is a cereal. Examples of cereals include rice, maize, wheat, barley, millet, rye, triticale, sorghum and oats.

The term "PLT transcription factor polypeptide" as defined herein refers to any polypeptide comprising in increasing order of preference at least 70%, 75%, 80%, 85%, 90%, 95%, 96%, 97%, 98% or 99% sequence identity to the AP2 domain represented by SEQ ID NO: 191.

Preferably the PLT transcription factor polypeptide of choice is a PLT transcription factor polypeptide that in its natural genetic environment is essentially expressed in the roots (below ground parts) of the plant.

Further preferably, the PLT transcription factor polypeptide comprises either one motif but preferably both of motif1 as represented by SEQ ID NO: 192 PK(V/L)(A/E)DFLG and motif 2 as represented by SEQ ID NO: 209: (V/L)FX(M/V) WN(D/E), wherein X may be any amino acid; preferably motif 2 has the sequence of SEQ ID NO: 193 (V/L)F(T/S/N) (M/V)WN(D/E).

Examples of PLT transcription factor polypeptides comprising (i) in increasing order of preference at least 70%, 75%, 80%, 85%, 90%, 95%, 96%, 97%, 98% or 99% sequence identity to the AP2 domain represented by SEQ ID NO: 191 are proteins represented by the sequences given in Table I in the examples section. Preferred examples are represented by SEQ ID NO: 176 and SEQ ID NO: 178.

The AP2 domain in a PLT transcription factor polypeptide may be identified using specialised databases e.g. SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAIPress, Menlo Park; Hulo et al., Nucl. Acids. Res. 32:D134-D137, (2004)) or Pfam (Bateman et al., Nucleic Acids Research 30(1): 276-280 (2002)). The AP2 domain of a PLT transcription factor comprises two repeats R1 and R2, each of about 68 amino acids and separated by a linker region (FIG. 13).

The AP2 domain as represented by SEQ ID NO: 191 may be identified using methods for the alignment of sequences for comparison as described hereinabove. In some instances, the default parameters may be adjusted to modify the stringency of the search. For example using BLAST, the statistical significance threshold (called "expect" value) for reporting matches against database sequences may be increased to show less stringent matches. This way, short nearly exact matches may be identified, including motif1 as represented by SEQ ID NO: 192 and motif 2 as represented by SEQ ID NO: 209, preferably as represented by SEQ ID NO: 193.

Homologues of a PLT transcription factor polypeptide may also be used to perform the methods of invention. Homologues (or homologous proteins) may readily be identified using routine techniques well known in the art, such as by sequence alignment. Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the alignment of two complete sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information. Homologues may readily be identified using, for example, the ClustalW multiple sequence alignment algorithm (version 1.83), with the default pairwise alignment parameters, and a scoring method in percentage. Minor manual editing may be performed to optimise alignment between conserved motifs, as would be apparent to a person skilled in the art.

Homologues also include orthologues and paralogues. Orthologues and paralogues may easily be found by performing a so-called reciprocal blast search. This may be done by a first BLAST involving BLASTing a query sequence (for example, SEQ ID NO: 175, SEQ ID NO: 176, SEQ ID NO: 177 or SEQ ID NO: 178) against any sequence database, such as the publicly available NCBI database. BLASTN or TBLASTX (using standard default values) may be used when starting from a nucleotide sequence and BLASTP or TBLASTN (using standard default values) may be used when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 175, SEQ ID NO: 176, SEQ ID NO: 177 or SEQ ID NO: 178, the second BLAST would therefore be against *Arabidopsis thaliana* sequences). The results of the first and second BLASTs are then compared. A paralogue is identified if a high-ranking hit from the first BLAST is from the same species as from which the query sequence is derived; an orthologue is identified if a high-ranking hit is not from the same species as from which the query sequence is derived. High-ranking hits are those having a low E-value. The lower the E-value, the more significant the score (or in other words the lower the chance that the hit was found by chance). Computation of the E-value is well known in the art. In the case of large families, ClustalW may be used, followed by a neighbour joining tree, to help visualize clustering of related genes and to identify orthologues and paralogues. In addition to E-values, comparisons are also scored by percentage identity. Percentage identity refers to the number of identical nucleotides (or amino acids) between the two compared nucleic acid (or polypeptide) sequences over a particular length. PLT transcription factor polypeptide homologues have in increasing order of preference at least 25%, 30%, 40%, 50%, 60%, 70%, 80%, 85%, 90%, 95%, 96%, 97%, 98% or 99% or more sequence identity or similarity (functional identity) to an unmodified PLT transcription factor polypeptide as represented by SEQ ID NO: 176 or SEQ ID NO: 178. Percentage identity between PLT transcription factor polypeptide homologues outside of the AP2 domain is reputedly low. Preferably, PLT transcription factor polypeptide homologues comprise an AP2 domain with in increasing order of preference at least 70%, 75%, 80%, 85%, 90%, 95%, 96%, 97%, 98% or 99% sequence identity to the AP2 domain represented by SEQ ID NO: 191. Further preferably, PLT transcription factor polypeptide homologues are as represented by SEQ ID NO: 180, SEQ ID NO: 182, SEQ ID NO: 184, SEQ ID NO: 186, SEQ ID NO: 188, SEQ ID NO: 200 and SEQ ID NO: 202.

The PLT polypeptide may be a derivative of SEQ ID NO: 176 or SEQ ID NO: 178. "Derivatives" include peptides, oligopeptides, polypeptides which may, compared to the amino acid sequence of the naturally-occurring form of the protein, such as the one presented in SEQ ID NO: 176 or SEQ ID NO: 178, comprise substitutions of amino acids with non-naturally occurring amino acid residues, or additions of non-naturally occurring amino acid residues. Derivatives of SEQ ID NO: 180, SEQ ID NO: 182, SEQ ID NO: 184, SEQ ID NO: 186, SEQ ID NO: 188, SEQ ID NO: 200 and SEQ ID NO: 202 are further examples which may be suitable for use in the methods of the invention provided that they have the same or similar biological activity.

Furthermore, PLT transcription factor polypeptides (at least in their native form) typically have DNA-binding activity and an activation domain. A person skilled in the art may easily determine the presence of an activation domain and DNA-binding activity using routine techniques and procedures. Proteins interacting with PLT transcription factor polypeptides (as, for example, in transcriptional complexes) may easily be identified using standard techniques for a person skilled in the art.

Examples of nucleic acids encoding PLT transcription factor polypeptides include but are not limited to those represented by any one of: SEQ ID NO: 175, SEQ ID NO: 177, SEQ ID NO: 179, SEQ ID NO: 181, SEQ ID NO: 183, SEQ ID NO: 185, SEQ ID NO: 187, SEQ ID NO: 199 and SEQ ID NO: 201. Variants of nucleic acids encoding PLT transcription factor polypeptides may be suitable for use in the methods of the invention provided that they have the same or similar biological activity. Suitable variants include portions of nucleic acids encoding PLT transcription factor polypeptides and/or nucleic acids capable of hybridising with nucleic acids/genes encoding PLT transcription factor polypeptides. Further variants include splice variants and allelic variants of nucleic acids encoding PLT transcription factor polypeptides.

The term "portion" as defined herein refers to a piece of DNA encoding a polypeptide comprising in increasing order of preference at least 70%, 75%, 80%, 85%, 90%, 95%, 96%, 97%, 98% or 99% sequence identity to the AP2 domain represented by SEQ ID NO: 191. The portion may further comprise either one motif but preferably both of motif1 as represented by SEQ ID NO: 192 and/or motif 2 as represented by SEQ ID NO: 209; preferably, motif 2 has the sequences as represented by SEQ ID NO: 193.

A portion may be prepared, for example, by making one or more deletions to a nucleic acid encoding a PLT transcription factor polypeptide. The portions may be used in isolated form or they may be fused to other coding (or non coding) sequences in order to, for example, produce a protein that combines several activities. When fused to other coding sequences, the resulting polypeptide produced upon translation may be bigger than that predicted for the PLT transcription factor portion. Preferably, the portion codes for a polypeptide with substantially the same biological activity as the PLT transcription factor polypeptides of SEQ ID NO: 176 and SEQ ID NO: 178.

Preferably, the portion is a portion of a nucleic acid as represented by any one of the sequences listed in Table I of the Examples. Most preferably the portion is a portion of a nucleic acid as represented by SEQ ID NO: 175 and SEQ ID NO: 177.

Another variant of a nucleic acid encoding a PLT transcription factor polypeptide, useful in the methods of the present invention, is a nucleic acid capable of hybridising under reduced stringency conditions, preferably under stringent conditions, with a probe derived from the nucleic acid as defined hereinbefore, which hybridising sequence encodes a polypeptide comprising in increasing order of preference at least 70%, 75%, 80%, 85%, 90%, 95%, 96%, 97%, 98% or 99% sequence identity to the AP2 domain represented by SEQ ID NO: 191. The hybridizing sequence may further comprise either one motif but preferably both of motif1 as represented by SEQ ID NO: 192 and/or motif 2 as represented by SEQ ID NO: 209, preferably as represented by SEQ ID NO: 193.

Preferably, the hybridising sequence is one that is capable of hybridising to a nucleic acid as represented by (or to probes derived from) any one of the sequences listed in Table I of the Examples, or to a portion of any of the aforementioned sequences (the target sequence). Most preferably the hybridising sequence is capable of hybridising to SEQ ID NO: 175 or to SEQ ID NO: 177 (or to probes derived therefrom). Probes are generally less than 1000 bp in length, preferably less than 500 bp in length. Commonly, probe lengths for DNA-DNA hybridisations such as Southern blotting, vary between 100 and 500 bp, whereas the hybridising region in probes for DNA-DNA hybridisations such as in PCR amplification generally are shorter than 50 but longer than 10 nucleotides.

The PLT transcription factor polypeptide may be encoded by a splice variant. The term "splice variant" as used herein encompasses variants of a nucleic acid sequence in which selected introns and/or exons have been excised, replaced, displaced or added, or in which introns have been shortened or lengthened. Such variants will be ones in which the substantial biological activity of the protein is retained, which may be achieved by selectively retaining functional segments of the protein. Such splice variants may be found in nature or may be manmade. Methods for making such splice variants are well known in the art.

Preferred splice variants are splice variants of the nucleic acid encoding a PLT transcription factor polypeptide comprising in increasing order of preference at least 70%, 75%, 80%, 85%, 90%, 95%, 96%, 97%, 98% or 99% sequence identity to the AP2 domain represented by SEQ ID NO: 191. Splice variants may further comprise either one motif but preferably both of motif1 as represented by SEQ ID NO: 192 and/or motif 2 as represented by SEQ ID NO: 209, preferably as represented by SEQ ID NO: 193.

Further preferred splice variants of nucleic acids encoding PLT transcription factor polypeptides comprising features as defined hereinabove are splice variants of a nucleic acid as represented by any one of the sequences listed in Table I of the Examples. Most preferred is a splice variant of a nucleic acid sequence as represented by SEQ ID NO: 175 and SEQ ID NO: 177.

The PLT transcription factor polypeptide may also be encoded by an allelic variant of a nucleic acid encoding a polypeptide comprising from comprising in increasing order of preference at least 70%, 75%, 80%, 85%, 90%, 95%, 96%, 97%, 98% or 99% sequence identity to the AP2 domain represented by SEQ ID NO: 191. The allelic variant may further comprise either one motif but preferably both of motif1 as represented by SEQ ID NO: 192 and/or motif 2 as represented by SEQ ID NO: 209, preferably as represented by SEQ ID NO: 193.

Preferred allelic variants of nucleic acids encoding PLT transcription factor polypeptides comprising features as defined hereinabove are splice variants of a nucleic acid as represented by any one of the sequences listed in Table I of the Examples. Most preferred is an allelic variant of a nucleic acid sequence as represented by SEQ ID NO: 175 and SEQ ID NO: 177.

The increase in expression of a nucleic acid encoding a PLT transcription factor polypeptide leads to raised corresponding mRNA or polypeptide levels, which could equate to raised activity of the PLT transcription factor polypeptide; or the activity may also be raised when there is no change in polypeptide levels, or even when there is a reduction in polypeptide levels. This may occur when the intrinsic properties of the polypeptide are altered, for example, by making mutant versions that are more active that the wild type polypeptide.

Directed evolution (or gene shuffling) may be used to generate variants of nucleic acids encoding PLT transcription factor polypeptides. This consists of iterations of DNA shuffling followed by appropriate screening and/or selection to generate variants of nucleic acids or portions thereof encoding PLT transcription factor polypeptides or homologues or portions thereof having an modified biological activity (Castle et al., (2004) Science 304(5674): 1151-4; U.S. Pat. Nos. 5,811,238 and 6,395,547).

Site-directed mutagenesis may be used to generate variants of nucleic acids encoding PLT transcription factor polypeptides. Several methods are available to achieve site-directed mutagenesis, the most common being PCR based methods (current protocols in molecular biology. Wiley Eds.).

Directed evolution and site-directed mutagenesis are examples of technologies that enable the generation of variants of nucleic acids encoding PLT transcription factor polypeptides with modified activity useful to perform the methods of the invention.

Nucleic acids encoding PLT transcription factor polypeptides may be derived from any natural or artificial source. The nucleic acid may be modified from its native form in composition and/or genomic environment through deliberate human manipulation. Preferably the PLT transcription factor nucleic acid is from a plant, preferably from a dicotyledonous plant, further preferably from the Brassicaceae family, more preferably from the *Arabidopsis* genus, most preferably the nucleic acid is from *Arabidopsis thaliana*.

The methods of the invention rely on increased expression of a nucleic acid encoding a PLT transcription factor polypeptide in a plant. The nucleic acid may be a full-length nucleic acid or may be a portion or a hybridising sequence or another nucleic acid variant as hereinbefore defined.

The methods of the invention rely on increased expression of a nucleic acid encoding a PLT transcription factor polypeptide in a plant.

The invention also provides genetic constructs and vectors to facilitate introduction and/or expression in a plant of the nucleic acid sequences useful in the methods according to the invention.

Therefore, there is provided a gene construct comprising:
  (i) A nucleic acid encoding a PLT transcription factor polypeptide as defined hereinabove;

(ii) One or more control sequences, of which at least one is a medium strength constitutive promoter.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells. The invention therefore provides use of a gene construct as defined hereinabove in the methods of the invention.

Plants are transformed with a vector comprising the sequence of interest (i.e., a nucleic acid encoding a PLT transcription factor polypeptide). The skilled artisan is well aware of the genetic elements that must be present on the vector in order to successfully transform, select and propagate host cells containing the sequence of interest. The sequence of interest is operably linked to one or more control sequences (at least to a promoter).

The nucleic acid encoding a PLT transcription factor polypeptide or variant thereof is operably linked to a constitutive promoter, preferably a medium strength constitutive promoter. A constitutive promoter is transcriptionally active during most, but not necessarily all, phases of its growth and development and is substantially ubiquitously expressed at moderate levels. Promoter strength and/or expression pattern can be analysed as described in the definitions section. The promoter strength and/or expression pattern can for example be compared to that of a well-characterised shoot preferred reference promoter, such as the Cab27 promoter (weak expression, GenBank AP004700) or the putative protochlorophyllid reductase promoter (strong expression, GenBank AL606456). Preferably the promoter used in the methods of the present invention is derived from a plant, further preferably a monocotyledonous plant. Most preferred is use of a GOS2 promoter (from rice) (SEQ ID NO: 194 or alternatively SEQ ID NO: 210). It should be clear that the applicability of the present invention is not restricted to the nucleic acid represented by SEQ ID NO: 175 or SEQ ID NO: 177, nor is the applicability of the invention restricted to expression of a nucleic acid encoding a PLT transcription factor polypeptide when driven by a GOS2 promoter. Examples of other constitutive promoters that may also be used to drive expression of a nucleic acid encoding a PLT transcription factor polypeptide are shown in the definitions section.

Optionally, one or more terminator sequences (also a control sequence) may be used in the construct introduced into a plant. Additional regulatory elements may include transcriptional as well as translational enhancers. Those skilled in the art will be aware of terminator and enhancer sequences that may be suitable for use in performing the invention. Other control sequences (besides promoter, enhancer, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1. The genetic construct may optionally comprise a selectable marker gene.

The present invention also encompasses plants obtainable by the methods according to the present invention. The present invention therefore provides plants, plant parts or plant cells thereof obtainable by the method according to the present invention, which plants or parts or cells thereof comprise a nucleic acid transgene encoding a PLT transcription factor polypeptide under the control of a constitutive promoter, preferably a non-viral constitutive promoter.

The invention also provides a method for the production of transgenic plants having increased yield relative to control plants, comprising introduction and preferential expression of a nucleic acid encoding a PLT transcription factor polypeptide in a plant.

More specifically, the present invention provides a method for the production of transgenic plants having increased yield which method comprises:
(i) introducing and expressing a nucleic acid encoding a PLT transcription factor polypeptide in a plant; and
(ii) cultivating the plant cell under conditions promoting plant growth and development.

The nucleic acid may be introduced directly into a plant cell or into the plant itself (including introduction into a tissue, organ or any other part of a plant). According to a preferred feature of the present invention, the nucleic acid is preferably introduced into a plant by transformation.

Generally after transformation, plant cells or cell groupings are selected for the presence of one or more markers which are encoded by plant-expressible genes co-transferred with the gene of interest, following which the transformed material is regenerated into a whole plant. Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, or quantitative PCR, all techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid encoding a PLT transcription factor polypeptide. Preferred host cells according to the invention are plant cells.

The invention furthermore extends to harvestable parts of a plant such as, but not limited to seeds, leaves, fruits, flowers, stems, rhizomes, tubers and bulbs. The invention furthermore relates to products derived, preferably directly derived, from a harvestable part of such a plant, such as dry pellets or powders, oil, fat and fatty acids, starch or proteins.

The present invention also encompasses use of nucleic acids encoding PLT transcription factor polypeptides and use of PLT transcription factor polypeptides in increasing plant yield as defined hereinabove in the methods of the invention.

The increased expression of a nucleic acid encoding a PLT transcription factor polypeptide may be performed by introducing a genetic modification (preferably in the locus of a PLT transcription factor gene). The locus of a gene as defined herein is taken to mean a genomic region, which includes the gene of interest and 10 KB up- or downstream of the coding region.

The genetic modification may be introduced by alternative methods as the one described hereinabove, for example, by any one (or more) of the following: T-DNA activation, TILLING and homologous recombination. Following introduction of the genetic modification, there follows an optional step of selecting for increased expression of a nucleic acid encoding a PLT transcription factor polypeptide, which increased expression gives plants having increased yield.

T-DNA activation tagging results in transgenic plants that show dominant phenotypes due to modified expression of genes close to the introduced promoter. The promoter to be introduced a medium strength constitutive promoter capable of increasing expression of the nucleic acid encoding a PLT transcription factor polypeptide in a plant.

A genetic modification may also be introduced in the locus of a gene encoding a PLT transcription factor polypeptide using the technique of TILLING (Targeted Induced Local Lesions In Genomes).

The effects of the invention may also be reproduced using homologous recombination. The nucleic acid to be introduced (which may be a nucleic acid encoding a PLT transcription factor polypeptide or variant thereof as hereinbefore defined) is targeted to the locus of a PLT gene. The nucleic acid to be targeted may be an improved allele used to replace the endogenous gene or may be introduced in addition to the endogenous gene.

T-DNA activation, TILLING and homologous recombination are examples of technologies that enable the generation of genetic modifications comprising increasing expression of a nucleic acid encoding a PLT transcription factor polypeptide in plants.

Nucleic acids encoding PLT transcription factor polypeptides, or PLT transcription factor polypeptides, may find use in breeding programmes in which a DNA marker is identified which may be genetically linked to a PLT transcription factor gene. The nucleic acids/genes, or the PLT transcription factor polypeptides may be used to define a molecular marker. This DNA or protein marker may then be used in breeding programmes to select plants having increased yield as defined hereinabove in the methods of the invention.

Allelic variants of a PLT transcription factor nucleic acid/ gene may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give increased yield. Selection is typically carried out by monitoring growth performance of plants containing different allelic variants of the sequence in question. Growth performance may be monitored in a greenhouse or in the field. Further optional steps include crossing plants in which the superior allelic variant was identified with another plant. This could be used, for example, to make a combination of interesting phenotypic features.

A nucleic acid encoding a PLT transcription factor polypeptide may also be used as probes for genetically and physically mapping the genes that they are a part of, and as markers for traits linked to those genes. Such information may be useful in plant breeding in order to develop lines with desired phenotypes. Such use of PLT transcription factor nucleic acids requires only a nucleic acid sequence of at least 15 nucleotides in length. The PLT transcription factor nucleic acids may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the PLT transcription factor nucleic acids. The resulting banding patterns may then be subjected to genetic analyses using computer programs such as MapMaker (Lander et al. (1987) Genomics 1: 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the PLT transcription factor nucleic acid in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridisation (FISH) mapping (Trask (1991) Trends Genet. 7:149-154). Although current methods of FISH mapping favor use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acids. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having increased yield, as described hereinbefore. This increased yield may also be combined with other economically advantageous traits, such as further yield-enhancing traits, tolerance to other abiotic and biotic stresses, traits modifying various architectural features and/or biochemical and/or physiological features.

Detailed Description of bHLH

Surprisingly, it has now been found that modulating expression in a plant of a nucleic acid encoding a particular class of bHLH transcription factor gives plants having enhanced yield-related traits relative to control plants. The particular class of bHLH transcription factor suitable for enhancing yield-related traits in plants is described in detail below.

The present invention provides a method for enhancing yield-related traits in plants relative to control plants, comprising modulating expression in a plant of a nucleic acid encoding a particular class of bHLH transcription factor.

A preferred method for modulating (preferably, increasing) expression of a nucleic acid encoding a bHLH transcription factor is by introducing and expressing in a plant a nucleic acid encoding a particular class of bHLH transcription factor as further defined below.

The nucleic acid to be introduced into a plant (and therefore useful in performing the methods of the invention) is any nucleic acid encoding the type of bHLH transcription factor which will now be described. A bHLH transcription factor as defined herein refers to a polypeptide represented by any one of SEQ ID NO 213, SEQ ID NO 215, SEQ ID NO: 217, SEQ ID NO: 219, SEQ ID NO 225, SEQ ID NO: 297, SEQ ID NO: 299 and SEQ ID NO: 301. The invention is illustrated by transforming plants with the *Oryza sativa* sequence represented by SEQ ID NO: 212, encoding the polypeptide of SEQ ID NO: 213. SEQ ID NO: 215 from *Oryza sativa* (encoded by SEQ ID NO: 214) and SEQ ID NO: 217 from *Oryza sativa* (encoded by SEQ ID NO: 216) are paralogues of the polypeptide of SEQ ID NO: 213. SEQ ID NO: 219 from *Arabidopsis thaliana* (encoded by SEQ ID NO: 218) and SEQ ID NO: 225 from *Arabidopsis thaliana* (encoded by SEQ ID NO: 224) are orthologues of the polypeptide of SEQ ID NO: 213. SEQ ID NO: 221 from *Arabidopsis thaliana* (encoded by SEQ ID NO: 220) and SEQ ID NO: 223 from *Arabidopsis thaliana* (encoded by SEQ ID NO: 222) are variants of SEQ ID NO: 218 and SEQ ID NO: 219.

Orthologues and paralogues may easily be found by performing a so-called reciprocal blast search. Typically this involves a first BLAST involving BLASTing a query sequence (for example, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 224 or SEQ ID NO: 225) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 212, SEQ ID NO: 213, SEQ ID NO: 214, SEQ ID NO: 215, SEQ ID NO: 216 or SEQ ID NO: 217, the second BLAST would therefore be against *Oryza* sequences; where the query sequence is SEQ ID NO: 218, SEQ ID NO: 219, SEQ ID NO: 224 or SEQ ID NO: 225, the second BLAST would therefore be against *Arabidopsis* sequences). The results of the first and second BLASTs are then compared. A paralogue is identified if a high-ranking hit from the first blast is from the same species as from which the query sequence is derived, a BLAST back then ideally results in the query sequence as highest hit; an orthologue is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. Preferably the score is greater than 50, more preferably greater than 100; and preferably the E-value is less than e-5, more preferably less than e-6. An example detailing the identification of orthologues and paralogues is given in Example 31 and Example 30 respectively herein. In the case of large families, ClustalW may be used, followed by a neighbour joining tree, to help visualize clustering of related genes and to identify orthologues and paralogues.

Examples of orthologues obtained by the BLAST procedure mentioned above are SEQ ID NO: 227 from *Medicago truncatula* (encoded by SEQ ID NO: 226) and SEQ ID NO: 229 from *Hordeum vulgare* (encoded by SEQ ID NO: 228). Further orthologues and paralogues may readily be identified using the BLAST procedure described above and by following the procedure given in the Examples section.

The proteins represented by SEQ ID NO: 297, 299 and 301 were hitherto unknown. Therefore, the invention also provides hitherto unknown bHLH transcription factors and bHLH transcription factor-encoding nucleic acids.

According to a further embodiment of the present invention, there is therefore provided an isolated nucleic acid molecule comprising:
(i) a nucleic acid represented by any one of SEQ ID NO: 296, SEQ ID NO: 298 and SEQ ID NO: 300;
(ii) the complement of a nucleic acid represented by any one of SEQ ID NO: 296, SEQ ID NO: 298 and SEQ ID NO: 300;
(iii) a nucleic acid encoding a bHLH transcription factor having (a) in increasing order of preference, at least 50%, 55%, 60%, 65%, 70%, 75%, 80%, 85%, 90%, 95%, 96%, 97%, 98%, 99% or more sequence identity to the amino acid sequence represented by any one of SEQ ID NO: 297, SEQ ID NO: 299 and SEQ ID NO: 301, and (b) a bHLH domain.

According to a further embodiment of the present invention, there is also provided an isolated polypeptide comprising:
(i) an amino acid sequence represented by any one of SEQ ID NO: 297, SEQ ID NO: 299 and SEQ ID NO: 301;
(ii) an amino acid sequence having (a) in increasing order of preference, at least 50%, 55%, 60%, 65%, 70%, 75%, 80%, 85%, 90%, 95%, 96%, 97%, 98%, 99% or more sequence identity to any one of the amino acid sequences represented by SEQ ID NO: 297, SEQ ID NO: 299 and SEQ ID NO: 301, and (b) a bHLH domain;
(iii) derivatives of any of the amino acid sequences given in (i) or (ii) above.

The polypeptides represented by any one of SEQ ID NO 213, SEQ ID NO 215, SEQ ID NO: 217, SEQ ID NO: 219, SEQ ID NO 221, SEQ ID NO 223, SEQ ID NO 225, SEQ ID NO: 227, SEQ ID NO: 229, SEQ ID NO: 297, SEQ ID NO: 299, SEQ ID NO: 301, or orthologues or paralogues of any of the aforementioned SEQ ID NOs, all comprise a bHLH domain.

bHLH domains are well known in the art and may readily be identified by persons skilled in the art. The family is defined by a bHLH signature domain, which consists of 60 or so amino acids with two functionally distinct regions. A basic region, located at the N-terminal end of the domain, is involved in DNA binding and consists of 15 or so amino acids with a high number of basic residues. An HLH region, at the C-terminal end, functions as a dimerization domain and mainly comprises hydrophobic residues that form two amphipathic helices separated by a loop region of variable sequence and length.

A bHLH domain may be identified using methods for the alignment of sequences for comparison. In some instances, default parameters may be adjusted to modify the stringency of the search. For example using BLAST, the statistical significance threshold (called E-value) for reporting matches against database sequences may be increased to show less stringent matches. In this way, short nearly exact matches may be identified.

Methods for the alignment of sequences for comparison are well known in the art, such methods include GAP, BEST-FIT, BLAST, FASTA and TFASTA. GAP uses the algorithm of Needleman and Wunsch ((1970) J Mol Biol 48: 443-453) to find the global (over the whole the sequence) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Minor manual editing may be performed to optimise alignment between conserved motifs, as would be apparent to a person skilled in the art.

Specialist databases also exist for the identification of domains. The bHLH domain in a bHLH transcription factor may be identified using, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAIPress, Menlo Park; Hulo et al., Nucl. Acids. Res. 32:D134-D137, (2004)) or Pfam (Bateman et al., Nucleic Acids Research 30(1): 276-280 (2002)). The HLH domain structure in the InterPro database is designated IPR001092 and IPR011598; PF00010 in the Pfam database; SM00353 in the SMART database and PS50888 in the PROSITE database. Furthermore, the alignment shown in FIG. 18 highlights the bHLH domain of bHLH transcription factors useful in the methods of the invention.

The polypeptides represented by any one of SEQ ID NO 213, SEQ ID NO 215, SEQ ID NO: 217, SEQ ID NO: 219, SEQ ID NO 225, SEQ ID NO: 297, SEQ ID NO: 299, SEQ ID NO: 301 or orthologues or paralogues of any of the aforementioned SEQ ID NOs, typically exhibit considerable sequence divergence outside of the conserved bHLH domain.

FIG. 19a is a matrix showing the overall similarities and identities (in bold) of the bHLH type proteins described above. Even though the identities appear to be relatively low, polypeptides having sequence identity falling within the ranges shown in the matrix may be taken to be orthologues or paralogues of any of SEQ ID NO 213, SEQ ID NO 215, SEQ ID NO: 217, SEQ ID NO: 219 or SEQ ID NO 225; this may be confirmed by the reciprocal blast procedure described above. Typically, nucleic acids encoding bHLH transcription factors useful in the methods of the invention have, in increasing order of preference, at least 13%, 15%, 20%, 25%, 30%, 35%, 40%, 45%, 50%, 55%, 60%, 65%, 70%, 75%, 80%, 85%, 90%, 95% or more sequence identity to the bHLH transcription factors represented by any one of SEQ ID NO 213, SEQ ID NO 215, SEQ ID NO: 217, SEQ ID NO: 219 or SEQ ID NO 225.

The matrix shown in FIG. 19b shows similarities and identities (in bold) over the bHLH domain, where of course the values are higher than when considering full length proteins. Typically, nucleic acids encoding bHLH transcription factors useful in the methods of the invention have bHLH domains having, in increasing order of preference, at least 25%, 30%, 35%, 40%, 45%, 50%, 55%, 60%, 65%, 70%, 75%, 80%, 85%, 90%, 95% or more sequence identity to the bHLH domain of any one of the polypeptides represented by any one of SEQ ID NO 213, SEQ ID NO 215, SEQ ID NO: 217, SEQ ID NO: 219 or SEQ ID NO 225.

A pattern of amino acids, termed a 5-9-13 configuration, may be found at three positions within the basic region of the bHLH domain (see FIG. 4 of Heim et al., 2003 (Mol. Biol. Evol. 20(5):735-747) and FIG. 18 herein where three upwardly pointing arrows show the configuration). The polypeptides represented by any one of SEQ ID NO 213, SEQ ID NO 215, SEQ ID NO: 217, SEQ ID NO: 219, SEQ ID NO 225, SEQ ID NO: 297, SEQ ID NO: 299, SEQ ID NO: 301 or orthologues or paralogues of any of the aforementioned SEQ ID NOs, preferably comprise a K/R ER configuration, more preferably an RER configuration, within the bHLH domain, typically within the basic region of the domain. The presence of this configuration is not a prerequisite to performing the methods of the invention, therefore some variation in the K/R ER configuration is acceptable. *Arabidopsis* bHLH polypeptides were grouped into twelve subfamilies according to structural similarities (see FIG. 4 of Heim et al., 2003). Members of group IX constitute bHLH polypeptides having an RER configuration. Furthermore, one member of Group VI comprises an RER configuration.

The polypeptides represented by any one of SEQ ID NO 213, SEQ ID NO 215, SEQ ID NO: 217, SEQ ID NO: 219, SEQ ID NO 225, SEQ ID NO: 297, SEQ ID NO: 299, SEQ ID NO: 301 or orthologues or paralogues of any of the aforementioned SEQ ID NOs, may also comprise (in addition to a bHLH domain and optionally a K/R ER 5-9-13 motif, preferably an RER motif) a domain designated PFB26111 (see Pfam database). The domain is also indicated in FIG. 18.

Typically, nucleic acids encoding bHLH transcription factors (as defined above) having a bHLH domain and having, in increasing order of preference, at least 50%, 55%, 60%, 65%, 70%, 75%, 80%, 85%, 90%, 95% or more sequence identity to the PFB26111 domain (see FIG. 18) of any one of the polypeptides represented by any one of SEQ ID NO 213, SEQ ID NO 215, SEQ ID NO: 217, SEQ ID NO: 219, SEQ ID NO 225, SEQ ID NO: 297, SEQ ID NO: 299, or SEQ ID NO: 301 are useful in the methods of the invention.

Nucleic acids encoding the polypeptides represented by any one of SEQ ID NO 213, SEQ ID NO 215, SEQ ID NO: 217, SEQ ID NO: 219, SEQ ID NO 225, SEQ ID NO: 297, SEQ ID NO: 299, SEQ ID NO: 301, or orthologues or paralogues of any of the aforementioned SEQ ID NOs, need not be full-length nucleic acids, since performance of the methods of the invention does not rely on the use of full length nucleic acid sequences. Examples of nucleic acids suitable for use in performing the methods of the invention include but are not limited to those represented by any one of: SEQ ID NO: 212, SEQ ID NO: 214, SEQ ID NO: 216, SEQ ID NO: 218, SEQ ID NO: 220, SEQ ID NO: 222, SEQ ID NO: 224, SEQ ID NO: 226, SEQ ID NO: 228, SEQ ID NO: 296, SEQ ID NO: 298, and SEQ ID NO: 300. Nucleic acid variants may also be useful in practising the methods of the invention. Examples of such nucleic acid variants include portions of nucleic acids encoding a bHLH transcription factor as defined herein, splice variants of nucleic acids encoding a bHLH transcription factor as defined herein, allelic variants of nucleic acids encoding a bHLH transcription factor as defined herein and variants of nucleic acids encoding a bHLH transcription factor as defined herein that are obtained by gene shuffling. The terms portion, splice variant, allelic variant and gene shuffling will now be described.

A portion of a nucleic acids encoding a bHLH transcription factor as defined herein may be prepared, for example, by making one or more deletions to the nucleic acid. The portions may be used in isolated form or they may be fused to other coding (or non coding) sequences in order to, for example, produce a protein that combines several activities. When fused to other coding sequences, the resultant polypeptide produced upon translation may be bigger than that predicted for the bHLH transcription factor portion.

According to the present invention, there is provided a method for enhancing yield-related traits in plants, comprising introducing and expressing in a plant a portion of a nucleic acid encoding a bHLH transcription factor represented by any of SEQ ID NO 213, SEQ ID NO 215, SEQ ID NO: 217, SEQ ID NO: 219, SEQ ID NO 225, SEQ ID NO: 297, SEQ ID NO: 299, SEQ ID NO: 301, or a portion of a nucleic acid encoding orthologues, paralogues or homologues of any of the aforementioned SEQ ID NOs.

Portions useful in the methods of the invention, encode a polypeptide having a bHLH domain (as described above) and having substantially the same biological activity as the bHLH transcription factor represented by any of SEQ ID NO 213, SEQ ID NO 215, SEQ ID NO: 217, SEQ ID NO: 219, SEQ ID NO 225, SEQ ID NO: 297, SEQ ID NO: 299, SEQ ID NO: 301, or orthologues or paralogues of any of the aforementioned SEQ ID NOs. The portion is typically at least 150 consecutive nucleotides in length, preferably at least 300 consecutive nucleotides in length, more preferably at least 400 consecutive nucleotides in length and most preferably at least 500 consecutive nucleotides in length. Preferably, the portion is a portion of a nucleic acid as represented by any one of SEQ ID NO: 212, SEQ ID NO: 214, SEQ ID NO: 216, SEQ ID NO: 218, SEQ ID NO: 220, SEQ ID NO: 222, SEQ ID NO: 224, SEQ ID NO: 226, SEQ ID NO: 228, SEQ ID NO: 296, SEQ ID NO: 298, and SEQ ID NO: 300. Most preferably the portion is a portion of a nucleic acid as represented by SEQ ID NO: 212.

Another nucleic acid variant useful in the methods of the invention, is a nucleic acid capable of hybridising under reduced stringency conditions, preferably under stringent conditions, with a nucleic acid encoding a bHLH transcription factor as defined herein, or a with a portion as defined herein.

Hybridising sequences useful in the methods of the invention, encode a polypeptide having a bHLH domain (as described above) and having substantially the same biological activity as the bHLH transcription factor represented by any of SEQ ID NO 213, SEQ ID NO 215, SEQ ID NO: 217, SEQ ID NO: 219, SEQ ID NO 225, SEQ ID NO: 297, SEQ ID NO: 299, SEQ ID NO: 301 or having substantially the same biological activity as orthologues or paralogues of any of the aforementioned SEQ ID NOs. The hybridising sequence is typically at least 150 consecutive nucleotides in length, preferably at least 300 consecutive nucleotides in length, more preferably at least 400 consecutive nucleotides in length and most preferably at least 500 consecutive nucleotides in length. Preferably, the hybridising sequence is one that is capable of hybridising to any of the nucleic acids represented by SEQ ID NO: 212, SEQ ID NO: 214, SEQ ID NO: 216, SEQ ID NO: 218, SEQ ID NO: 220, SEQ ID NO: 222, SEQ ID NO: 224, SEQ ID NO: 226, SEQ ID NO: 228, SEQ ID NO: 296, SEQ ID NO: 298, and SEQ ID NO: 300 or to a portion of any of the aforementioned sequences, a portion being as defined above. Most preferably the hybridising sequence is capable of hybridising to a nucleic acid as represented by SEQ ID NO: 212, or to portions thereof.

According to the present invention, there is provided a method for enhancing yield-related traits in plants, comprising introducing and expressing in a plant a nucleic acid capable of hybridizing to a nucleic acid encoding a bHLH transcription factor represented by any of SEQ ID NO 213, SEQ ID NO 215, SEQ ID NO: 217, SEQ ID NO: 219, SEQ ID NO 225, SEQ ID NO: 297, SEQ ID NO: 299, SEQ ID NO: 301, or comprising introducing and expressing in a plant a nucleic acid capable of hybridising to a nucleic acid encoding an orthologue, paralogue or homologue of any of the aforementioned SEQ ID NOs.

Another nucleic acid variant useful in the methods of the invention is a splice variant encoding a bHLH transcription factor as defined hereinabove.

According to the present invention, there is provided a method for enhancing yield-related traits in plants, comprising introducing and expressing in a plant a splice variant of a nucleic acid encoding a bHLH transcription factor represented by any of SEQ ID NO 213, SEQ ID NO 215, SEQ ID NO: 217, SEQ ID NO: 219, SEQ ID NO 225, SEQ ID NO: 297, SEQ ID NO: 299, and SEQ ID NO: 301, or a splice variant of a nucleic acid encoding an orthologue, paralogue or homologue of any of the aforementioned SEQ ID NOs.

Preferred splice variants are splice variants of a nucleic acid encoding bHLH transcription factor represented by any of SEQ ID NO 213, SEQ ID NO 215, SEQ ID NO: 217, SEQ ID NO: 219, SEQ ID NO 225, SEQ ID NO: 297, SEQ ID NO: 299, and SEQ ID NO: 301, or splice variants encoding orthologues or paralogues of any of the aforementioned SEQ ID NOs. Further preferred are splice variants of nucleic acids represented by any one of SEQ ID NO: 212, SEQ ID NO: 214, SEQ ID NO: 216, SEQ ID NO: 218, SEQ ID NO: 220, SEQ ID NO: 222, SEQ ID NO: 224, SEQ ID NO: 226, SEQ ID NO: 228, SEQ ID NO: 296, SEQ ID NO: 298, and SEQ ID NO: 300. Most preferred is a splice variant of a nucleic acid as represented by SEQ ID NO: 212.

Another nucleic acid variant useful in performing the methods of the invention is an allelic variant of a nucleic acid encoding a bHLH transcription factor as defined hereinabove.

According to the present invention, there is provided a method for enhancing yield-related traits in plants, comprising introducing and expressing in a plant an allelic variant of a nucleic acid encoding a bHLH transcription factor represented by any of SEQ ID NO 213, SEQ ID NO 215, SEQ ID NO: 217, SEQ ID NO: 219, SEQ ID NO 225, SEQ ID NO: 297, SEQ ID NO: 299, and SEQ ID NO: 301, or comprising introducing and expressing in a plant an allelic variant of a nucleic acid encoding an orthologue, paralogue or homologue of any of the aforementioned SEQ ID NOs.

The allelic variant may be an allelic variant of a nucleic acid encoding a bHLH transcription factor represented by any of SEQ ID NO 213, SEQ ID NO 215, SEQ ID NO: 217, SEQ ID NO: 219, SEQ ID NO 225, SEQ ID NO: 297, SEQ ID NO: 299, and SEQ ID NO: 301, or an allelic variants of a nucleic acid encoding orthologues or paralogues of any of the aforementioned SEQ ID NOs. Further preferred are allelic variants of nucleic acids represented by any one of SEQ ID NO: 212, SEQ ID NO: 214, SEQ ID NO: 216, SEQ ID NO: 218, SEQ ID NO: 220, SEQ ID NO: 222, SEQ ID NO: 224, SEQ ID NO: 226 and SEQ ID NO: 228, SEQ ID NO: 296, SEQ ID NO: 298, SEQ ID NO: 300. Most preferred is an allelic variant of a nucleic acid as represented by SEQ ID NO: 212.

A further nucleic acid variant useful in the methods of the invention is a nucleic acid variant obtained by gene shuffling. Gene shuffling or directed evolution may also be used to generate variants of nucleic acids encoding bHLH transcription factors as defined above.

According to the present invention, there is provided a method for enhancing yield-related traits in plants, comprising introducing and expressing in a plant a variant of a nucleic acid encoding a bHLH transcription factor represented by any of SEQ ID NO 213, SEQ ID NO 215, SEQ ID NO: 217, SEQ ID NO: 219, SEQ ID NO 225, SEQ ID NO: 297, SEQ ID NO: 299, SEQ and ID NO: 301, or comprising introducing and expressing in a variant of a nucleic acid encoding an orthologue, paralogue or homologue of any of the aforementioned SEQ ID NOs, which nucleic acid is obtained by gene shuffling.

Furthermore, nucleic acid variants may also be obtained by site-directed mutagenesis. Several methods are available to achieve site-directed mutagenesis, the most common being PCR based methods (current protocols in molecular biology. Wiley Eds.).

Also useful in the methods of the invention are nucleic acids encoding homologues of any one of the amino acids represented by SEQ ID NO 213, SEQ ID NO 215, SEQ ID NO: 217, SEQ ID NO: 219, SEQ ID NO 225, SEQ ID NO: 297, SEQ ID NO: 299, SEQ ID NO: 301 or orthologues or paralogues of any of the aforementioned SEQ ID NOs.

Also useful in the methods of the invention are nucleic acids encoding derivatives of any one of the amino acids represented by SEQ ID NO 213, SEQ ID NO 215, SEQ ID NO: 217, SEQ ID NO: 219, SEQ ID NO 225, SEQ ID NO: 297, SEQ ID NO: 299, SEQ ID NO: 301 or orthologues or paralogues of any of the aforementioned SEQ ID NOs. Derivatives of SEQ ID NO: 215, SEQ ID NO: 217, SEQ ID NO: 219, SEQ ID NO: 221, SEQ ID NO: 223, SEQ ID NO: 225, SEQ ID NO: 227 and SEQ ID NO: 229, SEQ ID NO: 297, SEQ ID NO: 299, SEQ ID NO: 301 are further examples which may be suitable for use in the methods of the invention Furthermore, bHLH transcription factors (at least in their native form) typically have DNA-binding activity and an activation domain. A person skilled in the art may easily determine the presence of an activation domain and DNA-binding activity using routine tools and techniques.

Nucleic acids encoding bHLH transcription factors may be derived from any natural or artificial source. The nucleic acid may be modified from its native form in composition and/or genomic environment through deliberate human manipulation. Preferably the bHLH transcription factor-encoding nucleic acid is from a plant, further preferably from a monocot, more preferably from the Poaceae family, most preferably the nucleic acid is from *Oryza sativa*.

Any reference herein to a bHLH transcription factor is therefore taken to mean a bHLH transcription factor as defined above. Any nucleic acid encoding such a bHLH transcription factor is suitable for use in performing the methods of the invention.

The present invention also encompasses plants or parts thereof (including plant cells) obtainable by the methods according to the present invention. The plants or parts thereof comprise a nucleic acid transgene encoding a bHLH transcription factor as defined above.

The invention also provides genetic constructs and vectors to facilitate introduction and/or expression of the nucleic acid sequences useful in the methods according to the invention, in a plant.

Therefore, there is provided a gene construct comprising:
(i) Any nucleic acid encoding a bHLH-type transcription factor as defined hereinabove;
(ii) One or more control sequences operably liked to the nucleic acid of (i).

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells. The invention therefore provides use of a gene construct as defined hereinabove in the methods of the invention.

Plants are transformed with a vector comprising the sequence of interest (i.e., a nucleic acid encoding a bHLH-type transcription factor). The skilled artisan is well aware of the genetic elements that must be present on the vector in order to successfully transform, select and propagate host cells containing the sequence of interest. The sequence of interest is operably linked to one or more control sequences (at least to a promoter).

Advantageously, any type of promoter, whether natural or synthetic, may be used to drive expression of the nucleic acid sequence. The promoter may be an inducible promoter, i.e. having induced or increased transcription initiation in response to a developmental, chemical, environmental or physical stimulus. The promoter may be a tissue-specific promoter, i.e. one that is capable of preferentially initiating transcription in certain tissues, such as the leaves, roots, seed tissue etc.

According to one preferred feature of the invention, the nucleic acid encoding a bHLH-type transcription factor is operably linked to a constitutive promoter. A constitutive promoter is transcriptionally active during most but not necessarily all phases of its growth and development and is substantially ubiquitously expressed. The constitutive promoter is preferably a GOS2 promoter, more preferably the constitutive promoter is a rice GOS2 promoter, further preferably the constitutive promoter is represented by a nucleic acid sequence substantially similar to SEQ ID NO: 230 or SEQ ID NO: 233, most preferably the constitutive promoter is as represented by SEQ ID NO: 233.

It should be clear that the applicability of the present invention is not restricted to the bHLH transcription factor-encoding nucleic acid represented by SEQ ID NO: 212, nor is the applicability of the invention restricted to expression of a such a bHLH transcription factor-encoding nucleic acid when driven by a GOS2 promoter. Examples of other constitutive promoters which may also be used perform the methods of the invention are shown in the definitions section.

Optionally, one or more terminator sequences (also a control sequence) may be used in the construct introduced into a plant. Additional regulatory elements may include transcriptional as well as translational enhancers. Those skilled in the art will be aware of terminator and enhancer sequences that may be suitable for use in performing the invention. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1. Other control sequences (besides promoter, enhancer, silencer, intron sequences, 3'UTR and/or 5'UTR regions) may be protein and/or RNA stabilizing elements. The genetic construct may optionally comprise a selectable marker gene.

The invention also provides a method for the production of transgenic plants having enhanced yield-related traits relative to control plants, comprising introduction and expression in a plant of any nucleic acid encoding a bHLH-type transcription factor polypeptide as defined hereinabove.

More specifically, the present invention provides a method for the production of transgenic plants having enhanced yield-related traits, which method comprises:
(i) introducing and expressing a nucleic acid encoding a bHLH-type transcription factor (as defined herein) in a plant cell; and
(ii) cultivating the plant cell under conditions promoting plant growth and development.

The nucleic acid may be introduced directly into a plant cell or into the plant itself (including introduction into a tissue, organ or any other part of a plant). According to a preferred feature of the present invention, the nucleic acid is preferably introduced into a plant by transformation.

Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, or quantitative PCR, all techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid encoding a bHLH transcription factor as defined hereinabove. Preferred host cells according to the invention are plant cells.

The invention also extends to harvestable parts of a plant such as, but not limited to seeds, leaves, fruits, flowers, stems, rhizomes, tubers and bulbs. The invention furthermore relates to products derived, preferably directly derived, from a harvestable part of such a plant, such as dry pellets or powders, oil, fat and fatty acids, starch or proteins.

According to a preferred feature of the invention, the modulated expression is increased expression.

As mentioned above, a preferred method for modulating (preferably, increasing) expression of a nucleic acid encoding a bHLH transcription factor is by introducing and expressing in a plant a nucleic acid encoding a bHLH transcription factor; however the effects of performing the method, i.e. enhancing yield-related traits may also be achieved using other well known techniques. A description of some of these techniques will now follow.

One such technique is T-DNA activation tagging. The resulting transgenic plants show dominant phenotypes due to modified expression of genes close to the introduced promoter. The effects of the invention may also be reproduced using the technique of TILLING (Targeted Induced Local Lesions In Genomes). The effects of the invention may also be reproduced using homologous recombination.

Reference herein to the term enhanced yield-related traits is taken to mean an increase in biomass (weight) of one or more parts of a plant, which may include aboveground (harvestable) parts and/or (harvestable) parts below ground.

In particular, such harvestable parts are seeds, and performance of the methods of the invention results in plants having increased seed yield relative to the seed yield of control plants.

Taking corn as an example, a yield increase may be manifested as one or more of the following: increase in the number of plants established per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

Since the transgenic plants according to the present invention have increased yield, it is likely that these plants exhibit an increased growth rate (during at least part of their life cycle), relative to the growth rate of corresponding wild type plants at a corresponding stage in their life cycle. The increased growth rate may be specific to one or more parts of a plant (including seeds), or may be throughout substantially the whole plant. A plant having an increased growth rate may even exhibit early flowering. The increase in growth rate may take place at one or more stages in the life cycle of a plant or during substantially the whole plant life cycle. Increased growth rate during the early stages in the life cycle of a plant may reflect enhanced vigour (increased seedling vigor at emergence). The increase in growth rate may alter the harvest cycle of a plant allowing plants to be sown later and/or harvested sooner than would otherwise be possible. If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of corn plants followed by, for example, the sowing and optional harvesting of soy bean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi and insects.

In particular, the methods of the present invention may be performed under non-stress conditions or under conditions of mild drought to give plants having increased yield relative to control plants. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signaling pathways and cellular responses, such as the production of stress proteins, up-regulation of anti-oxidants, accumulation of compatible solutes and growth arrest. The term "non-stress" conditions as used herein are those environmental conditions that allow optimal growth of plants. Persons skilled in the art are aware of normal soil conditions and climatic conditions for a given location.

Performance of the methods of the invention gives plants grown under non-stress conditions or under mild drought conditions increased yield relative to control plants grown under comparable conditions. Therefore, according to the present invention, there is provided a method for increasing yield in plants grown under non-stress conditions or under mild drought conditions, which method comprises increasing expression in a plant of a nucleic acid encoding a bHLH transcription factor.

Performance of the methods of the invention gives plants grown under conditions of nutrient deficiency, particularly under conditions of nitrogen deficiency, increased yield relative to control plants grown under comparable conditions. Therefore, according to the present invention, there is provided a method for increasing yield in plants grown under conditions of nutrient deficiency, which method comprises increasing expression in a plant of a nucleic acid encoding a MADS15 polypeptide. Nutrient deficiency may result from a lack or excess of nutrients such as nitrogen, phosphates and other phosphorous-containing compounds, potassium, calcium, cadmium, magnesium, manganese, iron and boron, amongst others.

According to a preferred feature of the present invention, performance of the methods of the invention gives plants having an increased growth rate relative to control plants, particularly during the early stages of plant development (typically three weeks post germination in the case of rice and maize, but this will vary from species to species) leading to early vigour. Therefore, according to the present invention, there is provided a method for increasing the growth rate of plants, which method comprises modulating, preferably increasing, expression in a plant of a nucleic acid encoding a bHLH transcription factor. The present invention therefore also provides a method for obtaining plants having early vigour relative to control plants, which method comprises modulating, preferably increasing, expression in a plant of a nucleic acid encoding a bHLH transcription factor.

Early vigour may also result from or be manifested as increased plant fitness relative to control plants due to, for example, the plants being better adapted to their environment (i.e. being more able to cope with various abiotic or biotic stress factors). Plants having early vigour also show better establishment of the crop (with the crop growing in uniform manner, i.e. with the majority of plants reaching the various stages of development at substantially the same time), and show better growth and often better yield. Early vigour may be determined by measuring various factors, such as seedling growth rate, thousand kernel weight, percentage germination, percentage emergence, seedling height, root length and shoot biomass and many more.

The methods of the invention are advantageously applicable to any plant.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs. According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, triticale, sorghum and oats. Plants in which early vigour is a particularly desirably trait include rice, maize, wheat, sunflower, sorghum.

The present invention also encompasses use of nucleic acids encoding bHLH transcription factors and use of bHLH transcription factor polypeptides in enhancing yield-related traits.

Nucleic acids encoding bHLH transcription factor polypeptides, or bHLH transcription factors themselves, may find use in breeding programmes in which a DNA marker is identified which may be genetically linked to a bHLH transcription factor-encoding gene. The nucleic acids/genes, or the bHLH transcription factors themselves may be used to define a molecular marker. This DNA or protein marker may then be used in breeding programmes to select plants having increased yield as defined hereinabove in the methods of the invention.

Allelic variants of a bHLH transcription factor-encoding acid/gene may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give increased yield. Selection is typically carried out by monitoring growth performance of plants containing different allelic variants of the sequence in question. Growth performance may be monitored in a greenhouse or in the field. Further optional steps include crossing plants in which the superior allelic variant was identified with another plant. This could be used, for example, to make a combination of interesting phenotypic features.

A nucleic acid encoding a bHLH transcription factor may also be used as probes for genetically and physically mapping the genes that they are a part of, and as markers for traits linked to those genes. Such information may be useful in plant breeding in order to develop lines with desired phenotypes. Such use of bHLH transcription factor encoding nucleic acids requires only a nucleic acid sequence of at least 15 nucleotides in length. The bHLH transcription factor encoding nucleic acids may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the bHLH transcription factor encoding nucleic acids. The resulting banding patterns may then be subjected to genetic analyses using computer programs such as MapMaker (Lander et al. (1987) Genomics 1: 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the bHLH transcription factor encoding nucleic acid in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridisation (FISH) mapping (Trask (1991) Trends Genet. 7:149-154). Although current methods of FISH mapping favor use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acids. Examples include allele-specific amplification (Kazazian (1989) J. Lab. Clin. Med. 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having enhanced yield-related traits, as described hereinbefore. These traits may also be combined with other economically advantageous traits, such as further yield-enhancing traits, tolerance to other abiotic and biotic stresses, traits modifying various architectural features and/or biochemical and/or physiological features.

Detailed Description of SPL15

Surprisingly, it has now been found that increasing expression in a plant of a nucleic acid encoding an SPL15 transcription factor polypeptide gives plants having enhanced yield related traits, particularly increased yield, relative to control plants. Therefore, the invention provides a method for enhancing yield related traits in particular for increasing yield in plants relative to control plants, comprising increasing expression in a plant of a nucleic acid encoding an SPL15 transcription factor polypeptide.

A preferred method for increasing expression of a nucleic acid encoding a SPL15 transcription factor polypeptide is by introducing and expressing in a plant a nucleic acid encoding a SPL15 transcription factor polypeptide.

The term "SPL15 transcription factor polypeptide" as defined herein refers to a polypeptide comprising from N-terminal to C-terminal: (i) Motif 1 as represented by SEQ ID NO: 276; and (ii) in increasing order of preference at least 65%, 70%, 75%, 80%, 85%, 90%, 95% or 98% sequence identity to the SPL DBD represented by SEQ ID NO: 277; and (iii) Motif 2 as represented by SEQ ID NO: 278.

The most conserved amino acids within Motif 1 are XLXF-GXXXYFX, and within Motif 2 DSXXALSLLSX (where X is a specified subset of amino acids differing for each position, as presented in SEQ ID NO: 276 and SEQ ID NO: 277). Within Motif 1 and Motif 2, are allowed one or more conservative change at any position, and/or one, two or three non-conservative change(s) at any position.

Additionally, the SPL15 transcription factor polypeptide may comprise any one or both of the following: (a) a G/S rich stretch preceding the SPL DBD; and (b) the W(S/T)L tripeptide at the C-terminal end of the polypeptide.

An example of an SPL15 transcription polypeptide as defined hereinabove comprising from N-terminal to C-terminal: (i) Motif 1 as represented by SEQ ID NO: 276; and (ii) in increasing order of preference at least 65%, 70%, 75%, 80%, 85%, 90%, 95% or 98% sequence identity to the SPL DBD represented by SEQ ID NO: 277; and (iii) Motif 2 as represented by SEQ ID NO: 278; and additionally comprising: (a) a G/S rich stretch preceding the SPL DBD; and (b) the W(S/T)L tripeptide at the C-terminal end of the polypeptide, is represented as in SEQ ID NO: 235. Further such examples are represented by any one of SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, SEQ ID NO: 255, SEQ ID NO: 257, SEQ ID NO: 259, SEQ ID NO: 261, SEQ ID NO: 263, SEQ ID NO: 283, SEQ ID NO: 285, SEQ ID NO: 287 or orthologues or paralogues of any of the aforementioned SEQ ID NOs. The invention is illustrated by transforming plants with the *Arabidopsis thaliana* sequence represented by SEQ ID NO: 234, encoding the polypeptide of SEQ ID NO: 235. SEQ ID NO: 237 from *Arabidopsis thaliana* (encoded by SEQ ID NO: 236) is a paralogue of the polypeptide of SEQ ID NO: 235. SEQ ID NO: 239 (encoded by SEQ ID NO: 238, from *Aquilegia formosa x Aquilegia pubescens*), SEQ ID NO: 241 (encoded by SEQ ID NO: 240, from *Gossypium hirsutum*), SEQ ID NO: 243 (encoded by SEQ ID NO: 242, from *Ipomoea nil*), SEQ ID NO: 245 (encoded by SEQ ID NO: 244, from *Lactuca sativa*), SEQ ID NO: 247 (encoded by SEQ ID NO: 246, from *Malus domestica*), SEQ ID NO: 249 (encoded by SEQ ID NO: 248, from *Medicago truncatula*), SEQ ID NO: 251 (encoded by SEQ ID NO: 250, from *Nicotiana bentamiana*), SEQ ID NO: 253 (encoded by SEQ ID NO: 252, from *Oryza sativa*), SEQ ID NO: 255 (encoded by SEQ ID NO: 254, from *Oryza sativa*), SEQ ID NO: 257 (encoded by SEQ ID NO: 256, from *Solanum tuberosum* SEQ ID NO: 259 (encoded by SEQ ID NO: 258, from *Vitis vinifera*), SEQ ID NO: 261 (encoded by SEQ ID NO: 260, from *Zea mays*), SEQ ID NO: 263 (encoded by SEQ ID NO: 262, *Zea mays*), SEQ ID NO: 283 (encoded by SEQ ID NO: 282, *Brassica rapa*), SEQ ID NO: 285 (encoded by SEQ ID NO: 284, *Glycine max*), and SEQ ID NO: 287 (encoded by SEQ ID NO: 286, *Populus tremuloides*) are orthologues of the polypeptide of SEQ ID NO: 235.

Orthologues and paralogues may easily be found by performing a so-called reciprocal blast search. This may be done by a first BLAST involving BLASTing a query sequence (for example, SEQ ID NO: 234 or SEQ ID NO: 235) against any sequence database, such as the publicly available NCBI database. BLASTN or TBLASTX (using standard default values) may be used when starting from a nucleotide sequence and BLASTP or TBLASTN (using standard default values) may be used when starting from a polypeptide sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 234 or SEQ ID NO: 235, the second BLAST would therefore be against *Arabidopsis* sequences). The results of the first and second BLASTs are then compared. A paralogue is identified if a high-ranking hit from the first BLAST is from the same species as from which the query sequence is derived, a BLAST back then ideally results in the query sequence as highest hit (besides itself); an orthologue is identified if a high-ranking hit in the first BLAST is not from the same species as from which the query sequence is derived and preferably results upon BLAST back in the query sequence amongst the highest hits. High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. An example detailing the identification of orthologues and paralogues is given in Example 41. In the case of large families, ClustalW may be used, followed by a neighbour joining tree, to help visualize clustering of related genes and to identify orthologues and paralogues. In FIG. 22, the SPL15 transcription factor polypeptide paralogues and orthologues cluster together.

The polypeptides represented by any one of SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, SEQ ID NO: 255, SEQ ID NO: 257, SEQ ID NO: 259, SEQ ID NO: 261, SEQ ID NO: 263, SEQ ID NO: 283, SEQ ID NO: 285, SEQ ID NO: 287, or orthologues or paralogues of any of the aforementioned SEQ ID NOs, all comprise an SPL DBD having, in increasing order of preference, at least 65%, 70%, 75%, 80%, 85%, 90%, 95% or 98% sequence identity to the SPL15 DBD represented by SEQ ID NO: 277.

SPL DBDs are well known in the art and may readily be identified by persons skilled in the art. A SPL DBD may be identified using methods for the alignment of sequences for comparison. Methods for the alignment of sequences for comparison include GAP, BESTFIT, BLAST, FASTA and TFASTA. GAP uses the algorithm of Needleman and Wunsch ((1970) J Mol Biol 48: 443-453) to find the alignment of two complete sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information. Homologues may readily be identified using, for example, the ClustalW multiple sequence alignment algorithm (version 1.83) available at GenomeNet service at the Kyoto University Bioinformatics Center, with the default pairwise alignment parameters, and a scoring method in percentage. Minor manual editing may be performed to optimise alignment between conserved motifs, as would be apparent to a person skilled in the art. The alignment shown in FIGS. 23 and 24 highlight the SPL DBD in SPL15 transcription factor polypeptides. Preferably, SPL15 transcription factor polypeptides useful in the methods of the invention comprise an SPL DBD having, in increasing order of preference, at least 65%, 70%, 75%, 80%, 85%, 90%, 95% or 98% sequence identity to the SPL DBD represented by SEQ ID NO: 277.

In some instances, default parameters may be adjusted to modify the stringency of the search. For example using BLAST, the statistical significance threshold (called "expect" value) for reporting matches against database sequences may be increased to show less stringent matches. In this way, short nearly exact matches may be identified. Motif 1 as represented by SEQ ID NO: 276 and Motif 2 as represented by SEQ ID NO: 278 both comprised in the SPL15 transcription factor polypeptides useful in the methods of the invention may be identified this way (FIG. 24). Within Motif 1 and Motif 2, are allowed one or more conservative change at any position, and/or one, two or three non-conservative change(s) at any position. The W(S/T)L tripeptide at the C-terminal end of the polypeptide may likewise be identified (FIG. 24).

Special databases also exist for the identification of domains. The SPL DBD in a SPL15 transcription factor polypeptide may be identified using, for example, SMART (Schultz et al. (1998) Proc. Natl. Acad. Sci. USA 95, 5857-5864; Letunic et al. (2002) Nucleic Acids Res 30, 242-244; hosted by the EMBL at Heidelberg, Germany), InterPro (Mulder et al., (2003) Nucl. Acids. Res. 31, 315-318; hosted by the European Bioinformatics Institute (EBI) in the United Kingdom), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAIPress, Menlo Park; Hulo et al., Nucl. Acids. Res. 32: D134-D137, (2004), The ExPASy proteomics server is provided as a service to the scientific community (hosted by the Swiss Institute of Bioinformatics (SIB) in Switzerland) or Pfam (Bateman et al., Nucleic Acids Research 30(1): 276-280 (2002), hosted by the Sanger Institute in the United Kingdom). The SPL DBD in the InterPro database is designated IPR004333, PF03110 in the Pfam database and PS51141 in the PROSITE database.

Furthermore, the presence of G/S rich stretch preceding the SPL DBD may also readily be identified (FIG. 24). Primary amino acid composition (in %) to determine if a polypeptide domain is rich in specific amino acids may be calculated using software programs from the ExPASy server, in particular the ProtParam tool (Gasteiger E et al. (2003) ExPASy: the proteomics server for in-depth protein knowledge and analysis. Nucleic Acids Res 31:3784-3788). The composition of the protein of interest may then be compared to the average amino acid composition (in %) in the Swiss-Prot Protein Sequence data bank. Within this databank, the average Gly (G) and Ser (E) content are both of 6.9% (adding up to 13.8%). As an example, the G/S rich stretch preceding the SPL DBD of SEQ ID NO: 235 contains 14.5% of G and 25.5% of S (adding up to 40%). As defined herein, a G/S rich stretch has a combined G and S content (in % terms) above that found in the average amino acid composition (in % terms) of the proteins in the Swiss-Prot Protein Sequence. Both G and S belong to the category of very small amino acids.

The nucleic acid encoding the polypeptides represented by any one of SEQ ID NO: 235, SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, SEQ ID NO: 255, SEQ ID NO: 257, SEQ ID NO: 259, SEQ ID NO: 261, SEQ ID NO: 263, SEQ ID NO: 283, SEQ ID NO: 285, SEQ ID NO: 287, or orthologues or paralogues of any of the aforementioned SEQ ID NOs, need not be full-length nucleic acids, since performance of the methods of the invention does not rely on the use of full length nucleic acid sequences. Furthermore, examples of nucleic acids suitable for use in performing the methods of the invention include but are not limited to those represented by any one of: SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256, SEQ ID NO: 258, SEQ ID NO: 260, SEQ ID NO: 262, SEQ ID NO: 282, SEQ ID NO: 284 and SEQ ID NO: 286. Nucleic acid variants may also be useful in practising the methods of the invention. Examples of such variants include portions of nucleic acids, splice variants, allelic variants either naturally occurring or obtained by DNA manipulation.

A portion may be prepared, for example, by making one or more deletions to a nucleic acid encoding a SPL15 transcription factor polypeptide as defined hereinabove. The portions may be used in isolated form or they may be fused to other coding (or non coding) sequences in order to, for example, produce a protein that combines several activities. When fused to other coding sequences, the resultant polypeptide produced upon translation may be bigger than that predicted for the SPL15 transcription factor portion. Portions useful in the methods of the invention, encode an SPL15 transcription factor polypeptide (as described above) and having substantially the same biological activity as the SPL15 transcription factor polypeptide represented by any of SEQ ID NO: 235, SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, SEQ ID NO: 255, SEQ ID NO: 257, SEQ ID NO: 259, SEQ ID NO: 261, SEQ ID NO: 263, SEQ ID NO: 283, SEQ ID NO: 285, SEQ ID NO: 287, or orthologues or paralogues of any of the aforementioned SEQ ID NOs. Examples of portions may include the nucleotides encoding Motif 1 as represented by SEQ ID NO: 276, in increasing order of preference at least 65%, 70%, 75%, 80%, 85%, 90%, 95% or 98% sequence identity to the SPL DBD represented by SEQ ID NO: 277, and Motif 2 as represented by SEQ ID NO: 278. Portions may additionally include nucleotides encoding the G/S rich stretch or the W(S/T)L tripeptide (but not necessarily the nucleotides encoding the amino acid sequences between any of these). The portion is typically at least 250 nucleotides in length, preferably at least 500 nucleotides in length, more preferably at least 750 nucleotides in length and most preferably at least 1000 nucleotides in length. Preferably, the portion is a portion of a nucleic acid as represented by any one of SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256, SEQ ID NO: 258, SEQ ID NO: 260, SEQ ID NO: 262, SEQ ID NO: 282, SEQ ID NO: 284 and SEQ ID NO: 286. Most preferably the portion is a portion of a nucleic acid as represented by SEQ ID NO: 234.

Another nucleic acid variant useful in the methods of the invention, is a nucleic acid capable of hybridising under reduced stringency conditions, preferably under stringent conditions, with a nucleic acid encoding a SPL15 transcription factor polypeptide as defined hereinabove, or a with a portion as defined hereinabove.

Hybridising sequences useful in the methods of the invention, encode a polypeptide comprising from N-terminal to C-terminal: (i) Motif 1 as represented by SEQ ID NO: 276; and (ii) in increasing order of preference at least 65%, 70%, 75%, 80%, 85%, 90%, 95% or 98% sequence identity to the SPL DBD represented by SEQ ID NO: 277; and (iii) Motif 2 as represented by SEQ ID NO: 278, and having substantially the same biological activity as the SPL15 transcription factor polypeptides represented by SEQ ID NO: 235, SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, SEQ ID NO: 255, SEQ ID NO: 257, SEQ ID NO: 259, SEQ ID NO: 261, SEQ ID NO: 263, SEQ ID NO: 283, SEQ ID NO: 285, SEQ ID NO: 287, or orthologues or paralogues of any of the aforementioned SEQ ID NOs. The hybridising sequence is typically at least 250 nucleotides in length, preferably at least 500 nucleotides in length, more preferably at least 750 nucleotides in length and most preferably at least 1000 nucleotides in length. Preferably, the hybridising sequence is one that is capable of hybridising to any of the nucleic acids represented by SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256, SEQ ID NO: 258, SEQ ID NO: 260, SEQ ID NO: 262, SEQ ID NO: 282, SEQ ID NO: 284 and SEQ ID NO: 286, or to a portion of any of the aforementioned sequences, a portion being as defined above. Most preferably the hybridising sequence is capable of hybridising to SEQ ID NO: 234, or to portions thereof.

Another nucleic acid variant useful in the methods of the invention is a splice variant encoding a SPL15 transcription factor polypeptide as defined hereinabove.

Preferred splice variants are splice variants of a nucleic acid encoding SPL15 transcription factor polypeptide represented by any of SEQ ID NO: 235, SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, SEQ ID NO: 255, SEQ ID NO: 257, SEQ ID NO: 259, SEQ ID NO: 261, SEQ ID NO: 263, SEQ ID NO: 283, SEQ ID NO: 285, or SEQ ID NO: 287, or splice variants encoding orthologues or paralogues of any of the aforementioned SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256, SEQ ID NO: 258, SEQ ID NO: 260, SEQ ID NO: 262, SEQ ID NO: 282, SEQ ID NO: 284 and SEQ ID NO: 286. Most preferred is a splice variant of a nucleic acid as represented by SEQ ID NO: 234.

Another nucleic acid variant useful in performing the methods of the invention is an allelic variant of a nucleic acid encoding a SPL15 transcription factor polypeptide as defined hereinabove.

The allelic variant may be an allelic variant of a nucleic acid encoding a SPL15 transcription factor polypeptide represented by any of SEQ ID NO: 235, SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, SEQ ID NO: 255, SEQ ID NO: 257, SEQ ID NO: 259, SEQ ID NO: 261, SEQ ID NO: 263, SEQ ID NO: 283, SEQ ID NO: 285, or SEQ ID NO: 287, or an allelic variant of a nucleic acid encoding orthologues or paralogues of any of the aforementioned SEQ ID NOs. Further preferred are allelic variants of nucleic acids represented by any one of SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256, SEQ ID NO: 258, SEQ ID NO: 260, SEQ ID NO: 262, SEQ ID NO: 282, SEQ ID NO: 284 and SEQ ID NO: 286. Most preferred is an allelic variant of a nucleic acid as represented by SEQ ID NO: 234.

A further nucleic acid variant useful in the methods of the invention is a nucleic acid variant obtained by gene shuffling. Gene shuffling or directed evolution may also be used to generate variants of nucleic acids encoding SPL15 transcription factor polypeptides as defined above.

Furthermore, nucleic acid variants may also be obtained by site-directed mutagenesis. Several methods are available to achieve site-directed mutagenesis, the most common being PCR based methods (Current Protocols in Molecular Biology. Wiley (Eds)).

Also useful in the methods of the invention are nucleic acids encoding homologues of any one of the amino acids represented by SEQ ID NO: 235, SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, SEQ ID NO: 255, SEQ ID NO: 257, SEQ ID NO: 259, SEQ ID NO: 261, SEQ ID NO: 263, SEQ ID NO: 283, SEQ ID NO: 285, SEQ ID NO: 287, or orthologues or paralogues of any of the aforementioned SEQ ID NOs.

Also useful in the methods of the invention are nucleic acids encoding derivatives of any one of the amino acids represented by SEQ ID NO: 235, SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, SEQ ID NO: 255, SEQ ID NO: 257, SEQ ID NO: 259, SEQ ID NO: 261 SEQ ID NO: 263, SEQ ID NO: 283, SEQ ID NO: 285, SEQ ID NO: 287, or orthologues or paralogues of any of the aforementioned SEQ ID NOs. "Derivatives" include peptides, oligopeptides, polypeptides which may, compared to the amino acid sequence of the naturally-occurring form of the protein, such as the one presented in SEQ ID NO: 235, comprise substitutions of amino acids with non-naturally occurring amino acid residues, or additions of non-naturally occurring amino acid residues.

Furthermore, SPL15 transcription factor polypeptides (at least in their native form) typically have DNA-binding activity and an activation domain. A person skilled in the art may easily determine the presence of an activation domain and DNA-binding activity using routine tools and techniques.

Nucleic acids encoding SPL15 transcription factor polypeptides may be derived from any natural or artificial source. The nucleic acid may be modified from its native form in composition and/or genomic environment through deliberate human manipulation. Preferably the SPL15 transcription factor polypeptide-encoding nucleic acid is from a plant, further preferably from a dicot, more preferably from the Brassicacea family, most preferably the nucleic acid is from *Arabidopsis thaliana*.

Any reference herein to a SPL15 transcription factor polypeptide is therefore taken to mean a SPL15 transcription factor peptide as defined above. Any nucleic acid encoding such a SPL15 transcription factor polypeptide is suitable for use in performing the methods of the invention.

The invention also provides genetic constructs and vectors to facilitate introduction and/or expression of the nucleic acid sequences useful in the methods according to the invention, in a plant.

Therefore, there is provided a gene construct comprising:
(i) A nucleic acid encoding a SPL15 transcription factor polypeptide as defined hereinabove;

(ii) One or more control sequences operably liked to the nucleic acid of (i).

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells. The invention therefore provides use of a gene construct as defined hereinabove in the methods of the invention.

Plants are transformed with a vector comprising the sequence of interest (i.e., a nucleic acid encoding a SPL15 transcription factor polypeptide). The skilled artisan is well aware of the genetic elements that must be present on the vector in order to successfully transform, select and propagate host cells containing the sequence of interest. The sequence of interest is operably linked to one or more control sequences (at least to a promoter).

Advantageously, any type of promoter, whether natural or synthetic, may be used to drive expression of the nucleic acid sequence. The promoter may be an inducible promoter, i.e. having induced or increased transcription initiation in response to a developmental, chemical, environmental or physical stimulus. The promoter may be a tissue-specific promoter, i.e. one that is capable of preferentially initiating transcription in certain tissues, such as the leaves, roots, seed tissue etc.

According to the invention, the nucleic acid encoding a SPL15 transcription factor polypeptide is operably linked to a constitutive promoter. The constitutive promoter is preferably a HMGB (high mobility group B) promoter, more preferably the constitutive promoter is a rice HMGB promoter, further preferably the constitutive promoter is represented by a nucleic acid sequence substantially similar to SEQ ID NO: 279, most preferably the constitutive promoter is as represented by SEQ ID NO: 279 or SEQ ID NO: 294.

It should be clear that the applicability of the present invention is not restricted to the nucleic acid encoding an SPL15 transcription factor polypeptide as represented by SEQ ID NO: 234, nor is the applicability of the invention restricted to expression of a such nucleic acid encoding an SPL15 transcription factor polypeptide when driven by a HMGB promoter. Examples of other constitutive promoters which may also be used perform the methods of the invention are shown in the definitions section.

Additional regulatory elements for increasing expression of nucleic acids or genes, or gene products, may include transcriptional as well as translational enhancers. Those skilled in the art will be aware of terminator and enhancer sequences that may be suitable for use in performing the invention. Other control sequences (besides promoter, enhancer, silencer, intron sequences, 3'UTR and/or 5'UTR regions) may be protein and/or RNA stabilizing elements. Such sequences would be known or may readily be obtained by a person skilled in the art. Optionally, one or more terminator sequences (also a control sequence) may be used in the construct introduced into a plant.

An intron sequence may also be added to the 5' untranslated region (UTR) or the coding sequence of the partial coding sequence to increase the amount of the mature message that accumulates in the cytosol.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

The genetic construct may optionally comprise a selectable marker gene.

The invention also provides a method for the production of transgenic plants having increased yield relative to control plants, comprising introduction and expression in a plant of a nucleic acid encoding a SPL15 transcription factor polypeptide as defined hereinabove.

More specifically, the present invention provides a method for the production of transgenic plants having increased yield relative to control plants, which method comprises:
  (i) introducing and expressing a nucleic acid encoding a SPL15 transcription factor polypeptide in a plant cell; and
  (ii) cultivating the plant cell under conditions promoting plant growth and development.

The nucleic acid may be introduced directly into a plant cell or into the plant itself (including introduction into a tissue, organ or any other part of a plant). According to a preferred feature of the present invention, the nucleic acid is preferably introduced into a plant by transformation. Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, or quantitative PCR, all techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid encoding a SPL15 transcription factor polypeptide as defined hereinabove. Preferred host cells according to the invention are plant cells.

The invention also extends to harvestable parts of a plant such as, but not limited to seeds, leaves, fruits, flowers, stems, rhizomes, tubers and bulbs. The invention furthermore relates to products derived, preferably directly derived, from a harvestable part of such a plant, such as dry pellets or powders, oil, fat and fatty acids, starch or proteins.

As mentioned above, a preferred method for increasing expression of a nucleic acid encoding a SPL15 transcription factor polypeptide is by introducing and expressing in a plant a nucleic acid encoding a SPL15 transcription factor polypeptide; however the effects of performing the method, i.e. increasing yield, may also be achieved using other well known techniques. A description of some of these techniques will now follow.

One such technique is T-DNA activation tagging. The resulting transgenic plants show dominant phenotypes due to modified expression of genes close to the introduced promoter.

The effects of the invention may also be reproduced using the technique of TILLING (Targeted Induced Local Lesions In Genomes).

The effects of the invention may also be reproduced using homologous recombination.

"Increased yield" as defined herein is taken to mean an increase in biomass (weight) of one or more parts of a plant, which may include aboveground (harvestable) parts and/or (harvestable) parts below ground.

In particular, such harvestable parts include vegetative biomass and/or seeds, and performance of the methods of the invention results in plants having increased yield (in vegetative biomass and/or seed) relative to the yield of control plants.

Taking corn as an example, a yield increase may be manifested as one or more of the following: increase in the number of plants per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

Since the transgenic plants according to the present invention have increased yield, it is likely that these plants exhibit an increased growth rate (during at least part of their life cycle), relative to the growth rate of corresponding wild type plants at a corresponding stage in their life cycle. The increased growth rate may be specific to one or more parts of a plant (including seeds), or may be throughout substantially the whole plant. A plant having an increased growth rate may even exhibit early flowering. The increase in growth rate may alter the harvest cycle of a plant allowing plants to be sown later and/or harvested sooner than would otherwise be possible. If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of corn plants followed by, for example, the sowing and optional harvesting of soy bean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

According to a preferred feature of the present invention, performance of the methods of the invention gives plants having an increased growth rate relative to control plants. Therefore, according to the present invention, there is provided a method for increasing the growth rate of plants, which method comprises increasing expression in a plant of a nucleic acid encoding a SPL15 transcription factor polypeptide An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi and insects.

In particular, the methods of the present invention may be performed under non-stress conditions or under conditions of mild drought to give plants having increased yield relative to control plants. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signaling pathways and cellular responses, such as the production of stress proteins, up-regulation of anti-oxidants, accumulation of compatible solutes and growth arrest. The term "non-stress" conditions as used herein are those environmental conditions that allow optimal growth of plants. Persons skilled in the art are aware of normal soil conditions and climatic conditions for a given location.

Performance of the methods of the invention gives plants grown under non-stress conditions or under mild drought conditions increased yield relative to control plants grown under comparable conditions. Therefore, according to the present invention, there is provided a method for increasing yield in plants grown under non-stress conditions or under mild drought conditions, which method comprises increasing expression in a plant of a nucleic acid encoding a MADS15 polypeptide.

Performance of the methods of the invention gives plants grown under conditions of nutrient deficiency, particularly under conditions of nitrogen deficiency, increased yield relative to control plants grown under comparable conditions. Therefore, according to the present invention, there is provided a method for increasing yield in plants grown under conditions of nutrient deficiency, which method comprises increasing expression in a plant of a nucleic acid encoding a MADS15 polypeptide. Nutrient deficiency may result from a lack or excess of nutrients such as nitrogen, phosphates and other phosphorous-containing compounds, potassium, calcium, cadmium, magnesium, manganese, iron and boron, amongst others.

The methods of the invention are advantageously applicable to any plant.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs. According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, triticale, sorghum and oats.

The present invention also encompasses plants obtainable by the methods according to the present invention. The present invention therefore provides plants, parts and cells from such plants obtainable by the methods according to the present invention, which plants or parts or cells comprise a nucleic acid transgene encoding a SPL15 transcription factor polypeptide as defined above.

The present invention also encompasses use of nucleic acids encoding SPL15 transcription factor polypeptides in increasing yield in a plant compared to yield in a control plant.

One such use relates to increasing yield of plants, yield being defined as defined herein above. Yield may in particular include one or more of the following: increased aboveground biomass, increased number of flowers per panicle, increased seed yield, increased total number of seeds, increased number of filled seeds, increased thousand kernel weight (TKW) and increased harvest index.

Nucleic acids encoding SPL15 transcription factor polypeptides may find use in breeding programmes in which a DNA marker is identified which may be genetically linked to a gene encoding SPL15 transcription factor polypeptide. Nucleic acids encoding SPL15 transcription factor polypeptides may be used to define a molecular marker. This marker may then be used in breeding programmes to select plants having increased seed yield. The nucleic acids encoding SPL15 transcription factor polypeptides may be, for example, a nucleic acid as represented by any one of SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256, SEQ ID NO: 258, SEQ ID NO: 260, SEQ ID NO: 262, SEQ ID NO: 282, SEQ ID NO: 284 and SEQ ID NO: 286.

Allelic variants of a nucleic acid encoding an SPL15 transcription factor polypeptide may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give increased seed yield. Selection is typically carried out by monitoring growth performance of plants containing different allelic variants of the sequence in question, for example, different allelic variants of any one of SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256, SEQ ID NO: 258, SEQ ID NO: 260, SEQ ID NO: 262, SEQ ID NO: 282, SEQ ID NO: 284 and SEQ ID NO: 286. Growth performance may be monitored in a greenhouse or in the field. Further optional steps include crossing plants, in which the superior allelic variant was identified, with another plant. This could be used, for example, to make a combination of interesting phenotypic features.

Nucleic acids encoding SPL15 transcription factor polypeptides may also be used as probes for genetically and physically mapping the genes that they are a part of, and as markers for traits linked to those genes. Such information may be useful in plant breeding in order to develop lines with desired phenotypes. Such use of nucleic acids encoding SPL15 transcription factor polypeptides requires only a nucleic acid sequence of at least 15 nucleotides in length. The nucleic acids encoding SPL15 transcription factor polypeptides may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with a nucleic acid encoding SPL15 transcription factor polypeptide. The resulting banding patterns may then be subjected to genetic analyses using computer programs such as MapMaker (Lander et al. (1987) Genomics 1: 174-181) in order to construct a genetic map. In addition, the nucleic acid may be used to probe Southern blots containing restriction endonuclease-treated genomic DNAs of a set of individuals representing parent and progeny of a defined genetic cross. Segregation of the DNA polymorphisms is noted and used to calculate the position of the nucleic acid encoding SPL15 transcription factor polypeptide in the genetic map previously obtained using this population (Botstein et al. (1980) Am. J. Hum. Genet. 32: 314-331).

The production and use of plant gene-derived probes for use in genetic mapping is described in Bernatzky and Tanksley (GENETICS 112 (4): 887-898, 1986). Numerous publications describe genetic mapping of specific cDNA clones using the methodology outlined above or variations thereof.

For example, F2 intercross populations, backcross populations, randomly mated populations, near isogenic lines (NIL), and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridization (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acids. Examples include allele-specific amplification (Kazazian (1989) J. Lab. Clin. Med. 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having increased yield, as described hereinbefore. These traits may also be combined with other economically advantageous traits, such as further yield-increasing traits, tolerance to other abiotic and biotic stresses, traits modifying various architectural features and/or biochemical and/or physiological features.

DESCRIPTION OF FIGURES

The present invention will now be described with reference to the following figures in which:

FIG. 3 shows a multiple alignment of a number of HAL3 sequences from Arabidopsis thaliana AtHAL3b (At_NP_973994), Sorghum bicolor (Sb), Arabidopsis thaliana AtHAL3a (Ath0218), Gossipium hirsutum (Cg), Hordeum vulgare (Hy), Oryza sativa (Os), Vitis vinifera (Vv), Glycine max (Gm), Solanum tuberosum (St), Zea mays (Zm), and Pinus sp (Pg).

FIG. 4 details examples of sequences useful in performing the methods according to the present invention: SEQ ID NO: 1 and SEQ ID NO: 2 represent the nucleic acid sequence and the protein sequence of AtHAl3a. SEQ ID NO: 3 and SEQ ID NO: 4 are the sequences of the forward and reverse primers used to isolate the AtHAL3 gene. SEQ ID NO: 5 is the sequence of the beta expansin promoter used in the methods of the present invention. SEQ ID NO: 9 to SEQ ID NO: 42 represent examples of full length or partial DNA/protein sequences, useful in the methods of the invention or for isolating corresponding full length sequences. In some cases, sequences were assembled from EST sequences, with lesser quality sequencing. As a consequence, a few nucleic acid substitutions may be expected.

FIG. 6 shows a multiple alignment of various MADS15 proteins. The asterisks indicate identical amino acids, the colons represent highly conservative substitutions, the dots represent less conserved substitutions.

FIG. 8 details examples of sequences useful in performing the methods according to the present invention.

FIG. 11 details examples of sequences useful in performing the methods according to the present invention, or useful in isolating such sequences. Sequences may result from public EST assemblies, with lesser quality sequencing. As a consequence, a few nucleic acid substitutions may be expected. The start (ATG) and stop codons delimit the nucleic acid sequences when these encode full-length MADS15 polypeptides. However both 5' and 3' UTR may also be used for the performing the methods of the invention.

Figure 14:
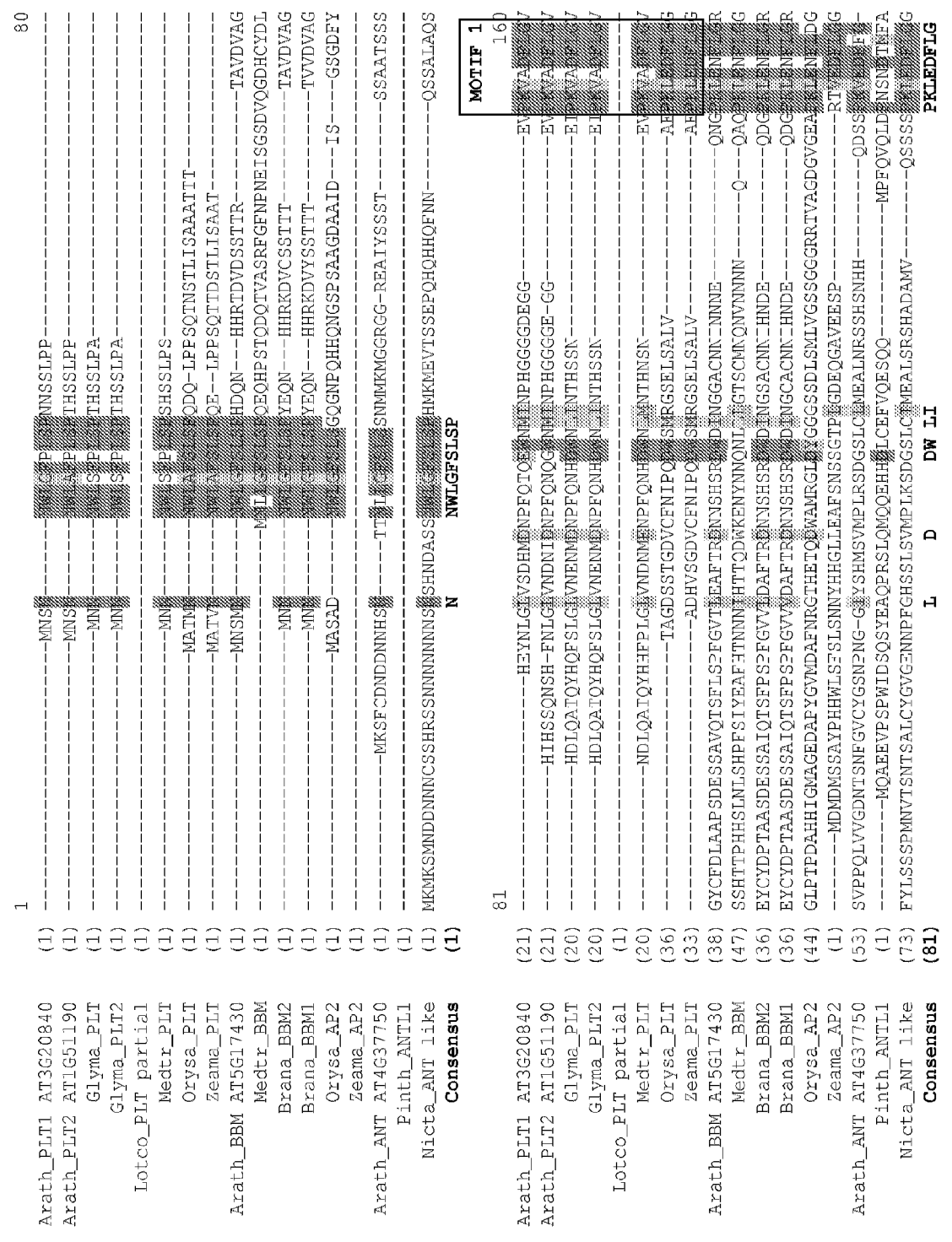
Figure 14:
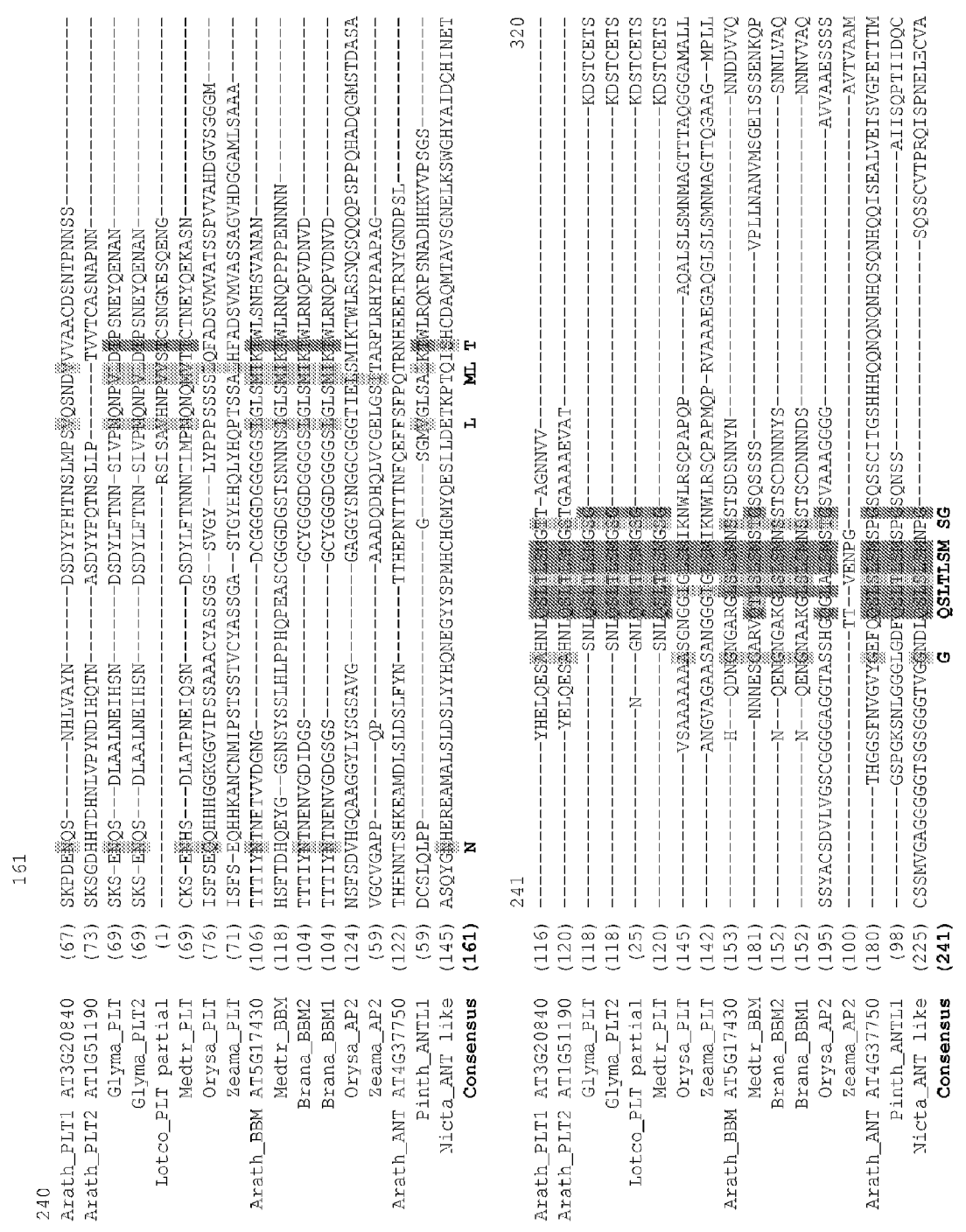
Figure 14:
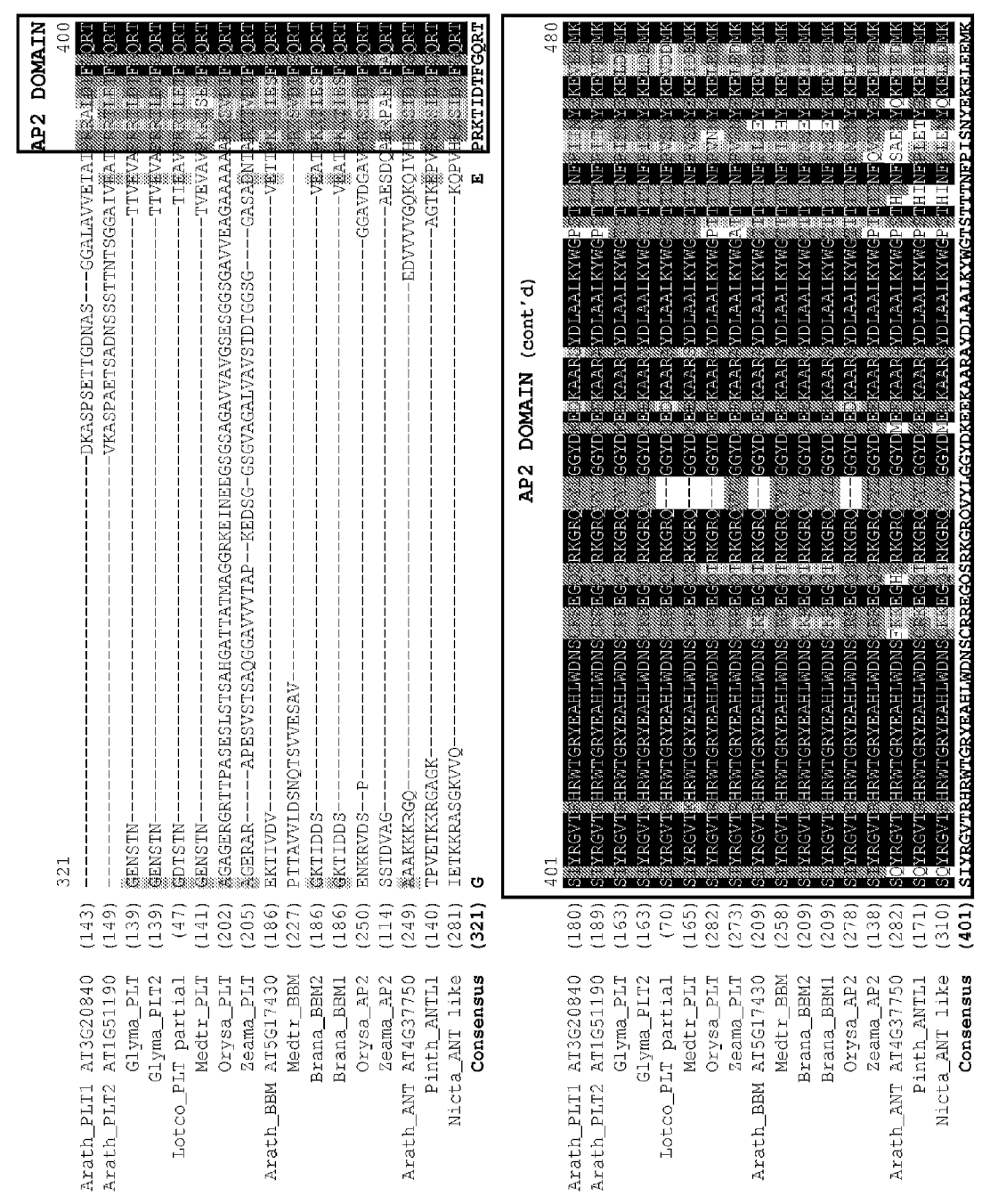
Figure 14:
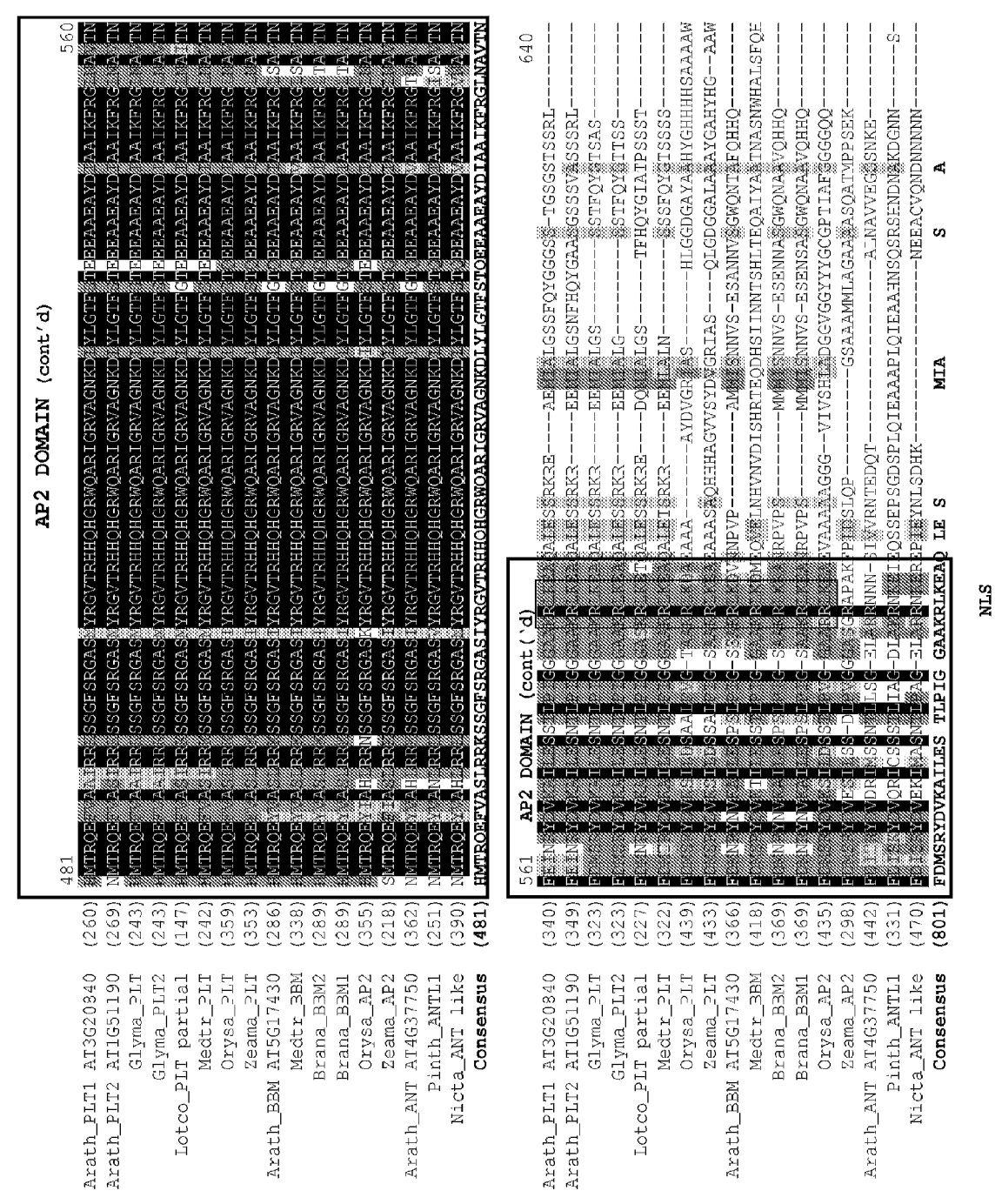
Figure 14:
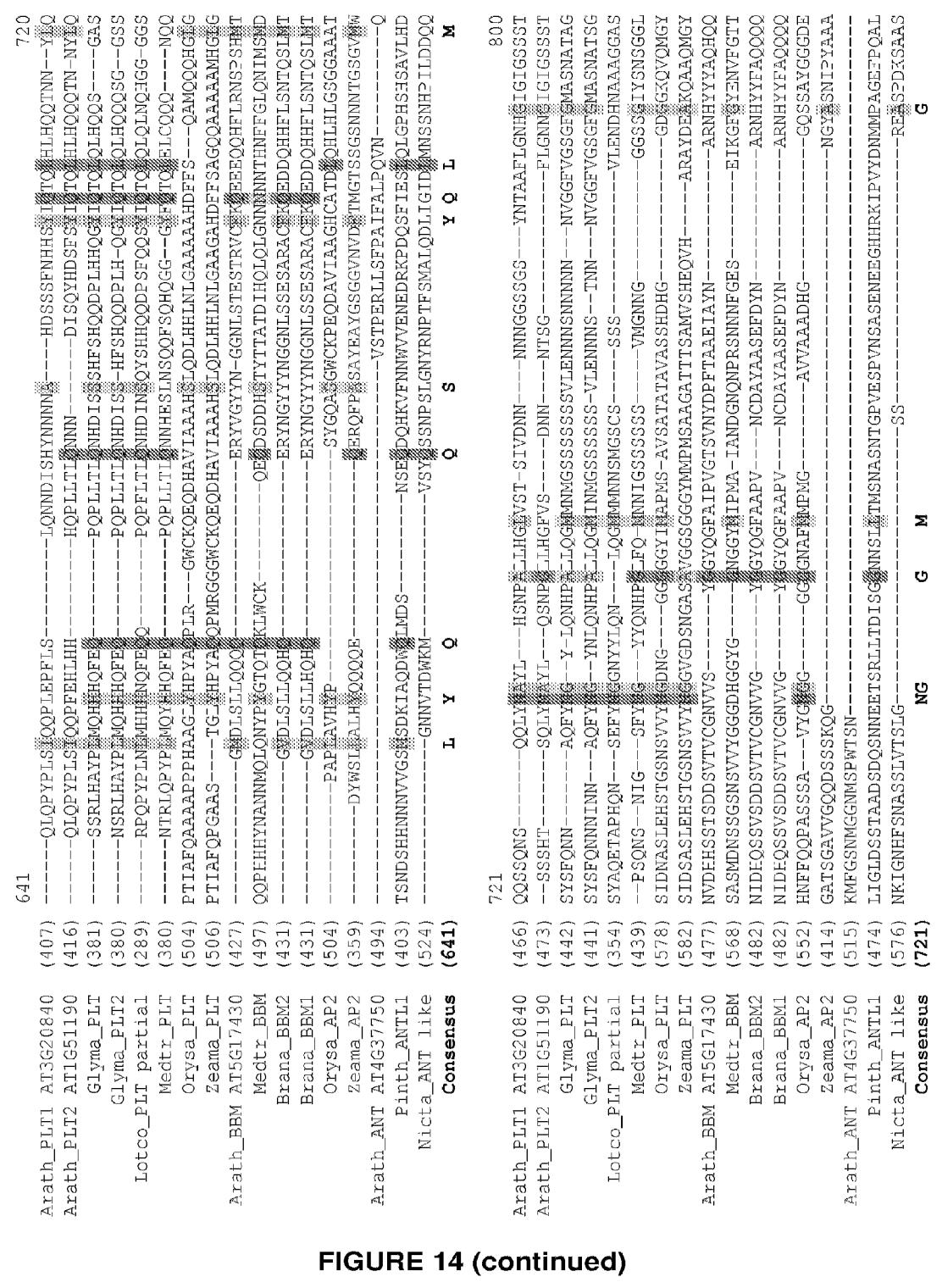
Figure 14:
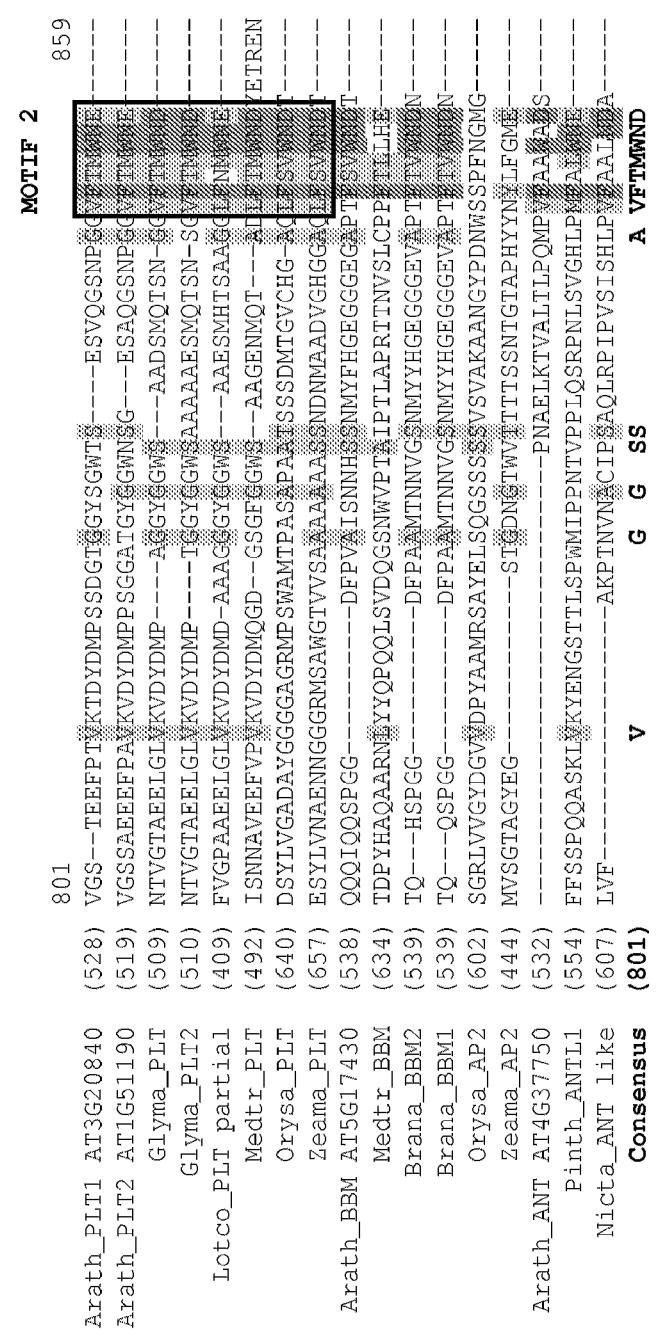

FIG. 14 is an alignment of PLT transcription factor polypeptide sequences (from Table 4), compared to other AP2 domain transcription factor polypeptides (from Table 4 below). The nuclear localisation signal (NLS), motif 1 PK(V/

L)(A/E)DFLG and motif 2 (V/L)FX(M/V)WN(D/E) are boxed. Identical residues are blackened, conservative residues are grayed.

TABLE 4

AP2 domain transcription factor polypeptides aligned against the PLT transcription factor polypeptides used to perform the methods of the invention.

| Name | NCBI accession number | Source |
|---|---|---|
| Arath_ANT | NM_119937 | Arabidopsis thaliana |
| Arath_BBM | NM_121749.1 | Arabidopsis thaliana |
| Brana_BBM1 | AF317904 | Brassica napus |
| Brana_BBM2 | AF317905 | Brassica napus |
| Medtr_AP2 BBM | AY899909 | Medicago truncatula |
| Nicta_ANT like | AY461432 | Nicotiana tabacum |
| Orysa_AP2 | XM_473084 | Oryza sativa |
| Pinth_ANTL1 | AB101585 | Pinus thunbergii |
| Zeama_AP2 | AY109146.1 | Zea mays |

Figure 15:
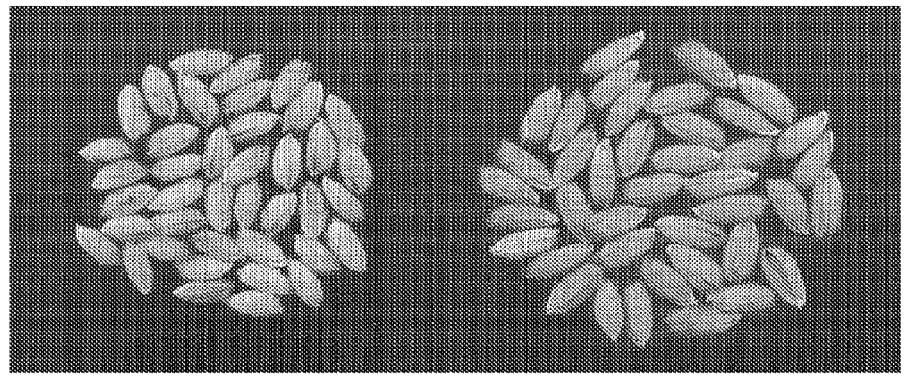

FIG. 15 is a photograph of 40 seeds from a control plant (left) compared to 40 seeds from a transgenic plant with increased expression of a PLT transcription factor polypeptide.

Figure 16:
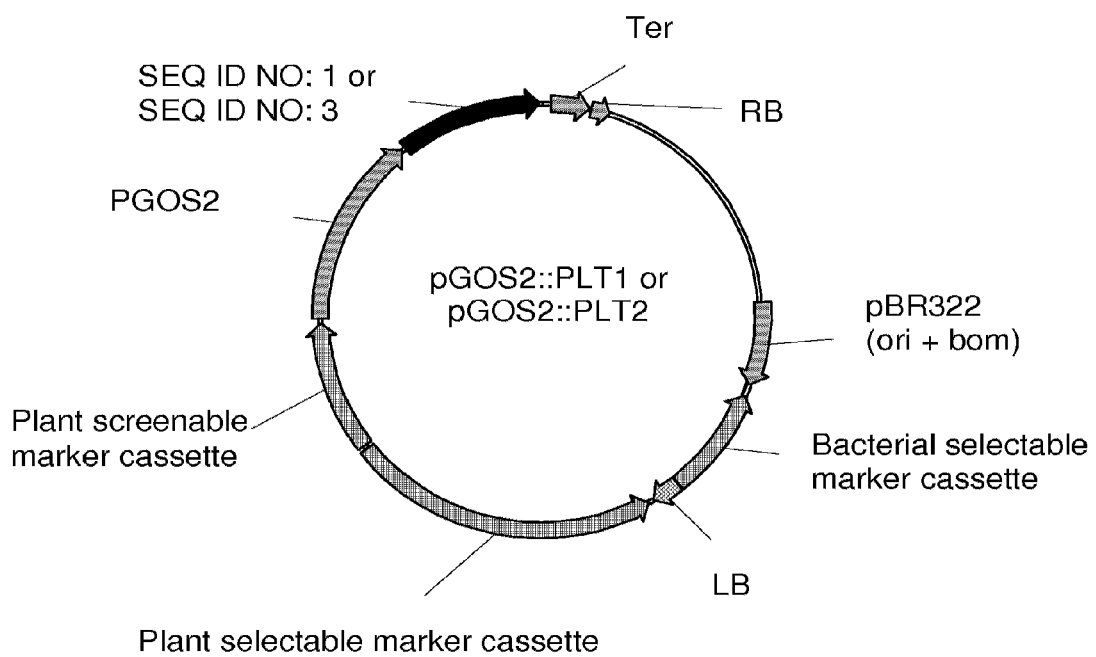

FIG. 16 shows a binary vector pGOS2::PLT, for increased expression in *Oryza sativa* of an *Oryza sativa* PLT transcription factor nucleic acid under the control of a GOS2 promoter.

FIG. 17 details examples of sequences useful in performing the methods according to the present invention (SEQ ID NO: 175 to SEQ ID NO: 188). Partial sequences (SEQ ID NO: 189 and SEQ ID NO: 190) useful in isolating corresponding full length sequences are also presented.

Figure 18:
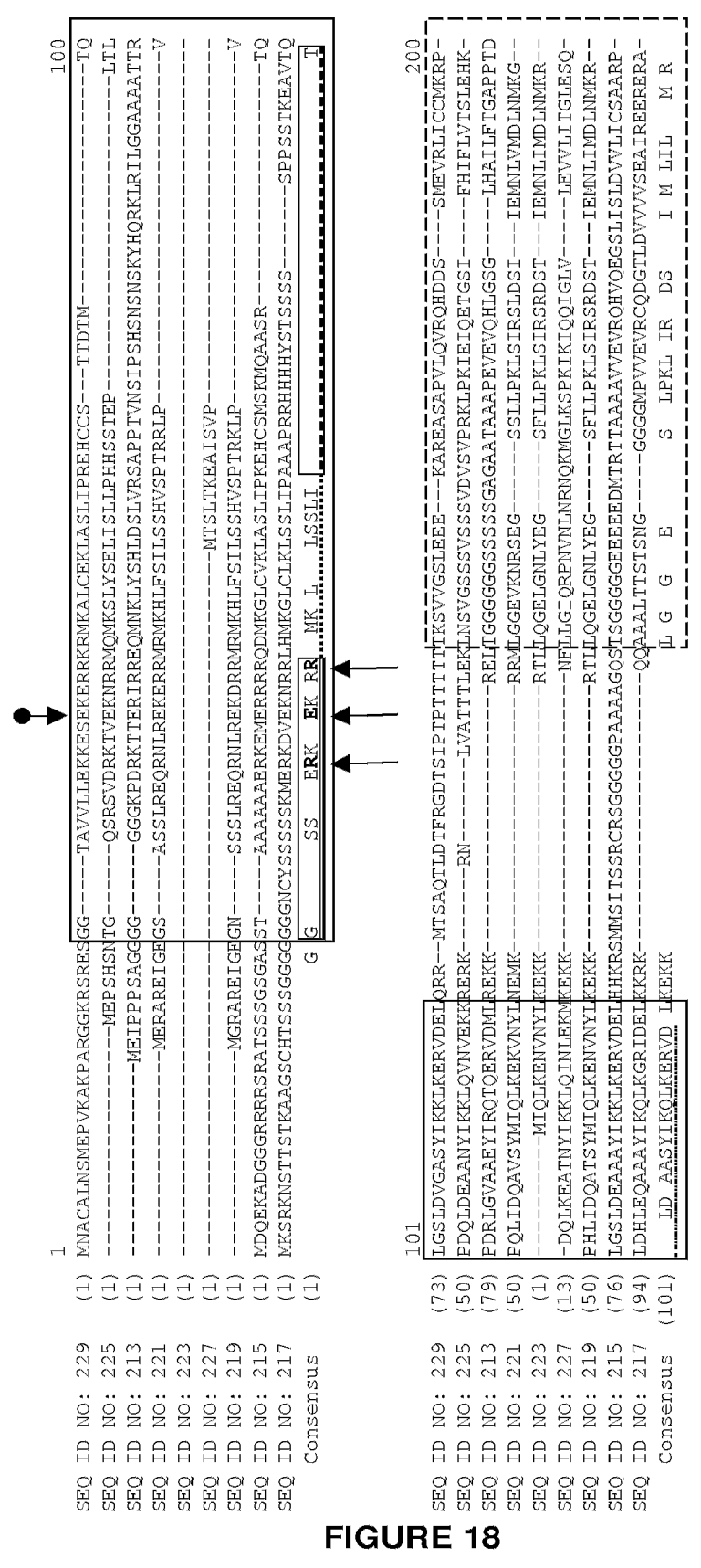

FIG. 18 shows an alignment of bHLH transcription factors as defined hereinabove. The sequences were aligned using AlignX program from Vector NTI suite (InforMax, Bethesda, Md.). Multiple alignment was done with a gap opening penalty of 10 and a gap extension of 0.01. Minor manual editing was also carried out where necessary to better position some conserved regions. The bHLH domain is indicated within the solid box and the PFB26111 domain is indicated within the dashed box. Also indicated by the three upwardly pointing arrows is the 5-9-13 configuration (K/R ER). The single downwardly pointing arrow indicates the glutamic acid reside for recognition of the E-BOX.

FIG. 19 shows a matrix of similarity and identity between bHLH transcription factors from various species. Percentage identity is shown in bold. FIG. 19a is a matrix over full length sequences and FIG. 19b is a matrix over the bHLH domain only. More details are provided in Example 34.

Figure 20:
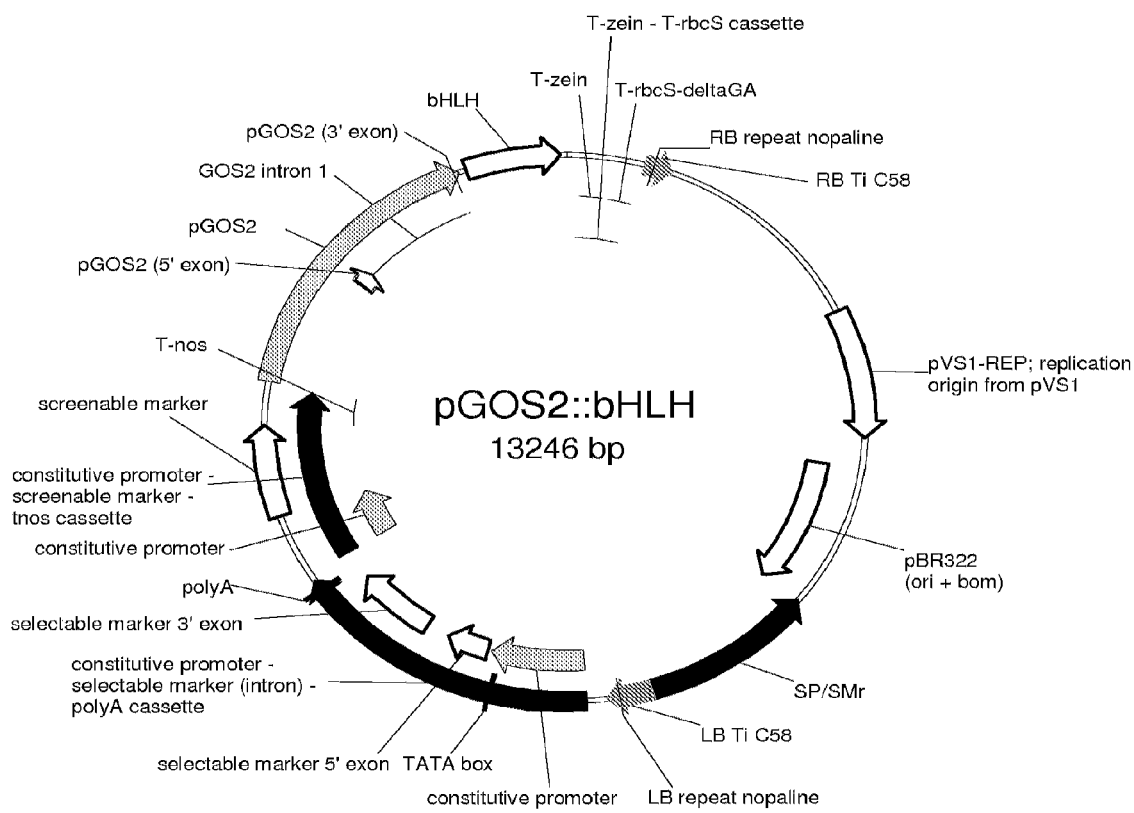

FIG. 20 shows a binary vector pGOS2::bHLH, for increased expression in *Oryza sativa* of an *Oryza sativa* bHLH transcription factor-encoding nucleic acid under the control of a GOS2 promoter.

FIG. 21 details examples of sequences useful in performing the methods according to the present invention.

Figure 22:
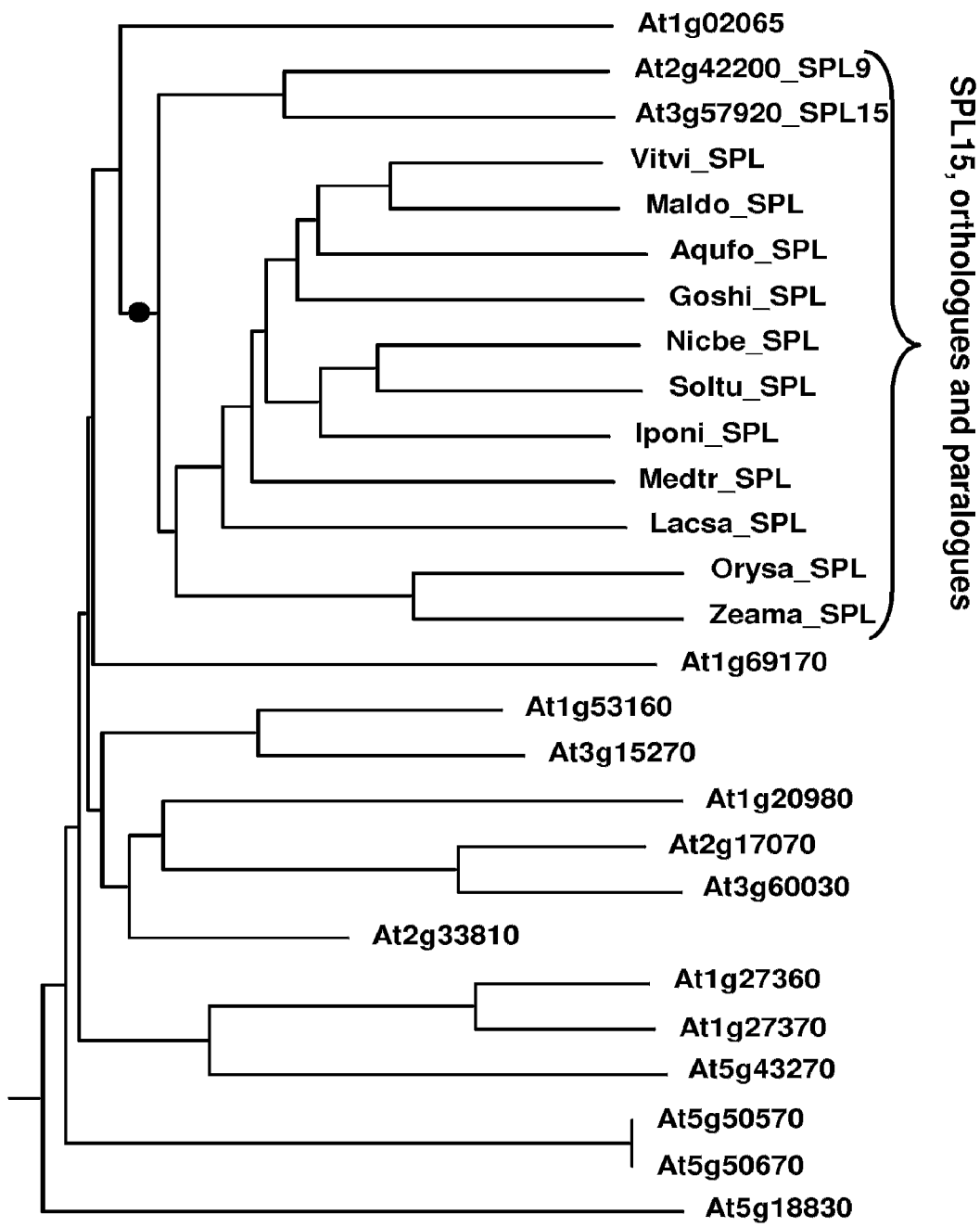

FIG. 22 Neighbour-joining tree output after a multiple sequence alignment of all *Arabidopsis thaliana* SPL transcription factor polypeptides and of SPL15 transcription factor polypeptide orthologues using CLUSTAL W (1.83) (at GenomeNet service at the Kyoto University Bioinformatics Center), and default values (Blosum 62 as weight matrix, gap open penalty of 10; gap extension penalty of 0.05). *Arabidopsis thaliana* SPL15 transcription factor polypeptide clusters with the other SPL15 transcription factor polypeptide orthologues and paralogues, as shown by the curly bracket.

Figure 23:
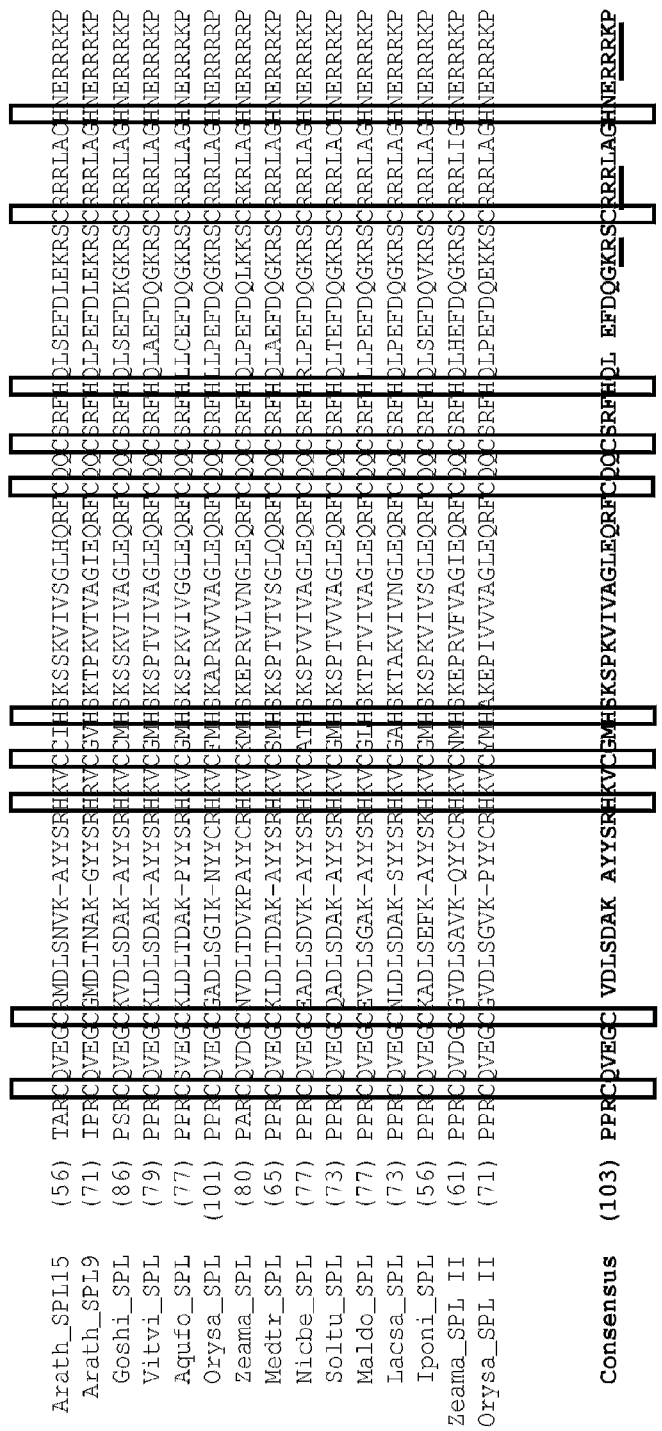

FIG. 23 shows an alignment of the DNA-binding domain (DBD) of SPL15 transcription factor polypeptide orthologues and paralogs. The sequences were aligned using AlignX program from Vector NTI suite (InforMax, Bethesda, Md.). Multiple alignment was done with a gap opening penalty of 10 and a gap extension of 0.01. The conserved Cys and His residues involved in zinc ion binding are boxed. The bipartite nuclear localization signal (NLS) is underlined.

Figures 24, 25:
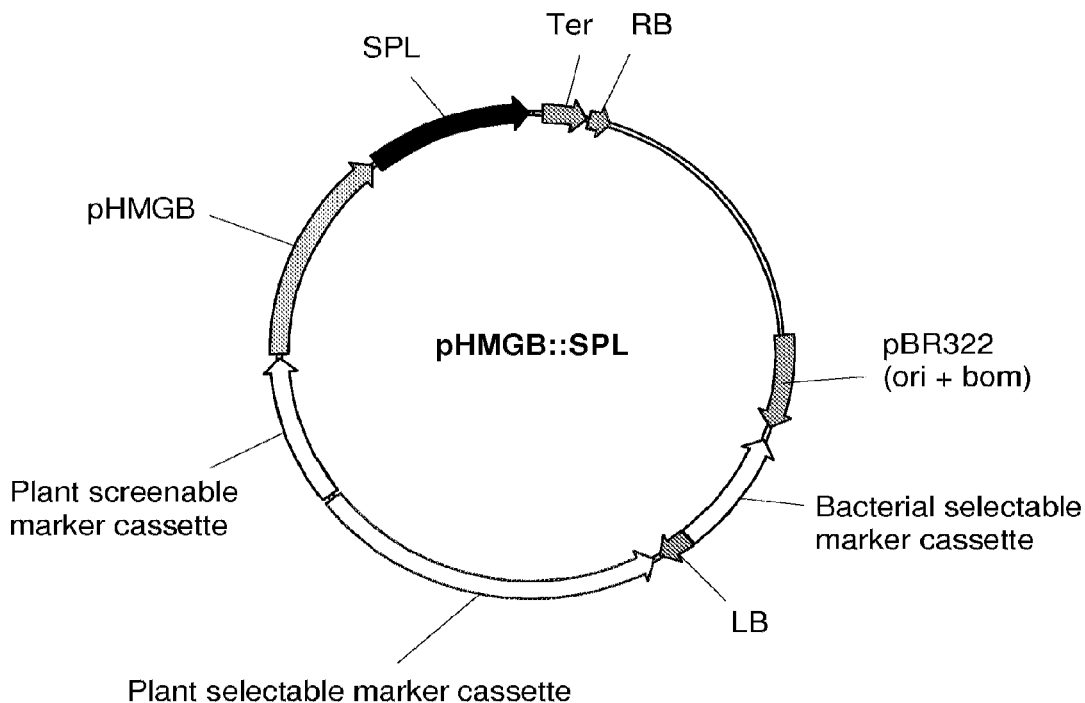

FIG. 24 is an alignment of SPL15 transcription factor polypeptide orthologues and paralogues. The sequences were aligned using AlignX program from Vector NTI suite (InforMax, Bethesda, Md.). Multiple alignment was done with a gap opening penalty of 10 and a gap extension of 0.01. Minor manual editing was also carried out where necessary to better position some conserved regions. The three main characterized domains, from N-terminal to C-terminal, are boxed and identified as Motif 1, the SPL DNA binding domain and Motif 2. Additionally, the G/S rich stretch preceding the SPL DBD is marked with Xs and the W(S/T)L tripeptide at the C-terminal end of the polypeptide also boxed.

FIG. 25 shows a binary vector pHMGB::SPL15, for increased expression in *Oryza sativa* of an *Arabidopsis thaliana* nucleic acid encoding an SPL15 transcription factor polypeptide under the control of an HMGB promoter.

FIG. 26 details examples of sequences useful in performing the methods according to the present invention.

EXAMPLES

The present invention will now be described with reference to the following examples, which are by way of illustration alone. The following examples are not intended to completely define or otherwise limit the scope of the invention.

DNA manipulation: unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

Example Section A

HAL3

Example 1

Identification of Sequences Related to the Nucleic Acid Sequence Used in the Methods of the Invention Sequences (full length cDNA, ESTs or genomic) related to the nucleic acid sequence used in the methods of the present invention were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid or polypeptide sequences to sequence databases and by calculating the statistical significance of matches. For example, the polypeptide encoded by the nucleic acid of the present invention was used for the TBLASTN algorithm, with default settings and the filter to ignore low complexity sequences set off. The output of the analysis was viewed by pairwise comparison, and ranked according to the probability score (E-value), where the score reflect the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search. For example the E-value may be increased to show less stringent matches. This way, short nearly exact matches may be identified.

Table A provides a list of nucleic acid sequences related to the nucleic acid sequence used in the methods of the present invention.

TABLE A

Examples of HAL3 polypeptides:

| Plant Source | Nucleic acid SEQ ID NO: | Protein SEQ ID NO: |
| --- | --- | --- |
| Arabidopsis thaliana | 9 | 10 |
| Oryza sativa | 11 | 12 |
| Triticum aestivum | 13 | 14 |
| Zea mays | 15 | 16 |
| Picea abies | 17 | 18 |
| Brassica napus | 19 | 20 |
| Brassica oleracea | 21 | 22 |
| Nicotiana tabacum | 23 | 24 |
| Solanum tuberosum | 25 | 26 |
| Glycine max | 27 | 28 |
| Vitis vinifera | 29 | 30 |
| Hordeum vulgare | 31 | 32 |
| Gossypium hirsutum | 33 | 34 |
| Sorghum bicolor | 35 | 36 |
| Lycopersicon esculentum | 37 | 38 |
| Arabidopsis thaliana | 39 | 40 |
| Pinus sp. | 41 | 42 |

In some instances, related sequences have tentatively been assembled and publicly disclosed by research institutions, such as The Institute for Genomic Research (TIGR). The Eukaryotic Gene Orthologs (EGO) database may be used to identify such related sequences, either by keyword search or by using the BLAST algorithm with the nucleic acid or polypeptide sequence of interest.

Example 2

Cloning of the Nucleic Acid Sequence Used in the Methods of the Invention

The nucleic acid sequence used in the methods of the invention was amplified by PCR using as template a custom-made *Arabidopsis thaliana* seedlings cDNA library (in pCMV Sport 6.0; Invitrogen, Paisley, UK). PCR was performed using Hifi Taq DNA polymerase in standard conditions, using 200 ng of template in a 50 µl PCR mix. The primers used were prm00957

(SEQ ID NO: 3; sense, start codon in bold:
5' aaaaagcaggctcacaatggagaatgggaaagagac 3')
and prm00958 (SEQ ID NO: 4; reverse,
complementary,:
5' agaaagctgggttggttttaactagttccaccg 3'), which include the AttB sites for Gateway recombination. The amplified PCR fragment was purified also using standard methods. The first step of the Gateway procedure, the BP reaction, was then performed, during which the PCR fragment recombines in vivo with the pDONR201 plasmid to produce, according to the Gateway terminology, an "entry clone", pHAL3. Plasmid pDONR201 was purchased from Invitrogen, as part of the Gateway® technology.

Example 3

Expression Vector Construction

The entry clone pHAL3 was subsequently used in an LR reaction with pEXP, a destination vector used for *Oryza sativa* transformation. This vector contains as functional elements within the T-DNA borders: a plant selectable marker; a screenable marker expression cassette; and a Gateway cassette intended for LR in vivo recombination with the nucleic acid sequence of interest already cloned in the entry clone. A rice beta expansin promoter (SEQ ID NO: 5) for shoot-specific expression was located upstream of this Gateway cassette.

Figures 1, 2:
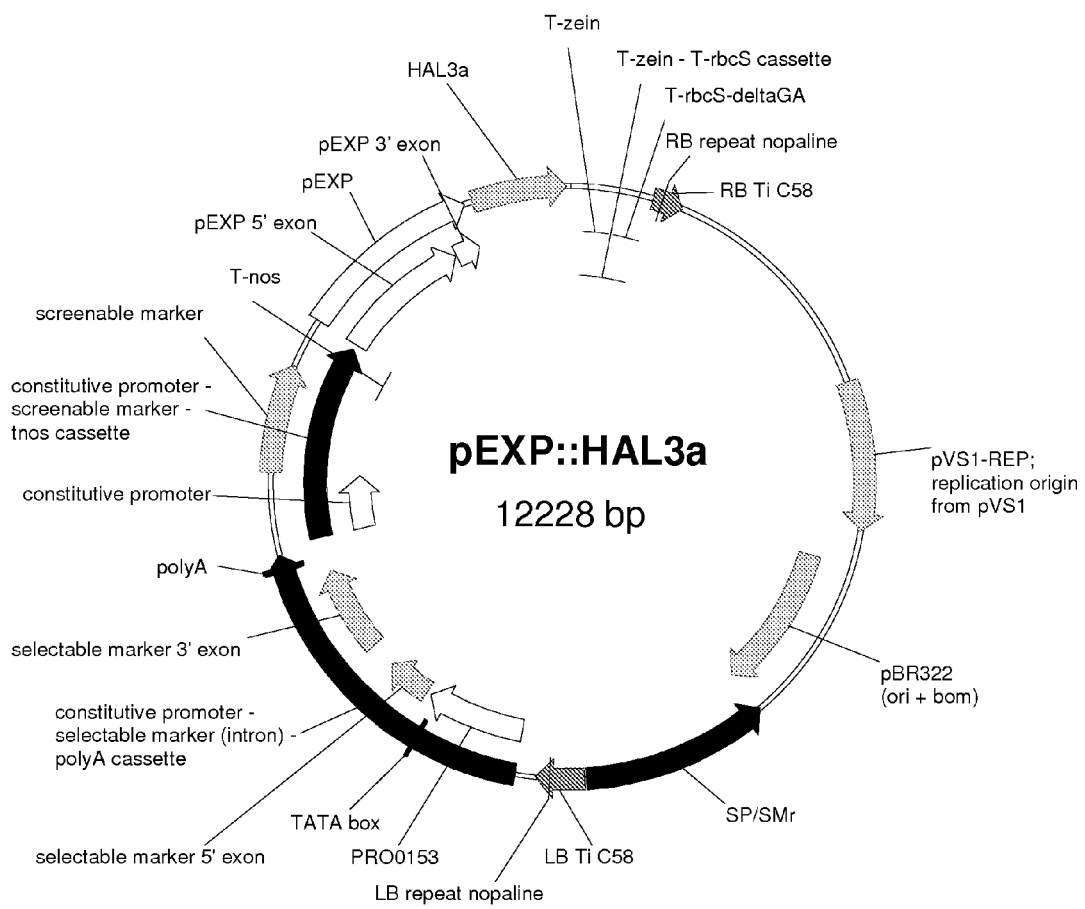
FIG. 1 represents the schematic structure of the AtHAL3a polypeptide comprising from N-terminus to C-terminus (i) the substrate binding helix (single underlined), (ii) the insertion His motif (double underlined), (iii) the PXMNXXMW motif (dotted) and (iv) the substrate recognition clamp (wave underlined). The N-terminal and C-terminal ends of the HAL3 proteins are not very conserved.
FIG. 2 shows a binary vector pEXP::HAL3, for increased expression in Oryza sativa of an Arabidopsis thaliana HAL3 nucleic acid under the control of a beta expansin promoter.
Figure 5:
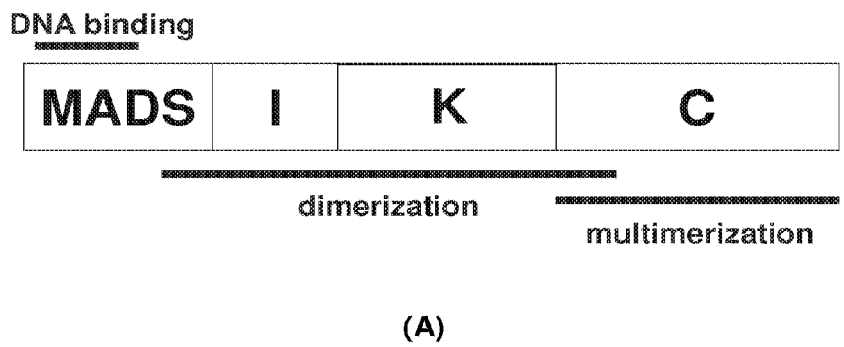
FIG. 5 (A) shows the domain structure of the MADS15 protein, (B) represents the sequence of SEQ ID NO: 44 with the MADS domain in bold and the keratin domain in italics. Between the MADS domain and the keratin, the intervening domain is located while the C-domain is located C-terminally of the keratin domain.

After the LR recombination step, the resulting expression vector pEXP::HAL3 (FIG. 2) was transformed into *Agrobacterium* strain LBA4044 and subsequently to *Oryza sativa* plants.

Example 4

Crop Transformation

The transformed *Agrobacterium* containing the expression vectors were used independently to transform *Oryza sativa* plants. Mature dry seeds of the rice japonica cultivar Nipponbare were dehusked. Sterilization was carried out by incubating for one minute in 70% ethanol, followed by 30 minutes in 0.2% $HgCl_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

*Agrobacterium* strain LBA4404 containing the expression vector was used for co-cultivation. *Agrobacterium* was inoculated on AB medium with the appropriate antibiotics and cultured for 3 days at 28° C. The bacteria were then collected and suspended in liquid co-cultivation medium to a density ($OD_{600}$) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges 1996, Chan et al. 1993, Hiei et al. 1994).

Corn Transformation

Transformation of maize (*Zea mays*) is performed with a modification of the method described by Ishida et al. (1996) Nature Biotech 14(6): 745-50. Transformation is genotype-dependent in corn and only specific genotypes are amenable to transformation and regeneration. The inbred line A188 (University of Minnesota) or hybrids with A188 as a parent are good sources of donor material for transformation, but other genotypes can be used successfully as well. Ears are harvested from corn plant approximately 11 days after pollination (DAP) when the length of the immature embryo is about 1 to 1.2 mm. Immature embryos are cocultivated with *Agrobacterium tumefaciens* containing the expression vector, and transgenic plants are recovered through organogenesis. Excised embryos are grown on callus induction medium, then maize regeneration medium, containing the selection agent (for example imidazolinone but various selection markers can be used). The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Wheat Transformation

Transformation of wheat is performed with the method described by Ishida et al. (1996) Nature Biotech 14(6): 745-50. The cultivar Bobwhite (available from CIMMYT, Mexico) is commonly used in transformation. Immature embryos are co-cultivated with *Agrobacterium tumefaciens* containing the expression vector, and transgenic plants are recovered through organogenesis. After incubation with *Agrobacterium*, the embryos are grown in vitro on callus induction medium, then regeneration medium, containing the selection agent (for example imidazolinone but various selection markers can be used). The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Soybean Transformation

Soybean is transformed according to a modification of the method described in the Texas A&M U.S. Pat. No. 5,164,310. Several commercial soybean varieties are amenable to transformation by this method. The cultivar Jack (available from the Illinois Seed foundation) is commonly used for transformation. Soybean seeds are sterilised for in vitro sowing. The hypocotyl, the radicle and one cotyledon are excised from seven-day old young seedlings. The epicotyl and the remaining cotyledon are further grown to develop axillary nodes. These axillary nodes are excised and incubated with *Agrobacterium tumefaciens* containing the expression vector. After the cocultivation treatment, the explants are washed and transferred to selection media. Regenerated shoots are excised and placed on a shoot elongation medium. Shoots no longer than 1 cm are placed on rooting medium until roots develop. The rooted shoots are transplanted to soil in the greenhouse. T1 seeds are produced from plants that exhibit tolerance to the selection agent and that contain a single copy of the T-DNA insert.

Rapeseed/Canola Transformation

Cotyledonary petioles and hypocotyls of 5-6 day old young seedling are used as explants for tissue culture and transformed according to Babic et al. (1998, Plant Cell Rep 17: 183-188). The commercial cultivar Westar (Agriculture Canada) is the standard variety used for transformation, but other varieties can also be used. Canola seeds are surface-sterilized for in vitro sowing. The cotyledon petiole explants with the cotyledon attached are excised from the in vitro seedlings, and inoculated with *Agrobacterium* (containing the expression vector) by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with *Agrobacterium*, the petiole explants are transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MS0) for root induction. The rooted shoots are transplanted to soil in the greenhouse. T1 seeds are produced from plants that exhibit tolerance to the selection agent and that contain a single copy of the T-DNA insert.

Alfalfa Transformation

A regenerating clone of alfalfa (*Medicago sativa*) is transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown D C W and A Atanassov (1985. Plant Cell Tissue Organ Culture 4: 111-112). Alternatively, the RA3 variety (University of Wisconsin) has been selected for use in tissue culture (Walker et al., 1978 Am J Bot 65:654-659). Petiole explants are cocultivated with an overnight culture of *Agrobacterium tumefaciens* C58C1 pMP90 (McKersie et al., 1999 Plant Physiol 119: 839-847) or LBA4404 containing the expression vector. The explants are cocultivated for 3 d in the dark on SH induction medium containing 288 mg/L Pro, 53 mg/L thioproline, 4.35 g/L $K_2SO_4$, and 100 μm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings were transplanted into pots and grown in a greenhouse. T1 seeds are produced from plants that exhibit tolerance to the selection agent and that contain a single copy of the T-DNA insert.

Example 5

Evaluation Procedure 5.1 Evaluation Setup

Approximately 30 independent T0 rice transformants were generated. The primary transformants were transferred from a tissue culture chamber to a greenhouse for growing and harvest of T1 seed. Seven events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions. Greenhouse conditions were of shorts days (12 hours light), 28° C. in the light and 22° C. in the dark, and a relative humidity of 70%.

Four T1 events were further evaluated in the T2 generation following the same evaluation procedure as for the T1 generation but with more individuals per event. From the stage of sowing until the stage of maturity the plants were passed several times through a digital imaging cabinet. At each time point digital images (2048×1536 pixels, 16 million colours) were taken of each plant from at least 6 different angles.

5.2 Statistical Analysis: t Test and F Test

A two factor ANOVA (analysis of variants) was used as a statistical model for the overall evaluation of plant phenotypic characteristics. An F test was carried out on all the parameters measured of all the plants of all the events transformed with the gene of the present invention. The F test was carried out to check for an effect of the gene over all the transformation events and to verify for an overall effect of the gene, also known as a global gene effect. The threshold for significance for a true global gene effect was set at a 5% probability level for the F test. A significant F test value points to a gene effect, meaning that it is not only the mere presence or position of the gene that is causing the differences in phenotype.

To check for an effect of the genes within an event, i.e., for a line-specific effect, a t-test was performed within each event using data sets from the transgenic plants and the corresponding null plants. "Null plants" or "null segregants" or "nullizygotes" are the plants treated in the same way as the transgenic plant, but from which the transgene has segregated. Null plants can also be described as the homozygous negative transformed plants. The threshold for significance for the t-test is set at 10% probability level. The results for some events can be above or below this threshold. This is based on the hypothesis that a gene might only have an effect in certain positions in the genome, and that the occurrence of this position-dependent effect is not uncommon. This kind of gene effect is also named herein a "line effect of the gene". The p-value is obtained by comparing the t-value to the t-distribution or alternatively, by comparing the F-value to the F-distribution. The p-value then gives the probability that the null hypothesis (i.e., that there is no effect of the transgene) is correct.

Example 6

Evaluation Results

The mature primary panicles were harvested, counted, bagged, barcode-labeled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed yield (total seed weight) was measured by weighing all filled husks harvested from a plant. Total seed number per plant was measured by counting the number of husks harvested from a plant. The harvest index (HI) in the present invention is defined as the ratio between the total seed yield and the above ground area ($mm^2$), multiplied by a factor $10^6$. The total number of flowers per panicle as defined in the present invention is the ratio between the total number of seeds and the number of mature primary panicles. The seed fill rate as defined in the present invention is the proportion (expressed as a %) of the number of filled seeds over the total number of seeds (or florets).

As presented in Table B, the seed yield, number of filled seeds and harvest index are increased in the transgenic plants preferentially expressing a nucleic acid encoding a HAL3 polypeptide in the shoot, compared to control plants.

Table B shows the average yield increase (total seed weight), increase in number of filled seeds and increase of harvest index in percent, calculated from the transgenic events compared to control plants, in the T1 generation

TABLE B

| parameters | % increase | p-value |
|---|---|---|
| Total seed weight | 14 | 0.0072 |
| Number of filled seeds | 15 | 0.0052 |
| Harvest Index | 10 | 0.0093 |

Example 7

Early Vigour Evaluation Results

Early vigour was determined by counting the total number of pixels from aboveground plant parts discriminated from the background. This value was averaged for the pictures taken on the same time point from different angles and was converted to a physical surface value expressed in square mm by calibration. The results described below are for plants three weeks post-germination.

Plant early vigour (as determined by aboveground area) was seen in six out of seven events of the T1 generation, with an overall increase in aboveground area for transgenic seedlings of 27% compared to control plants. Four of these T1 events were further evaluated in the T2 generation, and all four of these events gave an increase in aboveground area for transgenic seedlings compared to control plants, with an overall increase in aboveground area for transgenic seedlings of 33% compared to control plants. The results were also shown to be statistically significant with the p-value from the F-test being lower than 0.0001 (T2 generation) indicating that the effect seen is likely due to the transgene rather than the position of the gene or a line effect, see table C.

TABLE C

| parameters | % increase | p-value |
|---|---|---|
| Early vigour | 33 | 0.0000 |

Example Section B

MADS15 Upregulated

Example 8

Identification of Sequences Related to SEQ ID NO: 43 and SEQ ID NO: 44

Sequences (full length cDNA, ESTs or genomic) related to SEQ ID NO: 43 and/or protein sequences related to SEQ ID NO: 44 were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid or polypeptide sequences to sequence databases and by calculating the statistical significance of matches. The polypeptide encoded by SEQ ID NO: 43 was used for the TBLASTN algorithm, with default settings and the filter to ignore low complexity sequences set off. The output of the analysis was viewed by pairwise comparison, and ranked according to the probability score (E-value), where the score reflects the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search.

In addition to the publicly available nucleic acid sequences available at NCBI, proprietary sequence databases are also searched following the same procedure as described herein above.

Table D provides a list of nucleic acid and protein sequences related to the nucleic acid sequence as represented by SEQ ID NO: 43 and the protein sequence represented by SEQ ID NO: 44.

TABLE D

Nucleic acid sequences related to the nucleic acid sequence (SEQ ID NO: 43) useful in the methods of the present invention, and the corresponding deduced polypeptides.

| name | source organism | SEQ ID NO: nucl/protein | database accession number |
|---|---|---|---|
| VRN-H1 | Hordeum vulgare | 52/53 | AAW82995 |
| m5 | Hordeum vulgare | 54/55 | CAB97352 |
| TaMADS#11 | Triticum aestivum | 56/57 | BAA33457 |
| TaVRT-1 | Triticum aestivum | 58/59 | AAP33790 |
| AP1 | Triticum monococcum | 60/61 | AAO72630 |
| VRN-A1 | Triticum aestivum | 62/63 | AAW73222 |
| MADS1 | Lolium perenne | 64/65 | AAO45873 |
| MADS1 | Lolium temulentum | 66/67 | AAD10625 |
| m15 | Zea mays | 68/69 | CAD23408 |
| m4 | Zea mays | 70/71 | CAD23417 |
| RMADS211 | Oryza sativa | 72/73 | AAS59822 |
| MADS14 | Oryza sativa | 74/75 | AAF19047 |
| Mads2 | Dendrocalamus latiflorus | 76/77 | AAR32119 |
| Mads1 | Dendrocalamus latiflorus | 78/79 | AAR32118 |
| mads3 | Zea mays | 80/81 | AAG43200 |
| SbMADS2 | Sorghum bicolor | 82/83 | AAB50181 |
| ZAP1 | Zea mays | 84/85 | AAB00081 |
| MADS2 | Lolium temulentum | 86/87 | AAD10626 |
| MADS2 | Lolium perenne | 88/89 | AAO45874 |
| m8 | Hordeum vulgare | 90/91 | CAB97354 |
| FDRMADS3 | Oryza sativa | 92/93 | AAL09473 |
| MADS15 | Oryza sativa | 94/95 | AAL09473 |
| TvFL2 | Tradescantia virginiana | 96/97 | AAP83415 |
| TvFL1 | Tradescantia virginiana | 98/99 | AAP83414 |
| TvFL3 | Tradescantia virginiana | 100/101 | AAP83416 |
| SQUA1 | Elaeis guineensis | 102/103 | AAQ03221 |
| AIFL | Allium sp. | 104/105 | AAP83362 |
| DOMADS2 | Dendrobium grex | 106/107 | AAF13261 |

Example 9

Alignment of Relevant Polypeptide Sequences

AlignX from the Vector NTI (Invitrogen) is based on the popular Clustal algorithm of progressive alignment (Thompson et al. (1997) Nucleic Acids Res 25:4876-4882; Chenna et al. (2003). Nucleic Acids Res 31:3497-3500). A phylogenetic tree can be constructed using a neighbour-joining clustering algorithm. Default values are for the gap open penalty of 10, for the gap extension penalty of 0.1 and the selected weight matrix is Blosum 62 (if polypeptides are aligned).

Figure 6:
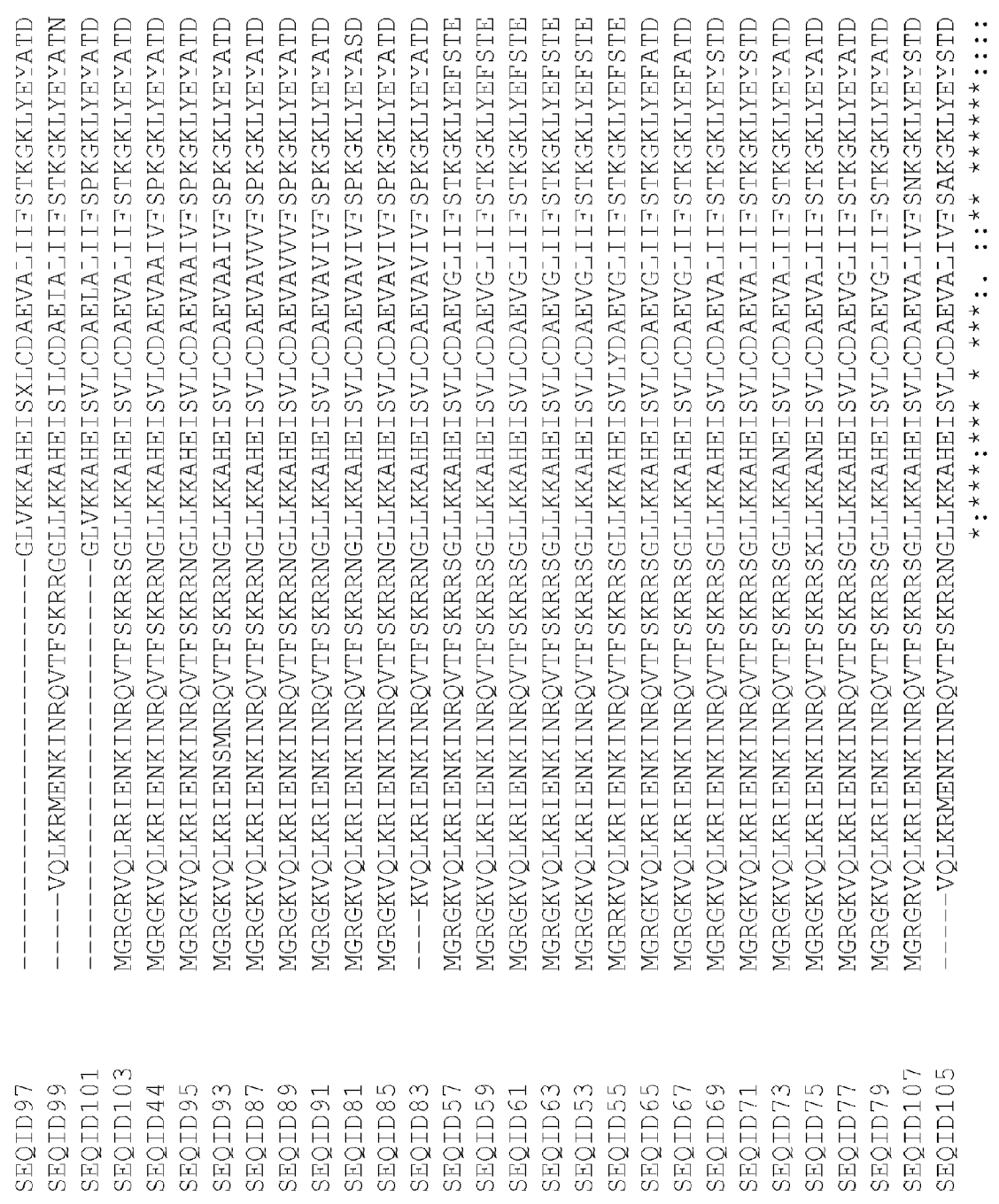
Figure 6:
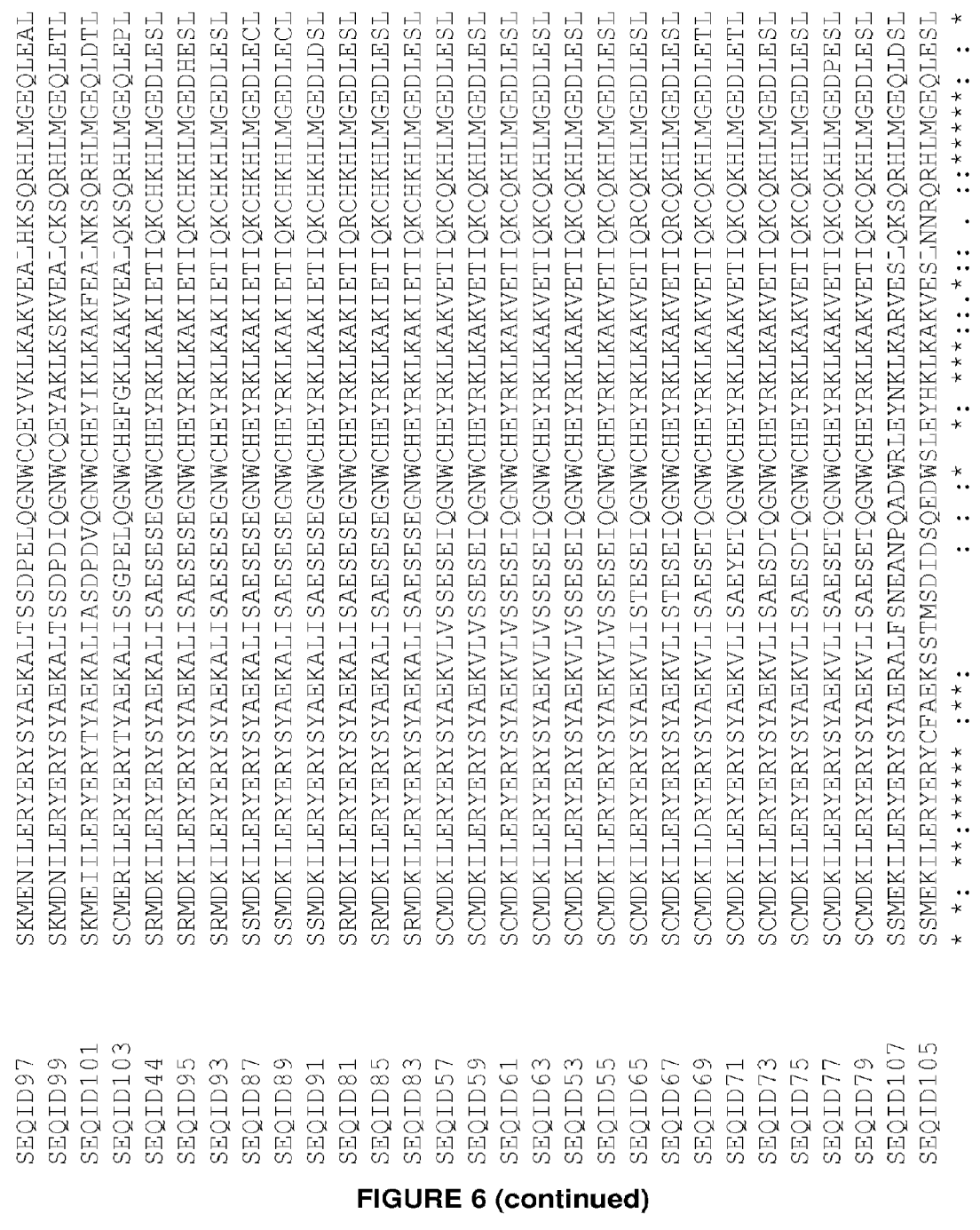
Figure 6:
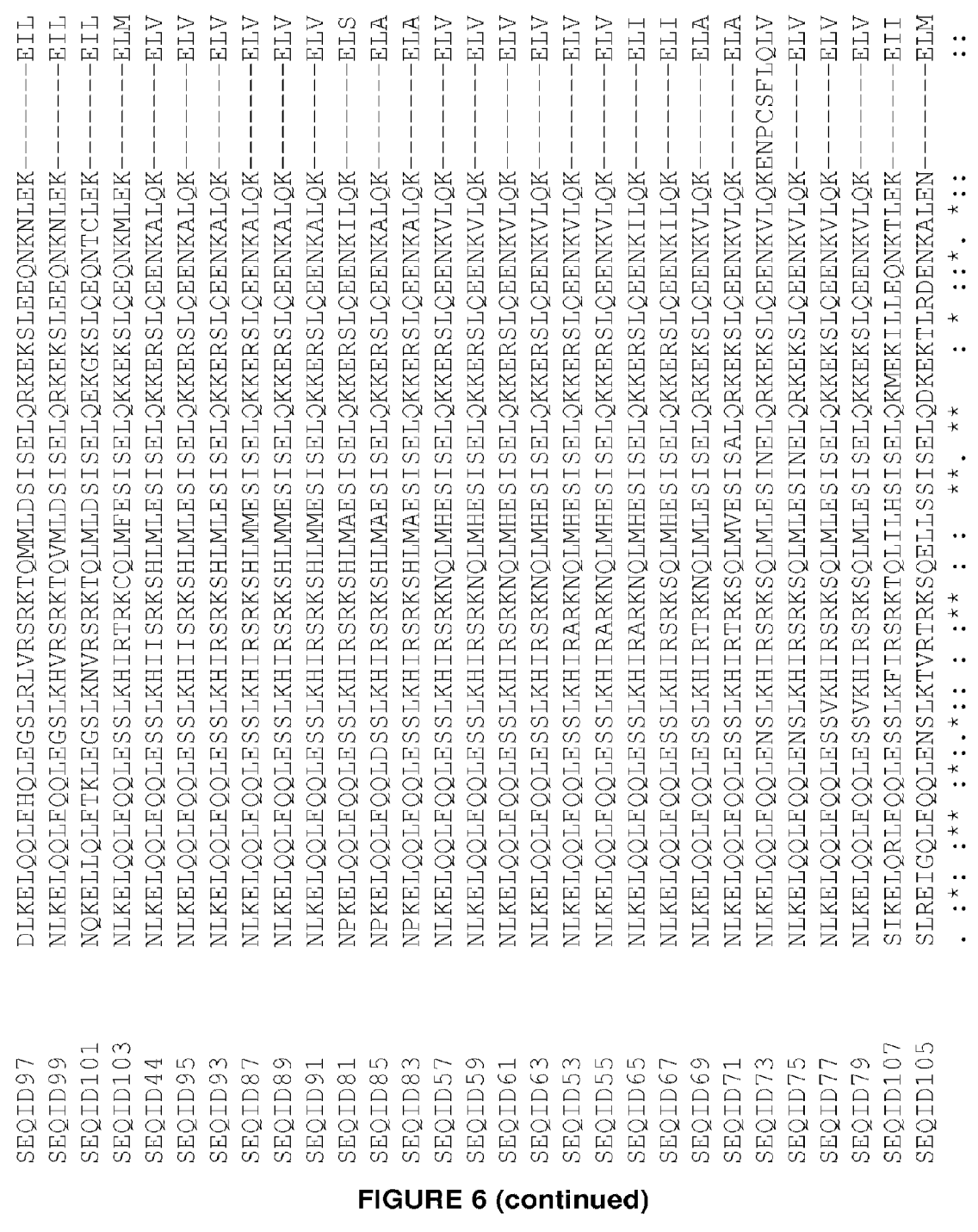

The result of the multiple sequence alignment using polypeptides relevant in identifying the ones useful in performing the methods of the invention is shown in FIG. 6.

Example 10

Calculation of Global Percentage Identity Between Polypeptide Sequences Useful in Performing the Methods of the Invention Global percentages of similarity and identity between full length polypeptide sequences useful in performing the methods of the invention were determined using one of the methods available in the art, the MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:
Scoring matrix: Blosum62
First Gap: 12
Extending gap: 2

Results of the software analysis are shown in Table E for the global similarity and identity over the full length of the polypeptide sequences (excluding the partial polypeptide sequences). Percentage identity is given above the diagonal and percentage similarity is given below the diagonal.

The percentage identity between the polypeptide sequences useful in performing the methods of the invention can be as low as 40% amino acid identity compared to SEQ ID NO: 44.

TABLE E

MatGAT results for global similarity and identity over the full length of the polypeptide sequences.

|    | | 1 | 2 | 3 | 4 | 5 | 6 | 7 | 8 | 9 | 10 | 11 | 12 | 13 |
|----|---|---|---|---|---|---|---|---|---|---|----|----|----|----|
| 1. | SEQID44 |      | 70.8 | 70.0 | 70.4 | 70.4 | 71.5 | 71.5 | 70.1 | 71.6 | 71.9 | 72.3 | 71.5 | 73.0 |
| 2. | SEQID53 | 77.2 |      | 99.2 | 96.3 | 96.3 | 95.5 | 95.1 | 87.0 | 86.2 | 80.6 | 80.2 | 81.0 | 82.9 |
| 3. | SEQID55 | 76.4 | 99.2 |      | 95.5 | 95.5 | 94.7 | 94.3 | 86.2 | 85.4 | 79.8 | 79.4 | 80.2 | 82.1 |
| 4. | SEQID57 | 76.0 | 96.7 | 95.9 |      | 98.8 | 98.0 | 97.5 | 87.0 | 86.6 | 81.8 | 81.4 | 80.6 | 82.5 |
| 5. | SEQID59 | 76.4 | 97.1 | 96.3 | 99.2 |      | 98.0 | 98.0 | 87.0 | 86.6 | 81.8 | 81.4 | 80.6 | 82.5 |
| 6. | SEQID61 | 77.2 | 96.7 | 95.9 | 98.4 | 98.8 |      | 99.6 | 87.9 | 87.4 | 82.6 | 82.6 | 81.0 | 82.9 |
| 7. | SEQID63 | 77.2 | 96.3 | 95.5 | 98.0 | 98.8 | 99.6 |      | 87.4 | 87.0 | 82.2 | 82.2 | 80.6 | 82.5 |
| 8. | SEQID65 | 76.4 | 92.2 | 91.4 | 92.2 | 92.7 | 93.5 | 93.1 |      | 97.6 | 81.7 | 80.9 | 82.3 | 83.8 |
| 9. | SEQID67 | 76.8 | 92.7 | 91.8 | 92.2 | 92.7 | 93.5 | 93.1 | 98.8 |      | 81.3 | 81.7 | 82.3 | 83.8 |
| 10.| SEQID69 | 79.4 | 87.3 | 86.5 | 89.0 | 89.0 | 89.4 | 89.0 | 88.2 | 88.2 |      | 93.5 | 83.8 | 85.8 |
| 11.| SEQID71 | 79.4 | 87.3 | 86.5 | 89.0 | 89.0 | 89.4 | 89.0 | 86.9 | 87.3 | 97.1 |      | 83.8 | 85.8 |
| 12.| SEQID73 | 80.1 | 88.1 | 87.4 | 86.6 | 87.0 | 87.4 | 87.0 | 88.5 | 88.1 | 91.3 | 90.9 |      | 96.4 |
| 13.| SEQID75 | 79.8 | 89.8 | 89.0 | 88.6 | 89.0 | 89.4 | 89.0 | 90.7 | 90.2 | 93.5 | 93.1 | 96.4 |      |
| 14.| SEQID77 | 79.8 | 91.8 | 91.0 | 91.4 | 91.8 | 92.6 | 92.2 | 90.6 | 90.2 | 91.8 | 91.4 | 93.3 | 95.1 |
| 15.| SEQID79 | 80.1 | 92.2 | 91.4 | 91.8 | 92.2 | 93.0 | 92.6 | 91.0 | 90.6 | 92.2 | 91.8 | 93.7 | 95.5 |
| 16.| SEQID81 | 86.3 | 79.3 | 78.5 | 77.8 | 78.1 | 78.9 | 78.9 | 77.0 | 77.0 | 81.9 | 80.7 | 80.7 | 80.7 |
| 17.| SEQID85 | 85.7 | 76.9 | 76.2 | 76.6 | 76.9 | 77.7 | 77.7 | 75.5 | 75.1 | 80.2 | 79.1 | 79.1 | 79.1 |
| 18.| SEQID87 | 89.1 | 78.2 | 77.4 | 79.3 | 79.7 | 79.7 | 80.1 | 78.2 | 77.8 | 82.8 | 80.8 | 81.6 | 80.8 |
| 19.| SEQID89 | 89.5 | 78.2 | 77.4 | 78.9 | 78.9 | 79.3 | 79.3 | 78.5 | 78.2 | 83.1 | 81.2 | 82.0 | 81.2 |
| 20.| SEQID91 | 85.9 | 75.4 | 74.6 | 75.7 | 75.7 | 76.4 | 76.4 | 75.4 | 74.6 | 79.3 | 78.6 | 79.0 | 79.0 |
| 21.| SEQID93 | 91.8 | 73.0 | 72.3 | 73.8 | 73.8 | 74.5 | 74.5 | 73.0 | 73.0 | 76.0 | 76.8 | 78.3 | 76.4 |
| 22.| SEQID95 | 99.6 | 76.8 | 76.0 | 76.0 | 76.0 | 76.8 | 76.8 | 76.0 | 75.7 | 78.7 | 79.0 | 79.8 | 79.4 |
| 23.| SEQID103| 75.3 | 82.8 | 82.0 | 81.6 | 82.0 | 82.4 | 82.4 | 84.4 | 84.4 | 82.4 | 82.4 | 85.4 | 84.0 |
| 24.| SEQID107| 70.4 | 77.3 | 76.5 | 76.5 | 74.5 | 77.3 | 76.1 | 74.9 | 74.9 | 76.5 | 75.7 | 75.1 | 77.3 |

|    | | 14 | 15 | 16 | 17 | 18 | 19 | 20 | 21 | 22 | 23 | 24 |
|----|---|----|----|----|----|----|----|----|----|----|----|----|
| 1. | SEQID44 | 72.7 | 73.0 | 82.1 | 82.2 | 87.4 | 87.7 | 82.5 | 90.3 | 99.6 | 64.7 | 56.7 |
| 2. | SEQID53 | 84.6 | 85.0 | 70.7 | 68.9 | 71.3 | 71.3 | 68.8 | 65.2 | 70.4 | 71.0 | 61.0 |
| 3. | SEQID55 | 83.7 | 84.1 | 70.0 | 68.1 | 70.5 | 70.5 | 68.1 | 64.4 | 69.7 | 69.3 | 60.2 |
| 4. | SEQID57 | 85.8 | 86.2 | 70.4 | 69.6 | 72.4 | 72.4 | 69.6 | 65.5 | 70.0 | 69.7 | 62.0 |
| 5. | SEQID59 | 85.8 | 86.2 | 70.7 | 69.6 | 72.4 | 72.4 | 69.6 | 65.5 | 70.0 | 70.1 | 61.5 |
| 6. | SEQID61 | 87.0 | 87.4 | 71.1 | 70.0 | 72.4 | 72.4 | 70.3 | 67.2 | 71.2 | 70.9 | 62.5 |
| 7. | SEQID63 | 86.6 | 87.0 | 71.1 | 70.0 | 72.8 | 72.4 | 70.3 | 67.2 | 71.2 | 70.9 | 61.8 |
| 8. | SEQID65 | 85.7 | 86.1 | 70.5 | 69.3 | 71.4 | 71.8 | 69.3 | 66.8 | 69.8 | 71.8 | 60.7 |
| 9. | SEQID67 | 85.7 | 86.1 | 71.2 | 70.1 | 72.1 | 72.5 | 68.6 | 66.0 | 70.5 | 71.8 | 60.7 |
| 10.| SEQID69 | 84.9 | 85.3 | 71.5 | 71.4 | 73.9 | 74.3 | 69.9 | 67.8 | 71.9 | 71.8 | 62.5 |
| 11.| SEQID71 | 84.5 | 84.9 | 71.5 | 71.4 | 73.6 | 73.9 | 69.6 | 69.3 | 71.9 | 72.2 | 61.0 |
| 12.| SEQID73 | 89.3 | 89.7 | 72.0 | 71.1 | 72.4 | 72.8 | 69.9 | 68.0 | 71.2 | 71.9 | 60.2 |
| 13.| SEQID75 | 91.5 | 91.9 | 73.0 | 71.8 | 73.9 | 74.3 | 70.7 | 68.3 | 72.7 | 72.0 | 60.6 |
| 14.| SEQID77 |      | 99.6 | 71.9 | 71.1 | 73.6 | 73.6 | 69.9 | 67.8 | 72.7 | 73.3 | 61.8 |
| 15.| SEQID79 | 99.6 |      | 72.2 | 71.4 | 73.9 | 73.9 | 70.3 | 68.2 | 72.7 | 73.7 | 62.2 |
| 16.| SEQID81 | 79.3 | 79.6 |      | 93.4 | 81.9 | 82.3 | 79.0 | 76.8 | 81.8 | 64.3 | 56.8 |
| 17.| SEQID85 | 77.7 | 78.0 | 96.3 |      | 82.5 | 82.9 | 81.3 | 77.0 | 81.9 | 63.6 | 57.2 |
| 18.| SEQID87 | 80.5 | 80.8 | 87.4 | 86.1 |      | 99.6 | 88.4 | 82.5 | 87.0 | 64.6 | 58.0 |
| 19.| SEQID89 | 80.5 | 80.8 | 87.8 | 86.4 | 99.6 |      | 88.8 | 82.9 | 87.4 | 64.6 | 58.0 |
| 20.| SEQID91 | 76.8 | 77.2 | 86.2 | 88.0 | 90.2 | 90.6 |      | 77.5 | 82.1 | 62.7 | 55.8 |
| 21.| SEQID93 | 76.0 | 76.4 | 83.3 | 82.1 | 85.4 | 85.8 | 81.5 |      | 89.9 | 61.0 | 54.1 |
| 22.| SEQID95 | 79.8 | 79.8 | 85.9 | 85.3 | 88.8 | 89.1 | 85.5 | 91.4 |      | 64.3 | 56.3 |
| 23.| SEQID103| 84.8 | 85.2 | 75.2 | 73.6 | 75.9 | 75.9 | 73.6 | 72.3 | 74.9 |      | 70.1 |
| 24.| SEQID107| 78.5 | 78.9 | 71.5 | 71.4 | 72.8 | 72.8 | 70.3 | 67.4 | 70.0 | 82.4 |      |

Example 11

Identification of Domains Comprised in Polypeptide Sequences Useful in Performing the Methods of the Invention The Integrated Resource of Protein Families, Domains and Sites (InterPro) database is an integrated interface for the commonly used signature databases for text- and sequence-based searches. The InterPro database combines these databases, which use different methodologies and varying degrees of biological information about well-characterized proteins to derive protein signatures. Collaborating databases include SWISS-PROT, PROSITE, TrEMBL, PRINTS, Propom and Pfam, Smart and TIGRFAMs. Interpro is hosted at the European Bioinformatics Institute in the United Kingdom.

The results of the InterPro scan of the polypeptide sequence as represented by SEQ ID NO: 44 are presented in Table F.

TABLE F

InterPro scan results of the polypeptide sequence as represented by SEQ ID NO: 44

| Database | Accession number | Accession name |
|---|---|---|
| PRINTS | PR00404 | MADSDOMAIN |
| PFAM | PF00319 | SRF-TF |
| SMART | SM00432 | MADS |
| PROFILE | PS50066 | MADS_BOX_2 |
| SUPERFAMILY | SSF55455 | SRF-like |
| PFAM | PF01486 | K-box |
| SUPERFAMILY | SSF46589 | tRNA-binding arm |
| PANTHER | PTHR11945 | MADS BOX PROTEIN |
| PANTHER | PTHR11945:SF19 | MADS BOX PROTEIN |

Example 12

Topology Prediction of the Polypeptide Sequences Useful in Performing the Methods of the Invention (Subcellular Localization, Transmembrane . . . )

TargetP 1.1 predicts the subcellular location of eukaryotic proteins. The location assignment is based on the predicted presence of any of the N-terminal pre-sequences: chloroplast transit peptide (cTP), mitochondrial targeting peptide (mTP) or secretory pathway signal peptide (SP). Scores on which the final prediction is based are not really probabilities, and they do not necessarily add to one. However, the location with the highest score is the most likely according to TargetP, and the relationship between the scores (the reliability class) may be an indication of how certain the prediction is. The reliability class (RC) ranges from 1 to 5, where 1 indicates the strongest prediction. TargetP is maintained at the server of the Technical University of Denmark.

For the sequences predicted to contain an N-terminal pre-sequence a potential cleavage site can also be predicted.

A number of parameters were selected, such as organism group (non-plant or plant), cutoff sets (none, predefined set of cutoffs, or user-specified set of cutoffs), and the calculation of prediction of cleavage sites (yes or no).

The results of TargetP 1.1 analysis of the polypeptide sequence as represented by SEQ ID NO: 44 are presented Table G. The "plant" organism group has been selected, no cutoffs defined, and the predicted length of the transit peptide requested. The subcellular localization of the polypeptide sequence as represented by SEQ ID NO: 44 may be the cytoplasm or nucleus, no transit peptide is predicted.

TABLE G

TargetP 1.1 analysis of the polypeptide sequence as represented by SEQ ID NO: 44

| | |
|---|---|
| Length (AA) | 267 |
| Chloroplastic transit peptide | 0.088 |
| Mitochondrial transit peptide | 0.492 |
| Secretory pathway signal peptide | 0.046 |
| Other subcellular targeting | 0.655 |
| Predicted Location | Chloroplastic |
| Reliability class | 5 |
| Predicted transit peptide length | / |

Many other algorithms can be used to perform such analyses, including:
ChloroP 1.1 hosted on the server of the Technical University of Denmark;
Protein Prowler Subcellular Localisation Predictor version 1.2 hosted on the server of the Institute for Molecular Bioscience, University of Queensland, Brisbane, Australia;
PENCE Proteome Analyst PA-GOSUB 2.5 hosted on the server of the University of Alberta, Edmonton, Alberta, Canada;
TMHMM, hosted on the server of the Technical University of Denmark

Example 13

Assay Related to the Polypeptide Sequences Useful in Performing the Methods of the Invention Lim et al. (PMB 44, 513-527, 2000) describe two assays for measuring protein-protein interactions that may be applied to MADS15. In the yeast two-hybrid assay, a truncated form of MADS1 (comprising the complete MADS box, the I- and K-domain but lacking the C-terminal part of the C-domain) was used as bait to test interaction with MADS15. In the in vitro pull-down assay, GST and GST-fused MADS1 proteins were produced and immobilised on glutathione Sepharose 4B. The resin-bound GST/GST-MADS1 was mixed with $^{35}$S-labeled MADS15 proteins or fragments thereof. After washing, the interacting proteins were eluted and analysed by SDS-PAGE. A person skilled in the art will appreciate that the MADS15 protein may be used as bait in the two-hybrid screen or may be immobilised on glutathione resin as well. Furthermore, a MADS15 protein, when used according to the methods of the present invention, will result in increased root yield in rice, measured as an increased ratio of root biomass over shoot biomass.

Example 14

Cloning of Nucleic Acid Sequence as Represented by SEQ ID NO: 43

The Oryza sativa MADS15 gene was amplified by PCR using as template an Oryza sativa seedling cDNA library (Invitrogen, Paisley, UK). After reverse transcription of RNA extracted from seedlings, the cDNAs were cloned into pCMV Sport 6.0. Average insert size of the bank was 1.5 kb and the original number of clones was of the order of $1.59 \times 10^7$ cfu. Original titer was determined to be $9.6 \times 10^5$ cfu/ml after first amplification of $6 \times 10^{11}$ cfu/ml. After plasmid extraction, 200 ng of template was used in a 50 µl PCR mix. Primers prm06892 (SEQ ID NO: 45; sense, start codon in bold, AttB1 site in italic: 5'-ggggacaagtttgtacaaaaaagcaggcttaaaca atgggcgggggaaggt-3') and prm06893 (SEQ ID NO: 46; reverse, complementary, AttB2 site in italic: 5'-ggggac-cactttgtacaagaaagctgggtttggccgacgacgacgac-3'), which include the AttB sites for Gateway recombination, were used for PCR amplification. PCR was performed using Hifi Taq DNA polymerase in standard conditions. A PCR fragment of around 915 bp was amplified and purified also using standard methods. The first step of the Gateway procedure, the BP reaction, was then performed, during which the PCR fragment recombines in vivo with the pDONR201 plasmid to produce, according to the Gateway terminology, an "entry clone", pMADS15. Plasmid pDONR201 was purchased from Invitrogen, as part of the Gateway® technology.

Example 15

Expression Vector Construction Using the Nucleic Acid Sequence as Represented by SEQ ID NO: 43

The entry clone pMADS15 was subsequently used in an LR reaction with pGOS2, a destination vector used for Oryza

*sativa* transformation. This vector contains as functional elements within the T-DNA borders: a plant selectable marker; a screenable marker expression cassette; and a Gateway cassette intended for LR in vivo recombination with the nucleic acid sequence of interest already cloned in the entry clone. A rice GOS2 promoter (SEQ ID NO: 108, alternatively, SEQ ID NO: 47 is equally useful) for constitutive expression was located upstream of this Gateway cassette.

Figure 7:
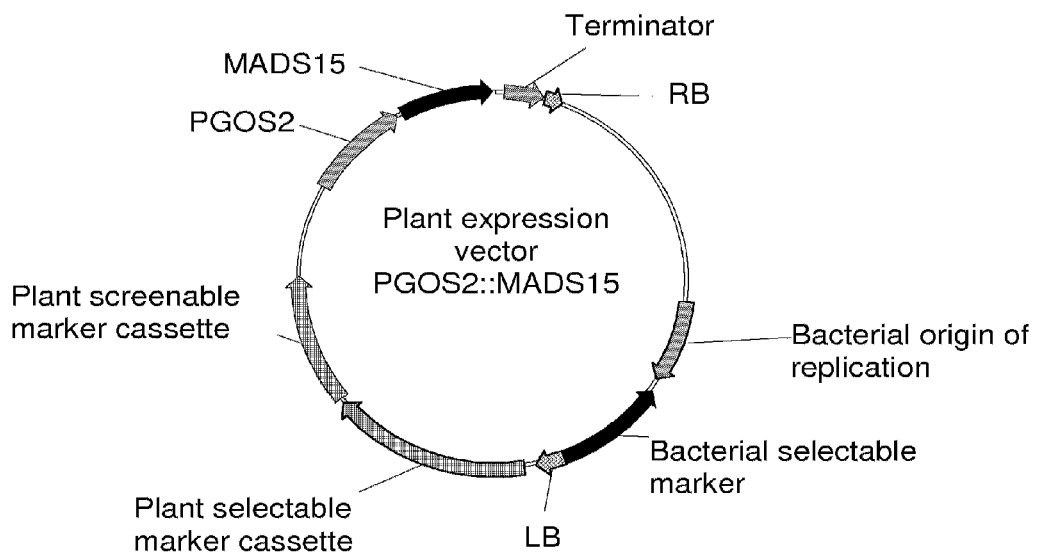
FIG. 7 shows the binary vector for increased expression in Oryza sativa of an Oryza sativa MADS15 protein-encoding nucleic acid under the control of a GOS2 promoter.
Figure 9:
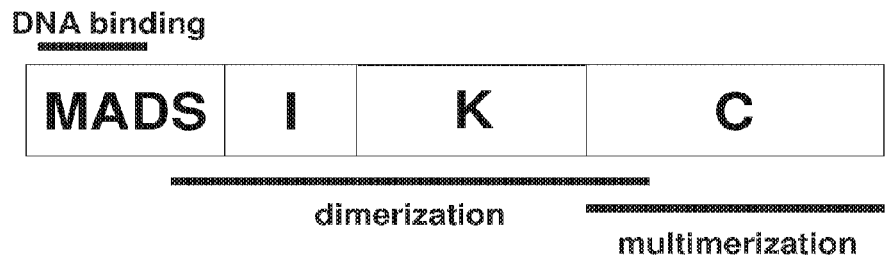
FIG. 9 is a schematic representation of a full-length OsMADS15 polypeptide. The typical domains (M, MADS; I, intervening domain; K, keratin K-box region; C, variable C-terminal region) are indicated, the lines above and below the diagram show the regions of the protein involved in DNA binding, dimerisation and in multimerisation with interacting proteins.

After the LR recombination step, the resulting expression vector pGOS2::MADS15 (FIG. 7) was transformed into *Agrobacterium* strain LBA4044 according to methods well known in the art.

Example 16

Plant Transformation

Rice Transformation

The *Agrobacterium* containing the expression vector was used to transform *Oryza sativa* plants. Mature dry seeds of the rice japonica cultivar Nipponbare were dehusked. Sterilization was carried out by incubating for one minute in 70% ethanol, followed by 30 minutes in 0.2% $HgCl_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

*Agrobacterium* strain LBA4404 containing the expression vector was used for co-cultivation. *Agrobacterium* was inoculated on AB medium with the appropriate antibiotics and cultured for 3 days at 28° C. The bacteria were then collected and suspended in liquid co-cultivation medium to a density ($OD_{600}$) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges 1996, Chan et al. 1993, Hiei et al. 1994).

Corn Transformation

Transformation of maize (*Zea mays*) is performed with a modification of the method described by Ishida et al. (1996) Nature Biotech 14(6): 745-50. Transformation is genotype-dependent in corn and only specific genotypes are amenable to transformation and regeneration. The inbred line A188 (University of Minnesota) or hybrids with A188 as a parent are good sources of donor material for transformation, but other genotypes can be used successfully as well. Ears are harvested from corn plant approximately 11 days after pollination (DAP) when the length of the immature embryo is about 1 to 1.2 mm. Immature embryos are cocultivated with *Agrobacterium tumefaciens* containing the expression vector, and transgenic plants are recovered through organogenesis. Excised embryos are grown on callus induction medium, then maize regeneration medium, containing the selection agent (for example imidazolinone but various selection markers can be used). The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Wheat Transformation

Transformation of wheat is performed with the method described by Ishida et al. (1996) Nature Biotech 14(6): 745-50. The cultivar Bobwhite (available from CIMMYT, Mexico) is commonly used in transformation. Immature embryos are co-cultivated with *Agrobacterium tumefaciens* containing the expression vector, and transgenic plants are recovered through organogenesis. After incubation with *Agrobacterium*, the embryos are grown in vitro on callus induction medium, then regeneration medium, containing the selection agent (for example imidazolinone but various selection markers can be used). The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Soybean Transformation

Soybean is transformed according to a modification of the method described in the Texas A&M U.S. Pat. No. 5,164,310. Several commercial soybean varieties are amenable to transformation by this method. The cultivar Jack (available from the Illinois Seed foundation) is commonly used for transformation. Soybean seeds are sterilised for in vitro sowing. The hypocotyl, the radicle and one cotyledon are excised from seven-day old young seedlings. The epicotyl and the remaining cotyledon are further grown to develop axillary nodes. These axillary nodes are excised and incubated with *Agrobacterium tumefaciens* containing the expression vector. After the cocultivation treatment, the explants are washed and transferred to selection media. Regenerated shoots are excised and placed on a shoot elongation medium. Shoots no longer than 1 cm are placed on rooting medium until roots develop. The rooted shoots are transplanted to soil in the greenhouse. T1 seeds are produced from plants that exhibit tolerance to the selection agent and that contain a single copy of the T-DNA insert.

Rapeseed/Canola Transformation

Cotyledonary petioles and hypocotyls of 5-6 day old young seedling are used as explants for tissue culture and transformed according to Babic et al. (1998, Plant Cell Rep 17: 183-188). The commercial cultivar Westar (Agriculture Canada) is the standard variety used for transformation, but other varieties can also be used. Canola seeds are surface-sterilized for in vitro sowing. The cotyledon petiole explants with the cotyledon attached are excised from the in vitro seedlings, and inoculated with *Agrobacterium* (containing the expression vector) by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with *Agrobacterium*, the petiole explants are transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MS0) for root induction. The rooted shoots are transplanted to soil in the greenhouse. T1 seeds are produced from plants that exhibit tolerance to the selection agent and that contain a single copy of the T-DNA insert.

Alfalfa Transformation

A regenerating clone of alfalfa (*Medicago sativa*) is transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown D C W and A Atanassov (1985. Plant Cell Tissue Organ Culture 4: 111-112). Alternatively, the RA3 variety (University of Wisconsin) has been selected for use in tissue culture (Walker et al., 1978 Am J Bot 65:654-659). Petiole explants are cocultivated with an overnight culture of *Agrobacterium tumefaciens* C58C1 pMP90 (McKersie et al., 1999 Plant Physiol 119: 839-847) or LBA4404 containing the expression vector. The explants are cocultivated for 3 d in the dark on SH induction medium containing 288 mg/L Pro, 53 mg/L thioproline, 4.35 g/L K2S04, and 100 µm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings were transplanted into pots and grown in a greenhouse. T1 seeds are produced from plants that exhibit tolerance to the selection agent and that contain a single copy of the T-DNA insert.

Example 17

Phenotypic Evaluation Procedure 17.1 Evaluation Setup

Approximately 35 independent T0 rice transformants were generated. The primary transformants were transferred from a tissue culture chamber to a greenhouse for growing and harvest of T1 seed. Six events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions. Greenhouse conditions were of shorts days (12 hours light), 28° C. in the light and 22° C. in the dark, and a relative humidity of 70%.

Four T1 events were further evaluated in the T2 generation following the same evaluation procedure as for the T1 generation but with more individuals per event. From the stage of sowing until the stage of maturity the plants were passed several times through a digital imaging cabinet. At each time point digital images (2048×1536 pixels, 16 million colours) were taken of each plant from at least 6 different angles.

17.2 Statistical analysis: F-Test

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and to verify for an overall effect of the gene, also known as a global gene effect. The threshold for significance for a true global gene effect was set at a 5% probability level for the F-test. A significant F-test value points to a gene effect, meaning that it is not only the mere presence or position of the gene that is causing the differences in phenotype.

To check for an effect of the genes within an event, i.e., for a line-specific effect, a t-test was performed within each event using data sets from the transgenic plants and the corresponding null plants. "Null plants" or "null segregants" or "nullizygotes" are the plants treated in the same way as the transgenic plant, but from which the transgene has segregated. Null plants can also be described as the homozygous negative transformed plants. The threshold for significance for the t-test is set at 10% probability level. The results for some events can be above or below this threshold. This is based on the hypothesis that a gene might only have an effect in certain positions in the genome, and that the occurrence of this position-dependent effect is not uncommon. This kind of gene effect is also named herein a "line effect of the gene". The p-value is obtained by comparing the t-value to the t-distribution or alternatively, by comparing the F-value to the F-distribution. The p-value then gives the probability that the null hypothesis (i.e., that there is no effect of the transgene) is correct.

17.3 Parameters Measured

From the stage of sowing until the stage of maturity the plants were passed several times through a digital imaging cabinet. At each time point digital images (2048×1536 pixels, 16 million colours) were taken of each plant from at least 6 different angles.

The plant aboveground area (or leafy biomass) was determined by counting the total number of pixels on the digital images from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The above ground area is the area measured at the time point at which the plant had reached its maximal leafy biomass. The early vigour is the plant (seedling) aboveground area three weeks post-germination. Increase in root biomass is expressed as an increase in total root biomass (measured as maximum biomass of roots observed during the lifespan of a plant); or as an increase in the root/shoot index (measured as the ratio between root biomass and shoot biomass in the period of active growth of root and shoot).

Example 18

Results of the Phenotypic Evaluation of the Transgenic Plants

Upon analysis of the plants as described above, the inventors found that plants transformed with the MADS15 gene construct had a higher root yield, expressed as root/shoot index, compared to plants lacking the MADS15 transgene. The increase was 9.4% (p-value 0.0207) in T1 and 25.7% (p-value 0.0002) in T2. The p-values show that the increases were significant.

Example Section C

MADS15 Down-Regulated

See also Examples 8 to 13 for the identification and characterisation of MADS15 related sequences.

Example 19

Gene Cloning

The *Oryza sativa* MADS15 gene was amplified by PCR using as template an *Oryza sativa* seedling cDNA library (Invitrogen, Paisley, UK). After reverse transcription of RNA extracted from seedlings, the cDNAs were cloned into pCMV Sport 6.0. Average insert size of the bank was 1.5 kb and the original number of clones was of the order of $1.59 \times 10^7$ cfu. Original titer was determined to be $9.6 \times 10^5$ cfu/ml after first amplification of $6 \times 10^{11}$ cfu/ml. After plasmid extraction, 200 ng of template was used in a 50 µl PCR mix. Primers prm06892 (SEQ ID NO: 111; sense, start codon in bold, AttB1 site in italic: -ggggacaagtttgtacaaaaaagcag-gcttaaacaatggg cgggggaaggt-3') and prm06893 (SEQ ID NO: 112; reverse, complementary, AttB2 site in italic: 5'-ggggac-cactttgtacaagaaagctgggtttggccgacgacgacgac-3'), which include the AttB sites for Gateway recombination, were used for PCR amplification. PCR was performed using Hifi Taq DNA polymerase in standard conditions. A PCR fragment of around 915 bp was amplified and purified also using standard methods. The PCR fragment was subsequently used for the preparation of a hairpin construct, using techniques known in the art. The first step of the Gateway procedure, the BP reaction, was then performed, during which the hairpin construct recombines in vivo with the pDONR201 plasmid to produce, according to the Gateway terminology, an "entry clone", pMADS15hp. Plasmid pDONR201 was purchased from Invitrogen, as part of the Gateway® technology.

Example 20

Vector Construction

The entry clone pMADS15hp was subsequently used in an LR reaction with p01519, a destination vector for the inverted repeat construct. This vector contains as functional elements within the T-DNA borders: a plant selectable marker; a screenable marker expression cassette; and a Gateway cassette intended for LR in vivo recombination such that the sequence of interest from the entry clone is integrated as an inverted repeat. A rice GOS2 promoter (SEQ ID NO: 174, alternatively, SEQ ID NO: 113 is equally useful) for constitutive expression was located upstream of this Gateway cassette.

Figure 10:
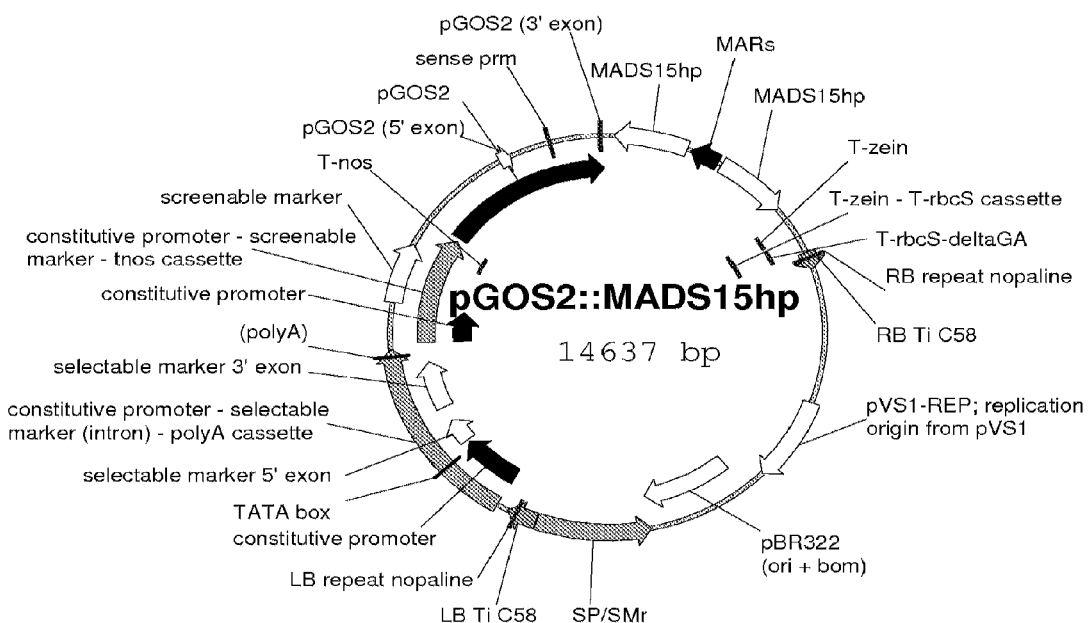
FIG. 10 shows the binary vector pGOS::MADS15hp for MADS15 RNA silencing in Oryza sativa, using a hairpin construct under the control of a constitutive promoter (GOS2).
Figure 12:
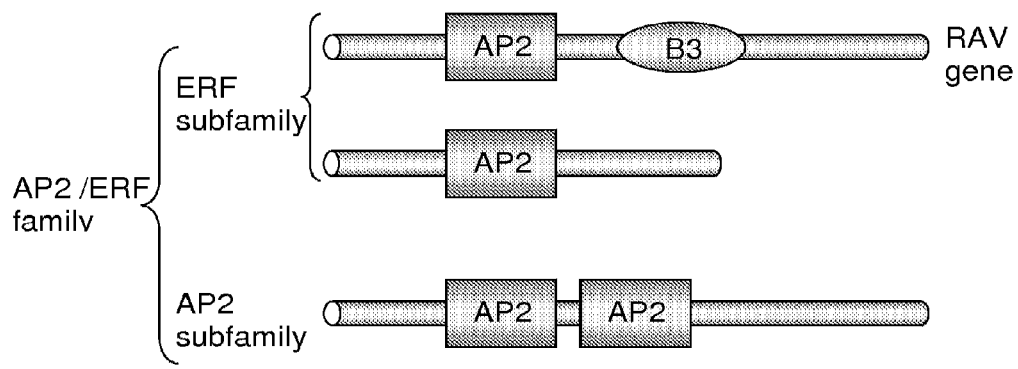
FIG. 12 shows the schematic classification of the AP2/ERF transcription factor polypeptides according to the domains present: the AP2 subfamily with two AP2 repeats and the ERF subfamily with only one AP2 repeat. The ERF subfamily is further subdivided into transcription factors comprising a B3 domain in addition to the AP2 repeat (called RAV), or not. The PLT transcription factor polypeptides belong to the AP2 subfamily with two AP2 repeats.
Figure 13:
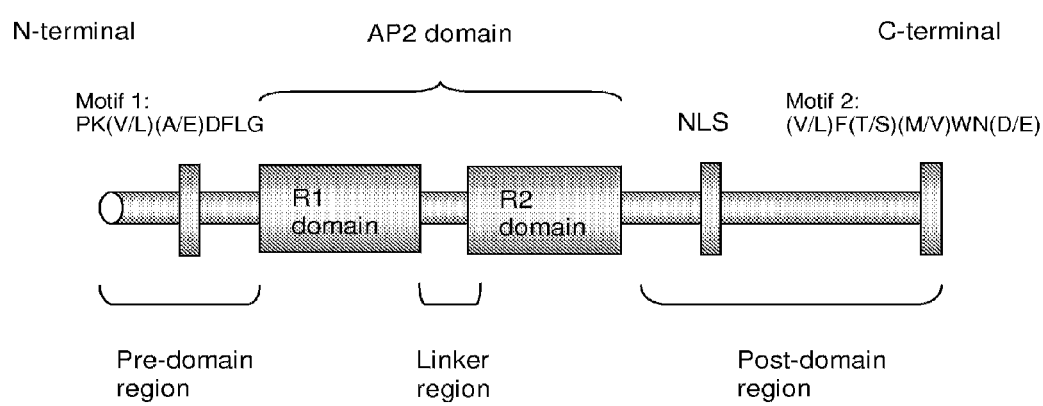
FIG. 13 represents a schematic presentation of the PLT transcription factor polypeptide structure. The AP2 domain comprises the two AP2 repeats (boxed) separated by a linker region. The approximate positions of the nuclear localisation signal (NLS), of motif 1 PK(V/L)(A/E)DFLG and of motif 2 (V/L)FX(M/V)WN(D/E) are marked as boxes.

After the LR recombination step, the resulting expression vector with the inverted repeat, FIG. 10) were transformed into *Agrobacterium* strain LBA4044 and subsequently to *Oryza sativa* plants.

Example 21

Plant Transformation

Rice Transformation

The *Agrobacterium* containing the expression vector was used to transform *Oryza sativa* plants. Mature dry seeds of the rice japonica cultivar Nipponbare were dehusked. Sterilization was carried out by incubating for one minute in 70% ethanol, followed by 30 minutes in 0.2% $HgCl_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

*Agrobacterium* strain LBA4404 containing the expression vector was used for co-cultivation. *Agrobacterium* was inoculated on AB medium with the appropriate antibiotics and cultured for 3 days at 28° C. The bacteria were then collected and suspended in liquid co-cultivation medium to a density ($OD_{600}$) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges 1996, Chan et al. 1993, Hiei et al. 1994).

Corn Transformation

Transformation of maize (*Zea mays*) is performed with a modification of the method described by Ishida et al. (1996) Nature Biotech 14(6): 745-50. Transformation is genotype-dependent in corn and only specific genotypes are amenable to transformation and regeneration. The inbred line A188 (University of Minnesota) or hybrids with A188 as a parent are good sources of donor material for transformation, but other genotypes can be used successfully as well. Ears are harvested from corn plant approximately 11 days after pollination (DAP) when the length of the immature embryo is about 1 to 1.2 mm. Immature embryos are cocultivated with *Agrobacterium tumefaciens* containing the expression vector, and transgenic plants are recovered through organogenesis.

Excised embryos are grown on callus induction medium, then maize regeneration medium, containing the selection agent (for example imidazolinone but various selection markers can be used). The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Wheat Transformation

Transformation of wheat is performed with the method described by Ishida et al. (1996) Nature Biotech 14(6): 745-50. The cultivar Bobwhite (available from CIMMYT, Mexico) is commonly used in transformation. Immature embryos are co-cultivated with *Agrobacterium tumefaciens* containing the expression vector, and transgenic plants are recovered through organogenesis. After incubation with *Agrobacterium*, the embryos are grown in vitro on callus induction medium, then regeneration medium, containing the selection agent (for example imidazolinone but various selection markers can be used). The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Soybean Transformation

Soybean is transformed according to a modification of the method described in the Texas A&M U.S. Pat. No. 5,164,310. Several commercial soybean varieties are amenable to transformation by this method. The cultivar Jack (available from the Illinois Seed foundation) is commonly used for transformation. Soybean seeds are sterilised for in vitro sowing. The hypocotyl, the radicle and one cotyledon are excised from seven-day old young seedlings. The epicotyl and the remaining cotyledon are further grown to develop axillary nodes. These axillary nodes are excised and incubated with *Agrobacterium tumefaciens* containing the expression vector. After the cocultivation treatment, the explants are washed and transferred to selection media. Regenerated shoots are excised and placed on a shoot elongation medium. Shoots no longer than 1 cm are placed on rooting medium until roots develop. The rooted shoots are transplanted to soil in the greenhouse. T1 seeds are produced from plants that exhibit tolerance to the selection agent and that contain a single copy of the T-DNA insert.

Rapeseed/Canola Transformation

Cotyledonary petioles and hypocotyls of 5-6 day old young seedling are used as explants for tissue culture and transformed according to Babic et al. (1998, Plant Cell Rep 17: 183-188). The commercial cultivar Westar (Agriculture Canada) is the standard variety used for transformation, but other varieties can also be used. Canola seeds are surface-sterilized for in vitro sowing. The cotyledon petiole explants with the cotyledon attached are excised from the in vitro seedlings, and inoculated with *Agrobacterium* (containing the expression vector) by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with *Agrobacterium*, the petiole explants are transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MS0) for root induction. The rooted shoots are transplanted to soil in the greenhouse. T1 seeds are produced from plants that exhibit tolerance to the selection agent and that contain a single copy of the T-DNA insert.

Alfalfa Transformation

A regenerating clone of alfalfa (*Medicago sativa*) is transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown D C W and A Atanassov (1985. Plant Cell Tissue Organ Culture 4: 111-112). Alternatively, the RA3 variety (University of Wisconsin) has been selected for use in tissue culture (Walker et al., 1978 Am J Bot 65:654-659). Petiole explants are cocultivated with an overnight culture of *Agrobacterium tumefaciens* C58C1 pMP90 (McKersie et al., 1999 Plant Physiol 119: 839-847) or LBA4404 containing the expression vector. The explants are cocultivated for 3 d in the dark on SH induction medium containing 288 mg/L Pro, 53 mg/L thioproline, 4.35 g/L K2SO4, and 100 μm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings were transplanted into pots and grown in a greenhouse. T1 seeds are produced from plants that exhibit tolerance to the selection agent and that contain a single copy of the T-DNA insert.

Example 22

Evaluation Methods of Plants Transformed with the MADS15 Inverted Repeat Under Control of the Rice GOS2 Promoter Approximately 15 to 20 independent T0 rice transformants were generated. The primary transformants were transferred from a tissue culture chamber to a greenhouse for growing and harvest of T1 seed. Eight events for the inverted repeat construct of which the T1 progeny segregated 3:1 for presence/absence of the transgene, were retained. For each of these events, approximately 10 T1 seedlings containing the transgene (hetero- and homozygotes) and approximately 10 T1 seedlings lacking the transgene (nullizygotes) were selected by monitoring visual marker expression. The selected T1 plants were transferred to a greenhouse. Each plant received a unique barcode label to link unambiguously the phenotyping data to the corresponding plant. The selected T1 plants were grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes were grown side-by-side at random positions.

From the stage of sowing until the stage of maturity the plants were passed several times through a digital imaging cabinet. At each time point digital images (2048×1536 pixels, 16 million colours) were taken of each plant from at least 6 different angles.

The plant aboveground area (or leafy biomass) was determined by counting the total number of pixels on the digital images from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The Areamax is the above ground area at the time point at which the plant had reached its maximal leafy biomass.

The mature primary panicles were harvested, bagged, barcode-labelled and then dried for three days in the oven at 37° C. The panicles were then threshed and all the seeds collected. The filled husks were separated from the empty ones using an air-blowing device. After separation, both seed lots were then counted using a commercially available counting machine. The empty husks were discarded. The filled husks were weighed on an analytical balance and the cross-sectional area of the seeds was measured using digital imaging. This procedure resulted in the set of the following seed-related parameters:

The flowers-per-panicle is a parameter estimating the average number of florets per panicle on a plant, derived from the number of total seeds divided by the number of first panicles. The tallest panicle and all the panicles that overlapped with the tallest panicle when aligned vertically, were considered as first panicles and were counted manually. The number of filled seeds was determined by counting the number of filled husks that remained after the separation step. The total seed yield (total seed weight) was measured by weighing all filled husks harvested from a plant. Total seed number per plant was measured by counting the number of husks harvested from a plant and corresponds to the number of florets per plant. These parameters were derived in an automated way from the digital images using image analysis software and were analysed statistically. Individual seed parameters (including width, length, area, weight) were measured using a custom-made device consisting of two main components, a weighing and imaging device, coupled to software for image analysis.

A two factor ANOVA (analyses of variance) corrected for the unbalanced design was used as statistical model for the overall evaluation of plant phenotypic characteristics. An F-test was carried out on all the parameters measured of all the plants of all the events transformed with that gene. The F-test was carried out to check for an effect of the gene over all the transformation events and to verify for an overall effect of the gene, also named herein "global gene effect". If the value of the F test shows that the data are significant, than it is concluded that there is a "gene" effect, meaning that not only presence or the position of the gene is causing the effect. The threshold for significance for a true global gene effect is set at 5% probability level for the F test.

To check for an effect of the genes within an event, i.e., for a line-specific effect, a t-test was performed within each event using data sets from the transgenic plants and the corresponding null plants. "Null plants" or "null segregants" or "nullizygotes" are the plants treated in the same way as the transgenic plant, but from which the transgene has segregated. Null plants can also be described as the homozygous negative transformed plants. The threshold for significance for the t-test is set at 10% probability level. The results for some events can be above or below this threshold. This is based on the hypothesis that a gene might only have an effect in certain positions in the genome, and that the occurrence of this position-dependent effect is not uncommon. This kind of gene effect is also named herein a "line effect of the gene". The p-value is obtained by comparing the t-value to the t-distribution or alternatively, by comparing the F-value to the F-distribution. The p-value then gives the probability that the null hypothesis (i.e., that there is no effect of the transgene) is correct.

Example 23

Measurement of Yield-Related Parameters for the Inverted Repeat Construct Transformants Upon analysis of the seeds as described above, the inventors found that plants transformed with the hairpin MADS15 gene construct had a higher seed yield, expressed as number of filled seeds, total weight of seeds, total number of seeds, and flowers per panicle, compared to plants lacking the MADS15 transgene, whereas the plants transformed with the sense MADS15 gene construct showed opposite effects. The p-values show that the increases were significant.

The results obtained for plants in the T1 generation are summarised in Table H, which represent the mean values for all the tested lines:

TABLE H

|  | % difference | p-value |
| --- | --- | --- |
| number of filled seeds | +122 | 0.0000 |
| total weight of seeds | +112 | 0.0000 |
| total number of seeds | +27 | 0.0000 |
| flowers per panicle | +25 | 0.0000 |

Example Section D

PLT

Example 24

Identification of Sequences Related to the Nucleic Acid Sequence Used in the Methods of the Invention Sequences (full length cDNA, ESTs or genomic) related to the nucleic acid sequence used in the methods of the present invention were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid or polypeptide sequences to sequence databases and by calculating the statistical significance of matches. For example, the polypeptide encoded by the nucleic acid of the present invention was used for the TBLASTN algorithm, with default settings and the filter to ignore low complexity sequences set off. The output of the analysis was viewed by pairwise comparison, and ranked according to the probability score (E-value), where the score reflect the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search. For example the E-value may be increased to show less stringent matches. This way, short nearly exact matches may be identified.

The Table I below provides a list of nucleic acid sequences related to the nucleic acid sequence used in the methods of the present invention.

TABLE I nucleic acid sequences related to the nucleic acid sequence used in the methods of the present invention

| Name | Nucleic acid SEQ ID NO | Polypeptide SEQ ID NO | | NCBI accession number | Source organism |
|---|---|---|---|---|---|
| Arath_PLT1 | 175 | 176 | full length | NM_112975 (At3g20840) | *Arabidopsis thaliana* |
| Arath_PLT2 | 177 | 178 | full length | NM_103997 (At1g51190) | *Arabidopsis thaliana* |
| Glyma_PLT | 179 | 180 | full length | BU964973.1 CA783156.1 BM309051.1 BM309377.1 | *Glycine max* |
| Glyma_PLT2 | 181 | 182 | full length | BU926204.1 BU547204.1 CA783156.1 BU927164.1 | *Glycine max* |
| Medtr_PLT | 183 | 184 | full length | AC144930.20 | *Medicago truncatula* |
| Orysa_PLT | 185 | 186 | full length | NM_190301 | *Oryza sativa* |
| Zeama_PLT | 187 | 188 | full length | CS155772.1 | *Zea mays* |
| Lotco_PLT | 189 | 190 | partial | AP007400 | *Lotus corniculatus* |
| Poptr_PLT I | 199 | 200 | full length | scaff_III.1595 | *Populus tremuloides* |
| Poptr_PLT II | 201 | 202 | full length | scaff_I.328 | *Populus tremuloides* |
| Vitvi_PLT | 203 | 204 | partial | AM469514 | *Vitis vinifera* |
| Brana_PLT | 205 | 206 | partial | CN730825 | *Brassica napus* |
| Phaco_PLT | 207 | 208 | partial | CA902624.1| | *Phaseolus coccineus* |

In some instances, related sequences have tentatively been assembled and publicly disclosed by research institutions, such as The Institute for Genomic Research (TIGR). The Eukaryotic Gene Orthologs (EGO) database may be used to identify such related sequences, either by keyword search or by using the BLAST algorithm with the nucleic acid or polypeptide sequence of interest.

Example 25

Cloning of the Nucleic Acid Sequences Used in the Methods of the Invention

The nucleic acid sequences used in the methods of the invention were amplified by PCR using as template a custom-made *Arabidopsis thaliana* cDNA library made starting from RNA extracted from different tissues (in pCMV Sport 6.0; Invitrogen, Paisley, UK). PCR was performed using Hifi Taq DNA polymerase in standard conditions, using 200 ng of template in a 50 µl PCR mix. The primers used to amplify SEQ ID NO: 175 (PLT1) were prm08180 (SEQ ID NO: 195; sense, start codon in bold, AttB1 site in italic: 5' *GGGGA-CAAGTTTGTA CAAAAAAGCAGGCTTAAAC*AATGAT-CAATCCACACGGTG 3') and prm08181 (SEQ ID NO: 196; reverse, complementary, AttB2 site in italic: 5' *GGGGAC-CACTTTGTACAAGAAAG CTGGGTTCCTTGTTTACT-CATTCCACA* 3'), which include the AttB sites for Gateway recombination. The primers used to amplify SEQ ID NO: 177 (PLT2) were prm08182 (SEQ ID NO: 197; sense, start codon in bold, AttB1 site in italic: 5'*GGGGACAAGTTTGTA- CAAAAAAGCAGGCTTAAAC*AATGAATTCTAACA ACTGGCTC 3') and prm08183 (SEQ ID NO: 198; reverse, complementary, AttB2 site in italic: 5' *GGGGACCACTTTG-TACAAGAAAGCTGGGTTCATCTTTTAT-TCATTCCACA* 3'), The amplified PCR fragments were purified also using standard methods. The first step of the Gateway procedure, the BP reaction, was then performed, during which the PCR fragment recombines in vivo with the pDONR201 plasmid to produce, according to the Gateway terminology, an "entry clone", pPLT1 for SEQ ID NO: 175 and pPLT2 for SEQ ID NO: 177. Plasmid pDONR201 was purchased from Invitrogen, as part of the Gateway® technology.

Example 26

Expression Vector Construction

The entry clones pPLT1 and pPLT2 were subsequently used in an LR reaction with destination vectors used for *Oryza sativa* transformation. A first vector contains as functional elements within the T-DNA borders: a plant selectable marker; a screenable marker expression cassette; and a Gateway cassette intended for LR in vivo recombination with the nucleic acid sequence of interest already cloned in the entry clone. A rice constitutive promoter, a GOS2 promoter (SEQ ID NO: 210, alternatively SEQ ID NO: 194 is equally useful) was located upstream of this Gateway cassette.

A second vector contains the same functional elements within the T-DNA borders: a plant selectable marker; a screenable marker expression cassette; and a Gateway cassette intended for LR in vivo recombination with the nucleic acid sequence of interest already cloned in the entry clone. A rice promoter for expression in meristems, an MT promoter (SEQ ID NO: 211) (PRO0126) was located upstream of this Gateway cassette.

After the LR recombination step, the resulting expression vectors, pGOS2::PLT1, pGOS2; PLT2, pMT::PLT1 and pMT::PLT2 (FIG. 16 shows the construct with the GOS2 promoter) were independently transformed into *Agrobacte-*

*rium* strain LBA4044 and subsequently to *Oryza sativa* plants. Transformed rice plants were allowed to grow and were then examined for the parameters described below.

Example 27

Crop Transformation

The transformed *Agrobacterium* containing the expression vectors were used independently to transform *Oryza sativa* plants. Mature dry seeds of the rice japonica cultivar Nipponbare were dehusked. Sterilization was carried out by incubating for one minute in 70% ethanol, followed by 30 minutes in 0.2% $HgCl_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

*Agrobacterium* strain LBA4404 containing the expression vector was used for co-cultivation. *Agrobacterium* was inoculated on AB medium with the appropriate antibiotics and cultured for 3 days at 28° C. The bacteria were then collected and suspended in liquid co-cultivation medium to a density ($OD_{600}$) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 35 independent T0 rice transformants were generated for one construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges 1996, Chan et al. 1993, Hiei et al. 1994).

Corn Transformation

Transformation of maize (*Zea mays*) is performed with a modification of the method described by Ishida et al. (1996) Nature Biotech 14(6): 745-50. Transformation is genotype-dependent in corn and only specific genotypes are amenable to transformation and regeneration. The inbred line A188 (University of Minnesota) or hybrids with A188 as a parent are good sources of donor material for transformation, but other genotypes can be used successfully as well. Ears are harvested from corn plant approximately 11 days after pollination (DAP) when the length of the immature embryo is about 1 to 1.2 mm. Immature embryos are cocultivated with *Agrobacterium tumefaciens* containing the expression vector, and transgenic plants are recovered through organogenesis. Excised embryos are grown on callus induction medium, then maize regeneration medium, containing the selection agent (for example imidazolinone but various selection markers can be used). The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Wheat Transformation

Transformation of wheat is performed with the method described by Ishida et al. (1996) Nature Biotech 14(6): 745-50. The cultivar Bobwhite (available from CIMMYT, Mexico) is commonly used in transformation. Immature embryos are co-cultivated with *Agrobacterium tumefaciens* containing the expression vector, and transgenic plants are recovered through organogenesis. After incubation with *Agrobacterium*, the embryos are grown in vitro on callus induction medium, then regeneration medium, containing the selection agent (for example imidazolinone but various selection markers can be used). The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Soybean Transformation

Soybean is transformed according to a modification of the method described in the Texas A&M U.S. Pat. No. 5,164,310. Several commercial soybean varieties are amenable to transformation by this method. The cultivar Jack (available from the Illinois Seed foundation) is commonly used for transformation. Soybean seeds are sterilised for in vitro sowing. The hypocotyl, the radicle and one cotyledon are excised from seven-day old young seedlings. The epicotyl and the remaining cotyledon are further grown to develop axillary nodes. These axillary nodes are excised and incubated with *Agrobacterium tumefaciens* containing the expression vector. After the cocultivation treatment, the explants are washed and transferred to selection media. Regenerated shoots are excised and placed on a shoot elongation medium. Shoots no longer than 1 cm are placed on rooting medium until roots develop. The rooted shoots are transplanted to soil in the greenhouse. T1 seeds are produced from plants that exhibit tolerance to the selection agent and that contain a single copy of the T-DNA insert.

Rapeseed/Canola Transformation

Cotyledonary petioles and hypocotyls of 5-6 day old young seedling are used as explants for tissue culture and transformed according to Babic et al. (1998, Plant Cell Rep 17: 183-188). The commercial cultivar Westar (Agriculture Canada) is the standard variety used for transformation, but other varieties can also be used. Canola seeds are surface-sterilized for in vitro sowing. The cotyledon petiole explants with the cotyledon attached are excised from the in vitro seedlings, and inoculated with *Agrobacterium* (containing the expression vector) by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with *Agrobacterium*, the petiole explants are transferred to MSBAP-3 medium containing 3 mg/l BAP, cefotaxime, carbenicillin, or timentin (300 mg/l)

for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MS0) for root induction. The rooted shoots are transplanted to soil in the greenhouse. T1 seeds are produced from plants that exhibit tolerance to the selection agent and that contain a single copy of the T-DNA insert.

Alfalfa Transformation

A regenerating clone of alfalfa (*Medicago sativa*) is transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown D C W and A Atanassov (1985. Plant Cell Tissue Organ Culture 4: 111-112). Alternatively, the RA3 variety (University of Wisconsin) has been selected for use in tissue culture (Walker et al., 1978 Am J Bot 65:654-659). Petiole explants are cocultivated with an overnight culture of *Agrobacterium tumefaciens* C58C1 pMP90 (McKersie et al., 1999 Plant Physiol 119: 839-847) or LBA4404 containing the expression vector. The explants are cocultivated for 3 d in the dark on SH induction medium containing 288 mg/L Pro, 53 mg/L thioproline, 4.35 g/L $K_2SO_4$, and 100 μm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings were transplanted into pots and grown in a greenhouse. T1 seeds are produced from plants that exhibit tolerance to the selection agent and that contain a single copy of the T-DNA insert.

Example 28

Phenotypic Evaluation Procedure 28.1 Evaluation Setup
Evaluation in Normal Growth Conditions The primary transformants were transferred from a tissue culture chamber to a greenhouse for growing and harvest of T1 seed. Six events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions. Greenhouse conditions were of shorts days (12 hours light), 28° C. in the light and 22° C. in the dark, and a relative humidity of 70%.

Evaluation Under Reduced Nitrogen Availability

The rice plants were grown in potting soil as under normal conditions except for the nutrient solution. The pots were watered from transplantation to maturation with a specific nutrient solution containing reduced N nitrogen (N) content, usually between 7 to 8 times less. The rest of the cultivation (plant maturation, seed harvest) was the same as for plants not grown under abiotic stress.

28.2 Statistical Analysis: F-Test

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and to verify for an overall effect of the gene, also known as a global gene effect. The threshold for significance for a true global gene effect was set at a 5% probability level for the F-test. A significant F-test value points to a gene effect, meaning that it is not only the mere presence or position of the gene that is causing the differences in phenotype.

To check for an effect of the genes within an event, i.e., for a line-specific effect, a t-test was performed within each event using data sets from the transgenic plants and the corresponding null plants. "Null plants" or "null segregants" or "nullizygotes" are the plants treated in the same way as the transgenic plant, but from which the transgene has segregated. Null plants can also be described as the homozygous negative transformed plants. The threshold for significance for the t-test is set at 10% probability level. The results for some events can be above or below this threshold. This is based on the hypothesis that a gene might only have an effect in certain positions in the genome, and that the occurrence of this position-dependent effect is not uncommon. This kind of gene effect is also named herein a "line effect of the gene". The p-value is obtained by comparing the t-value to the t-distribution or alternatively, by comparing the F-value to the F-distribution. The p-value then gives the probability that the null hypothesis (i.e., that there is no effect of the transgene) is correct.

28.3 Parameters Measured
Biomass-Related Parameter Measurement

From the stage of sowing until the stage of maturity the plants were passed several times through a digital imaging cabinet. At each time point digital images (2048×1536 pixels, 16 million colours) were taken of each plant from at least 6 different angles.

The plant aboveground area (or leafy biomass, areamax) was determined by counting the total number of pixels on the digital images from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The above ground area is the area measured at the time point at which the plant had reached its maximal leafy biomass. The early vigour is the plant (seedling) aboveground area three weeks post-germination. Increase in root biomass is expressed as an increase in total root biomass (measured as maximum biomass of roots observed during the lifespan of a plant); or as an increase in the root/shoot index (measured as the ratio between root mass and shoot mass in the period of active growth of root and shoot).

Seed-Related Parameter Measurements

The mature primary panicles were harvested, counted, bagged, barcode-labelled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed yield was measured by weighing all filled husks harvested from a plant. Total seed number per plant was measured by counting the number of husks harvested from a plant. Thousand Kernel Weight (TKW) is extrapolated from the number of filled seeds counted and their total weight. The Harvest Index (HI) in the present invention is defined as the ratio between the total seed yield and the above ground area (mm$^2$), multiplied by a factor $10^6$. The total number of flowers per panicle as defined in the present invention is the ratio between the total number of seeds and the number of mature primary panicles. The seed fill rate as defined in the present invention is the proportion (expressed as a %) of the number of filled seeds over the total number of seeds (or florets).

Example 29

Results of the Phenotypic Evaluation of the Transgenic Plants 29.1 Results of the Phenotypic Evaluation of the Transgenics Plants Grown Under Normal Growth Conditions, Expressing Either PLT1 or PLT2 Nucleic Acid Sequence Under the Control of a Constitutive Promoter The TKW measurement results of the T1 seeds of PLT1 and PLT2 transgenic rice plants grown under normal growth conditions, are shown in Table J, in absolute values (averaged events) and as a percentage compared to wild type plants. A substantial increase in TKW is observed for the transgenic seeds containing either construct, compared to wild type seeds.

TABLE J

Results of TKW measurements of the T1 seeds of PLT1 and PLT2 transgenic plants grown under normal growth conditions.

|  | TKW (g) | % increase |
|---|---|---|
| PLT1 transgenics | 0.0290 | 16% |
| PLT2 transgenics | 0.0288 | 15% |
| WT | 0.0250 | |

Individual seed parameters (including width, length, area, weight) were measured using a custom-made device consisting of two main components, a weighing and imaging device, coupled to software for image analysis.

The seed area and seed length measurement results of T1 seeds of PLT1 and PLT2 transgenic rice plants are shown in Table K in absolute values (averaged events) and as a percentage compared to wild type plants. A clear increase in both seed area and seed length is observed for the transgenic seeds containing either construct, compared to wild type seeds.

TABLE K

Results of seed area and seed length measurements of the T1 seeds of PLT1 and PLT2 transgenic plants grown under normal growth conditions.

|  | Seed area (mm$^2$) | % increase | Seed length (mm) | % increase |
|---|---|---|---|---|
| PLT1 transgenics | 27.60 | 12% | 9.4 | 13% |
| PLT2 transgenics | 27.35 | 11% | 9.4 | 13% |
| WT | 24.56 | | 8.3 | |

Seed width was not significantly affected on the T1 seeds of the PLT and PLT2 transgenic plants (data not shown).

29.2 Results of the Phenotypic Evaluation of the Transgenics Plants Grown Under Reduced Nitrogen Availability Conditions, Expressing Either PLT1 or PLT2 Nucleic Acid Sequence Under the Control of a Constitutive Promoter The TKW measurement results of the T1 seeds of PLT1 and PLT2 transgenic rice plants grown under reduced nitrogen availability conditions, are shown in Table L, in absolute values (averaged events) and as a percentage compared to wild type plants. A substantial increase in TKW is observed for the transgenic seeds containing either construct, compared to wild type seeds.

TABLE L

Results of TKW measurements of the T1 seeds of PLT1 and PLT2 transgenic plants grown under reduced nitrogen availability conditions.

|  | TKW (g) | % increase |
|---|---|---|
| PLT1 transgenics | 0.0295 | 12% |
| PLT2 transgenics | 0.0278 | 8% |
| WT | 0.0256 | |

29.3 Results of the Phenotypic Evaluation of the Transgenics Plants Grown Under Normal Growth Conditions, Expressing PLT2 Nucleic Acid Sequence Under the Control of a Meristem-Specific Promoter The TKW measurement results of the T1 seeds PLT2 transgenic rice plants grown under normal growth conditions, expressing PLT2 nucleic acid sequence under the control of a meristem-specific promoter, are shown in Table M, in absolute values (averaged events) and as a percentage compared to wild type plants. A substantial increase in TKW is observed for the transgenic seeds containing the construct, compared to wild type seeds.

TABLE M

Results of TKW measurements of the T1 seeds of PLT2 transgenic plants grown under normal growth conditions, expressing PLT2 nucleic acid sequence under the control of a mersitem-specific promoter.

|  | TKW (g) | % increase |
|---|---|---|
| PLT2 transgenics | 0.0263 | 3% |
| WT | 0.0254 | |

Example Section E bHLH

Example 30

Identification of Paralogues of the bHLH of SEQ ID NO: 213 in Rice

SEQ ID 2 was used to search for paralogues in the rice genome using a BLASTP algorithm used to perform similarity searches of a protein query sequence to a given database of protein sequences. The protein database queried corresponded to the rice proteome of the MIPS institute, the MIPS *Oryza sativa* Database (MOsDB), comprising 59,712 sequences; 27,051,637 total letters. Results were ranked according to highest similarity as determined from highest score and lowest e-value. Hits identifying bHLH protein sequences paralogous to SEQ ID NO: 2 had a score of at least 50 and an e-value lower than e-05. Pairwise alignments between the query sequence and the de novo identified paralogues are shown below.

| | | Smallest Sum |
| | High | Probability |
| Sequences producing High-scoring Segment Pairs: | Score | P(N) | N |
|---|---|---|---|
| 9629.m00093\|protein Helix-loop-helix DNA-binding domain, . . . | 1132 | 1.3e-115 | 1 |
| 9629.m00090\|protein Helix-loop-helix DNA-binding domain, . . . | 305 | 5.7e-28 | 1 |
| 9630.m01262\|protein Helix-loop-helix DNA-binding domain, . . . | 189 | 1.1e-15 | 1 |
| 9629.m07159\|protein Helix-loop-helix DNA-binding domain, . . . | 112 | 3.4e-05 | 1 |

Query: SEQID 2

>9629.m00093|protein Helix-loop-helix DNA-binding domain, putative
Length = 225

Score = 1132 (403.5 bits), Expect = 1.3e-115, P = 1.3e-115

Identities = 224/224 (100%), Positives = 224/224 (100%)

```
Query:      1   MKSRKNSTTSTKAAGSCHTSSSGGGGGGGNCYSSSSSKMERKDVEKNRRLHMKGLCLKLS       60
                MKSRKNSTTSTKAAGSCHTSSSGGGGGGGNCYSSSSSKMERKDVEKNRRLHMKGLCLKLS
Sbjct:      1   MKSRKNSTTSTKAAGSCHTSSSGGGGGGGNCYSSSSSKMERKDVEKNRRLHMKGLCLKLS       60

Query:     61   SLIPAAAPRRHHHHYSTSSSSSPPSSTKEAVTQLDHLEQAAAYIKQLKGRIDELKKRKQQ      120
                SLIPAAAPRRHHHHYSTSSSSSPPSSTKEAVTQLDHLEQAAAYIKQLKGRIDELKKRKQQ
Sbjct:     61   SLIPAAAPRRHHHHYSTSSSSSPPSSTKEAVTQLDHLEQAAAYIKQLKGRIDELKKRKQQ      120

Query:    121   AAALTTSTSNGGGGGMPVVEVRCQDGTLDVVVVSEAIREERERAVRLHEVIGVLEEEGAE      180
                AAALTTSTSNGGGGGMPVVEVRCQDGTLDVVVVSEAIREERERAVRLHEVIGVLEEEGAE
Sbjct:    121   AAALTTSTSNGGGGGMPVVEVRCQDGTLDVVVVSEAIREERERAVRLHEVIGVLEEEGAE      180

Query:    181   VVNASFSVVGDKIFYTLHSQALCSRIGLDASRVSHRLRNLLLQY                  224
                VVNASFSVVGDKIFYTLHSQALCSRIGLDASRVSHRLRNLLLQY
Sbjct:    181   VVNASFSVVGDKIFYTLHSQALCSRIGLDASRVSHRLRNLLLQY                  224
```

>9629.m00090|protein Helix-loop-helix DNA-binding domain, putative
Length = 363

Score = 305 (112.4 bits), Expect = 5.7e-28, P = 5.7e-28

Identities = 87/230 (37%), Positives = 126/230 (54%)

```
Query:     19   TSSSGGGGGGGNCYSSSSSKMERKDVEKNRRLHMKGLCLKLSSLIPAAAPRRHHHHYSTS       78
                TSSSG G       +++++  ERK++E+ RR MKGLC+KL+SLIP     + H   S
Sbjct:     18   TSSSGSGASS----TAAAAAERKEMERRRQDMKGLCVKLASLIP-----KEHCSMSKM       68

Query:     79   SSSSPPSSTKEAVTQLDHLEQAAAYIKQLKGRIDELKKRKQQ----------------AA      122
                ++S        TQL L++AAAYIK LK R+DEL    ++                  AA
Sbjct:     69   QAASR--------TQLGSLDEAAAYIKKLKERVDELHHKRSMMSITSSRCRSGGGGGPAA      120

Query:    123   ALTTSTSNGGGGGMPVVEVRCQDGTLDVVVVSEAIRE------------ERERAVRLHEV      170
                A   STS GGG    ++          VV V + ++E            R V+ H+V
Sbjct:    121   AAGQSTSGGGGGEEEEEDMTRTTAAAAVVEVRQHVQEGSLISLDVVLICSAARPVKFHDV      180

Query:    171   IGVLEEEGAEVVNASFSVVGDKIFYTLHSQALCSRIGLDASRVSHRLRNL            220
                I VLEEEGA++++A FS+     +YT++S+A  SRIG++ASR+S RLR L
Sbjct:    181   ITVLEEEGADIISANFSLAAHNFYYTIYSRAFSSRIGIEASRISERLRAL            230
```

>9630.m01262|protein Helix-loop-helix DNA-binding domain, putative
Length = 211

Score = 189 (71.6 bits), Expect = 1.1e-15, P = 1.1e-15

Identities = 66/214 (30%), Positives = 102/214 (47%)

```
Query:     21   SSGGGGGGGNCYSSSSSKMERKDVEKNRRLHMKGLCLKLSSLIPAAAPRRHH-HHYSTSS       79
                S+GGGGGGG         K +RK  E+ RR  M   L   L  SL+ +A P     +S S+
Sbjct:      7   SAGGGGGGG--------KPDRKTTERIRREQMNKLYSHLDSLVRSAPPTVNSIPSHSNSN       58

Query:     80   SSSPPSSTK------EAVTQLDHLEQAAAYIKQLKGRIDELKKRKQQ---AAALTTSTSN      130
                S             A  T+  D  L  AA  YI+Q +  R+D  L++KR++         +S+S+
Sbjct:     59   SKYHQRKLRILGGAAAATTRPDRLGVAAEYIRQTQERVDMLREKKRELTGGGGGSSSS          118

Query:    131   GGGGGM---PVVEVRCQDGTLDVVVVSEAIREERERAVRLHEVIGVLEEEGAEVVNASFS      187
                G G         P VEV+     L  ++  +  A   +       H  + +E+ G  +V NA FS
Sbjct:    119   GAGAATAAAPEVEVQHLGSGLHAILFTGAPPTD---GASFHRAVRAVEDAGGQVQNAHFS      175
```

```
Query:   188    VVGDKIFYTLHSQALCSRIGLDASRVSHRLRNLL                              221
                V G K  YT+H+       G++  RV  RL+  +
Sbjct:   176    VAGAKAVYTIHAMIGDGYGGIE--RVVQRLKEAI                              207
```

Example 31

Identification of Orthologues of the bHLH of SEQ ID NO: 213 in *Arabidopsis thaliana*

SEQ ID 2 was used to search for orthologues in the *Arabidopsis* genome using a BLASTP algorithm used to perform a similarity search of a protein query sequence to a given database of protein sequences. The protein database queried corresponded to the *Arabidopsis* proteome of the MIPS institute, the MIPS *Arabidopsis thaliana* database (MAtDB) comprising 26,735 sequences; 11,317,104 total letters. Results were ranked according to highest similarity as determined from highest score and lowest e-value. Hits identifying bHLH protein sequences orthologous to SEQ ID 2 had a score of at least 50 and an e-value lower than e-05. Pairwise alignments between the query sequence and the de novo identified orthologue are shown below.

```
                              Query: SEQID 2
                    Database: /home/data/blast/orgs_sets/arabi
                       26,735 sequences; 11,317,104 total letters.

Smallest
                                                                            Sum
                                                          High          Probability
Sequences producing High-scoring Segment Pairs:          Score       P(N)          N At1g10585 unknown protein                                 180       4.5e-15        1

At4g20970 hypothetical protein                            149       8.7e-12        1

At4g25410 putative protein                                118       2.0e-06        1

At5g51780 putative bHLH transcription factor (bHLH036)    105       1.5e-05        1

At5g51790 putative protein                                110       1.5e-05        1

>At1g10585 unknown protein
Length = 122

Score = 180 (68.4 bits), Expect = 4.5e-15, P = 4.5e-15

Identities = 38/119 (31%), Positives = 72/119 (60%)

Query:   106    QLKGRIDELKKRKQQAAALTTSTSNGGGGGMPVVEVRCQDGTLDVVVVSEAIREERERAV    165
                QLK  ++ LK++K+           G   +P + +R +D T+++ ++ + +   +R   V
Sbjct:   3      QLKENVNYLKEKKRTLLQGELGNLYEGSFLLPKLSIRSRDSTIEMNLIMD-LNMKR---V    58

Query:   166    RLHEVIGVLEEEGAEVVNASFSVVGDKIFYTLHSQALCSRIGLDASRVSHRLRNLLLQY     224
                 LHE++ +  EEEGA+V++A+   + D+  YT+ +QA+ SRIG+D SR+  R+R ++  Y
Sbjct:   59     MLHELVSIFEEEGAQVMSANLQNLNDRTTYTIIAQAIISRIGIDPSRIEERVRKIIYGY     117

>At4g20970 hypothetical protein
Length = 167

Score = 149 (57.5 bits), Expect = 8.7e-12, P = 8.7e-12

Identities = 49/171 (28), Positives = 86/171 (50%)

Query:   33     SSSSSKMERKDVEKNRRLHMKGLCLKLSSLIPAAAPRRHHHHYSTSSSSSPPSSTKEAVT    92
                +  S  ++RK VEKNRR+ MK L  +L SL+P         HH ST     + P      EA
Sbjct:   8      TGQSRSVDRKTVEKNRRMQMKSLYSELISLLP--------HHSSTEPLTLP-DQLDEAAN    58

Query:   93     QLDHLEQAAAYIKQLKGRI---DELKKRKQQ-AAALTTSTSNGGGGGMPVVEVRCQDGTL    148
                +   L+   ++ K  +    L+K    ++++++S        +P +E++  +  G++
Sbjct:   59     YIKKLQVNVEKKRERKRNLVATTTLEKLNSVGSSSVSSSVDVSVPRKLPKIEIQ-ETGSI    117

Query:   149    DVVVVSEAIREERERAVRLHEVIGVLEEE-GAEVVNASFSVVGDKIFYTLH            198
                 +  +  ++     E     E+I VL EE GAE+  +A  +S+V D  +F+TLH
Sbjct:   118    FHIFLVTSL----EHKFMFCEIIRVLTEELGAEITHAGYSIVDDAVFHTLH            164
```

Example 32

Identification of a bHLH from Medicago truncatula

The question to be addressed was whether the query sequence (SEQ ID NO: 227 from *Medicago truncatula*) was a bHLH polypeptide according to the definition applied herein. SEQ ID 227 was compared to the *Arabidopsis* proteome database of the MIPS institute.

Comparison was carried out using the BLASTP 2.0 MP-WashU algorithm, which performs similarity searches of a protein query sequence to a given database of protein sequences. (Reference: Gish, W. (1996-2002)). The parameters used in the comparison were E value 10 Cutoff score (S2): 56

The protein database queried corresponded to the *Arabidopsis* proteome of the MIPS institute comprising 26,735 sequences (Database: /home/data/blast/orgs_sets/arabi 26,735 sequences; 11,317,104 total letters). Results were ranked according to highest similarity as determined from highest score and lowest e-value. The first Hit identified (underlined in the alignment) corresponded to SEQ ID NO: 225 (At4g20970) indicating that the sequence is a bHLH polypeptide according to the definition applied herein. Pairwise alignments between the query sequence from *Medicago* and the first hit corresponding to the de novo identified bHLH are shown below.

BLASTP 2.0 MP-WashU [9 Sep. 2002] [decunix4.0-ev56-I32LPF64 2002-09-09T17:45:09]

Example 33

Identification of Sequences Related to the Nucleic Acid Sequence Used in the Methods of the Invention bHLH Sequences, whether nucleotide (full length cDNA, ESTs or genomic) or protein (full length or partial polypeptides), were used to identified other bHLH nucleotide or proteins sequences amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program was used to find regions of local similarity between sequences by comparing nucleic acid or polypeptide sequences to sequence databases and by calculating the statistical significance of matches. For example, the polypeptide encoded by SEQ ID NO: 213 was used as query to the nr (non-redundant: (Database: All GenBank+EMBL+DDBJ+PDB sequences (but no EST, STS, GSS, environmental samples or phase 0, 1 or 2 HTGS sequences) 3,819,973 sequences; 16,928,533,343 total letters) database sequence using the TBLASTN algorithm, with default settings and the filter to ignore low complexity sequences. The output of the analysis (shown below) was viewed by pairwise comparison, and ranked according to the probability score (E-value), where the score reflect the probability that a particular alignment occurs by chance (the lower the E-value, the more

```
                    Query = SEQ ID NO: 227
                         (140 letters)
            Database: /home/data/blast/orgs_sets/arabi
            26,735 sequences; 11,317,104 total letters.
              Searching....10....20....30....40....50....60....70....80....90....100% done
```

|  | High Score | Smallest Sum Probability P(N) | N |
|---|---|---|---|
| Sequences producing High-scoring Segment Pairs: |  |  |  |
| At4g20970 hypothetical protein | 248 | 2.8e-22 | 1 |
| At5g51780 putative bHLH transcription factor (bHLH036) | 103 | 6.5e-07 | 1 |
| At1g10585 unknown protein | 100 | 1.4e-06 | 1 |
| At4g25400 putative bHLH transcription factor (bHLH118) | 99 | 7.3e-06 | 1 |

```
>At4g20970 unknown protein
Length = 167

Score = 248 (92.4 bits), Expect = 2.8e-22, P = 2.8e-22

Identities = 52/123 (42%), Positives = 82/123 (66%)

Query:     7    EAISVPDQLKEATNYIKKLQINLEKMKEKKNFLLG---IQRPN------VNLNRNQKMGL    57
                E +++PDQL EA NYIKKLQ+N+EK +E+K  L+     +++ N      V+ + + +
Sbjct:    45    EPLTLPDQLDEAANYIKKLQVNVEKKRERKRNLVATTTLEKLNSVGSSSVSSSVDVSVPR   104

Query:    58    KSPKIKIQQIGLVLEVVLITGLESQFLFSETFRVLHEE-GVDIVNASYKVNEDSVFHSIH   116
                K PKI+IQ+ G +  + L+T LE +F+F  E  RVL EE G +I +A Y + +D+VFH++H
Sbjct:   105    KLPKIEIQETGSIFHIFLVTSLEHKFMFCEIIRVLTEELGAEITHAGYSIVDDAVFHTLH   164

Query:   117    CQV                                                         119
                C+V
Sbjct:   165    CKV                                                         166
``` significant the hit). In addition to E-values, comparisons were also scored by percentage identity. Percentage identity refers to the number of identical nucleotides (or amino acids) between the two compared nucleic acid (or polypeptide) sequences over a particular length.

Hits on the database identifying BHLH proteins produced a score of at least 50 and an e-value equal to or lower than e-05.

for DNA or protein sequences without needing pre-alignment of the data. The program performs a series of pair-wise alignments, calculates similarity and identity, and then places the results in a distance matrix.

Parameters used in the comparison were:
Scoring matrix: Blosum62
First Gap: 12
Extending gap: 2
Results are shown in FIG. 19a.

| Sequences producing significant alignments: | Score (Bits) | E Value |
|---|---|---|
| gi\|55765745\|ref\|NM_183508.2\| Oryza sativa (japonica cultivar-gro | 440 | 1e-121 |
| gi\|42821746\|dbj\|AK109432.2\| Oryza sativa (japonica cultivar-g . . . | 440 | 1e-121 |
| gi\|55769744\|ref\|XM_549862.1\| Oryza sativa (japonica cultivar-gro | 247 | 1e-105 |
| gi\|58530787\|dbj\|AP008207.1\| Oryza sativa (japonica cultivar-g . . . | 263 | 2e-68 |
| gi\|17385651\|dbj\|AP002845.3\| Oryza sativa (japonica cultivar-g . . . | 263 | 2e-68 |
| gi\|32980356\|dbj\|AK070332.1\| Oryza sativa (japonica cultivar-g . . . | 251 | 9e-65 |
| gi\|34894135\|ref\|NM_183504.1\| Oryza sativa (japonica cultivar-gro | 137 | 3e-30 |
| gi\|15293050\|gb\|AY050959.1\| Arabidopsis thaliana unknown prote . . . | 80.1 | 6e-16 |
| gi\|19340923\|ref\|NM_100934.2\| Arabidopsis thaliana transcripti . . . | 87.8 | 2e-15 |
| gi\|58531195\|dbj\|AP008214.1\| Oryza sativa (japonica cultivar-g . . . | 51.6 | 4e-13 |
| gi\|42408246\|dbj\|AP004557.3\| Oryza sativa (japonica cultivar-g . . . | 51.6 | 4e-13 |
| gi\|42408168\|dbj\|AP004376.3\| Oryza sativa (japonica cultivar-g . . . | 51.6 | 4e-13 |
| gi\|22328837\|ref\|NM_118215.2\| Arabidopsis thaliana DNA binding . . . | 78.2 | 1e-12 |
| gi\|7268888\|emb\|AL161554.2\|ATCHRIV54 Arabidopsis thaliana DNA chr | 77.8 | 2e-12 |
| gi\|5262774\|emb\|AL080282.1\|ATT13K14 Arabidopsis thaliana DNA c . . . | 77.8 | 2e-12 |
| gi\|50906596\|ref\|XM_464787.1\| Oryza sativa (japonica cultivar-gro | 77.0 | 3e-12 |

Example 34

Determination of Global Similarity and Identity Between bHLH Transcription Factors Global percentages similarity and identity between bHLH polypeptides was determined using the MatGAT software (BMC Bioinformatics. 2003 Jul. 10; 4:29. MatGAT: an application that generates similarity/identity matrices using protein or DNA sequences. Campanella J J, Bitincka L, Smalley J.). MatGAT software generates similarity/identity matrices Example 35

Determination of Global Similarity and Identity Between bHLH Domains in bHLH Polypeptides bHLH domains were mapped using the SMART software (Schultz et al. (1998) Proc. Natl. Acad. Sci. USA 95, 5857-5864; Letunic et al. (2006) Nucleic Acids Res 34, D257-D260). Smart software is available through EMBL institute (European Molecular Biology Laboratory (EMBL).

The sequences of the bHLH domain used are given below.

```
Hv_BHLH
KESEKERRKRMKALCEKLASLIPREHCCSTTDTMTQLGSLDVGASYIKKLKERVDE

OS_NP_908393_BHLH
KEMERRRQDMKGLCVKLASLIPKEHCSMSKMQAASRTQLGSLDEAAAYIKKLKERVDE

OS_NP_908397.1_BHLH
KDVEKNRRLHMKGLCLKLSSLI-
PAAAPRRHHHHYSTSSSSSPPSSTKEAVTQLDHLEQAAAYIKQLKGR
IDE

Os_XP_464787.1_BHLH
KTTERIRREQMNKLYSHLDSLVR-
SAPPTVNSIPSHSNSNSKYHQRKLRILGGAAAATTRPDRLGVAAEY
IRQTQERVDM
```

-continued

AT1G10585_bHLH
nlrekdrrmrmkhlfsilsshvsptrklpvphlidqatsymiqlkenvny

At4g20970_bHLH
KTVEKNRRMQMKSLYSELISLLPHHSSTEPLTLPDQLDEAANYIKKLQVNVEK

Global percentages of similarity and identity between bHLH domains of bHLH polypeptides were determined using the software and parameters described in Example 34. Results are shown in FIG. 19b.

Example 36

Cloning of the Nucleic Acid Sequence Used in the Methods of the Invention

The nucleic acid sequence used in the methods of the invention was amplified by PCR using as template a custom-made Oryza sativa seedlings cDNA library (in pCMV Sport 6.0; Invitrogen, Paisley, UK). PCR was performed using Hifi Taq DNA polymerase in standard conditions, using 200 ng of template in a 50 µl PCR mix. The primers used were prm06808 (SEQ ID NO: 231; sense, start codon in bold, AttB1 site in italic: 5'-ggggacaagtttgtacaaaaaagcag-gcttaaacaatgaagagcaggaagaacagc 3') and prm06809 (SEQ ID NO: 232; reverse, complementary, AttB2 site in italic: 5' ggggaccactttgtacaagaaagctgggtgcagagtgaaagagtggtgtg 3'), which include the AttB sites for Gateway recombination. The amplified PCR fragment was purified also using standard methods. The first step of the Gateway procedure, the BP reaction, was then performed, during which the PCR fragment recombines in vivo with the pDONR201 plasmid to produce, according to the Gateway terminology, an "entry clone", pbHLH. Plasmid pDONR201 was purchased from Invitrogen, as part of the Gateway® technology.

Example 37

Expression Vector Construction

The entry clone p076 was subsequently used in an LR reaction with pGOS2, a destination vector used for Oryza sativa transformation. This vector contains as functional elements within the T-DNA borders: a plant selectable marker; a screenable marker expression cassette; and a Gateway cassette intended for LR in vivo recombination with the nucleic acid sequence of interest already cloned in the entry clone. A rice GOS2 promoter (SEQ ID NO: 233, alternatively, SEQ ID NO: 230 is equally useful) for constitutive expression (internal reference PRO0129) was located upstream of this Gateway cassette.

After the LR recombination step, the resulting expression vector pGOS2::bHLH (FIG. 20) was transformed into Agrobacterium strain LBA4044 and subsequently to Oryza sativa plants.

Example 38

Plant Transformation

Rice Transformation
The Agrobacterium containing the expression vector was used to transform Oryza sativa plants. Mature dry seeds of the rice japonica cultivar Nipponbare were dehusked. Sterilization was carried out by incubating for one minute in 70% ethanol, followed by 30 minutes in 0.2% HgCl$_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

Agrobacterium strain LBA4404 containing the expression vector was used for co-cultivation. Agrobacterium was inoculated on AB medium with the appropriate antibiotics and cultured for 3 days at 28° C. The bacteria were then collected and suspended in liquid co-cultivation medium to a density (OD$_{600}$) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 30 independent T0 rice transformants were generated for one construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges 1996, Chan et al. 1993, Hiei et al. 1994).

Corn Transformation

Transformation of maize (Zea mays) is performed with a modification of the method described by Ishida et al. (1996) Nature Biotech 14(6): 745-50. Transformation is genotype-dependent in corn and only specific genotypes are amenable to transformation and regeneration. The inbred line A188 (University of Minnesota) or hybrids with A188 as a parent are good sources of donor material for transformation, but other genotypes can be used successfully as well. Ears are harvested from corn plant approximately 11 days after pollination (DAP) when the length of the immature embryo is about 1 to 1.2 mm. Immature embryos are cocultivated with Agrobacterium tumefaciens containing the expression vector, and transgenic plants are recovered through organogenesis. Excised embryos are grown on callus induction medium, then maize regeneration medium, containing the selection agent (for example imidazolinone but various selection markers can be used). The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Wheat Transformation

Transformation of wheat is performed with the method described by Ishida et al. (1996) Nature Biotech 14(6): 745-50. The cultivar Bobwhite (available from CIMMYT, Mexico) is commonly used in transformation. Immature embryos are co-cultivated with *Agrobacterium tumefaciens* containing the expression vector, and transgenic plants are recovered through organogenesis. After incubation with *Agrobacterium*, the embryos are grown in vitro on callus induction medium, then regeneration medium, containing the selection agent (for example imidazolinone but various selection markers can be used). The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Soybean Transformation

Soybean is transformed according to a modification of the method described in the Texas A&M U.S. Pat. No. 5,164,310. Several commercial soybean varieties are amenable to transformation by this method. The cultivar Jack (available from the Illinois Seed foundation) is commonly used for transformation. Soybean seeds are sterilised for in vitro sowing. The hypocotyl, the radicle and one cotyledon are excised from seven-day old young seedlings. The epicotyl and the remaining cotyledon are further grown to develop axillary nodes. These axillary nodes are excised and incubated with *Agrobacterium tumefaciens* containing the expression vector. After the cocultivation treatment, the explants are washed and transferred to selection media. Regenerated shoots are excised and placed on a shoot elongation medium. Shoots no longer than 1 cm are placed on rooting medium until roots develop. The rooted shoots are transplanted to soil in the greenhouse. T1 seeds are produced from plants that exhibit tolerance to the selection agent and that contain a single copy of the T-DNA insert.

Rapeseed/Canola Transformation

Cotyledonary petioles and hypocotyls of 5-6 day old young seedling are used as explants for tissue culture and transformed according to Babic et al. (1998, Plant Cell Rep 17: 183-188). The commercial cultivar Westar (Agriculture Canada) is the standard variety used for transformation, but other varieties can also be used. Canola seeds are surface-sterilized for in vitro sowing. The cotyledon petiole explants with the cotyledon attached are excised from the in vitro seedlings, and inoculated with *Agrobacterium* (containing the expression vector) by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with *Agrobacterium*, the petiole explants are transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MS0) for root induction. The rooted shoots are transplanted to soil in the greenhouse. T1 seeds are produced from plants that exhibit tolerance to the selection agent and that contain a single copy of the T-DNA insert.

Alfalfa Transformation

A regenerating clone of alfalfa (*Medicago sativa*) is transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown D C W and A Atanassov (1985. Plant Cell Tissue Organ Culture 4: 111-112). Alternatively, the RA3 variety (University of Wisconsin) has been selected for use in tissue culture (Walker et al., 1978 Am J Bot 65:654-659). Petiole explants are cocultivated with an overnight culture of *Agrobacterium tumefaciens* C58C1 pMP90 (McKersie et al., 1999 Plant Physiol 119: 839-847) or LBA4404 containing the expression vector. The explants are cocultivated for 3 d in the dark on SH induction medium containing 288 mg/L Pro, 53 mg/L thioproline, 4.35 g/L K2SO4, and 100 μm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings were transplanted into pots and grown in a greenhouse. T1 seeds are produced from plants that exhibit tolerance to the selection agent and that contain a single copy of the T-DNA insert.

Example 39

Evaluation Procedure 39.1 Evaluation Setup

Approximately 30 independent T0 rice transformants were generated. The primary transformants were transferred from a tissue culture chamber to a greenhouse for growing and harvest of T1 seed. Seven events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions. Greenhouse conditions were of shorts days (12 hours light), 28° C. in the light and 22° C. in the dark, and a relative humidity of 70%.

Four T1 events were further evaluated in the T2 generation following the same evaluation procedure as for the T1 generation but with more individuals per event. From the stage of sowing until the stage of maturity the plants were passed several times through a digital imaging cabinet. At each time point digital images (2048×1536 pixels, 16 million colours) were taken of each plant from at least 6 different angles.

39.2 Statistical Analysis: t-Test and F-Test

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and to verify for an overall effect of the gene, also known as a global gene effect. The threshold for significance for a true global gene effect was set at a 5% probability level for the F-test. A significant F-test value points to a gene effect, meaning that it is not only the mere presence or position of the gene that is causing the differences in phenotype.

To check for an effect of the genes within an event, i.e., for a line-specific effect, a t-test was performed within each event using data sets from the transgenic plants and the corresponding null plants. "Null plants" or "null segregants" or "nullizygotes" are the plants treated in the same way as the transgenic plant, but from which the transgene has segregated. Null plants can also be described as the homozygous negative transformed plants. The threshold for significance for the t-test is set at 10% probability level. The results for some events can be above or below this threshold. This is based on the hypothesis that a gene might only have an effect in certain positions in the genome, and that the occurrence of this position-dependent effect is not uncommon. This kind of gene effect is also named herein a "line effect of the gene". The p-value is obtained by comparing the t-value to the t-distribution or alternatively, by comparing the F-value to the F-distribution. The p-value then gives the probability that the null hypothesis (i.e., that there is no effect of the transgene) is correct.

Example 40

Evaluation Results

Early vigour was determined by counting the total number of pixels from aboveground plant parts discriminated from the background. This value was averaged for the pictures taken on the same time point from different angles and was converted to a physical surface value expressed in square mm by calibration. The results described below are for plants three weeks post-germination.

Early vigour (as determined by aboveground area) was seen in six out of seven events of the T1 generation, with an overall increase in aboveground area for transgenic seedlings of 22% compared to control plants. Four of these T1 events were further evaluated in the T2 generation, and all four of these events gave an increase in aboveground area for transgenic seedlings compared to control plants, with an overall increase in aboveground area for transgenic seedlings of 13% compared to control plants. The results were also shown to be statistically significant with the p-value from the F-test being 0.0007 (T2 generation) indicating that the effect seen is likely due to the transgene rather than the position of the gene or a line effect.

Example Section F

SPL15

Example 41

Identification of Sequences Related to the Nucleic Acid Sequence Used in the Methods of the Invention Sequences (full length cDNA, ESTs or genomic) related to the nucleic acid sequence used in the methods of the present invention were identified amongst those maintained in the Entrez Nucleotides database at the National Center for Biotechnology Information using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid or polypeptide sequences to sequence databases and by calculating the statistical significance of matches. The polypeptide encoded by the nucleic acid of the present invention was used for the TBLASTN algorithm, with default settings and the filter to ignore low complexity sequences set off. The output of the analysis was viewed by pairwise comparison, and ranked according to the probability score (E-value), where the score reflect the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search The Table N below provides a list of nucleic acid sequences related to the nucleic acid sequence used in the methods of the present invention.

TABLE N nucleic acid sequences related to the nucleic acid sequence (SEQ ID NO: 234) used in the methods of the present invention, and the corresponding deduced polypeptides

| Name | Nucleic acid SEQ ID NO | Polypeptide SEQ ID NO | Sequence length | NCBI accession number | Source organism |
|---|---|---|---|---|---|
| Arath_SPL15 (At3g57920) | 234 | 235 | Full length | NM_115654.1 | *Arabidopsis thaliana* |
| Arath_SPL9 (At2g42200) | 236 | 237 | Full length | AY150378 | *Arabidopsis thaliana* |
| Aqufo_SPL | 238 | 239 | Full length | contig of DR915312 DR949057.1 | *Aquilegia formosa* × *Aquilegia pubescens* |
| Goshi_SPL | 240 | 241 | Full length | DT566400 | *Gossypium hirsutum* |
| Iponi_SPL | 242 | 243 | Full length | contig of BJ576204.1 BJ556115 BJ567301 | *Ipomoea nil* |
| Lacsa_SPL | 244 | 245 | Full length | contig of DY966949 DW119178 | *Lactuca sativa* |
| Maldo_SPL | 246 | 247 | Full length | contig of CN891102.1 CO868185.1 CV523507 | *Malus domestica* |
| Medtr_SPL | 248 | 249 | Full length | spliced from AC170989.2 | *Medicago truncatula* |

TABLE N-continued nucleic acid sequences related to the nucleic acid sequence (SEQ ID NO: 234) used in the methods of the present invention, and the corresponding deduced polypeptides

| Name | Nucleic acid SEQ ID NO | Polypeptide SEQ ID NO | Sequence length | NCBI accession number | Source organism |
|---|---|---|---|---|---|
| Nicbe_SPL | 250 | 251 | Full length | contig of CK284078.1 CK294165 | Nicotiana bentamiana |
| Orysa_SPL | 252 | 253 | Full length | XM_483285 | Oryza sativa |
| Orysa_SPL II | 254 | 255 | Full length | spliced from AC108762 | Oryza sativa |
| Soltu_SPL | 256 | 257 | Full length | contig of CK246692.1 CK254420.1 | Solanum tuberosum |
| Vitvi_SPL | 258 | 259 | Full length | contig of CV098277 CV092812.1 | Vitis vinifera |
| Zeama_SPL | 260 | 261 | Full length | contig of EB160653 DY235599 DV029129 | Zea mays |
| Zeama_SPL II | 262 | 263 | Full length | contig of AJ011619 DV033513.1 DY532686.1 | Zea mays |
| Sorpr_SPL | 264 | 265 | Partial | BF422188 | Sorghum propinquium |
| Allce_SPL | 266 | 267 | Partial | CF444518.1 | Allium cepa |
| Antma_SPL | 268 | 269 | Partial | AMA011623 | Antirrhinum majus |
| Brana_SPL | 270 | 271 | Partial | CX189447 | Brassica napus |
| Sacof_SPL | 272 | 273 | Partial | contig of CA113070 CA254724 | Saccharum officinarum |
| Fesar_SPL | 274 | 275 | Partial | DT706587.1 | Festuca arundinacea |
| Brara_SPL | 282 | 283 | Full length | AC189445.1 | Brassica rapa |
| Glyma_SPL | 284 | 285 | Full length | CX708501.1 BG651519.1 | Glycine max |
| Poptr_SPL | 286 | 287 | Full length | scaff_XVI.416 | Populus tremuloides |
| Citcl_SPL | 288 | 289 | Partial | DY293795 | Citrus clementina |
| Betvu_SPL | 290 | 291 | Partial | BQ594361.1 | Beta vulgaris |
| Hevbr_SPL | 292 | 293 | Partial | EC604947 | Hevea brasiliensis |

Example 42

Determination of Global Similarity and Identity Between SPL15 Transcription Factors, and their SPL DBD Global percentages of similarity and identity between SPL15 transcription factors were determined using one of the methods available in the art, the MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line. The sequence of SEQ ID NO: 235 is indicated as number 5 in the matrix. Parameters used in the comparison were:

Scoring matrix: Blosum62
First Gap: 12
Extending gap: 2

Results of the software analysis are shown in Table O for the global similarity and identity over the full length of the SPL15 transcription factor polypeptides. Percentage identity is given above the diagonal and percentage similarity is given below the diagonal. Percentage identity between the SPL15 transcription factor paralogues and orthologues ranges between 30 and 70%, reflecting the relatively low sequence identity conservation between them outside of the SPL DBD.

TABLE O

MatGAT results for global similarity and identity over the full length of the SPL15 transcription factor polypeptides.

| Global similarity and identity over the full length of the SPL15 transcription factor polypeptides | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 1. Arath_SPL9 |  | 51.1 | 44.8 | 40.3 | 38.4 | 44 | 43.1 | 40.3 | 34.6 | 35.9 | 39.4 | 46.7 | 33.9 | 35.7 |
| 2. Arath_SPL15 | 63.2 |  | 39.4 | 39 | 33.7 | 40.1 | 40.3 | 35.1 | 31.3 | 33.7 | 36.5 | 39.6 | 30.5 | 31.9 |
| 3. Goshi_SPL | 58.9 | 53.2 |  | 47.3 | 43 | 54.4 | 46.9 | 52 | 41.3 | 40.2 | 50.1 | 59.8 | 39.5 | 39.1 |
| 4. Iponi_SPL | 53.3 | 55.9 | 61.7 |  | 43.9 | 50.9 | 46.8 | 56.1 | 33.6 | 37.2 | 56.7 | 53.5 | 36.3 | 38.7 |
| 5. Lacsa_SPL | 52 | 49.4 | 53.2 | 61.3 |  | 45.8 | 43.5 | 46.4 | 37 | 38.3 | 47.9 | 48.1 | 37.6 | 39.9 |
| 6. Maldo_SPL | 59.3 | 54.5 | 64.3 | 63.5 | 56.3 |  | 49.5 | 57.4 | 42 | 38.1 | 55.2 | 68.7 | 38.9 | 40.6 |
| 7. Medtr_SPL | 55.2 | 57.6 | 60.4 | 64.5 | 58.4 | 65.1 |  | 46.7 | 37.3 | 39.2 | 46.3 | 55.4 | 37.6 | 39.7 |
| 8. Nicbe_SPL | 58.2 | 51.6 | 63.8 | 66.8 | 56.8 | 70.8 | 62.9 |  | 36.9 | 40 | 66.6 | 62.1 | 38.2 | 37.5 |
| 9. Orysa_SPL | 48.7 | 42.2 | 54.2 | 47 | 47.2 | 53.2 | 49.2 | 51.8 |  | 62.4 | 37.3 | 40.7 | 59.5 | 54.9 |

TABLE O-continued

MatGAT results for global similarity and identity over the full length of the SPL15 transcription factor polypeptides.

| Global similarity and identity over the full length of the SPL15 transcription factor polypeptides | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 10. Orysa_SPL II | 49.9 | 45.8 | 53.4 | 49.1 | 48.9 | 51.1 | 53.4 | 53.2 | 72.2 | | 37.6 | 43.6 | 54.3 | 62.9 |
| 11. Soltu_SPL | 57.3 | 54 | 64 | 68.5 | 59.4 | 69.6 | 62.9 | 77.6 | 51.8 | 50.4 | | 60.7 | 36.9 | 37.9 |
| 12. Vitvi_SPL | 62.8 | 54.9 | 69.2 | 66 | 59.4 | 80.2 | 67.5 | 73.4 | 53.5 | 56.5 | 73.6 | | 42.2 | 40.8 |
| 13. Zeama_SPL | 47.3 | 43.3 | 55.2 | 48.8 | 49.3 | 52 | 51.2 | 52.5 | 68.3 | 67.9 | 49.8 | 54 | | 54.9 |
| 14. Zeama_SPL II | 49.2 | 43.1 | 53.2 | 51.6 | 50.8 | 54.5 | 53.2 | 48.7 | 64.3 | 71.2 | 51.1 | 54.6 | 66.2 | |

Results of the software analysis are shown in Table P for the global similarity and identity over the SPL DBD of the SPL15 transcription factor polypeptides. Percentage identity is given above the diagonal and percentage similarity is given below the diagonal. Percentage identity between the SPL DBD of SPL15 transcription factor paralogues and orthologues ranges between 70% and 100%.

AttB2 site in lower case: 5' ggggaccactttgtacaagaaagctgggtTGATGAAGATCTTAAAAGGTGA 3'), which include the AttB sites for Gateway recombination. The amplified PCR fragment was purified also using standard methods. The first step of the Gateway procedure, the BP reaction, was then performed, during which the PCR fragment recombines in vivo with the pDONR201 plasmid to produce, according to

TABLE P

MatGAT results for global similarity and identity over the SPL DBD of the SPL15 transcription factor polypeptides.

| Global similarity and identity over the SPL DBD of the SPL15 transcription factor polypeptides | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 1. SPL\DBD\Aqufo_SPL | | 75.6 | 79.5 | 84.8 | 85.9 | 87.2 | 85.9 | 88.5 | 84.6 | 80.8 | 78.2 | 85.9 | 91 | 76.9 |
| 2. SPL\DBD\Arath_SPL15 | 82.1 | | 78.2 | 83.5 | 82.1 | 78.2 | 76.9 | 78.2 | 79.5 | 71.8 | 74.4 | 79.5 | 79.5 | 71.8 |
| 3. SPL\DBD\Arath_SPL9 | 87.2 | 85.9 | | 77.2 | 78.2 | 82.1 | 82.1 | 79.5 | 78.2 | 76.9 | 78.2 | 79.5 | 80.8 | 76.9 |
| 4. SPL\DBD\Goshi_SPL | 88.6 | 91.1 | 86.1 | | 86.1 | 84.8 | 84.8 | 84.8 | 84.8 | 78.5 | 78.5 | 86.1 | 89.9 | 78.5 |
| 5. SPL\DBD\Iponi_SPL | 89.7 | 85.9 | 87.2 | 91.1 | | 84.6 | 84.6 | 85.9 | 85.9 | 80.8 | 79.5 | 87.2 | 89.7 | 78.2 |
| 6. SPL\DBD\Lacsa_SPL | 89.7 | 85.9 | 88.5 | 91.1 | 91 | | 88.5 | 84.6 | 85.9 | 80.8 | 79.5 | 85.9 | 89.7 | 78.2 |
| 7. SPL\DBD\Maldo_SPL | 92.3 | 82.1 | 88.5 | 89.9 | 91 | 91 | | 84.6 | 89.7 | 85.9 | 83.3 | 88.5 | 91 | 80.8 |
| 8. SPL\DBD\Medtr_SPL | 89.7 | 85.9 | 89.7 | 92.4 | 92.3 | 91 | 93.6 | | 84.6 | 79.5 | 78.2 | 88.5 | 93.6 | 78.2 |
| 9. SPL\DBD\Nicbe_SPL | 87.2 | 83.3 | 85.9 | 88.6 | 92.3 | 89.7 | 91 | 92.3 | | 84.6 | 82.1 | 88.5 | 89.7 | 80.8 |
| 10. SPL\DBD\Orysa_SPL | 87.2 | 80.8 | 84.6 | 84.8 | 88.5 | 85.9 | 89.7 | 85.9 | 89.7 | | 85.9 | 84.6 | 83.3 | 83.3 |
| 11. SPL\DBD\Orysa_SPL II | 84.6 | 82.1 | 87.2 | 83.5 | 85.9 | 84.6 | 88.5 | 85.9 | 88.5 | 92.3 | | 82.1 | 82.1 | 84.6 |
| 12. SPL\DBD\Soltu_SPL | 89.7 | 87.2 | 87.2 | 91.1 | 94.9 | 89.7 | 93.6 | 93.6 | 92.3 | 87.2 | 84.6 | | 93.6 | 80.8 |
| 13. SPL\DBD\Vitvi_SPL | 92.3 | 87.2 | 89.7 | 93.7 | 94.9 | 92.3 | 96.2 | 97.4 | 92.3 | 87.2 | 87.2 | 96.2 | | 82.1 |
| 14. SPL\DBD\Zeama_SPL II | 83.3 | 79.5 | 84.6 | 83.5 | 84.6 | 83.3 | 84.6 | 87.2 | 84.6 | 88.5 | 89.7 | 83.3 | 85.9 | |

Example 43

Cloning of the Nucleic Acid Sequence Used in the Methods of the Invention

DNA manipulation: unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfase (1993) by R. D. D. Croy, published by BIOS Scientific Publications Ltd (UK) and Blackwell Scientific Publications (UK).

The nucleic acid sequence used in the methods of the invention was amplified by PCR using as template a custom-made *Arabidopsis thaliana* mixed tissues cDNA library (in pCMV Sport 6.0; Invitrogen, Paisley, UK). PCR was performed using Hifi Taq DNA polymerase in standard conditions, using 200 ng of template in a 50 μl PCR mix. The primers used were prm07277 (SEQ ID NO: 280; sense, start codon in bold, AttB1 site in lower case: 5'-ggggacaagtttgtacaaaaaagcaggcttaaacaATGGAGTTGTTAATGTGTTCG 3') and prm07278 (SEQ ID NO: 281; reverse, complementary, the Gateway terminology, an "entry clone", pSPL15. Plasmid pDONR201 was purchased from Invitrogen, as part of the Gateway® technology.

Example 44

Expression Vector Construction

The entry clone p13075 was subsequently used in an LR reaction with p06659, a destination vector used for *Oryza sativa* transformation. This vector contains as functional elements within the T-DNA borders: a plant selectable marker; a screenable marker expression cassette; and a Gateway cassette intended for LR in vivo recombination with the nucleic acid sequence of interest already cloned in the entry clone. A rice HMGB promoter (SEQ ID NO: 294) for constitutive expression was located upstream of this Gateway cassette. Alternatively, the HMGB promoter represented by SEQ ID NO: 46 is equally useful. A similar construct was made with the SPL15 coding sequence under control of the constitutive GOS2 promoter (SEQ ID NO: 295).

After the LR recombination step, the resulting expression vector pHMGB::SPL15 (FIG. 26), or pGOS2::SPL15, was transformed into *Agrobacterium* strain LBA4044 and subsequently to *Oryza sativa* plants.

Example 45

Plant Transformation

Rice Transformation

The *Agrobacterium* containing the expression vector was used to transform *Oryza sativa* plants. Mature dry seeds of the rice japonica cultivar Nipponbare were dehusked. Sterilization was carried out by incubating for one minute in 70% ethanol, followed by 30 minutes in 0.2% $HgCl_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

*Agrobacterium* strain LBA4404 containing the expression vector was used for co-cultivation. *Agrobacterium* was inoculated on AB medium with the appropriate antibiotics and cultured for 3 days at 28° C. The bacteria were then collected and suspended in liquid co-cultivation medium to a density ($OD_{600}$) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 35 independent T0 rice transformants were generated for one construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges 1996, Chan et al. 1993, Hiei et al. 1994).

Corn Transformation

Transformation of maize (*Zea mays*) is performed with a modification of the method described by Ishida et al. (1996) Nature Biotech 14(6): 745-50. Transformation is genotype-dependent in corn and only specific genotypes are amenable to transformation and regeneration. The inbred line A188 (University of Minnesota) or hybrids with A188 as a parent are good sources of donor material for transformation, but other genotypes can be used successfully as well. Ears are harvested from corn plant approximately 11 days after pollination (DAP) when the length of the immature embryo is about 1 to 1.2 mm. Immature embryos are cocultivated with *Agrobacterium tumefaciens* containing the expression vector, and transgenic plants are recovered through organogenesis. Excised embryos are grown on callus induction medium, then maize regeneration medium, containing the selection agent (for example imidazolinone but various selection markers can be used). The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Wheat Transformation

Transformation of wheat is performed with the method described by Ishida et al. (1996) Nature Biotech 14(6): 745-50. The cultivar Bobwhite (available from CIMMYT, Mexico) is commonly used in transformation. Immature embryos are co-cultivated with *Agrobacterium tumefaciens* containing the expression vector, and transgenic plants are recovered through organogenesis. After incubation with *Agrobacterium*, the embryos are grown in vitro on callus induction medium, then regeneration medium, containing the selection agent (for example imidazolinone but various selection markers can be used). The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Soybean Transformation

Soybean is transformed according to a modification of the method described in the Texas A&M U.S. Pat. No. 5,164,310. Several commercial soybean varieties are amenable to transformation by this method. The cultivar Jack (available from the Illinois Seed foundation) is commonly used for transformation. Soybean seeds are sterilised for in vitro sowing. The hypocotyl, the radicle and one cotyledon are excised from seven-day old young seedlings. The epicotyl and the remaining cotyledon are further grown to develop axillary nodes. These axillary nodes are excised and incubated with *Agrobacterium tumefaciens* containing the expression vector. After the cocultivation treatment, the explants are washed and transferred to selection media. Regenerated shoots are excised and placed on a shoot elongation medium. Shoots no longer than 1 cm are placed on rooting medium until roots develop. The rooted shoots are transplanted to soil in the greenhouse. T1 seeds are produced from plants that exhibit tolerance to the selection agent and that contain a single copy of the T-DNA insert.

Rapeseed/Canola Transformation

Cotyledonary petioles and hypocotyls of 5-6 day old young seedling are used as explants for tissue culture and transformed according to Babic et al. (1998, Plant Cell Rep 17: 183-188). The commercial cultivar Westar (Agriculture Canada) is the standard variety used for transformation, but other varieties can also be used. Canola seeds are surface-sterilized for in vitro sowing. The cotyledon petiole explants with the cotyledon attached are excised from the in vitro seedlings, and inoculated with *Agrobacterium* (containing the expression vector) by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with *Agrobacterium*, the petiole explants are transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MS0) for root induction. The rooted shoots are transplanted to soil in the greenhouse. T1 seeds are produced from plants that exhibit tolerance to the selection agent and that contain a single copy of the T-DNA insert.

Alfalfa Transformation

A regenerating clone of alfalfa (*Medicago sativa*) is transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown D C W and A Atanassov (1985. Plant Cell Tissue Organ Culture 4: 111-112). Alternatively, the RA3 variety (University of Wisconsin) has been selected for use in tissue culture (Walker et al., 1978 Am J Bot 65:654-659). Petiole explants are cocultivated with an overnight culture of *Agrobacterium tumefaciens* C58C1 pMP90 (McKersie et al., 1999 Plant Physiol 119: 839-847) or LBA4404 containing the expression vector. The explants are cocultivated for 3 d in the dark on SH induction medium containing 288 mg/L Pro, 53 mg/L thioproline, 4.35 g/L K2SO4, and 100 μm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings were transplanted into pots and grown in a greenhouse. T1 seeds are produced from plants that exhibit tolerance to the selection agent and that contain a single copy of the T-DNA insert.

Example 46

Evaluation Procedure 46.1 Evaluation Setup

Approximately 35 independent T0 rice transformants were generated. The primary transformants were transferred from a tissue culture chamber to a greenhouse for growing and harvest of T1 seed. Seven events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions. Greenhouse conditions were of shorts days (12 hours light), 28° C. in the light and 22° C. in the dark, and a relative humidity of 70%.

Five T1 events were further evaluated in the T2 generation following the same evaluation procedure as for the T1 generation but with more individuals per event. From the stage of sowing until the stage of maturity the plants were passed several times through a digital imaging cabinet. At each time point digital images (2048×1536 pixels, 16 million colours) were taken of each plant from at least 6 different angles.

The early vigour is the plant (seedling) aboveground area three weeks post-germination. Increase in root biomass is expressed as an increase in total root biomass (measured as maximum biomass of roots observed during the lifespan of a plant); or as an increase in the root/shoot index (measured as the ratio between root mass and shoot mass in the period of active growth of root and shoot).

46.2 Statistical Analysis: F-Test

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and to verify for an overall effect of the gene, also known as a global gene effect. The threshold for significance for a true global gene effect was set at a 5% probability level for the F-test. A significant F-test value points to a gene effect, meaning that it is not only the mere presence or position of the gene that is causing the differences in phenotype.

To check for an effect of the genes within an event, i.e., for a line-specific effect, a t-test was performed within each event using data sets from the transgenic plants and the corresponding null plants. "Null plants" or "null segregants" or "nullizygotes" are the plants treated in the same way as the transgenic plant, but from which the transgene has segregated. Null plants can also be described as the homozygous negative transformed plants. The threshold for significance for the t-test is set at 10% probability level. The results for some events can be above or below this threshold. This is based on the hypothesis that a gene might only have an effect in certain positions in the genome, and that the occurrence of this position-dependent effect is not uncommon. This kind of gene effect is also named herein a "line effect of the gene". The p-value is obtained by comparing the t-value to the t-distribution or alternatively, by comparing the F-value to the F-distribution. The p-value then gives the probability that the null hypothesis (i.e., that there is no effect of the transgene) is correct.

Example 47

Evaluation Results

The plant aboveground area (or leafy biomass) was determined by counting the total number of pixels on the digital images from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The above ground area is the time point at which the plant had reached its maximal leafy biomass.

The mature primary panicles were harvested, counted, bagged, barcode-labeled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed yield was measured by weighing all filled husks harvested from a plant. Total seed number per plant was measured by counting the number of husks harvested from a plant. Thousand kernel weight (TKW) is extrapolated from the number of filled seeds counted and their total weight. The harvest index (HI) in the present invention is defined as the ratio between the total seed yield and the above ground area (mm$^2$), multiplied by a factor 10$^6$. The total number of flowers per panicle as defined in the present invention is the ratio between the total number of seeds and the number of mature primary panicles. The seed fill rate as defined in the present invention is the proportion (expressed as a %) of the number of filled seeds over the total number of seeds (or florets).

As presented in Tables Q to W, the aboveground biomass, the number of flowers per panicle, the seed yield, the total number of seeds, the number of filled seeds, the thousand kernel weight (TKW) and harvest index are increased in the transgenic plants with increased expression a nucleic acid encoding a SPL15 transcription factor polypeptide, compared to suitable control plants. Results from the T1 and the T2 generations are shown.

Table Q shows the number of transgenic events with an increase in aboveground biomass, the percentage of this increase, as well as the statistical relevance of this increase according to the F-test.

TABLE Q

Number of transgenic events with an increase in aboveground biomass, the percentage of the increase, and P value of the F-test in T1 and T2 generation of transgenic rice with increased expression of a nucleic acid encoding an SPL15 transcription factor polypeptide.
Aboveground biomass

| | Number of events showing an increase | % Difference | P value of F test |
|---|---|---|---|
| T1 generation | 5 out of 7 | 5 | 0.0773 |
| T2 generation | 4 out of 5 | 7 | 0.0172 |

Table R shows the number of transgenic events with an increase in the total number of flowers per panicle, the percentage of this increase, as well as the statistical relevance of this increase according to the F-test.

TABLE R

Number of transgenic events with an increase in flowers per panicle, the percentage of the increase, and P value of the F-test in T1 and T2 generation of transgenic rice with increased expression of a nucleic acid encoding an SPL15 transcription factor polypeptide.
Flowers per panicle

| | Number of events showing an increase | % Difference | P value of F test |
|---|---|---|---|
| T1 generation | 6 out of 7 | 4 | 0.0447 |
| T2 generation | 4 out of 5 | 10 | 0.0013 |

Table S shows the number of transgenic events with an increase in total seed yield (total seed weight), the percentage of this increase, as well as the statistical relevance of this increase according to the F-test.

TABLE S

Number of transgenic events with an increase in seed yield, the percentage of the increase, and P value of the F-test in T1 and T2 generation of transgenic rice with increased expression of a nucleic acid encoding an SPL15 transcription factor polypeptide.
Seed yield

| | Number of events showing an increase | % Difference | P value of F test |
|---|---|---|---|
| T1 generation | 7 out of 7 | 15 | 0.0019 |
| T2 generation | 5 out of 5 | 21 | 0.0001 |

Table T shows the number of transgenic events with an increase in the total number of seeds, the percentage of this increase, as well as the statistical relevance of this increase according to the F-test.

TABLE T

Number of transgenic events with an increase in total number of seeds, the percentage of the increase, and P value of the F-test in T1 and T2 generation of transgenic rice with increased expression of a nucleic acid encoding an SPL15 transcription factor polypeptide.
Total number of seeds

| | Number of events showing an increase | % Difference | P value of F test |
|---|---|---|---|
| T1 generation | 6 out of 7 | 6 | 0.07 |
| T2 generation | 4 out of 5 | 13 | 0.0023 |

Table U shows the number of transgenic events with an increase in the number of filled seeds, the percentage of this increase, as well as the statistical relevance of this increase according to the F-test.

TABLE U

Number of transgenic events with an increase in number of filled seeds, the percentage of the increase, and P value of the F-test in T1 and T2 generation of transgenic rice with increased expression of a nucleic acid encoding an SPL15 transcription factor polypeptide.
Number of filled seeds

| | Number of events showing an increase | % Difference | P value of F test |
|---|---|---|---|
| T1 generation | 6 out of 7 | 14 | 0.0031 |
| T2 generation | 4 out of 5 | 19 | 0.0003 |

Table V shows the number of transgenic events with an increase in the harvest index, the percentage of this increase, as well as the statistical relevance of this increase according to the F-test.

TABLE V

Number of transgenic events with an increase in harvest index, the percentage of the increase, and P value of the F-test in T1 and T2 generation of transgenic rice with increased expression of a nucleic acid encoding an SPL15 transcription factor polypeptide.
Harvest index

| | Number of events showing an increase | % Difference | P value of F test |
|---|---|---|---|
| T1 generation | 7 out of 7 | 12 | 0.0003 |
| T2 generation | 4 out of 5 | 15 | 0.0001 |

Table W shows the number of transgenic events with an increase in the thousand kernel weight (TKW), the percentage of this increase, as well as the statistical relevance of this increase according to the F-test.

TABLE W

Number of transgenic events with an increase in thousand kernel weight (TKW), the percentage of the increase, and P value of the F-test in T1 and T2 generation of transgenic rice with increased expression of a nucleic acid encoding an SPL15 transcription factor polypeptide.
Thousand kernel weight

| | Number of events showing an increase | % Difference | P value of F test |
|---|---|---|---|
| T1 generation | 4 out of 7 | 2 | 0.0041 |
| T2 generation | 4 out of 5 | 1 | 0.0259 |

Example 48

Results of the Phenotypic Evaluation of the Transgenic Plants Expressing SEQ ID NO: 234 Under the Control of a Constitutive Promoter The results of the evaluation of transgenic rice plants expressing the nucleic acid sequence useful in performing the methods of the invention, under the control of the constitutive GOS2 promoter, are presented in Table X. The percentage difference between the transgenics and the corresponding nullizygotes is also shown.

The transgenic plants expressing the nucleic acid sequence useful in performing the methods of the invention, have increased early vigour and increased TKW compared to the control plants (in this case, the nullizygotes).

TABLE X

Results of the evaluation of T1 generation transgenic rice plants expressing the nucleic acid sequence useful in performing the methods of the invention, under the control of a strong constitutive GOS2 promoter.

| Trait | % Increase of the best events in T1 generation |
| --- | --- |
| Increased early vigour | 17% |
| Total seed yield (per plant) | 18% |
| Total number of filled seeds | 19% |
| Increased seed fill rate | 10% |
| Increased harvest index | 15% |

The invention claimed is:

1. A method for enhancing seed yield in a plant relative to a control plant, comprising reducing expression of an endogenous MADS15 gene in plants, and selecting a plant having increased seed yield relative to a control plant, wherein said reduced expression is effected by RNA-mediated down-regulation of the MADS15 gene.

2. The method of claim 1, wherein said endogenous MADS15 gene encodes a protein comprising one or more of the motifs SEQ ID NO: 114, SEQ ID NO: 115, SEQ ID NO: 116, and SEQ ID NO: 117.

3. The method of claim 1, wherein said RNA-mediated downregulation is effected by introducing into the plant a MADS15 nucleic acid sequence thereby causing co-suppression.

4. The method of claim 1, wherein said RNA-mediated down-regulation is effected by an antisense MADS15 nucleic acid sequence.

5. The method of claim 1, wherein said reduced expression is effected by an inverted repeat of a MADS15 nucleic acid sequence, capable of forming a hairpin structure.

6. The method of claim 3, wherein said MADS15 nucleic acid sequence comprises a sufficient length of contiguous nucleotides of SEQ ID NO: 109 (OsMADS15) for reducing MADS15 gene expression.

7. The method of claim 3, wherein said MADS15 nucleic acid sequence comprises a sufficient length of contiguous nucleotides of a nucleic acid sequence encoding an orthologue or paralogue of OsMADS15 (SEQ ID NO: 110), wherein said orthologue or paralogue of OsMADS15 comprises the amino acid sequence of SEQ ID NO: 147, SEQ ID NO: 149, SEQ ID NO: 151, SEQ ID NO: 153, SEQ ID NO: 155, SEQ ID NO: 157, SEQ ID NO: 159 or SEQ ID NO: 161 for reducing MADS15 gene expression.

8. The method of claim 7, wherein said orthologue or paralogue of OsMADS15 (SEQ ID NO: 110) is encoded by the nucleic acid sequences of SEQ ID NO: 146, SEQ ID NO: 148, SEQ ID NO: 150, SEQ ID NO: 152, SEQ ID NO: 154, SEQ ID NO: 156, SEQ ID NO : 158 or SEQ ID NO: 160.

9. The method of claim 1, wherein said increased seed yield is:
    (a) increased seed biomass (seed weight),
    (b) increased number of flowers per plant, and/or
    (c) increased number of (filled) seeds.

10. A method of producing a plant having enhanced seed yield relative to a control plant, comprising transforming into a plant a construct comprising:
    (a) a MADS15 nucleic acid capable of silencing an endogenous MADS15 gene;
    (b) a GOS2 promoter capable of driving expression of the nucleic acid of (a); and
    (c) a transcription termination sequence,
    and selecting a transformed plant having enhanced seed yield relative to a control plant.

11. The method of claim 7, wherein said MADS15 nucleic acid sequence is operably linked to a GOS2 promoter.

12. The method of claim 7, wherein said MADS15 nucleic acid sequence is obtained from a monocotyledonous plant and is used to transform a monocotyledonous plant.

13. The method of claim 7, wherein said MADS15 nucleic acid sequence is obtained from a plant of the family Poaceae and is used to transform a plant of the family Poaceae.

14. The method of claim 7, wherein said MADS15 nucleic acid sequence is obtained from rice and used to transform a rice plant.

15. The method of claim 4, wherein said MADS15 nucleic acid sequence comprises a sufficient length of contiguous nucleotides of SEQ ID NO: 109 (OsMADS15) for reducing MADS15 gene expression.

16. The method of claim 5, wherein said MADS15 nucleic acid sequence comprises a sufficient length of contiguous nucleotides of SEQ ID NO: 109 (OsMADS15) for reducing MADS15 gene expression.

17. The method of claim 4, wherein said MADS15 nucleic acid sequence comprises a sufficient length of contiguous nucleotides of a nucleic acid sequence encoding an orthologue or paralogue of OsMADS15 (SEQ ID NO: 110), wherein said orthologue or paralogue of OsMADS15 comprises the amino acid sequence of SEQ ID NO: 147, SEQ ID NO: 149, SEQ ID NO: 151, SEQ ID NO: 153, SEQ ID NO: 155, SEQ ID NO: 157, SEQ ID NO: 159 or SEQ ID NO: 161 for reducing MADS15 gene expression.

18. The method of claim 5, wherein said MADS15 nucleic acid sequence comprises a sufficient length of contiguous nucleotides of a nucleic acid sequence encoding an orthologue or paralogue of OsMADS15 (SEQ ID NO: 110), wherein said orthologue or paralogue of OsMADS15 comprises the amino acid sequence of SEQ ID NO: 147, SEQ ID NO: 149, SEQ ID NO: 151, SEQ ID NO: 153, SEQ ID NO: 155, SEQ ID NO: 157, SEQ ID NO: 159 or SEQ ID NO: 161 for reducing MADS15 gene expression.

19. The method of claim 17, wherein said orthologue or paralogue of OsMADS15 (SEQ ID NO: 110) is encoded by the nucleic acid sequence of SEQ ID NO: 146, SEQ ID NO: 148, SEQ ID NO: 150, SEQ ID NO: 152, SEQ ID NO: 154, SEQ ID NO: 156, SEQ ID NO: 158 or SEQ ID NO: 160.

20. The method of claim 18, wherein said orthologue or paralogue of OsMADS15 (SEQ ID NO: 110) is encoded by the nucleic acid sequence of SEQ ID NO: 146, SEQ ID NO: 148, SEQ ID NO: 150, SEQ ID NO: 152, SEQ ID NO: 154, SEQ ID NO: 156, SEQ ID NO: 158 or SEQ ID NO: 160.

21. The method of claim 17, wherein said MADS15 nucleic acid sequence is operably linked to a GOS2 promoter.

22. The method of claim 18, wherein said MADS15 nucleic acid sequence is operably linked to a GOS2 promoter.

23. The method of claim 17, wherein said MADS15 nucleic acid sequence is obtained from a monocotyledonous plant and is used to transform a monocotyledonous plant.

24. The method of claim 18, wherein said MADS15 nucleic acid sequence is obtained from a monocotyledonous plant and is used to transform a monocotyledonous plant.

25. The method of claim 17, wherein said MADS15 nucleic acid sequence is obtained from a plant of the family Poaceae and is used to transform a plant of the family Poaceae.

26. The method of claim 18, wherein said MADS15 nucleic acid sequence is obtained from a plant of the family Poaceae and is used to transform a plant of the family Poaceae.

27. The method of claim 17, wherein said MADS15 nucleic acid sequence is obtained from rice and used to transform a rice plant.

28. The method of claim 18, wherein said MADS15 nucleic acid sequence is obtained from rice and used to transform a rice plant.

* * * * *

```
                            SEQUENCE LISTING

<160> NUMBER OF SEQ ID NOS: 301

<210> SEQ ID NO 1
<211> LENGTH: 630
<212> TYPE: DNA
<213> ORGANISM: Arabidopsis thaliana

<400> SEQUENCE: 1
atggagaatg ggaaaagaga cagacaagac atggaagtga ataccacacc gaggaagcct      60
cgtgtactac tcgctgcaag tggaagcgtc gctgctatca aattcggcaa tctctgccat     120
tgcttcaccg aatgggcaga agtcagagcc gtcgttacga aatcatctct acatttcctc     180
gataaactct ctctcccaca agaagtgact ctgtatactg atgaagatga atggtctagc     240
tggaacaaga tcggtgatcc tgtccttcac atcgagctta gacgttgggc tgatgtttta     300
gtcattgctc ctttgtctgc taacacctta ggcaagattg ctggtgggct ttgtgataat     360
cttctgactt gcattatacg agcttgggac tataccaaac cactgtttgt tgctccagct     420
atgaatactt tgatgtggaa caatcctttc actgaaaggc atcttttgtc tcttgatgaa     480
ctgggaatca cacttattcc tcctatcaag aagagacttg cctgtggaga ctacggtaat     540
ggagctatgg ctgagccctc tcttatctat tccactgtca gactcttctg ggagtctcag     600
gctcatcagc aaaccggtgg aactagttaa                                      630

<210> SEQ ID NO 2
<211> LENGTH: 209
<212> TYPE: PRT
<213> ORGANISM: Arabidopsis thaliana

<400> SEQUENCE: 2

Met Glu Asn Gly Lys Arg Asp Arg Gln Asp Met Glu Val Asn Thr Thr
1               5                   10                  15

Pro Arg Lys Pro Arg Val Leu Leu Ala Ala Ser Gly Ser Val Ala Ala
                20                  25                  30

Ile Lys Phe Gly Asn Leu Cys His Cys Phe Thr Glu Trp Ala Glu Val
            35                  40                  45

Arg Ala Val Val Thr Lys Ser Ser Leu His Phe Leu Asp Lys Leu Ser
        50                  55                  60

Leu Pro Gln Glu Val Thr Leu Tyr Thr Asp Glu Asp Glu Trp Ser Ser
65                  70                  75                  80

Trp Asn Lys Ile Gly Asp Pro Val Leu His Ile Glu Leu Arg Arg Trp
                85                  90                  95
```

```
Ala Asp Val Leu Val Ile Ala Pro Leu Ser Ala Asn Thr Leu Gly Lys
            100                 105                 110

Ile Ala Gly Gly Leu Cys Asp Asn Leu Leu Thr Cys Ile Ile Arg Ala
            115                 120                 125

Trp Asp Tyr Thr Lys Pro Leu Phe Val Ala Pro Ala Met Asn Thr Leu
    130                 135                 140

Met Trp Asn Asn Pro Phe Thr Glu Arg His Leu Leu Ser Leu Asp Glu
145                 150                 155                 160

Leu Gly Ile Thr Leu Ile Pro Pro Ile Lys Lys Arg Leu Ala Cys Gly
                165                 170                 175

Asp Tyr Gly Asn Gly Ala Met Ala Glu Pro Ser Leu Ile Tyr Ser Thr
            180                 185                 190

Val Arg Leu Phe Trp Glu Ser Gln Ala His Gln Gln Thr Gly Gly Thr
        195                 200                 205

Ser

<210> SEQ ID NO 3
<211> LENGTH: 37
<212> TYPE: DNA
<213> ORGANISM: Artificial sequence
<220> FEATURE:
<223> OTHER INFORMATION: primer: prm00957

<400> SEQUENCE: 3
aaaaagcagg ctcacaatgg agaatgggaa aagagac                              37

<210> SEQ ID NO 4
<211> LENGTH: 33
<212> TYPE: DNA
<213> ORGANISM: Artificial sequence
<220> FEATURE:
<223> OTHER INFORMATION: primer: prm00958

<400> SEQUENCE: 4
agaaagctgg gttggtttta actagttcca ccg                                  33

<210> SEQ ID NO 5
<211> LENGTH: 1243
<212> TYPE: DNA
<213> ORGANISM: Oryza sativa

<400> SEQUENCE: 5
aaaaccaccg agggacctga tctgcaccgg ttttgatagt tgagggaccc gttgtgtctg      60
gttttccgat cgagggacga aaatcggatt cggtgtaaag ttaagggacc tcagatgaac     120
ttattccgga gcatgattgg aagggagga cataaggccc atgtcgcatg tgtttggacg      180
gtccagatct ccagatcact cagcaggatc ggccgcgttc gcgtagcacc cgcggtttga     240
ttcggcttcc cgcaaggcgg cggccggtgg ccgtgccgcc gtagcttccg ccggaagcga     300
gcacgccgcc gccgccgacc cggctctgcg tttgcaccgc cttgcacgcg atacatcggg     360
atagatagct actactctct ccgtttcaca atgtaaatca ttctactatt ttccacattc     420
atattgatgt taatgaatat agacatatat atctatttag attcattaac atcaatatga     480
atgtaggaaa tgctagaatg acttacattg tgaattgtga aatggacgaa gtacctacga     540
tggatggatg caggatcatg aaagaattaa tgcaagatcg tatctgccgc atgcaaaatc     600
ttactaattg cgctgcatat atgcatgaca gcctgcatgc gggcgtgtaa gcgtgttcat     660
ccattaggaa gtaaccttgt cattacttat accagtacta catactatat agtattgatt     720
tcatgagcaa atctacaaaa ctggaaagca ataaggaata cgggactgga aaagactcaa     780
```

```
cattaatcac caaatatttc gccttctcca gcagaatata tatctctcca tcttgatcac    840
tgtacacact gacagtgtac gcataaacgc agcagccagc ttaactgtcg tctcaccgtc    900
gcacactggc cttccatctc aggctagctt tctcagccac ccatcgtaca tgtcaactcg    960
gcgcgcgcac aggcacaaat tacgtacaaa acgcatgacc aaatcaaaac caccggagaa   1020
gaatcgctcc cgcgcgcggc ggcggcgcgc acgtacgaat gcacgcacgc acgcccaacc   1080
ccacgacacg atcgcgcgcg acgccggcga caccggccat ccacccgcgc cctcacctcg   1140
ccgactataa atacgtaggc atctgcttga tcttgtcatc catctcacca ccaaaaaaaa   1200
aggaaaaaaa aacaaaacac accaagccaa ataaaagcga caa                     1243
```

```
<210> SEQ ID NO 6
<211> LENGTH: 34
<212> TYPE: PRT
<213> ORGANISM: Artificial sequence
<220> FEATURE:
<223> OTHER INFORMATION: conserved motif 1
<220> FEATURE:
<221> NAME/KEY: VARIANT
<222> LOCATION: (1)..(1)
<223> OTHER INFORMATION: Xaa is Lys or Arg
<220> FEATURE:
<221> NAME/KEY: VARIANT
<222> LOCATION: (4)..(4)
<223> OTHER INFORMATION: Xaa is Val or Ile
<220> FEATURE:
<221> NAME/KEY: VARIANT
<222> LOCATION: (9)..(9)
<223> OTHER INFORMATION: Xaa is Ser or Thr
<220> FEATURE:
<221> NAME/KEY: VARIANT
<222> LOCATION: (14)..(14)
<223> OTHER INFORMATION: Xaa is Ala or Ser
<220> FEATURE:
<221> NAME/KEY: VARIANT
<222> LOCATION: (15)..(15)
<223> OTHER INFORMATION: Xaa is Ile, Met, or Val
<220> FEATURE:
<221> NAME/KEY: VARIANT
<222> LOCATION: (18)..(18)
<223> OTHER INFORMATION: Xaa is Gly, Glu, Ala, or Ser
<220> FEATURE:
<221> NAME/KEY: VARIANT
<222> LOCATION: (21)..(21)
<223> OTHER INFORMATION: Xaa is Cys or Val
<220> FEATURE:
<221> NAME/KEY: VARIANT
<222> LOCATION: (22)..(22)
<223> OTHER INFORMATION: Xaa is His, Arg, or Gly
<220> FEATURE:
<221> NAME/KEY: VARIANT
<222> LOCATION: (23)..(23)
<223> OTHER INFORMATION: Xaa is Cys, Ser, or Ile
<220> FEATURE:
<221> NAME/KEY: VARIANT
<222> LOCATION: (25)..(25)
<223> OTHER INFORMATION: Xaa is Thr or Ser
<220> FEATURE:
<221> NAME/KEY: VARIANT
<222> LOCATION: (26)..(26)
<223> OTHER INFORMATION: Xaa is Glu or Asp
<220> FEATURE:
<221> NAME/KEY: VARIANT
<222> LOCATION: (29)..(29)
<223> OTHER INFORMATION: Xaa is Glu or Asp
<220> FEATURE:
<221> NAME/KEY: VARIANT
<222> LOCATION: (31)..(31)
<223> OTHER INFORMATION: Xaa is Arg or Lys
<220> FEATURE:
<221> NAME/KEY: VARIANT
<222> LOCATION: (34)..(34)
<223> OTHER INFORMATION: Xaa is Val or Ala
```

-continued

```
<400> SEQUENCE: 6

Xaa Pro Arg Xaa Leu Leu Ala Ala Xaa Gly Ser Val Ala Xaa Xaa Lys
1               5                   10                  15

Phe Xaa Asn Leu Xaa Xaa Xaa Phe Xaa Xaa Trp Ala Xaa Val Xaa Ala
            20                  25                  30

Val Xaa

<210> SEQ ID NO 7
<211> LENGTH: 98
<212> TYPE: PRT
<213> ORGANISM: Artificial sequence
<220> FEATURE:
<223> OTHER INFORMATION: conserved motif 2
<220> FEATURE:
<221> NAME/KEY: VARIANT
<222> LOCATION: (8)..(8)
<223> OTHER INFORMATION: Xaa is Arg, Lys, or Gln
<220> FEATURE:
<221> NAME/KEY: VARIANT
<222> LOCATION: (12)..(12)
<223> OTHER INFORMATION: Xaa is Val or Ile
<220> FEATURE:
<221> NAME/KEY: VARIANT
<222> LOCATION: (13)..(13)
<223> OTHER INFORMATION: Xaa is Leu or Met
<220> FEATURE:
<221> NAME/KEY: VARIANT
<222> LOCATION: (14)..(14)
<223> OTHER INFORMATION: Xaa is Val or Ile
<220> FEATURE:
<221> NAME/KEY: VARIANT
<222> LOCATION: (24)..(24)
<223> OTHER INFORMATION: Xaa is Gly or Ala
<220> FEATURE:
<221> NAME/KEY: VARIANT
<222> LOCATION: (30)..(30)
<223> OTHER INFORMATION: Xaa is Leu or Met
<220> FEATURE:
<221> NAME/KEY: VARIANT
<222> LOCATION: (38)..(38)
<223> OTHER INFORMATION: Xaa is Ile or Val
<220> FEATURE:
<221> NAME/KEY: VARIANT
<222> LOCATION: (39)..(39)
<223> OTHER INFORMATION: Xaa is Ile or Val
<220> FEATURE:
<221> NAME/KEY: VARIANT
<222> LOCATION: (44)..(44)
<223> OTHER INFORMATION: Xaa is Tyr or Phe
<220> FEATURE:
<221> NAME/KEY: VARIANT
<222> LOCATION: (45)..(45)
<223> OTHER INFORMATION: Xaa is Thr, Ser, Asn, Asp, or Lys
<220> FEATURE:
<221> NAME/KEY: VARIANT
<222> LOCATION: (48)..(48)
<223> OTHER INFORMATION: Xaa is Leu, Phe, Met, or Ile
<220> FEATURE:
<221> NAME/KEY: VARIANT
<222> LOCATION: (50)..(50)
<223> OTHER INFORMATION: Xaa is Val or Ala
<220> FEATURE:
<221> NAME/KEY: VARIANT
<222> LOCATION: (57)..(57)
<223> OTHER INFORMATION: Xaa is Leu or Phe
<220> FEATURE:
<221> NAME/KEY: VARIANT
<222> LOCATION: (60)..(60)
<223> OTHER INFORMATION: Xaa is Asn or Ser
<220> FEATURE:
<221> NAME/KEY: VARIANT
<222> LOCATION: (65)..(65)
<223> OTHER INFORMATION: Xaa is Glu, Ser, Gln, or Ala
<220> FEATURE:
<221> NAME/KEY: VARIANT
```

-continued

```
<222> LOCATION: (66)..(66)
<223> OTHER INFORMATION: Xaa is Arg or Lys
<220> FEATURE:
<221> NAME/KEY: VARIANT
<222> LOCATION: (68)..(68)
<223> OTHER INFORMATION: Xaa is Leu, Phe, or Ile
<220> FEATURE:
<221> NAME/KEY: UNSURE
<222> LOCATION: (69)..(70)
<223> OTHER INFORMATION: Xaa can be any naturally occurring amino acid
<220> FEATURE:
<221> NAME/KEY: VARIANT
<222> LOCATION: (71)..(71)
<223> OTHER INFORMATION: Xaa is Leu, Ile, or Met
<220> FEATURE:
<221> NAME/KEY: VARIANT
<222> LOCATION: (72)..(72)
<223> OTHER INFORMATION: Xaa is Asp, Asn, or Ser
<220> FEATURE:
<221> NAME/KEY: VARIANT
<222> LOCATION: (73)..(73)
<223> OTHER INFORMATION: Xaa is Glu, Leu, or Gln
<220> FEATURE:
<221> NAME/KEY: VARIANT
<222> LOCATION: (74)..(74)
<223> OTHER INFORMATION: Xaa is Leu or Met
<220> FEATURE:
<221> NAME/KEY: VARIANT
<222> LOCATION: (76)..(76)
<223> OTHER INFORMATION: Xaa is Ile or Val
<220> FEATURE:
<221> NAME/KEY: VARIANT
<222> LOCATION: (77)..(77)
<223> OTHER INFORMATION: Xaa is Thr, Ser, Ala, or Ile
<220> FEATURE:
<221> NAME/KEY: VARIANT
<222> LOCATION: (79)..(79)
<223> OTHER INFORMATION: Xaa is Ile or Val
<220> FEATURE:
<221> NAME/KEY: VARIANT
<222> LOCATION: (82)..(82)
<223> OTHER INFORMATION: Xaa is Ile, Val, or Thr
<220> FEATURE:
<221> NAME/KEY: VARIANT
<222> LOCATION: (83)..(83)
<223> OTHER INFORMATION: Xaa is Lys, Thr, or Ser
<220> FEATURE:
<221> NAME/KEY: VARIANT
<222> LOCATION: (85)..(85)
<223> OTHER INFORMATION: Xaa is Arg, Thr, or Lys
<220> FEATURE:
<221> NAME/KEY: VARIANT
<222> LOCATION: (91)..(91)
<223> OTHER INFORMATION: Xaa is Tyr or His
<220> FEATURE:
<221> NAME/KEY: VARIANT
<222> LOCATION: (93)..(93)
<223> OTHER INFORMATION: Xaa is Asn or Thr
<220> FEATURE:
<221> NAME/KEY: VARIANT
<222> LOCATION: (97)..(97)
<223> OTHER INFORMATION: Xaa is Ala or Ser

<400> SEQUENCE: 7

Val Leu His Ile Glu Leu Arg Xaa Trp Ala Asp Xaa Xaa Xaa Ile Ala
1               5                   10                  15

Pro Leu Ser Ala Asn Thr Leu Xaa Lys Ile Ala Gly Gly Xaa Cys Asp
            20                  25                  30

Asn Leu Leu Thr Cys Xaa Xaa Arg Ala Trp Asp Xaa Xaa Lys Pro Xaa
        35                  40                  45

Phe Xaa Ala Pro Ala Met Asn Thr Xaa Met Trp Xaa Asn Pro Phe Thr
    50                  55                  60

Xaa Xaa His Xaa Xaa Xaa Xaa Xaa Xaa Gly Xaa Xaa Leu Xaa Pro
65                  70                  75                  80
```

```
Pro Xaa Xaa Lys Xaa Leu Ala Cys Gly Asp Xaa Gly Xaa Gly Ala Met
            85                  90                  95

Xaa Glu

<210> SEQ ID NO 8
<211> LENGTH: 171
<212> TYPE: PRT
<213> ORGANISM: Arabidopsis thaliana

<400> SEQUENCE: 8

Lys Pro Arg Val Leu Leu Ala Ala Ser Gly Ser Val Ala Ala Ile Lys
1               5                   10                  15

Phe Gly Asn Leu Cys His Cys Phe Thr Glu Trp Ala Glu Val Arg Ala
            20                  25                  30

Val Val Thr Lys Ser Ser Leu His Phe Leu Asp Lys Leu Ser Leu Pro
        35                  40                  45

Gln Glu Val Thr Leu Tyr Thr Asp Glu Asp Glu Trp Ser Ser Trp Asn
    50                  55                  60

Lys Ile Gly Asp Pro Val Leu His Ile Glu Leu Arg Arg Trp Ala Asp
65                  70                  75                  80

Val Leu Val Ile Ala Pro Leu Ser Ala Asn Thr Leu Gly Lys Ile Ala
                85                  90                  95

Gly Gly Leu Cys Asp Asn Leu Leu Thr Cys Ile Ile Arg Ala Trp Asp
            100                 105                 110

Tyr Thr Lys Pro Leu Phe Val Ala Pro Ala Met Asn Thr Leu Met Trp
        115                 120                 125

Asn Asn Pro Phe Thr Glu Arg His Leu Leu Ser Leu Asp Glu Leu Gly
    130                 135                 140

Ile Thr Leu Ile Pro Pro Ile Lys Lys Arg Leu Ala Cys Gly Asp Tyr
145                 150                 155                 160

Gly Asn Gly Ala Met Ala Glu Pro Ser Leu Ile
                165                 170

<210> SEQ ID NO 9
<211> LENGTH: 606
<212> TYPE: DNA
<213> ORGANISM: Arabidopsis thaliana

<400> SEQUENCE: 9
atgaatatgg aagtggatac agtaacaagg aagcctcgta tcttactagc tgcaagtgga      60
agtgtggctt caattaagtt cagtaatctc tgccattgtt tctcagaatg ggctgaagtc     120
aaagccgtcg cttcaaaatc atctctcaat ttcgttgata aaccttctct acctcagaat     180
gtgactctct atacagatga agatgaatgg tctagctgga caagattgg tgatcccgtt      240 cttcatatcg agctcagacg ctgggctgat gttatgatca ttgctccttt gtctgctaac     300
acattagcca agattgctgg tgggttatgt gataatctat tgacatgtat agtaagagca     360
tgggattata gcaaaccgtt gtttgttgca ccggcgatga cactttgat gtggaacaat      420 cctttcacag aacggcacct tgtcttgctt gatgaacttg gaatcaccct aattcctccc     480
atcaagaaga aactggcctg tggagactac ggtaatggcg caatggctga gccttctctg     540
atttattcca ctgttagact gttctgggag tcacaagctc gtaaacaaag agatggaacc     600
agttga                                                                606

<210> SEQ ID NO 10
<211> LENGTH: 201
<212> TYPE: PRT
```

<213> ORGANISM: Arabidopsis thaliana

<400> SEQUENCE: 10

```
Met Asn Met Glu Val Asp Thr Val Thr Arg Lys Pro Arg Ile Leu Leu
1               5                   10                  15
Ala Ala Ser Gly Ser Val Ala Ser Ile Lys Phe Ser Asn Leu Cys His
            20                  25                  30
Cys Phe Ser Glu Trp Ala Glu Val Lys Ala Val Ala Ser Lys Ser Ser
        35                  40                  45
Leu Asn Phe Val Asp Lys Pro Ser Leu Pro Gln Asn Val Thr Leu Tyr
    50                  55                  60
Thr Asp Glu Asp Glu Trp Ser Ser Trp Asn Lys Ile Gly Asp Pro Val
65                  70                  75                  80
Leu His Ile Glu Leu Arg Arg Trp Ala Asp Val Met Ile Ile Ala Pro
                85                  90                  95
Leu Ser Ala Asn Thr Leu Ala Lys Ile Ala Gly Gly Leu Cys Asp Asn
            100                 105                 110
Leu Leu Thr Cys Ile Val Arg Ala Trp Asp Tyr Ser Lys Pro Leu Phe
        115                 120                 125
Val Ala Pro Ala Met Asn Thr Leu Met Trp Asn Asn Pro Phe Thr Glu
    130                 135                 140
Arg His Leu Val Leu Leu Asp Glu Leu Gly Ile Thr Leu Ile Pro Pro
145                 150                 155                 160
Ile Lys Lys Lys Leu Ala Cys Gly Asp Tyr Gly Asn Gly Ala Met Ala
                165                 170                 175
Glu Pro Ser Leu Ile Tyr Ser Thr Val Arg Leu Phe Trp Glu Ser Gln
            180                 185                 190
Ala Arg Lys Gln Arg Asp Gly Thr Ser
        195                 200
```

<210> SEQ ID NO 11
<211> LENGTH: 1128
<212> TYPE: DNA
<213> ORGANISM: Oryza sativa

<400> SEQUENCE: 11

```
caaccaaagt ccaaaggcta ttctgaaccg aagtcctccc acaccaaaac ttcgaggccc    60
ccgtcgcggc accctcctcc gccgccggat ctccaccgga gtacggcgcc ggccaccccc   120
tcctcccccg gatcttcacc gccggtgaag tactgaggtg atgactacat cagagtcagt   180
acaagaaacc ttgggattgg atttccctca tcctagcaaa cctcgggtcc tccttgctgc   240
ctctggaagc gtcgctgcta taaaatttga gagcctttgc cgtagcttct cggaatgggc   300
agaagtcaga gccgtcgcca ccaaggcttc attacatttt attgatagaa cgtctctgcc   360
tagcaatatt attctttaca ctgatgatga tgaatggtct acctggaaga agataggga    420
tgaagttttg cacattgaac tgcgaaaatg ggcagatatc atggtgattg cgccattatc   480
agctaatacc ctagctaaga ttgctggtgg tttatgtgac aacctcttga catgcatagt   540
gagagcatgg gactacagca aaccactctt tgttgcccca gctatgaaca ccttcatgtg   600
gaacaacccg ttcaccagtc gtcatcttga acaatcaac ctgctaggta tatctttggt    660
ccctcccatt accaaaaggc tggcctgtgg tgattatggt aatggtgcaa tggctgagcc   720
ttctgtgatc gattccaccg tcaggcttgc ttgcaagaga cagccactta atacaaatag   780
ttcacctgtg gttcctgccg gcagaaacct cccatctagc tgatgcggca actattctgt   840
tcaagattaa actctggacc tagttttcta tggtaaagag tacttcgtgt cacaaaatga   900
```

```
aatgttaagt gatgtctatg tcggccaaca tagcaccttt attggccagt tgttgtacta    960
ctattagtga tatggtagga cgtggagatt ggagaaaggc tattgtccca gcactttaat   1020
gttgcttttc caaatttctt gtgacataat gctaaggtgc tgatgaatat gttcatgttg   1080
tagcactatt tttttctgca aatgtttgca aagactcgtg atggaatc               1128
```

<210> SEQ ID NO 12
<211> LENGTH: 220
<212> TYPE: PRT
<213> ORGANISM: Oryza sativa

<400> SEQUENCE: 12

```
Met Thr Thr Ser Glu Ser Val Gln Glu Thr Leu Gly Leu Asp Phe Pro
1               5                   10                  15

His Pro Ser Lys Pro Arg Val Leu Leu Ala Ala Ser Gly Ser Val Ala
            20                  25                  30

Ala Ile Lys Phe Glu Ser Leu Cys Arg Ser Phe Ser Glu Trp Ala Glu
        35                  40                  45

Val Arg Ala Val Ala Thr Lys Ala Ser Leu His Phe Ile Asp Arg Thr
    50                  55                  60

Ser Leu Pro Ser Asn Ile Ile Leu Tyr Thr Asp Asp Glu Trp Ser
65                  70                  75                  80

Thr Trp Lys Lys Ile Gly Asp Glu Val Leu His Ile Glu Leu Arg Lys
                85                  90                  95

Trp Ala Asp Ile Met Val Ile Ala Pro Leu Ser Ala Asn Thr Leu Ala
            100                 105                 110

Lys Ile Ala Gly Gly Leu Cys Asp Asn Leu Leu Thr Cys Ile Val Arg
        115                 120                 125

Ala Trp Asp Tyr Ser Lys Pro Leu Phe Val Ala Pro Ala Met Asn Thr
    130                 135                 140

Phe Met Trp Asn Asn Pro Phe Thr Ser Arg His Leu Glu Thr Ile Asn
145                 150                 155                 160

Leu Leu Gly Ile Ser Leu Val Pro Pro Ile Thr Lys Arg Leu Ala Cys
                165                 170                 175

Gly Asp Tyr Gly Asn Gly Ala Met Ala Glu Pro Ser Val Ile Asp Ser
            180                 185                 190

Thr Val Arg Leu Ala Cys Lys Arg Gln Pro Leu Asn Thr Asn Ser Ser
        195                 200                 205

Pro Val Val Pro Ala Gly Arg Asn Leu Pro Ser Ser
    210                 215                 220
```

<210> SEQ ID NO 13
<211> LENGTH: 1164
<212> TYPE: DNA
<213> ORGANISM: Triticum aestivum

<400> SEQUENCE: 13

```
gcacgagcag ccgcggagcc gccagagaca gacgctgccg ccgtcggccg tcctccgccc     60
tccagttgag cggttcaagc agagctgatg ctacatcag agccagtaca agagagtttg    120
gtggtgcact actcacaacc tagtaggccc cgggtcctcc ttgctgcttc aggaagtgta    180
gccgctataa aatttgagag cctttgccgt agcttctctg agtgggcgga tgtccgagct    240
gtggccacca cgccatcctt gcacttcgtt gatagatcat ctctaccaag tggcatcgtt    300
ctttacactg atgacgatga atggtctacc tggaagaaga taggagatga agtcttacac    360
atcgagctgc ggaaatgggc agacgttatg gtgatcgctc cattgtcagc aaatacctg    420
```

```
gctaagatcg ccggtgggtt atgcgacaac ctcttgacct gcatcgtgag agcgtgggac    480
tacagcaaac cgctctttgt tgccccagcc atgaacacgt taatgtggaa caacccattc    540
acggagcggc atcttcacac aatcaaccaa ctgggcatag ccttgatccc cccagttacc    600
aaaaggctgg cctgtggcga ttacgggaac ggcgcaatgg ccgaaacctc gcagatccat    660
acttccgtga ggctcgcgtg caagacgcaa ccgcacgatg cgagcagttc actcgcgggt    720
cctgtcagta ataaccggcc atctagctga tgcagcagtt ggccacttga ttgtcaagct    780
taggaatttg ttttatatgc agtgtgcatc tggagtgttg taacagattt ttttccaac     840 tagtgtttgt gtgtattgaa attgggggg aaaggctgtt gtcacaggat aacaataact    900 tcctcccctgc tcagtaatta tgagtctatt cagtttgtaa ttgtcggtgg gagtacaatt    960
atgctacaat attgtttgtt tgtgtgtgtg tgggagttgg ggagtgctgc tgccacagag   1020
atagcttcct ccctgcccag ccagtaatga tagtgattat tcagtttgta gttgtcagtg   1080
gaagtgtcca gcaaactttt ctactaccct ttgatattcc tggtacaaat gttggaacga   1140
ctgtcctaaa aaaaaaaaaa aaaa                                          1164
```

<210> SEQ ID NO 14
<211> LENGTH: 220
<212> TYPE: PRT
<213> ORGANISM: Triticum aestivum

<400> SEQUENCE: 14

```
Met Ala Thr Ser Glu Pro Val Gln Glu Ser Leu Val Val His Tyr Ser
1               5                   10                  15

Gln Pro Ser Arg Pro Arg Val Leu Leu Ala Ala Ser Gly Ser Val Ala
            20                  25                  30

Ala Ile Lys Phe Glu Ser Leu Cys Arg Ser Phe Ser Glu Trp Ala Asp
        35                  40                  45

Val Arg Ala Val Ala Thr Thr Pro Ser Leu His Phe Val Asp Arg Ser
    50                  55                  60

Ser Leu Pro Ser Gly Ile Val Leu Tyr Thr Asp Asp Glu Trp Ser
65                  70                  75                  80

Thr Trp Lys Lys Ile Gly Asp Glu Val Leu His Ile Glu Leu Arg Lys
                85                  90                  95

Trp Ala Asp Val Met Val Ile Ala Pro Leu Ser Ala Asn Thr Leu Ala
            100                 105                 110

Lys Ile Ala Gly Gly Leu Cys Asp Asn Leu Leu Thr Cys Ile Val Arg
        115                 120                 125

Ala Trp Asp Tyr Ser Lys Pro Leu Phe Val Ala Pro Ala Met Asn Thr
    130                 135                 140

Leu Met Trp Asn Asn Pro Phe Thr Glu Arg His Leu His Thr Ile Asn
145                 150                 155                 160

Gln Leu Gly Ile Ala Leu Ile Pro Pro Val Thr Lys Arg Leu Ala Cys
                165                 170                 175

Gly Asp Tyr Gly Asn Gly Ala Met Ala Glu Thr Ser Gln Ile His Thr
            180                 185                 190

Ser Val Arg Leu Ala Cys Lys Thr Gln Pro His Asp Ala Ser Ser Ser
        195                 200                 205

Leu Ala Gly Pro Val Ser Asn Asn Arg Pro Ser Ser
    210                 215                 220
```

<210> SEQ ID NO 15
<211> LENGTH: 1165

```
<212> TYPE: DNA
<213> ORGANISM: Zea mays

<400> SEQUENCE: 15
gcacgaggtc agatcgacct ggactttggc ggcagctact tctagaacgc ggcggcacgg      60
cagcaagcca gcaaggagaa cgcggcggca cgggcgtgct gctacttctg cttcctctcc     120
gacgcttgct gttgagcggt tcaagcagag ctgatggcta catcagagcc agtacaagag     180
agtttggtgg tgcactactc acaacctagt aggccccggg tcctccttgc tgcttcagga     240
agtgtagccg ctataaaatt tgagagcctt tgccgtagct tctctgagtg ggcggatgtc     300
cgagctgtgg ccaccacgcc atccttgcac ttcgttgata gatcatctct accaagtggc     360
atcgttcttt acactgatga cgatgaatgg tctacctgga agaagatagg agatgaagtc     420
ttacacatcg agctgcggaa atgggcagac gttatgGtga tcgctccatt gtcagcaaat     480
accctggcta agatcgccgg tgggttatgc gacaacctct tgacctgcat cgtgagagcg     540
tgggactaca gcaaaccgct ctttgttgcc ccagccatga acacgttaat gtggaacaac     600
ccattcacgg agcggcatct tcacacaatc aaccaactgg gcatagcctt gatccccca      660 gttaccaaaa ggctggcctg tggcgattac gggaacggcg caatggccga aacctcgcag     720
atccatactt ccgtgaggct cgcgtgcaag acgcaaccgc acgatgcgag cagttcactc     780
gcgggtcctg tcagtaataa ccggccatct agctgatgca gcagttggcc acttgattgt     840
caagcttagg aatttgtttt atatgcagtg tgcatctgga gtgttgtaac agatttttt      900 tccaactagt gtttgtgtgt attgaaattg gggggaaag gctgttgtca caggataaca     960
ataacttcct ccctgctcag taattatgag tctattcagt ttgtaattgt cggtgggagt    1020
acaattatgc tacaatattg tttgtttgtg tgtgtgtggg agttggggag tgctgctgcc    1080
acagagatag cttcctccct gcccagccag taatgatagt gattattcag tttgtaaaaa    1140
aaaaaaaaaa aaaaaaaaaa aaaaa                                          1165

<210> SEQ ID NO 16
<211> LENGTH: 220
<212> TYPE: PRT
<213> ORGANISM: Zea mays

<400> SEQUENCE: 16

Met Ala Thr Ser Glu Pro Val Gln Glu Ser Leu Val Val His Tyr Ser
1               5                   10                  15

Gln Pro Ser Arg Pro Arg Val Leu Leu Ala Ala Ser Gly Ser Val Ala
            20                  25                  30

Ala Ile Lys Phe Glu Ser Leu Cys Arg Ser Phe Ser Glu Trp Ala Asp
        35                  40                  45

Val Arg Ala Val Ala Thr Thr Pro Ser Leu His Phe Val Asp Arg Ser
    50                  55                  60

Ser Leu Pro Ser Gly Ile Val Leu Tyr Thr Asp Asp Glu Trp Ser
65                  70                  75                  80

Thr Trp Lys Lys Ile Gly Asp Glu Val Leu His Ile Glu Leu Arg Lys
                85                  90                  95

Trp Ala Asp Val Met Val Ile Ala Pro Leu Ser Ala Asn Thr Leu Ala
            100                 105                 110

Lys Ile Ala Gly Gly Leu Cys Asp Asn Leu Leu Thr Cys Ile Val Arg
        115                 120                 125

Ala Trp Asp Tyr Ser Lys Pro Leu Phe Val Ala Pro Ala Met Asn Thr
    130                 135                 140
```

```
Leu Met Trp Asn Asn Pro Phe Thr Glu Arg His Leu His Thr Ile Asn
145                 150                 155                 160

Gln Leu Gly Ile Ala Leu Ile Pro Pro Val Thr Lys Arg Leu Ala Cys
                165                 170                 175

Gly Asp Tyr Gly Asn Gly Ala Met Ala Glu Thr Ser Gln Ile His Thr
            180                 185                 190

Ser Val Arg Leu Ala Cys Lys Thr Gln Pro His Asp Ala Ser Ser Ser
        195                 200                 205

Leu Ala Gly Pro Val Ser Asn Asn Arg Pro Ser Ser
    210                 215                 220
```

<210> SEQ ID NO 17
<211> LENGTH: 631
<212> TYPE: DNA
<213> ORGANISM: Picea abies
<220> FEATURE:
<221> NAME/KEY: misc_feature
<222> LOCATION: (546)..(546)
<223> OTHER INFORMATION: n is a, c, g, or t

<400> SEQUENCE: 17

```
ggacgcgtgg gtactgtact gcatatagaa ctccggcaat gggctgatgc tatggtgatt      60
gctccactat cagcaaacac gcttgctaag atagcaggtg gcctatgcga caatctactg     120
acttgcataa tacgtgcatg ggactttaac aagcctctct tgtagctcc  tgcaatgaat     180
actttcatgt ggaacaaccc atttactcaa cggcatttgg actctatctc ggagatggga     240
gtatcactta tcccccctat aacaaagacg ttagcttgtg gtgattatgg aaatggtgca     300
atgtcagaac cttcctcaat agatacaact cttaggtttt cactcgatcc ttcaattaaa     360
tgaagtatct gatctccctt tctccaattc ttgttatgaa tctaacatgc ttagtactat     420
ggactgtggt atagactcag attcgtagct gggctagaca gcatgaaccc agctcgtgtg     480
tggctatgtt aagaaattct gatgataaac aatctcgaac ttatgattta tgtaacattt     540
gttccnccat tctggacact tacaagaact gtgtggatac tcctgcttat aagaaaatgt     600
gtcaatctac attgcatatc atctaatttg g                                    631
```

<210> SEQ ID NO 18
<211> LENGTH: 120
<212> TYPE: PRT
<213> ORGANISM: Picea abies

<400> SEQUENCE: 18

```
Gly Arg Val Gly Thr Val Leu His Ile Glu Leu Arg Gln Trp Ala Asp
1               5                   10                  15

Ala Met Val Ile Ala Pro Leu Ser Ala Asn Thr Leu Ala Lys Ile Ala
            20                  25                  30

Gly Gly Leu Cys Asp Asn Leu Leu Thr Cys Ile Ile Arg Ala Trp Asp
        35                  40                  45

Phe Asn Lys Pro Leu Phe Val Ala Pro Ala Met Asn Thr Phe Met Trp
    50                  55                  60

Asn Asn Pro Phe Thr Gln Arg His Leu Asp Ser Ile Ser Glu Met Gly
65                  70                  75                  80

Val Ser Leu Ile Pro Pro Ile Thr Lys Thr Leu Ala Cys Gly Asp Tyr
                85                  90                  95

Gly Asn Gly Ala Met Ser Glu Pro Ser Ser Ile Asp Thr Thr Leu Arg
            100                 105                 110

Phe Ser Leu Asp Pro Ser Ile Lys
    115                 120
```

<210> SEQ ID NO 19
<211> LENGTH: 769
<212> TYPE: DNA
<213> ORGANISM: Brassica napus

<400> SEQUENCE: 19

```
gagatctgta agggttttca aaaagagcca tggagaacgg gaaaagagac agagaagaca      60
tggaagtgca gctctcccct agaaagcccc gcgtactcct cgcagcaacc ggaagcgtcg     120
ccgccatcaa attcggcaac ctctgccact gcttcacaga gtgggcggaa gtgagagccg     180
tcgtctcgaa atcgtctctc cacttcctcg acaagctctc tctcccacag gaagtgactc     240
tctacaccga cgaagacgag tggtcgagct ggaacaagat cggcgatccc gtgcttcaca     300
tcgagctcag acgctgggct gacgtcatgg tcatcgctcc tttgtctgct aacactttag     360
ccaagatagc tggtgggatg tgtgataatc ttctgacttg tatcataaga gcttgggatt     420
atagcaaacc gcttttcgtt gcgccggcta tgaatacttt gatgtggaac aatcctttta     480
cggagaggca tcttttgtcg cttgatgagc ttggaatcac tcttattcct ccgatcaaga     540
agaggttggc ttgtggtgac tatggtaatg gcgcgatggc tgagccgtct cttatctatt     600
ccactgttag actcttctgg gagtctcagg ctcatcagca aagtggtgga actagttaat     660
accatgatgg ttttgcactt tgcaatggtt ggtcagtgtc atagattgtt ctgtctgaaa     720
tgctcgtcct tgtatatgtt aagaacagct gtctgggttg atgtctctt                 769
```

<210> SEQ ID NO 20
<211> LENGTH: 209
<212> TYPE: PRT
<213> ORGANISM: Brassica napus

<400> SEQUENCE: 20

```
Met Glu Asn Gly Lys Arg Asp Arg Glu Asp Met Glu Val Gln Leu Ser
1               5                   10                  15

Pro Arg Lys Pro Arg Val Leu Leu Ala Ala Thr Gly Ser Val Ala Ala
            20                  25                  30

Ile Lys Phe Gly Asn Leu Cys His Cys Phe Thr Glu Trp Ala Glu Val
        35                  40                  45

Arg Ala Val Val Ser Lys Ser Ser Leu His Phe Leu Asp Lys Leu Ser
    50                  55                  60

Leu Pro Gln Glu Val Thr Leu Tyr Thr Asp Glu Asp Glu Trp Ser Ser
65                  70                  75                  80

Trp Asn Lys Ile Gly Asp Pro Val Leu His Ile Glu Leu Arg Arg Trp
                85                  90                  95

Ala Asp Val Met Val Ile Ala Pro Leu Ser Ala Asn Thr Leu Ala Lys
            100                 105                 110

Ile Ala Gly Gly Met Cys Asp Asn Leu Leu Thr Cys Ile Ile Arg Ala
        115                 120                 125

Trp Asp Tyr Ser Lys Pro Leu Phe Val Ala Pro Ala Met Asn Thr Leu
    130                 135                 140

Met Trp Asn Asn Pro Phe Thr Glu Arg His Leu Leu Ser Leu Asp Glu
145                 150                 155                 160

Leu Gly Ile Thr Leu Ile Pro Pro Ile Lys Lys Arg Leu Ala Cys Gly
                165                 170                 175

Asp Tyr Gly Asn Gly Ala Met Ala Glu Pro Ser Leu Ile Tyr Ser Thr
            180                 185                 190

Val Arg Leu Phe Trp Glu Ser Gln Ala His Gln Gln Ser Gly Gly Thr
```

Ser

<210> SEQ ID NO 21
<211> LENGTH: 636
<212> TYPE: DNA
<213> ORGANISM: Brassica oleracea
<220> FEATURE:
<223> OTHER INFORMATION: var. alboglabra
<220> FEATURE:
<221> NAME/KEY: misc_feature
<222> LOCATION: (622)..(622)
<223> OTHER INFORMATION: n is a, c, g, or t

<400> SEQUENCE: 21

```
gacgcgtggg cggacgcgtg ggggtttttc aaaaagagcc atggagaacg ggaaaagaga      60
cagagaagac atggaagtgc agctctcccc tagaaagccc cgcgtactcc tcgcagcaac     120
cggaagcgtc gccgccatca aattcggcaa cctctgccac tgcttcacag agtgggcgga     180
agtgagagcc gtcgtctcga aatcgtctct ccacttcctc gacaagctct ctctcccaca     240
ggaagtgact ctctacaccg acgaagacga gtggtcgagc tggaacaaga tcggcgatcc     300
cgtgcttcac atcgagctca gacgctgggc tgacgtcatg gtcatcgctc ctttgtctgc     360
taacacttta gccaagatag ctggtgggat gtgtgataat cttctgactt gtatcataag     420
agcttgggat tatagcaaac cgcttttcgt tgcgccggct atgaatactt tgatgtggaa     480
caatcctttt acgagaggc atcttttgtc gcttgatgag cttggaatca ctcttattcc     540
tccgatcaag aagaggttgg cttgtggtga ctatggtaat ggcgcgatgg ctgagccgtc     600
tcttatctat tccactgtta gnctcttctg ggagtc                               636
```

<210> SEQ ID NO 22
<211> LENGTH: 198
<212> TYPE: PRT
<213> ORGANISM: Brassica oleracea
<220> FEATURE:
<223> OTHER INFORMATION: var. alboglabra
<220> FEATURE:
<221> NAME/KEY: UNSURE
<222> LOCATION: (194)..(194)
<223> OTHER INFORMATION: Xaa can be any naturally occurring amino acid

<400> SEQUENCE: 22

```
Met Glu Asn Gly Lys Arg Asp Arg Glu Asp Met Glu Val Gln Leu Ser
1               5                   10                  15

Pro Arg Lys Pro Arg Val Leu Leu Ala Ala Thr Gly Ser Val Ala Ala
            20                  25                  30

Ile Lys Phe Gly Asn Leu Cys His Cys Phe Thr Glu Trp Ala Glu Val
        35                  40                  45

Arg Ala Val Val Ser Lys Ser Ser Leu His Phe Leu Asp Lys Leu Ser
    50                  55                  60

Leu Pro Gln Glu Val Thr Leu Tyr Thr Asp Glu Asp Glu Trp Ser Ser
65                  70                  75                  80

Trp Asn Lys Ile Gly Asp Pro Val Leu His Ile Glu Leu Arg Arg Trp
                85                  90                  95

Ala Asp Val Met Val Ile Ala Pro Leu Ser Ala Asn Thr Leu Ala Lys
            100                 105                 110

Ile Ala Gly Gly Met Cys Asp Asn Leu Leu Thr Cys Ile Ile Arg Ala
        115                 120                 125

Trp Asp Tyr Ser Lys Pro Leu Phe Val Ala Pro Ala Met Asn Thr Leu
    130                 135                 140
```

```
Met Trp Asn Asn Pro Phe Thr Glu Arg His Leu Leu Ser Leu Asp Glu
145                 150                 155                 160

Leu Gly Ile Thr Leu Ile Pro Pro Ile Lys Lys Arg Leu Ala Cys Gly
                165                 170                 175

Asp Tyr Gly Asn Gly Ala Met Ala Glu Pro Ser Leu Ile Tyr Ser Thr
            180                 185                 190

Val Xaa Leu Phe Trp Glu
        195

<210> SEQ ID NO 23
<211> LENGTH: 958
<212> TYPE: DNA
<213> ORGANISM: Nicotiana tabacum

<400> SEQUENCE: 23
ggagctgtgt tgccgcagaa ggagcaagaa ttgttggtgc ttcaaggata attggtgttg     60
atttaattcc tagcagattt gatttagatt agggtagata tggagacttc agagatggaa    120
ccggttcaga ttaacaatgc accgaggaga cctcgcattc tgcttgcagc aagtggaagt    180
gtggctgcta tcaagtttgc cagtctatgc cgttccttta ctgattgggc tgaagttaaa    240
gcggttgcta caaaagcttc tcttcatttc atagacaaag cttcacttcc ggaagatgtc    300
attctttata ctgatgagga tgaatggtca acttggacga agataggtga ccgtgtgcta    360
cacatcgagc tccggaggtg ggctgatatt atgattattg ccccctttgtc agcaaataca    420 cttgggaaga ttgctggtgg actatgtgat aacttgttaa cctgcatcgt acgagcatgg    480
gactacgata aaccccttttt cgtggcacca gcaatgaata cattgatgtg aataatcca    540 ttcacagaaa agcaccttat ggcaattgat gagcttggga tctctctcat accaccagta    600
tcaaagagac tagcctgtgg agattacggg aatggagcaa tggctgaacc gtctctgatc    660
ttccaagctg taagactcta ttatgacgca caattacgat caggtggcag caacgtggcg    720
tgatccacag gtcatgaaat tcattcatc ggtttgtaca agtgatagaa gttgttgaaa    780
ttcaggacca ggagcccagc tgtgttattt tctcctaaa ttcttcacct ccctagtatc    840
tttcttgtgt cctagagcta cttttcaatca aggttcatgt tcattttagt cgataaaatg    900
agaatatcac gtaactgctg ttactaatgg atgtgatcat gatcatgaac atgaaaaa     958

<210> SEQ ID NO 24
<211> LENGTH: 207
<212> TYPE: PRT
<213> ORGANISM: Nicotiana tabacum

<400> SEQUENCE: 24

Met Glu Thr Ser Glu Met Glu Pro Val Gln Ile Asn Asn Ala Pro Arg
1               5                   10                  15

Arg Pro Arg Ile Leu Leu Ala Ala Ser Gly Ser Val Ala Ala Ile Lys
                20                  25                  30

Phe Ala Ser Leu Cys Arg Ser Phe Thr Asp Trp Ala Glu Val Lys Ala
            35                  40                  45

Val Ala Thr Lys Ala Ser Leu His Phe Ile Asp Lys Ala Ser Leu Pro
        50                  55                  60

Glu Asp Val Ile Leu Tyr Thr Asp Glu Asp Trp Ser Trp Thr
65                  70                  75                  80

Lys Ile Gly Asp Arg Val Leu His Ile Glu Leu Arg Arg Trp Ala Asp
                85                  90                  95

Ile Met Ile Ile Ala Pro Leu Ser Ala Asn Thr Leu Gly Lys Ile Ala
```

```
                        100                 105                 110
Gly Gly Leu Cys Asp Asn Leu Leu Thr Cys Ile Val Arg Ala Trp Asp
        115                 120                 125

Tyr Asp Lys Pro Leu Phe Val Ala Pro Ala Met Asn Thr Leu Met Trp
130                 135                 140

Asn Asn Pro Phe Thr Glu Lys His Leu Met Ala Ile Asp Glu Leu Gly
145                 150                 155                 160

Ile Ser Leu Ile Pro Pro Val Ser Lys Arg Leu Ala Cys Gly Asp Tyr
                165                 170                 175

Gly Asn Gly Ala Met Ala Glu Pro Ser Leu Ile Phe Gln Ala Val Arg
            180                 185                 190

Leu Tyr Tyr Asp Ala Gln Leu Arg Ser Gly Gly Ser Asn Val Ala
        195                 200                 205

<210> SEQ ID NO 25
<211> LENGTH: 1016
<212> TYPE: DNA
<213> ORGANISM: Solanum tuberosum

<400> SEQUENCE: 25
```

| | | | | | |
|---|---|---|---|---|---|
| gaattgatcg | gcgccggact | tcgatcaccg | tcggcgtttc | taagccgtcg | ccggaactaa | 60 |
| gccggagaaa | atctcaatca | agtgagctaa | gcactcggcg | tttcaacttc | tggttataaa | 120 |
| tttattaaag | cctttgctcc | attaggttag | gtagatacgg | atcctatgac | ttcagagatg | 180 |
| gaaccagttc | agattaatgg | tgcacctagg | agacctcgta | ttctgctggc | agcaagtgga | 240 |
| agtgtggctg | caattaagtt | tgcaaatcta | tgtggttgtt | tttctgaatg | ggcagaagtt | 300 |
| aaagcagttg | caacaaaacc | ttctcttcat | ttcatagaca | aagcttcact | tccggaagat | 360 |
| gccattctat | atactgatga | ggaggaatgg | tccacttgga | agaaaattgg | tgatagtgtg | 420 |
| ctacacattg | agctccgcag | gtgggctgat | attatggtta | ttccccttt | gtcagcaaac | 480 |
| acacttggga | agattgcagg | tggactatgt | gataacttgt | taacctgcat | cgtacgagca | 540 |
| tgggactaca | ataaaccccct | ttttgtggca | ccagccatga | atacattgat | gtggaataat | 600 |
| ccattcacag | aacgacacct | tatggtaatt | gatgagcttg | gaatctctct | cataccacca | 660 |
| gtttctaaaa | gactagcttg | tggagattat | ggaaacggcg | ctatggctga | accttctctc | 720 |
| atctactcaa | ctgtaagact | cttctatgag | tcacggtcac | aatcaggtgg | catcaacttg | 780 |
| gcttgatcca | cggatcatta | aattttattc | gtcggtttgt | acaagtggta | gaaattgttg | 840 |
| aaattcagga | cctggaacag | tgttacttag | catacaccag | ttgtgtttat | ttttctcctt | 900 |
| aattagtgtc | atgtttgtat | ccaagagctg | actttcaatc | aagtttcatg | ttcattgtag | 960 |
| tctattgact | ctgaatatta | tgcaactcta | tatagtaccc | gctactaatt | atgtat | 1016 |

```
<210> SEQ ID NO 26
<211> LENGTH: 206
<212> TYPE: PRT
<213> ORGANISM: Solanum tuberosum

<400> SEQUENCE: 26

Met Thr Ser Glu Met Glu Pro Val Gln Ile Asn Gly Ala Pro Arg Arg
1               5                   10                  15

Pro Arg Ile Leu Leu Ala Ala Ser Gly Ser Val Ala Ala Ile Lys Phe
                20                  25                  30

Ala Asn Leu Cys Gly Cys Phe Ser Glu Trp Ala Glu Val Lys Ala Val
            35                  40                  45

Ala Thr Lys Pro Ser Leu His Phe Ile Asp Lys Ala Ser Leu Pro Glu
```

```
                50                  55                  60
Asp Ala Ile Leu Tyr Thr Asp Glu Glu Trp Ser Thr Trp Lys Lys
 65                  70                  75                  80

Ile Gly Asp Ser Val Leu His Ile Glu Leu Arg Arg Trp Ala Asp Ile
                 85                  90                  95

Met Val Ile Ala Pro Leu Ser Ala Asn Thr Leu Gly Lys Ile Ala Gly
            100                 105                 110

Gly Leu Cys Asp Asn Leu Leu Thr Cys Ile Val Arg Ala Trp Asp Tyr
        115                 120                 125

Asn Lys Pro Leu Phe Val Ala Pro Ala Met Asn Thr Leu Met Trp Asn
    130                 135                 140

Asn Pro Phe Thr Glu Arg His Leu Met Val Ile Asp Glu Leu Gly Ile
145                 150                 155                 160

Ser Leu Ile Pro Pro Val Ser Lys Arg Leu Ala Cys Gly Asp Tyr Gly
                165                 170                 175

Asn Gly Ala Met Ala Glu Pro Ser Leu Ile Tyr Ser Thr Val Arg Leu
            180                 185                 190

Phe Tyr Glu Ser Arg Ser Gln Ser Gly Gly Ile Asn Leu Ala
        195                 200                 205

<210> SEQ ID NO 27
<211> LENGTH: 967
<212> TYPE: DNA
<213> ORGANISM: Glycine max

<400> SEQUENCE: 27
ggttgaacag aagagattta ggcagcccga accgacgatg ttgttttaa ctgacagcag      60
cacaaagcga acactaacac taacgtgaaa cgcgttgcgt tgtcggaaaa tcaccctcac    120
ctgatcactg tggaagtctc taggtgatgg ccggttcaga acctgttagg gcagagggag    180
agactatggc tgtggatgct gccccaagga agccccggat tctacttgct gctagtggga    240
gtgttgctgc tgtcaaattt gcaaatcttt gtcactgttt ctctgaatgg gcagatgtaa    300
gagcagtttc cacaagtgca tctttgcatt tcattgatag gcagcaatg cccaaggatg     360
taattctata cacggatgac aatgaatggt ctagttggaa gaaattaggt gatagcgtgc    420
ttcacattga gcttcgcaaa tgggctgata tcatggtcat cgctccatta tcagcaaaca    480
cccttggcaa gattgctgga gggttgtgtg acaatctact gacatgcatc gttcgagcct    540
gggactacag caagccattc tttgttgcac cagccatgaa cactttgatg tggaacaatc    600
ctttcactga gcggcatttc atctccattg atgagcttgg catttctctc atcccgcctg    660
ttacaaagag gttagcttgt ggggattatg gcaatggtgc catggctgaa ccctctacca    720
tttactcaac tgtaaggctc ttctatgagt caaaggctca gcaaggtaga gctgtggtaa    780
ccttaaggtg aatgaagggg tagtcctacg cccccattca tggtagtcaa tagcactcta    840
tagcaggata acggagcgca gcagccctga gttactatgg aagtcgaaat cgctgagcga    900
ttttcaataa ccgctgtagc ggctgcaata gtggtctaaa tacagctttt cgggtgctac    960
agcgcac                                                             967

<210> SEQ ID NO 28
<211> LENGTH: 214
<212> TYPE: PRT
<213> ORGANISM: Glycine max

<400> SEQUENCE: 28

Met Ala Gly Ser Glu Pro Val Arg Ala Glu Gly Glu Thr Met Ala Val
```

```
              1               5              10              15

Asp Ala Ala Pro Arg Lys Pro Arg Ile Leu Leu Ala Ala Ser Gly Ser
                 20                  25                  30

Val Ala Ala Val Lys Phe Ala Asn Leu Cys His Cys Phe Ser Glu Trp
                 35                  40                  45

Ala Asp Val Arg Ala Val Ser Thr Ser Ala Ser Leu His Phe Ile Asp
 50                  55                  60

Arg Ala Ala Met Pro Lys Asp Val Ile Leu Tyr Thr Asp Asp Asn Glu
 65                  70                  75                  80

Trp Ser Ser Trp Lys Lys Leu Gly Asp Ser Val Leu His Ile Glu Leu
                 85                  90                  95

Arg Lys Trp Ala Asp Ile Met Val Ile Ala Pro Leu Ser Ala Asn Thr
                100                 105                 110

Leu Gly Lys Ile Ala Gly Gly Leu Cys Asp Asn Leu Leu Thr Cys Ile
                115                 120                 125

Val Arg Ala Trp Asp Tyr Ser Lys Pro Phe Phe Val Ala Pro Ala Met
                130                 135                 140

Asn Thr Leu Met Trp Asn Asn Pro Phe Thr Glu Arg His Phe Ile Ser
145                 150                 155                 160

Ile Asp Glu Leu Gly Ile Ser Leu Ile Pro Pro Val Thr Lys Arg Leu
                165                 170                 175

Ala Cys Gly Asp Tyr Gly Asn Gly Ala Met Ala Glu Pro Ser Thr Ile
                180                 185                 190

Tyr Ser Thr Val Arg Leu Phe Tyr Glu Ser Lys Ala Gln Gln Gly Arg
                195                 200                 205

Ala Val Val Thr Leu Arg
    210

<210> SEQ ID NO 29
<211> LENGTH: 1067
<212> TYPE: DNA
<213> ORGANISM: Vitis vinifera

<400> SEQUENCE: 29
ttgggagaga tgccacggcc ctcattcgct ctcgatcccc gacctcggct tcactctctc      60 taatttccc  gagcaattct ccgagttgag gctgatttga agttaatga  tgatgacata     120 tgcagaacct tgagtccag  aagttgatgc gataccagtc aacattgctc ccagaagacc     180
ccggattcta cttgctgcta gtgggagtgt agctgctatg aagtttggga atctcgtcca     240 ttcttttgt  gaatgggcag aagtaagagc agttgtcaca aaggcttctt tacacttcat     300
tgatagagca gcactgccta aggatttata tctttacact gatgatgatg aatggtccag     360
ttggacaaaa ttaggagaca gtgtgcttca cattgagctc cgcaggtggg ctgatgtcat     420
ggtaatcgcc ccattatcag caaatacact tggcaagatt gccgggggac tgtgtgacaa     480
cctgctgaca tgcattgtgc gagcgtggga ctacagcaag ccaatgtttg ttgcgccagc     540
tatgaacacc ttcatgtgga ccaatccttt cacagaacgc catcttatga caattgatga     600
acttggaatt tctcttattc cacctgtcac taaaaggctg gcttgcggag attatgggac     660
tggtgcaatg gctgaacctt ttctcatcca ctcaaccgta agactcttct tggagacacg     720
ggctcaatca agtagcagta atgtgcagta attgggtatg ttaatctgt  ctgttggaga     780 agtcaccaga gagttggctg aaatggcatg ttggaaatgc taaacgtagt tcacttggac     840
cgcattgatt tgttatgac  cgtccattaa acttactacg tcttgtagat tgttggtatc     900
ggtggatttg catatcctgt ttctcaatat ttctagtagc gccttttgaa tgttatgtgc     960
```

```
cttgtgtatt aatggtgagg gagaatgtat cagtctccta aatttctcaa tctctgtgta   1020
gacatgcttg atgatacatt cctataaata gactctgatt tctgggc                1067
```

```
<210> SEQ ID NO 30
<211> LENGTH: 214
<212> TYPE: PRT
<213> ORGANISM: Vitis vinifera

<400> SEQUENCE: 30
```

```
Met Met Met Thr Tyr Ala Glu Pro Leu Ser Pro Glu Val Asp Ala Ile
1               5                   10                  15

Pro Val Asn Ile Ala Pro Arg Arg Pro Arg Ile Leu Leu Ala Ala Ser
            20                  25                  30

Gly Ser Val Ala Ala Met Lys Phe Gly Asn Leu Val His Ser Phe Cys
        35                  40                  45

Glu Trp Ala Glu Val Arg Ala Val Val Thr Lys Ala Ser Leu His Phe
    50                  55                  60

Ile Asp Arg Ala Ala Leu Pro Lys Asp Leu Tyr Leu Tyr Thr Asp Asp
65                  70                  75                  80

Asp Glu Trp Ser Ser Trp Thr Lys Leu Gly Asp Ser Val Leu His Ile
                85                  90                  95

Glu Leu Arg Arg Trp Ala Asp Val Met Val Ile Ala Pro Leu Ser Ala
            100                 105                 110

Asn Thr Leu Gly Lys Ile Ala Gly Gly Leu Cys Asp Asn Leu Leu Thr
        115                 120                 125

Cys Ile Val Arg Ala Trp Asp Tyr Ser Lys Pro Met Phe Val Ala Pro
    130                 135                 140

Ala Met Asn Thr Phe Met Trp Asn Pro Phe Thr Glu Arg His Leu
145                 150                 155                 160

Met Thr Ile Asp Glu Leu Gly Ile Ser Leu Ile Pro Pro Val Thr Lys
                165                 170                 175

Arg Leu Ala Cys Gly Asp Tyr Gly Thr Gly Ala Met Ala Glu Pro Phe
            180                 185                 190

Leu Ile His Ser Thr Val Arg Leu Phe Leu Glu Thr Arg Ala Gln Ser
        195                 200                 205

Ser Ser Ser Asn Val Gln
    210
```

```
<210> SEQ ID NO 31
<211> LENGTH: 1081
<212> TYPE: DNA
<213> ORGANISM: Hordeum vulgare

<400> SEQUENCE: 31
cggcacgagg ctccccaatt ccctccgccc gcggcgcgcc gctccgggca gcctcggtcg   60
ccgccgccgc cgccgctgcc tccacctacc gccggccgac gacgcccttc gaacctaccg  120
cctccgccgc catcttcaac cgcttatttg cctgcgctcc taccagatcg cctctgagtt  180
gagggctcca agtgaagcag atggctacat cagaaccggt acagcaaagc tgggagctgg  240
aatccagcag gcctcgggtc ctccttgctg cgtcagggag tgtagctgct ataaaattcg  300
agagcctctg ccgtatcttc tccgagtggg cggaagtccg agctgtggcg accaagtcag  360
cattgcactt tgttgacaga tcatctctgc caagcgacgt cgtcctttac actgatgatg  420
atgagtggtc tacctggaca aagataggag acgaggttct gcacatagag ctgcgaaagt  480
gggcagacat catggtgatc gccccttat cagcaaacac tctggccaag atcgccggcg  540
```

-continued

```
ggttatgcga caacctcctg acgtgcatta tccgagcgtg ggactacaag aagccgatct      600
tcgccgcgcc agccatgaac accttcatgt ggaacaaccc attcacggcg cgccacatcg      660
agaccatgaa ccaactgggc atctccctgg tcccgcccac cacgaaacgg ctggcctgcg      720
gcgactacgg gaacggcgcg atggctgagc cctcgcagat ccacacgact gtgaggctcg      780
cgtgcaagtc gcagacgttt ggcacgggca tttcgcccgc gcaccttcc agcggccacc       840 ccgtctagcc gatgcggtga tggtcactat gttcaggtgg tctagtactc gaggttttc       900 tatgccgccc acatcatcag ggtttgagaa agtgaagggt atcaccaggt gttctgttca      960
tcggtggtgt ctgtattaac cgaagtatcg tacctgtggg atatggatca gcttatttgt     1020
tatgtggtag tagacgttag ggcgtagacg tagagattgg ggaattgctg ttgctccagc     1080
c                                                                    1081
```

<210> SEQ ID NO 32
<211> LENGTH: 215
<212> TYPE: PRT
<213> ORGANISM: Hordeum vulgare

<400> SEQUENCE: 32

```
Met Ala Thr Ser Glu Pro Val Gln Gln Ser Trp Glu Leu Glu Ser Ser
1               5                   10                  15

Arg Pro Arg Val Leu Leu Ala Ala Ser Gly Ser Val Ala Ala Ile Lys
            20                  25                  30

Phe Glu Ser Leu Cys Arg Ile Phe Ser Glu Trp Ala Glu Val Arg Ala
        35                  40                  45

Val Ala Thr Lys Ser Ala Leu His Phe Val Asp Arg Ser Ser Leu Pro
    50                  55                  60

Ser Asp Val Val Leu Tyr Thr Asp Asp Glu Trp Ser Thr Trp Thr
65                  70                  75                  80

Lys Ile Gly Asp Glu Val Leu His Ile Glu Leu Arg Lys Trp Ala Asp
                85                  90                  95

Ile Met Val Ile Ala Pro Leu Ser Ala Asn Thr Leu Ala Lys Ile Ala
            100                 105                 110

Gly Gly Leu Cys Asp Asn Leu Leu Thr Cys Ile Ile Arg Ala Trp Asp
        115                 120                 125

Tyr Lys Lys Pro Ile Phe Ala Ala Pro Ala Met Asn Thr Phe Met Trp
    130                 135                 140

Asn Asn Pro Phe Thr Ala Arg His Ile Glu Thr Met Asn Gln Leu Gly
145                 150                 155                 160

Ile Ser Leu Val Pro Pro Thr Thr Lys Arg Leu Ala Cys Gly Asp Tyr
                165                 170                 175

Gly Asn Gly Ala Met Ala Glu Pro Ser Gln Ile His Thr Thr Val Arg
            180                 185                 190

Leu Ala Cys Lys Ser Gln Thr Phe Gly Thr Gly Ile Ser Pro Ala His
        195                 200                 205

Pro Ser Ser Gly His Pro Val
    210                 215
```

<210> SEQ ID NO 33
<211> LENGTH: 1175
<212> TYPE: DNA
<213> ORGANISM: Gossypium hirsutum

<400> SEQUENCE: 33

```
cccattgtca cctttagtgc tggtgagcat ttaagagagg gcagagcaac ggaggaaatc       60
```

```
cccttttttg tgcagtggaa gtaaaaatta cctaccatta gaaaaggaga aggattggta    120
aagtattgca gcgctccgta aaggcatttt ggtatagcaa gtagcagcaa ttcatcaaaa    180
ggcagcattt cttttttgcac caggggccct taaaaagct caactctcgc gcttctttgc    240
gtttcaaatc tctctgcaag tcgcaaggac atctgaagca gaaagcccag attcctctct    300
aatcttagat tccagatttg cataggttat ggcgtatcct gagcctcaag gtgcagatag    360
ggagatggtt aaggtcaatc ctaccccaag aaaaccccgg gttttactcg ctgccagtgg    420
aagtgtagct gccataaagt ttgggaatct ctgccattgt ttctctgaat gggcagaagt    480
aaaagcagtt gccacgaaag cttctttgca tttcattgac agagcatcac ttcctaagga    540
tctaaagctt tacactgatg aggaggaatg gtctagttgg gggaaaatag gtgacagtgt    600
gcttcacatt gagcttcgtc gatgggctga tattatggtc attgccccat tgtcagcaaa    660
cacacttggc aagattgctg gaggattatg tgacaatttg ttaacttgtg tcgtacgagc    720
atgggactac agcaagccaa tgtttgttgc accagctatg aacactttca tgtggagcaa    780
ccctttcaca gaaaagcatc tcatgacaat tgatgagctt ggtatttctc tcatcccccc    840
tgtctccaaa agactagctt gtggggacta tggaaacggc gcaatggcag aaccttctct    900
aatccactcg actgtaagat tattcttgga gtcacgacct caaccaagtg actgaagatc    960
tatttattcg ccatgaatta taaatactat attagttgta tggtagccca gttgactcta   1020
ggttgggtgt atgtctatta gctgtctaac aagcttattg tacatttata gttgcatttc   1080
cgagtttgct taactttgca tatcatgagg agtggtcttt gaatactgct gaaaatttga   1140
tcctgtaagc tgatgatact gatgagagtt ggcag                              1175

<210> SEQ ID NO 34
<211> LENGTH: 208
<212> TYPE: PRT
<213> ORGANISM: Gossypium hirsutum

<400> SEQUENCE: 34

Met Ala Tyr Pro Glu Pro Gln Gly Ala Asp Arg Glu Met Val Lys Val
1               5                   10                  15

Asn Pro Thr Pro Arg Lys Pro Arg Val Leu Leu Ala Ala Ser Gly Ser
            20                  25                  30

Val Ala Ala Ile Lys Phe Gly Asn Leu Cys His Cys Phe Ser Glu Trp
        35                  40                  45

Ala Glu Val Lys Ala Val Ala Thr Lys Ala Ser Leu His Phe Ile Asp
    50                  55                  60

Arg Ala Ser Leu Pro Lys Asp Leu Lys Leu Tyr Thr Asp Glu Glu Glu
65                  70                  75                  80

Trp Ser Ser Trp Gly Lys Ile Gly Asp Ser Val Leu His Ile Glu Leu
                85                  90                  95

Arg Arg Trp Ala Asp Ile Met Val Ile Ala Pro Leu Ser Ala Asn Thr
            100                 105                 110

Leu Gly Lys Ile Ala Gly Gly Leu Cys Asp Asn Leu Leu Thr Cys Val
        115                 120                 125

Val Arg Ala Trp Asp Tyr Ser Lys Pro Met Phe Val Ala Pro Ala Met
    130                 135                 140

Asn Thr Phe Met Trp Ser Asn Pro Phe Thr Glu Lys His Leu Met Thr
145                 150                 155                 160

Ile Asp Glu Leu Gly Ile Ser Leu Ile Pro Pro Val Ser Lys Arg Leu
                165                 170                 175
```

Ala Cys Gly Asp Tyr Gly Asn Gly Ala Met Ala Glu Pro Ser Leu Ile
            180                 185                 190

His Ser Thr Val Arg Leu Phe Leu Glu Ser Arg Pro Gln Pro Ser Asp
        195                 200                 205

<210> SEQ ID NO 35
<211> LENGTH: 1119
<212> TYPE: DNA
<213> ORGANISM: Sorghum bicolor

<400> SEQUENCE: 35

| | | | | | |
|---|---|---|---|---|---|
| gcacgagggc | tctctccgct | cacctccact | tccccgcccc | cgccccggtc | tccgtccttg | 60 |
| acacgggcgc | gcaccgtcc | gcctccgact | gacccggagc | cgactcgacc | ttgttcagga | 120 |
| gggagggaga | gcccgaaccg | cggcggggcg | ggagggctcc | ttttcgtttg | ccccgccgga | 180 |
| gggccagccg | ccccatgggc | cggtcgcctg | agcgcgctac | gtatcagctc | atcgaccggc | 240 |
| ggaaagctga | gcgttagcgg | agctgatggc | tacatcagag | ccagtacaag | agaatttggc | 300 |
| gatggactac | tcacaaccta | gtaagcctcg | ggtactcctt | gctgcttcag | gaagtgtagc | 360 |
| cgctataaaa | tttgagaacc | tttgtcgtag | tttctctgag | tgggcggatg | tccgagccgt | 420 |
| ggccaccgca | tcatctttgc | actttattga | tagatcatct | cttccaagtg | acattgttct | 480 |
| ttacactgat | gatgatgagt | ggtctacctg | gaagaagata | ggagatgaag | ttttacacat | 540 |
| tgagctgcgt | aaatgggcag | atattatggt | gattgctccg | ttatcagcaa | atacccctggc | 600 |
| taagatcgcc | ggtgggttat | gtgacaacct | cttaacatgc | atcgtgagag | cgtgggacta | 660 |
| cagcaaaccg | ctctttgttg | ccccagctat | gaacacatta | atgtggaaca | acccattcac | 720 |
| agagcgtcat | cttcaaacga | tcaaccaact | gggcataatc | ttgatccccc | cagttaccaa | 780 |
| aaggttggct | tgtggcgatc | acgggaatgg | tgcaatggct | gaaacctcgc | agatctatac | 840 |
| ttctgtgagg | cttgcatgga | agacgcaacc | acatgatgca | agcagttcac | ttgtggttcc | 900 |
| tgtcagtaat | aaccgcccat | ctagctggtg | tttgacctct | taattaagag | cttaggaatt | 960 |
| tgttttatct | gcagtgtgca | tcttgatgtt | agaaatgttg | taccaatttt | ttttaaccag | 1020 |
| tgttttagtg | tgtattgtga | tgagaatgtg | gggaaaggaa | ggttgtcagt | tgtcacggtg | 1080 |
| ataaattact | gccagctcag | tatcgatagt | gaggatgag | | | 1119 |

<210> SEQ ID NO 36
<211> LENGTH: 225
<212> TYPE: PRT
<213> ORGANISM: Sorghum bicolor

<400> SEQUENCE: 36

Met Ala Thr Ser Glu Pro Val Gln Glu Asn Leu Ala Met Asp Tyr Ser
1               5                   10                  15

Gln Pro Ser Lys Pro Arg Val Leu Leu Ala Ala Ser Gly Ser Val Ala
            20                  25                  30

Ala Ile Lys Phe Glu Asn Leu Cys Arg Ser Phe Ser Glu Trp Ala Asp
        35                  40                  45

Val Arg Ala Val Ala Thr Ala Ser Ser Leu His Phe Ile Asp Arg Ser
    50                  55                  60

Ser Leu Pro Ser Asp Ile Val Leu Tyr Thr Asp Asp Glu Trp Ser
65                  70                  75                  80

Thr Trp Lys Lys Ile Gly Asp Glu Val Leu His Ile Glu Leu Arg Lys
                85                  90                  95

Trp Ala Asp Ile Met Val Ile Ala Pro Leu Ser Ala Asn Thr Leu Ala
            100                 105                 110

```
Lys Ile Ala Gly Gly Leu Cys Asp Asn Leu Leu Thr Cys Ile Val Arg
        115                 120                 125

Ala Trp Asp Tyr Ser Lys Pro Leu Phe Val Ala Pro Ala Met Asn Thr
130                 135                 140

Leu Met Trp Asn Asn Pro Phe Thr Glu Arg His Leu Gln Thr Ile Asn
145                 150                 155                 160

Gln Leu Gly Ile Ile Leu Ile Pro Pro Val Thr Lys Arg Leu Ala Cys
                165                 170                 175

Gly Asp His Gly Asn Gly Ala Met Ala Glu Thr Ser Gln Ile Tyr Thr
            180                 185                 190

Ser Val Arg Leu Ala Trp Lys Thr Gln Pro His Asp Ala Ser Ser Ser
        195                 200                 205

Leu Val Val Pro Val Ser Asn Asn Arg Pro Ser Ser Trp Cys Leu Thr
    210                 215                 220

Ser
225

<210> SEQ ID NO 37
<211> LENGTH: 975
<212> TYPE: DNA
<213> ORGANISM: Lycopersicon esculentum

<400> SEQUENCE: 37
ctacaattga tcggcgccgg actttgatca ccgtcggcgt ttctaagccg ttgccggact      60
atgccggagc aaatctcaat caagtgagct aaccactctg tgtttcaact tctggttata    120
aatttttta  agcctttgct ccgttaggtt aggtagatac ggatcctatg acttcagaga    180
tggaaccagt tcagattaat ggtgcaccta ggagacctcg tattctgctg gcagcaagtg    240
gaagtgtggc ttcaattaag tttgctaatc tatgtcgttg ttttctgaa  tgggcagaag    300
ttaaagcagt tgcaacgaaa ccttctcttc atttcataga caaagcttcg cttccggaag    360
atgtcattct ttatactgat gaggaggaat ggtccacttg gtgcagattg gtgatagtgt    420
gctacacatt gagctccgca gatgggctga tattatggtt attgcccctt tgtcagcaaa    480
cacacttggg aagattgcag gtggactatg tgataacttg ttaacctgca tcgtacgagc    540
atgggactac aataaacccc tttttgtggc accagccatg aatacattga tgtgaataa    600
tccattcaca gaacgacacc ttatggtaat tgatgagctt ggaatctctc tcatacccc     660
agtttcaaaa agactagcat gtggagatta tggaaatggc gctatggctg aaccttctct    720
catttactca actgtaagac tcttttatga gtcacggtca caatcaggtg gcatcaactt    780
ggcttgattc gcagatcatt aaattttatt catcggtttg tacaagtggt aaaaattgtt    840
gaaattcagg acctggaaca gtgttactta gcatacacca gttgggttta ttttctcct    900
aaattcttca cctctttaac ttgtgtcatg tttgtatcca agcggtaact ttcaatcaag    960
tttcatgttc attgt                                                    975

<210> SEQ ID NO 38
<211> LENGTH: 206
<212> TYPE: PRT
<213> ORGANISM: Lycopersicon esculentum
<220> FEATURE:
<221> NAME/KEY: UNSURE
<222> LOCATION: (74)..(74)
<223> OTHER INFORMATION: Xaa can be any naturally occurring amino acid

<400> SEQUENCE: 38

Met Thr Ser Glu Met Glu Pro Val Gln Ile Asn Gly Ala Pro Arg Arg
```

|     | 1   |     |     |     | 5   |     |     |     |     | 10  |     |     |     |     | 15  |
| --- | --- | --- | --- | --- | --- | --- | --- | --- | --- | --- | --- | --- | --- | --- | --- |

Pro Arg Ile Leu Leu Ala Ala Ser Gly Ser Val Ala Ser Ile Lys Phe
                20                      25                      30

Ala Asn Leu Cys Arg Cys Phe Ser Glu Trp Ala Glu Val Lys Ala Val
            35                      40                      45

Ala Thr Lys Pro Ser Leu His Phe Ile Asp Lys Ala Ser Leu Pro Glu
        50                      55                      60

Asp Val Ile Leu Tyr Thr Asp Glu Glu Xaa Met Val His Leu Val Gln
65                      70                      75                      80

Ile Gly Asp Ser Val Leu His Ile Glu Leu Arg Arg Trp Ala Asp Ile
                85                      90                      95

Met Val Ile Ala Pro Leu Ser Ala Asn Thr Leu Gly Lys Ile Ala Gly
            100                     105                     110

Gly Leu Cys Asp Asn Leu Leu Thr Cys Ile Val Arg Ala Trp Asp Tyr
        115                     120                     125

Asn Lys Pro Leu Phe Val Ala Pro Ala Met Asn Thr Leu Met Trp Asn
    130                     135                     140

Asn Pro Phe Thr Glu Arg His Leu Met Val Ile Asp Glu Leu Gly Ile
145                     150                     155                     160

Ser Leu Ile Pro Pro Val Ser Lys Arg Leu Ala Cys Gly Asp Tyr Gly
                165                     170                     175

Asn Gly Ala Met Ala Glu Pro Ser Leu Ile Tyr Ser Thr Val Arg Leu
            180                     185                     190

Phe Tyr Glu Ser Arg Ser Gln Ser Gly Gly Ile Asn Leu Ala
        195                     200                     205

<210> SEQ ID NO 39
<211> LENGTH: 1395
<212> TYPE: DNA
<213> ORGANISM: Arabidopsis thaliana

<400> SEQUENCE: 39

| atggcgaaaa cagctcttac tcctcccgcg tctggttccg aagttccaag atccggtaca | 60 |
| actggagatg cgtctggcaa caaacctcaa acgatgcca ccggcgtctc agctactgat | 120 |
| actgcttctc agaaacgcgg tcgtggtcga ccgccaaagg ctaaatctga ctcttcccaa | 180 |
| atcggtgccg tttctgcgaa ggcgagtact aaaccaagtg gtcgtccgaa agaaacgta | 240 |
| gctcaggctg ttccttctac gtctgtggcg gcggctgtga agaaacgtgg tagggcaaag | 300 |
| aggtcgactg taacggcggc tgtggttact actgctactg gagagggttc tagaaaacga | 360 |
| gggaggccaa agaaagatga cgtggcggct gcaactgttc cagcagaaac tgtggtggct | 420 |
| ccagctaaga gacgtggaag gaaacctact gtcgaagtag ctgcacagcc tgtgcgcagg | 480 |
| actaggaagg tattcgggtt ttctatgcat gaacaaaaga gcacttcagt ggcaccggta | 540 |
| gctgcaaacg tcggagatct caagaaaaga accgcactct acaaaagaa agtgaaggaa | 600 |
| gctgcagcta agttgaaaca agcagtaaca gcaattgacg aggtccagaa gttagcggat | 660 |
| ggaatattga ccagcgatga cgtcgacttc tctgttttgt tttcaaactt aaagaccctc | 720 |
| gcggcatttg atttcgattt ccgattaggg ttcctcgcag atcctccttc ctcggctata | 780 |
| gagaagaaga tgaatatgga agtggataca gtaacaagga agcctcgtat cttactagct | 840 |
| gcaagtggaa gtgtggcttc aattaagttc agtaatctct gccattgttt ctcagaatgg | 900 |
| gctgaagtca aagccgtcgc ttcaaaatca tctctcaatt tcgttgataa accttctcta | 960 |
| cctcagaatg tgactctcta tacagatgaa gatgaatggt ctagctggaa caagattggt | 1020 |

-continued

```
gatcccgttc ttcatatcga gctcagacgc tgggctgatg ttatgatcat tgctcctttg    1080
tctgctaaca cattagccaa gattgctggt gggttatgtg ataatctatt gacatgtata    1140
gtaagagcat gggattatag caaaccgttg tttgttgcac cggcgatgaa cactttgatg    1200
tggaacaatc ctttcacaga acggcacctt gtcttgcttg atgaacttgg aatcacccta    1260
attcctccca tcaagaagaa actggcctgt ggagactacg gtaatggcgc aatggctgag    1320
ccttctctga tttattccac tgttagactg ttctgggagt cacaagctcg taaacaaaga    1380
gatggaacca gttga                                                     1395
```

<210> SEQ ID NO 40
<211> LENGTH: 464
<212> TYPE: PRT
<213> ORGANISM: Arabidopsis thaliana

<400> SEQUENCE: 40

```
Met Ala Lys Thr Ala Leu Thr Pro Pro Ala Ser Gly Ser Glu Val Pro
1               5                   10                  15

Arg Ser Gly Thr Pro Gly Asp Ala Ser Gly Asn Lys Pro Gln Thr Asp
            20                  25                  30

Ala Thr Gly Val Ser Ala Thr Asp Thr Ala Ser Gln Lys Arg Gly Arg
        35                  40                  45

Gly Arg Pro Pro Lys Ala Lys Ser Asp Ser Ser Gln Ile Gly Ala Val
    50                  55                  60

Ser Ala Lys Ala Ser Thr Lys Pro Ser Gly Arg Pro Lys Arg Asn Val
65                  70                  75                  80

Ala Gln Ala Val Pro Ser Thr Ser Val Ala Ala Val Lys Lys Arg
                85                  90                  95

Gly Arg Ala Lys Arg Ser Thr Val Thr Ala Ala Val Val Thr Thr Ala
            100                 105                 110

Thr Gly Glu Gly Ser Arg Lys Arg Gly Arg Pro Lys Lys Asp Asp Val
        115                 120                 125

Ala Ala Ala Thr Val Pro Ala Glu Thr Val Val Ala Pro Ala Lys Arg
    130                 135                 140

Arg Gly Arg Lys Pro Thr Val Glu Val Ala Ala Gln Pro Val Arg Arg
145                 150                 155                 160

Thr Arg Lys Val Phe Gly Phe Ser Met His Glu Gln Lys Ser Thr Ser
                165                 170                 175

Val Ala Pro Val Ala Ala Asn Val Gly Asp Leu Lys Lys Arg Thr Ala
            180                 185                 190

Leu Leu Gln Lys Lys Val Lys Glu Ala Ala Ala Lys Leu Lys Gln Ala
        195                 200                 205

Val Thr Ala Ile Asp Glu Val Gln Lys Leu Ala Asp Gly Ile Leu Thr
    210                 215                 220

Ser Asp Asp Val Asp Phe Ser Val Leu Phe Ser Asn Leu Lys Thr Leu
225                 230                 235                 240

Ala Ala Phe Asp Phe Asp Phe Arg Leu Gly Phe Leu Ala Asp Pro Pro
                245                 250                 255

Ser Ser Ala Ile Glu Lys Lys Met Asn Met Glu Val Asp Thr Val Thr
            260                 265                 270

Arg Lys Pro Arg Ile Leu Leu Ala Ala Ser Gly Ser Val Ala Ser Ile
        275                 280                 285

Lys Phe Ser Asn Leu Cys His Cys Phe Ser Glu Trp Ala Glu Val Lys
    290                 295                 300

Ala Val Ala Ser Lys Ser Ser Leu Asn Phe Val Asp Lys Pro Ser Leu
```

```
            305                 310                 315                 320
Pro Gln Asn Val Thr Leu Tyr Thr Asp Glu Asp Glu Trp Ser Ser Trp
                    325                 330                 335

Asn Lys Ile Gly Asp Pro Val Leu His Ile Glu Leu Arg Arg Trp Ala
                340                 345                 350

Asp Val Met Ile Ile Ala Pro Leu Ser Ala Asn Thr Leu Ala Lys Ile
            355                 360                 365

Ala Gly Gly Leu Cys Asp Asn Leu Leu Thr Cys Ile Val Arg Ala Trp
        370                 375                 380

Asp Tyr Ser Lys Pro Leu Phe Val Ala Pro Ala Met Asn Thr Leu Met
385                 390                 395                 400

Trp Asn Asn Pro Phe Thr Glu Arg His Leu Val Leu Leu Asp Glu Leu
                405                 410                 415

Gly Ile Thr Leu Ile Pro Pro Ile Lys Lys Lys Leu Ala Cys Gly Asp
            420                 425                 430

Tyr Gly Asn Gly Ala Met Ala Glu Pro Ser Leu Ile Tyr Ser Thr Val
        435                 440                 445

Arg Leu Phe Trp Glu Ser Gln Ala Arg Lys Gln Arg Asp Gly Thr Ser
    450                 455                 460
```

<210> SEQ ID NO 41
<211> LENGTH: 1182
<212> TYPE: DNA
<213> ORGANISM: Pinus sp.

<400> SEQUENCE: 41

```
atattgaaac tcatttttaa acacttattc tgcactataa gaagcagcag gcccccagaa      60
atatgagctt catacacaca acgggggagt aatcagcacc atcaaagggg ggatttgcgg     120
caattgtgag atcaagtgga ggaagctgga atagatctaa atctaggccc ttgaggagaa     180
tgctctccta atggtggttt taaaaatcaa tactctagtg caaaacatgg atgcaacaaa     240
ttctcaacct gatgaacctg aagggatgc taattcatct cagaaaccac gaatcattct      300
agcagccagc gggagtgtgg cagcaataaa atttggaatt cttgcccatt gtctatgtca     360
atgggcagaa gtcaaagcag tggtcacaaa atctgctttg catttcattg acaagatgtc     420
tcttccggct aatgttaagc tctacactga tgaaaatgaa tggtctagct ggagcaaaat     480
aggtgatact gtactgcata tagaactccg gcaatgggct gatgctatgg tgattgctcc     540
actctcagca aacacgcttg ctaagatagc aggtggccta tgcgacaatc tacttacttg     600
catagtacgt gcatgggact ttaacaagcc tctctttgta gctcctgcaa tgaatacttt     660
catgtggaac aatccattta ctcaacggca tttggactca atctcagagc tcggactatc     720
acttatcccc ccaataacaa agaagttagc ttgtggtgat tatggaaatg gtgcaatggc     780
tgaaccttct acgatagata caactcttag gttttcactt gatccttcaa ttgtatgaag     840
tgtctgatgt cccgttcaac aattcttgtt atgaatctaa catgcttagt acaatggact     900
atggtataga cccagatagt gtttcttggt agctgggtta gacagcatga actcagcttg     960
tgtgtggtga agttaagttc tgatgataaa caatcatgaa cttgtgattt tatgtaacat    1020
ttgctcattt attctggaca cttacaagaa ctgtgtggat actcctgctt ataagagaat    1080
gtgtcaaact actatgcaaa tcatctaatt tggaacttga tgatgtaaga ggagtatgca    1140
ctttattttc ttccctgtga taattattaa tctctatgat tg                       1182
```

<210> SEQ ID NO 42
<211> LENGTH: 215

```
<212> TYPE: PRT
<213> ORGANISM: Pinus sp.

<400> SEQUENCE: 42

Met Val Val Leu Lys Ile Asn Thr Leu Val Gln Asn Met Asp Ala Thr
1               5                   10                  15

Asn Ser Gln Pro Asp Glu Pro Gly Arg Asp Ala Asn Ser Ser Gln Lys
            20                  25                  30

Pro Arg Ile Ile Leu Ala Ala Ser Gly Ser Val Ala Ala Ile Lys Phe
        35                  40                  45

Gly Ile Leu Ala His Cys Leu Cys Gln Trp Ala Glu Val Lys Ala Val
    50                  55                  60

Val Thr Lys Ser Ala Leu His Phe Ile Asp Lys Met Ser Leu Pro Ala
65                  70                  75                  80

Asn Val Lys Leu Tyr Thr Asp Glu Asn Glu Trp Ser Trp Ser Lys
                85                  90                  95

Ile Gly Asp Thr Val Leu His Ile Glu Leu Arg Gln Trp Ala Asp Ala
                100                 105                 110

Met Val Ile Ala Pro Leu Ser Ala Asn Thr Leu Ala Lys Ile Ala Gly
            115                 120                 125

Gly Leu Cys Asp Asn Leu Leu Thr Cys Ile Val Arg Ala Trp Asp Phe
    130                 135                 140

Asn Lys Pro Leu Phe Val Ala Pro Ala Met Asn Thr Phe Met Trp Asn
145                 150                 155                 160

Asn Pro Phe Thr Gln Arg His Leu Asp Ser Ile Ser Glu Leu Gly Leu
                165                 170                 175

Ser Leu Ile Pro Pro Ile Thr Lys Lys Leu Ala Cys Gly Asp Tyr Gly
            180                 185                 190

Asn Gly Ala Met Ala Glu Pro Ser Thr Ile Asp Thr Leu Arg Phe
    195                 200                 205

Ser Leu Asp Pro Ser Ile Val
    210             215

<210> SEQ ID NO 43
<211> LENGTH: 804
<212> TYPE: DNA
<213> ORGANISM: Oryza sativa

<400> SEQUENCE: 43 atgggggcggg ggaaggtgca gctgaagcgg atagagaaca agatcaacag gcaggtgacg      60
ttctccaaga ggaggaatgg attgctgaag aaggcgcacg agatctccgt cctctgcgac     120
gccgaggtcg ccgccatcgt cttctccccc aagggcaagc tctacgagta cgccactgac     180
tccaggatgg acaaaatcct tgaacgttat gagcgctatt catatgctga aaaggctctt     240
atttcagctg aatccgagag tgagggaaat tggtgccatg aatacaggaa acttaaggca     300
aagattgaga ccatacaaaa atgtcacaaa cacctcatgg gagaggatct agaatccctg     360
aatctcaaag aactccaaca gctagagcag cagctggaga gttcattgaa gcacataata     420
tcaagaaaga gccaccttat gcttgagtcc atttccgagc tgcagaaaaa ggagaggtca     480
ctgcaggagg agaacaaggc tctgcagaag gaactggtgg agaggcagaa gaatgtgagg     540
ggccagcagc aagtagggca gtgggaccaa acccaggtcc aggcccaggc caagcccaa     600 ccccaagccc agacaagctc ctcctcctcc tccatgctga gggatcagca ggcacttctt     660
ccaccacaaa atatctgcta cccgccggtg atgatgggcg agagaaatga tgcggcggcg     720
gcggcggcgg tggcggcgca gggccaggtg caactccgca tcggaggtct tccgccatgg     780
```
atgctgagcc acctcaatgc ttaa                                              804

<210> SEQ ID NO 44
<211> LENGTH: 267
<212> TYPE: PRT
<213> ORGANISM: Oryza sativa

<400> SEQUENCE: 44

Met Gly Arg Gly Lys Val Gln Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Ala Ile Val Phe
        35                  40                  45

Ser Pro Lys Gly Lys Leu Tyr Glu Tyr Ala Thr Asp Ser Arg Met Asp
    50                  55                  60

Lys Ile Leu Glu Arg Tyr Glu Arg Tyr Ser Tyr Ala Glu Lys Ala Leu
65                  70                  75                  80

Ile Ser Ala Glu Ser Glu Ser Glu Gly Asn Trp Cys His Glu Tyr Arg
                85                  90                  95

Lys Leu Lys Ala Lys Ile Glu Thr Ile Gln Lys Cys His Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Ile Ser Arg Lys Ser
    130                 135                 140

His Leu Met Leu Glu Ser Ile Ser Glu Leu Gln Lys Lys Glu Arg Ser
145                 150                 155                 160

Leu Gln Glu Glu Asn Lys Ala Leu Gln Lys Glu Leu Val Glu Arg Gln
                165                 170                 175

Lys Asn Val Arg Gly Gln Gln Val Gly Trp Asp Gln Thr Gln
            180                 185                 190

Val Gln Ala Gln Ala Gln Ala Gln Pro Gln Ala Gln Thr Ser Ser Ser
        195                 200                 205

Ser Ser Ser Met Leu Arg Asp Gln Gln Ala Leu Leu Pro Pro Gln Asn
    210                 215                 220

Ile Cys Tyr Pro Pro Val Met Met Gly Glu Arg Asn Asp Ala Ala Ala
225                 230                 235                 240

Ala Ala Ala Val Ala Ala Gln Gly Gln Val Gln Leu Arg Ile Gly Gly
                245                 250                 255

Leu Pro Pro Trp Met Leu Ser His Leu Asn Ala
            260                 265

<210> SEQ ID NO 45
<211> LENGTH: 52
<212> TYPE: DNA
<213> ORGANISM: Artificial sequence
<220> FEATURE:
<223> OTHER INFORMATION: primer

<400> SEQUENCE: 45
ggggacaagt ttgtacaaaa aagcaggctt aaacaatggg gcggggggaag gt              52

<210> SEQ ID NO 46
<211> LENGTH: 47
<212> TYPE: DNA
<213> ORGANISM: Artificial sequence
<220> FEATURE:

<223> OTHER INFORMATION: primer

<400> SEQUENCE: 46
ggggaccact tgtacaaga aagctgggtt tggccgacga cgacgac    47

<210> SEQ ID NO 47
<211> LENGTH: 2193
<212> TYPE: DNA
<213> ORGANISM: Oryza sativa

<400> SEQUENCE: 47

| aatccgaaaa gtttctgcac cgttttcacc ccctaactaa caatataggg aacgtgtgct | 60 |
|---|---|
| aaatataaaa tgagacctta tatatgtagc gctgataact agaactatgc aagaaaaact | 120 |
| catccaccta ctttagtggc aatcgggcta aataaaaaag agtcgctaca ctagtttcgt | 180 |
| tttccttagt aattaagtgg gaaaatgaaa tcattattgc ttagaatata cgttcacatc | 240 |
| tctgtcatga agttaaatta ttcgaggtag ccataattgt catcaaactc ttcttgaata | 300 |
| aaaaaatctt tctagctgaa ctcaatgggt aaagagagag atttttttta aaaaatagaa | 360 |
| atgaagatat tctgaacgta ttggcaaaga tttaaacata taattatata attttatagt | 420 |
| ttgtgcattc gtcatatcgc acatcattaa ggacatgtct tactccatcc aatttttat | 480 |
| ttagtaatta aagacaattg acttattttt attatttatc tttttcgat tagatgcaag | 540 |
| gtacttacgc acacactttg tgctcatgtg catgtgtgag tgcacctcct caatacacgt | 600 |
| tcaactagca acacatctct aatatcactc gcctatttaa tacatttagg tagcaatatc | 660 |
| tgaattcaag cactccacca tcaccagacc acttttaata atatctaaaa tacaaaaaat | 720 |
| aattttacag aatagcatga aaagtatgaa acgaactatt taggtttttc acatacaaaa | 780 |
| aaaaaagaa ttttgctcgt gcgcgagcgc caatctccca tattgggcac acaggcaaca | 840 |
| acagagtggc tgcccacaga acaacccaca aaaaacgatg atctaacgga ggacagcaag | 900 |
| tccgcaacaa cctttaaca gcaggctttg cggccaggag agaggaggag aggcaaagaa | 960 |
| aaccaagcat cctcctcctc ccatctataa attcctcccc ccttttcccc tctctatata | 1020 |
| ggaggcatcc aagccaagaa gagggagagc accaaggaca cgcgactagc agaagccgag | 1080 |
| cgaccgcctt cttcgatcca tatcttccgg tcgagttctt ggtcgatctc ttccctcctc | 1140 |
| cacctcctcc tcacagggta tgtgcccttc ggttgttctt ggatttattg ttctaggttg | 1200 |
| tgtagtacgg gcgttgatgt taggaaaggg gatctgtatc tgtgatgatt cctgttcttg | 1260 |
| gatttgggat agagggggttc ttgatgttgc atgttatcgg ttcggtttga ttagtagtat | 1320 |
| ggttttcaat cgtctggaga gctctatgga aatgaaatgg tttagggtac ggaatcttgc | 1380 |
| gattttgtga gtaccttttg tttgaggtaa atcagagca ccggtgattt tgcttggtgt | 1440 |
| aataaaagta cggttgtttg gtcctcgatt ctggtagtga tgcttctcga tttgacgaag | 1500 |
| ctatcctttg tttattccct attgaacaaa ataatccaa ctttgaagac ggtcccgttg | 1560 |
| atgagattga atgattgatt cttaagcctg tccaaaattt cgcagctggc ttgtttagat | 1620 |
| acagtagtcc ccatcacgaa attcatggaa acagttataa tcctcaggaa caggggattc | 1680 |
| cctgttcttc cgatttgctt tagtcccaga attttttttc ccaaatatct taaaaagtca | 1740 |
| ctttctggtt cagttcaatg aattgattgc tacaaataat gcttttatag cgttatccta | 1800 |
| gctgtagttc agtaataggg taatacccct atagtttagt caggagaaga acttatccga | 1860 |
| tttctgatct ccatttttaa ttatatgaaa tgaactgtag cataagcagt attcatttgg | 1920 |
| attatttttt ttattagctc tcaccccttc attattctga gctgaaagtc tggcatgaac | 1980 |

```
tgtcctcaat tttgttttca aattcacatc gattatctat gcattatcct cttgtatcta   2040
cctgtagaag tttcttttg gttattcctt gactgcttga ttacagaaag aaatttatga   2100
agctgtaatc gggatagtta tactgcttgt tcttatgatt catttccttt gtgcagttct   2160
tggtgtagct tgccactttc accagcaaag ttc                               2193
```

```
<210> SEQ ID NO 48
<211> LENGTH: 42
<212> TYPE: PRT
<213> ORGANISM: Artificial sequence
<220> FEATURE:
<223> OTHER INFORMATION: motif
<220> FEATURE:
<221> NAME/KEY: VARIANT
<222> LOCATION: (2)..(2)
<223> OTHER INFORMATION: Xaa is Leu or Val
<220> FEATURE:
<221> NAME/KEY: VARIANT
<222> LOCATION: (6)..(6)
<223> OTHER INFORMATION: Xaa is His or Asn
<220> FEATURE:
<221> NAME/KEY: VARIANT
<222> LOCATION: (10)..(10)
<223> OTHER INFORMATION: Xaa is Val or Ile
<220> FEATURE:
<221> NAME/KEY: VARIANT
<222> LOCATION: (12)..(12)
<223> OTHER INFORMATION: Xaa is Cys or Tyr
<220> FEATURE:
<221> NAME/KEY: VARIANT
<222> LOCATION: (16)..(16)
<223> OTHER INFORMATION: Xaa is Val, Ile, or Leu
<220> FEATURE:
<221> NAME/KEY: VARIANT
<222> LOCATION: (17)..(17)
<223> OTHER INFORMATION: Xaa is Ala or Gly
<220> FEATURE:
<221> NAME/KEY: VARIANT
<222> LOCATION: (18)..(18)
<223> OTHER INFORMATION: Xaa is Leu, Ala, or Val
<220> FEATURE:
<221> NAME/KEY: VARIANT
<222> LOCATION: (19)..(19)
<223> OTHER INFORMATION: Xaa is Ile or Val
<220> FEATURE:
<221> NAME/KEY: VARIANT
<222> LOCATION: (20)..(20)
<223> OTHER INFORMATION: Xaa is Ile or Val
<220> FEATURE:
<221> NAME/KEY: VARIANT
<222> LOCATION: (23)..(23)
<223> OTHER INFORMATION: Xaa is Thr, Pro, Ala, or Asn
<220> FEATURE:
<221> NAME/KEY: VARIANT
<222> LOCATION: (30)..(30)
<223> OTHER INFORMATION: Xaa is Tyr or Phe
<220> FEATURE:
<221> NAME/KEY: VARIANT
<222> LOCATION: (31)..(31)
<223> OTHER INFORMATION: Xaa is Ala or Ser
<220> FEATURE:
<221> NAME/KEY: VARIANT
<222> LOCATION: (32)..(32)
<223> OTHER INFORMATION: Xaa is Thr or Ser
<220> FEATURE:
<221> NAME/KEY: VARIANT
<222> LOCATION: (33)..(33)
<223> OTHER INFORMATION: Xaa is Asp, Asn, or Glu
<220> FEATURE:
<221> NAME/KEY: VARIANT
<222> LOCATION: (35)..(35)
<223> OTHER INFORMATION: Xaa is Lys, Cys, Arg, or Ser
<220> FEATURE:
<221> NAME/KEY: VARIANT
<222> LOCATION: (37)..(37)
<223> OTHER INFORMATION: Xaa is Asp or Glu
<220> FEATURE:
```

```
<221> NAME/KEY: VARIANT
<222> LOCATION: (38)..(38)
<223> OTHER INFORMATION: Xaa is Asn, Ile, Arg, or Lys
<220> FEATURE:
<221> NAME/KEY: VARIANT
<222> LOCATION: (41)..(41)
<223> OTHER INFORMATION: Xaa is Glu or Asp

<400> SEQUENCE: 48

Leu Xaa Lys Lys Ala Xaa Glu Ile Ser Xaa Leu Xaa Asp Ala Glu Xaa
1               5                   10                  15

Xaa Xaa Xaa Xaa Phe Ser Xaa Lys Gly Lys Leu Tyr Glu Xaa Xaa Xaa
            20                  25                  30

Xaa Ser Xaa Met Xaa Xaa Ile Leu Xaa Arg
        35                  40

<210> SEQ ID NO 49
<211> LENGTH: 19
<212> TYPE: PRT
<213> ORGANISM: Artificial sequence
<220> FEATURE:
<223> OTHER INFORMATION: motif
<220> FEATURE:
<221> NAME/KEY: VARIANT
<222> LOCATION: (4)..(4)
<223> OTHER INFORMATION: Xaa is Ala or Ser
<220> FEATURE:
<221> NAME/KEY: VARIANT
<222> LOCATION: (5)..(5)
<223> OTHER INFORMATION: Xaa is Lys or Arg
<220> FEATURE:
<221> NAME/KEY: VARIANT
<222> LOCATION: (6)..(6)
<223> OTHER INFORMATION: Xaa is Val or Ile
<220> FEATURE:
<221> NAME/KEY: VARIANT
<222> LOCATION: (8)..(8)
<223> OTHER INFORMATION: Xaa is Ala, Thr, or Ser
<220> FEATURE:
<221> NAME/KEY: VARIANT
<222> LOCATION: (9)..(9)
<223> OTHER INFORMATION: Xaa is Leu or Ile
<220> FEATURE:
<221> NAME/KEY: VARIANT
<222> LOCATION: (10)..(10)
<223> OTHER INFORMATION: Xaa is Gln or Asn
<220> FEATURE:
<221> NAME/KEY: VARIANT
<222> LOCATION: (11)..(11)
<223> OTHER INFORMATION: Xaa is Lys, Arg, or Asn
<220> FEATURE:
<221> NAME/KEY: VARIANT
<222> LOCATION: (12)..(12)
<223> OTHER INFORMATION: Xaa is Ser, Cys, or Arg
<220> FEATURE:
<221> NAME/KEY: VARIANT
<222> LOCATION: (13)..(13)
<223> OTHER INFORMATION: Xaa is Gln or His
<220> FEATURE:
<221> NAME/KEY: VARIANT
<222> LOCATION: (14)..(14)
<223> OTHER INFORMATION: Xaa is Arg or Lys

<400> SEQUENCE: 49

Lys Leu Lys Xaa Xaa Xaa Glu Xaa Xaa Xaa Xaa Xaa Xaa Xaa His Leu
1               5                   10                  15

Met Gly Glu

<210> SEQ ID NO 50
<211> LENGTH: 11
<212> TYPE: PRT
<213> ORGANISM: Artificial sequence
<220> FEATURE:
```

```
<223> OTHER INFORMATION: motif
<220> FEATURE:
<221> NAME/KEY: VARIANT
<222> LOCATION: (2)..(2)
<223> OTHER INFORMATION: Xaa is Pro, Gln, Val, or Ala
<220> FEATURE:
<221> NAME/KEY: VARIANT
<222> LOCATION: (6)..(6)
<223> OTHER INFORMATION: Xaa is Ser or Phe
<220> FEATURE:
<221> NAME/KEY: VARIANT
<222> LOCATION: (7)..(7)
<223> OTHER INFORMATION: Xaa is Ser or Phe
<220> FEATURE:
<221> NAME/KEY: VARIANT
<222> LOCATION: (8)..(8)
<223> OTHER INFORMATION: Xaa is Ser or Phe
<220> FEATURE:
<221> NAME/KEY: VARIANT
<222> LOCATION: (9)..(9)
<223> OTHER INFORMATION: Xaa is Ser or Phe
<220> FEATURE:
<221> NAME/KEY: VARIANT
<222> LOCATION: (10)..(10)
<223> OTHER INFORMATION: Xaa is Ser, Cys, or Phe
<220> FEATURE:
<221> NAME/KEY: VARIANT
<222> LOCATION: (11)..(11)
<223> OTHER INFORMATION: Xaa is Phe or Met

<400> SEQUENCE: 50

Gln Xaa Gln Thr Ser Xaa Xaa Xaa Xaa Xaa Xaa
1               5                   10

<210> SEQ ID NO 51
<211> LENGTH: 7
<212> TYPE: PRT
<213> ORGANISM: Artificial sequence
<220> FEATURE:
<223> OTHER INFORMATION: motif
<220> FEATURE:
<221> NAME/KEY: VARIANT
<222> LOCATION: (1)..(1)
<223> OTHER INFORMATION: Xaa is Gly, Ala, Val, or Leu
<220> FEATURE:
<221> NAME/KEY: VARIANT
<222> LOCATION: (2)..(2)
<223> OTHER INFORMATION: Xaa is Leu or Pro
<220> FEATURE:
<221> NAME/KEY: UNSURE
<222> LOCATION: (3)..(3)
<223> OTHER INFORMATION: Xaa can be any naturally occurring amino acid,
      preferably Leu, Pro or His
<220> FEATURE:
<221> NAME/KEY: UNSURE
<222> LOCATION: (6)..(6)
<223> OTHER INFORMATION: Xaa can be any naturally occurring amino acid,
      preferably Leu, Pro or His
<220> FEATURE:
<221> NAME/KEY: VARIANT
<222> LOCATION: (7)..(7)
<223> OTHER INFORMATION: Xaa is Ser or His

<400> SEQUENCE: 51

Xaa Xaa Xaa Trp Met Xaa Xaa
1               5

<210> SEQ ID NO 52
<211> LENGTH: 735
<212> TYPE: DNA
<213> ORGANISM: Hordeum vulgare

<400> SEQUENCE: 52
atggggcgcg ggaaggtgca gctgaagcgg atcgagaaca agatcaaccg ccaggtcacc      60
```

-continued

```
ttctccaagc gccgctcggg gctgctcaag aaggcgcacg agatctccgt gctctgcgac      120
gccgaggtcg gcctcatcat cttctccacc aagggaaagc tctacgagtt ctccaccgag      180
tcatgtatgg acaaaattct tgaacggtat gagcgctact cttatgcaga aaaggttctc      240
gtttcaagtg aatctgaaat tcagggaaac tggtgtcacg aatataggaa actgaaggcg      300
aaggttgaga caatacagaa atgtcaaaag catctcatgg gagaggatct tgaatctttg      360
aatctcaagg agttgcagca actggagcag cagctggaaa gctcactgaa acatatcaga      420
gccaggaaga accaacttat gcacgaatcc atttctgagc ttcagaagaa ggagaggtca      480
ctgcaggagg agaataaagt tctccagaag gaacttgtgg agaagcagaa ggcccaggcg      540
gcgcagcaag atcaaactca gcctcaaacc agctcttctt cttcttcctt catgatgagg      600
gatgctcccc ctgtcgcaga taccagcaat cacccagcgg cggcaggcga gagggcagag      660
gatgtggcag tgcagcctca ggtcccactc cggacggcgc ttccactgtg gatggtgagc      720
cacatcaacg gctga                                                      735
```

```
<210> SEQ ID NO 53
<211> LENGTH: 244
<212> TYPE: PRT
<213> ORGANISM: Hordeum vulgare

<400> SEQUENCE: 53

Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Gly Leu Ile Ile Phe
        35                  40                  45

Ser Thr Lys Gly Lys Leu Tyr Glu Phe Ser Thr Glu Ser Cys Met Asp
    50                  55                  60

Lys Ile Leu Glu Arg Tyr Glu Arg Tyr Ser Tyr Ala Glu Lys Val Leu
65                  70                  75                  80

Val Ser Ser Glu Ser Glu Ile Gln Gly Asn Trp Cys His Glu Tyr Arg
                85                  90                  95

Lys Leu Lys Ala Lys Val Glu Thr Ile Gln Lys Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Arg Ala Arg Lys Asn
    130                 135                 140

Gln Leu Met His Glu Ser Ile Ser Glu Leu Gln Lys Lys Glu Arg Ser
145                 150                 155                 160

Leu Gln Glu Glu Asn Lys Val Leu Gln Lys Glu Leu Val Glu Lys Gln
                165                 170                 175

Lys Ala Gln Ala Ala Gln Asp Gln Thr Gln Pro Gln Thr Ser Ser Ser
            180                 185                 190

Ser Ser Ser Ser Phe Met Met Arg Asp Ala Pro Pro Val Ala Asp Thr
        195                 200                 205

Ser Asn His Pro Ala Ala Ala Gly Glu Arg Ala Glu Asp Val Ala Val
    210                 215                 220

Gln Pro Gln Val Pro Leu Arg Thr Ala Leu Pro Leu Trp Met Val Ser
225                 230                 235                 240

His Ile Asn Gly
```

<210> SEQ ID NO 54
<211> LENGTH: 1196
<212> TYPE: DNA
<213> ORGANISM: Hordeum vulgare

<400> SEQUENCE: 54

```
ctctcccctc ccacttcacc caaccacctg acagccatgg ctccgccacc tcgcctccgc      60
ccgcgcctct gagagtagcc gtcgcggtcg ctcgctcgct cgctcgctgc tgccggtgtt     120
ggcccggtcc tcgagcggag atgggcgcag gaaggtgcag ctgaagcgga tcgagaaca     180
agatcaaccg ccaggtcacc ttctccaagc gccgctcggg gctgctcaag aaggcgcacg     240
agatctccgt gctctacgac gccgaggtcg gcctcatcat cttctccacc aagggaaagc     300
tctacgagtt ctccaccgag tcatgtatgg acaaaattct gaacggtat gagcgctact     360
cttatgcaga aaaggttctc gtttcaagtg aatctgaaat tcaggaaac tggtgtcacg     420
aatataggaa actgaaggcg aaggttgaga caatacagaa atgtcaaaag catctcatgg     480
gagaggatct tgaatctttg aatctcaagg agttgcagca actggagcag cagctggaaa     540
gctcactgaa acatatcaga gccaggaaga accaacttat gcacgaatcc atttctgagc     600
ttcagaagaa ggagaggtca ctgcaggagg agaataaagt tctccagaag gaacttgtgg     660
agaagcagaa ggcccaggcg cgcagcaag atcaaactca gcctcaaacc agctcttctt     720
cttcttcctt catgatgagg gatgctcccc ctgtcgcaga taccagcaat cacccagcgg     780
cggcaggcga gagggcagag gatgtggcag tgcagcctca ggtcccactc cggacggcgc     840
ttccactgtg gatggtgagc cacatcaacg gctgaaggc ttccagccca tgtaagcgta     900
ctattcagta cgagtaacaa gttgcagcgg ccagcctggt gtatcatgcg gttgcgaaca     960
tgctaacccc atggagggga gaggaaaaga aatcagagta aagcagcaag ctgcaggaat    1020
gtgtatattt cacttcgtcc acctcagttt cctttccacc tgggctgaga tggctgtacg    1080
agtaatctac catgtaattt atatgtagca tgagtgacga atttcaact ttcgatgata    1140
tccgttgctc ctgggtgttg tttctgtgaa ttaacctatc gaatatgagc gttgtg        1196
```

<210> SEQ ID NO 55
<211> LENGTH: 244
<212> TYPE: PRT
<213> ORGANISM: Hordeum vulgare

<400> SEQUENCE: 55

Met Gly Arg Arg Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Tyr Asp Ala Glu Val Gly Leu Ile Ile Phe
        35                  40                  45

Ser Thr Lys Gly Lys Leu Tyr Glu Phe Ser Thr Glu Ser Cys Met Asp
    50                  55                  60

Lys Ile Leu Glu Arg Tyr Glu Arg Tyr Ser Tyr Ala Glu Lys Val Leu
65                  70                  75                  80

Val Ser Ser Glu Ser Glu Ile Gln Gly Asn Trp Cys His Glu Tyr Arg
                85                  90                  95

Lys Leu Lys Ala Lys Val Glu Thr Ile Gln Lys Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Arg Ala Arg Lys Asn

```
                130                 135                 140
Gln Leu Met His Glu Ser Ile Ser Glu Leu Gln Lys Lys Glu Arg Ser
145                 150                 155                 160

Leu Gln Glu Glu Asn Lys Val Leu Gln Lys Glu Leu Val Glu Lys Gln
                165                 170                 175

Lys Ala Gln Ala Ala Gln Asp Gln Thr Gln Pro Gln Thr Ser Ser
            180                 185                 190

Ser Ser Ser Ser Phe Met Met Arg Asp Ala Pro Val Ala Asp Thr
                195                 200                 205

Ser Asn His Pro Ala Ala Ala Gly Glu Arg Ala Glu Asp Val Ala Val
        210                 215                 220

Gln Pro Gln Val Pro Leu Arg Thr Ala Leu Pro Leu Trp Met Val Ser
225                 230                 235                 240

His Ile Asn Gly

<210> SEQ ID NO 56
<211> LENGTH: 1161
<212> TYPE: DNA
<213> ORGANISM: Triticum aestivum

<400> SEQUENCE: 56
ggcacgagct ctctctctct ctctctctct ctctctctct ctctctcctc gtgccgaatt      60
cggcacgagc ggagatgggg cgcgggaagg tgcagctgaa gcggatcgag aacaagatca    120
accggcaggt gaccttctcc aagcgccgct cggggctgct caagaaggcg cacgagatct    180
ccgtgctctg cgacgccgag gtcggcctca tcatcttctc caccaaggga aagctctacg    240
agttctccac cgagtcatgt atggacaaaa ttcttgaacg gtatgagcgc tactcttatg    300
cagaaaaggt tctcgtttca agtgaatctg aaattcaggg aaactggtgt cacgaatata    360
ggaaactgaa ggcgaaggtt gagacaatac agaaatgtca aaagcatctg atgggagagg    420
atcttgaatc tttgaatctc aaggagttgc agcaactgga gcagcagctg aaagctcac    480 tgaaacatat cagatccagg aagaaccaac ttatgcacga atccatttct gagcttcaga    540
agaaggagag gtcactgcag gaggagaata agttctccca aaggaactc gtcgagaagc    600 agaaggccca gcggcgcaa caagatcaga ctcagcctca acaagctct tcttcttctt    660 ccttcatgat gagggatgct cccctgccg cagctaccag cattcatcca gcggcggcag    720
gcgagagggc aggggatgcg gcagtgcagc cgcaggcccc accccggacg ggcttccac    780 tgtgatggt gagccacatc aacgctgaa gggcttccag cccatataag cgtactattc    840
agtagagagt aacaagttgc accggccagt ctggtgtatg ttgcggttgc tagcacgcct    900
gaccccttgg aggggaaagg aaagaaatc agagtaaagt agcaagctgc agcgatgtgt    960
atatttcact ttgtccaccc cagtttccct cccagctggg ctcaatttac catgtaatct   1020
atatgtagct tgagtgatga attttcaagt ttccatgata cccgtctcta gtgggatgtt   1080
gtttatgtga attaacctat caaatatgag cattgtgtat attgtgattc ttgaaaataa   1140
ataaatcagg atctttgtct t                                             1161

<210> SEQ ID NO 57
<211> LENGTH: 244
<212> TYPE: PRT
<213> ORGANISM: Triticum aestivum

<400> SEQUENCE: 57

Met Gly Arg Gly Lys Val Gln Leu Lys Arg Ile Glu Asn Lys Ile Asn
1               5                   10                  15
```

```
Arg Gln Val Thr Phe Ser Lys Arg Arg Ser Gly Leu Leu Lys Lys Ala
             20                  25                  30

His Glu Ile Ser Val Leu Cys Asp Ala Glu Val Gly Leu Ile Ile Phe
         35                  40                  45

Ser Thr Lys Gly Lys Leu Tyr Glu Phe Ser Thr Glu Ser Cys Met Asp
 50                  55                  60

Lys Ile Leu Glu Arg Tyr Glu Arg Tyr Ser Tyr Ala Glu Lys Val Leu
 65                  70                  75                  80

Val Ser Ser Glu Ser Glu Ile Gln Gly Asn Trp Cys His Glu Tyr Arg
                 85                  90                  95

Lys Leu Lys Ala Lys Val Glu Thr Ile Gln Lys Cys Gln Lys His Leu
            100                 105                 110

Met Gly Glu Asp Leu Glu Ser Leu Asn Leu Lys Glu Leu Gln Gln Leu
            115                 120                 125

Glu Gln Gln Leu Glu Ser Ser Leu Lys His Ile Arg Ser Arg Lys Asn
130                 135                 140

Gln Leu Met His Glu Ser Ile Ser Glu Leu Gln Lys Lys Glu Arg Ser
145                 150                 155                 160

Leu Gln Glu Glu Asn Lys Val Leu Gln Lys Glu Leu Val Glu Lys Gln
                165                 170                 175

Lys Ala Gln Ala Ala Gln Gln Asp Gln Thr Gln Pro Gln Thr Ser Ser
            180                 185                 190

Ser Ser Ser Ser Phe Met Met Arg Asp Ala Pro Pro Ala Ala Ala Thr
            195                 200                 205

Ser Ile His Pro Ala Ala Ala Gly Glu Arg Ala Gly Asp Ala Ala Val
        210                 215                 220

Gln Pro Gln Ala Pro Pro Arg Thr Gly Leu Pro Leu Trp Met Val Ser
225                 230                 235                 240

His Ile Asn Gly

<210> SEQ ID NO 58
<211> LENGTH: 1210
<212> TYPE: DNA
<213> ORGANISM: Triticum aestivum

<400> SEQUENCE: 58
tccctctcct ccctctcttc cgcctcaccc aaccacctga cagccatggc tccgccccccc        60 cgccccccgcc tgcgcctgtc ggagtagccg tcgcggtctg ccggtgttgg aggcttgggg      120
tgtagggttg gccccgttct ccagcggaga tggggcgcgg gaaggtgcag ctgaagcgga      180
tcgagaacaa gatcaaccgg caggtgacct tctccaagcg ccgctcgggg ctgctcaaga      240
aggcgcacga gatctccgtg ctctgcgacg ccgaggtcgg cctcatcatc ttctccacca      300
agggaaagct ctacgagttc tccaccgagt catgtatgga caaaattctt gaacggtatg      360
agcgctactc ttatgcagaa aaggttctcg tttcaagtga atctgaaatt cagggaaact      420
ggtgtcacga atataggaaa ctgaaggcga aggttgagac aatacagaaa tgtcaaaagc      480
atctgatggg agaggatctt gaatctttga atctcaagga gttgcagcaa ctggagcagc      540
agctggaaag ctcactgaaa catatcagat ccaggaagaa ccaacttatg cacgaatcca      600
tttctgagct tcagaagaag gagaggtcac tgcaggagaa gaataaagtt ctccagaagg      660
aactcgtcga gaagcagaag gcccaggcgg cgcaacaaga tcagactcag cctcaaacaa      720
gctcttcttc ttcttcttcc atgatgaggg atgctccccc tgccgcaact accagcattc      780
atccagcggc atcaggagag agggcagagg atgcggcagt gcagccgcag gccccaccccc      840
```

```
ggacggggct tccactgtgg atggttagcc acatcaacgg ctgaagggct tccagcccat      900
ataagcgtac tattcagtag agagtaacaa gttgcaccgg ccagcctggt gtatgttgcg      960
gttgctagca tgcctgaccc cttggagggg aaaggaaaag aaatcagagt aaagtagcaa     1020
gctgcagtga tgtgtatatt tcactttgtc cacctcagtt tccctcccag ctgggctcaa     1080
tttaccatgt aatctatatg tagcttgagt gatgaatttt caagtttcca tgatacccgt     1140
ctcgagcggg tgttgtttat gtgaattaac ctatcaaata tgagcattgt gtaaaaaaaa     1200
aaaaaaaaaa                                                           1210
```

<210> SEQ ID NO 59
<211> LENGTH: 244
<212> TYPE: PRT
<213> ORGANISM: Triticum aestivum

<400> SEQUENCE: 59

```
Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Gly Leu Ile Ile Phe
        35                  40                  45

Ser Thr Lys Gly Lys Leu Tyr Glu Phe Ser Thr Glu Ser Cys Met Asp
    50                  55                  60

Lys Ile Leu Glu Arg Tyr Glu Arg Tyr Ser Tyr Ala Glu Lys Val Leu
65                  70                  75                  80

Val Ser Ser Glu Ser Glu Ile Gln Gly Asn Trp Cys His Glu Tyr Arg
                85                  90                  95

Lys Leu Lys Ala Lys Val Glu Thr Ile Gln Lys Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Arg Ser Arg Lys Asn
    130                 135                 140

Gln Leu Met His Glu Ser Ile Ser Glu Leu Gln Lys Lys Glu Arg Ser
145                 150                 155                 160

Leu Gln Glu Glu Asn Lys Val Leu Gln Lys Glu Leu Val Glu Lys Gln
                165                 170                 175

Lys Ala Gln Ala Ala Gln Gln Asp Gln Thr Gln Pro Gln Thr Ser Ser
            180                 185                 190

Ser Ser Ser Ser Phe Met Met Arg Asp Ala Pro Pro Ala Ala Thr Thr
        195                 200                 205

Ser Ile His Pro Ala Ala Ser Gly Glu Arg Ala Glu Asp Ala Ala Val
    210                 215                 220

Gln Pro Gln Ala Pro Pro Arg Thr Gly Leu Pro Leu Trp Met Val Ser
225                 230                 235                 240

His Ile Asn Gly
```

<210> SEQ ID NO 60
<211> LENGTH: 735
<212> TYPE: DNA
<213> ORGANISM: Triticum monococcum

<400> SEQUENCE: 60

```
atggggcgcg ggaaggtgca gctgaagcgg atcgagaaca agatcaaccg gcaggtgacc       60
```

```
ttctccaagc gccgctcggg gcttctcaag aaggcgcacg agatctccgt gctctgcgac    120
gccgaggtcg gcctcatcat cttctccacc aagggaaagc tctacgagtt ctccaccgag    180
tcatgtatgg acaaaattct tgaacggtat gagcgctatt cttatgcaga aaaggttctc    240
gtttcaagtg aatctgaaat tcagggaaac tggtgtcacg aatataggaa actgaaggcg    300
aaggttgaga caatacagaa atgtcaaaaa catctcatgg gagaggatct tgaatctttg    360
aatctcaagg agttgcagca actggagcag cagctggaaa gctcactgaa acatatcaga    420
tccaggaaga accaacttat gcacgaatcc atttctgagc tgcagaagaa ggagaggtca    480
ctgcaggagg agaataaagt tctccagaag gaactcgtgg agaagcagaa ggcccatgcg    540
gcgcagcaag atcaaactca gcctcaaacc agctcttctt cttcttcctt catgctgagg    600
gatgctcccc ctgccgcaaa taccagcatt catccagcgg cggcaggcga gagggcagag    660
gatgcggcag tgcagccgca ggccccaccc cggacggggc ttccaccgtg gatggtgagc    720
cacatcaacg ggtga                                                    735
```

<210> SEQ ID NO 61
<211> LENGTH: 244
<212> TYPE: PRT
<213> ORGANISM: Triticum monococcum

<400> SEQUENCE: 61

```
Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Gly Leu Ile Ile Phe
        35                  40                  45

Ser Thr Lys Gly Lys Leu Tyr Glu Phe Ser Thr Glu Ser Cys Met Asp
    50                  55                  60

Lys Ile Leu Glu Arg Tyr Glu Arg Tyr Ser Tyr Ala Glu Lys Val Leu
65                  70                  75                  80

Val Ser Ser Glu Ser Glu Ile Gln Gly Asn Trp Cys His Glu Tyr Arg
                85                  90                  95

Lys Leu Lys Ala Lys Val Glu Thr Ile Gln Lys Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Arg Ser Arg Lys Asn
    130                 135                 140

Gln Leu Met His Glu Ser Ile Ser Glu Leu Gln Lys Lys Glu Arg Ser
145                 150                 155                 160

Leu Gln Glu Glu Asn Lys Val Leu Gln Lys Glu Leu Val Glu Lys Gln
                165                 170                 175

Lys Ala His Ala Ala Gln Gln Asp Gln Thr Gln Pro Gln Thr Ser Ser
            180                 185                 190

Ser Ser Ser Ser Phe Met Leu Arg Asp Ala Pro Pro Ala Ala Asn Thr
        195                 200                 205

Ser Ile His Pro Ala Ala Ala Gly Glu Arg Ala Glu Asp Ala Ala Val
    210                 215                 220

Gln Pro Gln Ala Pro Pro Arg Thr Gly Leu Pro Pro Trp Met Val Ser
225                 230                 235                 240

His Ile Asn Gly
```

<210> SEQ ID NO 62
<211> LENGTH: 735
<212> TYPE: DNA
<213> ORGANISM: Triticum aestivum

<400> SEQUENCE: 62

```
atggggcggg ggaaggtgca gctgaagcgg atcgagaaca agatcaaccg gcaggtgacc      60
ttctccaagc gccgctcggg gcttctcaag aaggcgcacg agatctccgt gctctgcgac     120
gccgaggtcg gcctcatcat cttctccacc aagggaaagc tctacgagtt ctccaccgag     180
tcatgtatgg acaaaattct gaacggtat gagcgctatt cttatgcaga aaaggttctc      240
gtttcaagtg aatctgaaat tcaggaaac tggtgtcacg aatataggaa actgaaggcg      300
aaggttgaga caatacagaa atgtcaaaag catctcatgg gagaggatct tgaatctttg      360
aatctcaagg agttgcagca actggagcag cagctgaaaa gctcactgaa acatatcaga      420
tccaggaaga accaacttat gcacgaatcc atttctgagc ttcagaagaa ggagaggtca      480
ctgcaggagg agaataaagt tctccagaag gaactcgtgg agaagcagaa ggcccatgcg      540
gcgcagcaag atcaaactca gcctcaaacc agctcttcat cttcttcctt catgctgagg      600
gatgctcccc ctgccgcaaa taccagcatt catccagcgg caacaggcga gagggcagag      660
gatgcggcag tgcagccgca ggccccaccc cggacggggc ttccaccgtg gatggtgagc      720
cacatcaacg ggtga                                                      735
```

<210> SEQ ID NO 63
<211> LENGTH: 244
<212> TYPE: PRT
<213> ORGANISM: Triticum aestivum

<400> SEQUENCE: 63

```
Met Gly Arg Gly Lys Val Gln Leu Lys Arg Ile Glu Asn Lys Ile Asn
1               5                   10                  15

Arg Gln Val Thr Phe Ser Lys Arg Ser Gly Leu Leu Lys Lys Ala
            20                  25                  30

His Glu Ile Ser Val Leu Cys Asp Ala Glu Val Gly Leu Ile Ile Phe
        35                  40                  45

Ser Thr Lys Gly Lys Leu Tyr Glu Phe Ser Thr Glu Ser Cys Met Asp
    50                  55                  60

Lys Ile Leu Glu Arg Tyr Glu Arg Tyr Ser Tyr Ala Glu Lys Val Leu
65                  70                  75                  80

Val Ser Ser Glu Ser Glu Ile Gln Gly Asn Trp Cys His Glu Tyr Arg
                85                  90                  95

Lys Leu Lys Ala Lys Val Glu Thr Ile Gln Lys Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Arg Ser Arg Lys Asn
    130                 135                 140

Gln Leu Met His Glu Ser Ile Ser Glu Leu Gln Lys Lys Glu Arg Ser
145                 150                 155                 160

Leu Gln Glu Glu Asn Lys Val Leu Gln Lys Glu Leu Val Glu Lys Gln
                165                 170                 175

Lys Ala His Ala Ala Gln Gln Asp Gln Thr Gln Pro Gln Thr Ser Ser
            180                 185                 190

Ser Ser Ser Ser Phe Met Leu Arg Asp Ala Pro Pro Ala Ala Asn Thr
        195                 200                 205
```

```
Ser Ile His Pro Ala Ala Thr Gly Glu Arg Ala Glu Asp Ala Ala Val
    210                 215                 220

Gln Pro Gln Ala Pro Pro Arg Thr Gly Leu Pro Trp Met Val Ser
225                 230                 235                 240

His Ile Asn Gly

<210> SEQ ID NO 64
<211> LENGTH: 738
<212> TYPE: DNA
<213> ORGANISM: Lolium perenne

<400> SEQUENCE: 64
atggggcgcg gcaaggtgca gctcaagcgg atcgagaaca agatcaaccg ccaggtcacc        60
ttctccaagc gccgctcggg gctgctcaag aaggcgcacg agatctccgt gctctgcgac       120
gccgaggtcg ggctcatcat cttctccacc aagggaaagc tctacgagtt cgcaaccgac       180
tcatgtatgg acaaaattct tgagcggtat gagcgctact cctatgcaga gaaagtgctc       240
atttcaaccg aatctgaaat tcagggaaac tggtgtcatg aatataggaa actgaaggcg       300
aaggttgaga caatacagag atgtcaaaag catctaatgg gagaggatct tgaatcattg       360
aatctcaagg agttgcagca actagagcag cagctggaaa gttcactgaa acatattaga       420
gccagaaaga accagcttat gcacgaatcc atatctgagc ttcaaaagaa ggagaggtca       480
ctgcaggagg agaataaaat tctccagaag gaactcatag agaagcagaa ggcccacacg       540
cagcaagcgc agtgggagca aactcagccc caaaccagct cttcctcctc ctcctttatg       600
atgggggaag ctaccccagc aacaaattgc agtaatcccc cagcagcggc cagcgacaga       660
gcagaggatg cgacggggca gccttcagct cgcacggtgc ttccaccatg gatggtgagt       720
cacatcaaca atggctga                                                     738

<210> SEQ ID NO 65
<211> LENGTH: 245
<212> TYPE: PRT
<213> ORGANISM: Lolium perenne

<400> SEQUENCE: 65

Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
                20                  25                  30

His Glu Ile Ser Val Leu Cys Asp Ala Glu Val Gly Leu Ile Ile Phe
            35                  40                  45

Ser Thr Lys Gly Lys Leu Tyr Glu Phe Ala Thr Asp Ser Cys Met Asp
    50                  55                  60

Lys Ile Leu Glu Arg Tyr Glu Arg Tyr Ser Tyr Ala Glu Lys Val Leu
65                  70                  75                  80

Ile Ser Thr Glu Ser Glu Ile Gln Gly Asn Trp Cys His Glu Tyr Arg
                85                  90                  95

Lys Leu Lys Ala Lys Val Glu Thr Ile Gln Arg Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Arg Ala Arg Lys Asn
    130                 135                 140

Gln Leu Met His Glu Ser Ile Ser Glu Leu Gln Lys Lys Glu Arg Ser
145                 150                 155                 160
```

```
Leu Gln Glu Glu Asn Lys Ile Leu Gln Lys Glu Leu Ile Glu Lys Gln
                165                 170                 175

Lys Ala His Thr Gln Gln Ala Gln Trp Glu Gln Thr Gln Pro Gln Thr
            180                 185                 190

Ser Ser Ser Ser Ser Phe Met Met Gly Glu Ala Thr Pro Ala Thr
        195                 200                 205

Asn Cys Ser Asn Pro Ala Ala Ala Ser Asp Arg Ala Glu Asp Ala
        210                 215                 220

Thr Gly Gln Pro Ser Ala Arg Thr Val Leu Pro Pro Trp Met Val Ser
225                 230                 235                 240

His Ile Asn Asn Gly
                245

<210> SEQ ID NO 66
<211> LENGTH: 738
<212> TYPE: DNA
<213> ORGANISM: Lolium temulentum

<400> SEQUENCE: 66
atggggcgcg gcaaggtgca gctcaagcgg atcgagaaca agatcaaccg ccaggtcacc      60
ttctccaagc gccgctcagg cctgctcaag aaggcgcacg agatctccgt gctctgcgac     120
gcagaggtcg ggctcatcat cttctccacc aagggaaagc tctacgagtt cgccaccgac     180
tcatgtatgg acaaaattct tgagcggtat gagcgctact cctatgcaga gaaagtgctc     240
atttcaactg aatctgaaat tcagggaaac tggtgtcatg aatataggaa actgaaggcg     300
aaggttgaga caatacagag atgtcaaaag catctaatgg gagaggatct tgaatcattg     360
aatctcaagg agttgcagca actagagcag cagctggaaa gttcactgaa acatattaga     420
tccagaaaga gccagcttat gcacgaatcc atatctgagc ttcaaaagaa ggagaggtca     480
ctgcaagagg agaataaaat tctccagaag gaactcatag agaagcagaa ggcccacacg     540
cagcaagcgc agttggagca aactcagccc caaaccagct cttcctcctc ctcctttatg     600
atgggggaag ctaccccagc aacaaatcgc agtaatcccc cagcagcggc cagcgacaga     660
gcagaggatg cgacggggca gcctccagct cgcacggtgc ttccaccatg gatggtgagt     720
cacctcaaca atggctga                                                   738

<210> SEQ ID NO 67
<211> LENGTH: 245
<212> TYPE: PRT
<213> ORGANISM: Lolium temulentum

<400> SEQUENCE: 67

Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Gly Leu Ile Ile Phe
        35                  40                  45

Ser Thr Lys Gly Lys Leu Tyr Glu Phe Ala Thr Asp Ser Cys Met Asp
    50                  55                  60

Lys Ile Leu Glu Arg Tyr Glu Arg Tyr Ser Tyr Ala Glu Lys Val Leu
65                  70                  75                  80

Ile Ser Thr Glu Ser Glu Ile Gln Gly Asn Trp Cys His Glu Tyr Arg
                85                  90                  95

Lys Leu Lys Ala Lys Val Glu Thr Ile Gln Arg Cys Gln Lys His Leu
            100                 105                 110
```

```
Met Gly Glu Asp Leu Glu Ser Leu Asn Leu Lys Glu Leu Gln Gln Leu
            115                 120                 125

Glu Gln Gln Leu Glu Ser Ser Leu Lys His Ile Arg Ser Arg Lys Ser
    130                 135                 140

Gln Leu Met His Glu Ser Ile Ser Glu Leu Lys Lys Glu Arg Ser
145                 150                 155                 160

Leu Gln Glu Glu Asn Lys Ile Leu Gln Lys Glu Leu Ile Glu Lys Gln
                165                 170                 175

Lys Ala His Thr Gln Gln Ala Gln Leu Glu Gln Thr Gln Pro Gln Thr
            180                 185                 190

Ser Ser Ser Ser Ser Ser Phe Met Met Gly Glu Ala Thr Pro Ala Thr
            195                 200                 205

Asn Arg Ser Asn Pro Pro Ala Ala Ala Ser Asp Arg Ala Glu Asp Ala
            210                 215                 220

Thr Gly Gln Pro Pro Ala Arg Thr Val Leu Pro Pro Trp Met Val Ser
225                 230                 235                 240

His Leu Asn Asn Gly
                245

<210> SEQ ID NO 68
<211> LENGTH: 738
<212> TYPE: DNA
<213> ORGANISM: Zea mays

<400> SEQUENCE: 68
atggggcgcg ggaaggtgca gctgaagcgg atcgagaaca agatcaaccg ccaggtgacc      60
ttctccaagc gccgctcggg gctgctcaag aaggcgcacg agatctccgt gctctgcgac     120
gccgaggtcg cgctcatcat cttctccacc aaagggaagc tctacgagta ttccaccgat     180
tcatgtatgg acaaaattct tgaccggtac gagcgctact cctatgcaga aaaggttctt     240
atttcagcag aatctgaaac tcagggcaat tggtgccacg agtatagaaa actaaaggcg     300
aaggtcgaga caatacaaaa atgtcaaaag cacctcatgg gagaggatct tgaaacgttg     360
aatctcaaag agcttcagca actagagcag cagctggaga gttcactgaa acatatcaga     420
accaggaaga accaacttat gctcgagtca atttcggagc tccaacggaa ggagaagtcg     480
ctgcaggagg agaacaaggt tctgcagaag agctcgcgg agaagcagaa agcccagcgg     540
aagcaagtgc aatggggcca aacccaacag cagaccagtt cgtcttcctc gtgcttcgtg     600
ataagggaag ctgccccaac aacaaatatc agcattttc ctgtggcagc aggcgggagg     660
ttggtggaag gtgcagcagc gcagccacag gctcgcgttg gactaccacc atggatgctt     720
agccacctga gcagctga                                                   738

<210> SEQ ID NO 69
<211> LENGTH: 245
<212> TYPE: PRT
<213> ORGANISM: Zea mays

<400> SEQUENCE: 69

Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Ile Phe
        35                  40                  45

Ser Thr Lys Gly Lys Leu Tyr Glu Tyr Ser Thr Asp Ser Cys Met Asp
```

```
              50                  55                  60
Lys Ile Leu Asp Arg Tyr Glu Arg Tyr Ser Tyr Ala Glu Lys Val Leu
 65                  70                  75                  80

Ile Ser Ala Glu Ser Glu Thr Gln Gly Asn Trp Cys His Glu Tyr Arg
                 85                  90                  95

Lys Leu Lys Ala Lys Val Glu Thr Ile Gln Lys Cys Gln Lys His Leu
            100                 105                 110

Met Gly Glu Asp Leu Glu Thr Leu Asn Leu Lys Glu Leu Gln Gln Leu
            115                 120                 125

Glu Gln Gln Leu Glu Ser Ser Leu Lys His Ile Arg Thr Arg Lys Asn
        130                 135                 140

Gln Leu Met Leu Glu Ser Ile Ser Glu Leu Gln Arg Lys Glu Lys Ser
145                 150                 155                 160

Leu Gln Glu Glu Asn Lys Val Leu Gln Lys Glu Leu Ala Glu Lys Gln
                165                 170                 175

Lys Ala Gln Arg Lys Gln Val Gln Trp Gly Gln Thr Gln Gln Gln Thr
            180                 185                 190

Ser Ser Ser Ser Ser Cys Phe Val Ile Arg Glu Ala Ala Pro Thr Thr
        195                 200                 205

Asn Ile Ser Ile Phe Pro Val Ala Ala Gly Gly Arg Leu Val Glu Gly
    210                 215                 220

Ala Ala Ala Gln Pro Gln Ala Arg Val Gly Leu Pro Pro Trp Met Leu
225                 230                 235                 240

Ser His Leu Ser Ser
            245

<210> SEQ ID NO 70
<211> LENGTH: 738
<212> TYPE: DNA
<213> ORGANISM: Zea mays

<400> SEQUENCE: 70
atggggcgcg ggaaggtgca gctgaagcgg atcgagaaca agatcaaccg ccaggtgaca      60
ttctccaagc gccgctcggg gctactcaag aaggcgcacg agatctccgt gctctgcgac     120
gccgaggtcg cgctcatcat cttctccacc aagggcaagc tctacgagta ctctaccgat     180
tcatgtatgg acaaaattct tgaacggtat gagcgctact cctatgcaga aaaggttctc     240
atttccgcag aatatgaaac tcagggcaat tggtgccatg aatatagaaa actaaaggcg     300
aaggtcgaga caatacagaa atgtcaaaag cacctcatgg gagaggatct tgaaactttg     360
aatctcaaag agcttcagca actagagcag cagctggaga gttcactgaa acatatcaga     420
acaaggaaga gccagcttat ggtcgagtca atttcagcgc tccaacggaa ggagaagtca     480
ctgcaggagg agaacaaggt tctgcagaag gagctcgcgg agaagcagaa agaccagcgg     540
cagcaagtgc aacgggacca aactcaacag cagaccagtt cgtcttccac gtccttcatg     600
ttaagggaag ctgccccaac aacaaatgtc agcatcttcc ctgtggcagc aggcgggagg     660
gtggtggaag gggcagcagc gcagccgcag gctcgcgttg gactgccacc atggatgctt     720
agccatctga gctgctga                                                   738

<210> SEQ ID NO 71
<211> LENGTH: 245
<212> TYPE: PRT
<213> ORGANISM: Zea mays

<400> SEQUENCE: 71
```

Met Gly Arg Gly Lys Val Gln Leu Lys Arg Ile Glu Asn Lys Ile Asn
1               5                   10                  15

Arg Gln Val Thr Phe Ser Lys Arg Ser Gly Leu Leu Lys Lys Ala
            20                  25                  30

His Glu Ile Ser Val Leu Cys Asp Ala Glu Val Ala Leu Ile Ile Phe
                35                  40                  45

Ser Thr Lys Gly Lys Leu Tyr Glu Tyr Ser Thr Asp Ser Cys Met Asp
        50                  55                  60

Lys Ile Leu Glu Arg Tyr Glu Arg Tyr Ser Tyr Ala Glu Lys Val Leu
65                  70                  75                  80

Ile Ser Ala Glu Tyr Glu Thr Gln Gly Asn Trp Cys His Glu Tyr Arg
                85                  90                  95

Lys Leu Lys Ala Lys Val Glu Thr Ile Gln Lys Cys Gln Lys His Leu
                100                 105                 110

Met Gly Glu Asp Leu Glu Thr Leu Asn Leu Lys Glu Leu Gln Gln Leu
                115                 120                 125

Glu Gln Gln Leu Glu Ser Ser Leu Lys His Ile Arg Thr Arg Lys Ser
    130                 135                 140

Gln Leu Met Val Glu Ser Ile Ser Ala Leu Gln Arg Lys Glu Lys Ser
145                 150                 155                 160

Leu Gln Glu Glu Asn Lys Val Leu Gln Lys Glu Leu Ala Glu Lys Gln
                165                 170                 175

Lys Asp Gln Arg Gln Val Gln Arg Asp Gln Thr Gln Gln Thr
                180                 185                 190

Ser Ser Ser Ser Thr Ser Phe Met Leu Arg Glu Ala Ala Pro Thr Thr
    195                 200                 205

Asn Val Ser Ile Phe Pro Val Ala Ala Gly Gly Arg Val Val Glu Gly
                210                 215                 220

Ala Ala Ala Gln Pro Gln Ala Arg Val Gly Leu Pro Pro Trp Met Leu
225                 230                 235                 240

Ser His Leu Ser Cys
                245

<210> SEQ ID NO 72
<211> LENGTH: 762
<212> TYPE: DNA
<213> ORGANISM: Oryza sativa

<400> SEQUENCE: 72
atggggcggg gcaaggtgca gctgaagcgg atcgagaaca agatcaaccg gcaggtgacc      60
ttctccaagc gcaggtcggg gctgctcaag aaggcgaatg agatctccgt gctctgcgac     120
gccgaggtcg cgctcatcat cttctccacc aagggcaagc tctacgagta cgccaccgac     180
tcatgtatgg acaaaatcct tgaacgttat gagcgctact cctatgcaga aaaggtcctt     240
atttcagctg aatctgacac tcagggcaac tggtgccacg aatataggaa actgaaggct     300
aaggttgaga caatacagaa atgtcaaaag cacctcatgg gagaggatct tgaatctttg     360
aatctcaaag agctgcagca gctggagcag cagctgaaaa attcgttgaa acatatcaga     420
tccagaaaga gccaactaat gctcgagtcc attaacgagc ttcaacggaa ggaaaagtca     480
ctgcaggaga gaataaggt cctacagaaa gaaaaccctt gctccttcct acagctggtg     540
gagaagcaga agtccagaa gcaacaagtg caatgggacc agacacaacc tcaaacaagt     600
tcctcatcat cctccttcat gatgagggaa gcccttccaa caactaatat cagtaactac     660
cctgcagcag ctggcgaaag gatagaggat gtagcagcag ggcagccaca gcatgttcgc     720

```
attgggctgc caccatggat gctgagccac atcaacggct aa                          762
```

<210> SEQ ID NO 73
<211> LENGTH: 253
<212> TYPE: PRT
<213> ORGANISM: Oryza sativa

<400> SEQUENCE: 73

```
Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

Asn Glu Ile Ser Val Leu Cys Asp Ala Glu Val Ala Leu Ile Ile Phe
        35                  40                  45

Ser Thr Lys Gly Lys Leu Tyr Glu Tyr Ala Thr Asp Ser Cys Met Asp
    50                  55                  60

Lys Ile Leu Glu Arg Tyr Glu Arg Tyr Ser Tyr Ala Glu Lys Val Leu
65                  70                  75                  80

Ile Ser Ala Glu Ser Asp Thr Gln Gly Asn Trp Cys His Glu Tyr Arg
                85                  90                  95

Lys Leu Lys Ala Lys Val Glu Thr Ile Gln Lys Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Asn Ser Leu Lys His Ile Arg Ser Arg Lys Ser
    130                 135                 140

Gln Leu Met Leu Glu Ser Ile Asn Glu Leu Gln Arg Lys Glu Lys Ser
145                 150                 155                 160

Leu Gln Glu Glu Asn Lys Val Leu Gln Lys Glu Asn Pro Cys Ser Phe
                165                 170                 175

Leu Gln Leu Val Glu Lys Gln Lys Val Gln Lys Gln Val Gln Trp
            180                 185                 190

Asp Gln Thr Gln Pro Gln Thr Ser Ser Ser Ser Ser Phe Met Met
        195                 200                 205

Arg Glu Ala Leu Pro Thr Thr Asn Ile Ser Asn Tyr Pro Ala Ala Ala
    210                 215                 220

Gly Glu Arg Ile Glu Asp Val Ala Ala Gly Gln Pro Gln His Val Arg
225                 230                 235                 240

Ile Gly Leu Pro Pro Trp Met Leu Ser His Ile Asn Gly
                245                 250
```

<210> SEQ ID NO 74
<211> LENGTH: 741
<212> TYPE: DNA
<213> ORGANISM: Oryza sativa

<400> SEQUENCE: 74

```
atggggcggg gcaaggtgca gctgaagcgg atcgagaaca agatcaaccg gcaggtgacc       60
ttctccaagc gcaggtcaaa actgctcaag aaggcgaatg agatctccgt gctctgcgac      120
gccgaggtcg cgctcatcat cttctccacc aagggcaagc tctacgagta cgccaccgac      180
tcatgtatgg acaaaatcct tgaacgttat gagcgctact cctatgcaga aaaggtcctt      240
atttcagctg aatctgacac tcagggcaac tggtgccacg aatataggaa actgaaggct      300
aaggttgaga caatacagaa atgtcaaaag caccctcatgg gagaggatct tgaatctttg      360
aatctcaaag agctgcagca gctggagcag cagctggaaa attcgttgaa acatatcaga      420
```

```
tccagaaaga gccaactaat gctcgagtcc attaacgagc ttcaacggaa ggaaaagtca      480
ctgcaggagg agaataaggt cctacagaaa gaactggtgg agaagcagaa agtccagaag      540
caacaagtgc aatgggacca gacacaacct caaacaagtt cctcatcatc ctccttcatg      600
atgagggaag cccttccaac aactaatatc agtaactacc ctgcagcagc tggcgaaagg      660
atagaggatg tagcagcagg gcagccacag catgaacgca ttgggctgcc accatggatg      720
ctgagccaca tcaacggcta a                                                741

<210> SEQ ID NO 75
<211> LENGTH: 246
<212> TYPE: PRT
<213> ORGANISM: Oryza sativa

<400> SEQUENCE: 75

Met Gly Arg Gly Lys Val Gln Leu Lys Arg Ile Glu Asn Lys Ile Asn
1               5                   10                  15

Arg Gln Val Thr Phe Ser Lys Arg Arg Ser Lys Leu Leu Lys Lys Ala
            20                  25                  30

Asn Glu Ile Ser Val Leu Cys Asp Ala Glu Val Ala Leu Ile Ile Phe
        35                  40                  45

Ser Thr Lys Gly Lys Leu Tyr Glu Tyr Ala Thr Asp Ser Cys Met Asp
    50                  55                  60

Lys Ile Leu Glu Arg Tyr Glu Arg Tyr Ser Tyr Ala Glu Lys Val Leu
65                  70                  75                  80

Ile Ser Ala Glu Ser Asp Thr Gln Gly Asn Trp Cys His Glu Tyr Arg
                85                  90                  95

Lys Leu Lys Ala Lys Val Glu Thr Ile Gln Lys Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Asn Ser Leu Lys His Ile Arg Ser Arg Lys Ser
    130                 135                 140

Gln Leu Met Leu Glu Ser Ile Asn Glu Leu Gln Arg Lys Glu Lys Ser
145                 150                 155                 160

Leu Gln Glu Glu Asn Lys Val Leu Gln Lys Glu Leu Val Glu Lys Gln
                165                 170                 175

Lys Val Gln Lys Gln Val Gln Trp Asp Gln Thr Gln Pro Gln Thr
            180                 185                 190

Ser Ser Ser Ser Ser Ser Phe Met Met Arg Glu Ala Leu Pro Thr Thr
        195                 200                 205

Asn Ile Ser Asn Tyr Pro Ala Ala Ala Gly Glu Arg Ile Glu Asp Val
    210                 215                 220

Ala Ala Gly Gln Pro Gln His Glu Arg Ile Gly Leu Pro Pro Trp Met
225                 230                 235                 240

Leu Ser His Ile Asn Gly
                245

<210> SEQ ID NO 76
<211> LENGTH: 735
<212> TYPE: DNA
<213> ORGANISM: Dendrocalamus latiflorus

<400> SEQUENCE: 76
atggggcgcg ggaaggtgca gctgaagcgg atcgagaaca agatcaaccg gcaagtgact      60
ttctccaagc gccggtcggg gctgctcaag aaggcgcatg agatctccgt cctctgcgac     120
```

-continued

```
gccgaggtcg gccttatcat cttctccacc aagggcaagc tctacgagta cgccaccgac    180
tcatgtatgg acaaaattct tgaacggtac gagcgttact cctatgcaga aaaggttctt    240
atttcagccg aatctgaaac tcagggcaac tggtgtcacg aatataggaa actgaaggcg    300
aaggttgaga cgatacagaa atgtcaaaag cacctcatgg gagaggatcc tgaatctttg    360
aatctcaagg agctgcagca actcgagcag cagctggaaa gttcagtgaa acatatcaga    420
tccagaaaga gccagcttat gctcgagtcc atttccgagc ttcaaaagaa ggagaagtca    480
ctgcaggagg agaacaaggt tctgcagaag gaactcgtgg agaagcagca ggtccataaa    540
cggttagtgc aatgggacca aactcagccg caaactagtt cctcttcctc gtccttcatg    600
atgagggaag ctctcccaac aacaaatatc agtatttacg ctgcggcagc cggcgagagg    660
gcagaggacg cagcagggca gcctcagatt cacattgggc tgccgccatg gatggtgagc    720
cacatcaacg gctaa                                                    735
```

<210> SEQ ID NO 77
<211> LENGTH: 244
<212> TYPE: PRT
<213> ORGANISM: Dendrocalamus latiflorus

<400> SEQUENCE: 77

```
Met Gly Arg Gly Lys Val Gln Leu Lys Arg Ile Glu Asn Lys Ile Asn
 1               5                  10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Gly Leu Ile Ile Phe
        35                  40                  45

Ser Thr Lys Gly Lys Leu Tyr Glu Tyr Ala Thr Asp Ser Cys Met Asp
    50                  55                  60

Lys Ile Leu Glu Arg Tyr Glu Arg Tyr Ser Tyr Ala Glu Lys Val Leu
65                  70                  75                  80

Ile Ser Ala Glu Ser Glu Thr Gln Gly Asn Trp Cys His Glu Tyr Arg
                85                  90                  95

Lys Leu Lys Ala Lys Val Glu Thr Ile Gln Lys Cys Gln Lys His Leu
           100                 105                 110

Met Gly Glu Asp Pro Glu Ser Leu Asn Leu Lys Glu Leu Gln Gln Leu
       115                 120                 125

Glu Gln Gln Leu Glu Ser Ser Val Lys His Ile Arg Ser Arg Lys Ser
   130                 135                 140

Gln Leu Met Leu Glu Ser Ile Ser Glu Leu Gln Lys Glu Lys Leu Lys Ser
145                 150                 155                 160

Leu Gln Glu Glu Asn Lys Val Leu Gln Lys Glu Leu Val Glu Lys Gln
                165                 170                 175

Gln Val His Lys Arg Leu Val Gln Trp Asp Gln Thr Gln Pro Gln Thr
            180                 185                 190

Ser Ser Ser Ser Ser Ser Phe Met Met Arg Glu Ala Leu Pro Thr Thr
        195                 200                 205

Asn Ile Ser Ile Tyr Ala Ala Ala Ala Gly Glu Arg Ala Glu Asp Ala
    210                 215                 220

Ala Gly Gln Pro Gln Ile His Ile Gly Leu Pro Pro Trp Met Val Ser
225                 230                 235                 240

His Ile Asn Gly
```

<210> SEQ ID NO 78
<211> LENGTH: 735

<212> TYPE: DNA
<213> ORGANISM: Dendrocalamus latiflorus

<400> SEQUENCE: 78

```
atggggcgcg ggaaggtgca gctgaagcgg atcgagaaca agatcaaccg gcaagtgact      60
ttctccaagc gccggtcggg gctgctcaag aaggcgcatg agatctccgt cctctgcgac     120
gccgaggtcg gccttatcat cttctccacc aagggcaagc tctacgagta cgccaccgac     180
tcatgtatgg acaaaattct tgaacggtac gagcgttact cctatgcaga aaaggttctt     240
atttcagccg aatctgaaac tcagggcaac tggtgtcacg aatataggaa actgaaggcg     300
aaggttgaga cgatacagaa atgtcaaaag cacctcatgg gagaggatct tgaatctttg     360
aatctcaagg agctgcagca actcgagcag cagctggaaa gttcagtgaa acatatcaga     420
tccagaaaga gccagcttat gctcgagtcc atttccgagc ttcaaaagaa ggagaagtca     480
ctgcaggagg agaacaaggt tctgcagaag gaactcgtgg agaagcagca ggtccataaa     540
cggttagtgc aatgggacca aactcagccg caaactagtt cctcttcctc gtccttcatg     600
atgagggaag ctctcccaac aacaaatatc agtatttacg ctgcggcagc cggcgagagg     660
gcagaggaca cagcagggca gcctcagatt cacattgggc tgccgccatg gatggtgagc     720
cacatcaacg gctaa                                                      735
```

<210> SEQ ID NO 79
<211> LENGTH: 244
<212> TYPE: PRT
<213> ORGANISM: Dendrocalamus latiflorus

<400> SEQUENCE: 79

```
Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Gly Leu Ile Ile Phe
        35                  40                  45

Ser Thr Lys Gly Lys Leu Tyr Glu Tyr Ala Thr Asp Ser Cys Met Asp
    50                  55                  60

Lys Ile Leu Glu Arg Tyr Glu Arg Tyr Ser Tyr Ala Glu Lys Val Leu
65                  70                  75                  80

Ile Ser Ala Glu Ser Glu Thr Gln Gly Asn Trp Cys His Glu Tyr Arg
                85                  90                  95

Lys Leu Lys Ala Lys Val Glu Thr Ile Gln Lys Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Val Lys His Ile Arg Ser Arg Lys Ser
    130                 135                 140

Gln Leu Met Leu Glu Ser Ile Ser Glu Leu Gln Lys Lys Glu Lys Ser
145                 150                 155                 160

Leu Gln Glu Glu Asn Lys Val Leu Gln Lys Glu Leu Val Glu Lys Gln
                165                 170                 175

Gln Val His Lys Arg Leu Val Gln Trp Asp Gln Thr Gln Pro Gln Thr
            180                 185                 190

Ser Ser Ser Ser Ser Ser Phe Met Met Arg Glu Ala Leu Pro Thr Thr
        195                 200                 205

Asn Ile Ser Ile Tyr Ala Ala Ala Ala Gly Glu Arg Ala Glu Asp Ala
    210                 215                 220
```

Ala Gly Gln Pro Gln Ile His Ile Gly Leu Pro Pro Trp Met Val Ser
225                 230                 235                 240

His Ile Asn Gly

<210> SEQ ID NO 80
<211> LENGTH: 813
<212> TYPE: DNA
<213> ORGANISM: Zea mays

<400> SEQUENCE: 80

```
atggggcgcg gcaaggtgca gctgaagcgg atagagaaca agataaaccg gcaggtgacc      60
ttctccaagc gccggaacgg gctgctgaag aaggcgcacg agatctccgt cctctgcgac     120
gccgaggtcg ccgtcatcgt cttctccccc aagggcaagc tctacgagta cgcctccgac     180
tcccgcatgg acaaaattct agaacgttat gagcgatatt cctatgctga aaaggctctt     240
atttcagctg aatctgaaag tgagggaaat tggtgccacg aatacaggaa actgaaggcc     300
aaaattgaga ccatacaaag atgccacaag cacctgatgg gagaggatct agagtctttg     360
aatccaaaag agctccaaca actagagcag cagctggaga gctcactgaa gcacatcaga     420
tcaagaaaga gccaccttat ggccgagtca atttctgagc tacagaagaa ggagaggtca     480
ctgcaggagg agaacaagat tctacagaag gaactttcag agaggcagaa ggcggtcgct     540
agccggcagc agcagcagca gcaggtgcag tgggaccagc agacacaggt ccaggtccag     600
acaagctcat cgtcttcttc cttcatgatg aggcaggatc agcagggact gccacctcca     660
caaaacatct gcttcccgcc gttgagcatc ggagagagag gcgaagaggt ggctgcggcg     720
gcgcagcagc agctgcctcc tccggggcag gcgcaaccac agctccgcat cgcaggtctg     780
ccgccatgga tgctgagcca cctcaatgca taa                                   813
```

<210> SEQ ID NO 81
<211> LENGTH: 270
<212> TYPE: PRT
<213> ORGANISM: Zea mays

<400> SEQUENCE: 81

Met Gly Arg Gly Lys Val Gln Leu Lys Arg Ile Glu Asn Lys Ile Asn
1               5                  10                  15

Arg Gln Val Thr Phe Ser Lys Arg Arg Asn Gly Leu Leu Lys Lys Ala
                20                  25                  30

His Glu Ile Ser Val Leu Cys Asp Ala Glu Val Ala Val Ile Val Phe
            35                  40                  45

Ser Pro Lys Gly Lys Leu Tyr Glu Tyr Ala Ser Asp Ser Arg Met Asp
        50                  55                  60

Lys Ile Leu Glu Arg Tyr Glu Arg Tyr Ser Tyr Ala Glu Lys Ala Leu
65                  70                  75                  80

Ile Ser Ala Glu Ser Glu Ser Glu Gly Asn Trp Cys His Glu Tyr Arg
                85                  90                  95

Lys Leu Lys Ala Lys Ile Glu Thr Ile Gln Arg Cys His Lys His Leu
            100                 105                 110

Met Gly Glu Asp Leu Glu Ser Leu Asn Pro Lys Glu Leu Gln Gln Leu
        115                 120                 125

Glu Gln Gln Leu Glu Ser Ser Leu Lys His Ile Arg Ser Arg Lys Ser
    130                 135                 140

His Leu Met Ala Glu Ser Ile Ser Glu Leu Gln Lys Lys Glu Arg Ser
145                 150                 155                 160

```
Leu Gln Glu Glu Asn Lys Ile Leu Gln Lys Glu Leu Ser Glu Arg Gln
            165                 170                 175

Lys Ala Val Ala Ser Arg Gln Gln Gln Gln Val Gln Trp Asp
        180                 185                 190

Gln Gln Thr Gln Val Gln Val Gln Thr Ser Ser Ser Ser Ser Phe
        195                 200                 205

Met Met Arg Gln Asp Gln Gln Gly Leu Pro Pro Gln Asn Ile Cys
        210                 215                 220

Phe Pro Pro Leu Ser Ile Gly Glu Arg Gly Glu Val Ala Ala Ala
225                 230                 235                 240

Ala Gln Gln Gln Leu Pro Pro Pro Gly Gln Ala Gln Pro Gln Leu Arg
                245                 250                 255

Ile Ala Gly Leu Pro Pro Trp Met Leu Ser His Leu Asn Ala
            260                 265                 270

<210> SEQ ID NO 82
<211> LENGTH: 689
<212> TYPE: DNA
<213> ORGANISM: Sorghum bicolor

<400> SEQUENCE: 82
gcaaggtgca gctcaagcgg atagagaaca agataaaccg gcaggtgacc ttctccaagc     60
gccgcaacgg gctgctcaag aaggcgcacg agatctccgt cctctgcgac gccgaggtcg    120
ccgtcatcgt cttctccccc aagggcaagc tctatgagta cgccaccgac tcccgcatgg    180
acaaaattct cgaacgttat gagcgatatt cctatgctga aaaggctctt atttcagctg    240
aatctgaaag tgagggaaac tggtgccacg aatacaggaa actgaaggcc aaaattgaga    300
ccattcaaaa atgccacaag cacctgatgg gagaggatct agagtctttg aatcccaaag    360
agctccaaca actagagcag cagctggaga gctcactgaa gcacatcaga tcaagaaaga    420
gccaccttat ggctgagtct atttctgaac tacagaagaa ggagaggtca ctgcaggagg    480
agaacaaggc tctacagaag gaacttgcgg agaggcagaa ggcggccgcg agcaggcagc    540
agcagcaagg tgcagtggga ccagcagaca cagacccagg cccagacaag ctcatcatcg    600
tcctccttca tgatgaggca ggatcagcag ggtctgccgc ctccacaaaa catatgcttc    660
ccgccgctga taatcggaga gagaggtga                                     689

<210> SEQ ID NO 83
<211> LENGTH: 228
<212> TYPE: PRT
<213> ORGANISM: Sorghum bicolor

<400> SEQUENCE: 83

Lys Val Gln Leu Lys Arg Ile Glu Asn Lys Ile Asn Arg Gln Val Thr
1               5                   10                  15

Phe Ser Lys Arg Arg Asn Gly Leu Leu Lys Lys Ala His Glu Ile Ser
            20                  25                  30

Val Leu Cys Asp Ala Glu Val Ala Val Ile Val Phe Ser Pro Lys Gly
        35                  40                  45

Lys Leu Tyr Glu Tyr Ala Thr Asp Ser Arg Met Asp Lys Ile Leu Glu
    50                  55                  60

Arg Tyr Glu Arg Tyr Ser Tyr Ala Glu Lys Ala Leu Ile Ser Ala Glu
65                  70                  75                  80

Ser Glu Ser Glu Gly Asn Trp Cys His Glu Tyr Arg Lys Leu Lys Ala
                85                  90                  95

Lys Ile Glu Thr Ile Gln Lys Cys His Lys His Leu Met Gly Glu Asp
```

```
                        100                 105                 110
Leu Glu Ser Leu Asn Pro Lys Glu Leu Gln Gln Leu Glu Gln Gln Leu
                    115                 120                 125

Glu Ser Ser Leu Lys His Ile Arg Ser Arg Lys Ser His Leu Met Ala
            130                 135                 140

Glu Ser Ile Ser Glu Leu Gln Lys Lys Glu Arg Ser Leu Gln Glu Glu
145                 150                 155                 160

Asn Lys Ala Leu Gln Lys Glu Leu Ala Glu Arg Gln Lys Ala Ala Ala
                165                 170                 175

Ser Arg Gln Gln Gln Gln Gly Ala Val Gly Pro Ala Asp Thr Asp Pro
            180                 185                 190

Gly Pro Asp Lys Leu Ile Ile Val Leu Leu His Asp Glu Ala Gly Ser
        195                 200                 205

Ala Gly Ser Ala Ala Ser Thr Lys His Met Leu Pro Ala Ala Asp Asn
    210                 215                 220

Arg Arg Glu Arg
225

<210> SEQ ID NO 84
<211> LENGTH: 822
<212> TYPE: DNA
<213> ORGANISM: Zea mays

<400> SEQUENCE: 84
atggggcgcg gcaaggtaca gctgaagcgg atagagaaca agataaaccg gcaggtgacc      60
ttctccaagc gccggaacgg cctgctcaag aaggcgcacg agatctccgt cctctgcgat     120
gccgaggtcg ccgtcatcgt cttctccccc aagggcaagc tctacgagta cgccaccgac     180
tcccgcatgg acaaaattct tgaacgctat gagcgatatt cctatgctga aaaggctctt     240
atttcagctg aatctgaaag tgagggaaat tggtgccacg aatacaggaa actgaaggcc     300
aaaattgaga ccatacaaaa atgccacaag cacctgatgg gagaggatct agagtctttg     360
aatcccaaag agctccagca actagagcag cagctggata gctcactgaa gcacatcaga     420
tcaaggaaga gccaccttat ggccgagtct atttctgagc tacagaagaa ggagaggtca     480
ctgcaggagg agaacaaggc tctgcagaag gaacttgcgg agaggcagaa ggccgtcgcg     540
agccggcagc agcagcaaca gcagcaggtg cagtgggacc agcagacaca tgcccaggcc     600
cagacaagct catcatcgtc ctccttcatg atgaggcagg atcagcaggg actgccgcct     660
ccacacaaca tctgcttccc gccgttgaca atgggagata gagtgaagaa gctggctgcg     720
gcggcggcgg cgcagcagca gcagccactg ccggggcagg cgcaaccgca gctccgcatc     780
gcaggtctgc caccatggat gctgagccac ctcaatgcat aa                         822

<210> SEQ ID NO 85
<211> LENGTH: 273
<212> TYPE: PRT
<213> ORGANISM: Zea mays

<400> SEQUENCE: 85

Met Gly Arg Gly Lys Val Gln Leu Lys Arg Ile Glu Asn Lys Ile Asn
1               5                   10                  15

Arg Gln Val Thr Phe Ser Lys Arg Arg Asn Gly Leu Leu Lys Lys Ala
                20                  25                  30

His Glu Ile Ser Val Leu Cys Asp Ala Glu Val Ala Val Ile Val Phe
            35                  40                  45

Ser Pro Lys Gly Lys Leu Tyr Glu Tyr Ala Thr Asp Ser Arg Met Asp
```

```
              50                  55                  60
Lys Ile Leu Glu Arg Tyr Glu Arg Tyr Ser Tyr Ala Glu Lys Ala Leu
 65                  70                  75                  80

Ile Ser Ala Glu Ser Glu Ser Glu Gly Asn Trp Cys His Glu Tyr Arg
                 85                  90                  95

Lys Leu Lys Ala Lys Ile Glu Thr Ile Gln Lys Cys His Lys His Leu
            100                 105                 110

Met Gly Glu Asp Leu Glu Ser Leu Asn Pro Lys Glu Leu Gln Gln Leu
        115                 120                 125

Glu Gln Gln Leu Asp Ser Ser Leu Lys His Ile Arg Ser Arg Lys Ser
    130                 135                 140

His Leu Met Ala Glu Ser Ile Ser Glu Leu Gln Lys Lys Glu Arg Ser
145                 150                 155                 160

Leu Gln Glu Glu Asn Lys Ala Leu Gln Lys Glu Leu Ala Glu Arg Gln
                165                 170                 175

Lys Ala Val Ala Ser Arg Gln Gln Gln Gln Gln Gln Val Gln Trp
            180                 185                 190

Asp Gln Gln Thr His Ala Gln Ala Gln Thr Ser Ser Ser Ser Ser
        195                 200                 205

Phe Met Met Arg Gln Asp Gln Gln Gly Leu Pro Pro His Asn Ile
    210                 215                 220

Cys Phe Pro Pro Leu Thr Met Gly Asp Arg Gly Glu Glu Leu Ala Ala
225                 230                 235                 240

Ala Ala Ala Ala Gln Gln Gln Pro Leu Pro Gly Gln Ala Gln Pro
            245                 250                 255

Gln Leu Arg Ile Ala Gly Leu Pro Pro Trp Met Leu Ser His Leu Asn
            260                 265                 270

Ala

<210> SEQ ID NO 86
<211> LENGTH: 786
<212> TYPE: DNA
<213> ORGANISM: Lolium temulentum

<400> SEQUENCE: 86
atgggtcgcg gcaaggtgca gctgaagcgg atagagaaca agataaaccg tcaggtgaca     60
ttctccaagc gccgcaacgg gctactcaag aaggcgcacg agatctccgt cctctgcgac    120
gccgaggtcg ccgtcgtcgt cttctccccg aaagggaagc tctatgagta cgccactgac    180
tccagcatgg acaaaattct tgaacgttat gaacgctact cttatgctga aaaggctttg    240
atttcagctg aatctgaaag tgagggaaat tggtgccatg aatacaggaa gctgaaggcg    300
aagattgaga ctatacaaaa atgtcacaag caccctcatgg gggaggatct ggagtgtcta    360
aacctgaaag agctccaaca actagagcag cagctggaga gttcattgaa gcacatcaga    420
tcgagaaaga gccaccttat gatggagtcc atttctgagc tacagaagaa ggagcggtca    480
ctccaggagg agaacaaggc tctacagaag gaactggtgg agaggcagaa ggcggccagg    540
cagcagcagc aagagcagtg ggaccgtcag acccaaacac aacaagccca aaaccaacct    600
caggcccaga cgagctcatc atcttcctcc ttcatgatga gggatcagca ggcccatgct    660
caacaaaaca tctgttaccc gctggtgaca atgggtggag aggctgtggc cgcggcgcca    720
gggcagcagg ggcagcttcg catcggaggc ctgccaccat ggatgctgag ccacctcaac    780
gcttga                                                                786
```

```
<210> SEQ ID NO 87
<211> LENGTH: 261
<212> TYPE: PRT
<213> ORGANISM: Lolium temulentum

<400> SEQUENCE: 87

Met Gly Arg Gly Lys Val Gln Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Val Val Phe
        35                  40                  45

Ser Pro Lys Gly Lys Leu Tyr Glu Tyr Ala Thr Asp Ser Ser Met Asp
    50                  55                  60

Lys Ile Leu Glu Arg Tyr Glu Arg Tyr Ser Tyr Ala Glu Lys Ala Leu
65                  70                  75                  80

Ile Ser Ala Glu Ser Glu Ser Glu Gly Asn Trp Cys His Glu Tyr Arg
                85                  90                  95

Lys Leu Lys Ala Lys Ile Glu Thr Ile Gln Lys Cys His Lys His Leu
            100                 105                 110

Met Gly Glu Asp Leu Glu Cys Leu Asn Leu Lys Glu Leu Gln Gln Leu
        115                 120                 125

Glu Gln Gln Leu Glu Ser Ser Leu Lys His Ile Arg Ser Arg Lys Ser
    130                 135                 140

His Leu Met Met Glu Ser Ile Ser Glu Leu Gln Lys Lys Glu Arg Ser
145                 150                 155                 160

Leu Gln Glu Glu Asn Lys Ala Leu Gln Lys Glu Leu Val Glu Arg Gln
                165                 170                 175

Lys Ala Ala Arg Gln Gln Gln Glu Gln Trp Asp Arg Gln Thr Gln
            180                 185                 190

Thr Gln Gln Ala Gln Asn Gln Pro Gln Ala Gln Thr Ser Ser Ser Ser
        195                 200                 205

Ser Ser Phe Met Met Arg Asp Gln Gln Ala His Ala Gln Gln Asn Ile
    210                 215                 220

Cys Tyr Pro Leu Val Thr Met Gly Gly Glu Ala Val Ala Ala Ala Pro
225                 230                 235                 240

Gly Gln Gln Gly Gln Leu Arg Ile Gly Gly Leu Pro Pro Trp Met Leu
                245                 250                 255

Ser His Leu Asn Ala
            260

<210> SEQ ID NO 88
<211> LENGTH: 786
<212> TYPE: DNA
<213> ORGANISM: Lolium perenne

<400> SEQUENCE: 88
atgggtcgcg gcaaggtgca gctgaagcgg atagagaaca agataaaccg tcaggtgacc      60
ttctccaagc gccgcaacgg gctactcaag aaggcgcacg agatctccgt cctctgcgac     120
gccgaggtcg ccgtcgtcgt cttctccccg aaagggaagc tctatgagta cgccactgac     180
tccagcatgg acaaaattct gaacgttat gaacgctact cttatgctga aaaggctttg     240
atttcagctg aatctgaaag tgagggaaat tggtgccatg aatacaggaa actgaaggcg     300
aagattgaga ctatacaaaa atgtcacaag cacctcatgg gggaggatct ggagtgtcta     360
aacctgaaag agctccaaca actagagcag cagctggaga gttcattgaa gcacatcaga     420
```

-continued

```
tcgagaaaga gccaccttat gatggagtcc atttctgagc tacagaagaa ggagcggtca      480
ctccaggagg agaacaaggc tctacagaag gaactggtgg agaggcagaa ggcggccagg      540
cagcagcagc aagagcagtg ggaccgtcag acccaaacac aacaagccca aaaccaacct      600
caggcccaga cgagctcatc atcttcctcc ttcatgatga gggatcagca ggcccatgct      660
caacaaaaca tctgttaccc gccggtgaca atgggtggag aggctgtggc cgcggcgcca      720
gggcagcagg gcagcttcg catcggaggc ctgccaccat ggatgctgag ccacctcaac      780
gcttga                                                                786
```

<210> SEQ ID NO 89
<211> LENGTH: 261
<212> TYPE: PRT
<213> ORGANISM: Lolium perenne

<400> SEQUENCE: 89

```
Met Gly Arg Gly Lys Val Gln Leu Lys Arg Ile Glu Asn Lys Ile Asn
 1               5                  10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Val Val Phe
        35                  40                  45

Ser Pro Lys Gly Lys Leu Tyr Glu Tyr Ala Thr Asp Ser Ser Met Asp
    50                  55                  60

Lys Ile Leu Glu Arg Tyr Glu Arg Tyr Ser Tyr Ala Glu Lys Ala Leu
65                  70                  75                  80

Ile Ser Ala Glu Ser Glu Ser Glu Gly Asn Trp Cys His Glu Tyr Arg
                85                  90                  95

Lys Leu Lys Ala Lys Ile Glu Thr Ile Gln Lys Cys His Lys His Leu
            100                 105                 110

Met Gly Glu Asp Leu Glu Cys Leu Asn Leu Lys Glu Leu Gln Gln Leu
        115                 120                 125

Glu Gln Gln Leu Glu Ser Ser Leu Lys His Ile Arg Ser Arg Lys Ser
    130                 135                 140

His Leu Met Met Glu Ser Ile Ser Glu Leu Gln Lys Lys Glu Arg Ser
145                 150                 155                 160

Leu Gln Glu Glu Asn Lys Ala Leu Gln Lys Glu Leu Val Glu Arg Gln
                165                 170                 175

Lys Ala Ala Arg Gln Gln Gln Glu Gln Trp Asp Arg Gln Thr Gln
            180                 185                 190

Thr Gln Gln Ala Gln Asn Gln Pro Gln Ala Gln Thr Ser Ser Ser Ser
        195                 200                 205

Ser Ser Phe Met Met Arg Asp Gln Gln Ala His Ala Gln Gln Asn Ile
    210                 215                 220

Cys Tyr Pro Pro Val Thr Met Gly Gly Glu Ala Val Ala Ala Ala Pro
225                 230                 235                 240

Gly Gln Gln Gly Gln Leu Arg Ile Gly Gly Leu Pro Pro Trp Met Leu
                245                 250                 255

Ser His Leu Asn Ala
            260
```

<210> SEQ ID NO 90
<211> LENGTH: 831
<212> TYPE: DNA
<213> ORGANISM: Hordeum vulgare

<400> SEQUENCE: 90

-continued

```
atgggtcgcg gtaaggtgca gctgaagcgg atagagaaca agataaatcg gcaggtgacc      60
ttctccaagc gccgcaacgg gctcctgaag aaggcgcacg agatctccgt cctctgtgac     120
gcagaggtcg ccgtcatcgt cttctccccc aaaggcaagc tctatgagta cgccaccgac     180
tccagcatgg acaaaattct tgaacgttat gagcgctact cttatgctga aaaggctctt     240
atttcagctg aatctgaaag tgaggggaat tggtgtcatg aatacaggaa acttaaggcg     300
aagattgaga ccatacagaa gtgtcacaag cacctcatgg gagaggatct ggattctctg     360
aacctcaaag aactccaaca actggagcag cagctggaga gttcattgaa gcacatcaga     420
tcgagaaaga gccatcttat gatggagtcc atttctgagc tacagaagaa ggagaggtca     480
ctgcaggagg agaacaaggc cctacagaag gaactggtgg agaggcagaa ggcggccagc     540
aggcagcagc agctgcagca gcagcaacaa caacaacaaa tgcaatggga gcaccaagcc     600
cagacccaaa cccataccca tactcaaaac cagccccaag cccagactag ctcatcatct     660
tcctctttca tgatgaggga tcagcaggcc catgcccctc aacagaacat ttgtagctac     720
ccaccggtga cgatgggtgg ggaggcgacg gcggcggcgg cggcgccgga gcagcaggct     780
cagcttcgca tatgcctacc gccatggatg ctgagccacc tcaacgcttg a              831
```

<210> SEQ ID NO 91
<211> LENGTH: 276
<212> TYPE: PRT
<213> ORGANISM: Hordeum vulgare

<400> SEQUENCE: 91

```
Met Gly Arg Gly Lys Val Gln Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Val Ile Val Phe
        35                  40                  45

Ser Pro Lys Gly Lys Leu Tyr Glu Tyr Ala Thr Asp Ser Ser Met Asp
    50                  55                  60

Lys Ile Leu Glu Arg Tyr Glu Arg Tyr Ser Tyr Ala Glu Lys Ala Leu
65                  70                  75                  80

Ile Ser Ala Glu Ser Glu Ser Glu Gly Asn Trp Cys His Glu Tyr Arg
                85                  90                  95

Lys Leu Lys Ala Lys Ile Glu Thr Ile Gln Lys Cys His Lys His Leu
            100                 105                 110

Met Gly Glu Asp Leu Asp Ser Leu Asn Leu Lys Glu Leu Gln Gln Leu
        115                 120                 125

Glu Gln Gln Leu Glu Ser Ser Leu Lys His Ile Arg Ser Arg Lys Ser
    130                 135                 140

His Leu Met Met Glu Ser Ile Ser Glu Leu Gln Lys Lys Glu Arg Ser
145                 150                 155                 160

Leu Gln Glu Glu Asn Lys Ala Leu Gln Lys Glu Leu Val Glu Arg Gln
                165                 170                 175

Lys Ala Ala Ser Arg Gln Gln Gln Leu Gln Gln Gln Gln Gln Gln Gln
            180                 185                 190

Gln Met Gln Trp Glu His Gln Ala Gln Thr Gln Thr His Thr His Thr
        195                 200                 205

Gln Asn Gln Pro Gln Ala Gln Thr Ser Ser Ser Ser Ser Phe Met
    210                 215                 220

Met Arg Asp Gln Gln Ala His Ala Pro Gln Gln Asn Ile Cys Ser Tyr
```

```
                225                 230                 235                 240
Pro Pro Val Thr Met Gly Gly Glu Ala Thr Ala Ala Ala Ala Pro
                245                 250                 255
Glu Gln Gln Ala Gln Leu Arg Ile Cys Leu Pro Pro Trp Met Leu Ser
            260                 265                 270
His Leu Asn Ala
        275

<210> SEQ ID NO 92
<211> LENGTH: 804
<212> TYPE: DNA
<213> ORGANISM: Oryza sativa

<400> SEQUENCE: 92
atggggcggg ggaaggtgca gctgaagcgg atagagaact cgatgaaccg gcaggtgacg      60
ttctccaaga ggaggaatgg attgctgaag aaggcgcacg agatctccgt cctctgcgac     120
gccgaggtcg ccgccatcgt cttctccccc aagggcaagc tctacgagta cgccactgac     180
tccaggatgg acaaaatcct gaacgttatt gagcgctatt catatgctga aaaggctctt     240
atttcagctg aatctgagag tgagggaaat tggtgccatg aatacaggaa gcttaaggca     300
aagattgaga ccatacaaaa atgtcacaaa cacctcatgg gagaggatct agaatccctg     360
aatctcaaag aactccaaca gctagagcag cagctggaga gttcattgaa gcacataaga     420
tcaagaaaga gccaccttat gcttgagtcc atttccgagc tgcagaaaaa ggagaggtca     480
ctgcaggagg agaacaaggc tctgcagaag gaactggtgg agaggcagaa gaatgtgagg     540
ggccagcagc aagtagggca gtgggaccaa acccaggtcc aggcccaggc ccaagcccaa     600
ccccaagccc agacaagctt cttcttcttc ttcatgctga gggatcagca ggcacttctt     660
tcaccacaaa atatctgcta cccgccggtg atgatgggcc agagaaatga tgcggcggcg     720
cggcggcggt ggcggcccaa ggccaggtgc aacttccgca ttggaggctt ccgccatgg     780 atgctgagca ccttcaaggc ttaa                                            804

<210> SEQ ID NO 93
<211> LENGTH: 267
<212> TYPE: PRT
<213> ORGANISM: Oryza sativa

<400> SEQUENCE: 93

Met Gly Arg Gly Lys Val Gln Leu Lys Arg Ile Glu Asn Ser Met Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Ala Ile Val Phe
        35                  40                  45

Ser Pro Lys Gly Lys Leu Tyr Glu Tyr Ala Thr Asp Ser Arg Met Asp
    50                  55                  60

Lys Ile Leu Glu Arg Tyr Glu Arg Tyr Ser Tyr Ala Glu Lys Ala Leu
65                  70                  75                  80

Ile Ser Ala Glu Ser Glu Ser Glu Gly Asn Trp Cys His Glu Tyr Arg
                85                  90                  95

Lys Leu Lys Ala Lys Ile Glu Thr Ile Gln Lys Cys His Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Arg Ser Arg Lys Ser
```

```
                    130                 135                 140
His Leu Met Leu Glu Ser Ile Ser Glu Leu Gln Lys Lys Glu Arg Ser
145                 150                 155                 160

Leu Gln Glu Glu Asn Lys Ala Leu Gln Lys Glu Leu Val Glu Arg Gln
                165                 170                 175

Lys Asn Val Arg Gly Gln Gln Val Gly Gln Trp Asp Gln Thr Gln
            180                 185                 190

Val Gln Ala Gln Ala Gln Ala Gln Pro Gln Ala Gln Thr Ser Phe Phe
            195                 200                 205

Phe Phe Phe Met Leu Arg Asp Gln Gln Ala Leu Leu Ser Pro Gln Asn
            210                 215                 220

Ile Cys Tyr Pro Pro Val Met Met Gly Gln Arg Asn Asp Ala Ala Ala
225                 230                 235                 240

Arg Arg Arg Trp Arg Pro Lys Ala Arg Cys Asn Phe Arg Ile Gly Gly
                245                 250                 255

Phe Pro Pro Trp Met Leu Ser Thr Phe Lys Ala
            260                 265

<210> SEQ ID NO 94
<211> LENGTH: 804
<212> TYPE: DNA
<213> ORGANISM: Oryza sativa

<400> SEQUENCE: 94
atggggcggg ggaaggtgca gctgaagcgg atagagaaca agatcaacag gcaggtgacg      60
ttctccaaga ggaggaatgg attgctgaag aaggcgcacg agatctccgt cctctgcgac     120
gccgaggtcg ccgccatcgt cttctccccc aagggcaagc tctacgagta cgccactgac     180
tccaggatgg acaaaatcct tgaacgttat gagcgctatt catatgctga aaaggctctt     240
atttcagctg aatccgagag tgagggaaat tggtgccatg aatacaggaa acttaaggca     300
aagattgaga ccatacaaaa atgtcacaaa cacctcatgg agaggatca tgaatccctg      360 aatctcaaag aactccaaca gctagagcag cagctggaga gttcattgaa gcacataata     420
tcaagaaaga gccaccttat gcttgagtcc atttccgagc tgcagaaaaa ggagaggtca     480
ctgcaggagg agaacaaggc tctgcagaag gaactggtgg agaggcagaa gaatgtgagg     540
ggccagcagc aagtagggca gtgggaccaa acccaggtcc aggcccaggc caagcccaa      600 ccccaagccc agacaagctc ctcctcctcc tccatgctga gggatcagca ggcacttctt     660
ccaccacaaa atatctgcta cccgccggtg atgatgggcg agagaaatga tgcggcggcg     720
gcggcggcgg tggcggcgca gggccaggtg caactccgca tcggaggtct tccgccatgg     780
atgctgagcc acctcaatgc ttaa                                            804

<210> SEQ ID NO 95
<211> LENGTH: 267
<212> TYPE: PRT
<213> ORGANISM: Oryza sativa

<400> SEQUENCE: 95

Met Gly Arg Gly Lys Val Gln Leu Lys Arg Ile Glu Asn Lys Ile Asn
1               5                   10                  15

Arg Gln Val Thr Phe Ser Lys Arg Arg Asn Gly Leu Leu Lys Lys Ala
                20                  25                  30

His Glu Ile Ser Val Leu Cys Asp Ala Glu Val Ala Ala Ile Val Phe
            35                  40                  45

Ser Pro Lys Gly Lys Leu Tyr Glu Tyr Ala Thr Asp Ser Arg Met Asp
```

```
                50                  55                  60
Lys Ile Leu Glu Arg Tyr Glu Arg Tyr Ser Tyr Ala Glu Lys Ala Leu
 65                  70                  75                  80

Ile Ser Ala Glu Ser Glu Ser Glu Gly Asn Trp Cys His Glu Tyr Arg
                 85                  90                  95

Lys Leu Lys Ala Lys Ile Glu Thr Ile Gln Lys Cys His Lys His Leu
                100                 105                 110

Met Gly Glu Asp His Glu Ser Leu Asn Leu Lys Glu Leu Gln Gln Leu
            115                 120                 125

Glu Gln Gln Leu Glu Ser Ser Leu Lys His Ile Ile Ser Arg Lys Ser
        130                 135                 140

His Leu Met Leu Glu Ser Ile Ser Glu Leu Gln Lys Lys Glu Arg Ser
145                 150                 155                 160

Leu Gln Glu Glu Asn Lys Ala Leu Gln Lys Glu Leu Val Glu Arg Gln
                165                 170                 175

Lys Asn Val Arg Gly Gln Gln Gln Val Gly Trp Asp Gln Thr Gln
                180                 185                 190

Val Gln Ala Gln Ala Gln Ala Gln Pro Gln Ala Gln Thr Ser Ser Ser
            195                 200                 205

Ser Ser Ser Met Leu Arg Asp Gln Gln Ala Leu Leu Pro Pro Gln Asn
        210                 215                 220

Ile Cys Tyr Pro Pro Val Met Met Gly Glu Arg Asn Asp Ala Ala Ala
225                 230                 235                 240

Ala Ala Ala Val Ala Ala Gln Gly Gln Val Gln Leu Arg Ile Gly Gly
                245                 250                 255

Leu Pro Pro Trp Met Leu Ser His Leu Asn Ala
                260                 265
```

<210> SEQ ID NO 96
<211> LENGTH: 668
<212> TYPE: DNA
<213> ORGANISM: Tradescantia virginiana

<400> SEQUENCE: 96

```
gggctggtga agaaggctca tgagatctcd atkytrtgtg atgcygaggt tgcgcttatt      60
atttctcta ctaaaggcaa actatacgag tatgccactg attccaaaat ggaaaatatc     120
cttgaacgct atgaacgtta ctcatatgct gagaaggctt taacttcatc agatcctgaa     180
ttacagggaa attggtgcca agagtatgtt aaacttaagg ctaaggttga ggccttacat     240
aaaagccaaa ggcatcttat gggagagcaa ctagaagcgt tggatctcaa agaattgcag     300
caactagagc atcaacttga aggttctttg aggcttgtca ggtcaagaaa gactcaaatg     360
atgttggact ccatttccga acttcagagg aaggaaaagt ctctggaaga gcaaaacaag     420
aacctagaga aggagatttt ggagaagcag aaagaaaagg ctctggcaca ccaagctcac     480
tgggaacagc agaatcagcc actacaaagc actaattcgc ctccaaggcc cttcgtgatt     540
gcagaaactc atccaacact aaacattgga aatttccaag gtagaacaaa taccgtccat     600
gcagaagaaa gtctgcagcg tcagatgagg atcagcagca gcctactgcc mycmtggatg     660
mttcacma                                                              668
```

<210> SEQ ID NO 97
<211> LENGTH: 222
<212> TYPE: PRT
<213> ORGANISM: Tradescantia virginiana
<220> FEATURE:
<221> NAME/KEY: VARIANT

```
<222> LOCATION: (11)..(11)
<223> OTHER INFORMATION: Xaa can be any naturally occurring amino acid
<220> FEATURE:
<221> NAME/KEY: VARIANT
<222> LOCATION: (218)..(218)
<223> OTHER INFORMATION: Xaa can be any naturally occurring amino acid
<220> FEATURE:
<221> NAME/KEY: VARIANT
<222> LOCATION: (221)..(221)
<223> OTHER INFORMATION: Xaa can be any naturally occurring amino acid

<400> SEQUENCE: 97
```

Gly Leu Val Lys Lys Ala His Glu Ile Ser Xaa Leu Cys Asp Ala Glu
1               5                   10                  15

Val Ala Leu Ile Ile Phe Ser Thr Lys Gly Lys Leu Tyr Glu Tyr Ala
            20                  25                  30

Thr Asp Ser Lys Met Glu Asn Ile Leu Glu Arg Tyr Glu Arg Tyr Ser
        35                  40                  45

Tyr Ala Glu Lys Ala Leu Thr Ser Ser Asp Pro Glu Leu Gln Gly Asn
    50                  55                  60

Trp Cys Gln Glu Tyr Val Lys Leu Lys Ala Lys Val Glu Ala Leu His
65                  70                  75                  80

Lys Ser Gln Arg His Leu Met Gly Glu Gln Leu Glu Ala Leu Asp Leu
                85                  90                  95

Lys Glu Leu Gln Gln Leu Glu His Gln Leu Glu Gly Ser Leu Arg Leu
            100                 105                 110

Val Arg Ser Arg Lys Thr Gln Met Met Leu Asp Ser Ile Ser Glu Leu
        115                 120                 125

Gln Arg Lys Glu Lys Ser Leu Glu Glu Gln Asn Lys Asn Leu Glu Lys
    130                 135                 140

Glu Ile Leu Glu Lys Gln Lys Gly Lys Ala Leu Ala His Gln Ala His
145                 150                 155                 160

Trp Glu Gln Gln Asn Gln Pro Leu Gln Ser Thr Asn Ser Pro Pro Arg
                165                 170                 175

Pro Phe Val Ile Ala Glu Thr His Pro Thr Leu Asn Ile Gly Asn Phe
            180                 185                 190

Gln Gly Arg Thr Asn Thr Val His Ala Glu Glu Ser Leu Gln Arg Gln
        195                 200                 205

Met Arg Ile Ser Ser Ser Leu Leu Pro Xaa Trp Met Xaa His
    210                 215                 220

```
<210> SEQ ID NO 98
<211> LENGTH: 723
<212> TYPE: DNA
<213> ORGANISM: Tradescantia virginiana
<400> SEQUENCE: 98
gtgcagctga aacggatgga gaacaagatt aacaggcagg tgacgttttc taaacgtcga      60
ggagggctgc tgaagaaagc tcatgagatc tctattctat gtgatgctga gattgctctt    120
attattttct ctactaaagg gaagctctat gagtatgcca ccaattccaa aatggacaat    180
attcttgaac gctatgagcg ttactcatat gctgaaaagg ctctaacttc atcagatcct    240
gatatacagg gaaattggtg ccaagagtat gctaaactta gtctaaggt tgaggcttta    300
tgtaaaagcc aaaggcatct tatgggagag cagcttgaaa cattgaatct caagaattg    360
cagcaactag agcaacagct cgaaggttct ctaaagcatg tcaggtcaag aaagactcaa    420
gttatgctgg actctatttc tgaacttcag aggaaggaaa agtcactaga ggagcaaaac    480
aagaacctag agaaggagat tttggagaag cagaaaatca aggctcttgc acagcaggct    540
```

```
cactgggaac accagaatca accagcacca aggggttcac ctcctaggcc atttgtgatt    600
gcagagtctc atccgacact aaatattgga catttccaag gcaggacaaa tgcagtcgaa    660
gcagaagaaa atcagcagcc tcakatgaga atttgcagta gcctcctgcc ccctggatg    720 ctt                                                                  723
```

```
<210> SEQ ID NO 99
<211> LENGTH: 241
<212> TYPE: PRT
<213> ORGANISM: Tradescantia virginiana
<220> FEATURE:
<221> NAME/KEY: UNSURE
<222> LOCATION: (228)..(228)
<223> OTHER INFORMATION: Xaa can be any naturally occurring amino acid

<400> SEQUENCE: 99
```

```
Val Gln Leu Lys Arg Met Glu Asn Lys Ile Asn Arg Gln Val Thr Phe
1               5                   10                  15

Ser Lys Arg Arg Gly Gly Leu Leu Lys Lys Ala His Glu Ile Ser Ile
            20                  25                  30

Leu Cys Asp Ala Glu Ile Ala Leu Ile Ile Phe Ser Thr Lys Gly Lys
        35                  40                  45

Leu Tyr Glu Tyr Ala Thr Asn Ser Lys Met Asp Asn Ile Leu Glu Arg
    50                  55                  60

Tyr Glu Arg Tyr Ser Tyr Ala Glu Lys Ala Leu Thr Ser Ser Asp Pro
65                  70                  75                  80

Asp Ile Gln Gly Asn Trp Cys Gln Glu Tyr Ala Lys Leu Lys Ser Lys
                85                  90                  95

Val Glu Ala Leu Cys Lys Ser Gln Arg His Leu Met Gly Glu Gln Leu
            100                 105                 110

Glu Thr Leu Asn Leu Lys Glu Leu Gln Gln Leu Glu Gln Gln Leu Glu
        115                 120                 125

Gly Ser Leu Lys His Val Arg Ser Arg Lys Thr Gln Val Met Leu Asp
    130                 135                 140

Ser Ile Ser Glu Leu Gln Arg Lys Glu Lys Ser Leu Glu Glu Gln Asn
145                 150                 155                 160

Lys Asn Leu Glu Lys Glu Ile Leu Glu Lys Gln Lys Ile Lys Ala Leu
                165                 170                 175

Ala Gln Gln Ala His Trp Glu His Gln Asn Gln Pro Ala Pro Arg Gly
            180                 185                 190

Ser Pro Pro Arg Pro Phe Val Ile Ala Glu Ser His Pro Thr Leu Asn
        195                 200                 205

Ile Gly His Phe Gln Gly Arg Thr Asn Ala Val Glu Ala Glu Glu Asn
    210                 215                 220

Gln Gln Pro Xaa Met Arg Ile Cys Ser Ser Leu Leu Pro Pro Trp Met
225                 230                 235                 240

Leu
```

```
<210> SEQ ID NO 100
<211> LENGTH: 599
<212> TYPE: DNA
<213> ORGANISM: Tradescantia virginiana

<400> SEQUENCE: 100
gggctkgtga agaaagctca tgagatctcg gtactttgtg atgctgagct tgctcttatt     60
atcttctctc ccaaaggcaa gctctatgag tatgccaccg attccaaaat ggaaattatt    120
```

```
cttgaacgct atgaacgtta cacctacgct gaaaaagctt taattgcatc agatcctgat      180 gtacaggaa actggtgtca tgagtacatt aagcttaaag ctaaatttga ggccttgaat       240
aaaagccaga ggcatcttat gggagaacaa ctagatacgt tgaaccaaaa ggaattgctg     300
caactagaga ctaagcttga aggttctctg aaaaacgtca ggtcaagaaa gactcaactt    360
atgttggatt ccatttctga gcttcaagaa aagggaaagt cactccagga gcaaaacacc    420
tgcctagaaa aggagatttt gggaaaacag aaagacaagg ctcccaaaca gcatgttcag    480
tgggaaaaac agaatcaacc accacctacc tcttctgcgc caatgccatt cctcattggt    540
gatattcacc caaccctaa tatcagaaat ttccaaggca aacagtagc tgatgcaga       599
```

<210> SEQ ID NO 101
<211> LENGTH: 199
<212> TYPE: PRT
<213> ORGANISM: Tradescantia virginiana

<400> SEQUENCE: 101

Gly Leu Val Lys Lys Ala His Glu Ile Ser Val Leu Cys Asp Ala Glu
1               5                   10                  15

Leu Ala Leu Ile Ile Phe Ser Pro Lys Gly Lys Leu Tyr Glu Tyr Ala
            20                  25                  30

Thr Asp Ser Lys Met Glu Ile Ile Leu Glu Arg Tyr Glu Arg Tyr Thr
        35                  40                  45

Tyr Ala Glu Lys Ala Leu Ile Ala Ser Asp Pro Asp Val Gln Gly Asn
    50                  55                  60

Trp Cys His Glu Tyr Ile Lys Leu Lys Ala Lys Phe Glu Ala Leu Asn
65                  70                  75                  80

Lys Ser Gln Arg His Leu Met Gly Glu Gln Leu Asp Thr Leu Asn Gln
                85                  90                  95

Lys Glu Leu Leu Gln Leu Glu Thr Lys Leu Glu Gly Ser Leu Lys Asn
            100                 105                 110

Val Arg Ser Arg Lys Thr Gln Leu Met Leu Asp Ser Ile Ser Glu Leu
        115                 120                 125

Gln Glu Lys Gly Lys Ser Leu Gln Glu Gln Asn Thr Cys Leu Glu Lys
    130                 135                 140

Glu Ile Leu Gly Lys Gln Lys Asp Lys Ala Pro Lys Gln His Val Gln
145                 150                 155                 160

Trp Glu Lys Gln Asn Gln Pro Pro Pro Thr Ser Ser Ala Pro Met Pro
                165                 170                 175

Phe Leu Ile Gly Asp Ile His Pro Thr Pro Asn Ile Arg Asn Phe Gln
            180                 185                 190

Gly Arg Thr Val Ala Asp Ala
        195

<210> SEQ ID NO 102
<211> LENGTH: 753
<212> TYPE: DNA
<213> ORGANISM: Elaeis guineensis

<400> SEQUENCE: 102

```
atgggagag ggagggtgca gctgaggcgg atcgagaaca agataaaccg gcaggtgacg      60
ttctcgaagc gccggtcggg gctcctgaag aaagcccacg agatctccgt cctctgcgac    120
gccgaggtcg ccctcatcat cttctcgacc aagggcaagc tctacgagta cgccaccgac   180
tcctgcatga aaggattct tgaacgctat gaacgttaca cctatgcaga aaagcactga    240
atttcatctg gacccgaatt gcagggtaac tggtgccatg aatttggcaa actcaaagct    300
```

```
aaggttgagg ctttacaaaa aagccaaagg catctcatgg gtgagcaact tgagcccttg    360
aatctcaaag aactccagca actagagcaa cagcttgaaa gttctttaaa gcatataaga    420
accagaaagt gccaactcat gtttgaatcc atctctgagc ttcaaaaaaa ggaaaagtca    480
ctgcaggagc agaacaagat gctggagaag gagctcatgg agaagcagaa ggtgaaggca    540
ctaaaccagc aggcaccttg ggagcagcaa ggcccgccgc agacaagctc atcatcccca    600
acctccttcc tgatcggaga ctctctcccc accctgaata ttgggacata ccaatgtagc    660
ggaaatgaac atggggagga agcagcacaa ccccaggttc gtataggaaa cagcctgtta    720
ccaccttgga tgcttagcca cttgaacggg tag                                 753
```

<210> SEQ ID NO 103
<211> LENGTH: 250
<212> TYPE: PRT
<213> ORGANISM: Elaeis guineensis

<400> SEQUENCE: 103

```
Met Gly Arg Gly Arg Val Gln Leu Arg Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Ile Phe
        35                  40                  45

Ser Thr Lys Gly Lys Leu Tyr Glu Tyr Ala Thr Asp Ser Cys Met Glu
    50                  55                  60

Arg Ile Leu Glu Arg Tyr Glu Arg Tyr Thr Tyr Ala Glu Lys Ala Leu
65                  70                  75                  80

Ile Ser Ser Gly Pro Glu Leu Gln Gly Asn Trp Cys His Glu Phe Gly
                85                  90                  95

Lys Leu Lys Ala Lys Val Glu Ala Leu Gln Lys Ser Gln Arg His Leu
            100                 105                 110

Met Gly Glu Gln Leu Glu Pro Leu Asn Leu Lys Glu Leu Gln Gln Leu
        115                 120                 125

Glu Gln Gln Leu Glu Ser Ser Leu Lys His Ile Arg Thr Arg Lys Cys
    130                 135                 140

Gln Leu Met Phe Glu Ser Ile Ser Glu Leu Gln Lys Lys Glu Lys Ser
145                 150                 155                 160

Leu Gln Glu Gln Asn Lys Met Leu Glu Lys Glu Leu Met Glu Lys Gln
                165                 170                 175

Lys Val Lys Ala Leu Asn Gln Gln Ala Pro Trp Glu Gln Gln Gly Pro
            180                 185                 190

Pro Gln Thr Ser Ser Ser Pro Thr Ser Phe Leu Ile Gly Asp Ser
        195                 200                 205

Leu Pro Thr Leu Asn Ile Gly Thr Tyr Gln Cys Ser Gly Asn Glu His
    210                 215                 220

Gly Glu Glu Ala Ala Gln Pro Gln Val Arg Ile Gly Asn Ser Leu Leu
225                 230                 235                 240

Pro Pro Trp Met Leu Ser His Leu Asn Gly
                245                 250
```

<210> SEQ ID NO 104
<211> LENGTH: 699
<212> TYPE: DNA
<213> ORGANISM: Allium sp.

<400> SEQUENCE: 104

```
gtgcaattga agaggatgga aaacaagatt aatagacaag tgaccttctc aaaaagaaga      60
aatggtttgt tgaagaaagc tcatgagatt tcwgtgcttt gtgatgcaga agttgcactt     120
attgttttct ctgctaaagg aaaactctat gaatattcaa ctgattcaag tatggaaaaa     180
attctggaga ggtatgaacg ttattgcttt gcggagaaat catcaacaat gagtgacatt     240
gactcccagg aggattggag ccttgaatat cacaaactga aggctaaggt tgagagttta     300
aacaacaggc aaaggcatct tatgggagag caacttgaat ctctgagtct tcgagaaatt     360
ggacagcttg agcaacaact tgagaattct ctcaaaactg ttcggacgcg caagagccaa     420
gaattgttaa gttctatttc agagcttcag gacaaggaga aaactttgcg agatgagaac     480
aaagctttag aaaatgagct tatgaaaagg gccagggcaa aagctattct ggaacaacaa     540
gcacgatgga agcatcataa tcataaacaa caggataatc ttcataatcc aaatatcaac     600
attggaaatt accaaacaag gaacaatgag ggaggagttg agccagcaac ggatgttcaa     660
gtacgtgttg ttagaaattt gttgccccac tggatgctt                          699
```

<210> SEQ ID NO 105
<211> LENGTH: 233
<212> TYPE: PRT
<213> ORGANISM: Allium sp.

<400> SEQUENCE: 105

```
Val Gln Leu Lys Arg Met Glu Asn Lys Ile Asn Arg Gln Val Thr Phe
1               5                   10                  15

Ser Lys Arg Arg Asn Gly Leu Leu Lys Lys Ala His Glu Ile Ser Val
            20                  25                  30

Leu Cys Asp Ala Glu Val Ala Leu Ile Val Phe Ser Ala Lys Gly Lys
        35                  40                  45

Leu Tyr Glu Tyr Ser Thr Asp Ser Ser Met Glu Lys Ile Leu Glu Arg
    50                  55                  60

Tyr Glu Arg Tyr Cys Phe Ala Glu Lys Ser Ser Thr Met Ser Asp Ile
65                  70                  75                  80

Asp Ser Gln Glu Asp Trp Ser Leu Glu Tyr His Lys Leu Lys Ala Lys
                85                  90                  95

Val Glu Ser Leu Asn Asn Arg Gln Arg His Leu Met Gly Glu Gln Leu
            100                 105                 110

Glu Ser Leu Ser Leu Arg Glu Ile Gly Gln Leu Glu Gln Gln Leu Glu
        115                 120                 125

Asn Ser Leu Lys Thr Val Arg Thr Arg Lys Ser Gln Glu Leu Leu Ser
    130                 135                 140

Ser Ile Ser Glu Leu Gln Asp Lys Glu Lys Thr Leu Arg Asp Glu Asn
145                 150                 155                 160

Lys Ala Leu Glu Asn Glu Leu Met Lys Arg Ala Arg Ala Lys Ala Ile
                165                 170                 175

Leu Glu Gln Gln Ala Arg Trp Lys His His Asn His Lys Gln Gln Asp
            180                 185                 190

Asn Leu His Asn Pro Asn Ile Asn Ile Gly Asn Tyr Gln Thr Arg Asn
        195                 200                 205

Asn Glu Gly Gly Val Glu Pro Ala Thr Asp Val Gln Val Arg Val Val
    210                 215                 220

Arg Asn Leu Leu Pro His Trp Met Leu
225                 230
```

<210> SEQ ID NO 106

```
<211> LENGTH: 744
<212> TYPE: DNA
<213> ORGANISM: Dendrobium grex Madame Thong-IN

<400> SEQUENCE: 106
atgggtcgtg cagggtgca gctgaagcga atcgagaata aaataaaccg gcaggtgacg      60
ttctcgaagc ggagatctgg tttgcttaag aaggcgcacg agatctccgt gctctgtgac    120
gctgaagttg ctctgatcgt ttttccaat aagggaaagc tttatgagta ttccaccgat     180
tccagcatgg agaaaattct tgaacggtat gagcgttatt catatgctga agagcatta    240 ttttccaatg aggccaaccc ccaggctgat tggcgccttg aatataataa actgaaggca    300
agggttgaaa gcttacagaa gagccaaagg caccttatgg gggagcaact tgactccttg    360
agcattaaag aactccaacg tctagagcaa cagcttgaaa gttccttgaa gtttatacga    420
tccagaaaga cacagctcat actacattca atttccgagc tacaaaagat ggaaaaaata    480
ttgctggagc aaaacaagac cttagagaag gagattatag ctaaagagaa agccaaagct    540
ttggtgcagc atgccccatg ggagaagcaa aaccagtccc aatatagctc tgcactcccg    600
cctgtgattt cggattctgt cccaactccc accagcagaa cgtttcaagc cagagccaat    660
gaagaagaat caccctcagcc acagttaaga gtaagcaaca ctctgctgcc cccatggatg    720
ctcagtcata tgaatggaca ataa                                          744
```

```
<210> SEQ ID NO 107
<211> LENGTH: 247
<212> TYPE: PRT
<213> ORGANISM: Dendrobium grex Madame Thong-IN

<400> SEQUENCE: 107

Met Gly Arg Gly Arg Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Val Phe
        35                  40                  45

Ser Asn Lys Gly Lys Leu Tyr Glu Tyr Ser Thr Asp Ser Ser Met Glu
    50                  55                  60

Lys Ile Leu Glu Arg Tyr Glu Arg Tyr Ser Tyr Ala Glu Arg Ala Leu
65                  70                  75                  80

Phe Ser Asn Glu Ala Asn Pro Gln Ala Asp Trp Arg Leu Glu Tyr Asn
                85                  90                  95

Lys Leu Lys Ala Arg Val Glu Ser Leu Gln Lys Ser Gln Arg His Leu
            100                 105                 110

Met Gly Glu Gln Leu Asp Ser Leu Ser Ile Lys Glu Leu Gln Arg Leu
        115                 120                 125

Glu Gln Gln Leu Glu Ser Ser Leu Lys Phe Ile Arg Ser Arg Lys Thr
    130                 135                 140

Gln Leu Ile Leu His Ser Ile Ser Glu Leu Gln Lys Met Glu Lys Ile
145                 150                 155                 160

Leu Leu Glu Gln Asn Lys Thr Leu Glu Lys Glu Ile Ile Ala Lys Glu
                165                 170                 175

Lys Ala Lys Ala Leu Val Gln His Ala Pro Trp Glu Lys Gln Asn Gln
            180                 185                 190

Ser Gln Tyr Ser Ser Ala Leu Pro Pro Val Ile Ser Asp Ser Val Pro
        195                 200                 205

Thr Pro Thr Ser Arg Thr Phe Gln Ala Arg Ala Asn Glu Glu Glu Ser
```

```
                  210                 215                 220
Pro Gln Pro Gln Leu Arg Val Ser Asn Thr Leu Leu Pro Pro Trp Met
225                 230                 235                 240

Leu Ser His Met Asn Gly Gln
            245

<210> SEQ ID NO 108
<211> LENGTH: 2194
<212> TYPE: DNA
<213> ORGANISM: Oryza sativa

<400> SEQUENCE: 108
aatccgaaaa gtttctgcac cgttttcacc ccctaactaa caatataggg aacgtgtgct      60
aaatataaaa tgagaccttta tatatgtagc gctgataact agaactatgc aagaaaaact    120
catccaccta ctttagtggc aatcgggcta ataaaaaag agtcgctaca ctagtttcgt     180
tttccttagt aattaagtgg gaaaatgaaa tcattattgc ttagaatata cgttcacatc     240
tctgtcatga agttaaatta ttcgaggtag ccataattgt catcaaactc ttcttgaata     300
aaaaaatctt tctagctgaa ctcaatgggt aaagagagag atttttttta aaaaaataga     360
atgaagatat tctgaacgta ttggcaaaga tttaaacata taattatata attttatagt     420
ttgtgcattc gtcatatcgc acatcattaa ggacatgtct tactccatcc caattttat      480 ttagtaatta aagacaattg acttattttt attatttatc ttttttcgat tagatgcaag     540
gtacttacgc acacactttg tgctcatgtg catgtgtgag tgcacctcct caatacacgt     600
tcaactagca acacatctct aatatcactc gcctatttaa tacatttagg tagcaatatc     660
tgaattcaag cactccacca tcaccagacc acttttaata atatctaaaa tacaaaaaat     720
aattttacag aatagcatga aaagtatgaa acgaactatt taggttttc acatacaaaa     780 aaaaaaagaa ttttgctcgt gcgcgagcgc caatctccca tattgggcac acaggcaaca     840
acagagtggc tgcccacaga acaacccaca aaaaacgatg atctaacgga ggacagcaag     900
tccgcaacaa cctttttaaca gcaggctttg cggccaggag agaggaggag aggcaaagaa    960
aaccaagcat cctccttctc ccatctataa attcctcccc ccttttcccc tctctatata   1020
ggaggcatcc aagccaagaa gagggagagc accaaggaca cgcgactagc agaagccgag   1080
cgaccgcctt ctcgatccat atcttccggt cgagttcttg gtcgatctct tccctcctcc   1140
acctcctcct cacagggtat gtgcctccct tcggttgttc ttggatttat tgttctaggt   1200
tgtgtagtac gggcgttgat gttaggaaag gggatctgta tctgtgatga ttcctgttct   1260
tggatttggg atagaggggt tcttgatgtt gcatgttatc ggttcggttt gattagtagt   1320
atggttttca atcgtctgga gagctctatg gaaatgaaat ggtttaggga tcggaatctt   1380
gcgattttgt gagtaccttt tgtttgaggt aaaatcagag caccggtgat tttgcttggt   1440
gtaataaagt acggttgttt ggtcctcgat tctggtagtg atgcttctcg atttgacgaa   1500
gctatccttt gtttattccc tattgaacaa aaataatcca actttgaaga cggtcccgtt   1560
gatgagattg aatgattgat tcttaagcct gtccaaaatt tcgcagctgg cttgtttaga   1620
tacagtagtc cccatcacga aattcatgga aacagttata atcctcagga acagggatt    1680 ccctgttctt ccgatttgct ttagtcccag aattttttt cccaaatatc ttaaaaagtc   1740
actttctggt tcagttcaat gaattgattg ctacaaataa tgcttttata gcgttatcct   1800
agctgtagtt cagttaatag gtaataccccc tatagtttag tcaggagaag aacttatccg   1860
atttctgatc tccatttttta attatatgaa atgaactgta gcataagcag tattcatttg   1920
```

```
gattattttt ttattagct ctcacccctt cattattctg agctgaaagt ctggcatgaa    1980
ctgtcctcaa ttttgttttc aaattcacat cgattatcta tgcattatcc tcttgtatct    2040
acctgtagaa gtttcttttt ggttattcct tgactgcttg attacagaaa gaaatttatg    2100
aagctgtaat cgggatagtt atactgcttg ttcttatgat tcatttcctt tgtgcagttc    2160
ttggtgtagc ttgccacttt caccagcaaa gttc                                 2194
```

<210> SEQ ID NO 109
<211> LENGTH: 804
<212> TYPE: DNA
<213> ORGANISM: Oryza sativa

<400> SEQUENCE: 109

```
atggggcggg ggaaggtgca gctgaagcgg atagagaaca agatcaacag gcaggtgacg      60
ttctccaaga ggaggaatgg attgctgaag aaggcgcacg agatctccgt cctctgcgac     120
gccgaggtcg ccgccatcgt cttctccccc aagggcaagc tctacgagta cgccactgac     180
tccaggatgg acaaaatcct tgaacgttat gagcgctatt catatgctga aaaggctctt     240
atttcagctg aatccgagag tgagggaaat tggtgccatg aatacaggaa acttaaggca     300
aagattgaga ccatacaaaa atgtcacaaa cacctcatgg gagaggatct agaatccctg     360
aatctcaaag aactccaaca gctagagcag cagctggaga gttcattgaa gcacataata     420
tcaagaaaga gccaccttat gcttgagtcc atttccgagc tgcagaaaaa ggagaggtca     480
ctgcaggagg agaacaaggc tctgcagaag gaactggtgg agaggcagaa gaatgtgagg     540
ggccagcagc aagtagggca gtgggaccaa acccaggtcc aggcccaggc ccaagcccaa     600
ccccaagccc agacaagctc ctcctcctcc tccatgctga gggatcagca ggcacttctt     660
ccaccacaaa atatctgcta cccgccggtg atgatgggcg agagaaatga tgcggcggcg     720
gcggcggcgg tggcggcgca gggccaggtg caactccgca tcggaggtct tccgccatgg     780
atgctgagcc acctcaatgc ttaa                                             804
```

<210> SEQ ID NO 110
<211> LENGTH: 267
<212> TYPE: PRT
<213> ORGANISM: Oryza sativa

<400> SEQUENCE: 110

Met Gly Arg Gly Lys Val Gln Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Ala Ile Val Phe
        35                  40                  45

Ser Pro Lys Gly Lys Leu Tyr Glu Tyr Ala Thr Asp Ser Arg Met Asp
    50                  55                  60

Lys Ile Leu Glu Arg Tyr Glu Arg Tyr Ser Tyr Ala Glu Lys Ala Leu
65                  70                  75                  80

Ile Ser Ala Glu Ser Glu Ser Glu Gly Asn Trp Cys His Glu Tyr Arg
                85                  90                  95

Lys Leu Lys Ala Lys Ile Glu Thr Ile Gln Lys Cys His Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Ile Ser Arg Lys Ser
    130                 135                 140

```
His Leu Met Leu Glu Ser Ile Ser Glu Leu Gln Lys Lys Glu Arg Ser
145                 150                 155                 160

Leu Gln Glu Glu Asn Lys Ala Leu Gln Lys Glu Leu Val Arg Gln
            165                 170                 175

Lys Asn Val Arg Gly Gln Gln Val Gly Gln Trp Asp Gln Thr Gln
        180                 185                 190

Val Gln Ala Gln Ala Gln Ala Gln Pro Gln Ala Gln Thr Ser Ser Ser
    195                 200                 205

Ser Ser Ser Met Leu Arg Asp Gln Gln Ala Leu Leu Pro Pro Gln Asn
    210                 215                 220

Ile Cys Tyr Pro Pro Val Met Met Gly Glu Arg Asn Asp Ala Ala Ala
225                 230                 235                 240

Ala Ala Ala Val Ala Ala Gln Gly Gln Val Gln Leu Arg Ile Gly Gly
            245                 250                 255

Leu Pro Pro Trp Met Leu Ser His Leu Asn Ala
        260                 265
```

<210> SEQ ID NO 111
<211> LENGTH: 52
<212> TYPE: DNA
<213> ORGANISM: Artificial sequence
<220> FEATURE:
<223> OTHER INFORMATION: primer

<400> SEQUENCE: 111

```
ggggacaagt ttgtacaaaa aagcaggctt aaacaatggg gcggggaag gt        52
```

<210> SEQ ID NO 112
<211> LENGTH: 47
<212> TYPE: DNA
<213> ORGANISM: Artificial sequence
<220> FEATURE:
<223> OTHER INFORMATION: primer

<400> SEQUENCE: 112

```
ggggaccact ttgtacaaga aagctgggtt tggccgacga cgacgac              47
```

<210> SEQ ID NO 113
<211> LENGTH: 2193
<212> TYPE: DNA
<213> ORGANISM: Oryza sativa

<400> SEQUENCE: 113

```
aatccgaaaa gtttctgcac cgttttcacc ccctaactaa caatataggg aacgtgtgct    60
aaatataaaa tgagacctta tatatgtagc gctgataact agaactatgc aagaaaaact   120
catccaccta ctttagtggc aatcgggcta ataaaaaag agtcgctaca ctagtttcgt    180
tttccttagt aattaagtgg gaaaatgaaa tcattattgc ttagaatata cgttcacatc   240
tctgtcatga agttaaatta ttcgaggtag ccataattgt catcaaactc ttcttgaata   300
aaaaaatctt tctagctgaa ctcaatgggt aaagagagag atttttttta aaaaaataga   360
atgaagatat tctgaacgta ttggcaaaga tttaaacata taattatata attttatagt   420
ttgtgcattc gtcatatcgc acatcattaa ggacatgtct tactccatcc caatttttat   480
ttagtaatta aagacaattg acttattttt attatttatc tttttcgat tagatgcaag    540 gtacttacgc acacactttg tgctcatgtg catgtgtgag tgcacctcct caatacacgt   600
tcaactagca acacatctct aatatcactc gcctatttaa tacatttagg tagcaatatc   660
tgaattcaag cactccacca tcaccagacc acttttaata atatctaaaa tacaaaaaat   720
```

```
aattttacag aatagcatga aaagtatgaa acgaactatt taggttttc acatacaaaa       780 aaaaaaagaa ttttgctcgt gcgcgagcgc caatctccca tattgggcac acaggcaaca      840
acagagtggc tgcccacaga acaacccaca aaaaacgatg atctaacgga ggacagcaag      900
tccgcaacaa ccttttaaca gcaggctttg cggccaggag agaggaggag aggcaaagaa      960
aaccaagcat cctcctcctc ccatctataa attcctcccc ccttttcccc tctctatata     1020
ggaggcatcc aagccaagaa gagggagagc accaaggaca cgcgactagc agaagccgag     1080
cgaccgcctt cttcgatcca tatcttccgg tcgagttctt ggtcgatctc ttccctcctc     1140
cacctcctcc tcacagggta tgtgcccttc ggttgttctt ggatttattg ttctaggttg     1200
tgtagtacgg gcgttgatgt taggaaaggg gatctgtatc tgtgatgatt cctgttcttg     1260
gatttgggat agaggggttc ttgatgttgc atgttatcgg ttcggtttga ttagtagtat     1320
ggttttcaat cgtctggaga gctctatgga aatgaaatgg tttagggtac ggaatcttgc     1380
gattttgtga gtaccttttg tttgaggtaa atcagagca ccggtgattt tgcttggtgt      1440
aataaaagta cggttgtttg gtcctcgatt ctggtagtga tgcttctcga tttgacgaag     1500
ctatcctttg tttattccct attgaacaaa aataatccaa ctttgaagac ggtcccgttg     1560
atgagattga atgattgatt cttaagcctg tccaaaattt cgcagctggc ttgtttagat     1620
acagtagtcc ccatcacgaa attcatggaa acagttataa tcctcaggaa caggggattc     1680
cctgttcttc cgatttgctt tagtcccaga attttttttc ccaaatatct taaaaagtca     1740
ctttctggtt cagttcaatg aattgattgc tacaaataat gcttttatag cgttatccta     1800
gctgtagttc agttaatagg taatacccct atagtttagt caggagaaga acttatccga     1860
tttctgatct ccattttaa ttatatgaaa tgaactgtag cataagcagt attcatttgg      1920
attatttttt ttattagctc tcacccttc attattctga gctgaaagtc tggcatgaac      1980
tgtcctcaat tttgttttca aattcacatc gattatctat gcattatcct cttgtatcta     2040
cctgtagaag tttcttttg gttattcctt gactgcttga ttacagaaag aaatttatga      2100
agctgtaatc gggatagtta tactgcttgt tcttatgatt catttccttt gtgcagttct     2160
tggtgtagct tgccactttc accagcaaag ttc                                  2193
```

<210> SEQ ID NO 114
<211> LENGTH: 42
<212> TYPE: PRT
<213> ORGANISM: Artificial sequence
<220> FEATURE:
<223> OTHER INFORMATION: motif
<220> FEATURE:
<221> NAME/KEY: VARIANT
<222> LOCATION: (2)..(2)
<223> OTHER INFORMATION: Xaa is Leu or Val
<220> FEATURE:
<221> NAME/KEY: VARIANT
<222> LOCATION: (6)..(6)
<223> OTHER INFORMATION: Xaa is His or Asn
<220> FEATURE:
<221> NAME/KEY: VARIANT
<222> LOCATION: (10)..(10)
<223> OTHER INFORMATION: Xaa is Val or Ile
<220> FEATURE:
<221> NAME/KEY: VARIANT
<222> LOCATION: (12)..(12)
<223> OTHER INFORMATION: Xaa is Cys or Tyr
<220> FEATURE:
<221> NAME/KEY: VARIANT
<222> LOCATION: (16)..(16)
<223> OTHER INFORMATION: Xaa is Val, Ile, or Leu
<220> FEATURE:
<221> NAME/KEY: VARIANT

```
<222> LOCATION: (17)..(17)
<223> OTHER INFORMATION: Xaa is Ala or Gly
<220> FEATURE:
<221> NAME/KEY: VARIANT
<222> LOCATION: (18)..(18)
<223> OTHER INFORMATION: Xaa is Leu, Ala, or Val
<220> FEATURE:
<221> NAME/KEY: VARIANT
<222> LOCATION: (19)..(19)
<223> OTHER INFORMATION: Xaa is Ile or Val
<220> FEATURE:
<221> NAME/KEY: VARIANT
<222> LOCATION: (20)..(20)
<223> OTHER INFORMATION: Xaa is Ile or Val
<220> FEATURE:
<221> NAME/KEY: VARIANT
<222> LOCATION: (23)..(23)
<223> OTHER INFORMATION: Xaa is Thr, Pro, Ala, or Asn
<220> FEATURE:
<221> NAME/KEY: VARIANT
<222> LOCATION: (30)..(30)
<223> OTHER INFORMATION: Xaa is Tyr or Phe
<220> FEATURE:
<221> NAME/KEY: VARIANT
<222> LOCATION: (31)..(31)
<223> OTHER INFORMATION: Xaa is Ala or Ser
<220> FEATURE:
<221> NAME/KEY: VARIANT
<222> LOCATION: (32)..(32)
<223> OTHER INFORMATION: Xaa is Thr or Ser
<220> FEATURE:
<221> NAME/KEY: VARIANT
<222> LOCATION: (33)..(33)
<223> OTHER INFORMATION: Xaa is Asp, Asn, or Glu
<220> FEATURE:
<221> NAME/KEY: VARIANT
<222> LOCATION: (35)..(35)
<223> OTHER INFORMATION: Xaa is Lys, Cys, Arg, or Ser
<220> FEATURE:
<221> NAME/KEY: VARIANT
<222> LOCATION: (37)..(37)
<223> OTHER INFORMATION: Xaa is Asp or Glu
<220> FEATURE:
<221> NAME/KEY: VARIANT
<222> LOCATION: (38)..(38)
<223> OTHER INFORMATION: Xaa is Asn, Ile, Arg, or Lys
<220> FEATURE:
<221> NAME/KEY: VARIANT
<222> LOCATION: (41)..(41)
<223> OTHER INFORMATION: Xaa is Glu or Asp

<400> SEQUENCE: 114

Leu Xaa Lys Lys Ala Xaa Glu Ile Ser Xaa Leu Xaa Asp Ala Glu Xaa
1               5                   10                  15

Xaa Xaa Xaa Xaa Phe Ser Xaa Lys Gly Lys Leu Tyr Glu Xaa Xaa Xaa
            20                  25                  30

Xaa Ser Xaa Met Xaa Xaa Ile Leu Xaa Arg
        35                  40

<210> SEQ ID NO 115
<211> LENGTH: 19
<212> TYPE: PRT
<213> ORGANISM: Artificial sequence
<220> FEATURE:
<223> OTHER INFORMATION: motif
<220> FEATURE:
<221> NAME/KEY: VARIANT
<222> LOCATION: (4)..(4)
<223> OTHER INFORMATION: Xaa is Ala or Ser
<220> FEATURE:
<221> NAME/KEY: VARIANT
<222> LOCATION: (5)..(5)
<223> OTHER INFORMATION: Xaa is Lys or Arg
<220> FEATURE:
<221> NAME/KEY: VARIANT
<222> LOCATION: (6)..(6)
```

```
<223> OTHER INFORMATION: Xaa is Val or Ile
<220> FEATURE:
<221> NAME/KEY: VARIANT
<222> LOCATION: (8)..(8)
<223> OTHER INFORMATION: Xaa is Ala, Thr, or Ser
<220> FEATURE:
<221> NAME/KEY: VARIANT
<222> LOCATION: (9)..(9)
<223> OTHER INFORMATION: Xaa is Leu or Ile
<220> FEATURE:
<221> NAME/KEY: VARIANT
<222> LOCATION: (10)..(10)
<223> OTHER INFORMATION: Xaa is Gln or Asn
<220> FEATURE:
<221> NAME/KEY: VARIANT
<222> LOCATION: (11)..(11)
<223> OTHER INFORMATION: Xaa is Lys, Arg, or Asn
<220> FEATURE:
<221> NAME/KEY: VARIANT
<222> LOCATION: (12)..(12)
<223> OTHER INFORMATION: Xaa is Ser, Cys, or Arg
<220> FEATURE:
<221> NAME/KEY: VARIANT
<222> LOCATION: (13)..(13)
<223> OTHER INFORMATION: Xaa is Gln or His
<220> FEATURE:
<221> NAME/KEY: VARIANT
<222> LOCATION: (14)..(14)
<223> OTHER INFORMATION: Xaa is Arg or Lys

<400> SEQUENCE: 115

Lys Leu Lys Xaa Xaa Xaa Glu Xaa Xaa Xaa Xaa Xaa Xaa Xaa His Leu
1               5                   10                  15

Met Gly Glu

<210> SEQ ID NO 116
<211> LENGTH: 11
<212> TYPE: PRT
<213> ORGANISM: Artificial sequence
<220> FEATURE:
<223> OTHER INFORMATION: motif
<220> FEATURE:
<221> NAME/KEY: VARIANT
<222> LOCATION: (2)..(2)
<223> OTHER INFORMATION: Xaa is Pro, Gln, Val, or Ala
<220> FEATURE:
<221> NAME/KEY: VARIANT
<222> LOCATION: (6)..(6)
<223> OTHER INFORMATION: Xaa is Ser or Phe
<220> FEATURE:
<221> NAME/KEY: VARIANT
<222> LOCATION: (7)..(7)
<223> OTHER INFORMATION: Xaa is Ser or Phe
<220> FEATURE:
<221> NAME/KEY: VARIANT
<222> LOCATION: (8)..(8)
<223> OTHER INFORMATION: Xaa is Ser or Phe
<220> FEATURE:
<221> NAME/KEY: VARIANT
<222> LOCATION: (9)..(9)
<223> OTHER INFORMATION: Xaa is Ser or Phe
<220> FEATURE:
<221> NAME/KEY: VARIANT
<222> LOCATION: (10)..(10)
<223> OTHER INFORMATION: Xaa is Ser, Cys, or Phe
<220> FEATURE:
<221> NAME/KEY: VARIANT
<222> LOCATION: (11)..(11)
<223> OTHER INFORMATION: Xaa is Phe or Met

<400> SEQUENCE: 116

Gln Xaa Gln Thr Ser Xaa Xaa Xaa Xaa Xaa Xaa
1               5                   10

<210> SEQ ID NO 117
```

```
<211> LENGTH: 7
<212> TYPE: PRT
<213> ORGANISM: Artificial sequence
<220> FEATURE:
<223> OTHER INFORMATION: motif
<220> FEATURE:
<221> NAME/KEY: VARIANT
<222> LOCATION: (1)..(1)
<223> OTHER INFORMATION: Xaa is Gly, Ala, Val, or Leu
<220> FEATURE:
<221> NAME/KEY: VARIANT
<222> LOCATION: (2)..(2)
<223> OTHER INFORMATION: Xaa is Leu or Pro
<220> FEATURE:
<221> NAME/KEY: UNSURE
<222> LOCATION: (3)..(3)
<223> OTHER INFORMATION: Xaa can be any amino acid, preferably Leu, Phe
      or His
<220> FEATURE:
<221> NAME/KEY: UNSURE
<222> LOCATION: (6)..(6)
<223> OTHER INFORMATION: Xaa can be any naturally occuring amino acid,
      preferably Val or Leu
<220> FEATURE:
<221> NAME/KEY: VARIANT
<222> LOCATION: (7)..(7)
<223> OTHER INFORMATION: Xaa is Ser or His

<400> SEQUENCE: 117

Xaa Xaa Xaa Trp Met Xaa Xaa
1               5

<210> SEQ ID NO 118
<211> LENGTH: 735
<212> TYPE: DNA
<213> ORGANISM: Hordeum vulgare

<400> SEQUENCE: 118
atggggcgcg ggaaggtgca gctgaagcgg atcgagaaca agatcaaccg ccaggtcacc      60
ttctccaagc gccgctcggg gctgctcaag aaggcgcacg agatctccgt gctctgcgac     120
gccgaggtcg gcctcatcat cttctccacc aagggaaagc tctacgagtt ctccaccgag     180
tcatgtatgg acaaaattct gaacggtat gagcgctact cttatgcaga aaaggttctc      240
gtttcaagtg aatctgaaat tcagggaaac tggtgtcacg aatataggaa actgaaggcg     300
aaggttgaga caatacagaa atgtcaaaag catctcatgg gagaggatct tgaatctttg     360
aatctcaagg agttgcagca actggagcag cagctggaaa gctcactgaa acatatcaga     420
gccaggaaga accaacttat gcacgaatcc atttctgagc ttcagaagaa ggagaggtca     480
ctgcaggagg agaataaagt tctccagaag gaacttgtgg agaagcagaa ggcccaggcg     540
gcgcagcaag atcaaactca gcctcaaacc agctcttctt cttcttcctt catgatgagg     600
gatgctcccc ctgtcgcaga taccagcaat cacccagcgg cggcaggcga gagggcagag     660
gatgtggcag tgcagcctca ggtcccactc cggacggcgc ttccactgtg gatggtgagc     720
cacatcaacg gctga                                                     735

<210> SEQ ID NO 119
<211> LENGTH: 244
<212> TYPE: PRT
<213> ORGANISM: Hordeum vulgare

<400> SEQUENCE: 119

Met Gly Arg Gly Lys Val Gln Leu Lys Arg Ile Glu Asn Lys Ile Asn
1               5                   10                  15

Arg Gln Val Thr Phe Ser Lys Arg Ser Gly Leu Leu Lys Lys Ala
            20                  25                  30
```

```
His Glu Ile Ser Val Leu Cys Asp Ala Glu Val Gly Leu Ile Ile Phe
        35                  40                  45

Ser Thr Lys Gly Lys Leu Tyr Glu Phe Ser Thr Glu Ser Cys Met Asp
 50                  55                  60

Lys Ile Leu Glu Arg Tyr Glu Arg Tyr Ser Tyr Ala Glu Lys Val Leu
 65                  70                  75                  80

Val Ser Ser Glu Ser Glu Ile Gln Gly Asn Trp Cys His Glu Tyr Arg
                 85                  90                  95

Lys Leu Lys Ala Lys Val Glu Thr Ile Gln Lys Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Arg Ala Arg Lys Asn
    130                 135                 140

Gln Leu Met His Glu Ser Ile Ser Glu Leu Gln Lys Lys Glu Arg Ser
145                 150                 155                 160

Leu Gln Glu Glu Asn Lys Val Leu Gln Lys Glu Leu Val Glu Lys Gln
                165                 170                 175

Lys Ala Gln Ala Ala Gln Asp Gln Thr Gln Pro Gln Thr Ser Ser
            180                 185                 190

Ser Ser Ser Phe Met Met Arg Asp Ala Pro Val Ala Asp Thr
        195                 200                 205

Ser Asn His Pro Ala Ala Gly Glu Arg Ala Glu Asp Val Ala Val
    210                 215                 220

Gln Pro Gln Val Pro Leu Arg Thr Ala Leu Pro Leu Trp Met Val Ser
225                 230                 235                 240

His Ile Asn Gly

<210> SEQ ID NO 120
<211> LENGTH: 1196
<212> TYPE: DNA
<213> ORGANISM: Hordeum vulgare

<400> SEQUENCE: 120
ctctcccctc ccacttcacc caaccacctg acagccatgg ctccgccacc tcgcctccgc    60
ccgcgcctct gagagtagcc gtcgcggtcg ctcgctcgct cgctcgctgc tgccggtgtt   120
ggcccggtcc tcgagcggag atggggcgca ggaaggtgca gctgaagcgg atcgagaaca   180
agatcaaccg ccaggtcacc ttctccaagc gccgctcggg gctgctcaag aaggcgcacg   240
agatctccgt gctctacgac gccgaggtcg gcctcatcat cttctccacc aagggaaagc   300
tctacgagtt ctccaccgag tcatgtatgg acaaaattct gaacggtat gagcgctact   360
cttatgcaga aaaggttctc gtttcaagtg aatctgaaat tcagggaaac tggtgtcacg   420
aatataggaa actgaaggcg aaggttgaga caatacagaa atgtcaaaag catctcatgg   480
gagaggatct tgaatctttg aatctcaagg agttgcagca actggagcag cagctggaaa   540
gctcactgaa acatatcaga gccaggaaga accaacttat gcacgaatcc atttctgagc   600
ttcagaagaa ggagaggtca ctgcaggagg agaataaagt tctccagaag gaacttgtgg   660
agaagcagaa ggcccaggcg cgcagcaag atcaaactca gcctcaaacc agctcttctt   720
cttcttcctt catgatgagg gatgctcccc ctgtcgcaga taccagcaat cacccagcgg   780
cggcaggcga gagggcagag gatgtggcag tgcagcctca ggtcccactc cggacggcgc   840
ttccactgtg gatggtgagc cacatcaacg gctgaagggc ttccagccca tgtaagcgta   900
```

```
ctattcagta cgagtaacaa gttgcagcgg ccagcctggt gtatcatgcg gttgcgaaca    960
tgctaacccc atggagggga gaggaaaaga aatcagagta aagcagcaag ctgcaggaat   1020
gtgtatattt cacttcgtcc acctcagttt cctttccacc tgggctgaga tggctgtacg   1080
agtaatctac catgtaattt atatgtagca tgagtgacga attttcaact ttcgatgata   1140
tccgttgctc ctgggtgttg tttctgtgaa ttaacctatc gaatatgagc gttgtg       1196
```

<210> SEQ ID NO 121
<211> LENGTH: 244
<212> TYPE: PRT
<213> ORGANISM: Hordeum vulgare

<400> SEQUENCE: 121

```
Met Gly Arg Arg Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Tyr Asp Ala Glu Val Gly Leu Ile Ile Phe
        35                  40                  45

Ser Thr Lys Gly Lys Leu Tyr Glu Phe Ser Thr Glu Ser Cys Met Asp
    50                  55                  60

Lys Ile Leu Glu Arg Tyr Glu Arg Tyr Ser Tyr Ala Glu Lys Val Leu
65                  70                  75                  80

Val Ser Ser Glu Ser Glu Ile Gln Gly Asn Trp Cys His Glu Tyr Arg
                85                  90                  95

Lys Leu Lys Ala Lys Val Glu Thr Ile Gln Lys Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Arg Ala Arg Lys Asn
    130                 135                 140

Gln Leu Met His Glu Ser Ile Ser Glu Leu Gln Lys Lys Glu Arg Ser
145                 150                 155                 160

Leu Gln Glu Glu Asn Lys Val Leu Gln Lys Glu Leu Val Glu Lys Gln
                165                 170                 175

Lys Ala Gln Ala Ala Gln Gln Asp Gln Thr Gln Pro Gln Thr Ser Ser
            180                 185                 190

Ser Ser Ser Ser Phe Met Met Arg Asp Ala Pro Pro Val Ala Asp Thr
        195                 200                 205

Ser Asn His Pro Ala Ala Ala Gly Glu Arg Ala Glu Asp Val Ala Val
    210                 215                 220

Gln Pro Gln Val Pro Leu Arg Thr Ala Leu Pro Leu Trp Met Val Ser
225                 230                 235                 240

His Ile Asn Gly
```

<210> SEQ ID NO 122
<211> LENGTH: 1161
<212> TYPE: DNA
<213> ORGANISM: Triticum aestivum

<400> SEQUENCE: 122

```
ggcacgagct ctctctctct ctctctctct ctctctcctc gtgccgaatt              60
cggcacgagc ggagatgggg cgcgggaagg tgcagctgaa gcggatcgag aacaagatca   120
accggcaggt gaccttctcc aagcgccgct cggggctgct caagaaggcg cacgagatct   180
ccgtgctctg cgacgccgag gtcggcctca tcatcttctc caccaaggga aagctctacg   240
```

```
agttctccac cgagtcatgt atggacaaaa ttcttgaacg gtatgagcgc tactcttatg    300
cagaaaaggt tctcgtttca agtgaatctg aaattcaggg aaactggtgt cacgaatata    360
ggaaactgaa ggcgaaggtt gagacaatac agaaatgtca aaagcatctg atgggagagg    420
atcttgaatc tttgaatctc aaggagttgc agcaactgga gcagcagctg aaagctcac     480 tgaaacatat cagatccagg aagaaccaac ttatgcacga atccatttct gagcttcaga    540
agaaggagag gtcactgcag gaggagaata agttctcca gaaggaactc gtcgagaagc     600
agaaggccca ggcggcgcaa caagatcaga ctcagcctca acaagctct tcttcttctt     660 ccttcatgat gagggatgct ccccctgccg cagctaccag cattcatcca gcggcggcag    720
gcgagagggc aggggatgcg gcagtgcagc cgcaggcccc accccggacg gggcttccac    780
tgtggatggt gagccacatc aacggctgaa gggcttccag cccatataag cgtactattc    840
agtagagagt aacaagttgc accggccagt ctggtgtatg ttgcggttgc tagcacgcct    900
gaccccttgg aggggaaagg aaaagaaatc agagtaaagt agcaagctgc agcgatgtgt    960
atatttcact tgtccaccc cagtttccct cccagctggg ctcaatttac catgtaatct     1020
atatgtagct tgagtgatga atttcaagt ttccatgata cccgtctcta gtgggatgtt     1080
gtttatgtga attaacctat caaatatgag cattgtgtat attgtgattc ttgaaaataa    1140
ataaatcagg atctttgtct t                                              1161

<210> SEQ ID NO 123
<211> LENGTH: 244
<212> TYPE: PRT
<213> ORGANISM: Triticum aestivum

<400> SEQUENCE: 123

Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Gly Leu Ile Ile Phe
        35                  40                  45

Ser Thr Lys Gly Lys Leu Tyr Glu Phe Ser Thr Glu Ser Cys Met Asp
    50                  55                  60

Lys Ile Leu Glu Arg Tyr Glu Arg Tyr Ser Tyr Ala Glu Lys Val Leu
65                  70                  75                  80

Val Ser Ser Glu Ser Glu Ile Gln Gly Asn Trp Cys His Glu Tyr Arg
                85                  90                  95

Lys Leu Lys Ala Lys Val Glu Thr Ile Gln Lys Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Arg Ser Arg Lys Asn
    130                 135                 140

Gln Leu Met His Glu Ser Ile Ser Glu Leu Gln Lys Lys Glu Arg Ser
145                 150                 155                 160

Leu Gln Glu Glu Asn Lys Val Leu Gln Lys Glu Leu Val Glu Lys Gln
                165                 170                 175

Lys Ala Gln Ala Ala Gln Gln Asp Gln Thr Gln Pro Gln Thr Ser Ser
            180                 185                 190

Ser Ser Ser Ser Phe Met Met Arg Asp Ala Pro Pro Ala Ala Ala Thr
        195                 200                 205
```

Ser Ile His Pro Ala Ala Ala Gly Glu Arg Ala Gly Asp Ala Ala Val
            210                 215                 220

Gln Pro Gln Ala Pro Pro Arg Thr Gly Leu Pro Leu Trp Met Val Ser
225                 230                 235                 240

His Ile Asn Gly

<210> SEQ ID NO 124
<211> LENGTH: 1210
<212> TYPE: DNA
<213> ORGANISM: Triticum aestivum

<400> SEQUENCE: 124

```
tccctctcct ccctctcttc cgcctcaccc aaccacctga cagccatggc tccgcccccc    60
cgccccccgcc tgcgcctgtc ggagtagccg tcgcggtctg ccgtgttgg aggcttgggg   120
tgtagggttg gccccgttct ccagcggaga tggggcgcgg gaaggtgcag ctgaagcgga   180
tcgagaacaa gatcaaccgg caggtgacct tctccaagcg ccgctcgggg ctgctcaaga   240
aggcgcacga gatctccgtg ctctgcgacg ccgaggtcgg cctcatcatc ttctccacca   300
agggaaagct ctacgagttc tccaccgagt catgtatgga caaaattctt gaacggtatg   360
agcgctactc ttatgcagaa aaggttctcg tttcaagtga atctgaaatt cagggaaact   420
ggtgtcacga atataggaaa ctgaaggcga aggttgagac aatacagaaa tgtcaaaagc   480
atctgatggg agaggatctt gaatctttga atctcaagga gttgcagcaa ctggagcagc   540
agctggaaag ctcactgaaa catatcagat ccaggaagaa ccaacttatg cacgaatcca   600
tttctgagct tcagaagaag gagaggtcac tgcaggagga gaataaagtt ctccagaagg   660
aactcgtcga gaagcagaag gcccaggcgg cgcaacaaga tcagactcag cctcaaacaa   720
gctcttcttc ttcttccttc atgatgaggg atgctccccc tgccgcaact accagcattc   780
atccagcggc atcaggagag agggcagagg atgcggcagt gcagccgcag gccccacccc   840
ggacggggct tccactgtgg atggttagcc acatcaacgg ctgaagggct tccagcccat   900
ataagcgtac tattcagtag agagtaacaa gttgcaccgg ccagcctggt gtatgttgcg   960
gttgctagca tgcctgaccc cttggagggg aaaggaaaag aaatcagagt aaagtagcaa  1020
gctgcagtga tgtgtatatt tcactttgtc cacctcagtt tccctcccag ctgggctcaa  1080
tttaccatgt aatctatatg tagcttgagt gatgaatttt caagtttcca tgataccgt  1140
ctcgagcggg tgttgtttat gtgaattaac ctatcaaata tgagcattgt gtaaaaaaaa  1200
aaaaaaaaaa                                                        1210
```

<210> SEQ ID NO 125
<211> LENGTH: 244
<212> TYPE: PRT
<213> ORGANISM: Triticum aestivum

<400> SEQUENCE: 125

Met Gly Arg Gly Lys Val Gln Leu Lys Arg Ile Glu Asn Lys Ile Asn
1               5                   10                  15

Arg Gln Val Thr Phe Ser Lys Arg Ser Gly Leu Leu Lys Lys Ala
            20                  25                  30

His Glu Ile Ser Val Leu Cys Asp Ala Glu Val Gly Leu Ile Ile Phe
            35                  40                  45

Ser Thr Lys Gly Lys Leu Tyr Glu Phe Ser Thr Glu Ser Cys Met Asp
        50                  55                  60

Lys Ile Leu Glu Arg Tyr Glu Arg Tyr Ser Tyr Ala Glu Lys Val Leu
65                  70                  75                  80

Val Ser Ser Glu Ser Glu Ile Gln Gly Asn Trp Cys His Glu Tyr Arg
                85                  90                  95
Lys Leu Lys Ala Lys Val Glu Thr Ile Gln Lys Cys Gln Lys His Leu
            100                 105                 110
Met Gly Glu Asp Leu Glu Ser Leu Asn Leu Lys Glu Leu Gln Gln Leu
        115                 120                 125
Glu Gln Gln Leu Glu Ser Ser Leu Lys His Ile Arg Ser Arg Lys Asn
    130                 135                 140
Gln Leu Met His Glu Ser Ile Ser Glu Leu Gln Lys Lys Glu Arg Ser
145                 150                 155                 160
Leu Gln Glu Glu Asn Lys Val Leu Gln Lys Glu Leu Val Glu Lys Gln
                165                 170                 175
Lys Ala Gln Ala Ala Gln Gln Asp Gln Thr Gln Pro Gln Thr Ser Ser
            180                 185                 190
Ser Ser Ser Ser Phe Met Met Arg Asp Ala Pro Ala Ala Thr Thr
        195                 200                 205
Ser Ile His Pro Ala Ala Ser Gly Glu Arg Ala Glu Asp Ala Ala Val
    210                 215                 220
Gln Pro Gln Ala Pro Arg Thr Gly Leu Pro Leu Trp Met Val Ser
225                 230                 235                 240
His Ile Asn Gly

<210> SEQ ID NO 126
<211> LENGTH: 735
<212> TYPE: DNA
<213> ORGANISM: Triticum monococcum

<400> SEQUENCE: 126
atggggcgcg ggaaggtgca gctgaagcgg atcgagaaca agatcaaccg gcaggtgacc        60
ttctccaagc gccgctcggg gcttctcaag aaggcgcacg agatctccgt gctctgcgac       120
gccgaggtcg gcctcatcat cttctccacc aagggaaagc tctacgagtt ctccaccgag       180
tcatgtatgg acaaaattct tgaacggtat gagcgctatt cttatgcaga aaaggttctc       240
gtttcaagtg aatctgaaat tcagggaaac tggtgtcacg aatataggaa actgaaggcg       300
aaggttgaga caatacagaa atgtcaaaaa catctcatgg gagaggatct tgaatctttg       360
aatctcaagg agttgcagca actggagcag cagctggaaa gctcactgaa acatatcaga       420
tccaggaaga accaacttat gcacgaatcc atttctgagc tgcagaagaa ggagaggtca       480
ctgcaggagg agaataaagt tctccagaag gaactcgtgg agaagcagaa ggcccatgcg       540
gcgcagcaag atcaaactca gcctcaaacc agctcttctt cttcttcctt catgctgagg       600
gatgctcccc ctgccgcaaa taccagcatt catccagcgg cggcaggcga gagggcagag       660
gatgcggcag tgcagccgca ggccccaccc cggacggggc ttccaccgtg gatggtgagc       720
cacatcaacg ggtga                                                       735

<210> SEQ ID NO 127
<211> LENGTH: 244
<212> TYPE: PRT
<213> ORGANISM: Triticum monococcum

<400> SEQUENCE: 127

Met Gly Arg Gly Lys Val Gln Leu Lys Arg Ile Glu Asn Lys Ile Asn
1               5                   10                  15
Arg Gln Val Thr Phe Ser Lys Arg Arg Ser Gly Leu Leu Lys Lys Ala
            20                  25                  30

His Glu Ile Ser Val Leu Cys Asp Ala Glu Val Gly Leu Ile Ile Phe
    35                  40                  45

Ser Thr Lys Gly Lys Leu Tyr Glu Phe Ser Thr Glu Ser Cys Met Asp
 50                  55                  60

Lys Ile Leu Glu Arg Tyr Glu Arg Tyr Ser Tyr Ala Glu Lys Val Leu
 65                  70                  75                  80

Val Ser Ser Glu Ser Glu Ile Gln Gly Asn Trp Cys His Glu Tyr Arg
                 85                  90                  95

Lys Leu Lys Ala Lys Val Glu Thr Ile Gln Lys Cys Gln Lys His Leu
                100                 105                 110

Met Gly Glu Asp Leu Glu Ser Leu Asn Leu Lys Glu Leu Gln Gln Leu
            115                 120                 125

Glu Gln Gln Leu Glu Ser Ser Leu Lys His Ile Arg Ser Arg Lys Asn
130                 135                 140

Gln Leu Met His Glu Ser Ile Ser Glu Leu Gln Lys Lys Glu Arg Ser
145                 150                 155                 160

Leu Gln Glu Glu Asn Lys Val Leu Gln Lys Glu Leu Val Glu Lys Gln
                165                 170                 175

Lys Ala His Ala Ala Gln Gln Asp Gln Thr Gln Pro Gln Thr Ser Ser
                180                 185                 190

Ser Ser Ser Ser Phe Met Leu Arg Asp Ala Pro Ala Ala Asn Thr
            195                 200                 205

Ser Ile His Pro Ala Ala Ala Gly Glu Arg Ala Glu Asp Ala Ala Val
        210                 215                 220

Gln Pro Gln Ala Pro Pro Arg Thr Gly Leu Pro Pro Trp Met Val Ser
225                 230                 235                 240

His Ile Asn Gly

<210> SEQ ID NO 128
<211> LENGTH: 735
<212> TYPE: DNA
<213> ORGANISM: Triticum aestivum

<400> SEQUENCE: 128
atggggcggg ggaaggtgca gctgaagcgg atcgagaaca agatcaaccg gcaggtgacc    60
ttctccaagc gccgctcggg gcttctcaag aaggcgcacg atctccgt gctctgcgac     120
gccgaggtcg gcctcatcat cttctccacc aagggaaagc tctacgagtt ctccaccgag   180
tcatgtatgg acaaaattct tgaacggtat gagcgctatt cttatgcaga aaaggttctc   240
gtttcaagtg aatctgaaat tcagggaaac tggtgtcacg aatataggaa actgaaggcg   300
aaggttgaga caatacagaa atgtcaaaag catctcatgg gagaggatct tgaatctttg   360
aatctcaagg agttgcagca actggagcag cagctggaaa gctcactgaa acatatcaga   420
tccaggaaga accaacttat gcacgaatcc atttctgagc ttcagaagaa ggagaggtca   480
ctgcaggagg agaataaagt tctccagaag gaactcgtgg agaagcagaa ggcccatgcg   540
gcgcagcaag atcaaactca gcctcaaacc agctcttcat cttcttcctt catgctgagg   600
gatgctcccc ctgccgcaaa taccagcatt catccagcgg caacaggcga gagggcagag   660
gatgcggcag tgcagccgca ggccccaccc cggacggggc ttccaccgtg gatggtgagc   720
cacatcaacg ggtga                                                    735

<210> SEQ ID NO 129
<211> LENGTH: 244
<212> TYPE: PRT

<213> ORGANISM: Triticum aestivum

<400> SEQUENCE: 129

```
Met Gly Arg Gly Lys Val Gln Leu Lys Arg Ile Glu Asn Lys Ile Asn
1               5                   10                  15
Arg Gln Val Thr Phe Ser Lys Arg Arg Ser Gly Leu Leu Lys Lys Ala
            20                  25                  30
His Glu Ile Ser Val Leu Cys Asp Ala Glu Val Gly Leu Ile Ile Phe
        35                  40                  45
Ser Thr Lys Gly Lys Leu Tyr Glu Phe Ser Thr Glu Ser Cys Met Asp
    50                  55                  60
Lys Ile Leu Glu Arg Tyr Glu Arg Tyr Ser Tyr Ala Glu Lys Val Leu
65                  70                  75                  80
Val Ser Ser Glu Ser Glu Ile Gln Gly Asn Trp Cys His Glu Tyr Arg
                85                  90                  95
Lys Leu Lys Ala Lys Val Glu Thr Ile Gln Lys Cys Gln Lys His Leu
            100                 105                 110
Met Gly Glu Asp Leu Glu Ser Leu Asn Leu Lys Glu Leu Gln Gln Leu
        115                 120                 125
Glu Gln Gln Leu Glu Ser Ser Leu Lys His Ile Arg Ser Arg Lys Asn
    130                 135                 140
Gln Leu Met His Glu Ser Ile Ser Glu Leu Gln Lys Lys Glu Arg Ser
145                 150                 155                 160
Leu Gln Glu Glu Asn Lys Val Leu Gln Lys Glu Leu Val Glu Lys Gln
                165                 170                 175
Lys Ala His Ala Ala Gln Gln Asp Gln Thr Gln Pro Gln Thr Ser Ser
            180                 185                 190
Ser Ser Ser Ser Phe Met Leu Arg Asp Ala Pro Ala Ala Asn Thr
        195                 200                 205
Ser Ile His Pro Ala Ala Thr Gly Glu Arg Ala Glu Asp Ala Ala Val
    210                 215                 220
Gln Pro Gln Ala Pro Pro Arg Thr Gly Leu Pro Pro Trp Met Val Ser
225                 230                 235                 240
His Ile Asn Gly
```

<210> SEQ ID NO 130
<211> LENGTH: 738
<212> TYPE: DNA
<213> ORGANISM: Lolium perenne

<400> SEQUENCE: 130

```
atggggcgcg gcaaggtgca gctcaagcgg atcgagaaca agatcaaccg ccaggtcacc      60
ttctccaagc gccgctcggg gctgctcaag aaggcgcacg agatctccgt gctctgcgac     120
gccgaggtcg ggctcatcat cttctccacc aagggaaagc tctacgagtt cgcaaccgac     180
tcatgtatgg acaaaattct tgagcggtat gagcgctact cctatgcaga aaagtgctc      240
atttcaaccg aatctgaaat tcagggaaac tggtgtcatg aatataggaa actgaaggcg     300
aaggttgaga caatacagag atgtcaaaag catctaatgg gagaggatct tgaatcattg     360
aatctcaagg agttgcagca actagagcag cagctggaaa gttcactgaa acatattaga     420
gccagaaaga accagcttat gcacgaatcc atatctgagc ttcaaaagaa ggagaggtca     480
ctgcaggagg agaataaaat tctccagaag gaactcatag agaagcagaa ggcccacacg     540
cagcaagcgc agtgggagca aactcagccc caaaccagct cttcctcctc ctcctttatg     600
atgggggaag ctaccccagc aacaaattgc agtaatcccc cagcagcggc cagcgacaga     660
```

```
gcagaggatg cgacggggca gccttcagct cgcacggtgc ttccaccatg gatggtgagt    720
cacatcaaca atggctga                                                  738
```

<210> SEQ ID NO 131
<211> LENGTH: 245
<212> TYPE: PRT
<213> ORGANISM: Lolium perenne

<400> SEQUENCE: 131

```
Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Gly Leu Ile Ile Phe
        35                  40                  45

Ser Thr Lys Gly Lys Leu Tyr Glu Phe Ala Thr Asp Ser Cys Met Asp
    50                  55                  60

Lys Ile Leu Glu Arg Tyr Glu Arg Tyr Ser Tyr Ala Glu Lys Val Leu
65                  70                  75                  80

Ile Ser Thr Glu Ser Glu Ile Gln Gly Asn Trp Cys His Glu Tyr Arg
                85                  90                  95

Lys Leu Lys Ala Lys Val Glu Thr Ile Gln Arg Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Arg Ala Arg Lys Asn
    130                 135                 140

Gln Leu Met His Glu Ser Ile Ser Glu Leu Gln Lys Lys Glu Arg Ser
145                 150                 155                 160

Leu Gln Glu Glu Asn Lys Ile Leu Gln Lys Glu Leu Ile Glu Lys Gln
                165                 170                 175

Lys Ala His Thr Gln Gln Ala Gln Trp Glu Gln Thr Gln Pro Gln Thr
            180                 185                 190

Ser Ser Ser Ser Ser Ser Phe Met Met Gly Glu Ala Thr Pro Ala Thr
        195                 200                 205

Asn Cys Ser Asn Pro Pro Ala Ala Ala Ser Asp Arg Ala Glu Asp Ala
    210                 215                 220

Thr Gly Gln Pro Ser Ala Arg Thr Val Leu Pro Pro Trp Met Val Ser
225                 230                 235                 240

His Ile Asn Asn Gly
                245
```

<210> SEQ ID NO 132
<211> LENGTH: 738
<212> TYPE: DNA
<213> ORGANISM: Lolium temulentum

<400> SEQUENCE: 132

```
atggggcgcg gcaaggtgca gctcaagcgg atcgagaaca agatcaaccg ccaggtcacc     60
ttctccaagc gccgctcagg cctgctcaag aaggcgcacg agatctccgt gctctgcgac    120
gcagaggtcg ggctcatcat cttctccacc aagggaaagc tctacgagtt cgccaccgac    180
tcatgtatgg acaaaattct tgagcggtat gagcgctact cctatgcaga gaaagtgctc    240
atttcaactg aatctgaaat tcagggaaac tggtgtcatg aatataggaa actgaaggcg    300
aaggttgaga caatacagag atgtcaaaag catctaatgg gagaggatct tgaatcattg    360
```

```
aatctcaagg agttgcagca actagagcag cagctggaaa gttcactgaa acatattaga    420
tccagaaaga gccagcttat gcacgaatcc atatctgagc ttcaaaagaa ggagaggtca    480
ctgcaagagg agaataaaat tctccagaag gaactcatag agaagcagaa ggcccacacg    540
cagcaagcgc agttggagca aactcagccc caaaccagct cttcctcctc ctcctttatg    600 atggggaag ctaccccagc aacaaatcgc agtaatcccc cagcagcggc cagcgacaga     660
gcagaggatg cgacggggca gcctccagct cgcacggtgc ttccaccatg gatggtgagt    720
cacctcaaca atggctga                                                  738
```

```
<210> SEQ ID NO 133
<211> LENGTH: 245
<212> TYPE: PRT
<213> ORGANISM: Lolium temulentum

<400> SEQUENCE: 133

Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Gly Leu Ile Ile Phe
        35                  40                  45

Ser Thr Lys Gly Lys Leu Tyr Glu Phe Ala Thr Asp Ser Cys Met Asp
    50                  55                  60

Lys Ile Leu Glu Arg Tyr Glu Arg Tyr Ser Tyr Ala Glu Lys Val Leu
65                  70                  75                  80

Ile Ser Thr Glu Ser Glu Ile Gln Gly Asn Trp Cys His Glu Tyr Arg
                85                  90                  95

Lys Leu Lys Ala Lys Val Glu Thr Ile Gln Arg Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Arg Ser Arg Lys Ser
    130                 135                 140

Gln Leu Met His Glu Ser Ile Ser Glu Leu Gln Lys Lys Glu Arg Ser
145                 150                 155                 160

Leu Gln Glu Glu Asn Lys Ile Leu Gln Lys Glu Leu Ile Glu Lys Gln
                165                 170                 175

Lys Ala His Thr Gln Gln Ala Gln Leu Glu Gln Thr Gln Pro Gln Thr
            180                 185                 190

Ser Ser Ser Ser Ser Phe Met Met Gly Glu Ala Thr Pro Ala Thr
        195                 200                 205

Asn Arg Ser Asn Pro Pro Ala Ala Ala Ser Asp Arg Ala Glu Asp Ala
    210                 215                 220

Thr Gly Gln Pro Pro Ala Arg Thr Val Leu Pro Pro Trp Met Val Ser
225                 230                 235                 240

His Leu Asn Asn Gly
                245
```

```
<210> SEQ ID NO 134
<211> LENGTH: 738
<212> TYPE: DNA
<213> ORGANISM: Zea mays

<400> SEQUENCE: 134
atggggcgcg ggaaggtgca gctgaagcgg atcgagaaca agatcaaccg ccaggtgacc    60
```

-continued

```
ttctccaagc gccgctcggg gctgctcaag aaggcgcacg agatctccgt gctctgcgac    120
gccgaggtcg cgctcatcat cttctccacc aaagggaagc tctacgagta ttccaccgat    180
tcatgtatgg acaaaattct tgaccggtac gagcgctact cctatgcaga aaaggttctt    240
atttcagcag aatctgaaac tcagggcaat tggtgccacg agtatagaaa actaaaggcg    300
aaggtcgaga caatacaaaa atgtcaaaag cacctcatgg gagaggatct tgaaacgttg    360
aatctcaaag agcttcagca actagagcag cagctggaga gttcactgaa acatatcaga    420
accaggaaga accaacttat gctcgagtca atttcggagc tccaacggaa ggagaagtcg    480
ctgcaggagg agaacaaggt tctgcagaag gagctcgcgg agaagcagaa agcccagcgg    540
aagcaagtgc aatggggcca aacccaacag cagaccagtt cgtcttcctc gtgcttcgtg    600
ataagggaag ctgccccaac aacaaatatc agcattttc ctgtggcagc aggcgggagg    660
ttggtggaag gtgcagcagc gcagccacag gctcgcgttg gactaccacc atggatgctt    720
agccacctga gcagctga                                                   738
```

<210> SEQ ID NO 135
<211> LENGTH: 245
<212> TYPE: PRT
<213> ORGANISM: Zea mays

<400> SEQUENCE: 135

```
Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Ile Phe
        35                  40                  45

Ser Thr Lys Gly Lys Leu Tyr Glu Tyr Ser Thr Asp Ser Cys Met Asp
    50                  55                  60

Lys Ile Leu Asp Arg Tyr Glu Arg Tyr Ser Tyr Ala Glu Lys Val Leu
65                  70                  75                  80

Ile Ser Ala Glu Ser Glu Thr Gln Gly Asn Trp Cys His Glu Tyr Arg
                85                  90                  95

Lys Leu Lys Ala Lys Val Glu Thr Ile Gln Lys Cys Gln Lys His Leu
            100                 105                 110

Met Gly Glu Asp Leu Glu Thr Leu Asn Leu Lys Glu Leu Gln Gln Leu
        115                 120                 125

Glu Gln Gln Leu Glu Ser Ser Leu Lys His Ile Arg Thr Arg Lys Asn
    130                 135                 140

Gln Leu Met Leu Glu Ser Ile Ser Glu Leu Gln Arg Lys Glu Lys Ser
145                 150                 155                 160

Leu Gln Glu Glu Asn Lys Val Leu Gln Lys Glu Leu Ala Glu Lys Gln
                165                 170                 175

Lys Ala Gln Arg Lys Gln Val Gln Trp Gly Gln Thr Gln Gln Gln Thr
            180                 185                 190

Ser Ser Ser Ser Cys Phe Val Ile Arg Glu Ala Ala Pro Thr Thr
        195                 200                 205

Asn Ile Ser Ile Phe Pro Val Ala Ala Gly Arg Leu Val Glu Gly
    210                 215                 220

Ala Ala Ala Gln Pro Gln Ala Arg Val Gly Leu Pro Pro Trp Met Leu
225                 230                 235                 240

Ser His Leu Ser Ser
            245
```

<210> SEQ ID NO 136
<211> LENGTH: 738
<212> TYPE: DNA
<213> ORGANISM: Zea mays

<400> SEQUENCE: 136

```
atggggcgcg ggaaggtgca gctgaagcgg atcgagaaca agatcaaccg ccaggtgaca    60
ttctccaagc gccgctcggg gctactcaag aaggcgcacg agatctccgt gctctgcgac   120
gccgaggtcg cgctcatcat cttctccacc aagggcaagc tctacgagta ctctaccgat   180
tcatgtatgg acaaaattct gaacggtat gagcgctact cctatgcaga aaaggttctc   240
atttccgcag aatatgaaac tcagggcaat tggtgccatg aatatagaaa actaaaggcg   300
aaggtcgaga caatacagaa atgtcaaaag cacctcatgg gagaggatct tgaaactttg   360
aatctcaaag agcttcagca actagagcag cagctggaga gttcactgaa acatatcaga   420
acaaggaaga gccagcttat ggtcgagtca atttcagcgc tccaacggaa ggagaagtca   480
ctgcaggagg agaacaaggt tctgcagaag gagctcgcgg agaagcagaa agaccagcgg   540
cagcaagtgc aacgggacca aactcaacag cagaccagtt cgtcttccac gtccttcatg   600
ttaagggaag ctgccccaac aacaaatgtc agcatcttcc ctgtggcagc aggcgggagg   660
gtggtgaag gggcagcagc gcagccgcag gctcgcgttg gactgccacc atggatgctt   720
agccatctga gctgctga                                                 738
```

<210> SEQ ID NO 137
<211> LENGTH: 245
<212> TYPE: PRT
<213> ORGANISM: Zea mays

<400> SEQUENCE: 137

Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Ile Phe
        35                  40                  45

Ser Thr Lys Gly Lys Leu Tyr Glu Tyr Ser Thr Asp Ser Cys Met Asp
    50                  55                  60

Lys Ile Leu Glu Arg Tyr Glu Arg Tyr Ser Tyr Ala Glu Lys Val Leu
65                  70                  75                  80

Ile Ser Ala Glu Tyr Glu Thr Gln Gly Asn Trp Cys His Glu Tyr Arg
                85                  90                  95

Lys Leu Lys Ala Lys Val Glu Thr Ile Gln Lys Cys Gln Lys His Leu
            100                 105                 110

Met Gly Glu Asp Leu Glu Thr Leu Asn Leu Lys Glu Leu Gln Gln Leu
        115                 120                 125

Glu Gln Gln Leu Glu Ser Ser Leu Lys His Ile Arg Thr Arg Lys Ser
    130                 135                 140

Gln Leu Met Val Glu Ser Ile Ser Ala Leu Gln Arg Lys Glu Lys Ser
145                 150                 155                 160

Leu Gln Glu Glu Asn Lys Val Leu Gln Lys Leu Ala Glu Lys Gln
                165                 170                 175

Lys Asp Gln Arg Gln Gln Val Gln Arg Asp Gln Thr Gln Gln Thr
            180                 185                 190

Ser Ser Ser Ser Thr Ser Phe Met Leu Arg Glu Ala Ala Pro Thr Thr

|  | 195 |  |  |  | 200 |  |  |  | 205 |  |  |
|---|---|---|---|---|---|---|---|---|---|---|---|

Asn Val Ser Ile Phe Pro Val Ala Ala Gly Gly Arg Val Val Glu Gly
210                 215                 220

Ala Ala Ala Gln Pro Gln Ala Arg Val Gly Leu Pro Pro Trp Met Leu
225                 230                 235                 240

Ser His Leu Ser Cys
                245

<210> SEQ ID NO 138
<211> LENGTH: 762
<212> TYPE: DNA
<213> ORGANISM: Oryza sativa

<400> SEQUENCE: 138

```
atggggcggg gcaaggtgca gctgaagcgg atcgagaaca agatcaaccg gcaggtgacc      60
ttctccaagc gcaggtcggg gctgctcaag aaggcgaatg agatctccgt gctctgcgac     120
gccgaggtcg cgctcatcat cttctccacc aagggcaagc tctacgagta cgccaccgac     180
tcatgtatgg acaaaatcct tgaacgttat gagcgctact cctatgcaga aaaggtcctt     240
atttcagctg aatctgacac tcagggcaac tggtgccacg aatataggaa actgaaggct     300
aaggttgaga caatacagaa atgtcaaaag cacctcatgg gagaggatct tgaatctttg     360
aatctcaaag agctgcagca gctggagcag cagctggaaa attcgttgaa acatatcaga     420
tccagaaaga gccaactaat gctcgagtcc attaacgagc ttcaacggaa ggaaaagtca     480
ctgcaggagg agaataaggt cctacagaaa gaaaacccctt gctccttcct acagctggtg     540
gagaagcaga aagtccagaa gcaacaagtg caatgggacc agacacaacc tcaaacaagt     600
tcctcatcat cctccttcat gatgagggaa gcccttccaa caactaatat cagtaactac     660
cctgcagcag ctggcgaaag gatagaggat gtagcagcag ggcagccaca gcatgttcgc     720
attgggctgc caccatggat gctgagccac atcaacggct aa                        762
```

<210> SEQ ID NO 139
<211> LENGTH: 253
<212> TYPE: PRT
<213> ORGANISM: Oryza sativa

<400> SEQUENCE: 139

Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
                20                  25                  30

Asn Glu Ile Ser Val Leu Cys Asp Ala Glu Val Ala Leu Ile Ile Phe
            35                  40                  45

Ser Thr Lys Gly Lys Leu Tyr Glu Tyr Ala Thr Asp Ser Cys Met Asp
    50                  55                  60

Lys Ile Leu Glu Arg Tyr Glu Arg Tyr Ser Tyr Ala Glu Lys Val Leu
65                  70                  75                  80

Ile Ser Ala Glu Ser Asp Thr Gln Gly Asn Trp Cys His Glu Tyr Arg
                85                  90                  95

Lys Leu Lys Ala Lys Val Glu Thr Ile Gln Lys Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Asn Ser Leu Lys His Ile Arg Ser Arg Lys Ser
    130                 135                 140

-continued

Gln Leu Met Leu Glu Ser Ile Asn Glu Leu Gln Arg Lys Glu Lys Ser
145                 150                 155                 160

Leu Gln Glu Glu Asn Lys Val Leu Gln Lys Glu Asn Pro Cys Ser Phe
                165                 170                 175

Leu Gln Leu Val Glu Lys Gln Lys Val Gln Lys Gln Val Gln Trp
            180                 185                 190

Asp Gln Thr Gln Pro Gln Thr Ser Ser Ser Ser Ser Phe Met Met
            195                 200                 205

Arg Glu Ala Leu Pro Thr Thr Asn Ile Ser Asn Tyr Pro Ala Ala Ala
            210                 215                 220

Gly Glu Arg Ile Glu Asp Val Ala Ala Gly Pro Gln His Val Arg
225                 230                 235                 240

Ile Gly Leu Pro Pro Trp Met Leu Ser His Ile Asn Gly
                245                 250

<210> SEQ ID NO 140
<211> LENGTH: 741
<212> TYPE: DNA
<213> ORGANISM: Oryza sativa

<400> SEQUENCE: 140
atggggcggg gcaaggtgca gctgaagcgg atcgagaaca agatcaaccg gcaggtgacc      60
ttctccaagc gcaggtcaaa actgctcaag aaggcgaatg agatctccgt gctctgcgac     120
gccgaggtcg cgctcatcat cttctccacc aagggcaagc tctacgagta cgccaccgac     180
tcatgtatgg acaaaatcct tgaacgttat gagcgctact cctatgcaga aaaggtcctt     240
atttcagctg aatctgacac tcagggcaac tggtgccacg aatataggaa actgaaggct     300
aaggttgaga caatacagaa atgtcaaaag cacctcatgg gagaggatct tgaatctttg     360
aatctcaaag agctgcagca gctggagcag cagctggaaa attcgttgaa acatatcaga     420
tccagaaaga gccaactaat gctcgagtcc attaacgagc ttcaacggaa ggaaaagtca     480
ctgcaggagg agaataaggt cctacagaaa gaactggtgg agaagcagaa agtccagaag     540
caacaagtgc aatgggacca gacacaacct caaacaagtt cctcatcatc ctccttcatg     600
atgagggaag cccttccaac aactaatatc agtaactacc ctgcagcagc tggcgaaagg     660
atagaggatg tagcagcagg gcagccacag catgaacgca ttgggctgcc accatggatg     720
ctgagccaca tcaacggcta a                                               741

<210> SEQ ID NO 141
<211> LENGTH: 246
<212> TYPE: PRT
<213> ORGANISM: Oryza sativa

<400> SEQUENCE: 141

Met Gly Arg Gly Lys Val Gln Leu Lys Arg Ile Glu Asn Lys Ile Asn
1               5                   10                  15

Arg Gln Val Thr Phe Ser Lys Arg Arg Ser Lys Leu Leu Lys Lys Ala
            20                  25                  30

Asn Glu Ile Ser Val Leu Cys Asp Ala Glu Val Ala Leu Ile Ile Phe
        35                  40                  45

Ser Thr Lys Gly Lys Leu Tyr Glu Tyr Ala Thr Asp Ser Cys Met Asp
    50                  55                  60

Lys Ile Leu Glu Arg Tyr Glu Arg Tyr Ser Tyr Ala Glu Lys Val Leu
65                  70                  75                  80

Ile Ser Ala Glu Ser Asp Thr Gln Gly Asn Trp Cys His Glu Tyr Arg
                85                  90                  95

```
Lys Leu Lys Ala Lys Val Glu Thr Ile Gln Lys Cys Gln Lys His Leu
                100                 105                 110

Met Gly Glu Asp Leu Glu Ser Leu Asn Leu Lys Glu Leu Gln Gln Leu
            115                 120                 125

Glu Gln Gln Leu Glu Asn Ser Leu Lys His Ile Arg Ser Arg Lys Ser
        130                 135                 140

Gln Leu Met Leu Glu Ser Ile Asn Glu Leu Gln Arg Lys Glu Lys Ser
145                 150                 155                 160

Leu Gln Glu Glu Asn Lys Val Leu Gln Lys Glu Leu Val Glu Lys Gln
                165                 170                 175

Lys Val Gln Lys Gln Val Gln Trp Asp Gln Thr Gln Pro Gln Thr
            180                 185                 190

Ser Ser Ser Ser Ser Ser Phe Met Met Arg Glu Ala Leu Pro Thr Thr
        195                 200                 205

Asn Ile Ser Asn Tyr Pro Ala Ala Ala Gly Glu Arg Ile Glu Asp Val
    210                 215                 220

Ala Ala Gly Gln Pro Gln His Glu Arg Ile Gly Leu Pro Pro Trp Met
225                 230                 235                 240

Leu Ser His Ile Asn Gly
                245

<210> SEQ ID NO 142
<211> LENGTH: 735
<212> TYPE: DNA
<213> ORGANISM: Dendrocalamus latiflorus

<400> SEQUENCE: 142
atggggcgcg ggaaggtgca gctgaagcgg atcgagaaca agatcaaccg gcaagtgact     60
ttctccaagc gccggtcggg gctgctcaag aaggcgcatg agatctccgt cctctgcgac    120
gccgaggtcg gccttatcat cttctccacc aagggcaagc tctacgagta cgccaccgac    180
tcatgtatgg acaaaattct tgaacggtac gagcgttact cctatgcaga aaaggttctt    240
atttcagccg aatctgaaac tcagggcaac tggtgtcacg aatataggaa actgaaggcg    300
aaggttgaga cgatacagaa atgtcaaaag cacctcatgg gagaggatcc tgaatctttg    360
aatctcaagg agctgcagca actcgagcag cagctggaaa gttcagtgaa acatatcaga    420
tccagaaaga gccagcttat gctcgagtcc atttccgagc ttcaaaagaa ggagaagtca    480
ctgcaggagg agaacaaggt tctgcagaag gaactcgtgg agaagcagca ggtccataaa    540
cggttagtgc aatgggacca aactcagccg caaactagtt cctcttcctc gtccttcatg    600
atgagggaag ctctccccaac aacaaatatc agtatttacg ctgcggcagc cggcgagagg    660
gcagaggacg cagcagggca gcctcagatt cacattgggc tgccgccatg gatggtgagc    720
cacatcaacg gctaa                                                     735

<210> SEQ ID NO 143
<211> LENGTH: 244
<212> TYPE: PRT
<213> ORGANISM: Dendrocalamus latiflorus

<400> SEQUENCE: 143

Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Gly Leu Ile Ile Phe
```

```
                 35                  40                  45
Ser Thr Lys Gly Lys Leu Tyr Glu Tyr Ala Thr Asp Ser Cys Met Asp
 50                  55                  60

Lys Ile Leu Glu Arg Tyr Glu Arg Tyr Ser Tyr Ala Glu Lys Val Leu
 65                  70                  75                  80

Ile Ser Ala Glu Ser Glu Thr Gln Gly Asn Trp Cys His Glu Tyr Arg
                 85                  90                  95

Lys Leu Lys Ala Lys Val Glu Thr Ile Gln Lys Cys Gln Lys His Leu
                100                 105                 110

Met Gly Glu Asp Pro Glu Ser Leu Asn Leu Lys Glu Leu Gln Gln Leu
                115                 120                 125

Glu Gln Gln Leu Glu Ser Ser Val Lys His Ile Arg Ser Arg Lys Ser
                130                 135                 140

Gln Leu Met Leu Glu Ser Ile Ser Glu Leu Gln Lys Lys Glu Lys Ser
145                 150                 155                 160

Leu Gln Glu Glu Asn Lys Val Leu Gln Lys Glu Leu Val Glu Lys Gln
                165                 170                 175

Gln Val His Lys Arg Leu Val Gln Trp Asp Gln Thr Gln Pro Gln Thr
                180                 185                 190

Ser Ser Ser Ser Ser Ser Phe Met Met Arg Glu Ala Leu Pro Thr Thr
                195                 200                 205

Asn Ile Ser Ile Tyr Ala Ala Ala Ala Gly Glu Arg Ala Glu Asp Ala
                210                 215                 220

Ala Gly Gln Pro Gln Ile His Ile Gly Leu Pro Pro Trp Met Val Ser
225                 230                 235                 240

His Ile Asn Gly

<210> SEQ ID NO 144
<211> LENGTH: 735
<212> TYPE: DNA
<213> ORGANISM: Dendrocalamus latiflorus

<400> SEQUENCE: 144
atggggcgcg ggaaggtgca gctgaagcgg atcgagaaca agatcaaccg gcaagtgact      60
ttctccaagc gccggtcggg gctgctcaag aaggcgcatg agatctccgt cctctgcgac     120
gccgaggtcg gccttatcat cttctccacc aagggcaagc tctacgagta cgccaccgac     180
tcatgtatgg acaaaattct tgaacggtac gagcgttact cctatgcaga aaaggttctt     240
atttcagccg aatctgaaac tcagggcaac tggtgtcacg aatataggaa actgaaggcg     300
aaggttgaga cgatacagaa atgtcaaaag cacctcatgg gagaggatct tgaatctttg     360
aatctcaagg agctgcagca actcgagcag cagctggaaa gttcagtgaa acatatcaga     420
tccagaaaga gccagcttat gctcgagtcc atttccgagc ttcaaaagaa ggagaagtca     480
ctgcaggagg agaacaaggt tctgcagaag gaactcgtgg agaagcagca ggtccataaa     540
cggttagtgc aatgggacca aactcagccg caaactagtt cctcttcctc gtccttcatg     600
atgagggaag ctctcccaac aacaaatatc agtatttacg ctgcggcagc cggcgagagg     660
gcagaggacg cagcagggca gcctcagatt cacattgggc tgccgccatg gatggtgagc     720
cacatcaacg gctaa                                                     735

<210> SEQ ID NO 145
<211> LENGTH: 244
<212> TYPE: PRT
<213> ORGANISM: Dendrocalamus latiflorus
```

<400> SEQUENCE: 145

```
Met Gly Arg Gly Lys Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Gly Leu Ile Ile Phe
        35                  40                  45

Ser Thr Lys Gly Lys Leu Tyr Glu Tyr Ala Thr Asp Ser Cys Met Asp
50                  55                  60

Lys Ile Leu Glu Arg Tyr Glu Arg Tyr Ser Tyr Ala Glu Lys Val Leu
65                  70                  75                  80

Ile Ser Ala Glu Ser Glu Thr Gln Gly Asn Trp Cys His Glu Tyr Arg
                85                  90                  95

Lys Leu Lys Ala Lys Val Glu Thr Ile Gln Lys Cys Gln Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Val Lys His Ile Arg Ser Arg Lys Ser
130                 135                 140

Gln Leu Met Leu Glu Ser Ile Ser Glu Leu Gln Lys Lys Glu Lys Ser
145                 150                 155                 160

Leu Gln Glu Glu Asn Lys Val Leu Gln Lys Leu Val Glu Lys Gln
                165                 170                 175

Gln Val His Lys Arg Leu Val Gln Trp Asp Gln Thr Gln Pro Gln Thr
            180                 185                 190

Ser Ser Ser Ser Ser Phe Met Met Arg Glu Ala Leu Pro Thr Thr
        195                 200                 205

Asn Ile Ser Ile Tyr Ala Ala Ala Ala Gly Glu Arg Ala Glu Asp Ala
        210                 215                 220

Ala Gly Gln Pro Gln Ile His Ile Gly Leu Pro Pro Trp Met Val Ser
225                 230                 235                 240

His Ile Asn Gly
```

<210> SEQ ID NO 146
<211> LENGTH: 813
<212> TYPE: DNA
<213> ORGANISM: Zea mays

<400> SEQUENCE: 146

```
atggggcgcg gcaaggtgca gctgaagcgg atagagaaca agataaaccg gcaggtgacc        60
ttctccaagc gccggaacgg gctgctgaag aaggcgcacg agatctccgt cctctgcgac       120
gccgaggtcg ccgtcatcgt cttctccccc aagggcaagc tctacgagta cgcctccgac       180
tcccgcatgg acaaaattct agaacgttat gagcgatatt cctatgctga aaaggctctt       240
atttcagctg aatctgaaag tgagggaaat tggtgccacg aatacaggaa actgaaggcc       300
aaaattgaga ccatacaaag atgccacaag cacctgatgg gagaggatct agagtctttg       360
aatccaaaag agctccaaca actagagcag cagctggaga gctcactgaa gcacatcaga       420
tcaagaaaga gccaccttat ggccgagtca atttctgagc tacagaagaa ggagaggtca       480
ctgcaggagg agaacaagat tctacagaag gaactttcag agaggcagaa ggcggtcgct       540
agccggcagc agcagcagca gcaggtgcag tgggaccagc agacacaggt ccaggtccag       600
acaagctcat cgtcttcttc cttcatgatg aggcaggatc agcagggact gccacctcca       660
caaaacatct gcttccgcc gttgagcatc ggagagagag gcgaagaggt ggctgcggcg       720
```

```
gcgcagcagc agctgcctcc tccggggcag gcgcaaccac agctccgcat cgcaggtctg    780
ccgccatgga tgctgagcca cctcaatgca taa                                 813
```

<210> SEQ ID NO 147
<211> LENGTH: 270
<212> TYPE: PRT
<213> ORGANISM: Zea mays

<400> SEQUENCE: 147

```
Met Gly Arg Gly Lys Val Gln Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Val Ile Val Phe
        35                  40                  45

Ser Pro Lys Gly Lys Leu Tyr Glu Tyr Ala Ser Asp Ser Arg Met Asp
    50                  55                  60

Lys Ile Leu Glu Arg Tyr Glu Arg Tyr Ser Tyr Ala Glu Lys Ala Leu
65                  70                  75                  80

Ile Ser Ala Glu Ser Glu Ser Glu Gly Asn Trp Cys His Glu Tyr Arg
                85                  90                  95

Lys Leu Lys Ala Lys Ile Glu Thr Ile Gln Arg Cys His Lys His Leu
            100                 105                 110

Met Gly Glu Asp Leu Glu Ser Leu Asn Pro Lys Glu Leu Gln Gln Leu
        115                 120                 125

Glu Gln Gln Leu Glu Ser Ser Leu Lys His Ile Arg Ser Arg Lys Ser
    130                 135                 140

His Leu Met Ala Glu Ser Ile Ser Glu Leu Gln Lys Lys Glu Arg Ser
145                 150                 155                 160

Leu Gln Glu Glu Asn Lys Ile Leu Gln Lys Glu Leu Ser Glu Arg Gln
                165                 170                 175

Lys Ala Val Ala Ser Arg Gln Gln Gln Gln Val Gln Trp Asp
            180                 185                 190

Gln Gln Thr Gln Val Gln Val Gln Thr Ser Ser Ser Ser Ser Phe
        195                 200                 205

Met Met Arg Gln Asp Gln Gly Leu Pro Pro Gln Asn Ile Cys
    210                 215                 220

Phe Pro Pro Leu Ser Ile Gly Glu Arg Gly Glu Val Ala Ala Ala
225                 230                 235                 240

Ala Gln Gln Gln Leu Pro Pro Gly Gln Ala Gln Pro Gln Leu Arg
                245                 250                 255

Ile Ala Gly Leu Pro Pro Trp Met Leu Ser His Leu Asn Ala
            260                 265                 270
```

<210> SEQ ID NO 148
<211> LENGTH: 689
<212> TYPE: DNA
<213> ORGANISM: Sorghum bicolor

<400> SEQUENCE: 148

```
gcaaggtgca gctcaagcgg atagagaaca agataaaccg gcaggtgacc ttctccaagc    60
gccgcaacgg gctgctcaag aaggcgcacg agatctccgt cctctgcgac gccgaggtcg    120
ccgtcatcgt cttctccccc aagggcaagc tctatgagta cgccaccgac tcccgcatgg    180
acaaaattct cgaacgttat gagcgatatt cctatgctga aaaggctctt atttcagctg    240
```

```
aatctgaaag tgagggaaac tggtgccacg aatacaggaa actgaaggcc aaaattgaga       300
ccattcaaaa atgccacaag cacctgatgg gagaggatct agagtctttg aatcccaaag       360
agctccaaca actagagcag cagctggaga gctcactgaa gcacatcaga tcaagaaaga       420
gccaccttat ggctgagtct atttctgaac tacagaagaa ggagaggtca ctgcaggagg       480
agaacaaggc tctacagaag gaacttgcgg agaggcagaa ggcggccgcg agcaggcagc       540
agcagcaagg tgcagtggga ccagcagaca cagacccagg cccagacaag ctcatcatcg       600
tcctccttca tgatgaggca ggatcagcag ggtctgccgc ctccacaaaa catatgcttc       660
ccgccgctga taatcggaga gagaggtga                                        689

<210> SEQ ID NO 149
<211> LENGTH: 228
<212> TYPE: PRT
<213> ORGANISM: Sorghum bicolor

<400> SEQUENCE: 149

Lys Val Gln Leu Lys Arg Ile Glu Asn Lys Ile Asn Arg Gln Val Thr
1               5                   10                  15

Phe Ser Lys Arg Arg Asn Gly Leu Leu Lys Lys Ala His Glu Ile Ser
            20                  25                  30

Val Leu Cys Asp Ala Glu Val Ala Val Ile Val Phe Ser Pro Lys Gly
        35                  40                  45

Lys Leu Tyr Glu Tyr Ala Thr Asp Ser Arg Met Asp Lys Ile Leu Glu
    50                  55                  60

Arg Tyr Glu Arg Tyr Ser Tyr Ala Glu Lys Ala Leu Ile Ser Ala Glu
65                  70                  75                  80

Ser Glu Ser Glu Gly Asn Trp Cys His Glu Tyr Arg Lys Leu Lys Ala
                85                  90                  95

Lys Ile Glu Thr Ile Gln Lys Cys His Lys His Leu Met Gly Glu Asp
            100                 105                 110

Leu Glu Ser Leu Asn Pro Lys Glu Leu Gln Gln Leu Glu Gln Gln Leu
        115                 120                 125

Glu Ser Ser Leu Lys His Ile Arg Ser Arg Lys Ser His Leu Met Ala
    130                 135                 140

Glu Ser Ile Ser Glu Leu Gln Lys Lys Glu Arg Ser Leu Gln Glu Glu
145                 150                 155                 160

Asn Lys Ala Leu Gln Lys Glu Leu Ala Glu Arg Gln Lys Ala Ala Ala
                165                 170                 175

Ser Arg Gln Gln Gln Gly Ala Val Gly Pro Ala Asp Thr Asp Pro
            180                 185                 190

Gly Pro Asp Lys Leu Ile Ile Val Leu Leu His Asp Glu Ala Gly Ser
        195                 200                 205

Ala Gly Ser Ala Ala Ser Thr Lys His Met Leu Pro Ala Ala Asp Asn
    210                 215                 220

Arg Arg Glu Arg
225

<210> SEQ ID NO 150
<211> LENGTH: 822
<212> TYPE: DNA
<213> ORGANISM: Zea mays

<400> SEQUENCE: 150
atggggcgcg gcaaggtaca gctgaagcgg atagagaaca agataaaccg gcaggtgacc        60
ttctccaagc gccggaacgg cctgctcaag aaggcgcacg agatctccgt cctctgcgat       120
```

```
gccgaggtcg ccgtcatcgt cttctccccc aagggcaagc tctacgagta cgccaccgac      180
tcccgcatgg acaaaattct tgaacgctat gagcgatatt cctatgctga aaaggctctt      240
atttcagctg aatctgaaag tgagggaaat tggtgccacg aatacaggaa actgaaggcc      300
aaaattgaga ccatacaaaa atgccacaag cacctgatgg gagaggatct agagtctttg      360
aatcccaaag agctccagca actagagcag cagctggata gctcactgaa gcacatcaga      420
tcaaggaaga gccaccttat ggccgagtct atttctgagc tacagaagaa ggagaggtca      480
ctgcaggagg agaacaaggc tctgcagaag gaacttgcgg agaggcagaa ggccgtcgcg      540
agccggcagc agcagcaaca gcagcaggtg cagtgggacc agcagacaca tgcccaggcc      600
cagacaagct catcatcgtc ctccttcatg atgaggcagg atcagcaggg actgccgcct      660
ccacacaaca tctgcttccc gccgttgaca atggagagata gaggtgaaga gctggctgcg      720
gcggcggcgg cgcagcagca gcagccactg ccggggcagg cgcaaccgca gctccgcatc      780
gcaggtctgc caccatggat gctgagccac ctcaatgcat aa                         822
```

<210> SEQ ID NO 151
<211> LENGTH: 273
<212> TYPE: PRT
<213> ORGANISM: Zea mays

<400> SEQUENCE: 151

Met Gly Arg Gly Lys Val Gln Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Val Ile Val Phe
        35                  40                  45

Ser Pro Lys Gly Lys Leu Tyr Glu Tyr Ala Thr Asp Ser Arg Met Asp
    50                  55                  60

Lys Ile Leu Glu Arg Tyr Glu Arg Tyr Ser Tyr Ala Glu Lys Ala Leu
65                  70                  75                  80

Ile Ser Ala Glu Ser Glu Ser Glu Gly Asn Trp Cys His Glu Tyr Arg
                85                  90                  95

Lys Leu Lys Ala Lys Ile Glu Thr Ile Gln Lys Cys His Lys His Leu
            100                 105                 110

Met Gly Glu Asp Leu Glu Ser Leu Asn Pro Lys Glu Leu Gln Gln Leu
        115                 120                 125

Glu Gln Gln Leu Asp Ser Ser Leu Lys His Ile Arg Ser Arg Lys Ser
    130                 135                 140

His Leu Met Ala Glu Ser Ile Ser Glu Leu Gln Lys Lys Glu Arg Ser
145                 150                 155                 160

Leu Gln Glu Glu Asn Lys Ala Leu Gln Lys Glu Leu Ala Glu Arg Gln
                165                 170                 175

Lys Ala Val Ala Ser Arg Gln Gln Gln Gln Gln Val Gln Trp
            180                 185                 190

Asp Gln Gln Thr His Ala Gln Ala Gln Thr Ser Ser Ser Ser Ser
        195                 200                 205

Phe Met Met Arg Gln Asp Gln Gln Gly Leu Pro Pro His Asn Ile
    210                 215                 220

Cys Phe Pro Pro Leu Thr Met Gly Asp Arg Gly Glu Glu Leu Ala Ala
225                 230                 235                 240

Ala Ala Ala Ala Gln Gln Gln Gln Pro Leu Pro Gly Gln Ala Gln Pro
                245                 250                 255

```
Gln Leu Arg Ile Ala Gly Leu Pro Pro Trp Met Leu Ser His Leu Asn
        260                 265                 270

Ala

<210> SEQ ID NO 152
<211> LENGTH: 786
<212> TYPE: DNA
<213> ORGANISM: Lolium temulentum

<400> SEQUENCE: 152
atgggtcgcg gcaaggtgca gctgaagcgg atagagaaca agataaaccg tcaggtgaca      60
ttctccaagc gccgcaacgg gctactcaag aaggcgcacg agatctccgt cctctgcgac     120
gccgaggtcg ccgtcgtcgt cttctccccg aaagggaagc tctatgagta cgccactgac     180
tccagcatgg acaaaattct gaacgttatg aacgctact cttatgctga aaaggctttg     240
atttcagctg aatctgaaag tgagggaaat tggtgccatg aatacaggaa gctgaaggcg     300
aagattgaga ctatacaaaa atgtcacaag cacctcatgg gggaggatct ggagtgtcta     360
aacctgaaag agctccaaca actagagcag cagctggaga gttcattgaa gcacatcaga     420
tcgagaaaga gccaccttat gatggagtcc atttctgagc tacagaagaa ggagcggtca     480
ctccaggagg agaacaaggc tctacagaag gaactggtgg agaggcagaa ggcggccagg     540
cagcagcagc aagagcagtg ggaccgtcag acccaaacac aacaagccca aaaccaacct     600
caggcccaga cgagctcatc atcttcctcc ttcatgatga gggatcagca ggcccatgct     660
caacaaaaca tctgttaccc gctggtgaca atgggtggag aggctgtggc cgcggcgcca     720
gggcagcagg ggcagcttcg catcggaggc ctgccaccat ggatgctgag ccacctcaac     780
gcttga                                                                786

<210> SEQ ID NO 153
<211> LENGTH: 261
<212> TYPE: PRT
<213> ORGANISM: Lolium temulentum

<400> SEQUENCE: 153

Met Gly Arg Gly Lys Val Gln Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Val Val Val Phe
        35                  40                  45

Ser Pro Lys Gly Lys Leu Tyr Glu Tyr Ala Thr Asp Ser Ser Met Asp
    50                  55                  60

Lys Ile Leu Glu Arg Tyr Glu Arg Tyr Ser Tyr Ala Glu Lys Ala Leu
65                  70                  75                  80

Ile Ser Ala Glu Ser Glu Ser Glu Gly Asn Trp Cys His Glu Tyr Arg
                85                  90                  95

Lys Leu Lys Ala Lys Ile Glu Thr Ile Gln Lys Cys His Lys His Leu
            100                 105                 110

Met Gly Glu Asp Leu Glu Cys Leu Asn Leu Lys Glu Leu Gln Gln Leu
        115                 120                 125

Glu Gln Gln Leu Glu Ser Ser Leu Lys His Ile Arg Ser Arg Lys Ser
    130                 135                 140

His Leu Met Met Glu Ser Ile Ser Glu Leu Gln Lys Lys Glu Arg Ser
145                 150                 155                 160
```

```
Leu Gln Glu Glu Asn Lys Ala Leu Gln Lys Glu Leu Val Glu Arg Gln
                165                 170                 175

Lys Ala Ala Arg Gln Gln Gln Glu Gln Trp Asp Arg Gln Thr Gln
        180                 185                 190

Thr Gln Gln Ala Gln Asn Gln Pro Gln Ala Gln Thr Ser Ser Ser
        195                 200                 205

Ser Ser Phe Met Met Arg Asp Gln Gln Ala His Ala Gln Gln Asn Ile
        210                 215                 220

Cys Tyr Pro Leu Val Thr Met Gly Gly Glu Ala Val Ala Ala Pro
225                 230                 235                 240

Gly Gln Gln Gly Gln Leu Arg Ile Gly Gly Leu Pro Pro Trp Met Leu
        245                 250                 255

Ser His Leu Asn Ala
        260

<210> SEQ ID NO 154
<211> LENGTH: 786
<212> TYPE: DNA
<213> ORGANISM: Lolium perenne

<400> SEQUENCE: 154
atgggtcgcg gcaaggtgca gctgaagcgg atagagaaca agataaaccg tcaggtgacc      60
ttctccaagc gccgcaacgg gctactcaag aaggcgcacg agatctccgt cctctgcgac     120
gccgaggtcg ccgtcgtcgt cttctccccg aagggaagc tctatgagta cgccactgac      180
tccagcatga caaaattct tgaacgttat gaacgctact cttatgctga aaaggctttg      240
atttcagctg aatctgaaag tgagggaaat tggtgccatg aatacaggaa actgaaggcg     300
aagattgaga ctatacaaaa atgtcacaag caccctcatgg gggaggatct ggagtgtcta    360
aacctgaaag agctccaaca actagagcag cagctggaga gttcattgaa gcacatcaga    420
tcgagaaaga gccaccttat gatggagtcc atttctgagc tacagaagaa ggagcggtca    480
ctccaggagg agaacaaggc tctacagaag gaactggtgg agaggcagaa ggcggccagg    540
cagcagcagc aagagcagtg ggaccgtcag acccaaacac aacaagccca aaaccaacct    600
caggcccaga cgagctcatc atcttcctcc ttcatgatga gggatcagca ggcccatgct    660
caacaaaaca tctgttaccc gccggtgaca atgggtggag aggctgtggc cgcggcgcca    720
gggcagcagg ggcagcttcg catcggaggc ctgccaccat ggatgctgag ccacctcaac    780
gcttga                                                                786

<210> SEQ ID NO 155
<211> LENGTH: 261
<212> TYPE: PRT
<213> ORGANISM: Lolium perenne

<400> SEQUENCE: 155

Met Gly Arg Gly Lys Val Gln Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Val Val Val Phe
        35                  40                  45

Ser Pro Lys Gly Lys Leu Tyr Glu Tyr Ala Thr Asp Ser Ser Met Asp
    50                  55                  60

Lys Ile Leu Glu Arg Tyr Glu Arg Tyr Ser Tyr Ala Glu Lys Ala Leu
65                  70                  75                  80
```

```
Ile Ser Ala Glu Ser Glu Ser Glu Gly Asn Trp Cys His Glu Tyr Arg
                85                  90                  95

Lys Leu Lys Ala Lys Ile Glu Thr Ile Gln Lys Cys His Lys His Leu
            100                 105                 110

Met Gly Glu Asp Leu Glu Cys Leu Asn Leu Lys Glu Leu Gln Gln Leu
        115                 120                 125

Glu Gln Gln Leu Glu Ser Ser Leu Lys His Ile Arg Ser Arg Lys Ser
    130                 135                 140

His Leu Met Met Glu Ser Ile Ser Glu Leu Gln Lys Lys Glu Arg Ser
145                 150                 155                 160

Leu Gln Glu Glu Asn Lys Ala Leu Gln Lys Glu Leu Val Glu Arg Gln
                165                 170                 175

Lys Ala Ala Arg Gln Gln Gln Gln Glu Gln Trp Asp Arg Gln Thr Gln
            180                 185                 190

Thr Gln Gln Ala Gln Asn Gln Pro Gln Ala Gln Thr Ser Ser Ser Ser
        195                 200                 205

Ser Ser Phe Met Met Arg Asp Gln Gln Ala His Ala Gln Gln Asn Ile
    210                 215                 220

Cys Tyr Pro Pro Val Thr Met Gly Gly Glu Ala Val Ala Ala Ala Pro
225                 230                 235                 240

Gly Gln Gln Gly Gln Leu Arg Ile Gly Gly Leu Pro Pro Trp Met Leu
                245                 250                 255

Ser His Leu Asn Ala
            260

<210> SEQ ID NO 156
<211> LENGTH: 831
<212> TYPE: DNA
<213> ORGANISM: Hordeum vulgare

<400> SEQUENCE: 156
atgggtcgcg gtaaggtgca gctgaagcgg atagagaaca agataaatcg gcaggtgacc          60
ttctccaagc gccgcaacgg gctcctgaag aaggcgcacg agatctccgt cctctgtgac         120
gcagaggtcg ccgtcatcgt cttctccccc aaaggcaagc tctatgagta cgccaccgac         180
tccagcatgg acaaaattct tgaacgttat gagcgctact cttatgctga aaaggctctt         240
atttcagctg aatctgaaag tgaggggaat tggtgtcatg aatacaggaa acttaaggcg         300
aagattgaga ccatacagaa gtgtcacaag cacctcatgg gagaggatct ggattctctg         360
aacctcaaag aactccaaca actggagcag cagctggaga gttcattgaa gcacatcaga         420
tcgagaaaga gccatcttat gatggagtcc atttctgagc tacagaagaa ggagaggtca         480
ctgcaggaga gaacaaggc cctacagaag gaactggtgg agaggcagaa ggcggccagc         540
aggcagcagc agctgcagca gcagcaacaa caacaacaaa tgcaatggga gaccaagcc         600
cagacccaaa cccataccca tactcaaaac cagcccaag cccagactag ctcatcatct         660
tcctctttca tgatgaggga tcagcaggcc catgcccctc aacagaacat tgtagctac         720
ccaccggtga cgatgggtgg ggaggcgacg gcggcggcgg cggcgccgga gcagcaggct         780
cagcttcgca tatgcctacc gccatggatg ctgagccacc tcaacgcttg a                831

<210> SEQ ID NO 157
<211> LENGTH: 276
<212> TYPE: PRT
<213> ORGANISM: Hordeum vulgare

<400> SEQUENCE: 157
```

```
Met Gly Arg Gly Lys Val Gln Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Val Ile Val Phe
        35                  40                  45

Ser Pro Lys Gly Lys Leu Tyr Glu Tyr Ala Thr Asp Ser Ser Met Asp
    50                  55                  60

Lys Ile Leu Glu Arg Tyr Glu Arg Tyr Ser Tyr Ala Glu Lys Ala Leu
65                  70                  75                  80

Ile Ser Ala Glu Ser Glu Ser Glu Gly Asn Trp Cys His Glu Tyr Arg
                85                  90                  95

Lys Leu Lys Ala Lys Ile Glu Thr Ile Gln Lys Cys His Lys His Leu
            100                 105                 110

Met Gly Glu Asp Leu Asp Ser Leu Asn Leu Lys Glu Leu Gln Gln Leu
        115                 120                 125

Glu Gln Gln Leu Glu Ser Ser Leu Lys His Ile Arg Ser Arg Lys Ser
    130                 135                 140

His Leu Met Met Glu Ser Ile Ser Glu Leu Gln Lys Lys Glu Arg Ser
145                 150                 155                 160

Leu Gln Glu Glu Asn Lys Ala Leu Gln Lys Glu Leu Val Glu Arg Gln
                165                 170                 175

Lys Ala Ala Ser Arg Gln Gln Gln Leu Gln Gln Gln Gln Gln Gln Gln
            180                 185                 190

Gln Met Gln Trp Glu His Gln Ala Gln Thr Gln Thr His Thr His Thr
    195                 200                 205

Gln Asn Gln Pro Gln Ala Gln Thr Ser Ser Ser Ser Ser Ser Phe Met
210                 215                 220

Met Arg Asp Gln Gln Ala His Ala Pro Gln Gln Asn Ile Cys Ser Tyr
225                 230                 235                 240

Pro Pro Val Thr Met Gly Gly Glu Ala Thr Ala Ala Ala Ala Ala Pro
                245                 250                 255

Glu Gln Gln Ala Gln Leu Arg Ile Cys Leu Pro Pro Trp Met Leu Ser
            260                 265                 270

His Leu Asn Ala
        275
```

<210> SEQ ID NO 158
<211> LENGTH: 804
<212> TYPE: DNA
<213> ORGANISM: Oryza sativa

<400> SEQUENCE: 158

| | | |
|---|---|---|
| atgggcggg ggaaggtgca gctgaagcgg atagagaact cgatgaaccg gcaggtgacg | 60 |
| ttctccaaga ggaggaatgg attgctgaag aaggcgcacg agatctccgt cctctgcgac | 120 |
| gccgaggtcg ccgccatcgt cttctccccc aagggcaagc tctacgagta cgccactgac | 180 |
| tccaggatgg acaaaatcct tgaacgttat gagcgctatt catatgctga aaaggctctt | 240 |
| atttcagctg aatctgagag tgagggaaat tggtgccatg aatacaggaa gcttaaggca | 300 |
| aagattgaga ccatacaaaa atgtcacaaa caccttcatgg agaggatct agaatccctg | 360 |
| aatctcaaag aactccaaca gctagagcag cagctggaga gttcattgaa gcacataaga | 420 |
| tcaagaaaga gccaccttat gcttgagtcc atttccgagc tgcagaaaaa ggagaggtca | 480 |
| ctgcaggagg agaacaaggc tctgcagaag gaactggtgg agaggcagaa gattgtgagg | 540 |

```
ggccagcagc aagtagggca gtgggaccaa acccaggtcc aggcccaggc ccaagcccaa      600 cccccaagccc agacaagctt cttcttcttc ttcatgctga gggatcagca ggcacttctt      660
tcaccacaaa atatctgcta cccgccggtg atgatgggcc agagaaatga tgcggcggcg      720
cggcggcggt ggcggcccaa ggccaggtgc aacttccgca ttggaggctt ccgccatgg       780 atgctgagca ccttcaaggc ttaa                                              804
```

<210> SEQ ID NO 159
<211> LENGTH: 267
<212> TYPE: PRT
<213> ORGANISM: Oryza sativa

<400> SEQUENCE: 159

```
Met Gly Arg Gly Lys Val Gln Leu Lys Arg Ile Glu Asn Ser Met Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Ala Ile Val Phe
        35                  40                  45

Ser Pro Lys Gly Lys Leu Tyr Glu Tyr Ala Thr Asp Ser Arg Met Asp
    50                  55                  60

Lys Ile Leu Glu Arg Tyr Glu Arg Tyr Ser Tyr Ala Glu Lys Ala Leu
65                  70                  75                  80

Ile Ser Ala Glu Ser Glu Ser Glu Gly Asn Trp Cys His Glu Tyr Arg
                85                  90                  95

Lys Leu Lys Ala Lys Ile Glu Thr Ile Gln Lys Cys His Lys His Leu
            100                 105                 110

Met Gly Glu Asp Leu Glu Ser Leu Asn Leu Lys Glu Leu Gln Gln Leu
        115                 120                 125

Glu Gln Gln Leu Glu Ser Ser Leu Lys His Ile Arg Ser Arg Lys Ser
    130                 135                 140

His Leu Met Leu Glu Ser Ile Ser Glu Leu Gln Lys Lys Glu Arg Ser
145                 150                 155                 160

Leu Gln Glu Glu Asn Lys Ala Leu Gln Lys Glu Leu Val Glu Arg Gln
                165                 170                 175

Lys Asn Val Arg Gly Gln Gln Val Gly Gln Trp Asp Gln Thr Gln
            180                 185                 190

Val Gln Ala Gln Ala Gln Ala Gln Pro Gln Ala Gln Thr Ser Phe Phe
        195                 200                 205

Phe Phe Phe Met Leu Arg Asp Gln Gln Ala Leu Leu Ser Pro Gln Asn
    210                 215                 220

Ile Cys Tyr Pro Pro Val Met Met Gly Gln Arg Asn Asp Ala Ala Ala
225                 230                 235                 240

Arg Arg Arg Trp Arg Pro Lys Ala Arg Cys Asn Phe Arg Ile Gly Gly
                245                 250                 255

Phe Pro Pro Trp Met Leu Ser Thr Phe Lys Ala
            260                 265
```

<210> SEQ ID NO 160
<211> LENGTH: 804
<212> TYPE: DNA
<213> ORGANISM: Oryza sativa

<400> SEQUENCE: 160

```
atggggcggg ggaaggtgca gctgaagcgg atagagaaca agatcaacag gcaggtgacg      60
ttctccaaga ggaggaatgg attgctgaag aaggcgcacg agatctccgt cctctgcgac     120
```

```
gccgaggtcg ccgccatcgt cttctccccc aagggcaagc tctacgagta cgccactgac    180
tccaggatgg acaaaatcct tgaacgttat gagcgctatt catatgctga aaaggctctt    240
atttcagctg aatccgagag tgagggaaat tggtgccatg aatacaggaa acttaaggca    300
aagattgaga ccatacaaaa atgtcacaaa cacctcatgg gagaggatca tgaatccctg    360
aatctcaaag aactccaaca gctagagcag cagctggaga gttcattgaa gcacataata    420
tcaagaaaga gccaccttat gcttgagtcc atttccgagc tgcagaaaaa ggagaggtca    480
ctgcaggagg agaacaaggc tctgcagaag gaactggtgg agaggcagaa gaatgtgagg    540
ggccagcagc aagtagggca gtgggaccaa acccaggtcc aggcccaggc ccaagcccaa    600
ccccaagccc agacaagctc ctcctcctcc tccatgctga gggatcagca ggcacttctt    660
ccaccacaaa atatctgcta cccgccggtg atgatgggcg agagaaatga tgcggcggcg    720
gcggcggcgg tggcggcgca gggccaggtg caactccgca tcggaggtct tccgccatgg    780
atgctgagcc acctcaatgc ttaa                                           804
```

<210> SEQ ID NO 161
<211> LENGTH: 267
<212> TYPE: PRT
<213> ORGANISM: Oryza sativa

<400> SEQUENCE: 161

```
Met Gly Arg Gly Lys Val Gln Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Ala Ile Val Phe
        35                  40                  45

Ser Pro Lys Gly Lys Leu Tyr Glu Tyr Ala Thr Asp Ser Arg Met Asp
    50                  55                  60

Lys Ile Leu Glu Arg Tyr Glu Arg Tyr Ser Tyr Ala Glu Lys Ala Leu
65                  70                  75                  80

Ile Ser Ala Glu Ser Glu Ser Glu Gly Asn Trp Cys His Glu Tyr Arg
                85                  90                  95

Lys Leu Lys Ala Lys Ile Glu Thr Ile Gln Lys Cys His Lys His Leu
            100                 105                 110

Met Gly Glu Asp His Glu Ser Leu Asn Leu Lys Glu Leu Gln Gln Leu
        115                 120                 125

Glu Gln Gln Leu Glu Ser Ser Leu Lys His Ile Ile Ser Arg Lys Ser
    130                 135                 140

His Leu Met Leu Glu Ser Ile Ser Glu Leu Gln Lys Lys Glu Arg Ser
145                 150                 155                 160

Leu Gln Glu Glu Asn Lys Ala Leu Gln Lys Glu Leu Val Glu Arg Gln
                165                 170                 175

Lys Asn Val Arg Gly Gln Gln Val Gly Gln Trp Asp Gln Thr Gln
            180                 185                 190

Val Gln Ala Gln Ala Gln Ala Gln Pro Gln Ala Gln Thr Ser Ser Ser
        195                 200                 205

Ser Ser Ser Met Leu Arg Asp Gln Gln Ala Leu Leu Pro Pro Gln Asn
    210                 215                 220

Ile Cys Tyr Pro Pro Val Met Met Gly Glu Arg Asn Asp Ala Ala Ala
225                 230                 235                 240

Ala Ala Ala Val Ala Ala Gln Gly Gln Val Gln Leu Arg Ile Gly Gly
                245                 250                 255
```

```
Leu Pro Pro Trp Met Leu Ser His Leu Asn Ala
            260                 265
```

```
<210> SEQ ID NO 162
<211> LENGTH: 668
<212> TYPE: DNA
<213> ORGANISM: Tradescantia virginiana

<400> SEQUENCE: 162
gggctggtga agaaggctca tgagatctcd atkytrtgtg atgcyagggt tgcgcttatt     60
atttctcta ctaaaggcaa actatacgag tatgccactg attccaaaat ggaaaatatc    120
cttgaacgct atgaacgtta ctcatatgct gagaaggctt taacttcatc agatcctgaa    180
ttacagggaa attggtgcca agagtatgtt aaacttaagg ctaaggttga ggccttacat    240
aaaagccaaa ggcatcttat gggagagcaa ctagaagcgt tggatctcaa agaattgcag    300
caactagagc atcaacttga aggttctttg aggcttgtca ggtcaagaaa gactcaaatg    360
atgttggact ccatttccga acttcagagg aaggaaaagt ctctggaaga gcaaaacaag    420
aacctagaga aggagatttt ggagaagcag aaagaaaagg ctctggcaca ccaagctcac    480
tgggaacagc agaatcagcc actacaaagc actaattcgc ctccaaggcc cttcgtgatt    540
gcagaaactc atccaacact aaacattgga aatttccaag gtagaacaaa taccgtccat    600
gcagaagaaa gtctgcagcg tcagatgagg atcagcagca gcctactgcc mycmtggatg    660
mttcacma                                                              668
```

```
<210> SEQ ID NO 163
<211> LENGTH: 222
<212> TYPE: PRT
<213> ORGANISM: Tradescantia virginiana
<220> FEATURE:
<221> NAME/KEY: UNSURE
<222> LOCATION: (11)..(11)
<223> OTHER INFORMATION: Xaa can be any naturally occurring amino acid
<220> FEATURE:
<221> NAME/KEY: UNSURE
<222> LOCATION: (218)..(218)
<223> OTHER INFORMATION: Xaa can be any naturally occurring amino acid
<220> FEATURE:
<221> NAME/KEY: UNSURE
<222> LOCATION: (221)..(221)
<223> OTHER INFORMATION: Xaa can be any naturally occurring amino acid

<400> SEQUENCE: 163

Gly Leu Val Lys Lys Ala His Glu Ile Ser Xaa Leu Cys Asp Ala Glu
 1               5                  10                  15

Val Ala Leu Ile Ile Phe Ser Thr Lys Gly Lys Leu Tyr Glu Tyr Ala
            20                  25                  30

Thr Asp Ser Lys Met Glu Asn Ile Leu Glu Arg Tyr Glu Arg Tyr Ser
        35                  40                  45

Tyr Ala Glu Lys Ala Leu Thr Ser Ser Asp Pro Glu Leu Gln Gly Asn
    50                  55                  60

Trp Cys Gln Glu Tyr Val Lys Leu Lys Ala Lys Val Glu Ala Leu His
65                  70                  75                  80

Lys Ser Gln Arg His Leu Met Gly Glu Gln Leu Glu Ala Leu Asp Leu
                85                  90                  95

Lys Glu Leu Gln Gln Leu Glu His Gln Leu Glu Gly Ser Leu Arg Leu
            100                 105                 110

Val Arg Ser Arg Lys Thr Gln Met Met Leu Asp Ser Ile Ser Glu Leu
        115                 120                 125
```

```
Gln Arg Lys Glu Lys Ser Leu Glu Glu Gln Asn Lys Asn Leu Glu Lys
    130                 135                 140

Glu Ile Leu Glu Lys Gln Lys Glu Lys Ala Leu Ala His Gln Ala His
145                 150                 155                 160

Trp Glu Gln Gln Asn Gln Pro Leu Gln Ser Thr Asn Ser Pro Pro Arg
                165                 170                 175

Pro Phe Val Ile Ala Glu Thr His Pro Thr Leu Asn Ile Gly Asn Phe
            180                 185                 190

Gln Gly Arg Thr Asn Thr Val His Ala Glu Glu Ser Leu Gln Arg Gln
        195                 200                 205

Met Arg Ile Ser Ser Ser Leu Leu Pro Xaa Trp Met Xaa His
    210                 215                 220

<210> SEQ ID NO 164
<211> LENGTH: 723
<212> TYPE: DNA
<213> ORGANISM: Tradescantia virginiana

<400> SEQUENCE: 164
gtgcagctga acggatgga gaacaagatt aacaggcagg tgacgttttc taaacgtcga      60
ggagggctgc tgaagaaagc tcatgagatc tctattctat gtgatgctga gattgctctt     120
attattttct ctactaaagg gaagctctat gagtatgcca ccaattccaa atggacaat     180 attcttgaac gctatgagcg ttactcatat gctgaaaagg ctctaacttc atcagatcct     240
gatatacagg gaaattggtg ccaagagtat gctaaactta gtctaaggt tgaggcttta     300 tgtaaaagcc aaaggcatct tatgggagag cagcttgaaa cattgaatct caaagaattg     360
cagcaactag agcaacagct cgaaggttct ctaaagcatg tcaggtcaag aaagactcaa     420
gttatgctgg actctatttc tgaacttcag aggaaggaaa agtcactaga ggagcaaaac     480
aagaacctag agaaggagat tttggagaag cagaaaatca aggctcttgc acagcaggct     540
cactgggaac accagaatca accagcacca aggggttcac ctcctaggcc atttgtgatt     600
gcagagtctc atccgacact aaatattgga catttccaag gaggacaaa tgcagtcgaa     660 gcagaagaaa atcagcagcc tcakatgaga atttgcagta gcctcctgcc ccctggatg     720 ctt                                                                    723

<210> SEQ ID NO 165
<211> LENGTH: 241
<212> TYPE: PRT
<213> ORGANISM: Tradescantia virginiana
<220> FEATURE:
<221> NAME/KEY: UNSURE
<222> LOCATION: (228)..(228)
<223> OTHER INFORMATION: Xaa can be any naturally occurring amino acid

<400> SEQUENCE: 165

Val Gln Leu Lys Arg Met Glu Asn Lys Ile Asn Arg Gln Val Thr Phe
1               5                   10                  15

Ser Lys Arg Arg Gly Gly Leu Leu Lys Lys Ala His Glu Ile Ser Ile
            20                  25                  30

Leu Cys Asp Ala Glu Ile Ala Leu Ile Ile Phe Ser Thr Lys Gly Lys
        35                  40                  45

Leu Tyr Glu Tyr Ala Thr Asn Ser Lys Met Asp Asn Ile Leu Glu Arg
    50                  55                  60

Tyr Glu Arg Tyr Ser Tyr Ala Glu Lys Ala Leu Thr Ser Ser Asp Pro
65                  70                  75                  80

Asp Ile Gln Gly Asn Trp Cys Gln Glu Tyr Ala Lys Leu Lys Ser Lys
```

|  |  |  |  |  |  |  |  |  | 85 |  |  |  |  | 90 |  |  |  |  | 95 |  |  |
|---|---|---|---|---|---|---|---|---|---|---|---|---|---|---|---|---|---|---|---|---|---|

Val Glu Ala Leu Cys Lys Ser Gln Arg His Leu Met Gly Glu Gln Leu
                            100                 105                 110

Glu Thr Leu Asn Leu Lys Glu Leu Gln Gln Leu Glu Gln Gln Leu Glu
            115                 120                 125

Gly Ser Leu Lys His Val Arg Ser Arg Lys Thr Gln Val Met Leu Asp
        130                 135                 140

Ser Ile Ser Glu Leu Gln Arg Lys Glu Lys Ser Leu Glu Glu Gln Asn
145                 150                 155                 160

Lys Asn Leu Glu Lys Glu Ile Leu Glu Lys Gln Lys Ile Lys Ala Leu
                165                 170                 175

Ala Gln Gln Ala His Trp Glu His Gln Asn Gln Pro Ala Pro Arg Gly
            180                 185                 190

Ser Pro Pro Arg Pro Phe Val Ile Ala Glu Ser His Pro Thr Leu Asn
        195                 200                 205

Ile Gly His Phe Gln Gly Arg Thr Asn Ala Val Glu Ala Glu Asn
    210                 215                 220

Gln Gln Pro Xaa Met Arg Ile Cys Ser Ser Leu Leu Pro Pro Trp Met
225                 230                 235                 240

Leu

<210> SEQ ID NO 166
<211> LENGTH: 599
<212> TYPE: DNA
<213> ORGANISM: Tradescantia virginiana

<400> SEQUENCE: 166
gggctkgtga agaaagctca tgagatctcg gtactttgtg atgctgagct tgctcttatt       60
atcttctctc ccaaaggcaa gctctatgag tatgccaccg attccaaaat ggaaattatt      120
cttgaacgct atgaacgtta cacctacgct gaaaaagctt taattgcatc agatcctgat      180
gtacagggaa actggtgtca tgagtacatt aagcttaaag ctaaatttga ggccttgaat      240
aaaagccaga ggcatcttat gggagaacaa ctagatacgt tgaaccaaaa ggaattgctg      300
caactagaga ctaagcttga aggttctctg aaaaacgtca ggtcaagaaa gactcaactt      360
atgttggatt ccatttctga gcttcaagaa aagggaaagt cactccagga gcaaaacacc      420
tgcctagaaa aggagatttt gggaaaacag aaagacaagg ctcccaaaca gcatgttcag      480
tgggaaaaac agaatcaacc accacctacc tcttctgcgc aatgccattc ctcattggt      540 gatattcacc caacccctaa tatcagaaat ttccaaggca gaacagtagc tgatgcaga      599

<210> SEQ ID NO 167
<211> LENGTH: 199
<212> TYPE: PRT
<213> ORGANISM: Tradescantia virginiana

<400> SEQUENCE: 167

Gly Leu Val Lys Lys Ala His Glu Ile Ser Val Leu Cys Asp Ala Glu
1               5                   10                  15

Leu Ala Leu Ile Ile Phe Ser Pro Lys Gly Lys Leu Tyr Glu Tyr Ala
                20                  25                  30

Thr Asp Ser Lys Met Glu Ile Ile Leu Glu Arg Tyr Glu Arg Tyr Thr
            35                  40                  45

Tyr Ala Glu Lys Ala Leu Ile Ala Ser Asp Pro Asp Val Gln Gly Asn
        50                  55                  60

Trp Cys His Glu Tyr Ile Lys Leu Lys Ala Lys Phe Glu Ala Leu Asn

```
                65                  70                  75                  80
Lys Ser Gln Arg His Leu Met Gly Glu Gln Leu Asp Thr Leu Asn Gln
                    85                  90                  95

Lys Glu Leu Leu Gln Leu Glu Thr Lys Leu Glu Gly Ser Leu Lys Asn
                100                 105                 110

Val Arg Ser Arg Lys Thr Gln Leu Met Leu Asp Ser Ile Ser Glu Leu
            115                 120                 125

Gln Glu Lys Gly Lys Ser Leu Gln Glu Gln Asn Thr Cys Leu Glu Lys
        130                 135                 140

Glu Ile Leu Gly Lys Gln Lys Asp Lys Ala Pro Lys Gln His Val Gln
145                 150                 155                 160

Trp Glu Lys Gln Asn Gln Pro Pro Thr Ser Ser Ala Pro Met Pro
                165                 170                 175

Phe Leu Ile Gly Asp Ile His Pro Thr Pro Asn Ile Arg Asn Phe Gln
                180                 185                 190

Gly Arg Thr Val Ala Asp Ala
        195

<210> SEQ ID NO 168
<211> LENGTH: 753
<212> TYPE: DNA
<213> ORGANISM: Elaeis guineensis

<400> SEQUENCE: 168
atggggagag ggagggtgca gctgaggcgg atcgagaaca agataaaccg gcaggtgacg      60
ttctcgaagc gccggtcggg gctcctgaag aaagcccacg agatctccgt cctctgcgac     120
gccgaggtcg ccctcatcat cttctcgacc aagggcaagc tctacgagta cgccaccgac     180
tcctgcatgg aaaggattct tgaacgctat gaacgttaca cctatgcaga aaaagcacta     240
atttcatctg acccgaatt gcagggtaac tggtgccatg aatttggcaa actcaaagct     300
aaggttgagg ctttacaaaa aagccaaagg catctcatgg gtgagcaact tgagcccttg     360
aatctcaaag aactccagca actagagcaa cagcttgaaa gttcttttaaa gcatataaga     420 accagaaagt gccaactcat gtttgaatcc atctctgagc ttcaaaaaaa ggaaaagtca     480
ctgcaggagc agaacaagat gctggagaag gagctcatgg agaagcagaa ggtgaaggca     540
ctaaaccagc aggcacctttg ggagcagcaa ggccgccgc agacaagctc atcatcccca     600
acctccttcc tgatcggaga ctctctcccc accctgaata ttgggacata ccaatgtagc     660
ggaaatgaac atgggagga agcagcacaa ccccaggttc gtataggaaa cagcctgtta     720
ccaccttgga tgcttagcca cttgaacggg tag                                  753

<210> SEQ ID NO 169
<211> LENGTH: 250
<212> TYPE: PRT
<213> ORGANISM: Elaeis guineensis

<400> SEQUENCE: 169

Met Gly Arg Gly Arg Val Gln Leu Arg Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Ile Phe
        35                  40                  45

Ser Thr Lys Gly Lys Leu Tyr Glu Tyr Ala Thr Asp Ser Cys Met Glu
    50                  55                  60
```

```
Arg Ile Leu Glu Arg Tyr Glu Arg Tyr Thr Tyr Ala Glu Lys Ala Leu
 65                  70                  75                  80

Ile Ser Ser Gly Pro Glu Leu Gln Gly Asn Trp Cys His Glu Phe Gly
                 85                  90                  95

Lys Leu Lys Ala Lys Val Glu Ala Leu Gln Lys Ser Gln Arg His Leu
            100                 105                 110

Met Gly Glu Gln Leu Glu Pro Leu Asn Leu Lys Glu Leu Gln Gln Leu
        115                 120                 125

Glu Gln Gln Leu Glu Ser Ser Leu Lys His Ile Arg Thr Arg Lys Cys
130                 135                 140

Gln Leu Met Phe Glu Ser Ile Ser Glu Leu Gln Lys Lys Glu Lys Ser
145                 150                 155                 160

Leu Gln Glu Gln Asn Lys Met Leu Glu Lys Glu Leu Met Glu Lys Gln
                165                 170                 175

Lys Val Lys Ala Leu Asn Gln Gln Ala Pro Trp Glu Gln Gly Pro
            180                 185                 190

Pro Gln Thr Ser Ser Ser Pro Thr Ser Phe Leu Ile Gly Asp Ser
                195                 200                 205

Leu Pro Thr Leu Asn Ile Gly Thr Tyr Gln Cys Ser Gly Asn Glu His
    210                 215                 220

Gly Glu Glu Ala Ala Gln Pro Gln Val Arg Ile Gly Asn Ser Leu Leu
225                 230                 235                 240

Pro Pro Trp Met Leu Ser His Leu Asn Gly
                245                 250

<210> SEQ ID NO 170
<211> LENGTH: 699
<212> TYPE: DNA
<213> ORGANISM: Allium sp.

<400> SEQUENCE: 170
gtgcaattga agaggatgga aaacaagatt aatagacaag tgaccttctc aaaaagaaga      60
aatggtttgt tgaagaaagc tcatgagatt tcwgtgcttt gtgatgcaga agttgcactt     120
attgttttct ctgctaaagg aaaactctat gaatattcaa ctgattcaag tatggaaaaa     180
attctggaga ggtatgaacg ttattgcttt gcggagaaat catcaacaat gagtgacatt     240
gactcccagg aggattggag ccttgaatat cacaaactga aggctaaggt tgagagttta     300
aacaacaggc aaaggcatct tatgggagag caacttgaat ctctgagtct tcgagaaatt     360
ggacagcttg agcaacaact tgagaattct ctcaaaactg ttcggacgcg caagagccaa     420
gaattgttaa gttctatttc agagcttcag gacaaggaga aactttgcg atgagaac      480 aaagctttag aaaatgagct tatgaaaagg gccagggcaa aagctattct ggaacaacaa     540
gcacgatgga agcatcataa tcataaacaa caggataatc ttcataatcc aaatatcaac     600
attggaaatt accaaacaag gaacaatgag ggaggagttg agccagcaac ggatgttcaa     660
gtacgtgttg ttagaaattt gttgccccac tggatgctt                           699

<210> SEQ ID NO 171
<211> LENGTH: 233
<212> TYPE: PRT
<213> ORGANISM: Allium sp.

<400> SEQUENCE: 171

Val Gln Leu Lys Arg Met Glu Asn Lys Ile Asn Arg Gln Val Thr Phe
  1               5                  10                  15

Ser Lys Arg Arg Asn Gly Leu Leu Lys Lys Ala His Glu Ile Ser Val
```

|  |  |  | 20 |  |  |  | 25 |  |  |  | 30 |  |
|---|---|---|---|---|---|---|---|---|---|---|---|---|

Leu Cys Asp Ala Glu Val Ala Leu Ile Val Phe Ser Ala Lys Gly Lys
        35                  40                  45

Leu Tyr Glu Tyr Ser Thr Asp Ser Ser Met Glu Lys Ile Leu Glu Arg
50                      55                  60

Tyr Glu Arg Tyr Cys Phe Ala Glu Lys Ser Ser Thr Met Ser Asp Ile
65                      70                  75                  80

Asp Ser Gln Glu Asp Trp Ser Leu Glu Tyr His Lys Leu Lys Ala Lys
        85                  90                  95

Val Glu Ser Leu Asn Asn Arg Gln Arg His Leu Met Gly Glu Gln Leu
        100                105              110

Glu Ser Leu Ser Leu Arg Glu Ile Gly Gln Leu Glu Gln Gln Leu Glu
        115                120              125

Asn Ser Leu Lys Thr Val Arg Thr Arg Lys Ser Gln Glu Leu Leu Ser
        130                135              140

Ser Ile Ser Glu Leu Gln Asp Lys Glu Lys Thr Leu Arg Asp Glu Asn
145                    150                155              160

Lys Ala Leu Glu Asn Glu Leu Met Lys Arg Ala Arg Ala Lys Ala Ile
        165                170              175

Leu Glu Gln Gln Ala Arg Trp Lys His His Asn His Lys Gln Gln Asp
        180                185              190

Asn Leu His Asn Pro Asn Ile Asn Ile Gly Asn Tyr Gln Thr Arg Asn
        195                200              205

Asn Glu Gly Gly Val Glu Pro Ala Thr Asp Val Gln Val Arg Val Val
        210                215              220

Arg Asn Leu Leu Pro His Trp Met Leu
225                    230

<210> SEQ ID NO 172
<211> LENGTH: 744
<212> TYPE: DNA
<213> ORGANISM: Dendrobium grex Madame Thong-IN

<400> SEQUENCE: 172

```
atgggtcgtg caggatgca gctgaagcga atcgagaata aaataaaccg gcaggtgacg      60
ttctcgaagc ggagatctgg tttgcttaag aaggcgcacg agatctccgt gctctgtgac    120
gctgaagttg ctctgatcgt tttttccaat aagggaaagc tttatgagta ttccaccgat    180
tccagcatgg agaaaattct gaacggtat gagcgttatt catatgctga aagagcatta    240
ttttccaatg aggccaaccc ccaggctgat tggcgccttg aatataataa actgaaggca    300
agggttgaaa gcttacagaa gagccaaagg caccttatgg gggagcaact tgactccttg    360
agcattaaag aactccaacg tctagagcaa cagcttgaaa gttccttgaa gtttatacga    420
tccagaaaga cacagctcat actacattca atttccgagc tacaaaagat ggaaaaaata    480
ttgctggagc aaaacaagac cttagagaag agattatag ctaaagagaa agccaaagct    540
ttggtgcagc atgccccatg ggaagaagcaa accagtccc aatatagctc tgcactccg    600
cctgtgattt cggattctgt cccaactccc accagcagaa cgtttcaagc cagagccaat    660
gaagaagaat cacctcagcc acagttaaga gtaagcaaca ctctgctgcc cccatggatg    720
ctcagtcata tgaatggaca ataa                                          744
```

<210> SEQ ID NO 173
<211> LENGTH: 247
<212> TYPE: PRT
<213> ORGANISM: Dendrobium grex Madame Thong-IN

```
<400> SEQUENCE: 173

Met Gly Arg Gly Arg Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Val Phe
        35                  40                  45

Ser Asn Lys Gly Lys Leu Tyr Glu Tyr Ser Thr Asp Ser Ser Met Glu
    50                  55                  60

Lys Ile Leu Glu Arg Tyr Glu Arg Tyr Ser Tyr Ala Glu Arg Ala Leu
65                  70                  75                  80

Phe Ser Asn Glu Ala Asn Pro Gln Ala Asp Trp Arg Leu Glu Tyr Asn
                85                  90                  95

Lys Leu Lys Ala Arg Val Glu Ser Leu Gln Lys Ser Gln Arg His Leu
            100                 105                 110

Met Gly Glu Gln Leu Asp Ser Leu Ser Ile Lys Glu Leu Gln Arg Leu
        115                 120                 125

Glu Gln Gln Leu Glu Ser Ser Leu Lys Phe Ile Arg Ser Arg Lys Thr
    130                 135                 140

Gln Leu Ile Leu His Ser Ile Ser Glu Leu Gln Lys Met Glu Lys Ile
145                 150                 155                 160

Leu Leu Glu Gln Asn Lys Thr Leu Glu Lys Glu Ile Ile Ala Lys Glu
                165                 170                 175

Lys Ala Lys Ala Leu Val Gln His Ala Pro Trp Glu Lys Gln Asn Gln
            180                 185                 190

Ser Gln Tyr Ser Ser Ala Leu Pro Pro Val Ile Ser Asp Ser Val Pro
        195                 200                 205

Thr Pro Thr Ser Arg Thr Phe Gln Ala Arg Ala Asn Glu Glu Glu Ser
    210                 215                 220

Pro Gln Pro Gln Leu Arg Val Ser Asn Thr Leu Leu Pro Pro Trp Met
225                 230                 235                 240

Leu Ser His Met Asn Gly Gln
                245

<210> SEQ ID NO 174
<211> LENGTH: 2194
<212> TYPE: DNA
<213> ORGANISM: Oryza sativa

<400> SEQUENCE: 174
aatccgaaaa gtttctgcac cgttttcacc ccctaactaa caatataggg aacgtgtgct      60
aaatataaaa tgagacctta tatatgtagc gctgataact agaactatgc aagaaaaact     120
catccaccta ctttagtggc aatcgggcta aataaaaaag agtcgctaca ctagtttcgt     180
tttccttagt aattaagtgg gaaatgaaa  tcattattgc ttagaatata cgttcacatc     240
tctgtcatga agttaaatta ttcgaggtag ccataattgt catcaaactc ttccttaata     300
aaaaaatctt tctagctgaa ctcaatgggt aaagagagag attttttta  aaaaaataga    360 atgaagatat tctgaacgta ttggcaaaga tttaaacata taattatata attttatagt     420
ttgtgcattc gtcatatcgc acatcattaa ggacatgtct tactccatcc caattttat     480 ttagtaatta aagacaattg acttattttt attatttatc ttttttcgat tagatgcaag     540
gtacttacgc acacactttg tgctcatgtg catgtgtgag tgcacctcct caatacacgt     600
tcaactagca acacatctct aatatcactc gcctatttaa tacatttagg tagcaatatc     660
```

```
tgaattcaag cactccacca tcaccagacc acttttaata atatctaaaa tacaaaaaat    720
aattttacag aatagcatga aaagtatgaa acgaactatt taggtttttc acatacaaaa    780
aaaaaaagaa ttttgctcgt gcgcgagcgc caatctccca tattgggcac acaggcaaca    840
acagagtggc tgcccacaga acaacccaca aaaaacgatg atctaacgga ggacagcaag    900
tccgcaacaa ccttttaaca gcaggctttg cggccaggag agaggaggag aggcaaagaa    960
aaccaagcat cctccttctc ccatctataa attcctcccc ccttttcccc tctctatata   1020
ggaggcatcc aagccaagaa gagggagagc accaaggaca cgcgactagc agaagccgag   1080
cgaccgcctt ctcgatccat atcttccggt cgagttcttg gtcgatctct ccctcctcc    1140 acctcctcct cacagggtat gtgcctccct tcggttgttc ttggatttat tgttctaggt   1200
tgtgtagtac gggcgttgat gttaggaaag gggatctgta tctgtgatga ttcctgttct   1260
tggatttggg atagaggggt tcttgatgtt gcatgttatc ggttcggttt gattagtagt   1320
atggttttca atcgtctgga gagctctatg gaaatgaaat ggtttaggga tcggaatctt   1380
gcgattttgt gagtaccttt tgtttgaggt aaaatcagag caccggtgat tttgcttggt   1440
gtaataaagt acgttgttt ggtcctcgat tctggtagtg atgcttctcg atttgacgaa    1500
gctatccttt gtttattccc tattgaacaa aaataatcca actttgaaga cggtcccgtt   1560
gatgagattg aatgattgat tcttaagcct gtccaaaatt tcgcagctgg cttgtttaga   1620
tacagtagtc cccatcacga aattcatgga aacagttata atcctcagga cagggggatt   1680
ccctgttctt ccgatttgct ttagtcccag aattttttt cccaaatatc ttaaaaagtc    1740
actttctggt tcagttcaat gaattgattg ctacaaataa tgcttttata gcgttatcct   1800
agctgtagtt cagttaatag gtaataccc tatagtttag tcaggagaag aacttatccg    1860
atttctgatc tccattttta attatatgaa atgaactgta gcataagcag tattcatttg   1920 gattatttt tttattagct ctcacccctt cattattctg agctgaaagt ctggcatgaa    1980
ctgtcctcaa ttttgttttc aaattcacat cgattatcta tgcattatcc tcttgtatct   2040
acctgtagaa gttctttttt ggttattcct tgactgcttg attacagaaa gaaatttatg   2100
aagctgtaat cgggatagtt atactgcttg ttcttatgat tcatttcctt tgtgcagttc   2160
ttggtgtagc ttgccacttt caccagcaaa gttc                              2194
```

<210> SEQ ID NO 175
<211> LENGTH: 1725
<212> TYPE: DNA
<213> ORGANISM: Arabidopsis thaliana

<400> SEQUENCE: 175

```
atgaattcta caactggct tggctttcct ctttcaccga caactcttc tttgcctcct      60 catgaataca accttggctt ggtcagcgac catatggaca acccttttca aacacaagag    120
tggaatatga tcaatccaca cggtggagga ggagatgaag gaggagaggt tccaaaagtg    180
gccgattttc tcggtgtgag caaaccggac gaaaaccaat ccaaccacct agtagcttac    240
aacgactcag actactactt ccataccaat agcttgatgc ctagcgtcca atcaaacgat    300
gtcgttgtag cagcttgtga ctccaatact cctaacaaca gtagctatca tgagcttcaa    360
gagagtgctc acaatctaca gtcacttact ttgtccatgg ggaccaccgc tggtaataat    420
gttgtagaca aagcttcacc atccgagacc accggggata acgctagcgg tggagcacta    480
gccgttgttg agacggccac gccaagacgt gcattggaca ctttcggaca acgaacctcg    540
atctatcgtg gtgtcacaag acatcgatgg actggtcgat atgaggctca tctatgggat    600
```

-continued

```
aatagttgta gaagggaagg ccagtctagg aaaggaagac aagtttactt gggtggatat    660
gataaagaag ataaagcagc aagatcatat gatctagctg cacttaagta ctggggtccc    720
tcaactacta ctaatttccc cattacaaac tacgagaaag aagtagagga atgaagcac     780 atgacgaggc aagagttcgt ggctgccatt agaaggaaaa gtagtggatt tcgagaggc     840 gcttcgatgt atcgaggagt tacaaggcac caccaacatg gaagatgcaa gcaaggatc     900 ggccgagtcg ccgggaacaa agacctctac ttgggaactt ttagcactga ggaagaagca    960
gcagaagctt acgatatagc tgcaataaag tttagaggac ttaatgcagt gaccaacttc    1020
gagatcaacc ggtacgacgt gaaagccatt ctagagagta gcactcttcc catcggagga    1080
ggcgcagcta acggctcaa agaagctcaa gctcttgagt cttcaaggaa acgcgaggcg     1140
gagatgatag cccttggttc aagtttccag tacggtggtg gctcgagcac aggctctggc    1200
tccacctcat caagacttca gcttcaacct taccctctaa gcattcaaca accattagag    1260 cctttttctat ctcttcagaa caatgacatc tctcattaca acaacaacaa tgctcacgat   1320
tcctcctctt ttaatcacca tagctatatc cagacacaac ttcatctcca ccaacagacc    1380
aacaattact tgcagcaaca gtcgagccag aactctcagc agctctacaa tgcgtatctt    1440
catagcaatc cggctctgct tcatggactt gtctctacct ctatcgttga caacaataat    1500
aacaatggag gctctagtgg gagctacaac actgcagcat ttcttgggaa ccacggtatt    1560
ggtattgggt ccagctcgac tgttggatcg accgaggagt tccaaccgt taaaacagat    1620 tacgatatgc cttccagtga tggaaccgga gggtatagtg gttggaccag tgagtctgtt    1680 cagggggtcaa accctggtgg tgttttcact atgtggaatg agtaa                    1725
```

<210> SEQ ID NO 176
<211> LENGTH: 574
<212> TYPE: PRT
<213> ORGANISM: Arabidopsis thaliana

<400> SEQUENCE: 176

```
Met Asn Ser Asn Asn Trp Leu Gly Phe Pro Leu Ser Pro Asn Asn Ser
1               5                   10                  15

Ser Leu Pro Pro His Glu Tyr Asn Leu Gly Leu Val Ser Asp His Met
            20                  25                  30

Asp Asn Pro Phe Gln Thr Gln Glu Trp Asn Met Ile Asn Pro His Gly
        35                  40                  45

Gly Gly Gly Asp Glu Gly Gly Glu Val Pro Lys Val Ala Asp Phe Leu
    50                  55                  60

Gly Val Ser Lys Pro Asp Glu Asn Gln Ser Asn His Leu Val Ala Tyr
65                  70                  75                  80

Asn Asp Ser Asp Tyr Tyr Phe His Thr Asn Ser Leu Met Pro Ser Val
                85                  90                  95

Gln Ser Asn Asp Val Val Ala Ala Cys Asp Ser Asn Thr Pro Asn
            100                 105                 110

Asn Ser Ser Tyr His Glu Leu Gln Glu Ser Ala His Asn Leu Gln Ser
        115                 120                 125

Leu Thr Leu Ser Met Gly Thr Thr Ala Gly Asn Asn Val Val Asp Lys
    130                 135                 140

Ala Ser Pro Ser Glu Thr Thr Gly Asp Asn Ala Ser Gly Gly Ala Leu
145                 150                 155                 160

Ala Val Val Glu Thr Ala Thr Pro Arg Arg Ala Leu Asp Thr Phe Gly
                165                 170                 175
```

-continued

```
Gln Arg Thr Ser Ile Tyr Arg Gly Val Thr Arg His Arg Trp Thr Gly
            180                 185                 190

Arg Tyr Glu Ala His Leu Trp Asp Asn Ser Cys Arg Glu Gly Gln
        195                 200                 205

Ser Arg Lys Gly Arg Gln Val Tyr Leu Gly Gly Tyr Asp Lys Glu Asp
210                 215                 220

Lys Ala Ala Arg Ser Tyr Asp Leu Ala Ala Leu Lys Tyr Trp Gly Pro
225                 230                 235                 240

Ser Thr Thr Thr Asn Phe Pro Ile Thr Asn Tyr Glu Lys Glu Val Glu
                245                 250                 255

Glu Met Lys His Met Thr Arg Gln Glu Phe Val Ala Ala Ile Arg Arg
            260                 265                 270

Lys Ser Ser Gly Phe Ser Arg Gly Ala Ser Met Tyr Arg Gly Val Thr
        275                 280                 285

Arg His His Gln His Gly Arg Trp Gln Ala Arg Ile Gly Arg Val Ala
    290                 295                 300

Gly Asn Lys Asp Leu Tyr Leu Gly Thr Phe Ser Thr Glu Glu Glu Ala
305                 310                 315                 320

Ala Glu Ala Tyr Asp Ile Ala Ala Ile Lys Phe Arg Gly Leu Asn Ala
                325                 330                 335

Val Thr Asn Phe Glu Ile Asn Arg Tyr Asp Val Lys Ala Ile Leu Glu
            340                 345                 350

Ser Ser Thr Leu Pro Ile Gly Gly Ala Ala Lys Arg Leu Lys Glu
        355                 360                 365

Ala Gln Ala Leu Glu Ser Ser Arg Lys Arg Glu Ala Glu Met Ile Ala
370                 375                 380

Leu Gly Ser Ser Phe Gln Tyr Gly Gly Gly Ser Ser Thr Gly Ser Gly
385                 390                 395                 400

Ser Thr Ser Ser Arg Leu Gln Leu Gln Pro Tyr Pro Leu Ser Ile Gln
                405                 410                 415

Gln Pro Leu Glu Pro Phe Leu Ser Leu Gln Asn Asn Asp Ile Ser His
            420                 425                 430

Tyr Asn Asn Asn Ala His Asp Ser Ser Ser Phe Asn His His Ser
        435                 440                 445

Tyr Ile Gln Thr Gln Leu His Leu His Gln Thr Asn Asn Tyr Leu
    450                 455                 460

Gln Gln Gln Ser Ser Gln Asn Ser Gln Gln Leu Tyr Asn Ala Tyr Leu
465                 470                 475                 480

His Ser Asn Pro Ala Leu Leu His Gly Leu Val Ser Thr Ser Ile Val
                485                 490                 495

Asp Asn Asn Asn Asn Gly Gly Ser Ser Gly Ser Tyr Asn Thr Ala
            500                 505                 510

Ala Phe Leu Gly Asn His Gly Ile Gly Ile Gly Ser Ser Thr Val
        515                 520                 525

Gly Ser Thr Glu Glu Phe Pro Thr Val Lys Thr Asp Tyr Asp Met Pro
    530                 535                 540

Ser Ser Asp Gly Thr Gly Gly Tyr Ser Gly Trp Thr Ser Glu Ser Val
545                 550                 555                 560

Gln Gly Ser Asn Pro Gly Gly Val Phe Thr Met Trp Asn Glu
                565                 570
```

<210> SEQ ID NO 177
<211> LENGTH: 1707
<212> TYPE: DNA
<213> ORGANISM: Arabidopsis thaliana

<400> SEQUENCE: 177

```
atgaattcta caactggct cgcgttccct ctatcaccaa ctcactcttc tttgccgcct      60
cacattcact cttcacaaaa ttctcatttc aatctaggtt tggtcaacga caatatcgac    120
aaccctttc aaaaccaagg atggaatatg atcaatccac atggtggagg cggcgaaggt    180
ggagaggttc caaaagtggc tgatttctta ggagtgagca atcggggga tcatcacacc    240
gatcacaacc tcgtaccta taacgacatt catcaaacca acgcctccga ctactacttt    300
caaaccaata gcttgttacc tacagtcgtc acttgtgcct ctaatgctcc taataattat    360
gagcttcaag agagtgcaca caatttgcaa tctctcactc tctctatggg aagtactgga    420
gctgccgctg cagaagtcgc cactgtgaaa gcctcgccgg ctgagactag tgccgataat    480
agtagcagca ctaccaacac aagcggagga gccatcgttg aggctacacc gagacggact    540
ttggaaactt ttggacaacg aacctctatc tatcgtggag ttacaagaca tagatggacc    600
ggtagatatg aagctcatct ttgggataat agctgtagaa gagaaggaca atcaaggaaa    660
ggaagacaag tctacttagg tgggtatgac aaagaagaga agcagccag agcatatgat    720
ctagctgcac ttaaatattg gggtccctct actactacca acttccgat aactaactac    780
gagaaggaag tagaggagat gaaaaacatg acgagacaag agtttgtggc ttctataaga    840
aggaagagta gcggattctc gcgtggtgca tccatgtatc gtggagtaac aaggcatcat    900
caacatggaa gatggcaagc aaggatcggc cgagttgctg aaacaaaga tctctacttg    960
ggaacattca gcacggagga agaagcagca gaagcttatg acatagctgc gataaagttt   1020
cgaggtctaa acgcggttac aaactttgag ataaatcggt atgatgtgaa agccatcctg   1080
gagagcaaca cacttcctat aggaggtggt gcggctaaac ggctcaaaga agctcaagct   1140
ctagaatcat caagaaaacg agaggaaatg atagccctcg atcaaatttt ccatcaatat   1200
ggtgcagcga gcggctcgag ctctgttgct tccagctcta ggcttcagct tcaaccttac   1260
cctctaagca ttcaacaacc ttttgagcat cttcatcatc atcagccttt acttactcta   1320
cagaacaaca acgatatctc tcagtatcat gattccttta gttacattca gacgcagctt   1380
catcttcacc aacaacaaac caacaattac ttgcagtctt ctagtcacac ttcacagctc   1440
tacaatgctt atcttcagag taaccctggt ctgcttcatg gatttgtctc tgataataac   1500
aacacttcag ggtttcttgg aaacaatggg attggtattg ggtcaagctc taccgttgga   1560
tcatcggctg aggaagagtt tccagccgtg aaagtcgatt acgatatgcc tccttccggt   1620
ggagctacag ggtatggagg atggaatagt ggagagtctg ctcaaggatc gaatccagga   1680
ggtgttttca cgatgtggaa tgaataa                                      1707
```

<210> SEQ ID NO 178
<211> LENGTH: 568
<212> TYPE: PRT
<213> ORGANISM: Arabidopsis thaliana

<400> SEQUENCE: 178

```
Met Asn Ser Asn Asn Trp Leu Ala Phe Pro Leu Ser Pro Thr His Ser
1               5                   10                  15

Ser Leu Pro Pro His Ile His Ser Ser Gln Asn Ser His Phe Asn Leu
            20                  25                  30

Gly Leu Val Asn Asp Asn Ile Asp Asn Pro Phe Gln Asn Gln Gly Trp
        35                  40                  45

Asn Met Ile Asn Pro His Gly Gly Gly Glu Gly Gly Glu Val Pro
    50                  55                  60
```

```
Lys Val Ala Asp Phe Leu Gly Val Ser Lys Gly Asp His His Thr
 65                  70                  75                  80

Asp His Asn Leu Val Pro Tyr Asn Asp Ile His Gln Thr Asn Ala Ser
                  85                  90                  95

Asp Tyr Tyr Phe Gln Thr Asn Ser Leu Leu Pro Thr Val Val Thr Cys
            100                 105                 110

Ala Ser Asn Ala Pro Asn Asn Tyr Glu Leu Gln Glu Ser Ala His Asn
            115                 120                 125

Leu Gln Ser Leu Thr Leu Ser Met Gly Ser Thr Gly Ala Ala Ala
        130                 135                 140

Glu Val Ala Thr Val Lys Ala Ser Pro Ala Glu Thr Ser Ala Asp Asn
145                 150                 155                 160

Ser Ser Ser Thr Thr Asn Thr Ser Gly Gly Ala Ile Val Glu Ala Thr
                165                 170                 175

Pro Arg Arg Thr Leu Glu Thr Phe Gly Gln Arg Thr Ser Ile Tyr Arg
                180                 185                 190

Gly Val Thr Arg His Arg Trp Thr Gly Arg Tyr Glu Ala His Leu Trp
            195                 200                 205

Asp Asn Ser Cys Arg Arg Glu Gly Gln Ser Arg Lys Gly Arg Gln Val
        210                 215                 220

Tyr Leu Gly Gly Tyr Asp Lys Glu Glu Lys Ala Ala Arg Ala Tyr Asp
225                 230                 235                 240

Leu Ala Ala Leu Lys Tyr Trp Gly Pro Ser Thr Thr Thr Asn Phe Pro
                245                 250                 255

Ile Thr Asn Tyr Glu Lys Glu Val Glu Glu Met Lys Asn Met Thr Arg
                260                 265                 270

Gln Glu Phe Val Ala Ser Ile Arg Arg Lys Ser Ser Gly Phe Ser Arg
            275                 280                 285

Gly Ala Ser Met Tyr Arg Gly Val Thr Arg His His Gln His Gly Arg
        290                 295                 300

Trp Gln Ala Arg Ile Gly Arg Val Ala Gly Asn Lys Asp Leu Tyr Leu
305                 310                 315                 320

Gly Thr Phe Ser Thr Glu Glu Ala Ala Glu Ala Tyr Asp Ile Ala
                325                 330                 335

Ala Ile Lys Phe Arg Gly Leu Asn Ala Val Thr Asn Phe Glu Ile Asn
            340                 345                 350

Arg Tyr Asp Val Lys Ala Ile Leu Glu Ser Asn Thr Leu Pro Ile Gly
        355                 360                 365

Gly Gly Ala Ala Lys Arg Leu Lys Glu Ala Gln Ala Leu Glu Ser Ser
        370                 375                 380

Arg Lys Arg Glu Glu Met Ile Ala Leu Gly Ser Asn Phe His Gln Tyr
385                 390                 395                 400

Gly Ala Ala Ser Gly Ser Ser Ser Val Ala Ser Ser Ser Arg Leu Gln
                405                 410                 415

Leu Gln Pro Tyr Pro Leu Ser Ile Gln Gln Pro Phe Glu His Leu His
                420                 425                 430

His His Gln Pro Leu Leu Thr Leu Gln Asn Asn Asn Asp Ile Ser Gln
        435                 440                 445

Tyr His Asp Ser Phe Ser Tyr Ile Gln Thr Leu His Leu His Gln
        450                 455                 460

Gln Gln Thr Asn Asn Tyr Leu Gln Ser Ser Ser His Thr Ser Gln Leu
465                 470                 475                 480

Tyr Asn Ala Tyr Leu Gln Ser Asn Pro Gly Leu Leu His Gly Phe Val
```

485                 490                 495
Ser Asp Asn Asn Asn Thr Ser Gly Phe Leu Gly Asn Asn Gly Ile Gly
            500                 505                 510

Ile Gly Ser Ser Thr Val Gly Ser Ser Ala Glu Glu Glu Phe Pro
        515                 520                 525

Ala Val Lys Val Asp Tyr Asp Met Pro Pro Ser Gly Gly Ala Thr Gly
        530                 535                 540

Tyr Gly Gly Trp Asn Ser Gly Glu Ser Ala Gln Gly Ser Asn Pro Gly
545                 550                 555                 560

Gly Val Phe Thr Met Trp Asn Glu
            565

<210> SEQ ID NO 179
<211> LENGTH: 1662
<212> TYPE: DNA
<213> ORGANISM: Glycine max

<400> SEQUENCE: 179
atgaacaaca actggctttc gttccctctt tctcctactc attcttcctt accagctcat      60
gatcttcaag caactcaata tcatcaattt tcccttgggt tagtgaacga gaacatggat     120
aaccctttcc aaaatcatga ttggaatctg attaacaccc atagtagcaa cgaaattcca     180
aaagtggctg attttctagg agtgagcaag tctgaaaatc agtcagacct tgcagcctta     240
aacgaaattc attcaaatga ttcagattat ctgttcacaa caacagtctg gtgcctatg      300
caaaaccctg tgttggacac acctagcaat gagtatcaag aaaatgctaa tagtaatttg     360
caatcattga cattatccat gggaagtggt aaggattcaa catgtgaaac cagtggtgaa     420
aatagcacaa acactactgt tgaagttgca cctagaagaa ctttggatac attcgggcag     480
agaacatcca tatatcgtgg agtaactcga catagatgga ctggaaggta tgaagctcat     540
ctttgggata tagctgtag aagggaaggc caatcaagaa aaggacgcca agtttatttg     600
ggtggatatg ataaagaaga gaaagcagct agagcttatg atttagctgc actgaagtac     660
tggggggacat ccaccactac caactttcca attagcaact atgagaagga attggatgaa     720
atgaaacaca tgacgagaca agaatttgtt gccgccatta aaggaaaag cagtggtttc      780
tccaggggtg catcaatgta tcgtggagtt acaaggcatc accaacacgg aagatggcaa     840
gcaaggattg gcagagttgc aggaaacaaa gatctttact tgggaacttt cagtactgag     900
gaagaggctg cagaagcata cgacatagca gcgataaagt tcagaggtct caacgctgtc     960
acaaactttg acatgagccg ctacgacgtg aaagccattc ttgaaagcaa cactctccca    1020
ataggaggag gcgctgcaaa gcgtctgaaa gaagctcaag ctctagaatc ttcgagaaaa    1080
cgcgaagaga tgattgcact aggctcatct tccacgttcc aatacggaac ctcagcaagc    1140
tcttctaggc ttcacgctta ccctctaatg cagcaccacc accagttcga gcaacctcaa    1200
cctctgctaa ctcttcaaaa ccacgacata agttcttctc acttctctca ccagcaagac    1260
cctttgcatc atcagggtta catccaaacg cagcttcagt tgcaccagca gagtggcgct    1320
tcttcttata gctttcagaa taatgctcag ttctacaatg ttaccttca gaaccaccct      1380
gcattgcttc agggaatgat gaacatgggg tcttcttctt cttcctcatc tgtgttggag    1440
aataataata gtaacaataa taataataat gttggtgggt tgtgggaag tgggtttggt      1500
atggcttcga atgcaacggc ggggaacacg gtggggacag cggaggagtt agggctggtg    1560
aaggtggact atgacatgcc ggctggaggt tacgtggct ggtcggcggc ggactccatg      1620
cagacgtcaa atggtggggt gttcacaatg tggaatgatt aa                       1662

<210> SEQ ID NO 180
<211> LENGTH: 553
<212> TYPE: PRT
<213> ORGANISM: Glycine max

<400> SEQUENCE: 180

```
Met Asn Asn Asn Trp Leu Ser Phe Pro Leu Ser Pro Thr His Ser Ser
1               5                   10                  15

Leu Pro Ala His Asp Leu Gln Ala Thr Gln Tyr His Gln Phe Ser Leu
            20                  25                  30

Gly Leu Val Asn Glu Asn Met Asp Asn Pro Phe Gln Asn His Asp Trp
        35                  40                  45

Asn Leu Ile Asn Thr His Ser Ser Asn Glu Ile Pro Lys Val Ala Asp
50                  55                  60

Phe Leu Gly Val Ser Lys Ser Glu Asn Gln Ser Asp Leu Ala Ala Leu
65                  70                  75                  80

Asn Glu Ile His Ser Asn Asp Ser Asp Tyr Leu Phe Thr Asn Asn Ser
                85                  90                  95

Leu Val Pro Met Gln Asn Pro Val Leu Asp Thr Pro Ser Asn Glu Tyr
            100                 105                 110

Gln Glu Asn Ala Asn Ser Asn Leu Gln Ser Leu Thr Leu Ser Met Gly
        115                 120                 125

Ser Gly Lys Asp Ser Thr Cys Glu Thr Ser Gly Glu Asn Ser Thr Asn
130                 135                 140

Thr Thr Val Glu Val Ala Pro Arg Arg Thr Leu Asp Thr Phe Gly Gln
145                 150                 155                 160

Arg Thr Ser Ile Tyr Arg Gly Val Thr Arg His Arg Trp Thr Gly Arg
                165                 170                 175

Tyr Glu Ala His Leu Trp Asp Asn Ser Cys Arg Arg Glu Gly Gln Ser
            180                 185                 190

Arg Lys Gly Arg Gln Val Tyr Leu Gly Gly Tyr Asp Lys Glu Glu Lys
        195                 200                 205

Ala Ala Arg Ala Tyr Asp Leu Ala Ala Leu Lys Tyr Trp Gly Thr Ser
210                 215                 220

Thr Thr Thr Asn Phe Pro Ile Ser Asn Tyr Glu Lys Glu Leu Asp Glu
225                 230                 235                 240

Met Lys His Met Thr Arg Gln Glu Phe Val Ala Ala Ile Arg Arg Lys
                245                 250                 255

Ser Ser Gly Phe Ser Arg Gly Ala Ser Met Tyr Arg Gly Val Thr Arg
            260                 265                 270

His His Gln His Gly Arg Trp Gln Ala Arg Ile Gly Arg Val Ala Gly
        275                 280                 285

Asn Lys Asp Leu Tyr Leu Gly Thr Phe Ser Thr Glu Glu Ala Ala
290                 295                 300

Glu Ala Tyr Asp Ile Ala Ala Ile Lys Phe Arg Gly Leu Asn Ala Val
305                 310                 315                 320

Thr Asn Phe Asp Met Ser Arg Tyr Asp Val Lys Ala Ile Leu Glu Ser
                325                 330                 335

Asn Thr Leu Pro Ile Gly Gly Ala Ala Lys Arg Leu Lys Glu Ala
            340                 345                 350

Gln Ala Leu Glu Ser Ser Arg Lys Arg Glu Glu Met Ile Ala Leu Gly
        355                 360                 365

Ser Ser Ser Thr Phe Gln Tyr Gly Thr Ser Ala Ser Ser Arg Leu
370                 375                 380
```

```
His Ala Tyr Pro Leu Met Gln His His Gln Phe Glu Gln Pro Gln
385                 390                 395                 400

Pro Leu Leu Thr Leu Gln Asn His Asp Ile Ser Ser His Phe Ser
            405                 410                 415

His Gln Gln Asp Pro Leu His His Gln Gly Tyr Ile Gln Thr Gln Leu
        420                 425                 430

Gln Leu His Gln Gln Ser Gly Ala Ser Ser Tyr Ser Phe Gln Asn Asn
            435                 440                 445

Ala Gln Phe Tyr Asn Gly Tyr Leu Gln Asn His Pro Ala Leu Leu Gln
    450                 455                 460

Gly Met Met Asn Met Gly Ser Ser Ser Ser Ser Ser Val Leu Glu
465                 470                 475                 480

Asn Asn Asn Ser Asn Asn Asn Asn Asn Val Gly Gly Phe Val Gly
                485                 490                 495

Ser Gly Phe Gly Met Ala Ser Asn Ala Thr Ala Gly Asn Thr Val Gly
            500                 505                 510

Thr Ala Glu Glu Leu Gly Leu Val Lys Val Asp Tyr Asp Met Pro Ala
        515                 520                 525

Gly Gly Tyr Gly Gly Trp Ser Ala Ala Asp Ser Met Gln Thr Ser Asn
    530                 535                 540

Gly Gly Val Phe Thr Met Trp Asn Asp
545                 550

<210> SEQ ID NO 181
<211> LENGTH: 1674
<212> TYPE: DNA
<213> ORGANISM: Glycine max

<400> SEQUENCE: 181
atgaacaaca actggctttc gttccctctt tctcctactc attcttcctt accagctcat     60
gatcttcaag caactcaata tcatcaattt tcccttgggt tagtgaacga aacatggat    120 aacccttttcc aaaatcatga ttggaatctg attacaccc atagtagcaa cgaaattcca    180
aaagtggctg attttctagg agtgagcaag tctgaaaatc agtcagacct tgcagcctta    240
aacgaaattc attcaaatga ttcagattat ctgttcacaa caacagtct ggtgcctatg    300 caaaaccctg tgttggacac acctagcaat gagtatcaag aaaatgctaa tagtaatttg    360
caatcattga cattatccat gggaagtggt aaggattcaa catgtgaaac cagtggtgaa    420
aatagcacaa acactactgt tgaagttgca cctagaagaa cttggataca ttcgggcag    480 agaacatcca tatatcgtgg agtaactcga catagatgga ctggaaggta tgaagctcat    540
ctttgggata tagctgtag aagggaaggc caatcaagaa aaggacgcca agtttatttg    600
ggtggatatg ataagaaga gaaagcagct agggcttatg atttagctgc actgaagtac    660
tgggggacat ccaccactac caactttcca attagtaact atgagaagga ttggatgaa    720 atgaaacaca tgacgcgaca agaatttgtt gctgccatta aaggaaaag cagtggtttc    780 tccagggggtg catcaatgta tcgtggagtt acaaggcatc accaacacgg aagatggcaa    840
gcaagaattg gcagagttgc aggaaacaaa gatctttact tgggaacttt cagtactgaa    900
gaagaggctg ctgaagcata cgacatagct gcgataaagt tcagaggtct caacgctgtc    960
acaaactttg acatgagccg ctacgacgtg aaagccatcc ttgaaagcaa cactctccca   1020
ataggaggag gagctgcaaa agcgtctgaa gaagctcaag ctctagaatc ttcgagaaag   1080
cgcgaagaga tgattgcact aggatcatcc acattccaat atggaaccac aagctctaat   1140
```

```
tctaggctac atgcttaccc tctaatgcag caccaccacc agtttgaaca acctcaacct    1200
ctgctaactt tgcaaaacca tgatatcagt tctcacttct ctcaccagca agacccttg      1260 catcagggtt acatccaaac gcagcttcag ttgcaccagc agcagagtgg tggttcttct    1320
tcttatagct ttcagaataa taatataaat aatgctcagt tctataatgg ttataatctt   1380
cagaaccacc ctgcattgct tcagggaatg attaacatgg ggtcttcatc ttcttcatct   1440
gtgttggaga ataataatag taccaataat aatgttggtg ggtttgtggg aagtgggttt    1500
ggtatggctt ctaatgcaac gtcggggaac acggtgggga cggcggagga gctagggctg   1560
gtgaaggtgg actatgacat gccgactggt ggttacggtg gatggtcggc ggcggcggcg   1620
gcggagtcca tgcagacgtc gaatagtggg gtgttcacaa tgtggaatga ctga          1674
```

<210> SEQ ID NO 182
<211> LENGTH: 557
<212> TYPE: PRT
<213> ORGANISM: Glycine max

<400> SEQUENCE: 182

```
Met Asn Asn Asn Trp Leu Ser Phe Pro Leu Ser Pro Thr His Ser Ser
1               5                  10                  15

Leu Pro Ala His Asp Leu Gln Ala Thr Gln Tyr His Gln Phe Ser Leu
            20                  25                  30

Gly Leu Val Asn Glu Asn Met Asp Asn Pro Phe Gln Asn His Asp Trp
        35                  40                  45

Asn Leu Ile Asn Thr His Ser Ser Asn Glu Ile Pro Lys Val Ala Asp
    50                  55                  60

Phe Leu Gly Val Ser Lys Ser Glu Asn Gln Ser Asp Leu Ala Ala Leu
65                  70                  75                  80

Asn Glu Ile His Ser Asn Asp Ser Asp Tyr Leu Phe Thr Asn Asn Ser
                85                  90                  95

Leu Val Pro Met Gln Asn Pro Val Leu Asp Thr Pro Ser Asn Glu Tyr
            100                 105                 110

Gln Glu Asn Ala Asn Ser Asn Leu Gln Ser Leu Thr Leu Ser Met Gly
        115                 120                 125

Ser Gly Lys Asp Ser Thr Cys Glu Thr Ser Gly Glu Asn Ser Thr Asn
    130                 135                 140

Thr Thr Val Glu Val Ala Pro Arg Arg Thr Leu Asp Thr Phe Gly Gln
145                 150                 155                 160

Arg Thr Ser Ile Tyr Arg Gly Val Thr Arg His Arg Trp Thr Gly Arg
                165                 170                 175

Tyr Glu Ala His Leu Trp Asp Asn Ser Cys Arg Arg Glu Gly Gln Ser
            180                 185                 190

Arg Lys Gly Arg Gln Val Tyr Leu Gly Gly Tyr Asp Lys Glu Glu Lys
        195                 200                 205

Ala Ala Arg Ala Tyr Asp Leu Ala Ala Leu Lys Tyr Trp Gly Thr Ser
    210                 215                 220

Thr Thr Thr Asn Phe Pro Ile Ser Asn Tyr Glu Lys Glu Leu Asp Glu
225                 230                 235                 240

Met Lys His Met Thr Arg Gln Glu Phe Val Ala Ala Ile Arg Arg Lys
                245                 250                 255

Ser Ser Gly Phe Ser Arg Gly Ala Ser Met Tyr Arg Gly Val Thr Arg
            260                 265                 270

His His Gln His Gly Arg Trp Gln Ala Arg Ile Gly Arg Val Ala Gly
        275                 280                 285
```

```
Asn Lys Asp Leu Tyr Leu Gly Thr Phe Ser Thr Glu Glu Glu Ala Ala
        290                 295                 300

Glu Ala Tyr Asp Ile Ala Ala Ile Lys Phe Arg Gly Leu Asn Ala Val
305                 310                 315                 320

Thr Asn Phe Asp Met Ser Arg Tyr Asp Val Lys Ala Ile Leu Glu Ser
                325                 330                 335

Asn Thr Leu Pro Ile Gly Gly Ala Ala Lys Arg Leu Lys Glu Ala
            340                 345                 350

Gln Ala Leu Glu Ser Ser Arg Lys Arg Glu Glu Met Ile Ala Leu Gly
                355                 360                 365

Ser Ser Thr Phe Gln Tyr Gly Thr Thr Ser Ser Asn Ser Arg Leu His
    370                 375                 380

Ala Tyr Pro Leu Met Gln His His Gln Phe Glu Gln Pro Gln Pro
385                 390                 395                 400

Leu Leu Thr Leu Gln Asn His Asp Ile Ser Ser His Phe Ser His Gln
                405                 410                 415

Gln Asp Pro Leu His Gln Gly Tyr Ile Gln Thr Gln Leu Gln Leu His
            420                 425                 430

Gln Gln Gln Ser Gly Gly Ser Ser Ser Tyr Ser Phe Gln Asn Asn Asn
        435                 440                 445

Ile Asn Asn Ala Gln Phe Tyr Asn Gly Tyr Asn Leu Gln Asn His Pro
450                 455                 460

Ala Leu Leu Gln Gly Met Ile Asn Met Gly Ser Ser Ser Ser Ser Ser
465                 470                 475                 480

Val Leu Glu Asn Asn Asn Ser Thr Asn Asn Val Gly Gly Phe Val
                485                 490                 495

Gly Ser Gly Phe Gly Met Ala Ser Asn Ala Thr Ser Gly Asn Thr Val
            500                 505                 510

Gly Thr Ala Glu Glu Leu Gly Leu Val Lys Val Asp Tyr Asp Met Pro
        515                 520                 525

Thr Gly Gly Tyr Gly Gly Trp Ser Ala Ala Ala Ala Glu Ser Met
    530                 535                 540

Gln Thr Ser Asn Ser Gly Val Phe Thr Met Trp Asn Asp
545                 550                 555

<210> SEQ ID NO 183
<211> LENGTH: 1632
<212> TYPE: DNA
<213> ORGANISM: Medicago trunculata

<400> SEQUENCE: 183
atgaacaata actggctttc attccctctc tcaccttctc attcttcctt accttctaat    60
gatcttcaag caactcaata tcatcacttt cctcttggat tagtcaatga caacatggaa    120 aacccttttcc aaaatcatga ttggaatctg atgaacacac acaacagcaa tgaagttcca    180
aaggttgcgg attttctcgg tgtatgcaag tctgaaaatc actcagatct tgctacaccg    240
aacgaaattc aatctaatga ttcagattat ctgtttacaa ataacaatac tctcatgcca    300
atgcaaaacc aaatggttac aacatgcacc aatgagtatc aagaaaaggc tagtaatagt    360
aatttgcagt ctttgacatt atccatggga agtggtaaag attcaacatg tgaaactagt    420
ggtgaaaata gtacaaacac tgttgaagtt gctgttccta aagaacttc agagacattt    480 ggacaaagaa cttcgatata tcgcggtgta acaaaacata gatggactgg aaggtatgaa    540
gctcaccttt gggataacag ctgtagaagg gaaggtcagt cgagaaaagg ccgccaaggt    600
ggatatgata agaagagaa agctgctagg tcttatgatt tagctgcact taagtactgg    660
```

-continued

```
gggacatcca ccactaccaa ctttccagtt agcaactatg agaaggaaat agatgaaatg      720
aagcacatga caagacaaga atttgttgcc tctattagaa ggaaaagcag cggtttctct      780 agggggtgcat caatgtaccg tggagttaca aggcatcacc aacatggaag atggcaagca     840
aggattggca gagttgcagg aaataaagat ctatacttgg aactttcag cactgaagaa       900 gaggctgcag aagcatacga catagcagca ataaaattca gaggactcaa cgctgtaaca      960
aactttgaca tgactcgtta cgacgtgaaa gccattctcg aaagcaacac actgccaatt     1020
ggaggaggag ctgcaaaaag actaaaagaa gcacaagctc tagaaacttc gagaaaacgc     1080
gaagaaatgc ttgcacttaa ctcatcatct ttccaatatg aacatcaag ctctagtaac      1140 actagactcc aaccctaccc tctcatgcaa tatcatcacc aatttgaaca acctcaacca     1200
ttgctaacat tacaaaacaa ccatgaaagc ttgaattctc acaattctc tcaacaccaa      1260 ggtggtggtt atttccaaac acagcttgag ttgtgtcaac aacaaaacca acaaccatct     1320
cagaatagta acataggttc attctacaat ggttattatc agaatcatcc tggtttgttt     1380
cagatgaata atataggatc ttcttcttca tcttcggtga tgggaaataa tggtggtggt     1440
tctagtggga tttatagtaa tagtggaggg ttaattagta ataatgctgt tgaggaattt     1500
gtgccggtta aggttgatta tgacatgcaa ggtgatggaa gtggttttgg cggctggtcg     1560
gcggcaggag agaacatgca gactgctgat ttgtttacaa tgtggaatga ctatgagaca     1620
agagagaatt ag                                                        1632
```

<210> SEQ ID NO 184
<211> LENGTH: 557
<212> TYPE: PRT
<213> ORGANISM: Medicago trunculata

<400> SEQUENCE: 184

```
Met Asn Asn Asn Trp Leu Ser Phe Pro Leu Ser Pro Thr His Ser Ser
1               5                   10                  15

Leu Pro Ala His Asp Leu Gln Ala Thr Gln Tyr His Gln Phe Ser Leu
            20                  25                  30

Gly Leu Val Asn Glu Asn Met Asp Asn Pro Phe Gln Asn His Asp Trp
        35                  40                  45

Asn Leu Ile Asn Thr His Ser Ser Asn Glu Ile Pro Lys Val Ala Asp
    50                  55                  60

Phe Leu Gly Val Ser Lys Ser Glu Asn Gln Ser Asp Leu Ala Ala Leu
65                  70                  75                  80

Asn Glu Ile His Ser Asn Asp Ser Asp Tyr Leu Phe Thr Asn Asn Ser
                85                  90                  95

Leu Val Pro Met Gln Asn Pro Val Leu Asp Thr Pro Ser Asn Glu Tyr
            100                 105                 110

Gln Glu Asn Ala Asn Ser Asn Leu Gln Ser Leu Thr Leu Ser Met Gly
        115                 120                 125

Ser Gly Lys Asp Ser Thr Cys Glu Thr Ser Gly Glu Asn Ser Thr Asn
    130                 135                 140

Thr Thr Val Glu Val Ala Pro Arg Arg Thr Leu Asp Thr Phe Gly Gln
145                 150                 155                 160

Arg Thr Ser Ile Tyr Arg Gly Val Thr Arg His Arg Trp Thr Gly Arg
                165                 170                 175

Tyr Glu Ala His Leu Trp Asp Asn Ser Cys Arg Arg Glu Gly Gln Ser
            180                 185                 190

Arg Lys Gly Arg Gln Val Tyr Leu Gly Gly Tyr Asp Lys Glu Glu Lys
```

```
                195                 200                 205
Ala Ala Arg Ala Tyr Asp Leu Ala Ala Leu Lys Tyr Trp Gly Thr Ser
210                 215                 220

Thr Thr Thr Asn Phe Pro Ile Ser Asn Tyr Glu Lys Glu Leu Asp Glu
225                 230                 235                 240

Met Lys His Met Thr Arg Gln Glu Phe Val Ala Ile Arg Arg Lys
                245                 250                 255

Ser Ser Gly Phe Ser Arg Gly Ala Ser Met Tyr Arg Gly Val Thr Arg
                260                 265                 270

His His Gln His Gly Arg Trp Gln Ala Arg Ile Gly Arg Val Ala Gly
                275                 280                 285

Asn Lys Asp Leu Tyr Leu Gly Thr Phe Ser Thr Glu Glu Ala Ala
                290                 295                 300

Glu Ala Tyr Asp Ile Ala Ala Ile Lys Phe Arg Gly Leu Asn Ala Val
305                 310                 315                 320

Thr Asn Phe Asp Met Ser Arg Tyr Asp Val Lys Ala Ile Leu Glu Ser
                325                 330                 335

Asn Thr Leu Pro Ile Gly Gly Ala Ala Lys Arg Leu Lys Glu Ala
                340                 345                 350

Gln Ala Leu Glu Ser Ser Arg Lys Arg Glu Glu Met Ile Ala Leu Gly
                355                 360                 365

Ser Ser Thr Phe Gln Tyr Gly Thr Ser Ser Asn Ser Arg Leu His
                370                 375                 380

Ala Tyr Pro Leu Met Gln His His Gln Phe Glu Gln Pro Gln Pro
385                 390                 395                 400

Leu Leu Thr Leu Gln Asn His Asp Ile Ser Ser His Phe Ser His Gln
                405                 410                 415

Gln Asp Pro Leu His Gln Gly Tyr Ile Gln Thr Gln Leu Gln Leu His
                420                 425                 430

Gln Gln Gln Ser Gly Gly Ser Ser Tyr Ser Phe Gly Asn Asn Asn
                435                 440                 445

Ile Asn Asn Ala Gln Phe Tyr Asn Gly Tyr Asn Leu Gln Asn His Pro
450                 455                 460

Ala Leu Leu Gln Gly Met Ile Asn Met Gly Ser Ser Ser Ser Ser
465                 470                 475                 480

Val Leu Glu Asn Asn Asn Ser Thr Asn Asn Val Gly Gly Phe Val
                485                 490                 495

Gly Ser Gly Phe Gly Met Ala Ser Asn Ala Thr Ser Gly Asn Thr Val
                500                 505                 510

Gly Thr Ala Glu Glu Leu Gly Leu Val Lys Val Asp Tyr Asp Met Pro
515                 520                 525

Thr Gly Gly Tyr Gly Gly Trp Ser Ala Ala Ala Ala Glu Ser Met
530                 535                 540

Gln Thr Ser Asn Ser Gly Val Phe Thr Met Trp Asn Asp
545                 550                 555

<210> SEQ ID NO 185
<211> LENGTH: 2079
<212> TYPE: DNA
<213> ORGANISM: Oryza sativa

<400> SEQUENCE: 185
atggccacca tgaacaactg gctggccttc tccctctccc cgcaggatca gctcccgccg      60
tctcagacca actccactct catctccgcc gccgccacca ccaccaccgc cggcgactcc     120
```

```
tccaccggcg acgtctgctt caacatcccc caagattgga gcatgagggg atcggagctc    180
tcggcgctcg tcgccgagcc gaagctggag gacttcctcg gcggcatctc cttctcggag    240
cagcagcatc atcacggcgg caagggcggc gtgatcccga gcagcgccgc cgcttgctac    300
gcgagctccg gcagcagcgt cggctacctg taccctcctc aagctcatc ctcgctccag     360 ttcgccgact ccgtcatggt ggccacctcc tcgcccgtcg tcgcccacga cggcgtcagc    420
ggcggcggca tggtgagcgc cgccgccgcc gggcggcca gtggcaacgg cggcattggc     480
ctgtccatga tcaagaactg gctccggagc cagccggcgc cgcagccggc gcaggcgctg    540
tctctgtcca tgaacatggc ggggacgacg acggcgcagg gcggcggcgc catggcgctc    600
ctcgccggcg caggggagcg aggccggacg acgcccgcgt cagagagcct gtccacgtcg    660
gcgcacggag cgacgacggc gacgatggct ggtggtcgca aggagattaa cgaggaaggc    720
agcggcagcg ccggcgccgt ggttgccgtc ggctcggagt caggcggcag cggcgccgtg    780
gtggaggccg gcgcggcggc ggcggcggcg aggaagtccg tcgacacgtt cggccagaga    840
acatcgatct accgcggcgt gacaaggcat agatggacag ggaggtatga ggctcatctt    900
tgggacaaca gctgcagaag agagggccaa actcgcaagg gtcgtcaagg tggttatgac    960
aaagaggaaa aagctgctag agcttatgat ttggctgctc tcaaatactg ggcccgacg    1020 acgacgacaa attttccggt aaataactat gaaaaggagc tggaggagat gaagcacatg    1080
acaaggcagg agttcgtagc ctctttgaga aggaagagca gtggtttctc cagaggtgca    1140
tccatttacc gtggagtaac taggcatcac cagcatggga gatggcaagc aaggatagga    1200
agagttgcag ggaacaagga cctctacttg ggcaccttca gcacgcagga ggaggcggcg    1260
gaggcgtacg acatcgcggc gatcaagttc cgggggctca acgccgtcac caacttcgac    1320
atgagccgct acgacgtcaa gagcatcctc gacacgcctg ccctccccgt cggcaccgcc    1380
gccaagcgcc tcaaggacgc cgaggccgcc gccgcctacg acgtcggccg catcgcctcg    1440
cacctcggcg gcgacggcgc ctacgccgcg cattacggcc accaccacca ctcggccgcc    1500
gccgcctggc cgaccatcgc gttccaggcg gcggcggcgc cgccgccgca cgccgccggg    1560
ctttaccacc cgtacgcgca gccgctgcgt gggtggtgca agcaggagca ggaccacgcc    1620
gtgatcgcgg cggcgcacag cctgcaggat ctccaccacc tcaacctcgg cgccgccgcc    1680
gccgcgcatg acttcttctc gcaggcgatg cagcagcagc acggcctcgg cagcatcgac    1740
aacgcgtcgc tcgagcacag caccggctcc aactccgtcg tctacaacgg cgacaatggc    1800
ggcggaggcg gcggctacat catggcgccg atgagcgccg tgtcggccac ggccaccgcg    1860
gtggcgagca gccacgatca cggcggcgac ggcgggaagc aggtgcagat ggggtacgac    1920
agctacctcg tcgcgcagag cgcctacggc ggcggcggcg ccgggaggat gccatcctgg    1980
gcgatgacgc cggcgtcggc gccggccgcc acgagcagca gcgacatgac cggagtctgc    2040
catggcgcac agctcttcag cgtctggaac gacacataa                          2079
```

<210> SEQ ID NO 186
<211> LENGTH: 692
<212> TYPE: PRT
<213> ORGANISM: Oryza sativa

<400> SEQUENCE: 186

Met Ala Thr Met Asn Asn Trp Leu Ala Phe Ser Leu Ser Pro Gln Asp
1               5                   10                  15

Gln Leu Pro Pro Ser Gln Thr Asn Ser Thr Leu Ile Ser Ala Ala Ala
            20                  25                  30

-continued

```
Thr Thr Thr Thr Ala Gly Asp Ser Thr Gly Asp Val Cys Phe Asn
         35                  40                  45

Ile Pro Gln Asp Trp Ser Met Arg Gly Ser Glu Leu Ser Ala Leu Val
 50                  55                  60

Ala Glu Pro Lys Leu Glu Asp Phe Leu Gly Gly Ile Ser Phe Ser Glu
 65                  70                  75                  80

Gln Gln His His His Gly Gly Lys Gly Val Ile Pro Ser Ser Ala
                 85                  90                  95

Ala Ala Cys Tyr Ala Ser Ser Gly Ser Ser Val Gly Tyr Leu Tyr Pro
                100                 105                 110

Pro Pro Ser Ser Ser Leu Gln Phe Ala Asp Ser Val Met Val Ala
                115                 120                 125

Thr Ser Ser Pro Val Val Ala His Asp Gly Val Ser Gly Gly Gly Met
    130                 135                 140

Val Ser Ala Ala Ala Ala Ala Ala Ser Gly Asn Gly Gly Ile Gly
145                 150                 155                 160

Leu Ser Met Ile Lys Asn Trp Leu Arg Ser Gln Pro Ala Pro Gln Pro
                165                 170                 175

Ala Gln Ala Leu Ser Leu Ser Met Asn Met Ala Gly Thr Thr Thr Ala
                180                 185                 190

Gln Gly Gly Gly Ala Met Ala Leu Leu Ala Gly Ala Gly Glu Arg Gly
                195                 200                 205

Arg Thr Thr Pro Ala Ser Glu Ser Leu Ser Thr Ser Ala His Gly Ala
    210                 215                 220

Thr Thr Ala Thr Met Ala Gly Gly Arg Lys Glu Ile Asn Glu Glu Gly
225                 230                 235                 240

Ser Gly Ser Ala Gly Ala Val Val Ala Val Gly Ser Glu Ser Gly Gly
                245                 250                 255

Ser Gly Ala Val Val Glu Ala Gly Ala Ala Ala Ala Arg Lys
                260                 265                 270

Ser Val Asp Thr Phe Gly Gln Arg Thr Ser Ile Tyr Arg Gly Val Thr
    275                 280                 285

Arg His Arg Trp Thr Gly Arg Tyr Glu Ala His Leu Trp Asp Asn Ser
290                 295                 300

Cys Arg Arg Glu Gly Gln Thr Arg Lys Gly Arg Gln Gly Gly Tyr Asp
305                 310                 315                 320

Lys Glu Glu Lys Ala Ala Arg Ala Tyr Asp Leu Ala Ala Leu Lys Tyr
                325                 330                 335

Trp Gly Pro Thr Thr Thr Asn Phe Pro Val Asn Asn Tyr Glu Lys
                340                 345                 350

Glu Leu Glu Glu Met Lys His Met Thr Arg Gln Glu Phe Val Ala Ser
                355                 360                 365

Leu Arg Arg Lys Ser Ser Gly Phe Ser Arg Gly Ala Ser Ile Tyr Arg
    370                 375                 380

Gly Val Thr Arg His His Gln His Gly Arg Trp Gln Ala Arg Ile Gly
385                 390                 395                 400

Arg Val Ala Gly Asn Lys Asp Leu Tyr Leu Gly Thr Phe Ser Thr Gln
                405                 410                 415

Glu Glu Ala Ala Glu Ala Tyr Asp Ile Ala Ala Ile Lys Phe Arg Gly
                420                 425                 430

Leu Asn Ala Val Thr Asn Phe Asp Met Ser Arg Tyr Asp Val Lys Ser
                435                 440                 445

Ile Leu Asp Ser Ala Ala Leu Pro Val Gly Thr Ala Ala Lys Arg Leu
    450                 455                 460
```

```
Lys Asp Ala Glu Ala Ala Ala Tyr Asp Val Gly Arg Ile Ala Ser
465                 470                 475                 480

His Leu Gly Gly Asp Gly Ala Tyr Ala Ala His Tyr Gly His His His
            485                 490                 495

His Ser Ala Ala Ala Ala Trp Pro Thr Ile Ala Phe Gln Ala Ala Ala
        500                 505                 510

Ala Pro Pro Pro His Ala Ala Gly Leu Tyr His Pro Tyr Ala Gln Pro
            515                 520                 525

Leu Arg Gly Trp Cys Lys Gln Glu Gln Asp His Ala Val Ile Ala Ala
        530                 535                 540

Ala His Ser Leu Gln Asp Leu His His Leu Asn Leu Gly Ala Ala Ala
545                 550                 555                 560

Ala Ala His Asp Phe Phe Ser Gln Ala Met Gln Gln His Gly Leu
            565                 570                 575

Gly Ser Ile Asp Asn Ala Ser Leu Glu His Ser Thr Gly Ser Asn Ser
            580                 585                 590

Val Val Tyr Asn Gly Asp Asn Gly Gly Gly Gly Gly Tyr Ile Met
        595                 600                 605

Ala Pro Met Ser Ala Val Ser Ala Thr Ala Thr Ala Val Ala Ser Ser
        610                 615                 620

His Asp His Gly Gly Asp Gly Gly Lys Gln Val Gln Met Gly Tyr Asp
625                 630                 635                 640

Ser Tyr Leu Val Gly Ala Asp Ala Tyr Gly Gly Gly Ala Gly Arg
            645                 650                 655

Met Pro Ser Trp Ala Met Thr Pro Ala Ser Ala Pro Ala Ala Thr Ser
            660                 665                 670

Ser Ser Asp Met Thr Gly Val Cys His Gly Ala Gln Leu Phe Ser Val
        675                 680                 685

Trp Asn Asp Thr
    690

<210> SEQ ID NO 187
<211> LENGTH: 2133
<212> TYPE: DNA
<213> ORGANISM: Zea mays

<400> SEQUENCE: 187
atggccactg tgaacaactg gctcgctttc tccctctccc cgcaggagct gccgccctcc      60
cagacgacgg actccacact catctcggcc gccaccgccg accatgtctc cggcgatgtc     120
tgcttcaaca tcccccaaga ttggagcatg aggggatcag agctttcggc gctcgtcgcg     180
gagccgaagc tggaggactt cctcggcggc atctccttct ccgagcagca tcacaaggcc     240
aactgcaaca tgatacccag cactagcagc acagtttgct acgcgagctc aggtgctagc     300
accggctacc atcaccagct gtaccaccag cccaccagct cagcgctcca cttcgcggac     360
tccgtaatgg tggcctcctc ggccggtgtc cacgacggcg gtgccatgct cagcgcggcc     420
gccgctaacg tgtcgctgg cgctgccagt gccaacggcg gcggcatcgg gctgtccatg     480
attaagaact ggctgcggag ccaaccggcg cccatgcagc cgagggtggc ggcggctgag     540
ggcgcgcagg gctctctttt gtccatgaac atggcgggga cgacccaagg cgctgctggc     600
atgccacttc tcgctggaga gcgcgcacgg gcgcccgaga gtgtatcgac gtcagcacag     660
ggtggagccg tcgtcgtcac ggcgccgaag gaggatagcg gtggcagcgg tgttgccggc     720
gctctagtag ccgtgagcac ggacacgggt ggcagcggcg gcgcgtcggc tgacaacacg     780
```

-continued

```
gcaaggaaga cggtggacac gttcgggcag cgcacgtcga tttaccgtgg cgtgacaagg    840
catagatgga ctgggagata tgaggcacat ctttgggata acagttgcag aagggaaggg    900
caaactcgta agggtcgtca agtctattta ggtggctatg ataaagagga gaaagctgct    960
agggcttatg atcttgctgc tctgaagtac tggggtgcca caacaacaac aaattttcca   1020
gtgagtaact acgaaaagga gctcgaggac atgaagcaca tgacaaggca ggagtttgta   1080
gcgtctctga gaaggaagag cagtggtttc tccagaggtg catccattta caggggagtg   1140
actaggcatc accaacatgg aagatggcaa gcacggattg gacgagttgc agggaacaag   1200
gatctttact tgggcacctt cagcacccag gaggaggcag cggaggcgta cgacatcgcg   1260
gcgatcaagt tccgcggcct caacgccgtc accaacttcg acatgagccg ctacgacgtg   1320
aagagcatcc tggacagcag cgccctcccc atcggcagcg ccgccaagcg cctcaaggag   1380
gccgaggccg cagcgtccgc gcagcaccac cacgccggcg tggtgagcta cgacgtcggc   1440
cgcatcgcct cgcagctcgg cgacggcgga gccctggcgg cggcgtacgg cgcgcactac   1500
cacggcgccg cctggccgac catcgcgttc cagccgggcg ccgccagcac aggcctgtac   1560
cacccgtacg cgcagcagcc aatgcgcggc ggcgggtggt gcaagcagga gcaggaccac   1620
gcggtgatcg cggccgcgca cagcctgcag gacctccacc acctgaacct gggcgcggcc   1680
ggcgcgcacg actttttctc ggcagggcag caggccgccg ccgctgcgat gcacggcctg   1740
ggtagcatcg acagtgcgtc gctcgagcac agcaccggct ccaactccgt cgtctacaac   1800
ggcggggtcg gcgacagcaa cggcgccagc gccgtcggcg gcagtggcgg tggctacatg   1860
atgccgatga gcgctgccgg agcaaccact acatcggcaa tggtgagcca cgagcaggtg   1920
catgcacggg cctacgacga agccaagcag gctgctcaga tggggtacga gagctacctg   1980
gtgaacgcgg agaacaatgg tggcggaagg atgtctgcat gggggactgt cgtgtctgca   2040
gccgcggcgg cagcagcaag cagcaacgac aacatggccg ccgacgtcgg ccatggcggc   2100
gcgcagctct tcagtgtctg gaacgacact taa                                2133

<210> SEQ ID NO 188
<211> LENGTH: 710
<212> TYPE: PRT
<213> ORGANISM: Zea mays

<400> SEQUENCE: 188

Met Ala Thr Val Asn Asn Trp Leu Ala Phe Ser Leu Ser Pro Gln Glu
1               5                   10                  15

Leu Pro Pro Ser Gln Thr Thr Asp Ser Thr Leu Ile Ser Ala Ala Thr
            20                  25                  30

Ala Asp His Val Ser Gly Asp Val Cys Phe Asn Ile Pro Gln Asp Trp
        35                  40                  45

Ser Met Arg Gly Ser Glu Leu Ser Ala Leu Val Ala Glu Pro Lys Leu
    50                  55                  60

Glu Asp Phe Leu Gly Gly Ile Ser Phe Ser Glu Gln His His Lys Ala
65                  70                  75                  80

Asn Cys Asn Met Ile Pro Ser Thr Ser Ser Thr Val Cys Tyr Ala Ser
                85                  90                  95

Ser Gly Ala Ser Thr Gly Tyr His His Gln Leu Tyr His Gln Pro Thr
            100                 105                 110

Ser Ser Ala Leu His Phe Ala Asp Ser Val Met Val Ala Ser Ser Ala
        115                 120                 125

Gly Val His Asp Gly Gly Ala Met Leu Ser Ala Ala Ala Ala Asn Gly
    130                 135                 140
```

-continued

```
Val Ala Gly Ala Ala Ser Ala Asn Gly Gly Ile Gly Leu Ser Met
145                 150                 155                 160

Ile Lys Asn Trp Leu Arg Ser Gln Pro Ala Pro Met Gln Pro Arg Val
                165                 170                 175

Ala Ala Ala Glu Gly Ala Gln Gly Leu Ser Leu Ser Met Asn Met Ala
            180                 185                 190

Gly Thr Thr Gln Gly Ala Ala Gly Met Pro Leu Leu Ala Gly Glu Arg
        195                 200                 205

Ala Arg Ala Pro Glu Ser Val Ser Thr Ser Ala Gln Gly Gly Ala Val
    210                 215                 220

Val Val Thr Ala Pro Lys Glu Asp Ser Gly Ser Gly Val Ala Gly
225                 230                 235                 240

Ala Leu Val Ala Val Ser Thr Asp Thr Gly Ser Gly Gly Ala Ser
                245                 250                 255

Ala Asp Asn Thr Ala Arg Lys Thr Val Asp Thr Phe Gly Gln Arg Thr
            260                 265                 270

Ser Ile Tyr Arg Gly Val Thr Arg His Arg Trp Thr Gly Arg Tyr Glu
        275                 280                 285

Ala His Leu Trp Asp Asn Ser Cys Arg Arg Glu Gly Gln Thr Arg Lys
    290                 295                 300

Gly Arg Gln Val Tyr Leu Gly Gly Tyr Asp Lys Glu Glu Lys Ala Ala
305                 310                 315                 320

Arg Ala Tyr Asp Leu Ala Ala Leu Lys Tyr Trp Gly Ala Thr Thr Thr
                325                 330                 335

Thr Asn Phe Pro Val Ser Asn Tyr Glu Lys Glu Leu Glu Asp Met Lys
            340                 345                 350

His Met Thr Arg Gln Glu Phe Val Ala Ser Leu Arg Arg Lys Ser Ser
        355                 360                 365

Gly Phe Ser Arg Gly Ala Ser Ile Tyr Arg Gly Val Thr Arg His His
    370                 375                 380

Gln His Gly Arg Trp Gln Ala Arg Ile Gly Arg Val Ala Gly Asn Lys
385                 390                 395                 400

Asp Leu Tyr Leu Gly Thr Phe Ser Thr Gln Glu Ala Ala Glu Ala
                405                 410                 415

Tyr Asp Ile Ala Ala Ile Lys Phe Arg Gly Leu Asn Ala Val Thr Asn
            420                 425                 430

Phe Asp Met Ser Arg Tyr Asp Val Lys Ser Ile Leu Asp Ser Ser Ala
        435                 440                 445

Leu Pro Ile Gly Ser Ala Ala Lys Arg Leu Lys Glu Ala Glu Ala Ala
    450                 455                 460

Ala Ser Ala Gln His His His Ala Gly Val Val Ser Tyr Asp Val Gly
465                 470                 475                 480

Arg Ile Ala Ser Gln Leu Gly Asp Gly Ala Leu Ala Ala Tyr
                485                 490                 495

Gly Ala His Tyr His Gly Ala Ala Trp Pro Thr Ile Ala Phe Gln Pro
            500                 505                 510

Gly Ala Ala Ser Thr Gly Leu Tyr His Pro Tyr Ala Gln Gln Pro Met
        515                 520                 525

Arg Gly Gly Gly Trp Cys Lys Gln Glu Gln Asp His Ala Val Ile Ala
    530                 535                 540

Ala Ala His Ser Leu Gln Asp Leu His His Leu Asn Leu Gly Ala Ala
545                 550                 555                 560

Gly Ala His Asp Phe Phe Ser Ala Gly Gln Gln Ala Ala Ala Ala Ala
```

-continued

```
                565                 570                 575
Met His Gly Leu Gly Ser Ile Asp Ser Ala Ser Leu Glu His Ser Thr
                    580                 585                 590

Gly Ser Asn Ser Val Val Tyr Asn Gly Gly Val Gly Asp Ser Asn Gly
            595                 600                 605

Ala Ser Ala Val Gly Gly Ser Gly Gly Gly Tyr Met Met Pro Met Ser
        610                 615                 620

Ala Ala Gly Ala Thr Thr Thr Ser Ala Met Val Ser His Glu Gln Val
625                 630                 635                 640

His Ala Arg Ala Tyr Asp Glu Ala Lys Gln Ala Ala Gln Met Gly Tyr
                645                 650                 655

Glu Ser Tyr Leu Val Asn Ala Glu Asn Asn Gly Gly Gly Arg Met Ser
            660                 665                 670

Ala Trp Gly Thr Val Val Ser Ala Ala Ala Ala Ala Ala Ala Ser Ser
        675                 680                 685

Asn Asp Asn Met Ala Ala Asp Val Gly His Gly Ala Gln Leu Phe
    690                 695                 700

Ser Val Trp Asn Asp Thr
705                 710

<210> SEQ ID NO 189
<211> LENGTH: 1374
<212> TYPE: DNA
<213> ORGANISM: Lotus corniculatus

<400> SEQUENCE: 189
agatctctct ctgcagtgca caatccagtg gtaagcacat gtagtaatgg taatgagtct     60
caagaaaatg gtaatggtaa tttgcaatcg ttgacattat ccatgggaag tggtaaggat    120
tcaacatgtg aaaccagtgg tgacactagt accaacacta tcgaagctgt gcctagaaga    180
accttggaga catttgggca agaacatcta tatatcgag gtgtaacaag acatagatgg     240
accggaaggt atgaagctca cctttgggac aatagctgta gaagggaagg acagtcaagg    300
aaaggtcgcc aagtggata tgataaagaa gacaaagcag ctagggccta tgatttagct    360
gcccttaagt actgggggac atccactact accaactttc cggttagcaa ctatgagaag    420
gaagtggatg acatgaagca tatgacaaga caagaatttg tggcttccat agaaggaaa    480 agcagtggtt tctcgagggg tgcttcaatg tatcgtggag ttacaaggca tcatcaacat    540
gggaggtggc aagcaaggat tggaagagtt gcaggaaaca aagatcttta cttgggaact    600
ttcggtactg aggaagaggc ggcagaagct tacgacatag ctgcgataaa gttcagaggc    660
cttaacgcca tcaccaactt tgacatgaac cgttacgatg tgaaagccat tctagagagc    720
aacaccctcc caatcggagg aggagcttca aaaaggctaa agaaactca agctctggaa    780 tcttcaagaa aacgtgaaga tcagatgatt gcactcggct caacatttca tcaatacgga    840
attgcaaccc catcaagctc tacaaggcca caaccttacc cgctaaacct aatgcatcat    900
cacaatcagt ttgaacaaca gcctcaacca tttctaacct acaaaaacca tgacattaat    960
tctcaatact cccatcatca gcaggaccct tcgtttcagc agagttacat tcaaacacag   1020
cttcagttgc agttgaatca acacggtggt ggtggttcta gttatgctca agaaacagct   1080
cctcatcaga acagtgagtt ctataatggt ggaaattatt accttcagaa ccttcaggaa   1140
atgatgatga acaatagtat ggggtcttgt tcttcatcgt ctgtgttgga gaatgatcat   1200
aatgctgctg ctggtgggc ttcttttgtg ggtcccgcag cggaggaact tgggttggtt   1260
aaggttgatt atgacatgga tgctgctgct ggcggtggtt atggtggttg gtcagcggcg   1320
```
gagtccatgc acacgtcggc ggctggtggt ttgtttacta tgtggaatga gtga      1374

<210> SEQ ID NO 190
<211> LENGTH: 457
<212> TYPE: PRT
<213> ORGANISM: Lotus corniculatus

<400> SEQUENCE: 190

```
Arg Ser Leu Ser Ala Val His Asn Pro Val Val Ser Thr Cys Ser Asn
1               5                   10                  15

Gly Asn Glu Ser Gln Glu Asn Gly Asn Gly Asn Leu Gln Ser Leu Thr
            20                  25                  30

Leu Ser Met Gly Ser Gly Lys Asp Ser Thr Cys Glu Thr Ser Gly Asp
        35                  40                  45

Thr Ser Thr Asn Thr Ile Glu Ala Val Pro Arg Arg Thr Leu Glu Thr
    50                  55                  60

Phe Gly Gln Arg Thr Ser Ile Tyr Arg Gly Val Thr Arg His Arg Trp
65                  70                  75                  80

Thr Gly Arg Tyr Glu Ala His Leu Trp Asp Asn Ser Cys Arg Arg Glu
                85                  90                  95

Gly Gln Ser Arg Lys Gly Arg Gln Gly Gly Tyr Asp Lys Glu Asp Lys
            100                 105                 110

Ala Ala Arg Ala Tyr Asp Leu Ala Ala Leu Lys Tyr Trp Gly Thr Ser
        115                 120                 125

Thr Thr Thr Asn Phe Pro Val Ser Asn Tyr Glu Lys Glu Val Asp Asp
    130                 135                 140

Met Lys His Met Thr Arg Gln Glu Phe Val Ala Ser Ile Arg Arg Lys
145                 150                 155                 160

Ser Ser Gly Phe Ser Arg Gly Ala Ser Met Tyr Arg Gly Val Thr Arg
                165                 170                 175

His His Gln His Gly Arg Trp Gln Ala Arg Ile Gly Arg Val Ala Gly
            180                 185                 190

Asn Lys Asp Leu Tyr Leu Gly Thr Phe Gly Thr Glu Glu Ala Ala
        195                 200                 205

Glu Ala Tyr Asp Ile Ala Ala Ile Lys Phe Arg Gly Leu Asn Ala Ile
    210                 215                 220

Thr Asn Phe Asp Met Asn Arg Tyr Asp Val Lys Ala Ile Leu Glu Ser
225                 230                 235                 240

Asn Thr Leu Pro Ile Gly Gly Ala Ser Lys Arg Leu Lys Glu Thr
                245                 250                 255

Gln Ala Leu Glu Ser Ser Arg Lys Arg Glu Asp Gln Met Ile Ala Leu
            260                 265                 270

Gly Ser Thr Phe His Gln Tyr Gly Ile Ala Thr Pro Ser Ser Ser Thr
        275                 280                 285

Arg Pro Gln Pro Tyr Pro Leu Asn Leu Met His His Asn Gln Phe
    290                 295                 300

Glu Gln Gln Pro Gln Pro Phe Leu Thr Leu Gln Asn His Asp Ile Asn
305                 310                 315                 320

Ser Gln Tyr Ser His His Gln Asp Pro Ser Phe Gln Ser Tyr
                325                 330                 335

Ile Gln Thr Gln Leu Gln Leu Gln Leu Asn Gln His Gly Gly Gly
            340                 345                 350

Ser Ser Tyr Ala Gln Glu Thr Ala Pro His Gln Asn Ser Glu Phe Tyr
        355                 360                 365
```

```
Asn Gly Gly Asn Tyr Tyr Leu Gln Asn Leu Gln Gly Met Met Met Asn
    370                 375                 380

Asn Ser Met Gly Ser Cys Ser Ser Ser Val Leu Glu Asn Asp His
385                 390                 395                 400

Asn Ala Ala Gly Gly Ala Ser Phe Val Gly Pro Ala Ala Glu Glu
                405                 410                 415

Leu Gly Leu Val Lys Val Asp Tyr Asp Met Asp Ala Ala Ala Gly Gly
            420                 425                 430

Gly Tyr Gly Gly Trp Ser Ala Ala Glu Ser Met His Thr Ser Ala Ala
        435                 440                 445

Gly Gly Leu Phe Thr Met Trp Asn Glu
    450                 455

<210> SEQ ID NO 191
<211> LENGTH: 202
<212> TYPE: PRT
<213> ORGANISM: Artificial sequence
<220> FEATURE:
<223> OTHER INFORMATION: AP2 domain of Arath_PLT1 and Arath_PLT2
<220> FEATURE:
<221> NAME/KEY: VARIANT
<222> LOCATION: (4)..(4)
<223> OTHER INFORMATION: Xaa is Ala or Thr
<220> FEATURE:
<221> NAME/KEY: VARIANT
<222> LOCATION: (6)..(6)
<223> OTHER INFORMATION: Xaa is Asp or Glu
<220> FEATURE:
<221> NAME/KEY: VARIANT
<222> LOCATION: (57)..(57)
<223> OTHER INFORMATION: Xaa is Asp or Glu
<220> FEATURE:
<221> NAME/KEY: VARIANT
<222> LOCATION: (62)..(62)
<223> OTHER INFORMATION: Xaa is Ser or Ala
<220> FEATURE:
<221> NAME/KEY: VARIANT
<222> LOCATION: (93)..(93)
<223> OTHER INFORMATION: Xaa is His or Asn
<220> FEATURE:
<221> NAME/KEY: VARIANT
<222> LOCATION: (102)..(102)
<223> OTHER INFORMATION: Xaa is Ala or Ser
<220> FEATURE:
<221> NAME/KEY: VARIANT
<222> LOCATION: (187)..(187)
<223> OTHER INFORMATION: Xaa is Ser or Asn

<400> SEQUENCE: 191

Pro Arg Arg Xaa Leu Xaa Thr Phe Gly Gln Arg Thr Ser Ile Tyr Arg
1               5                   10                  15

Gly Val Thr Arg His Arg Trp Thr Gly Arg Tyr Glu Ala His Leu Trp
            20                  25                  30

Asp Asn Ser Cys Arg Arg Glu Gly Gln Ser Arg Lys Gly Arg Gln Val
        35                  40                  45

Tyr Leu Gly Gly Tyr Asp Lys Glu Xaa Lys Ala Ala Arg Xaa Tyr Asp
    50                  55                  60

Leu Ala Ala Leu Lys Tyr Trp Gly Pro Ser Thr Thr Thr Asn Phe Pro
65                  70                  75                  80

Ile Thr Asn Tyr Glu Lys Glu Val Glu Glu Met Lys Xaa Met Thr Arg
                85                  90                  95

Gln Glu Phe Val Ala Xaa Ile Arg Arg Lys Ser Ser Gly Phe Ser Arg
            100                 105                 110

Gly Ala Ser Met Tyr Arg Gly Val Thr Arg His His Gln His Gly Arg
        115                 120                 125
```

```
Trp Gln Ala Arg Ile Gly Arg Val Ala Gly Asn Lys Asp Leu Tyr Leu
        130                 135                 140

Gly Thr Phe Ser Thr Glu Glu Ala Ala Glu Ala Tyr Asp Ile Ala
145                 150                 155                 160

Ala Ile Lys Phe Arg Gly Leu Asn Ala Val Thr Asn Phe Glu Ile Asn
                165                 170                 175

Arg Tyr Asp Val Lys Ala Ile Leu Glu Ser Xaa Thr Leu Pro Ile Gly
            180                 185                 190

Gly Gly Ala Ala Lys Arg Leu Lys Glu Ala
            195                 200

<210> SEQ ID NO 192
<211> LENGTH: 8
<212> TYPE: PRT
<213> ORGANISM: Artificial sequence
<220> FEATURE:
<223> OTHER INFORMATION: motif 1
<220> FEATURE:
<221> NAME/KEY: VARIANT
<222> LOCATION: (3)..(3)
<223> OTHER INFORMATION: Xaa is Val or Leu
<220> FEATURE:
<221> NAME/KEY: VARIANT
<222> LOCATION: (4)..(4)
<223> OTHER INFORMATION: Xaa is Ala or Glu

<400> SEQUENCE: 192

Pro Lys Xaa Xaa Asp Phe Leu Gly
1               5

<210> SEQ ID NO 193
<211> LENGTH: 7
<212> TYPE: PRT
<213> ORGANISM: Artificial sequence
<220> FEATURE:
<223> OTHER INFORMATION: motif 2
<220> FEATURE:
<221> NAME/KEY: VARIANT
<222> LOCATION: (1)..(1)
<223> OTHER INFORMATION: Xaa is Val or Leu
<220> FEATURE:
<221> NAME/KEY: VARIANT
<222> LOCATION: (3)..(3)
<223> OTHER INFORMATION: Xaa is Thr or Ser
<220> FEATURE:
<221> NAME/KEY: VARIANT
<222> LOCATION: (4)..(4)
<223> OTHER INFORMATION: Xaa is Met or Val
<220> FEATURE:
<221> NAME/KEY: VARIANT
<222> LOCATION: (7)..(7)
<223> OTHER INFORMATION: Xaa is Asp or Glu

<400> SEQUENCE: 193

Xaa Phe Xaa Xaa Trp Asn Xaa
1               5

<210> SEQ ID NO 194
<211> LENGTH: 2193
<212> TYPE: DNA
<213> ORGANISM: Oryza sativa

<400> SEQUENCE: 194
aatccgaaaa gtttctgcac cgttttcacc ccctaactaa caatataggg aacgtgtgct      60
aaatataaaa tgagaccttta tatgtagc gctgataact agaactatgc aagaaaaact     120
catccaccta ctttagtggc aatcgggcta aataaaaaag agtcgctaca ctagtttcgt    180
tttccttagt aattaagtgg gaaaatgaaa tcattattgc ttagaatata cgttcacatc    240
```

```
tctgtcatga agttaaatta ttcgaggtag ccataattgt catcaaactc ttcttgaata    300
aaaaaatctt tctagctgaa ctcaatgggt aaagagagag attttttta aaaaatagga    360 atgaagatat tctgaacgta ttggcaaaga tttaaacata taattatata attttatagt    420
ttgtgcattc gtcatatcgc acatcattaa ggacatgtct tactccatcc caatttttat    480
ttagtaatta aagacaattg acttatttt attatttatc tttttcgat tagatgcaag      540 gtacttacgc acacactttg tgctcatgtg catgtgtgag tgcacctcct caatacacgt    600
tcaactagca acacatctct aatatcactc gcctatttaa tacatttagg tagcaatatc    660
tgaattcaag cactccacca tcaccagacc acttttaata atatctaaaa tacaaaaaat    720
aattttacag aatagcatga aaagtatgaa acgaactatt taggttttc acatacaaaa     780 aaaaaaagaa ttttgctcgt gcgcgagcgc caatctccca tattgggcac acaggcaaca    840
acagagtggc tgcccacaga acaacccaca aaaaacgatg atctaacgga ggacagcaag    900
tccgcaacaa cctttaacaa gcaggctttg cggccaggag agaggaggag aggcaaagaa    960
aaccaagcat cctcctcctc ccatctataa attcctcccc ccttttcccc tctctatata    1020
ggaggcatcc aagccaagaa gagggagagc accaaggaca cgcgactagc agaagccgag    1080
cgaccgcctt cttcgatcca tatcttccgg tcgagttctt ggtcgatctc ttccctcctc    1140
cacctcctcc tcacagggta tgtgcccttc ggttgttctt ggattattg ttctaggttg     1200 tgtagtacgg gcgttgatgt taggaaaggg gatctgtatc tgtgatgatt cctgttcttg    1260
gatttgggat agaggggttc ttgatgttgc atgttatcgg ttcggtttga ttagtagtat    1320
ggttttcaat cgtctggaga gctctatgga aatgaaatgg tttagggtac ggaatcttgc    1380
gattttgtga gtacccttttg tttgaggtaa atcagagca ccggtgattt tgcttggtgt     1440
aataaaagta cggttgtttg gtcctcgatt ctggtagtga tgcttctcga tttgacgaag    1500
ctatcctttg tttattccct attgaacaaa aataatccaa ctttgaagac ggtcccgttg    1560
atgagattga atgattgatt cttaagcctg tccaaaattt cgcagctggc ttgtttagat    1620
acagtagtcc ccatcacgaa attcatggaa acagttataa tcctcaggaa caggggattc    1680
cctgttcttc cgatttgctt tagtcccaga attttttttc ccaaatatct taaaaagtca    1740
ctttctggtt cagttcaatg aattgattgc tacaaataat gcttttatag cgttatccta    1800
gctgtagttc agtaataggg taatacccct atagtttagt caggagaaga acttatccga    1860
tttctgatct ccatttttaa ttatatgaaa tgaactgtag cataagcagt attcatttgg    1920
attatttttt ttattagctc tcacccttc attattctga gctgaaagtc tggcatgaac     1980
tgtcctcaat tttgttttca aattcacatc gattatctat gcattatcct cttgtatcta    2040
cctgtagaag tttcttttg gttattcctt gactgcttga ttacagaaag aaatttatga     2100
agctgtaatc gggatagtta tactgcttgt tcttatgatt catttccttt gtgcagttct    2160
tggtgtagct tgccactttc accagcaaag ttc                                 2193
```

<210> SEQ ID NO 195
<211> LENGTH: 54
<212> TYPE: DNA
<213> ORGANISM: Artificial sequence
<220> FEATURE:
<223> OTHER INFORMATION: primer: PRM08180

<400> SEQUENCE: 195

```
ggggacaagt ttgtacaaaa aagcaggctt aaacaatgat caatccacac ggtg           54
```

-continued

<210> SEQ ID NO 196
<211> LENGTH: 50
<212> TYPE: DNA
<213> ORGANISM: Artificial sequence
<220> FEATURE:
<223> OTHER INFORMATION: primer: PRM08181

<400> SEQUENCE: 196
ggggaccact ttgtacaaga aagctgggtt ccttgtttac tcattccaca        50

<210> SEQ ID NO 197
<211> LENGTH: 56
<212> TYPE: DNA
<213> ORGANISM: Artificial sequence
<220> FEATURE:
<223> OTHER INFORMATION: primer: PRM08182

<400> SEQUENCE: 197
ggggacaagt ttgtacaaaa aagcaggctt aaacaatgaa ttctaacaac tggctc        56

<210> SEQ ID NO 198
<211> LENGTH: 50
<212> TYPE: DNA
<213> ORGANISM: Artificial sequence
<220> FEATURE:
<223> OTHER INFORMATION: primer: PRM08183

<400> SEQUENCE: 198
ggggaccact ttgtacaaga aagctgggtt catcttttat tcattccaca        50

<210> SEQ ID NO 199
<211> LENGTH: 1638
<212> TYPE: DNA
<213> ORGANISM: Populus tremuloides

<400> SEQUENCE: 199
atgaattcta caactggct ttcatttcct ctttctccta ctcatccttc cttgcctgct        60
catctacatg catcccaccc tcatcaattc tctctagggt tagtcaatga taatatggaa       120
aacccatttc aaactcaaga gtggagtctt cttaacactc atcaaggcaa caatgaagtg       180
ccaaaggttg cagactttct tggtgtgagc aaatctgaga atcaatcaga tcttgtagcc       240
ttcaatgaaa ttcaagctaa tgaatctgac tatctctttt caaacaatag tctagtacca       300
gtccaaaatg ctgttgtagg cgccaataat acctttgagt ttcaagaaaa tgctagcaat       360
ttgcagtcat taacattgtc tatgggcagt gctagtggta aggttctac atgtgaaccc       420 agtggggata atagcactaa tactgttgaa gctgctgcac aagaagaac tttggataca       480 tttgggcaaa gaacatccat atatcgtggt gtaacaaggc atcgatggac aggaaggtat       540
gaagctcatt tatgggataa tagttgcaga agagaaggtc aatctaggaa aggaagacag       600
ggtggctatg acaaagaaga aaaggcagct agggcttatg atcttgctgc acttaagtac       660
tggggaacat ccaccactac caattttcca atcagcaact acgagaaaga aatagaggaa       720
atgaagcaca tgaccaggca agaatttgtg gcctccatta gaaggaagag tagtggcttc       780 tctagggtg catccatgta tcgtggagtt acaaggcatc accagcatgg tagatggcaa       840
gcaaggatag gcagagttgc aggaaacaaa gatctctact tgggaacttt tagcactgag       900
gaggaggctg cagaagctta tgacatagca gcaataaagt ttagagggct taatgcagtg       960
actaactttg acatgaatcg atatgatgtg aagagcattc ttgaaagcaa tactttgcca      1020
attggaggag gggcagccaa acggctaaag gaggctcaag caattgaatc atcacgaaaa      1080
agagaagaaa tgattgctct tggctcaagt tttccatatg gatcaacttc aagctctagc      1140

```
aggctacaag cttaccctct aatgcagaca ccatttgagc aacctcaacc tttacttact    1200
ctacaaaatc aagacatttc tcagtacact caggattcct catcattcca ccaaaatttc    1260
cttcaaacac agcttcattt gcaccagcaa tctacagggt ctaatttcct gcataaccaa    1320
tcaaaccaaa accctcaata ttacaatagt tatatccaaa acaatccagc tttacttcat    1380
ggattgtgga acatgggttc ttcatcatct gtaatggaga ataatggaag ttctagtggg    1440
agctatagta ctggaggtta tctgggaaat gggctgggaa tggcttccaa ttcaacaggg    1500
tctaatgcag taggatcagc cgaggaactt gcacttgtca agttgattta tgatatgcct    1560
tctagtggct atggaagctg gtctggggac tcagtccagg gatccaatcc aggtgttttc    1620
actatgtgga atgagtga                                                  1638
```

<210> SEQ ID NO 200
<211> LENGTH: 545
<212> TYPE: PRT
<213> ORGANISM: Populus tremuloides

<400> SEQUENCE: 200

```
Met Asn Ser Asn Asn Trp Leu Ser Phe Pro Leu Ser Pro Thr His Pro
1               5                   10                  15

Ser Leu Pro Ala His Leu His Ala Ser His Pro His Gln Phe Ser Leu
                20                  25                  30

Gly Leu Val Asn Asp Asn Met Glu Asn Pro Phe Gln Thr Gln Glu Trp
            35                  40                  45

Ser Leu Leu Asn Thr His Gln Gly Asn Asn Glu Val Pro Lys Val Ala
        50                  55                  60

Asp Phe Leu Gly Val Ser Lys Ser Glu Asn Gln Ser Asp Leu Val Ala
65                  70                  75                  80

Phe Asn Glu Ile Gln Ala Asn Glu Ser Asp Tyr Leu Phe Ser Asn Asn
                85                  90                  95

Ser Leu Val Pro Val Gln Asn Ala Val Val Gly Ala Asn Asn Thr Phe
            100                 105                 110

Glu Phe Gln Glu Asn Ala Ser Asn Leu Gln Ser Leu Thr Leu Ser Met
        115                 120                 125

Gly Ser Ala Ser Gly Lys Gly Ser Thr Cys Glu Pro Ser Gly Asp Asn
130                 135                 140

Ser Thr Asn Thr Val Glu Ala Ala Pro Arg Arg Thr Leu Asp Thr
145                 150                 155                 160

Phe Gly Gln Arg Thr Ser Ile Tyr Arg Gly Val Thr Arg His Arg Trp
                165                 170                 175

Thr Gly Arg Tyr Glu Ala His Leu Trp Asp Asn Ser Cys Arg Arg Glu
            180                 185                 190

Gly Gln Ser Arg Lys Gly Arg Gln Gly Gly Tyr Asp Lys Glu Glu Lys
        195                 200                 205

Ala Ala Arg Ala Tyr Asp Leu Ala Ala Leu Lys Tyr Trp Gly Thr Ser
    210                 215                 220

Thr Thr Thr Asn Phe Pro Ile Ser Asn Tyr Glu Lys Glu Ile Glu Glu
225                 230                 235                 240

Met Lys His Met Thr Arg Gln Glu Phe Val Ala Ser Ile Arg Arg Lys
                245                 250                 255

Ser Ser Gly Phe Ser Arg Gly Ala Ser Met Tyr Arg Gly Val Thr Arg
            260                 265                 270

His His Gln His Gly Arg Trp Gln Ala Arg Ile Gly Arg Val Ala Gly
        275                 280                 285
```

```
Asn Lys Asp Leu Tyr Leu Gly Thr Phe Ser Thr Glu Glu Ala Ala
    290                 295                 300

Glu Ala Tyr Asp Ile Ala Ala Ile Lys Phe Arg Gly Leu Asn Ala Val
305                 310                 315                 320

Thr Asn Phe Asp Met Asn Arg Tyr Asp Val Lys Ser Ile Leu Glu Ser
                325                 330                 335

Asn Thr Leu Pro Ile Gly Gly Gly Ala Ala Lys Arg Leu Lys Glu Ala
            340                 345                 350

Gln Ala Ile Glu Ser Ser Arg Lys Arg Glu Glu Met Ile Ala Leu Gly
        355                 360                 365

Ser Ser Phe Pro Tyr Gly Ser Thr Ser Ser Ser Arg Leu Gln Ala
    370                 375                 380

Tyr Pro Leu Met Gln Thr Pro Phe Glu Gln Pro Gln Pro Leu Leu Thr
385                 390                 395                 400

Leu Gln Asn Gln Asp Ile Ser Gln Tyr Thr Gln Asp Ser Ser Ser Phe
                405                 410                 415

His Gln Asn Phe Leu Gln Thr Gln Leu His Leu His Gln Ser Thr
            420                 425                 430

Gly Ser Asn Phe Leu His Asn Gln Ser Asn Gln Asn Pro Gln Tyr Tyr
        435                 440                 445

Asn Ser Tyr Ile Gln Asn Asn Pro Ala Leu Leu His Gly Leu Trp Asn
450                 455                 460

Met Gly Ser Ser Ser Val Met Glu Asn Asn Gly Ser Ser Ser Gly
465                 470                 475                 480

Ser Tyr Ser Thr Gly Gly Tyr Leu Gly Asn Gly Leu Gly Met Ala Ser
                485                 490                 495

Asn Ser Thr Gly Ser Asn Ala Val Gly Ser Ala Glu Glu Leu Ala Leu
            500                 505                 510

Val Lys Val Asp Tyr Asp Met Pro Ser Ser Gly Tyr Gly Ser Trp Ser
        515                 520                 525

Gly Asp Ser Val Gln Gly Ser Asn Pro Gly Val Phe Thr Met Trp Asn
    530                 535                 540

Glu
545

<210> SEQ ID NO 201
<211> LENGTH: 1515
<212> TYPE: DNA
<213> ORGANISM: Populus tremuloides

<400> SEQUENCE: 201
atgttttttt tttgtttcc tttagagtgg agtcttctta acactcaagg caacaatgaa      60
gtgccaaagg ttgcagattt tcttggtgta agtaaatctg agaatcaatc agatctcgta     120
gccttcaatg aaattcaagc cagtgattct gagtatctct tttcaagcaa tagtctgttg     180
ccggtccaaa atgctgtggt agccgccagt actaactacg aatttcaaga aaatcctagc     240
aatttgcagt cattaacatt gtctatgggc agtgctagtg gtaagggttc taaatgtgaa     300
accagtggtg ataatagtac taattctgtc gaagctgctg ctccaagaag gactttggat     360
acatttggtc aaagaacatc catctatcgt ggtgtaacaa ggcatcgatg gacaggaagg     420
tatgaagctc atttatggga taatagttgc agaagagaag gtcaatccag aaaggaaga     480 caaggtggct atgacaaaga agacaaggct gctagggctt atgatcttgc tgcacttaag     540
tactggggaa catcgaccac taccaatttt cctatcagca actatgagaa agaactagag     600
```

```
gacatgaaga acatgaccag acaagaattt gtggcctcca ttagaaggaa gagtagtggc    660
ttctctaggg gtgcatccat gtatcgtgga gtcacaaggc atcaccaaca tggaagatgg    720
caagcaagaa ttggtagagt tgcaggaaac aaagatctct acttgggaac ttttagcact    780
gaggaggagg ctgcagaagc ttatgacata gcagcaataa agtttagagg cttaatgca     840 gtgactaatt ttgacatgaa tcgatatgat gtgaaaagca ttcttgagag caatagtttg    900
ccaattggag gaggggcagc caaaaggcta aggaggctc aagcaatcga atcgtcacaa     960
aaacgagaag aaatgattgc tcttggatca agttatccat atggatcaac ttcaagctct   1020
agtcgacaac aagcttactc tctaatgcag aaaccatttg agcaacctca acctttactt   1080
actctacaaa atcaagacat ttctcagtac actcaagatt cttcatttca gcaaaattac   1140
cttcaaacac agcttcattt gcaccagcta tctgcagggt ctaatttcct gcataataac   1200
caatcaagcc aaaatcctca gtattacaac agctatatcc aaaacaatcc cactttgctt   1260
catggattgt ggaacatggg ttcttcatca tctctaatgg agaataatgg cagttctagt   1320
gggagttata gtactgtcgg ttatctggga atgggttgg gaatggctac caattcaaca    1380
gggtctaatg cagtagctga ggaacttcca cttgttaaga tagattatga tatgccttct   1440
ggtggctatg gaagttggtc tggggaatca gttcagggat ccaacccagg tgttttaca    1500 atgtggaatg agtga                                                    1515

<210> SEQ ID NO 202
<211> LENGTH: 504
<212> TYPE: PRT
<213> ORGANISM: Populus tremuloides

<400> SEQUENCE: 202

Met Phe Phe Phe Leu Phe Pro Leu Glu Trp Ser Leu Leu Asn Thr Gln
1               5                   10                  15

Gly Asn Asn Glu Val Pro Lys Val Ala Asp Phe Leu Gly Val Ser Lys
            20                  25                  30

Ser Glu Asn Gln Ser Asp Leu Val Ala Phe Asn Glu Ile Gln Ala Ser
        35                  40                  45

Asp Ser Glu Tyr Leu Phe Ser Ser Asn Ser Leu Leu Pro Val Gln Asn
    50                  55                  60

Ala Val Val Ala Ala Ser Thr Asn Tyr Glu Phe Gln Glu Asn Pro Ser
65                  70                  75                  80

Asn Leu Gln Ser Leu Thr Leu Ser Met Gly Ser Ala Ser Gly Lys Gly
                85                  90                  95

Ser Lys Cys Glu Thr Ser Gly Asp Asn Ser Thr Asn Ser Val Glu Ala
            100                 105                 110

Ala Ala Pro Arg Arg Thr Leu Asp Thr Phe Gly Gln Arg Thr Ser Ile
        115                 120                 125

Tyr Arg Gly Val Thr Arg His Arg Trp Thr Gly Arg Tyr Glu Ala His
    130                 135                 140

Leu Trp Asp Asn Ser Cys Arg Arg Glu Gly Gln Ser Arg Lys Gly Arg
145                 150                 155                 160

Gln Gly Gly Tyr Asp Lys Glu Asp Lys Ala Ala Arg Ala Tyr Asp Leu
                165                 170                 175

Ala Ala Leu Lys Tyr Trp Gly Thr Ser Thr Thr Thr Asn Phe Pro Ile
            180                 185                 190

Ser Asn Tyr Glu Lys Glu Leu Glu Asp Met Lys Asn Met Thr Arg Gln
        195                 200                 205

Glu Phe Val Ala Ser Ile Arg Arg Lys Ser Ser Gly Phe Ser Arg Gly
```

```
              210                 215                 220
Ala Ser Met Tyr Arg Gly Val Thr Arg His His Gln His Gly Arg Trp
225                 230                 235                 240

Gln Ala Arg Ile Gly Arg Val Ala Gly Asn Lys Asp Leu Tyr Leu Gly
                245                 250                 255

Thr Phe Ser Thr Glu Glu Ala Ala Glu Ala Tyr Asp Ile Ala Ala
                260                 265                 270

Ile Lys Phe Arg Gly Leu Asn Ala Val Thr Asn Phe Asp Met Asn Arg
                275                 280                 285

Tyr Asp Val Lys Ser Ile Leu Glu Ser Asn Ser Leu Pro Ile Gly Gly
                290                 295                 300

Gly Ala Lys Arg Leu Lys Glu Ala Gln Ala Ile Glu Ser Ser Gln
305                 310                 315                 320

Lys Arg Glu Glu Met Ile Ala Leu Gly Ser Ser Tyr Pro Tyr Gly Ser
                325                 330                 335

Thr Ser Ser Ser Arg Gln Gln Ala Tyr Ser Leu Met Gln Lys Pro
                340                 345                 350

Phe Glu Gln Pro Gln Pro Leu Leu Thr Leu Gln Asn Gln Asp Ile Ser
                355                 360                 365

Gln Tyr Thr Gln Asp Ser Ser Phe Gln Gln Asn Tyr Leu Gln Thr Gln
                370                 375                 380

Leu His Leu His Gln Leu Ser Ala Gly Ser Asn Phe Leu His Asn Asn
385                 390                 395                 400

Gln Ser Ser Gln Asn Pro Gln Tyr Tyr Asn Ser Tyr Ile Gln Asn Asn
                405                 410                 415

Pro Thr Leu Leu His Gly Leu Trp Asn Met Gly Ser Ser Ser Leu
                420                 425                 430

Met Glu Asn Asn Gly Ser Ser Ser Gly Ser Tyr Ser Thr Val Gly Tyr
                435                 440                 445

Leu Gly Asn Gly Leu Gly Met Ala Thr Asn Ser Thr Gly Ser Asn Ala
                450                 455                 460

Val Ala Glu Glu Leu Pro Leu Val Lys Ile Asp Tyr Asp Met Pro Ser
465                 470                 475                 480

Gly Gly Tyr Gly Ser Trp Ser Gly Glu Ser Val Gln Gly Ser Asn Pro
                485                 490                 495

Gly Val Phe Thr Met Trp Asn Glu
                500

<210> SEQ ID NO 203
<211> LENGTH: 785
<212> TYPE: DNA
<213> ORGANISM: Vitis vinifera

<400> SEQUENCE: 203
tcttgataaa tcccaaaact gactgtgtag gtactgagga ggaagctgca gaagcctatg      60
atattgcagc aataaagttc agaggcctta atgcagtgac caactttgac atgaatcgat     120
acgatgtgaa gagcattctt gaaagcaaca ctcttccgat aggtggggga gcggccaagc     180
ggctaaagga ggctcaagca attgaatcat caagaaaacg ggaagaaatg atagccctag     240
gttcaagttt ccaatatggg agctcgagct ctagcaggtt acagacatat cctctaatgc     300
agcagcagtt tgagcaacct cagcctttac taacattaca gaaccaagaa ccattactaa     360
ctttgcaaaa ccctgaaatt tctcagtacc cccaagactc ccagtttcac caaaactaca     420
tccaaactca gttgcagttg caccagcaat ctgggtcgta cctgaaccat tcaagccaaa     480
```

```
gtcctcagtt ctacaacagt tacctccaca acaacccggc tcttcttcat gggctgatga      540
gtatgggctc ttcttcatct gtcatggaga ataatgggag ttctagtggg agttacaatg      600
gaggmtactt caataatgga cttggggttg cttcgaattc tacggtggct agtgcagtag      660
gatcagcaga ggagcttccc ctcatcaagg ttgattacga tatgccggcc gcaggctatg      720
gcagctggtc aggtgactca gttcagggac agaatgctgg agttttttaca atgtggaatg      780 actga                                                                  785
```

<210> SEQ ID NO 204
<211> LENGTH: 260
<212> TYPE: PRT
<213> ORGANISM: Vitis vinifera

<400> SEQUENCE: 204

```
Leu Ile Asn Pro Lys Thr Asp Cys Val Gly Thr Glu Glu Glu Ala Ala
1               5                   10                  15

Glu Ala Tyr Asp Ile Ala Ala Ile Lys Phe Arg Gly Leu Asn Ala Val
            20                  25                  30

Thr Asn Phe Asp Met Asn Arg Tyr Asp Val Lys Ser Ile Leu Glu Ser
        35                  40                  45

Asn Thr Leu Pro Ile Gly Gly Ala Ala Lys Arg Leu Lys Glu Ala
    50                  55                  60

Gln Ala Ile Glu Ser Ser Arg Lys Arg Glu Glu Met Ile Ala Leu Gly
65                  70                  75                  80

Ser Ser Phe Gln Tyr Gly Ser Ser Ser Ser Arg Leu Gln Thr Tyr
                85                  90                  95

Pro Leu Met Gln Gln Gln Phe Glu Gln Pro Gln Pro Leu Leu Thr Leu
            100                 105                 110

Gln Asn Gln Glu Pro Leu Leu Thr Leu Gln Asn Pro Glu Ile Ser Gln
        115                 120                 125

Tyr Pro Gln Asp Ser Gln Phe His Gln Asn Tyr Ile Gln Thr Gln Leu
    130                 135                 140

Gln Leu His Gln Gln Ser Gly Ser Tyr Leu Asn His Ser Ser Gln Ser
145                 150                 155                 160

Pro Gln Phe Tyr Asn Ser Tyr Leu His Asn Asn Pro Ala Leu Leu His
                165                 170                 175

Gly Leu Met Ser Met Gly Ser Ser Ser Val Met Glu Asn Asn Gly
            180                 185                 190

Ser Ser Ser Gly Ser Tyr Asn Gly Gly Tyr Phe Asn Asn Gly Leu Gly
        195                 200                 205

Val Ala Ser Asn Ser Thr Val Ala Ser Ala Val Gly Ser Ala Glu Glu
    210                 215                 220

Leu Pro Leu Ile Lys Val Asp Tyr Asp Met Pro Ala Ala Gly Tyr Gly
225                 230                 235                 240

Ser Trp Ser Gly Asp Ser Val Gln Gly Gln Asn Ala Gly Val Phe Thr
                245                 250                 255

Met Trp Asn Asp
            260
```

<210> SEQ ID NO 205
<211> LENGTH: 150
<212> TYPE: DNA
<213> ORGANISM: brassica napus

<400> SEQUENCE: 205

```
ggaacatcgg ccgaggaaga gtttcccacg gttaaagttg attacgatat gcctccttta      60
```

```
ggtggagcca cagggtgtga acgatggact aatggagaga atggtcaggg gtcaaatcca    120
ggaggtgtct tcacaatgtg gaatgaataa                                    150

<210> SEQ ID NO 206
<211> LENGTH: 49
<212> TYPE: PRT
<213> ORGANISM: Brassica napus

<400> SEQUENCE: 206

Gly Thr Ser Ala Glu Glu Phe Pro Thr Val Lys Val Asp Tyr Asp
1               5                   10                  15

Met Pro Pro Leu Gly Gly Ala Thr Gly Cys Glu Arg Trp Thr Asn Gly
            20                  25                  30

Glu Asn Gly Gln Gly Ser Asn Pro Gly Gly Val Phe Thr Met Trp Asn
        35                  40                  45

Glu

<210> SEQ ID NO 207
<211> LENGTH: 162
<212> TYPE: DNA
<213> ORGANISM: Phaseolus coccineus

<400> SEQUENCE: 207
tcgaatgcat cgtcgggtaa tgcggtgggc acggcggagg aacttggatt ggtgaaagtt    60
gactatgaca tgccggccgg aggttacggt ggttggtcgg cggcggcggc ggaatccatg   120
cagacgtcaa atggtggggt gttcacaatg tggaatgagt ga                      162

<210> SEQ ID NO 208
<211> LENGTH: 53
<212> TYPE: PRT
<213> ORGANISM: Phaseolus coccineus

<400> SEQUENCE: 208

Ser Asn Ala Ser Ser Gly Asn Ala Val Gly Thr Ala Glu Glu Leu Gly
1               5                   10                  15

Leu Val Lys Val Asp Tyr Asp Met Pro Ala Gly Gly Tyr Gly Gly Trp
            20                  25                  30

Ser Ala Ala Ala Ala Glu Ser Met Gln Thr Ser Asn Gly Gly Val Phe
        35                  40                  45

Thr Met Trp Asn Glu
    50

<210> SEQ ID NO 209
<211> LENGTH: 7
<212> TYPE: PRT
<213> ORGANISM: Artificial sequence
<220> FEATURE:
<223> OTHER INFORMATION: Motif 2
<220> FEATURE:
<221> NAME/KEY: VARIANT
<222> LOCATION: (1)..(1)
<223> OTHER INFORMATION: Xaa is Val or Leu
<220> FEATURE:
<221> NAME/KEY: UNSURE
<222> LOCATION: (3)..(3)
<223> OTHER INFORMATION: Xaa can be any naturally occurring amino acid
<220> FEATURE:
<221> NAME/KEY: VARIANT
<222> LOCATION: (4)..(4)
<223> OTHER INFORMATION: Xaa is Met or Val
<220> FEATURE:
<221> NAME/KEY: VARIANT
<222> LOCATION: (7)..(7)
```

<223> OTHER INFORMATION: Xaa is Asp or Glu

<400> SEQUENCE: 209

Xaa Phe Xaa Xaa Trp Asn Xaa
1               5

<210> SEQ ID NO 210
<211> LENGTH: 2194
<212> TYPE: DNA
<213> ORGANISM: Oryza sativa

<400> SEQUENCE: 210

| | | | | | |
|---|---|---|---|---|---|
| aatccgaaaa | gtttctgcac | cgttttcacc | ccctaactaa | caatataggg | aacgtgtgct | 60 |
| aaatataaaa | tgagaccttta | tatatgtagc | gctgataact | agaactatgc | aagaaaaact | 120 |
| catccaccta | ctttagtggc | aatcgggcta | aataaaaaag | agtcgctaca | ctagtttcgt | 180 |
| tttccttagt | aattaagtgg | gaaaatgaaa | tcattattgc | ttagaatata | cgttcacatc | 240 |
| tctgtcatga | agttaaatta | ttcgaggtag | ccataattgt | catcaaactc | ttcttgaata | 300 |
| aaaaaatctt | tctagctgaa | ctcaatgggt | aaagagagag | attttttta | aaaaaataga | 360 |
| atgaagatat | tctgaacgta | ttggcaaaga | tttaaacata | taattatata | attttatagt | 420 |
| ttgtgcattc | gtcatatcgc | acatcattaa | ggacatgtct | tactccatcc | caatttttat | 480 |
| ttagtaatta | aagacaattg | acttattttt | attatttatc | ttttttcgat | tagatgcaag | 540 |
| gtacttacgc | acacactttg | tgctcatgtg | catgtgtgag | tgcacctcct | caatacacgt | 600 |
| tcaactagca | acacatctct | aatatcactc | gcctatttaa | tacatttagg | tagcaatatc | 660 |
| tgaattcaag | cactccacca | tcaccagacc | acttttaata | atatctaaaa | tacaaaaaat | 720 |
| aatttttacag | aatagcatga | aaagtatgaa | acgaactatt | taggttttt | acatacaaaa | 780 |
| aaaaaaagaa | tttttgctcgt | gcgcgagcgc | caatctccca | tattgggcac | acaggcaaca | 840 |
| acagagtggc | tgcccacaga | acaacccaca | aaaaacgatg | atctaacgga | ggacagcaag | 900 |
| tccgcaacaa | ccttttaaca | gcaggctttg | cggccaggag | agaggaggag | aggcaaagaa | 960 |
| aaccaagcat | cctccttctc | ccatctataa | attcctcccc | ccttttcccc | tctctatata | 1020 |
| ggaggcatcc | aagccaagaa | gagggagagc | accaaggaca | cgcgactagc | agaagccgag | 1080 |
| cgaccgcctt | ctcgatccat | atcttccggt | cgagttcttg | gtcgatctct | tccctcctcc | 1140 |
| acctcctcct | cacagggtat | gtgcctccct | tcggttgttc | ttggatttat | tgttctaggt | 1200 |
| tgtgtagtac | gggcgttgat | gttaggaaag | gggatctgta | tctgtgatga | ttcctgttct | 1260 |
| tggatttggg | atagagggggt | tcttgatgtt | gcatgttatc | ggttcggttt | gattagtagt | 1320 |
| atggttttca | atcgtctgga | gagctctatg | gaaatgaaat | ggtttaggga | tcggaatctt | 1380 |
| gcgattttgt | gagtaccttt | tgtttgaggt | aaaatcagag | caccggtgat | tttgcttggt | 1440 |
| gtaataaagt | acggttgttt | ggtcctcgat | tctggtagtg | atgcttctcg | atttgacgaa | 1500 |
| gctatccttt | gttattccc | tattgaacaa | aaataatcca | actttgaaga | cggtcccgtt | 1560 |
| gatgagattg | aatgattgat | tcttaagcct | gtccaaaatt | tcgcagctgg | cttgttttaga | 1620 |
| tacagtagtc | cccatcacga | aattcatgga | aacagttata | atcctcagga | acaggggatt | 1680 |
| ccctgttctt | ccgatttgct | ttagtcccag | aatttttttt | cccaaatatc | ttaaaaagtc | 1740 |
| actttctggt | tcagttcaat | gaattgattg | ctacaaataa | tgcttttata | gcgttatcct | 1800 |
| agctgtagtt | cagttaatag | gtaatacccc | tatagtttag | tcaggagaag | aacttatccg | 1860 |
| atttctgatc | tccattttta | attatatgaa | atgaactgta | gcataagcag | tattcatttg | 1920 |
| gattattttt | tttattagct | ctcaccccctt | cattattctg | agctgaaagt | ctggcatgaa | 1980 |

| | |
|---|---:|
| ctgtcctcaa ttttgttttc aaattcacat cgattatcta tgcattatcc tcttgtatct | 2040 |
| acctgtagaa gtttctttt ggttattcct tgactgcttg attacagaaa gaaatttatg | 2100 |
| aagctgtaat cgggatagtt atactgcttg ttcttatgat tcatttcctt tgtgcagttc | 2160 |
| ttggtgtagc ttgccacttt caccagcaaa gttc | 2194 |

<210> SEQ ID NO 211
<211> LENGTH: 1245
<212> TYPE: DNA
<213> ORGANISM: Oryza sativa

<400> SEQUENCE: 211

| | |
|---|---:|
| cttgttgttg atctgtgccc ccaagaagaa taacactcta ctcttacttg ttggaaaaaa | 60 |
| atagtattag caaccacgca tatgcaaatt ttaatgcagt aataataaga gatggatcga | 120 |
| tcgttttcca gctcttgtat atgtgactgg ccctgcttta tgtgtgtagt gttaatttca | 180 |
| gctttagcag tacgtgatta gtgatggaca ataattgtcg cagacgtatc tatcaattgc | 240 |
| tcctgttgtg tgatgcttta actgttggaa tcaaagttgc gttgcctttg ttgttatgag | 300 |
| gaggaatata tatgttgggg caggaaaaga tggaggaga tcgttctc catatcctta | 360 |
| tcatcggcct cgtcactgct cgcagtttaa cttttggtg atgcgagcga tggtcagcca | 420 |
| tatatatact cccatgctgc atgctagtaa tcaatatacg ccttgtaaaa gtaaacgatc | 480 |
| gtctagtaat tgcaatatca taggggtagc cattgacaga gatctacata gatagagggg | 540 |
| gaacaagaat tgcactcca cagatgctcc actcattcac ctttactaat ttatatcttt | 600 |
| tgatgtttga tcgatcgatc gatccgtccg tcggtgtctc gacgaataaa aactgcaaat | 660 |
| cgaactgtat gtatataata tagcgtcgta aattaaatta aattaaatcg aactgaatac | 720 |
| tacatgtcga agcaagaatt agttcaacta aaagatttag ttttttccggt tgcaatatct | 780 |
| gtgaaattaa ttgaagaaat taagaagaaa actggagaga tatatatatg gatgagacaa | 840 |
| aatgagataa gacgcatgat ggtccctcgg atgatgtcgt ccgttcctta tttccattcc | 900 |
| atggcagctg ctatcgctat ctagtgcgcg cggcatctcc aatcccatcc attctagtgg | 960 |
| tcgatctagc tactactgag tattgttttt tcttcttttt actactgttg attattctgc | 1020 |
| aactgcagtt agatgcttgc tactcctaca tcgatctctc tcgcgcgggc gtatgcattg | 1080 |
| cattcactac tgatgatccg tgggtgtagt gtgggtggct ataaataggg cagggtgcgg | 1140 |
| ttgccattgc tcctcaggcc agcaactgag aagctccata caagtaagca gcagctagtt | 1200 |
| gccgacaagg ccagagaagg aagaagaagc tctcatcatc atcac | 1245 |

<210> SEQ ID NO 212
<211> LENGTH: 675
<212> TYPE: DNA
<213> ORGANISM: Oryza sativa

<400> SEQUENCE: 212

| | |
|---|---:|
| atgaagagca ggaagaacag cacgacgagc acaaaagcag caggcagctg ccacaccagc | 60 |
| agcagcggag gaggaggagg cggcggcaac tgctatagca gcagcagtag caagatggag | 120 |
| cgcaaggatg tggagaagaa tcggcgcctc cacatgaagg gtctctgcct caagctctcc | 180 |
| tccctcatcc ccgccgccgc tccccgccgc catcaccacc actactccac ctcctcctcc | 240 |
| tcatcgccgc cctcctccac caaggaggct gtgacgcagc tggatcacct ggagcaggcg | 300 |
| gcggcgtaca tcaagcagct caaggggagg atcgacgagc tgaagaagag gaagcagcag | 360 |
| gcggcggcac tcaccaccag caccagcaat ggcggcggcg gcgggatgcc ggtggtggag | 420 |

```
gtgcggtgcc aggatgggac gctggacgtg gtggtggtga gcgaggcgat cagggaggag     480
agggagaggg cggtgcggct gcacgaggtg atcggcgtgc tggaggaaga aggcgcggag     540
gtggtgaacg ccagcttctc cgtcgtcggc gacaagatct tctacactct ccactcccag     600
gcgctctgct ccaggatcgg cctcgacgcc tccagggtct cccacaggct gcgcaacctc     660
ctcctccaat attaa                                                     675
```

<210> SEQ ID NO 213
<211> LENGTH: 224
<212> TYPE: PRT
<213> ORGANISM: Oryza sativa

<400> SEQUENCE: 213

```
Met Lys Ser Arg Lys Asn Ser Thr Thr Ser Thr Lys Ala Ala Gly Ser
1               5                   10                  15

Cys His Thr Ser Ser Ser Gly Gly Gly Gly Gly Gly Asn Cys Tyr
                20                  25                  30

Ser Ser Ser Ser Ser Lys Met Glu Arg Lys Asp Val Glu Lys Asn Arg
            35                  40                  45

Arg Leu His Met Lys Gly Leu Cys Leu Lys Leu Ser Ser Leu Ile Pro
        50                  55                  60

Ala Ala Ala Pro Arg Arg His His His Tyr Ser Thr Ser Ser Ser
65                  70                  75                  80

Ser Ser Pro Pro Ser Ser Thr Lys Glu Ala Val Thr Gln Leu Asp His
                85                  90                  95

Leu Glu Gln Ala Ala Ala Tyr Ile Lys Gln Leu Lys Gly Arg Ile Asp
                100                 105                 110

Glu Leu Lys Lys Arg Lys Gln Gln Ala Ala Ala Leu Thr Thr Ser Thr
            115                 120                 125

Ser Asn Gly Gly Gly Gly Gly Met Pro Val Val Glu Val Arg Cys Gln
130                 135                 140

Asp Gly Thr Leu Asp Val Val Val Ser Glu Ala Ile Arg Glu Glu
145                 150                 155                 160

Arg Glu Arg Ala Val Arg Leu His Glu Val Ile Gly Val Leu Glu Glu
                165                 170                 175

Glu Gly Ala Glu Val Val Asn Ala Ser Phe Ser Val Val Gly Asp Lys
            180                 185                 190

Ile Phe Tyr Thr Leu His Ser Gln Ala Leu Cys Ser Arg Ile Gly Leu
        195                 200                 205

Asp Ala Ser Arg Val Ser His Arg Leu Arg Asn Leu Leu Leu Gln Tyr
    210                 215                 220
```

<210> SEQ ID NO 214
<211> LENGTH: 696
<212> TYPE: DNA
<213> ORGANISM: Oryza sativa

<400> SEQUENCE: 214

```
atggatcagg agaaggcgga cggcggcggc aggaggagga ggagcagggc gacgagtagc      60
agcggcagcg gcgcgagcag cacgcggcgc ggcggcggcg cggagaggaa ggagatggag     120
cgcaggaggc ggcaggacat gaaggcctc tgcgtcaagc tcgcctctct catccccaaa     180
gaacactgct ccatgtccaa gatgcaggcg gcgtctagga cccagctggg cagcctggac     240
gaagcggcgg cctacatcaa gaagctcaag gaaagggtgg acgagctgca ccacaagagg     300
agcatgatga gtatcacatc atcgcgctgc cgctcaggag gaggaggagg accagctgct     360
```

```
gctgctggcc agtcgacgag cggcggcggc ggcggggaag aagaagaaga agatatgacg    420
aggacgacgg cggcggcggc ggtggtggag gtgcggcagc acgtgcagga ggggtcgctg    480
atcagcttgg acgtggtgct gatctgcagc gcagcgaggc cggtcaagtt ccacgacgtc    540
atcaccgtcc tcgaggaaga aggcgccgac atcatctccg ccaacttctc cctcgccgcc    600
cacaatttct actacaccat ctactccagg gcctttagct caagaattgg catagaggct    660
tcgaggattt ctgagagact acgggcattg gtatga                              696
```

<210> SEQ ID NO 215
<211> LENGTH: 231
<212> TYPE: PRT
<213> ORGANISM: Oryza sativa

<400> SEQUENCE: 215

```
Met Asp Gln Glu Lys Ala Asp Gly Gly Gly Arg Arg Arg Ser Arg
1               5                   10                  15

Ala Thr Ser Ser Ser Gly Ser Gly Ala Ser Ser Thr Ala Ala Ala
                20                  25                  30

Ala Ala Glu Arg Lys Glu Met Glu Arg Arg Arg Gln Asp Met Lys
                35                  40                  45

Gly Leu Cys Val Lys Leu Ala Ser Leu Ile Pro Lys Glu His Cys Ser
    50                  55                  60

Met Ser Lys Met Gln Ala Ala Ser Arg Thr Gln Leu Gly Ser Leu Asp
65                  70                  75                  80

Glu Ala Ala Ala Tyr Ile Lys Lys Leu Lys Arg Val Asp Glu Leu
                85                  90                  95

His His Lys Arg Ser Met Met Ser Ile Thr Ser Ser Arg Cys Arg Ser
                100                 105                 110

Gly Gly Gly Gly Gly Pro Ala Ala Ala Gly Gln Ser Thr Ser Gly
                115                 120                 125

Gly Gly Gly Gly Glu Glu Glu Glu Asp Met Thr Arg Thr Thr Ala
            130                 135                 140

Ala Ala Ala Val Val Glu Val Arg Gln His Val Gln Glu Gly Ser Leu
145                 150                 155                 160

Ile Ser Leu Asp Val Val Leu Ile Cys Ser Ala Ala Arg Pro Val Lys
                165                 170                 175

Phe His Asp Val Ile Thr Val Leu Glu Glu Glu Gly Ala Asp Ile Ile
                180                 185                 190

Ser Ala Asn Phe Ser Leu Ala Ala His Asn Phe Tyr Tyr Thr Ile Tyr
                195                 200                 205

Ser Arg Ala Phe Ser Ser Arg Ile Gly Ile Glu Ala Ser Arg Ile Ser
    210                 215                 220

Glu Arg Leu Arg Ala Leu Val
225                 230
```

<210> SEQ ID NO 216
<211> LENGTH: 633
<212> TYPE: DNA
<213> ORGANISM: Oryza sativa

<400> SEQUENCE: 216

```
atggagatcc cgccgccgtc agctggtggc ggaggcggcg gcggcaagcc cgaccggaag    60
acgacggagc gcatccgccg cgagcagatg aacaagctct actccccacct cgactccctc   120 gtccgctccg ctccccccac agttaattcc attccttcac attcaaattc aaattcaaaa    180
```

```
taccatcaaa gaaaattacg gattctcggt ggggcggcgg cggcgacgac gaggccggac    240
aggttggggg tggcggcgga gtacataagg cagacgcagg agagggtgga catgctgagg    300
gagaagaaga gggagctcac cggcggcggc ggcggcggct cctcgtcgtc gtccggcgcc    360
ggggcggcca cggccgccgc gccggaggtg gaggtgcagc acctgggctc cggcctgcac    420
gccatcctct tcaccggcgc gccgcccacc gacggcgcct ccttccaccg cgccgtccgc    480
gccgtcgagg acgccggcgg ccaggtgcag aacgcgcact ctccgtcgc cggcgccaag     540 gccgtctaca ccatccacgc catgattgga gatggatatg gaggcattga gagggtggtg    600
cagagattaa aggaagcaat acggagcaac taa                                 633
```

<210> SEQ ID NO 217
<211> LENGTH: 210
<212> TYPE: PRT
<213> ORGANISM: Oryza sativa

<400> SEQUENCE: 217

```
Met Glu Ile Pro Pro Ser Ala Gly Gly Gly Gly Gly Gly Gly Lys
1               5                   10                  15

Pro Asp Arg Lys Thr Thr Glu Arg Ile Arg Arg Glu Gln Met Asn Lys
            20                  25                  30

Leu Tyr Ser His Leu Asp Ser Leu Val Arg Ser Ala Pro Pro Thr Val
        35                  40                  45

Asn Ser Ile Pro Ser His Ser Asn Ser Asn Ser Lys Tyr His Gln Arg
    50                  55                  60

Lys Leu Arg Ile Leu Gly Gly Ala Ala Ala Thr Thr Arg Pro Asp
65                  70                  75                  80

Arg Leu Gly Val Ala Ala Glu Tyr Ile Arg Gln Thr Gln Glu Arg Val
                85                  90                  95

Asp Met Leu Arg Glu Lys Lys Arg Glu Leu Thr Gly Gly Gly Gly
            100                 105                 110

Gly Ser Ser Ser Ser Gly Ala Gly Ala Ala Thr Ala Ala Ala Pro
        115                 120                 125

Glu Val Glu Val Gln His Leu Gly Ser Gly Leu His Ala Ile Leu Phe
    130                 135                 140

Thr Gly Ala Pro Pro Thr Asp Gly Ala Ser Phe His Arg Ala Val Arg
145                 150                 155                 160

Ala Val Glu Asp Ala Gly Gly Gln Val Gln Asn Ala His Phe Ser Val
                165                 170                 175

Ala Gly Ala Lys Ala Val Tyr Thr Ile His Ala Met Ile Gly Asp Gly
            180                 185                 190

Tyr Gly Gly Ile Glu Arg Val Val Gln Arg Leu Lys Glu Ala Ile Arg
        195                 200                 205

Ser Asn
    210
```

<210> SEQ ID NO 218
<211> LENGTH: 546
<212> TYPE: DNA
<213> ORGANISM: Arabidopsis thaliana

<400> SEQUENCE: 218

```
atggggagag caagagaaat aggagaagga aactcatcgt cgttaaggga caacgaaac     60 ctcagagaga aggatcgaag gatgcgcatg aaacatctct tctctatact ttcttctcat    120
gtttctccca ctcgcaagtt accagtgcct caccttatag atcaagcgac atcatacatg    180
```

```
atccaattga agagaatgt  aaattatttg aaagagaaga aaaggacatt gttacaagga    240
gaactcggga atctctacga agggtcgttt cttctaccca aactcagtat tcgttcgcgg    300
gattcgacca tagaaatgaa tctgatcatg gatctaaaca tgaaaagagt aatgttacac    360
gagcttgtga gtattttga  agaagaagga gctcaagtaa tgagtgctaa tcttcagaac    420
ttgaatgata ggaccactta cacaatcata gcccaggcta tcattagtcg gattggcatt    480
gatccatcaa ggatagaaga gagagtacgg aaaatcatct atggatatat atattttgaa    540
gcatga                                                                546
```

<210> SEQ ID NO 219
<211> LENGTH: 188
<212> TYPE: PRT
<213> ORGANISM: Arabidopsis thaliana

<400> SEQUENCE: 219

```
Met Gly Arg Ala Arg Glu Ile Gly Glu Gly Asn Ser Ser Ser Leu Arg
1               5                   10                  15

Glu Gln Arg Asn Leu Arg Glu Lys Asp Arg Arg Met Arg Met Lys His
                20                  25                  30

Leu Phe Ser Ile Leu Ser Ser His Val Ser Pro Thr Arg Lys Leu Pro
            35                  40                  45

Val Pro His Leu Ile Asp Gln Ala Thr Ser Tyr Met Ile Gln Leu Lys
        50                  55                  60

Glu Asn Val Asn Tyr Leu Lys Glu Lys Lys Arg Thr Leu Leu Gln Gly
65                  70                  75                  80

Glu Leu Gly Asn Leu Tyr Glu Gly Ser Phe Leu Leu Pro Lys Leu Ser
                85                  90                  95

Ile Arg Ser Arg Asp Ser Thr Ile Glu Met Asn Leu Ile Met Asp Leu
            100                 105                 110

Asn Met Lys Arg Val Met Leu His Glu Leu Val Ser Ile Phe Glu Glu
        115                 120                 125

Glu Gly Ala Gln Val Met Ser Ala Asn Leu Gln Asn Leu Asn Asp Arg
    130                 135                 140

Thr Thr Tyr Thr Ile Ile Ala Gln Val Pro His Pro His Ala Tyr Ala
145                 150                 155                 160

Ile Ile Ser Arg Ile Gly Ile Asp Pro Ser Arg Ile Glu Glu Arg Val
                165                 170                 175

Arg Lys Ile Ile Tyr Gly Tyr Ile Tyr Phe Glu Ala
            180                 185
```

<210> SEQ ID NO 220
<211> LENGTH: 525
<212> TYPE: DNA
<213> ORGANISM: Arabidopsis thaliana

<400> SEQUENCE: 220

```
atggaaagag cgagagaaat aggagaagga agcgcatcgt cattacggga caacgaaac     60 ctcagagaga agaacgacg  aatgcgcatg aaacatctct ctccatact  ctcttctcat    120 gtttctccca ctcgtaggtt gccagtgcct caacttatag atcaagcggt atcatacatg    180
atccaactga agagaaggt  aaactatttg aatgagatga aaggagaat  gttaggagga    240 gaagtcaaaa atcgctctga agggtcgtct cttctgccaa aactcagtat tcgttcactg    300
gattcgatca tagaaatgaa tctggttatg gatctaaaca tgaaaggagt aatgttacac    360
aagcttgtga gtgtttttga agaagaagga gctcaagtga tgagtgctaa tcttcagaac    420
```

```
ttgaatgata ggacctttta tacaatcata gcccaggcta tcatatgtcg gatcgggatt    480
gatccatcaa ggatagaaga gagattaagg gatataatct catga                   525

<210> SEQ ID NO 221
<211> LENGTH: 174
<212> TYPE: PRT
<213> ORGANISM: Arabidopsis thaliana

<400> SEQUENCE: 221

Met Glu Arg Ala Arg Glu Ile Gly Glu Gly Ser Ala Ser Ser Leu Arg
1               5                   10                  15

Glu Gln Arg Asn Leu Arg Glu Lys Glu Arg Arg Met Arg Met Lys His
            20                  25                  30

Leu Phe Ser Ile Leu Ser Ser His Val Ser Pro Thr Arg Arg Leu Pro
        35                  40                  45

Val Pro Gln Leu Ile Asp Gln Ala Val Ser Tyr Met Ile Gln Leu Lys
    50                  55                  60

Glu Lys Val Asn Tyr Leu Asn Glu Met Lys Arg Arg Met Leu Gly Gly
65                  70                  75                  80

Glu Val Lys Asn Arg Ser Glu Gly Ser Ser Leu Leu Pro Lys Leu Ser
                85                  90                  95

Ile Arg Ser Leu Asp Ser Ile Ile Glu Met Asn Leu Val Met Asp Leu
            100                 105                 110

Asn Met Lys Gly Val Met Leu His Lys Leu Val Ser Val Phe Glu Glu
        115                 120                 125

Glu Gly Ala Gln Val Met Ser Ala Asn Leu Gln Asn Leu Asn Asp Arg
    130                 135                 140

Thr Phe Tyr Thr Ile Ala Gln Ala Ile Cys Arg Ile Gly Ile
145                 150                 155                 160

Asp Pro Ser Arg Ile Glu Glu Arg Leu Arg Asp Ile Ile Ser
                165                 170

<210> SEQ ID NO 222
<211> LENGTH: 369
<212> TYPE: DNA
<213> ORGANISM: Arabidopsis thaliana

<400> SEQUENCE: 222
atgatccaat tgaaagagaa tgtaaattat ttgaaagaga agaaaaggac attgttacaa    60
ggagaactcg ggaatctcta cgaagggtcg tttcttctac ccaaactcag tattcgttcg    120
cgggattcga ccatagaaat gaatctgatc atggatctaa acatgaaaag agtaatgtta    180
cacgagcttg tgagtatttt tgaagaagaa ggagctcaag taatgagtgc taatcttcag    240
aacttgaatg ataggaccac ttacacaatc atagcccagg ctatcattag tcggattggc    300
attgatccat caaggataga agagagagta cggaaaatca tctatggata tatatatttt    360
gaagcatga                                                            369

<210> SEQ ID NO 223
<211> LENGTH: 122
<212> TYPE: PRT
<213> ORGANISM: Arabidopsis thaliana

<400> SEQUENCE: 223

Met Ile Gln Leu Lys Glu Asn Val Asn Tyr Leu Lys Glu Lys Lys Arg
1               5                   10                  15

Thr Leu Leu Gln Gly Glu Leu Gly Asn Leu Tyr Glu Gly Ser Phe Leu
            20                  25                  30
```

```
Leu Pro Lys Leu Ser Ile Arg Ser Arg Asp Ser Thr Ile Glu Met Asn
            35                  40                  45

Leu Ile Met Asp Leu Asn Met Lys Arg Val Met Leu His Glu Leu Val
 50                  55                  60

Ser Ile Phe Glu Glu Glu Gly Ala Gln Val Met Ser Ala Asn Leu Gln
 65                  70                  75                  80

Asn Leu Asn Asp Arg Thr Thr Tyr Thr Ile Ile Ala Gln Ala Ile Ile
                 85                  90                  95

Ser Arg Ile Gly Ile Asp Pro Ser Arg Ile Glu Glu Arg Val Arg Lys
            100                 105                 110

Ile Ile Tyr Gly Tyr Ile Tyr Phe Glu Ala
            115                 120

<210> SEQ ID NO 224
<211> LENGTH: 573
<212> TYPE: DNA
<213> ORGANISM: Arabidopsis thaliana

<400> SEQUENCE: 224
atggagccga gccattcaaa cacaggtcaa tcaagatctg tagatcgcaa aacggttgag      60
aaaaatagaa ggatgcaaat gaagtctctc tactcagaac tcatctctct tcttcctcat     120
cattcttcta cggagccttt aacactacct gatcagctag atgaagctgc aaactacatc     180
aagaagctac aagtgaacgt ggagaaaaag agagaaagga aaggaaccct cgttgcgact     240
acaactttgg agaaactgaa ttccgtcgga tcttcatcgg tttcgtcgag cgtcgatgtc     300
tccgtgccaa gaaagctgcc aaaaatcgag attcaagaaa ctggttccat ttttcacatc     360
tttcttgtga caagcttgga acacaagttt atgttttgtg agatcattcg tgttctcacc     420
gaggaattag agctgagat cactcatgct ggatactcca ttgttgatga tgctgtcttc     480
cacacccttc actgcaaggt ggaagaacac gattatggag ctaggagtca aattcctgaa     540
agactggaga agattgtgaa cagtgttcac taa                                  573

<210> SEQ ID NO 225
<211> LENGTH: 190
<212> TYPE: PRT
<213> ORGANISM: Arabidopsis thaliana

<400> SEQUENCE: 225

Met Glu Pro Ser His Ser Asn Thr Gly Gln Ser Arg Ser Val Asp Arg
  1               5                  10                  15

Lys Thr Val Glu Lys Asn Arg Arg Met Gln Met Lys Ser Leu Tyr Ser
             20                  25                  30

Glu Leu Ile Ser Leu Leu Pro His His Ser Ser Thr Glu Pro Leu Thr
            35                  40                  45

Leu Pro Asp Gln Leu Asp Glu Ala Ala Asn Tyr Ile Lys Lys Leu Gln
 50                  55                  60

Val Asn Val Glu Lys Lys Arg Glu Arg Lys Asn Leu Val Ala Thr
 65                  70                  75                  80

Thr Thr Leu Glu Lys Leu Asn Ser Val Gly Ser Ser Val Ser Ser
             85                  90                  95

Ser Val Asp Val Ser Val Pro Arg Lys Leu Pro Lys Ile Glu Ile Gln
            100                 105                 110

Glu Thr Gly Ser Ile Phe His Ile Phe Leu Val Thr Ser Leu Glu His
            115                 120                 125

Lys Phe Met Phe Cys Glu Ile Ile Arg Val Leu Thr Glu Glu Leu Gly
```

```
                    130                 135                 140
Ala Glu Ile Thr His Ala Gly Tyr Ser Ile Val Asp Asp Ala Val Phe
145                 150                 155                 160

His Thr Leu His Cys Lys Val Glu Glu His Asp Tyr Gly Ala Arg Ser
                165                 170                 175

Gln Ile Pro Glu Arg Leu Glu Lys Ile Val Asn Ser Val His
            180                 185                 190

<210> SEQ ID NO 226
<211> LENGTH: 423
<212> TYPE: DNA
<213> ORGANISM: Medicago truncatula

<400> SEQUENCE: 226
atgacatctc taacaaagga ggcgatttca gtgccggatc agctaaagga agcaacaaac      60
tacataaaga aattgcagat caacctggag aaaatgaagg aaaagaagaa ttttctacta     120
ggaattcaaa ggccaaatgt gaatttgaat agaaaccaga gatgggatt aaagtctcca     180 aaaattaaga tacaacaaat tggtttagtc ttagaggttg ttctaataac tggattggag     240
tctcagtttt tgttcagcga aacctttcga gttcttcatg aagaaggagt tgatattgtt     300
aatgctagtt ataaggtcaa tgaagattct gttttccatt caatacactg ccaggtagga     360
gaatttggca atgaagctgc aagaatatct gagagattga agaagtttat gcaagactat     420
tag                                                                   423

<210> SEQ ID NO 227
<211> LENGTH: 140
<212> TYPE: PRT
<213> ORGANISM: Medicago truncatula

<400> SEQUENCE: 227

Met Thr Ser Leu Thr Lys Glu Ala Ile Ser Val Pro Asp Gln Leu Lys
1               5                   10                  15

Glu Ala Thr Asn Tyr Ile Lys Lys Leu Gln Ile Asn Leu Glu Lys Met
            20                  25                  30

Lys Glu Lys Lys Asn Phe Leu Leu Gly Ile Gln Arg Pro Asn Val Asn
        35                  40                  45

Leu Asn Arg Asn Gln Lys Met Gly Leu Lys Ser Pro Lys Ile Lys Ile
50                  55                  60

Gln Gln Ile Gly Leu Val Leu Glu Val Val Leu Ile Thr Gly Leu Glu
65                  70                  75                  80

Ser Gln Phe Leu Phe Ser Glu Thr Phe Arg Val Leu His Glu Glu Gly
                85                  90                  95

Val Asp Ile Val Asn Ala Ser Tyr Lys Val Asn Glu Asp Ser Val Phe
            100                 105                 110

His Ser Ile His Cys Gln Val Gly Glu Phe Gly Asn Glu Ala Ala Arg
        115                 120                 125

Ile Ser Glu Arg Leu Lys Lys Phe Met Gln Asp Tyr
    130                 135                 140

<210> SEQ ID NO 228
<211> LENGTH: 882
<212> TYPE: DNA
<213> ORGANISM: Hordeum vulgare

<400> SEQUENCE: 228
atgaatgcct gcgctctgaa ctcgatggag ccggtgaagg cgaagccggc gaggggcggg      60
```

-continued

```
aagaggagca gggagagcgg cggcacggcg gtggtgctgc tggagaagaa ggagtcggag    120
aaggagagga ggaagcgcat gaaggcgctc tgcgagaagc tcgcatccct catcccaagg    180
gaacactgct gctccaccac tgatacaatg acccagctag gcagcctgga tgtgggggca    240
tcgtatatca agaagctgaa ggagagggtc gatgagctac aacgtaggat gacctctgcg    300
cagaccttgg ataccttcag aggagacact agcatcccaa cgcccactac caccactacc    360
acgaaaagcg ttgtagggtc gctggaagaa gagaaagctc gggaggcatc ggcacccgta    420
ttgcaggtgc ggcaacacga cgattcaagc atggaggtga gattgatatg ctgcatgaag    480
aggccgatca agtccatga ggtgatcacc atccatgagg aagaaggtgc tgagatcatc    540
aacgccaatc actctgttgc tggccaaaaa atgttctaca ctatacactc tcgggcctct    600
agctcgagaa ttggcataga tgttccaagg gtttctgaac gactgcgagc attgctccaa    660
ctttattcgc atgaaaatca ggcaccgtcg tgcatgcaca caatcaagt cctcaggtac    720 aatgatgggg ccaacgcgac tcctcccaag gagctcgtcg gcaacaatga tataggtgga    780
accaacaagg tggcaaacca cgagtgtgag tcttgggttg agcaagacca agtgatgtgg    840
agttccctgc ttgcgtcaat atcaccagag ttgctcgagt ag                      882
```

<210> SEQ ID NO 229
<211> LENGTH: 293
<212> TYPE: PRT
<213> ORGANISM: Hordeum vulgare

<400> SEQUENCE: 229

```
Met Asn Ala Cys Ala Leu Asn Ser Met Glu Pro Val Lys Ala Lys Pro
1               5                   10                  15

Ala Arg Gly Gly Lys Arg Ser Arg Glu Ser Gly Gly Thr Ala Val Val
            20                  25                  30

Leu Leu Glu Lys Lys Glu Ser Glu Lys Glu Arg Arg Lys Arg Met Lys
        35                  40                  45

Ala Leu Cys Glu Lys Leu Ala Ser Leu Ile Pro Arg Glu His Cys Cys
    50                  55                  60

Ser Thr Thr Asp Thr Met Thr Gln Leu Gly Ser Leu Asp Val Gly Ala
65                  70                  75                  80

Ser Tyr Ile Lys Lys Leu Lys Glu Arg Val Asp Glu Leu Gln Arg Arg
                85                  90                  95

Met Thr Ser Ala Gln Thr Leu Asp Thr Phe Arg Gly Asp Thr Ser Ile
            100                 105                 110

Pro Thr Pro Thr Thr Thr Thr Thr Lys Ser Val Val Gly Ser Leu
        115                 120                 125

Glu Glu Glu Lys Ala Arg Glu Ala Ser Ala Pro Val Leu Gln Val Arg
    130                 135                 140

Gln His Asp Asp Ser Ser Met Glu Val Arg Leu Ile Cys Cys Met Lys
145                 150                 155                 160

Arg Pro Ile Lys Leu His Glu Val Ile Thr Ile His Glu Glu Gly
                165                 170                 175

Ala Glu Ile Ile Asn Ala Asn His Ser Val Ala Gly Gln Lys Met Phe
            180                 185                 190

Tyr Thr Ile His Ser Arg Ala Ser Ser Arg Ile Gly Ile Asp Val
        195                 200                 205

Pro Arg Val Ser Glu Arg Leu Arg Ala Leu Leu Gln Leu Tyr Ser His
    210                 215                 220

Glu Asn Gln Ala Pro Ser Cys Met His Asn Asn Gln Val Leu Arg Tyr
225                 230                 235                 240
```

Asn Asp Gly Ala Asn Ala Thr Pro Pro Lys Glu Leu Val Gly Asn Asn
                245                 250                 255

Asp Ile Gly Gly Thr Asn Lys Val Ala Asn His Glu Cys Glu Ser Trp
            260                 265                 270

Val Glu Gln Asp Gln Val Met Trp Ser Ser Leu Leu Ala Ser Ile Ser
        275                 280                 285

Pro Glu Leu Leu Glu
    290

<210> SEQ ID NO 230
<211> LENGTH: 2193
<212> TYPE: DNA
<213> ORGANISM: Oryza sativa

<400> SEQUENCE: 230

| | | | | | |
|---|---|---|---|---|---|
| aatccgaaaa | gtttctgcac | cgttttcacc | ccctaactaa | caatataggg | aacgtgtgct | 60 |
| aaatataaaa | tgagacctta | tatatgtagc | gctgataact | agaactatgc | aagaaaaact | 120 |
| catccaccta | ctttagtggc | aatcgggcta | aataaaaaag | agtcgctaca | ctagtttcgt | 180 |
| tttccttagt | aattaagtgg | gaaaatgaaa | tcattattgc | ttagaatata | cgttcacatc | 240 |
| tctgtcatga | agttaaatta | ttcgaggtag | ccataattgt | catcaaactc | ttcttgaata | 300 |
| aaaaaatctt | tctagctgaa | ctcaatgggt | aagagagag | attttttta | aaaaaataga | 360 |
| atgaagatat | tctgaacgta | ttggcaaaga | tttaaacata | taattatata | attttatagt | 420 |
| ttgtgcattc | gtcatatcgc | acatcattaa | ggacatgtct | tactccatcc | caattttat | 480 |
| ttagtaatta | aagacaattg | acttattttt | attatttatc | tttttcgat | tagatgcaag | 540 |
| gtacttacgc | acacactttg | tgctcatgtg | catgtgtgag | tgcacctcct | caatacacgt | 600 |
| tcaactagca | acacatctct | aatatcactc | gcctatttaa | tacatttagg | tagcaatatc | 660 |
| tgaattcaag | cactccacca | tcaccagacc | acttttaata | atatctaaaa | tacaaaaaat | 720 |
| aattttacag | aatagcatga | aaagtatgaa | acgaactatt | taggttttc | acatacaaaa | 780 |
| aaaaaaagaa | ttttgctcgt | gcgcgagcgc | caatctccca | tattgggcac | acaggcaaca | 840 |
| acagagtggc | tgcccacaga | acaacccaca | aaaaacgatg | atctaacgga | ggacagcaag | 900 |
| tccgcaacaa | cctttaaca | gcaggctttg | cggccaggag | agaggaggag | aggcaaagaa | 960 |
| aaccaagcat | cctcctcctc | ccatctataa | attcctcccc | ccttttcccc | tctctatata | 1020 |
| ggaggcatcc | aagccaagaa | gagggagagc | accaaggaca | cgcgactagc | agaagccgag | 1080 |
| cgaccgcctt | cttcgatcca | tatcttccgg | tcgagttctt | ggtcgatctc | ttccctcctc | 1140 |
| cacctcctcc | tcacagggta | tgtgcccttc | ggttgttctt | ggattattg | ttctaggttg | 1200 |
| tgtagtacgg | gcgttgatgt | taggaaaggg | gatctgtatc | tgtgatgatt | cctgttcttg | 1260 |
| gatttgggat | agaggggttc | ttgatgttgc | atgttatcgg | ttcggtttga | ttagtagtat | 1320 |
| ggttttcaat | cgtctggaga | gctctatgga | aatgaaatgg | tttagggtac | ggaatcttgc | 1380 |
| gattttgtga | gtacctttg | tttgaggtaa | aatcagagca | ccggtgattt | tgcttggtgt | 1440 |
| aataaaagta | cggttgtttg | gtcctcgatt | ctggtagtga | tgcttctcga | tttgacgaag | 1500 |
| ctatcctttg | tttattccct | attgaacaaa | aataatccaa | ctttgaagac | ggtcccgttg | 1560 |
| atgagattga | atgattgatt | cttaagcctg | tccaaaattt | cgcagctggc | ttgtttagat | 1620 |
| acagtagtcc | ccatcacgaa | attcatggaa | acagttataa | tcctcaggaa | caggggattc | 1680 |
| cctgttcttc | cgatttgctt | tagtcccaga | attttttttc | ccaaatatct | taaaaagtca | 1740 |
| ctttctggtt | cagttcaatg | aattgattgc | tacaaataat | gcttttatag | cgttatccta | 1800 |

```
gctgtagttc agttaatagg taatacccct atagtttagt caggagaaga acttatccga    1860
tttctgatct ccattttttaa ttatatgaaa tgaactgtag cataagcagt attcatttgg   1920
attatttttt ttattagctc tcacccttc attattctga gctgaaagtc tggcatgaac     1980
tgtcctcaat tttgttttca aattcacatc gattatctat gcattatcct cttgtatcta   2040
cctgtagaag tttcttttg gttattcctt gactgcttga ttacagaaag aaatttatga    2100
agctgtaatc gggatagtta tactgcttgt tcttatgatt catttccttt gtgcagttct    2160
tggtgtagct tgccactttc accagcaaag ttc                                 2193

<210> SEQ ID NO 231
<211> LENGTH: 56
<212> TYPE: DNA
<213> ORGANISM: Artificial sequence
<220> FEATURE:
<223> OTHER INFORMATION: primer: prm06808

<400> SEQUENCE: 231
ggggacaagt ttgtacaaaa aagcaggctt aaacaatgaa gagcaggaag aacagc         56

<210> SEQ ID NO 232
<211> LENGTH: 50
<212> TYPE: DNA
<213> ORGANISM: Artificial sequence
<220> FEATURE:
<223> OTHER INFORMATION: primer: prm06809

<400> SEQUENCE: 232
ggggaccact ttgtacaaga aagctgggtg cagagtgaaa gagtggtgtg                 50

<210> SEQ ID NO 233
<211> LENGTH: 2194
<212> TYPE: DNA
<213> ORGANISM: Oryza sativa

<400> SEQUENCE: 233
aatccgaaaa gtttctgcac cgttttcacc ccctaactaa caatataggg aacgtgtgct      60
aaatataaaa tgagacctta tatgtagc gctgataact agaactatgc aagaaaaact      120
catccaccta cttagtggc aatcgggcta aataaaaag agtcgctaca ctagtttcgt      180
tttccttagt aattaagtgg gaaaatgaaa tcattattgc ttagaatata cgttcacatc    240
tctgtcatga agttaaatta ttcgaggtag ccataattgt catcaaactc ttcttgaata    300
aaaaaatctt tctagctgaa ctcaatgggt aaagagagag atttttttta aaaaaataga    360
atgaagatat tctgaacgta ttggcaaaga tttaaacata taattatata atttttatagt   420 ttgtgcattc gtcatatcgc acatcattaa ggacatgtct tactccatcc caatttttat    480
ttagtaatta aagacaattg acttattttt attatttatc ttttttcgat tagatgcaag    540
gtacttacgc acacactttg tgctcatgtg catgtgtgag tgcacctcct caatacacgt    600
tcaactagca acacatctct aatatcactc gcctatttaa tacatttagg tagcaatatc    660
tgaattcaag cactccacca tcaccagacc acttttaata atatctaaaa tacaaaaaat    720
aattttacag aatagcatga aaagtatgaa acgaactatt taggttttttc acatacaaaa    780 aaaaaaagaa ttttgctcgt gcgcgagcgc caatctccca tattgggcac acaggcaaca    840
acagagtggc tgcccacaga acaacccaca aaaacgatg atctaacgga ggacagcaag      900
tccgcaacaa cctttttaaca gcaggctttg cggccaggag agaggaggag aggcaaagaa    960
aaccaagcat cctccttctc ccatctataa attcctcccc ccttttcccc tctctatata    1020
```

```
ggaggcatcc aagccaagaa gagggagagc accaaggaca cgcgactagc agaagccgag      1080
cgaccgcctt ctcgatccat atcttccggt cgagttcttg gtcgatctct tccctcctcc      1140
acctcctcct cacagggtat gtgcctccct tcggttgttc ttggatttat tgttctaggt      1200
tgtgtagtac gggcgttgat gttaggaaag gggatctgta tctgtgatga ttcctgttct      1260
tggatttggg atagagggt  tcttgatgtt gcatgttatc ggttcggttt gattagtagt      1320
atggttttca atcgtctgga gagctctatg gaaatgaaat ggtttaggga tcggaatctt      1380
gcgattttgt gagtaccttt tgtttgaggt aaaatcagag caccggtgat tttgcttggt      1440
gtaataaagt acgttgttt  ggtcctcgat tctggtagtg atgcttctcg atttgacgaa      1500
gctatccttt gtttattccc tattgaacaa aaataatcca actttgaaga cggtcccgtt      1560
gatgagattg aatgattgat tcttaagcct gtccaaaatt tcgcagctgg cttgtttaga      1620
tacagtagtc cccatcacga aattcatgga aacagttata atcctcagga acaggggatt      1680
ccctgttctt ccgatttgct ttagtcccag aattttttt  cccaaatatc ttaaaaagtc      1740
actttctggt tcagttcaat gaattgattg ctacaaataa tgctttttata gcgttatcct      1800 agctgtagtt cagttaatag gtaataccccc tatagtttag tcaggagaag aacttatccg      1860
atttctgatc tccatttta  attatatgaa atgaactgta gcataagcag tattcatttg      1920
gattattttt tttattagct ctcaccccctt cattattctg agctgaaagt ctggcatgaa      1980
ctgtcctcaa ttttgtttc  aaattcacat cgattatcta tgcattatcc tcttgtatct      2040
acctgtagaa gttctttttt ggttattcct tgactgcttg attacagaaa gaaatttatg      2100
aagctgtaat cgggatagtt atactgcttg ttcttatgat tcatttcctt tgtgcagttc      2160
ttggtgtagc ttgccacttt caccagcaaa gttc                                 2194

<210> SEQ ID NO 234
<211> LENGTH: 1065
<212> TYPE: DNA
<213> ORGANISM: Arabidopsis thaliana

<400> SEQUENCE: 234
atggagttgt taatgtgttc gggtcaggcc gagtcaggtg gttcctcttc caccgagtct        60
tcttcactca gtggtggact caggtttggt cagaagatct acttcgagga tggatccgga       120
tccagaagca agaaccgggt caataccgtt cgtaagtcgt ctaccacggc gaggtgccaa       180
gtggaaggtt gtagaatgga tctaagcaat gttaaagctt attactcgag acacaaagtt       240
tgttgcattc actctaaatc atctaaagtc attgtctctg gtcttcatca aaggttttgt       300
caacaatgta gcaggtttca ccagcttttct gagtttgact tggagaaaag aagttgtcgc       360
agaagactcg cttgtcataa cgaacgacga agaaaaccac aacccacaac ggctcttttc       420
acttctcatt actctcgaat cgctccatct ctttacggaa accccaatgc tgcaatgatt       480
aaaagcgttt tgggagatcc tactgcgtgg tcaaccgcaa gatcagtgat gcagcggcct       540
ggaccgtggc agattaatcc agttagggaa acccatccac acatgaatgt tttatcacat       600
ggaagctcaa gctttactac atgtccagag atgataaaca acaatagcac agattcaagc       660
tgtgctctct ctcttctgtc aaactcatac ccaattcatc agcagcaact tcagacacca       720
acaaatacat ggcgaccatc ttctggtttc gactcgatga tctcattctc cgataaggtt       780
acaatggctc agccaccgcc catttcaacc catcagccgc ccatctcaac acatcagcag       840
tacctcagcc aaacttggga agtcatcgcg ggcgaaaaga gcaattcaca ttatatgtct       900
cctgtgagtc aaatctcgga gccagcagat ttccagataa gcaatggcac cacaatgggt       960
```

```
ggatttgagc tgtatcttca tcagcaggtt ctgaagcaat acatggaacc cgagaacaca    1020
agagcttatg actcctctcc tcaacatttc aattggtctc tttga                    1065
```

<210> SEQ ID NO 235
<211> LENGTH: 354
<212> TYPE: PRT
<213> ORGANISM: Arabidopsis thaliana

<400> SEQUENCE: 235

```
Met Glu Leu Leu Met Cys Ser Gly Gln Ala Glu Ser Gly Gly Ser Ser
1               5                   10                  15

Ser Thr Glu Ser Ser Ser Leu Ser Gly Gly Leu Arg Phe Gly Gln Lys
            20                  25                  30

Ile Tyr Phe Glu Asp Gly Ser Gly Ser Arg Ser Lys Asn Arg Val Asn
        35                  40                  45

Thr Val Arg Lys Ser Ser Thr Thr Ala Arg Cys Gln Val Glu Gly Cys
    50                  55                  60

Arg Met Asp Leu Ser Asn Val Lys Ala Tyr Tyr Ser Arg His Lys Val
65                  70                  75                  80

Cys Cys Ile His Ser Lys Ser Lys Val Ile Val Ser Gly Leu His
                85                  90                  95

Gln Arg Phe Cys Gln Gln Cys Ser Arg Phe His Gln Leu Ser Glu Phe
            100                 105                 110

Asp Leu Glu Lys Arg Ser Cys Arg Arg Leu Ala Cys His Asn Glu
        115                 120                 125

Arg Arg Arg Lys Pro Gln Pro Thr Thr Ala Leu Phe Thr Ser His Tyr
    130                 135                 140

Ser Arg Ile Ala Pro Ser Leu Tyr Gly Asn Pro Asn Ala Ala Met Ile
145                 150                 155                 160

Lys Ser Val Leu Gly Asp Pro Thr Ala Trp Ser Thr Ala Arg Ser Val
                165                 170                 175

Met Gln Arg Pro Gly Pro Trp Gln Ile Asn Pro Val Arg Glu Thr His
            180                 185                 190

Pro His Met Asn Val Leu Ser His Gly Ser Ser Ser Phe Thr Thr Cys
        195                 200                 205

Pro Glu Met Ile Asn Asn Asn Ser Thr Asp Ser Ser Cys Ala Leu Ser
    210                 215                 220

Leu Leu Ser Asn Ser Tyr Pro Ile His Gln Gln Leu Gln Thr Pro
225                 230                 235                 240

Thr Asn Thr Trp Arg Pro Ser Ser Gly Phe Asp Ser Met Ile Ser Phe
                245                 250                 255

Ser Asp Lys Val Thr Met Ala Gln Pro Pro Ile Ser Thr His Gln
            260                 265                 270

Pro Pro Ile Ser Thr His Gln Gln Tyr Leu Ser Gln Thr Trp Glu Val
        275                 280                 285

Ile Ala Gly Glu Lys Ser Asn Ser His Tyr Met Ser Pro Val Ser Gln
    290                 295                 300

Ile Ser Glu Pro Ala Asp Phe Gln Ile Ser Asn Gly Thr Thr Met Gly
305                 310                 315                 320

Gly Phe Glu Leu Tyr Leu His Gln Gln Val Leu Lys Gln Tyr Met Glu
                325                 330                 335

Pro Glu Asn Thr Arg Ala Tyr Asp Ser Ser Pro Gln His Phe Asn Trp
            340                 345                 350

Ser Leu
```

<210> SEQ ID NO 236
<211> LENGTH: 1128
<212> TYPE: DNA
<213> ORGANISM: Arabidopsis thaliana

<400> SEQUENCE: 236

```
atggagatgg gttccaactc gggtccgggt catggtccgg gtcaggcaga gtcgggtggt      60
tcctccactg agtcatcctc tttcagtgga gggctcatgt ttggccagaa gatctacttc     120
gaggacggtg gtggtggatc cgggtcttct tcctcaggtg gtcgttcaaa cagacgtgtc     180
cgtggaggcg gtcgggtca gtcgggtcag ataccaaggt gccaagtgga aggttgtggg      240
atggatctaa ccaatgcaaa aggttattac tcgagacacc gagtttgtgg agtgcactct     300
aaaacaccta aagtcactgt ggctggtatc gaacagaggt tttgtcaaca gtgcagcagg     360
tttcatcagc ttccggaatt tgacctagag aaaaggagtt gccgcaggag actcgctggt     420
cataatgagc gacgaaggaa gccacagcct gcgtctctct ctgtgttagc ttctcgttac     480
gggaggatcg caccttcgct ttacgaaaat ggtgatgctg aatgaatgg aagctttctt      540
gggaaccaag ataggatg ccaagttca gaaacattgg atacaagagt gatgaggcgg       600
ccagtgtcgt caccgtcatg gcagatcaat ccaatgaatg tatttagtca aggttcagtt     660
ggtgaggag gacaagctt ctcatctcca gagattatgg acactaaact agagagctac       720
aagggaattg gcgactcaaa ctgtgctctc tctcttctgt caaatccaca tcaaccacat     780
gacaacaaca caacaacaa caacaacaac aacaacaaca caatacatg gcgagcttct      840
tcaggttttg gcccgatgac ggttacaatg gctcaaccac cacctgcacc tagccagcat     900
cagtatctga acccgccttg gtattcaag gacaatgata tgatatgtc tcctgttttg      960
aatttaggtc gatacaccga ccagataat tgtcagataa gtagtggcac ggcaatgggt     1020
gagttcgagt tatctgatca ccatcatcaa gtaggagac agtacatgga agatgagaac     1080
acaagggctt atgactcttc ttctcaccat accaactggt ccctctga               1128
```

<210> SEQ ID NO 237
<211> LENGTH: 375
<212> TYPE: PRT
<213> ORGANISM: Arabidopsis thaliana

<400> SEQUENCE: 237

```
Met Glu Met Gly Ser Asn Ser Gly Pro Gly His Gly Pro Gly Gln Ala
  1               5                  10                  15

Glu Ser Gly Gly Ser Ser Thr Glu Ser Ser Ser Phe Ser Gly Gly Leu
             20                  25                  30

Met Phe Gly Gln Lys Ile Tyr Phe Glu Asp Gly Gly Gly Ser Gly
         35                  40                  45

Ser Ser Ser Ser Gly Gly Arg Ser Asn Arg Arg Val Arg Gly Gly
     50                  55                  60

Ser Gly Gln Ser Gly Gln Ile Pro Arg Cys Gln Val Glu Gly Cys Gly
 65                  70                  75                  80

Met Asp Leu Thr Asn Ala Lys Gly Tyr Tyr Ser Arg His Arg Val Cys
                 85                  90                  95

Gly Val His Ser Lys Thr Pro Lys Val Thr Val Ala Gly Ile Glu Gln
            100                 105                 110

Arg Phe Cys Gln Gln Cys Ser Arg Phe His Gln Leu Pro Glu Phe Asp
        115                 120                 125

Leu Glu Lys Arg Ser Cys Arg Arg Arg Leu Ala Gly His Asn Glu Arg
```

```
                130                 135                 140
Arg Arg Lys Pro Gln Pro Ala Ser Leu Ser Val Leu Ala Ser Arg Tyr
145                 150                 155                 160

Gly Arg Ile Ala Pro Ser Leu Tyr Glu Asn Gly Asp Ala Gly Met Asn
                165                 170                 175

Gly Ser Phe Leu Gly Asn Gln Glu Ile Gly Trp Pro Ser Ser Arg Thr
                180                 185                 190

Leu Asp Thr Arg Val Met Arg Pro Val Ser Ser Pro Ser Trp Gln
            195                 200                 205

Ile Asn Pro Met Asn Val Phe Ser Gln Gly Ser Val Gly Gly Gly
        210                 215                 220

Thr Ser Phe Ser Ser Pro Glu Ile Met Asp Thr Lys Leu Glu Ser Tyr
225                 230                 235                 240

Lys Gly Ile Gly Asp Ser Asn Cys Ala Leu Ser Leu Leu Ser Asn Pro
                245                 250                 255

His Gln Pro His Asp Asn Asn Asn Asn Asn Asn Asn Asn Asn Asn
            260                 265                 270

Asn Asn Asn Thr Trp Arg Ala Ser Ser Gly Phe Gly Pro Met Thr Val
            275                 280                 285

Thr Met Ala Gln Pro Pro Ala Pro Ser Gln His Gln Tyr Leu Asn
290                 295                 300

Pro Pro Trp Val Phe Lys Asp Asn Asp Asn Asp Met Ser Pro Val Leu
305                 310                 315                 320

Asn Leu Gly Arg Tyr Thr Glu Pro Asp Asn Cys Gln Ile Ser Ser Gly
                325                 330                 335

Thr Ala Met Gly Glu Phe Glu Leu Ser Asp His His His Gln Ser Arg
                340                 345                 350

Arg Gln Tyr Met Glu Asp Glu Asn Thr Arg Ala Tyr Asp Ser Ser Ser
            355                 360                 365

His His Thr Asn Trp Ser Leu
370                 375

<210> SEQ ID NO 238
<211> LENGTH: 1149
<212> TYPE: DNA
<213> ORGANISM: Aquilegia formosa x Aquilegia pubescens

<400> SEQUENCE: 238
atggaaatgg gttccagctc tttcgctggt ggtgggggta agggtgcttc tggttcatct      60
gattcttcac tgaatggttt gaaatttggg aagaaaatct actttgaaga tgtgggtatt     120
ggagttttag gcaagtcaag tgttgggtct ccgtcaattt tggtttctga agctcggttg     180
ccaccggctt cgtcggtgaa aagggtaga ggggttttgc aaggacaacc acctagatgt      240
tctgttgaag ttgtaagct tgatcttact gatgctaagc cttattactc aaggcacaaa     300
gtctgtggta tgcactctaa atctcctaaa gtaattgttg tggtttgga gcagaggttt     360 tgccagcagt gtagcagatt tcatctactc tgtgaatttg accaaggcaa gcgaagctgt     420
cgtagacgtc tagctggcca caatgagcgt cgaagaaaac cacaacctgg atcaatattt     480
tcaccgcgct atggtcgtgt gtcaccatct ttccaagaaa atagcaccag aggaggagt     540 tttctaatgg acttcacagc gtacccaagg ctggcaggaa gggatgcatg caaacagta     600 aaagccggca attgggcaga tggaaaccaa acctctccta ttaagaagct tctcccacat     660
caatggcaag gcaattcaga gaatcctcct cctattgtct attctcaggc acctcacccg     720
tatctgcaag gtgtggctag tggatcaatt ttttccagta caagaatacc ttcagccgag     780
```

-continued

```
tgttttgctg gtgtctctga ctccagctgt gctctctctc ttctgtcaaa tcaaccatgg    840
aaccccagaa accagacttc cgatttggag gtgaataaca tagtgaacgg tgaaggggta    900
tccatggcaa gatctatagc acctcatagt gctgtagtca ccaacttcac gaacaacaca    960 tggaattta agggcaacag tgaagttagt ggcagttccc atgaaattcc acgtcaggtg   1020
tcgcagccag tcaccaatca tttctccagt gagctcgatc tagctcagca ggggaacagg   1080
cagtacatgg agatccggca ttcaagggat tttggttctt ccactcacca gatgcactgg   1140
tctctttga                                                          1149
```

<210> SEQ ID NO 239
<211> LENGTH: 382
<212> TYPE: PRT
<213> ORGANISM: Aquilegia formosa x Aquilegia pubescens

<400> SEQUENCE: 239

```
Met Glu Met Gly Ser Ser Ser Phe Ala Gly Gly Gly Lys Gly Ala
1               5                   10                  15

Ser Gly Ser Ser Asp Ser Ser Leu Asn Gly Leu Lys Phe Gly Lys Lys
                20                  25                  30

Ile Tyr Phe Glu Asp Val Gly Ile Gly Val Leu Gly Lys Ser Ser Val
            35                  40                  45

Gly Ser Pro Ser Ile Leu Val Ser Glu Ala Arg Leu Pro Pro Ala Ser
        50                  55                  60

Ser Val Lys Lys Gly Arg Gly Val Leu Gln Gly Gln Pro Pro Arg Cys
65                  70                  75                  80

Ser Val Glu Gly Cys Lys Leu Asp Leu Thr Asp Ala Lys Pro Tyr Tyr
                85                  90                  95

Ser Arg His Lys Val Cys Gly Met His Ser Lys Ser Pro Lys Val Ile
            100                 105                 110

Val Gly Gly Leu Glu Gln Arg Phe Cys Gln Gln Cys Ser Arg Phe His
        115                 120                 125

Leu Leu Cys Glu Phe Asp Gln Gly Lys Arg Ser Cys Arg Arg Arg Leu
    130                 135                 140

Ala Gly His Asn Glu Arg Arg Arg Lys Pro Gln Pro Gly Ser Ile Phe
145                 150                 155                 160

Ser Pro Arg Tyr Gly Arg Val Ser Pro Ser Phe Gln Glu Asn Ser Thr
                165                 170                 175

Arg Gly Gly Gly Phe Leu Met Asp Phe Thr Ala Tyr Pro Arg Leu Ala
            180                 185                 190

Gly Arg Asp Ala Trp Gln Thr Val Lys Ala Gly Asn Trp Ala Asp Gly
        195                 200                 205

Asn Gln Thr Ser Pro Ile Lys Lys Leu Leu Pro His Gln Trp Gln Gly
    210                 215                 220

Asn Ser Glu Asn Pro Pro Pro Ile Val Tyr Ser Gln Ala Pro His Pro
225                 230                 235                 240

Tyr Leu Gln Gly Val Ala Ser Gly Ser Ile Phe Ser Ser Thr Arg Ile
                245                 250                 255

Pro Ser Ala Glu Cys Phe Ala Gly Val Ser Asp Ser Ser Cys Ala Leu
            260                 265                 270

Ser Leu Leu Ser Asn Gln Pro Trp Asn Pro Arg Asn Gln Thr Ser Asp
        275                 280                 285

Leu Glu Val Asn Asn Ile Val Asn Gly Glu Gly Val Ser Met Ala Arg
    290                 295                 300
```

```
Ser Ile Ala Pro His Ser Ala Val Val Thr Asn Phe Thr Asn Asn Thr
305                 310                 315                 320

Trp Asn Phe Lys Gly Asn Ser Glu Val Ser Gly Ser Ser His Glu Ile
            325                 330                 335

Pro Arg Gln Val Ser Gln Pro Val Thr Asn His Phe Ser Glu Leu
        340                 345                 350

Asp Leu Ala Gln Gln Gly Asn Arg Gln Tyr Met Glu Ile Arg His Ser
        355                 360                 365

Arg Asp Phe Gly Ser Ser Thr His Gln Met His Trp Ser Leu
    370                 375                 380

<210> SEQ ID NO 240
<211> LENGTH: 1170
<212> TYPE: DNA
<213> ORGANISM: Gossypium hirsutum

<400> SEQUENCE: 240
atggaaatgg gttcgggctc tttgactgag tcgggcggtt ctcccaccaa ctcttccgcc      60
gagtcactca acggcttgaa gttcggtaaa aagatctact ttgaggatac agccgctgtc     120
gccgccgccg ctggtggtaa aagtgttggt ggtggtgcaa acatagggac tccatccaag     180
tccggtccag catcttcaag cttagccggg tcgtgtagga aagccagggt tgatggaatg     240
gcgcaagggg ttctgccttc taggtgtcaa gtagaagggt gtaaagtgga tctgagtgat     300
gctaaggctt actattcaag gcataaggtt tgttgtatgc actctaagtc atctaaagtc     360
attgttgctg gtctcgagca agatttttgt cagcagtgta gcagatttca tcagcttttct    420 gaatttgaca aagggaaacg gagttgtcgt agacggcttg caggtcacaa tgagcgacgc     480
aggaaaccac cacctggatc attatttttcc tctccttatg gccggctttc ttcctctatt     540
attgaaaatg gcagtagagg tggaagcttt atagtggatt tctcagcata cccaaggctt     600
tcaggaaggg atgcatggcc agcagctcga tcgttagaat gcataactgg aaatcgaagc     660
acagccactg gaagctcatt ttcacatcca cggcaaaaca actccagcaa acctcctcat     720
gaccatttct tgcaaggttc accatgtggg actagtttct ccagcactgg aatttctcca     780
ggagaatgct tcacagggtc tggtgactca agctgtgctc tctctcttct gtcaaatcaa     840
ccgtggggct ccaggaacca ggctttgaat ttttctgtaa atggcgtgat aagtactgaa     900
gggtcctctg cggcacaacc aacaacgctt catggtgcag ttgtgaaccc ttattcaaat     960
gcctctttgg atttcaatgg cagtgacact gttcgcagtt ctcacaagat gctgccacac    1020
ctagatttgg gtcaaatccc agaccctgtt aactgtcaat tctctagtga ccttgagttg    1080
tctcaacaaa gctggaggtc atatatcgaa catgagcagt ccggggcagc ctatgacgac    1140
tccatgcagc atatccactg gacgctctaa                                     1170

<210> SEQ ID NO 241
<211> LENGTH: 389
<212> TYPE: PRT
<213> ORGANISM: Gossypium hirsutum

<400> SEQUENCE: 241

Met Glu Met Gly Ser Gly Ser Leu Thr Glu Ser Gly Gly Ser Pro Thr
1               5                   10                  15

Asn Ser Ser Ala Glu Ser Leu Asn Gly Leu Lys Phe Gly Lys Lys Ile
            20                  25                  30

Tyr Phe Glu Asp Thr Ala Ala Val Ala Ala Ala Gly Gly Lys Ser
        35                  40                  45
```

```
Val Gly Gly Gly Ala Asn Ile Gly Thr Pro Ser Lys Ser Gly Pro Ala
 50                  55                  60

Ser Ser Ser Leu Ala Gly Ser Cys Arg Lys Ala Arg Val Asp Gly Met
 65                  70                  75                  80

Ala Gln Gly Val Leu Pro Ser Arg Cys Gln Val Glu Gly Cys Lys Val
                 85                  90                  95

Asp Leu Ser Asp Ala Lys Ala Tyr Tyr Ser Arg His Lys Val Cys Cys
            100                 105                 110

Met His Ser Lys Ser Lys Val Ile Val Ala Gly Leu Glu Gln Arg
            115                 120                 125

Phe Cys Gln Gln Cys Ser Arg Phe His Gln Leu Ser Glu Phe Asp Lys
            130                 135                 140

Gly Lys Arg Ser Cys Arg Arg Leu Ala Gly His Asn Glu Arg Arg
145                 150                 155                 160

Arg Lys Pro Pro Pro Gly Ser Leu Phe Ser Ser Pro Tyr Gly Arg Leu
                165                 170                 175

Ser Ser Ser Ile Ile Glu Asn Gly Ser Arg Gly Gly Ser Phe Ile Val
                180                 185                 190

Asp Phe Ser Ala Tyr Pro Arg Leu Ser Gly Arg Asp Ala Trp Pro Ala
            195                 200                 205

Ala Arg Ser Leu Glu Cys Ile Thr Gly Asn Arg Ser Thr Ala Thr Gly
210                 215                 220

Ser Ser Phe Ser His Pro Arg Gln Asn Asn Ser Ser Lys Pro Pro His
225                 230                 235                 240

Asp His Phe Leu Gln Gly Ser Pro Cys Gly Thr Ser Phe Ser Ser Thr
                245                 250                 255

Gly Ile Ser Pro Gly Glu Cys Phe Thr Gly Ser Gly Asp Ser Ser Cys
                260                 265                 270

Ala Leu Ser Leu Leu Ser Asn Gln Pro Trp Gly Ser Arg Asn Gln Ala
            275                 280                 285

Leu Asn Phe Ser Val Asn Gly Val Ile Ser Thr Glu Gly Ser Ser Ala
            290                 295                 300

Ala Gln Pro Thr Thr Leu His Gly Ala Val Val Asn Pro Tyr Ser Asn
305                 310                 315                 320

Ala Ser Leu Asp Phe Asn Gly Ser Asp Thr Val Arg Ser Ser His Lys
                325                 330                 335

Met Leu Pro His Leu Asp Leu Gly Gln Ile Pro Asp Pro Val Asn Cys
            340                 345                 350

Gln Phe Ser Ser Asp Leu Glu Leu Ser Gln Gln Ser Trp Arg Ser Tyr
            355                 360                 365

Ile Glu His Glu Gln Ser Gly Ala Ala Tyr Asp Asp Ser Met Gln His
            370                 375                 380

Ile His Trp Thr Leu
385

<210> SEQ ID NO 242
<211> LENGTH: 1017
<212> TYPE: DNA
<213> ORGANISM: Ipomoea nil

<400> SEQUENCE: 242
atggaactgg gttcttcttc ttcttctacc tctacctccg ccgactcctc atccgacggc      60
ttgaagttcg gcaaaaaagt ctactttgaa gatgcgggtg gtgggagtgg tgggtcgtcg     120
ctgccggcca agagagggag gagcgcggtg gcgcaaggcg acagccacc caggtgccag      180
```

```
gtggaagggt gcaaggcaga tctgagtgaa tttaaggctt attactcaaa gcataaagtt    240
tgtggtatgc actccaagtc tcctaaggtc attgtttctg ggcttgaaca gagattctgc    300
cagcagtgca gcaggtttca tcaattgagt gaatttgatc aagtaaaaag gagctgccgt    360
aggcgtttgg ctggtcataa tgagcgtcgt aggaagcccc cacttggatc catattgtcc    420
acacattatg ggactctttc ttcttcaatg tttggaaaca atggccactt tgtgatggat    480
ttcgcctcat acccatatcc gggtggtaag ggctcatggc ggccaagtac caatggcgtg    540
gggaactttc ttcaacaacc atggcagaga aactctgaag atcccccacc caagcttctt    600
ttgctaggtt cggatgctgc tgctagggct acttatccca gtccttgtgg agaatacttc    660
aatggggtct cggattccac ccgtgctctc tctcttctgt caaactcaaa tcagccctgg    720
ggctcgagaa accaacaacc ctctggtctc ggggttaata gcttacttaa cactgatgga    780
acgcttgctg ttcatccatc cggttcccat gctgccgtta tcaatgaatt ttcttcaagt    840 ccatgggggtt ttaaaggcaa tcaagccact accagctcag ataagatcct tcctgatagt    900
cactattctg gtgagctcga gatgatggct catcaacaaa ctggacgagc atacatggga    960
atggagtact cgacgggtta tgattcttct gtccagaatg tgcactggac tctctga     1017

<210> SEQ ID NO 243
<211> LENGTH: 338
<212> TYPE: PRT
<213> ORGANISM: Ipomoea nil

<400> SEQUENCE: 243

Met Glu Leu Gly Ser Ser Ser Ser Thr Ser Thr Ser Ala Asp Ser
1               5                   10                  15

Ser Ser Asp Gly Leu Lys Phe Gly Lys Lys Val Tyr Phe Glu Asp Ala
            20                  25                  30

Gly Gly Gly Ser Gly Gly Ser Ser Leu Pro Ala Lys Arg Gly Arg Ser
        35                  40                  45

Ala Val Ala Gln Gly Gly Gln Pro Pro Arg Cys Gln Val Glu Gly Cys
    50                  55                  60

Lys Ala Asp Leu Ser Glu Phe Lys Ala Tyr Tyr Ser Lys His Lys Val
65                  70                  75                  80

Cys Gly Met His Ser Lys Ser Pro Lys Val Ile Val Ser Gly Leu Glu
                85                  90                  95

Gln Arg Phe Cys Gln Gln Cys Ser Arg Phe His Gln Leu Ser Glu Phe
            100                 105                 110

Asp Gln Val Lys Arg Ser Cys Arg Arg Leu Ala Gly His Asn Glu
        115                 120                 125

Arg Arg Arg Lys Pro Pro Leu Gly Ser Ile Leu Ser Thr His Tyr Gly
    130                 135                 140

Thr Leu Ser Ser Ser Met Phe Gly Asn Asn Gly His Phe Val Met Asp
145                 150                 155                 160

Phe Ala Ser Tyr Pro Tyr Pro Gly Gly Lys Gly Ser Trp Arg Pro Ser
                165                 170                 175

Thr Asn Gly Val Gly Asn Phe Leu Gln Gln Pro Trp Gln Arg Asn Ser
            180                 185                 190

Glu Asp Pro Pro Pro Lys Leu Leu Leu Leu Gly Ser Asp Ala Ala Ala
        195                 200                 205

Arg Ala Thr Tyr Pro Ser Pro Cys Gly Glu Tyr Phe Asn Gly Val Ser
    210                 215                 220

Asp Ser Thr Arg Ala Leu Ser Leu Leu Ser Asn Ser Asn Gln Pro Trp
225                 230                 235                 240
```

```
Gly Ser Arg Asn Gln Gln Pro Ser Gly Leu Gly Val Asn Ser Leu Leu
            245                 250                 255

Asn Thr Asp Gly Thr Leu Ala Val His Pro Ser Gly Ser His Ala Ala
            260                 265                 270

Val Ile Asn Glu Phe Ser Ser Pro Trp Gly Phe Lys Gly Asn Gln
            275                 280                 285

Ala Thr Thr Ser Ser Asp Lys Ile Leu Pro Asp Ser His Tyr Ser Gly
            290                 295                 300

Glu Leu Glu Met Met Ala His Gln Gln Thr Gly Arg Ala Tyr Met Gly
305                 310                 315                 320

Met Glu Tyr Ser Thr Gly Tyr Asp Ser Ser Val Gln Asn Val His Trp
                325                 330                 335

Thr Leu

<210> SEQ ID NO 244
<211> LENGTH: 1035
<212> TYPE: DNA
<213> ORGANISM: Lactuca sativa

<400> SEQUENCE: 244
atggagatgg gtggttcgag tggttcttcg gagtcgcaac tgctcaaaat tggtttgcaa      60
ttcgggaaag aaatctattt tgaggatgtg ggagttggag ctcaggttaa atccgatgat     120
gggttgtctc cggcgagcgg cggcgatgct gctggagggc gcagaagaa agggagaact     180
gctggtgggg tggtgagtgg ttttggacaa cagcaaccac cgaggtgtca ggtgaaggt     240
tgtaatctgg atctgagtga tgctaaaagt tactattcaa ggcacaaagt tgtggtgct     300
cattcgaaaa cggctaaggt cattgttaat ggccttgaac agagattctg ccaacagtgc    360
agcaggttcc atcaactacc agagtttgac cagggaaaaa gaagctgcag agacgattg     420
gctgggcaca tgaacgtag aagaaagcca tctctgctat ccactcgcta tggaactgtc     480
tcctcctcaa tctttgaaaa caatgggaat tctggaggct ttctaatgga cttttcgtca    540
tgctcaagag gaaggattca gtggccagga caagggcgg caccaccgcc tcgagccgcc    600
atcgacctcc caattgccgg agaaaagttc ccaccgcttc atggcaaag caacctggat    660
aatccacctc cttatgttcc accaggaggg tgttttaatg gagtccatga ggactccaac    720
tgtgctctct ctcttctgtc aaatcactca tctggctcaa ggaaccaatc cctgagccat    780
gagtactata tcaaccctga agctggtgca tatgtgcacc agcttcatca accaacaacc    840
ggaaccggag ctgggttcgg aaccatggtt gaggtcaccg ccactggctg gtatacgag     900
acccatgatg cccatttggg tttgggtcac gtcccacagt ctggtggtgg ctactctggt    960
gaggttggac ttggtccaca tggtgggga aggcgatatg actcatctgt tgaccacatt    1020
gactggtcac tttga                                                   1035

<210> SEQ ID NO 245
<211> LENGTH: 344
<212> TYPE: PRT
<213> ORGANISM: Lactuca sativa

<400> SEQUENCE: 245

Met Glu Met Gly Gly Ser Ser Gly Ser Ser Glu Ser Gln Leu Leu Lys
1               5                   10                  15

Ile Gly Leu Gln Phe Gly Lys Glu Ile Tyr Phe Glu Asp Val Gly Val
            20                  25                  30

Gly Ala Gln Val Lys Ser Asp Asp Gly Leu Ser Pro Ala Ser Gly Gly
```

```
                 35                  40                  45
Asp Ala Ala Gly Gly Pro Gln Lys Lys Gly Arg Thr Ala Gly Val
 50                  55                  60

Val Ser Gly Phe Gly Gln Gln Pro Pro Arg Cys Gln Val Glu Gly
 65                  70                  75                  80

Cys Asn Leu Asp Leu Ser Asp Ala Lys Ser Tyr Tyr Ser Arg His Lys
                 85                  90                  95

Val Cys Gly Ala His Ser Lys Thr Ala Lys Val Ile Val Asn Gly Leu
                100                 105                 110

Glu Gln Arg Phe Cys Gln Gln Cys Ser Arg Phe His Gln Leu Pro Glu
                115                 120                 125

Phe Asp Gln Gly Lys Arg Ser Cys Arg Arg Leu Ala Gly His Asn
130                 135                 140

Glu Arg Arg Arg Lys Pro Ser Leu Leu Ser Thr Arg Tyr Gly Thr Val
145                 150                 155                 160

Ser Ser Ser Ile Phe Glu Asn Asn Gly Asn Ser Gly Gly Phe Leu Met
                165                 170                 175

Asp Phe Ser Ser Cys Ser Arg Gly Arg Ile Gln Trp Pro Gly Thr Arg
                180                 185                 190

Ala Ala Pro Pro Arg Ala Ala Ile Asp Leu Pro Ile Ala Gly Glu
                195                 200                 205

Lys Phe Pro Pro Leu Pro Trp Gln Ser Asn Leu Asp Asn Pro Pro
210                 215                 220

Tyr Val Pro Pro Gly Gly Cys Phe Asn Gly Val His Glu Asp Ser Asn
225                 230                 235                 240

Cys Ala Leu Ser Leu Leu Ser Asn His Ser Ser Gly Ser Arg Asn Gln
                245                 250                 255

Ser Leu Ser His Glu Tyr Tyr Ile Asn Pro Glu Ala Gly Ala Tyr Val
                260                 265                 270

His Gln Leu His Gln Pro Thr Thr Gly Thr Gly Ala Gly Phe Gly Thr
                275                 280                 285

Met Val Glu Val Thr Ala Thr Gly Trp Val Tyr Glu Thr His Asp Ala
290                 295                 300

His Leu Gly Leu Gly His Val Pro Gln Ser Gly Gly Tyr Ser Gly
305                 310                 315                 320

Glu Val Gly Leu Gly Pro His Gly Gly Gly Arg Arg Tyr Asp Ser Ser
                325                 330                 335

Val Asp His Ile Asp Trp Ser Leu
                340

<210> SEQ ID NO 246
<211> LENGTH: 1137
<212> TYPE: DNA
<213> ORGANISM: Malus domestica

<400> SEQUENCE: 246
atggaaatgg gctcgagttc taagaccgag tcagcgagct cttcctcctc ttcgccgccc      60
aactcctccg ctgagtcact caacggcttg aaattcggcc ggaaaatcta ctttgaggat     120
gggggttttg agctctgca caaatcatca tgcgggtctg ctgctgggtc ttcctccgcc      180
ggggctacgc cgccaaagaa gcaaggggc ggcggaaatt gggtcagcc gccgcggtgt       240 caggtggagg gctgcgaggt agatctgagt ggtgccaaag cttactattc aggcacaaa     300 gtctgtggct gcactctaa aactcccact gtcattgttg ctggtcttga acagaggttt     360
tgccaacagt gtagcaggtt tcatttactt cctgaatttg atcaaggaaa acgtagttgt   420
```

```
cgtagacgct tggctgggca taatgagcgt cgtagaaaac cacctccagg atccatactg    480
tctacgcgtg gcagactttc ttcgtctctc tacgaaaaca gcagcagaat tggaagcttt    540
ctgatggact tcactgcata cccaaggttt tctgggaggg atacatggac aacaagaacc    600
tctgagcgag cacctgttaa tcaaaatgcc aatgacgcag gaagtttct acaacagccg     660 tggcagagca actctgatat ttctacatcc ggcttttacc tacaaggttc agcaggcggg    720
actagttatc ctggtcctgg aattcctcca ggagaatgtg tcacagtagt cactgactca    780
agctgtgctc tctctcttct gtcaaatcag ccatggggct ctcgaaaccg agtattgggt    840
gctgggatga attccttgat gaacactcaa ggggtacctg tggctcaacc agtccctcat    900
tctgcaacct ccaatcactt tccgaccact tcgtggggtt tcaaaggaaa tgaaaatggt    960
agcagctcac acgggatgct tccagatctg gtctcggtc aaatctcgca gccgcttagc    1020
agtcagtact ctggtgtgct ggagctgtct caacagggta ggaggcagca acacatggaa    1080
ctcggacaca ccagggcta tgactccacc agtcagcaga tgcactggtc actttaa      1137
```

<210> SEQ ID NO 247
<211> LENGTH: 378
<212> TYPE: PRT
<213> ORGANISM: Malus domestica

<400> SEQUENCE: 247

```
Met Glu Met Gly Ser Ser Ser Lys Thr Glu Ser Ala Ser Ser Ser Ser
1               5                   10                  15

Ser Ser Pro Pro Asn Ser Ser Ala Glu Ser Leu Asn Gly Leu Lys Phe
            20                  25                  30

Gly Arg Lys Ile Tyr Phe Glu Asp Gly Gly Phe Gly Ala Leu His Lys
        35                  40                  45

Ser Ser Cys Gly Ser Ala Ala Gly Ser Ser Ala Gly Ala Thr Pro
    50                  55                  60

Pro Lys Lys Gln Arg Gly Gly Asn Leu Gly Gln Pro Pro Arg Cys
65                  70                  75                  80

Gln Val Glu Gly Cys Glu Val Asp Leu Ser Gly Lys Ala Tyr Tyr
                85                  90                  95

Ser Arg His Lys Val Cys Gly Leu His Ser Lys Thr Pro Thr Val Ile
                100                 105                 110

Val Ala Gly Leu Glu Gln Arg Phe Cys Gln Gln Cys Ser Arg Phe His
            115                 120                 125

Leu Leu Pro Glu Phe Asp Gln Gly Lys Arg Ser Cys Arg Arg Leu
130                 135                 140

Ala Gly His Asn Glu Arg Arg Arg Lys Pro Pro Gly Ser Ile Leu
145                 150                 155                 160

Ser Thr Arg Gly Arg Leu Ser Ser Ser Leu Tyr Glu Asn Ser Ser Arg
                165                 170                 175

Ile Gly Ser Phe Leu Met Asp Phe Thr Ala Tyr Pro Arg Phe Ser Gly
            180                 185                 190

Arg Asp Thr Trp Thr Thr Arg Ser Glu Arg Ala Pro Val Asn Gln
        195                 200                 205

Asn Ala Asn Asp Ala Gly Lys Phe Leu Gln Gln Pro Trp Gln Ser Asn
    210                 215                 220

Ser Asp Ile Ser Thr Ser Gly Phe Tyr Leu Gln Gly Ser Ala Gly Gly
225                 230                 235                 240

Thr Ser Tyr Pro Gly Pro Gly Ile Pro Pro Gly Glu Cys Val Thr Val
                245                 250                 255
```

```
Val Thr Asp Ser Ser Cys Ala Leu Ser Leu Leu Ser Asn Gln Pro Trp
            260                 265                 270

Gly Ser Arg Asn Arg Val Leu Gly Ala Gly Met Asn Ser Leu Met Asn
        275                 280                 285

Thr Gln Gly Val Pro Val Ala Gln Pro Val Pro His Ser Ala Thr Ser
    290                 295                 300

Asn His Phe Pro Thr Thr Ser Trp Gly Phe Lys Gly Asn Glu Asn Gly
305                 310                 315                 320

Ser Ser Ser His Gly Met Leu Pro Asp Leu Gly Leu Gly Gln Ile Ser
            325                 330                 335

Gln Pro Leu Ser Ser Gln Tyr Ser Gly Val Leu Glu Leu Ser Gln Gln
        340                 345                 350

Gly Arg Arg Gln Gln His Met Glu Leu Gly His Thr Arg Gly Tyr Asp
    355                 360                 365

Ser Thr Ser Gln Gln Met His Trp Ser Leu
370                 375

<210> SEQ ID NO 248
<211> LENGTH: 1014
<212> TYPE: DNA
<213> ORGANISM: Medicago trunculata

<400> SEQUENCE: 248
atggattcag gaggcaactc ttcttcagaa gagtcctcac ttaatggctt gaaatttggc      60
caacgaatct atttcgaaga tacagctctt actgctgctt ctgctgctgc tgctagtact     120
accattgctg ctggttctcc ttcttcttct ggttcaaaga aggaagagg tgggtcagtt     180 caacattctc aaccacctag tgtcaagtt gaaggatgta aactagatct gactgatgct     240
aaagcttact attctagaca caaagtttgt agcatgcact ctaaatcccc tactgttact     300
gtttctggtc ttcaacaaag gttttgtcaa caatgtagca gatttcatca gcttgctgag     360
tttgatcaag gaaaagaag ttgtcggaga cgactagctg gtcataatga gcgtcgcaga     420
aagcccccac ccagctctct cttaacctca cgttttgcca ggctttcttc gtctgttttt     480
ggtaacagcg acagaggtgg cagcttttg atggaatttg cttcaaatcc gaaacatagt     540
ctgaggaatt cacccggaaa tcaaaccaca gcaatcggtt ggccttggcc ggggaacacg     600
gagtcgccat ctagcaacct tttcttgcaa ggttcggtgg gtgggacaag cttccctggt     660
gccaggcatc ctcccgagga aacttacact ggagtcacag attcaaactg tgctctctct     720
cttctgtcaa atcaaacatg gggttctcaa aacacagaac caagtcctgg attgaataac     780
atgctgaatt tcaacgggac acccatgaca caacttggta catcttctca tggtgtagcc     840
atgcatcaaa ttccaaacaa ttacgaggtt gtccctgatc ttggtcgggg tcacattttg     900
catcctcttg gtagccaaca ctctggcgag cttgatctgt tgcagcaggg aaggaggcat     960
tatatggatg tagaacattc cagggcctat gaatcttctc agtggtcact gtaa         1014

<210> SEQ ID NO 249
<211> LENGTH: 337
<212> TYPE: PRT
<213> ORGANISM: Medicago trunculata

<400> SEQUENCE: 249

Met Asp Ser Gly Gly Asn Ser Ser Glu Glu Ser Ser Leu Asn Gly
1               5                   10                  15

Leu Lys Phe Gly Gln Arg Ile Tyr Phe Glu Asp Thr Ala Leu Thr Ala
            20                  25                  30
```

```
Ala Ser Ala Ala Ala Ser Thr Thr Ile Ala Ala Gly Ser Pro Ser
             35                  40                  45

Ser Ser Gly Ser Lys Lys Gly Arg Gly Gly Ser Val Gln His Ser Gln
 50                  55                  60

Pro Pro Arg Cys Gln Val Glu Gly Cys Lys Leu Asp Leu Thr Asp Ala
 65                  70                  75                  80

Lys Ala Tyr Tyr Ser Arg His Lys Val Cys Ser Met His Ser Lys Ser
                 85                  90                  95

Pro Thr Val Thr Val Ser Gly Leu Gln Gln Arg Phe Cys Gln Gln Cys
            100                 105                 110

Ser Arg Phe His Gln Leu Ala Glu Phe Asp Gln Gly Lys Arg Ser Cys
        115                 120                 125

Arg Arg Arg Leu Ala Gly His Asn Glu Arg Arg Lys Pro Pro
    130                 135                 140

Ser Ser Leu Leu Thr Ser Arg Phe Ala Arg Leu Ser Ser Ser Val Phe
145                 150                 155                 160

Gly Asn Ser Asp Arg Gly Gly Ser Phe Leu Met Glu Phe Ala Ser Asn
                165                 170                 175

Pro Lys His Ser Leu Arg Asn Ser Pro Gly Asn Gln Thr Thr Ala Ile
            180                 185                 190

Gly Trp Pro Trp Pro Gly Asn Thr Glu Ser Pro Ser Asn Leu Phe
        195                 200                 205

Leu Gln Gly Ser Val Gly Gly Thr Ser Phe Pro Gly Ala Arg His Pro
    210                 215                 220

Pro Glu Glu Thr Tyr Thr Gly Val Thr Asp Ser Asn Cys Ala Leu Ser
225                 230                 235                 240

Leu Leu Ser Asn Gln Thr Trp Gly Ser Gln Thr Glu Pro Ser Pro
                245                 250                 255

Gly Leu Asn Asn Met Leu Asn Phe Asn Gly Thr Pro Met Thr Gln Leu
            260                 265                 270

Gly Thr Ser Ser His Gly Val Ala Met His Gln Ile Pro Asn Asn Tyr
        275                 280                 285

Glu Val Val Pro Asp Leu Gly Arg Gly His Ile Leu His Pro Leu Gly
    290                 295                 300

Ser Gln His Ser Gly Glu Leu Asp Leu Leu Gln Gln Gly Arg Arg His
305                 310                 315                 320

Tyr Met Asp Val Glu His Ser Arg Ala Tyr Glu Ser Ser Gln Trp Ser
                325                 330                 335

Leu

<210> SEQ ID NO 250
<211> LENGTH: 1143
<212> TYPE: DNA
<213> ORGANISM: Nicotiana bentamiana

<400> SEQUENCE: 250
atggaacttc tggcttctgc ttcttcttct acttctacta attctacttc ccctgactct      60
cctcccaaca ctttaaaatt tggtcaaaaa atctactttg agcatgttgg acttcagcac     120
ctcaaatcag caactgggtc gtcgtcgtca tcgccgccgg tcatcggaac tccggcgccg     180
gcgatgtcca agaaaggaag aggggqtggt gtagttcaag gtcggcaacc acctaggtgt     240
caagttgaag ggtgtgaagc agatctgagt gatgttaagg cttactattc aaggcacaaa     300
gtctgtgcta cacattctaa gtctcctgtg gtcattgttg ctggtcttga acaaagattt     360
```

-continued

```
tgtcaacagt gtagcaggtt tcatcggttg ccagaatttg accaagggaa acgcagttgc    420
cgcaggcgcc tagcaggcca taatgagcgt cggaggaaac ctccacctgg atctcttttg    480
tctaatcgct atggaagtct ttcttcatca atatttgaaa acaatggcag atctggaagt    540
tttctggttg acttcactgc atatccgaat ctcactggag gtgcatggcc aaatactaga    600
tcatctgatc gaggatggga taatcaatcc actgcgtcag ggaagcttct ccaaagtcat    660
tggctgaaca gttctgaaaa tccgacatcc gaccttgttc tgcaaggttc agttgctagg    720
ggtgccaatt attctggtcc tggtattatt ccttccggaa actgcttctc tggagtctca    780
gattccaatg gtgctctctc tcttctgtca aatgagccat ggggctcgag gaaccaatcc    840
tctagcctcg gggttaacgg cttggtcaac actgatggcg gacataccgt tcacccatcg    900
ggttcccatg ctgctcctgt caatcactac tcaggccctc tatggggatt aaaggaaat    960
gaagctagta gcagttcaca tgcaataacct cctgatctcg ggctgggtca catttctcaa   1020
catgctgtca atcagtactc tggtgagcct gggatggctc agcacagtgg aagacagtac   1080
atgggactgg agcattcaaa gggttataat tcttctgttc agaatgtgca ctggacactt   1140
tga                                                                  1143
```

<210> SEQ ID NO 251
<211> LENGTH: 380
<212> TYPE: PRT
<213> ORGANISM: Nicotiana bentamiana

<400> SEQUENCE: 251

```
Met Glu Leu Leu Ala Ser Ala Ser Ser Thr Ser Thr Asn Ser Thr
1               5                   10                  15

Ser Pro Asp Ser Pro Asn Thr Leu Lys Phe Gly Gln Lys Ile Tyr
            20                  25                  30

Phe Glu His Val Gly Leu Gln His Leu Lys Ser Ala Thr Gly Ser Ser
                35                  40                  45

Ser Ser Ser Pro Pro Val Ile Gly Thr Pro Ala Pro Ala Met Ser Lys
    50                  55                  60

Lys Gly Arg Gly Gly Val Val Gln Gly Arg Gln Pro Pro Arg Cys
65              70                  75                  80

Gln Val Glu Gly Cys Glu Ala Asp Leu Ser Asp Val Lys Ala Tyr Tyr
                85                  90                  95

Ser Arg His Lys Val Cys Ala Thr His Ser Lys Ser Pro Val Val Ile
            100                 105                 110

Val Ala Gly Leu Glu Gln Arg Phe Cys Gln Gln Cys Ser Arg Phe His
        115                 120                 125

Arg Leu Pro Glu Phe Asp Gln Gly Lys Arg Ser Cys Arg Arg Leu
    130                 135                 140

Ala Gly His Asn Glu Arg Arg Arg Lys Pro Pro Gly Ser Leu Leu
145                 150                 155                 160

Ser Asn Arg Tyr Gly Ser Leu Ser Ser Ile Phe Glu Asn Asn Gly
                165                 170                 175

Arg Ser Gly Ser Phe Leu Val Asp Phe Thr Ala Tyr Pro Asn Leu Thr
            180                 185                 190

Gly Gly Ala Trp Pro Asn Thr Arg Ser Ser Asp Arg Gly Trp Asp Asn
        195                 200                 205

Gln Ser Thr Ala Ser Gly Lys Leu Leu Gln Ser His Trp Leu Asn Ser
    210                 215                 220

Ser Glu Asn Pro Thr Ser Asp Leu Val Leu Gln Gly Ser Val Ala Arg
225                 230                 235                 240
```

```
Gly Ala Asn Tyr Ser Gly Pro Gly Ile Ile Pro Ser Gly Asn Cys Phe
                245                 250                 255

Ser Gly Val Ser Asp Ser Asn Gly Ala Leu Ser Leu Leu Ser Asn Glu
            260                 265                 270

Pro Trp Gly Ser Arg Asn Gln Ser Ser Leu Gly Val Asn Gly Leu
        275                 280                 285

Val Asn Thr Asp Gly Gly His Thr Val His Pro Ser Gly Ser His Ala
    290                 295                 300

Ala Pro Val Asn His Tyr Ser Gly Pro Leu Trp Gly Phe Lys Gly Asn
305                 310                 315                 320

Glu Ala Ser Ser Ser His Ala Ile Pro Pro Asp Leu Gly Leu Gly
                325                 330                 335

His Ile Ser Gln His Ala Val Asn Gln Tyr Ser Gly Glu Pro Gly Met
            340                 345                 350

Ala Gln His Ser Gly Arg Gln Tyr Met Gly Leu Glu His Ser Lys Gly
        355                 360                 365

Tyr Asn Ser Ser Val Gln Asn Val His Trp Thr Leu
    370                 375                 380

<210> SEQ ID NO 252
<211> LENGTH: 1254
<212> TYPE: DNA
<213> ORGANISM: Oryza sativa

<400> SEQUENCE: 252
atggagatgg ccagtggagg aggcgccgcc gccgccgccg gcggcggagt aggcggcagc      60
ggcggcggtg gtggtggagg ggacgagcac cgccagctgc acgtctcaa gttcggcaag     120 aagatctact tcgaggacgc cgccgcggca gcaggcggcg gcggcactgg cagtggcagt     180
ggcagcgcga gcgccgcgcc gccgtcctcg tcttccaagg cggcgggtgg tggacgcggc     240 ggaggggggca agaacaaggg gaagggcgtg gccgcggcgc cgccaccgcc gccgccgccg     300
ccgccgcggt gccaggtgga ggggtgcggc gcggatctga gcgggatcaa gaactactac     360
tgccgccaca aggtgtgctt catgcattcc aaggctcccc gcgtcgtcgt cgccggcctc     420
gagcagcgct tctgccagca gtgcagcagg ttccacctgc tgcctgaatt tgaccaagga     480
aaacgcagct gccgcagacg ccttgcaggt cataatgagc gccggaggag gccgcaaacc     540
cctttggcat cacgctacgg tcgactagct gcatctgttg gtgagcatcg caggttcaga     600
agctttacgt tggatttctc ctacccaagg gttccaagca gcgtaaggaa tgcatggcca     660
gcaattcaac caggcgatcg gatctccggt ggtatccagt ggcacaggaa cgtagctcct     720
catggtcact ctagtgcagt ggcgggatat ggtgccaaca catacagcgg ccaaggtagc     780
tcttcttcag gccaccggt gttcgctggc ccaaatctcc ctccaggtgg atgtctcgca     840
ggggtcggtg ccgccaccga ctcgagctgt gctctctctc ttctgtcaac ccagccatgg     900
gatactacta cccacagtgc cgctgccagc acaaccagg ctgcagccat gtccactacc     960
accagctttg atggcaatcc tgtggcaccc tccgccatgg cggtagcta catggcacca    1020 agcccctgga caggttctcg gggccatgag ggtggtggtc ggagcgtggc gcaccagcta    1080
ccacatgaag tctcacttga tgaggtgcac cctggtccta gccatcatgc ccacttctcc    1140
ggtgagcttg agcttgctct gcaggggaac ggtccagccc cagcaccacg catcgatcct    1200
gggtccggca gcaccttcga ccaaaccagc aacacgatgg attggtctct gtag           1254

<210> SEQ ID NO 253
```

```
<211> LENGTH: 417
<212> TYPE: PRT
<213> ORGANISM: Oryza sativa

<400> SEQUENCE: 253

Met Glu Met Ala Ser Gly Gly Ala Ala Ala Ala Gly Gly
1               5                   10                  15

Val Gly Gly Ser Gly Gly Gly Gly Gly Asp Glu His Arg Gln
            20                  25                  30

Leu His Gly Leu Lys Phe Gly Lys Ile Tyr Phe Glu Asp Ala Ala
                35                  40                  45

Ala Ala Ala Gly Gly Gly Thr Gly Ser Gly Ser Ala Ser
        50                  55                  60

Ala Ala Pro Pro Ser Ser Ser Lys Ala Ala Gly Gly Gly Arg Gly
65                  70                  75                  80

Gly Gly Gly Lys Asn Lys Gly Lys Gly Val Ala Ala Ala Pro Pro
                85                  90                  95

Pro Pro Pro Pro Pro Arg Cys Gln Val Glu Gly Cys Gly Ala Asp
            100                 105                 110

Leu Ser Gly Ile Lys Asn Tyr Tyr Cys Arg His Lys Val Cys Phe Met
                115                 120                 125

His Ser Lys Ala Pro Arg Val Val Val Ala Gly Leu Glu Gln Arg Phe
130                 135                 140

Cys Gln Gln Cys Ser Arg Phe His Leu Leu Pro Glu Phe Asp Gln Gly
145                 150                 155                 160

Lys Arg Ser Cys Arg Arg Leu Ala Gly His Asn Glu Arg Arg
                165                 170                 175

Arg Pro Gln Thr Pro Leu Ala Ser Arg Tyr Gly Arg Leu Ala Ala Ser
            180                 185                 190

Val Gly Glu His Arg Arg Phe Arg Ser Phe Thr Leu Asp Phe Ser Tyr
                195                 200                 205

Pro Arg Val Pro Ser Ser Val Arg Asn Ala Trp Pro Ala Ile Gln Pro
            210                 215                 220

Gly Asp Arg Ile Ser Gly Gly Ile Gln Trp His Arg Asn Val Ala Pro
225                 230                 235                 240

His Gly His Ser Ser Ala Val Ala Gly Tyr Gly Ala Asn Thr Tyr Ser
                245                 250                 255

Gly Gln Gly Ser Ser Ser Ser Gly Pro Pro Val Phe Ala Gly Pro Asn
                260                 265                 270

Leu Pro Pro Gly Gly Cys Leu Ala Gly Val Gly Ala Ala Thr Asp Ser
            275                 280                 285

Ser Cys Ala Leu Ser Leu Leu Ser Thr Gln Pro Trp Asp Thr Thr Thr
290                 295                 300

His Ser Ala Ala Ala Ser His Asn Gln Ala Ala Met Ser Thr Thr
305                 310                 315                 320

Thr Ser Phe Asp Gly Asn Pro Val Ala Pro Ser Ala Met Ala Gly Ser
                325                 330                 335

Tyr Met Ala Pro Ser Pro Trp Thr Gly Ser Arg Gly His Glu Gly Gly
            340                 345                 350

Gly Arg Ser Val Ala His Gln Leu Pro His Glu Val Ser Leu Asp Glu
                355                 360                 365

Val His Pro Gly Pro Ser His His Ala His Phe Ser Gly Glu Leu Glu
            370                 375                 380

Leu Ala Leu Gln Gly Asn Gly Pro Ala Pro Ala Pro Arg Ile Asp Pro
385                 390                 395                 400
```

Gly Ser Gly Ser Thr Phe Asp Gln Thr Ser Asn Thr Met Asp Trp Ser
                405                 410                 415

Leu

<210> SEQ ID NO 254
<211> LENGTH: 1182
<212> TYPE: DNA
<213> ORGANISM: Oryza sativa

<400> SEQUENCE: 254

```
atggcgaccg gcggcagcgg cggcggcggc ggaggtggag gtggtggtga cgatgtccac      60
gggctcaagt tcggcaagaa gatctacttc gagcaggacg cggcggcgtc ggcgtcggcg     120
gcggcggtgg agtcgtcgtc gacgtcgtcg ggcggaggcg gcaagaaggg gaagggcgtg     180
gcggcggcgg cggcgccccc gccgccgctg ccgccgaggt gccaggtgga gggttgcggc     240
gtggatctga gcggcgtcaa gccgtactac tgccgccaca aggtgtgcta catgcacgcc     300
aaggagccca tcgtcgtcgt cgccggcctc gagcagcgct tctgccaaca gtgcagcagg     360
ttccaccaat tacctgaatt tgatcaagaa aaaaaaagct gccgcagacg ccttgcaggt     420
cacaatgaac gccggaggaa gccgacacct ggacctcttt cttctcgcta tggccggctt     480
gctgcatcct ttcatgaaga gccaggcagg tccagaagct tgtggtagaa tttctcatac     540
ccaagggttc aagcagtgtg agggatgcg tggcctgcta ttcagcccag cgatcgcatg      600
tccggttcaa tccagtggca aggggccat gaactccatc ctcaccgcag cgcagttgcg      660
ggatacagtg atcaccatgc gttcagcagc catggtggct cagcggctgg ggcaccaatg     720
ctccaccacc cagcctttga gctcacctca ggtggatgtc tcgcgggagt cgccaccgac     780
tccagctgtg ctctctctct tctgtcaact cagccatggg atactaccca agcaccagc      840
agccacaacc ggtccccgcc aatgtcgtca acggccagcg ccttcggagg cggcaacaac     900
ccggtgtcgc cctcggtcat ggcaagcaac tacatggcgg cgagcccgg ctggaacagc      960
tccagccggg gccatgacgg cgccaggaac gtgcacctgc cgccaccgca cggggttgtg    1020
ctgaacgagg tccctccggg ctctgtccac acggccatt tctccggcga gctcgagctc    1080
gcactgcagg gaggtgcccc gtccaaccgg ccggaagccg agcatggctc cggcagcggc    1140
gccttcagcc actccaccaa tgccatgaac tggtctctgt ag                      1182
```

<210> SEQ ID NO 255
<211> LENGTH: 393
<212> TYPE: PRT
<213> ORGANISM: Oryza sativa

<400> SEQUENCE: 255

Met Ala Thr Gly Gly Ser Gly Gly Gly Gly Gly Gly Gly Gly Gly Gly
1               5                   10                  15

Asp Asp Val His Gly Leu Lys Phe Gly Lys Lys Ile Tyr Phe Glu Gln
                20                  25                  30

Asp Ala Ala Ala Ser Ala Ser Ala Ala Val Glu Ser Ser Ser Thr
            35                  40                  45

Ser Ser Gly Gly Gly Gly Lys Lys Gly Lys Gly Val Ala Ala Ala
        50                  55                  60

Ala Pro Pro Pro Leu Pro Pro Arg Cys Gln Val Glu Gly Cys Gly
65                  70                  75                  80

Val Asp Leu Ser Gly Val Lys Pro Tyr Tyr Cys Arg His Lys Val Cys
                85                  90                  95

-continued

```
Tyr Met His Ala Lys Glu Pro Ile Val Val Ala Gly Leu Glu Gln
            100                 105                 110

Arg Phe Cys Gln Gln Cys Ser Arg Phe His Gln Leu Pro Glu Phe Asp
        115                 120                 125

Gln Glu Lys Lys Ser Cys Arg Arg Leu Ala Gly His Asn Glu Arg
    130                 135                 140

Arg Arg Lys Pro Thr Pro Gly Pro Leu Ser Ser Arg Tyr Gly Arg Leu
145                 150                 155                 160

Ala Ala Ser Phe His Glu Pro Gly Arg Ser Arg Ser Phe Val Val
            165                 170                 175

Asp Phe Ser Tyr Pro Arg Val Pro Ser Ser Val Arg Asp Ala Trp Pro
            180                 185                 190

Ala Ile Gln Pro Ser Asp Arg Met Ser Gly Ser Ile Gln Trp Gln Gly
            195                 200                 205

Gly His Glu Leu His Pro His Arg Ser Ala Val Ala Gly Tyr Ser Asp
            210                 215                 220

His His Ala Phe Ser Ser His Gly Gly Ser Ala Ala Gly Ala Pro Met
225                 230                 235                 240

Leu His His Pro Ala Phe Glu Leu Thr Ser Gly Gly Cys Leu Ala Gly
            245                 250                 255

Val Ala Thr Asp Ser Ser Cys Ala Leu Ser Leu Leu Ser Thr Gln Pro
            260                 265                 270

Trp Asp Thr Thr Gln Ser Thr Ser Ser His Asn Arg Ser Pro Pro Met
            275                 280                 285

Ser Ser Thr Ala Ser Ala Phe Gly Gly Gly Asn Asn Pro Val Ser Pro
    290                 295                 300

Ser Val Met Ala Ser Asn Tyr Met Ala Ala Ser Pro Gly Trp Asn Ser
305                 310                 315                 320

Ser Ser Arg Gly His Asp Gly Ala Arg Asn Val His Leu Pro Pro Pro
            325                 330                 335

His Gly Val Val Leu Asn Glu Val Pro Pro Gly Ser Val His His Gly
            340                 345                 350

His Phe Ser Gly Glu Leu Glu Leu Ala Leu Gln Gly Gly Ala Pro Ser
            355                 360                 365

Asn Arg Pro Glu Ala Glu His Gly Ser Gly Ser Gly Ala Phe Ser His
            370                 375                 380

Ser Thr Asn Ala Met Asn Trp Ser Leu
385                 390
```

```
<210> SEQ ID NO 256
<211> LENGTH: 1119
<212> TYPE: DNA
<213> ORGANISM: Solanum tuberosum

<400> SEQUENCE: 256
atggaactgg gttcagtttc ttcttctggt aattcaagct catctgattc tttgaatggt    60
ttgaagtttg gtaagaaaat ctactttgga aatgtgggtg ttggagttca ggtcaagaat   120
ggaagtgggt cgtcgccggt gaccggagat gggaacatgc caccggctcc ggcgacgact   180
aagaggggga ggggtggggtt ggtgcagggt ggtcatccac taggtgtca agttgaaggt   240 tgtcaggcag atctgagtga tgctaaggct actattcaa ggcataaagt ttgtggtatg   300
cactctaagt ctcctactgt tgttgttgct ggtcttgaac agaggttttg ccaacagtgt   360
agcaggttcc atcaattaac tgaattcgac caggggaaaa ggagttgccg caggagactg   420
gcatgccata tgagcgtcg taggaagcct ccatctggat ctcttttctc tacacactac   480
```

-continued

```
gggaatcttt cttcatcaat atttgaaaat aatagcagca gatccggaag ctttctggtc    540
gacttcagct cacaccaaaa tgtcaatgat agttcatggc caaatactcg agcatctgaa    600
caaggatggg atcatcaatc atcagggaag ttccttcaac gtccttggct gaataactct    660
gaaaatgctg ccagtgagct tgttttgcaa ggttcagcta ccaggaccag ttatcctagt    720
gttccttctg gagactattt tcctggagtc tcagattcaa gtggtgctct ctctcttctg    780
tcaaatcggt cctggggatc aaggaatcga tctccaagtc ttggggttaa cagccaagtt    840
cacattgatg gggtacacac cattcaacct tcaggttctc atggtgcacc taccaatcac    900
ttctcaagcc cttcattgag ttttaaagga aatgaagcta gcagcagttc acatgagatg    960
cctcctgatc tcggtttggg tcaaatgtta caagcttctg ataatccata ctgtggcgag   1020
cttgggatgg ctcagcatgg tgatggacga caatacatgg aactggacca gtccaagggt   1080
tatcatcctt ctgttcagaa tgtgcactgg actctttga                          1119
```

<210> SEQ ID NO 257
<211> LENGTH: 372
<212> TYPE: PRT
<213> ORGANISM: Solanum tuberosum

<400> SEQUENCE: 257

```
Met Glu Leu Gly Ser Val Ser Ser Gly Asn Ser Ser Ser Asp
1               5                   10                  15

Ser Leu Asn Gly Leu Lys Phe Gly Lys Lys Ile Tyr Phe Gly Asn Val
                20                  25                  30

Gly Val Gly Val Gln Val Lys Asn Gly Ser Gly Ser Ser Pro Val Thr
            35                  40                  45

Gly Asp Gly Asn Met Pro Pro Ala Pro Ala Thr Thr Lys Arg Gly Arg
        50                  55                  60

Gly Gly Leu Val Gln Gly Gly His Pro Pro Arg Cys Gln Val Glu Gly
65                  70                  75                  80

Cys Gln Ala Asp Leu Ser Asp Ala Lys Ala Tyr Tyr Ser Arg His Lys
                85                  90                  95

Val Cys Gly Met His Ser Lys Ser Pro Thr Val Val Val Ala Gly Leu
            100                 105                 110

Glu Gln Arg Phe Cys Gln Gln Cys Ser Arg Phe His Gln Leu Thr Glu
        115                 120                 125

Phe Asp Gln Gly Lys Arg Ser Cys Arg Arg Arg Leu Ala Cys His Asn
    130                 135                 140

Glu Arg Arg Arg Lys Pro Pro Ser Gly Ser Leu Phe Ser Thr His Tyr
145                 150                 155                 160

Gly Asn Leu Ser Ser Ser Ile Phe Glu Asn Asn Ser Ser Arg Ser Gly
                165                 170                 175

Ser Phe Leu Val Asp Phe Ser Ser His Gln Asn Val Asn Asp Ser Ser
            180                 185                 190

Trp Pro Asn Thr Arg Ala Ser Glu Gln Gly Trp Asp His Gln Ser Ser
        195                 200                 205

Gly Lys Phe Leu Gln Arg Pro Trp Leu Asn Asn Ser Glu Asn Ala Ala
    210                 215                 220

Ser Glu Leu Val Leu Gln Gly Ser Ala Thr Arg Thr Ser Tyr Pro Ser
225                 230                 235                 240

Val Pro Ser Gly Asp Tyr Phe Pro Gly Val Ser Asp Ser Ser Gly Ala
                245                 250                 255

Leu Ser Leu Leu Ser Asn Arg Ser Trp Gly Ser Arg Asn Arg Ser Pro
```

```
                260               265               270
Ser Leu Gly Val Asn Ser Gln Val His Ile Asp Gly Val His Thr Ile
            275               280               285

Gln Pro Ser Gly Ser His Gly Ala Pro Thr Asn His Phe Ser Ser Pro
        290               295               300

Ser Leu Ser Phe Lys Gly Asn Glu Ala Ser Ser Ser His Glu Met
305               310               315               320

Pro Pro Asp Leu Gly Leu Gly Gln Met Leu Gln Ala Ser Asp Asn Pro
                325               330               335

Tyr Cys Gly Glu Leu Gly Met Ala Gln His Gly Asp Gly Arg Gln Tyr
            340               345               350

Met Glu Leu Asp Gln Ser Lys Gly Tyr His Pro Ser Val Gln Asn Val
        355               360               365

His Trp Thr Leu
    370
```

<210> SEQ ID NO 258
<211> LENGTH: 1140
<212> TYPE: DNA
<213> ORGANISM: Vitis vinifera

<400> SEQUENCE: 258

```
atggaaaggg gttcgagctc tttgaccgtt tccagctctt cggccaactc gtctgagtcg    60
ctcaacgggt tgaaatttgg gcagaagata tattttgaag atttggcgt tggagctccg    120
gccaaatcgg gaaccggctc ctcctcctcc tcctctgccg ccggctccgg tggtcgccca   180
cctccggcgc cgccaaagaa ggtaagaggt agtgggttg ttcagggagg ccaaccaccg    240
aggtgtcaag ttgaagggtg taaactagat ctgagtgatg ccaaagctta ctattcaagg    300
cataaagtgt gtggtatgca ttcgaagtct ccaacggtca ttgttgcggg ccttgagcag    360
aggttttgcc agcagtgtag cagatttcat cagcttgccg aatttgacca ggaaaacga    420
agttgtcgta ggcgcctggc tggtcataat gagcgtcgca ggaagccacc acctggatct    480
ttattgtcct cacgctatgg gcgactttct tcatccattt ttgaaaacag cagcagggtg    540
ggaggaggct ttctgatgga ctttgctgca tacccaaggc atcccgagag ggatacttgg    600
ccaactacaa gagcatctga tgggtacct ggaaatcaaa ccactgcgat gggaaggttt    660
cttccacatc catggcagag caactctgag aatcctctct ttctgcaagg ttcagccggc   720
gggaccagct ttcatggtcc tggaattcct tcaggagaat gtttcacagg gcctccgac    780
tcaagctgtg ctctctctct tctgtcaaat cagccatgga gctccaggaa tcgagcatct   840
ggtcttggag caaacagctt catgaatcct gaaggggcat ccatggcgca acccacagct   900
cctcatagtg cagctatcaa tcacttccca agcacctcgt gggatttcaa gggcaatgaa   960
ggtagtagca gttcgcagga gatgccacct gatcttggtc ttggtcaaat ttcacagcct  1020
attaatagcc agttctcagg tggggcgag ttgccccaac agagtggaag caatacatg    1080
gaactcgagc actccagggc ttatgacact tccactcagc agatgcactg gtcactttag  1140
```

<210> SEQ ID NO 259
<211> LENGTH: 379
<212> TYPE: PRT
<213> ORGANISM: Vitis vinifera

<400> SEQUENCE: 259

```
Met Glu Arg Gly Ser Ser Ser Leu Thr Val Ser Ser Ser Ala Asn
1               5                   10                  15
```

| | | | | | | | | | | | |
|---|---|---|---|---|---|---|---|---|---|---|---|
|Ser|Ser|Glu|Ser|Leu|Asn|Gly|Leu|Lys|Phe|Gly|Gln|Lys|Ile|Tyr|Phe|
| | | |20 | | | |25 | | | |30 | | | | |
|Glu|Asp|Leu|Gly|Val|Gly|Ala|Pro|Ala|Lys|Ser|Gly|Thr|Gly|Ser|Ser|
| | | |35 | | | |40 | | | |45 | | | | |

```
Ser Ser Glu Ser Leu Asn Gly Leu Lys Phe Gly Gln Lys Ile Tyr Phe
             20                  25                  30
Glu Asp Leu Gly Val Gly Ala Pro Ala Lys Ser Gly Thr Gly Ser Ser
             35                  40                  45
Ser Ser Ser Ala Ala Gly Ser Gly Gly Arg Pro Pro Ala Pro
 50                  55                  60
Pro Lys Lys Val Arg Gly Ser Gly Val Val Gln Gly Gln Pro Pro
 65                  70                  75                  80
Arg Cys Gln Val Glu Gly Cys Lys Leu Asp Leu Ser Asp Ala Lys Ala
                 85                  90                  95
Tyr Tyr Ser Arg His Lys Val Cys Gly Met His Ser Lys Ser Pro Thr
                100                 105                 110
Val Ile Val Ala Gly Leu Glu Gln Arg Phe Cys Gln Gln Cys Ser Arg
                115                 120                 125
Phe His Gln Leu Ala Glu Phe Asp Gln Gly Lys Arg Ser Cys Arg Arg
                130                 135                 140
Arg Leu Ala Gly His Asn Glu Arg Arg Arg Lys Pro Pro Pro Gly Ser
145                 150                 155                 160
Leu Leu Ser Ser Arg Tyr Gly Arg Leu Ser Ser Ser Ile Phe Glu Asn
                165                 170                 175
Ser Ser Arg Val Gly Gly Gly Phe Leu Met Asp Phe Ala Ala Tyr Pro
                180                 185                 190
Arg His Pro Glu Arg Asp Thr Trp Pro Thr Thr Arg Ala Ser Asp Arg
                195                 200                 205
Val Pro Gly Asn Gln Thr Thr Ala Met Gly Arg Phe Leu Pro His Pro
                210                 215                 220
Trp Gln Ser Asn Ser Glu Asn Pro Leu Phe Leu Gln Gly Ser Ala Gly
225                 230                 235                 240
Gly Thr Ser Phe His Gly Pro Gly Ile Pro Ser Gly Glu Cys Phe Thr
                245                 250                 255
Gly Ala Ser Asp Ser Ser Cys Ala Leu Ser Leu Leu Ser Asn Gln Pro
                260                 265                 270
Trp Ser Arg Asn Arg Ala Ser Gly Leu Gly Ala Asn Ser Phe Met
                275                 280                 285
Asn Pro Glu Gly Ala Ser Met Ala Gln Pro Thr Ala Pro His Ser Ala
290                 295                 300
Ala Ile Asn His Phe Pro Ser Thr Ser Trp Asp Phe Lys Gly Asn Glu
305                 310                 315                 320
Gly Ser Ser Ser Gln Glu Met Pro Pro Asp Leu Gly Leu Gly Gln
                325                 330                 335
Ile Ser Gln Pro Ile Asn Ser Gln Phe Ser Gly Gly Gly Glu Leu Pro
                340                 345                 350
Gln Gln Ser Gly Arg Gln Tyr Met Glu Leu Glu His Ser Arg Ala Tyr
                355                 360                 365
Asp Thr Ser Thr Gln Gln Met His Trp Ser Leu
    370                 375
```

<210> SEQ ID NO 260
<211> LENGTH: 1209
<212> TYPE: DNA
<213> ORGANISM: Zea mays

<400> SEQUENCE: 260
atggagtccg gcggtggcgg ggacgaccag ctgcacggcc tcaagttcgg caagaagatc    60
tacttcgagg acgccgccgg ctccagcagc ggcagcagca gcggcggtgg cagcgcgccc   120

```
gcgcctccag cgacgcagca gccgtcgccg ccggccgctt cgcctagggc cccggccggc      180
ggcggcagga ggggcagggc cgcggccggc ggcgcgggcc cctcgacggc gcccgcgccc      240
gcgcgctgcc aggtcgacgg ctgcaacgtt gacctcaccg acgtcaagcc cgcctactac      300
tgccgccaca aggtgtgcaa aatgcactcc aaggagcccc gcgtcctcgt caacggcctc      360
gagcagcgct tctgccagca gtgcagcagg ttccaccagc tgcctgaatt cgaccagcta      420
aagaagagct gccgcaaacg cctcgcaggc cacaacgagc gccggaggag gccgccgcct      480
ggacccettg cgtcacgata cggccgtcac gctgcgtcgc tcggcgagcc cggcaggctc      540
agaagcttca tgctggattt ctcgtacccg agggtctcaa gcgccatgag gggtgggttt      600
cccgcggtga gggccggtgg tgaaagggtg cctggcggga tccagtggca agcgggcttg      660
gatcctcgtc accaccaagg cgcggtcgcg ggatacggcg cccactatgg gagcgagggt      720
ggtagctcgt cgtcggcgag gccgccggtg ttccctggcc cggagctgcc cccaggtgga      780
tgccttgcag gagtccccgc ggactccagc tgtgctctct ctcttctgtc aactcagcca      840
tgggatgctg cccacagcca cagccacagc cacgctgcgc caacagcggg tttcgacggc      900
ggcagccctg tggcgccctc cctcatggcg gcgagtagcc acatcgcgcc gagcccctgg      960
accgagaccg actcctgggg ccacgaaggc gggcggagcg tgcctcagct gccacctgac     1020
gacgtccccc tcggcgaggt gcactccggc tcgagcagcc accacggcca gttctcaggt     1080
gagctcgagc tcgccctgca gggaaacagg ccagcgccag ggtcggcggc accgccagcg     1140
ccgcgcaata atcagggctc cgcgggcacg ttcgaccagg ctggcaacac gatggactgg     1200
tcgctctag                                                             1209
```

<210> SEQ ID NO 261
<211> LENGTH: 402
<212> TYPE: PRT
<213> ORGANISM: Zea mays

<400> SEQUENCE: 261

```
Met Glu Ser Gly Gly Gly Gly Asp Asp Gln Leu His Gly Leu Lys Phe
1               5                   10                  15

Gly Lys Lys Ile Tyr Phe Glu Asp Ala Ala Gly Ser Ser Ser Gly Ser
                20                  25                  30

Ser Ser Gly Gly Gly Ser Ala Pro Ala Pro Ala Thr Gln Gln Pro
            35                  40                  45

Ser Pro Pro Ala Ala Ser Pro Arg Ala Pro Ala Gly Gly Gly Arg Arg
        50                  55                  60

Gly Arg Ala Ala Ala Gly Gly Ala Gly Pro Ser Thr Ala Pro Ala Pro
65                  70                  75                  80

Ala Arg Cys Gln Val Asp Gly Cys Asn Val Asp Leu Thr Asp Val Lys
                85                  90                  95

Pro Ala Tyr Tyr Cys Arg His Lys Val Cys Lys Met His Ser Lys Glu
            100                 105                 110

Pro Arg Val Leu Val Asn Gly Leu Glu Gln Arg Phe Cys Gln Gln Cys
        115                 120                 125

Ser Arg Phe His Gln Leu Pro Glu Phe Asp Gln Leu Lys Lys Ser Cys
    130                 135                 140

Arg Lys Arg Leu Ala Gly His Asn Glu Arg Arg Arg Pro Pro
145                 150                 155                 160

Gly Pro Leu Ala Ser Arg Tyr Gly Arg His Ala Ala Ser Leu Gly Glu
                165                 170                 175
```

```
Pro Gly Arg Leu Arg Ser Phe Met Leu Asp Phe Ser Tyr Pro Arg Val
            180                 185                 190

Ser Ser Ala Met Arg Gly Gly Phe Pro Ala Val Arg Ala Gly Gly Glu
        195                 200                 205

Arg Val Pro Gly Gly Ile Gln Trp Gln Ala Gly Leu Asp Pro Arg His
    210                 215                 220

His Gln Gly Ala Val Ala Gly Tyr Gly Ala His Tyr Gly Ser Glu Gly
225                 230                 235                 240

Gly Ser Ser Ser Ala Arg Pro Pro Val Phe Pro Gly Pro Glu Leu
                245                 250                 255

Pro Pro Gly Gly Cys Leu Ala Gly Val Pro Ala Asp Ser Ser Cys Ala
        260                 265                 270

Leu Ser Leu Leu Ser Thr Gln Pro Trp Asp Ala His Ser His Ser
    275                 280                 285

His Ser His Ala Ala Pro Thr Ala Gly Phe Asp Gly Gly Ser Pro Val
290                 295                 300

Ala Pro Ser Leu Met Ala Ala Ser Ser Tyr Ile Ala Pro Ser Pro Trp
305                 310                 315                 320

Thr Glu Thr Asp Ser Trp Gly His Glu Gly Gly Arg Ser Val Pro Gln
                325                 330                 335

Leu Pro Pro Asp Asp Val Pro Leu Gly Glu Val His Ser Gly Ser Ser
            340                 345                 350

Ser His His Gly Gln Phe Ser Gly Glu Leu Glu Leu Ala Leu Gln Gly
        355                 360                 365

Asn Arg Pro Ala Pro Gly Ser Ala Ala Pro Pro Ala Pro Arg Asn Asn
    370                 375                 380

Gln Gly Ser Ala Gly Thr Phe Asp Gln Ala Gly Asn Thr Met Asp Trp
385                 390                 395                 400

Ser Leu

<210> SEQ ID NO 262
<211> LENGTH: 1137
<212> TYPE: DNA
<213> ORGANISM: Zea mays

<400> SEQUENCE: 262
atggcgaccg gcggcggcag cagcaggagc gacgacgtgc gcgggctcaa gtttggcaag      60
aagatctact tcgagcagga cggcgggagc gggagcgggg cggggcggt gggcggcagg      120 aaggggaagg gcgtggccac cggtggcgcg aggccggcgt ccgccgcctc cgcagcccag      180
ccgccgaggt gccaggtgga cgggtgcggc gtggatctga cgccgtcaa gcagtactac      240 tgccggcaca aggtgtgcaa catgcactcc aaggagccgc gcgtcttcgt cgccggcatc      300
gagcagcgct tctgccaaca gtgcagcagg ttccaccagc tacatgaatt tgaccaaggg      360
aaacgtagct gccgccgccg cctcatcggt cacaacgagc gccggaggaa gccaccacct      420
ggacctctca cttcacgata tggccggctc gctgcatcac ttcaagagcc tggcaggttc      480
agaagcttcc tgctcgactt ctcgtaccca agggttccaa gcagcgtgag ggatgcgtgg      540
ccaggaatcc agcacggtgg cgacaggatg ctgggcaccg tccagtggca tgggcaccaa      600
gaacctcctc acccacaccg cagtgcagct gctggctatg caaccatgc tgcatacaac      660 tgccatggcg gcttggtagc aggcggggcc ccaatgctct cctctgccgc ctttgagctc      720
ccgcctggcg gatgtgtcgc gggagttgcc gccgactcca gctgtgctct ctctcttctg      780
tcaactcagc catgggacac gacctcccac gaccaccggt ccccagcaat gcccgcggcc      840
```

```
ggcgccttcg acggcacccc ggtggcgccg tccgtcatgg cgagcagcta cgcggcgtcg    900
agcgcctgga cgggctcgcg ggaccccgct gccgacggcg ccaggaacgc gcagcgtctc    960
gacgatgctc tgcacctggt ccacccaggc tccgcggcgg tccacttctc cggcgagctc   1020
gagctcgccc tgcagggaag cggcgggccg ccacacctgc cgcgcgtcga ccatggcggc   1080
tccggcggcg gcaccttcaa ccattccacc accagcgcga tgaactggtc cctgtag     1137
```

<210> SEQ ID NO 263
<211> LENGTH: 378
<212> TYPE: PRT
<213> ORGANISM: Zea mays

<400> SEQUENCE: 263

```
Met Ala Thr Gly Gly Ser Ser Arg Ser Asp Asp Val Arg Gly Leu
1               5                   10                  15

Lys Phe Gly Lys Lys Ile Tyr Phe Glu Gln Asp Gly Gly Ser Gly Ser
                20                  25                  30

Gly Ala Gly Ala Val Gly Gly Arg Lys Gly Lys Gly Val Ala Thr Gly
            35                  40                  45

Gly Ala Arg Pro Ala Ser Ala Ala Ser Ala Ala Gln Pro Pro Arg Cys
    50                  55                  60

Gln Val Asp Gly Cys Gly Val Asp Leu Ser Ala Val Lys Gln Tyr Tyr
65                  70                  75                  80

Cys Arg His Lys Val Cys Asn Met His Ser Lys Glu Pro Arg Val Phe
                85                  90                  95

Val Ala Gly Ile Glu Gln Arg Phe Cys Gln Gln Cys Ser Arg Phe His
            100                 105                 110

Gln Leu His Glu Phe Asp Gln Gly Lys Arg Ser Cys Arg Arg Arg Leu
        115                 120                 125

Ile Gly His Asn Glu Arg Arg Arg Lys Pro Pro Gly Pro Leu Thr
    130                 135                 140

Ser Arg Tyr Gly Arg Leu Ala Ala Ser Leu Gln Glu Pro Gly Arg Phe
145                 150                 155                 160

Arg Ser Phe Leu Leu Asp Phe Ser Tyr Pro Arg Val Pro Ser Ser Val
                165                 170                 175

Arg Asp Ala Trp Pro Gly Ile Gln His Gly Gly Asp Arg Met Leu Gly
            180                 185                 190

Thr Val Gln Trp His Gly His Gln Glu Pro Pro His Pro His Arg Ser
        195                 200                 205

Ala Ala Ala Gly Tyr Gly Asn His Ala Ala Tyr Asn Cys His Gly Gly
    210                 215                 220

Leu Val Ala Gly Gly Ala Pro Met Leu Ser Ser Ala Ala Phe Glu Leu
225                 230                 235                 240

Pro Pro Gly Gly Cys Val Ala Gly Val Ala Ala Asp Ser Ser Cys Ala
                245                 250                 255

Leu Ser Leu Leu Ser Thr Gln Pro Trp Asp Thr Ser His Asp His
            260                 265                 270

Arg Ser Pro Ala Met Pro Ala Ala Gly Ala Phe Asp Gly Thr Pro Val
        275                 280                 285

Ala Pro Ser Val Met Ala Ser Ser Tyr Ala Ala Ser Ser Ala Trp Thr
    290                 295                 300

Gly Ser Arg Asp Pro Ala Ala Asp Gly Ala Arg Asn Ala Gln Arg Leu
305                 310                 315                 320

Asp Asp Ala Leu His Leu Val His Pro Gly Ser Ala Ala Val His Phe
                325                 330                 335
```

```
Ser Gly Glu Leu Glu Leu Ala Leu Gln Gly Ser Gly Gly Pro Pro His
            340                 345                 350

Leu Pro Arg Val Asp His Gly Ser Gly Gly Gly Thr Phe Asn His
            355                 360                 365

Ser Thr Thr Ser Ala Met Asn Trp Ser Leu
            370                 375

<210> SEQ ID NO 264
<211> LENGTH: 403
<212> TYPE: DNA
<213> ORGANISM: Sorghum propinquum

<400> SEQUENCE: 264
atggagtccg gtggcgccag tggcggcggc ggcggggacg accagctgca cggcctcaag      60
ttcggcaaga agatctactt cgaggacgcc gccgcggtcg gctccagcag cggtggcggt     120
ggcggtggca gtggcagtgc tagcgcgacc cccgcgcctc agcgacgca gcagccgtcc      180 ccgccgcagg ccgcttcgcc cagggcagcc agcggcggcg gcggcaggag gggcagggcc     240
gcgggcggcc cctccccggc gcccgcgccc gcgcgctgcc aggtcgacgg ctgcaacgtg     300
gacctcaccg acgtcaagcc ctactactgc cgccacaagg tctgcaaaat gcactccaag     360
gagccccgcg tcgtcgtcaa cggcctcgag cagcgcttct gcc                       403

<210> SEQ ID NO 265
<211> LENGTH: 134
<212> TYPE: PRT
<213> ORGANISM: Sorghum propinquum

<400> SEQUENCE: 265

Met Glu Ser Gly Gly Ala Ser Gly Gly Gly Gly Asp Asp Gln Leu
  1               5                  10                  15

His Gly Leu Lys Phe Gly Lys Lys Ile Tyr Phe Glu Asp Ala Ala Ala
             20                  25                  30

Val Gly Ser Ser Ser Gly Gly Gly Gly Gly Ser Gly Ser Ala Ser
             35                  40                  45

Ala Thr Pro Ala Pro Pro Ala Thr Gln Gln Pro Ser Pro Pro Gln Ala
 50                  55                  60

Ala Ser Pro Arg Ala Ala Ser Gly Gly Gly Gly Arg Arg Gly Arg Ala
 65                  70                  75                  80

Ala Gly Gly Pro Ser Pro Ala Pro Ala Pro Ala Arg Cys Gln Val Asp
                 85                  90                  95

Gly Cys Asn Val Asp Leu Thr Asp Val Lys Pro Tyr Tyr Cys Arg His
                100                 105                 110

Lys Val Cys Lys Met His Ser Lys Glu Pro Arg Val Val Val Asn Gly
                115                 120                 125

Leu Glu Gln Arg Phe Cys
    130

<210> SEQ ID NO 266
<211> LENGTH: 732
<212> TYPE: DNA
<213> ORGANISM: Allium cepa

<400> SEQUENCE: 266
atggaaatgg ttcgagctc tgagccaatt tctgactctc tcgatgggct cacattcggc       60
gaaaaaattt actttgaaga ttccactacc agtactgcaa gtactactag caatacaatt     120
gctgctcctc ccaaaaaggg aaaatcttta gcttcttcgt ccactaatat caactctaat     180
```

```
cagcaacaaa taagcatacc tagatgccag gttgaaggat gcaaagttga tttgactgga      240
gctaaagcct attactgcag gcataaggtt tgcggagttc attcaaaatc accaaaagtt      300
gtggttgctg gaattgaaca gaggttttgt cagcagtgca gcaggttcca ccagttgcaa      360
gaatttgacc aaggaaaaag aagctgccgc agacgcctag ctggacacaa tgagcgtcgt      420
agaaagccgc ctccaggccc ttcccgttat ggaaggatgt catcatctgt ctatgatggc      480
agtaacagat tcagaggatt cctgatggac ttcagttacc cgaggcccat acagcctcct      540
ccaggagatc atctatggcc tagactgtcc aacattccat catacccagc aaacccaaac      600
actgcatcta acattcatgt tgctcaaccg tacatgcatg caatgaatca ctacagttcc      660
gagcttccac acaggaatac atggtctggc gtctgcgact tgagctgtgc tctctctctt      720
ctgtcactca ac                                                         732
```

<210> SEQ ID NO 267
<211> LENGTH: 244
<212> TYPE: PRT
<213> ORGANISM: Allium cepa

<400> SEQUENCE: 267

```
Met Glu Met Gly Ser Ser Ser Glu Pro Ile Ser Asp Ser Leu Asp Gly
1               5                   10                  15

Leu Thr Phe Gly Glu Lys Ile Tyr Phe Glu Asp Ser Thr Thr Ser Thr
            20                  25                  30

Ala Ser Thr Thr Ser Asn Thr Ile Ala Ala Pro Pro Lys Lys Gly Lys
        35                  40                  45

Ser Leu Ala Ser Ser Ser Thr Asn Ile Asn Ser Asn Gln Gln Gln Ile
    50                  55                  60

Ser Ile Pro Arg Cys Gln Val Glu Gly Cys Lys Val Asp Leu Thr Gly
65                  70                  75                  80

Ala Lys Ala Tyr Tyr Cys Arg His Lys Val Cys Gly Val His Ser Lys
                85                  90                  95

Ser Pro Lys Val Val Val Ala Gly Ile Glu Gln Arg Phe Cys Gln Gln
            100                 105                 110

Cys Ser Arg Phe His Gln Leu Gln Glu Phe Asp Gln Gly Lys Arg Ser
        115                 120                 125

Cys Arg Arg Leu Ala Gly His Asn Glu Arg Arg Lys Pro Pro
    130                 135                 140

Pro Gly Pro Ser Arg Tyr Gly Arg Met Ser Ser Ser Val Tyr Asp Gly
145                 150                 155                 160

Ser Asn Arg Phe Arg Gly Phe Leu Met Asp Phe Ser Tyr Pro Arg Pro
                165                 170                 175

Ile Gln Pro Pro Pro Gly Asp His Leu Trp Pro Arg Leu Ser Asn Ile
            180                 185                 190

Pro Ser Tyr Pro Ala Asn Pro Asn Thr Ala Ser Asn Ile His Val Ala
        195                 200                 205

Gln Pro Tyr Met His Ala Met Asn His Tyr Ser Ser Glu Leu Pro His
    210                 215                 220

Arg Asn Thr Trp Ser Gly Val Cys Asp Leu Ser Cys Ala Leu Ser Leu
225                 230                 235                 240

Leu Ser Leu Asn
```

<210> SEQ ID NO 268
<211> LENGTH: 969
<212> TYPE: DNA

<213> ORGANISM: Antirrhinum majus

<400> SEQUENCE: 268

```
tcagctgctg gtggagcaga ggaatctctc aatgggttga agtttggcaa gaaaatatac      60
tttgaggagg ctaaggcaaa gaaagggaag agtaccggtg gggtggttag gtgccaggtg     120
gagggggtgtg aggtagatct gagtgatgct aaggcttact atttgagaca caaagtttgt    180
agtatgcatt caaagtctcc aaaggtcatt gttgctggaa tagaacaaag gttttgccag     240
cagtgcagca ggttccatca attgcctgaa tttgaccaag aaaacggag ttgccgcaga      300
cgccttgcag gccacaacga acgtcggagg aagccatctc caggatctat gatgtctcct     360
tactatggaa gtctttctcc aaccttattt gataaccaaa atagaactgg aggcttttg      420
atggacttca gcacttaccc aaatctcgct gggaaagatt catggccaaa tacaatacc     480
gaacgaggat tgggaggtcc agcaagtcca tggcagagcg acatgcaaaa tcctgtacct    540
gagttttgc gaggtacaac aaataggcca agttttctg gtcttggagt atcttccgaa      600
gaatgtttta gcggagtctc taattccagc actgctctct ctcttctgtc aaatcagtcc    660
tggggctcca gaaactcgaa caattttctt ggtaccaatg gaaacgggcc aaccatagtt   720
cagccgtcta ttaaccctgg tgccacaatt ggacagttta cctgtccctc ttgggtttt    780
ggaggcaacc cagctgataa caccctccat gatatgcctc ccaatctgaa tttaggacaa    840
ttttctcact ccagtaacag tcactatact ggagagcctg gggtagtcca actgagccac   900
ggacaattcc aggacctcga tcactcaaga ggctatgatt cttccgttca ggacatgcat    960
tggtcactt                                                             969
```

<210> SEQ ID NO 269
<211> LENGTH: 323
<212> TYPE: PRT
<213> ORGANISM: Antirrhinum majus

<400> SEQUENCE: 269

```
Ser Ala Ala Gly Gly Ala Glu Glu Ser Leu Asn Gly Leu Lys Phe Gly
  1               5                  10                  15

Lys Lys Ile Tyr Phe Glu Glu Ala Lys Ala Lys Lys Gly Lys Ser Thr
             20                  25                  30

Gly Gly Val Val Arg Cys Gln Val Glu Gly Cys Glu Val Asp Leu Ser
         35                  40                  45

Asp Ala Lys Ala Tyr Tyr Leu Arg His Lys Val Cys Ser Met His Ser
     50                  55                  60

Lys Ser Pro Lys Val Ile Val Ala Gly Ile Glu Gln Arg Phe Cys Gln
 65                  70                  75                  80

Gln Cys Ser Arg Phe His Gln Leu Pro Glu Phe Asp Gln Gly Lys Arg
                 85                  90                  95

Ser Cys Arg Arg Arg Leu Ala Gly His Asn Glu Arg Arg Arg Lys Pro
            100                 105                 110

Ser Pro Gly Ser Met Met Ser Pro Tyr Tyr Gly Ser Leu Ser Pro Thr
        115                 120                 125

Leu Phe Asp Asn Gln Asn Arg Thr Gly Gly Phe Leu Met Asp Phe Ser
    130                 135                 140

Thr Tyr Pro Asn Leu Ala Gly Lys Asp Ser Trp Pro Asn Thr Ile Pro
145                 150                 155                 160

Glu Arg Gly Leu Gly Gly Pro Ala Ser Pro Trp Gln Ser Asp Met Gln
                165                 170                 175

Asn Pro Val Pro Glu Phe Leu Arg Gly Thr Thr Asn Arg Pro Ser Phe
```

```
                    180                 185                 190
Ser Gly Leu Gly Val Ser Ser Glu Glu Cys Phe Ser Gly Val Ser Asn
            195                 200                 205

Ser Ser Thr Ala Leu Ser Leu Leu Ser Asn Gln Ser Trp Gly Ser Arg
        210                 215                 220

Asn Ser Asn Asn Phe Leu Gly Thr Asn Gly Asn Gly Pro Thr Ile Val
225                 230                 235                 240

Gln Pro Ser Ile Asn Pro Gly Ala Thr Ile Gly Gln Phe Thr Cys Pro
                245                 250                 255

Ser Trp Gly Phe Gly Gly Asn Pro Ala Asp Asn Thr Ser His Asp Met
            260                 265                 270

Pro Pro Asn Leu Asn Leu Gly Gln Phe Ser His Ser Ser Asn Ser His
        275                 280                 285

Tyr Thr Gly Glu Pro Gly Val Val Gln Leu Ser His Gly Gln Phe Gln
    290                 295                 300

Asp Leu Asp His Ser Arg Gly Tyr Asp Ser Ser Val Gln Asp Met His
305                 310                 315                 320

Trp Ser Leu

<210> SEQ ID NO 270
<211> LENGTH: 633
<212> TYPE: DNA
<213> ORGANISM: Brassica napus

<400> SEQUENCE: 270
gacttggaga aagaagttg tagaagacgt ctagcttgtc ataacgaaag aagaagaaag      60
ccccaagcaa caacagcagc tcttttggct tctggttact ctagaatcgc tccatctctt    120
tacggaagcg ttttgggaga tcctacaacg tggtcaaccg caagatctgt gatgggacgg    180
tccgcaccgt gggatagcca tcaactgatg aacgttttgt cacagggaag ttcaaggttt    240
agtataacat acccagagat ggtgaacaat aatagcacag actcaagctg tgctctctct    300
cttctgtcaa actcaaacac aactcagcag cagcagcaga catcaaccaa tgcttacttg    360
atggacgcag aaagggttac aatggctaag tcaccgcctg tttcagtaca caatcagtac    420
tcgaaacaaa cctgggagtt catgtcaggc gaaagagca attggccttg tgtgtcgtcc      480
cctgttttgg gactgagaca aatctctgag ccagatgatg acctccagtt cctgatgagc    540
aatggcacca caatgggtgg attcgagctg aacctacagc aggagcaggt tctgaggcaa    600
tactcttcta ctcaaaattt tacttggcct ctt                                 633

<210> SEQ ID NO 271
<211> LENGTH: 211
<212> TYPE: PRT
<213> ORGANISM: Brassica napus

<400> SEQUENCE: 271

Asp Leu Glu Lys Arg Ser Cys Arg Arg Arg Leu Ala Cys His Asn Glu
1               5                   10                  15

Arg Arg Arg Lys Pro Gln Ala Thr Thr Ala Ala Leu Leu Ala Ser Gly
            20                  25                  30

Tyr Ser Arg Ile Ala Pro Ser Leu Tyr Gly Ser Val Leu Gly Asp Pro
        35                  40                  45

Thr Thr Trp Ser Thr Ala Arg Ser Val Met Gly Arg Ser Ala Pro Trp
    50                  55                  60

Asp Ser His Gln Leu Met Asn Val Leu Ser Gln Gly Ser Ser Arg Phe
65                  70                  75                  80
```

Ser Ile Thr Tyr Pro Glu Met Val Asn Asn Ser Thr Asp Ser Ser
            85                  90                  95

Cys Ala Leu Ser Leu Leu Ser Asn Ser Asn Thr Thr Gln Gln Gln Gln
            100                 105                 110

Gln Thr Ser Thr Asn Ala Tyr Leu Met Asp Ala Glu Arg Val Thr Met
            115                 120                 125

Ala Lys Ser Pro Pro Val Ser Val His Asn Gln Tyr Ser Lys Gln Thr
        130                 135                 140

Trp Glu Phe Met Ser Gly Glu Lys Ser Asn Trp Pro Cys Val Ser Ser
145                 150                 155                 160

Pro Val Leu Gly Leu Arg Gln Ile Ser Glu Pro Asp Asp Asp Leu Gln
                165                 170                 175

Phe Leu Met Ser Asn Gly Thr Thr Met Gly Gly Phe Glu Leu Asn Leu
            180                 185                 190

Gln Gln Glu Gln Val Leu Arg Gln Tyr Ser Ser Thr Gln Asn Phe Thr
        195                 200                 205

Trp Pro Leu
    210

<210> SEQ ID NO 272
<211> LENGTH: 852
<212> TYPE: DNA
<213> ORGANISM: Saccharum officinarum

<400> SEQUENCE: 272
ctcgtcgtca acggcctcga gcagcgcttc tgccagcagt gcagcaggtt ccaccagctg      60
cctgaatttg accaactaaa gaaaagctgc cgcagacgtc ttgcaggcca caatgaacgc     120
cggaggaggc cacctcctgg acctcttgca tcacgatatg gtcgccttgc tgcatcattt     180
ggtgagcccg gcaggttccg aagctttatg ttggatttct catacccaag ggttccaggc     240
accatgaggg atgggtttcc ggcagttcga cctggcgaaa gggtgcctgg tagtatccag     300
tggcaagcgg gcttagatcc tcatcatcat caaagcgcgg tcgcaggata cggtgcccac     360
tcatatggga gccagggtag ctcgtcgtcg tcaaggccac cggtgttccc tggtccagag     420
ctccccccag gtggatgtct tgcaggagtc ccctcggact ctagctgtgc tctctctctt     480
ctgtcaactc agccatggga tactacccac agcgccggcc acagccatgc tggatcaatg     540
cctgcaacag caggttttga cggcaaccct gtggcaccct ccctcatggc gagtagctac     600
attgcgccaa gccctggac tgactccgg ggccatgaag gcgggcggaa cgtgcctcag      660
ttgccacctg acgtccccct cagcgaggtg cactctggct caagcagcca tcacggccag     720
ttctcaggtg agctcgagct tgccctgcag ggaaacaggc cagcaccagg gtcagcgcca     780
gcgccgcgca atgatcaggg ctccacgggc acgttcgacc agtccggcaa cacaatggac     840
tggtcgctct ag                                                        852

<210> SEQ ID NO 273
<211> LENGTH: 283
<212> TYPE: PRT
<213> ORGANISM: Saccharum officinarum

<400> SEQUENCE: 273

Leu Val Val Asn Gly Leu Glu Gln Arg Phe Cys Gln Gln Cys Ser Arg
1               5                   10                  15

Phe His Gln Leu Pro Glu Phe Asp Gln Leu Lys Lys Ser Cys Arg Arg
            20                  25                  30

```
Arg Leu Ala Gly His Asn Glu Arg Arg Arg Pro Pro Pro Gly Pro
            35                  40                  45
Leu Ala Ser Arg Tyr Gly Arg Leu Ala Ala Ser Phe Gly Glu Pro Gly
    50                  55                  60
Arg Phe Arg Ser Phe Met Leu Asp Phe Ser Tyr Pro Arg Val Pro Gly
65                  70                  75                  80
Thr Met Arg Asp Gly Phe Pro Ala Val Arg Pro Gly Glu Arg Val Pro
                85                  90                  95
Gly Ser Ile Gln Trp Gln Ala Gly Leu Asp Pro His His Gln Ser
                100                 105                 110
Ala Val Ala Gly Tyr Gly Ala His Ser Tyr Gly Ser Gln Gly Ser Ser
            115                 120                 125
Ser Ser Ser Arg Pro Pro Val Phe Pro Gly Pro Glu Leu Pro Pro Gly
130                 135                 140
Gly Cys Leu Ala Gly Val Pro Ser Asp Ser Ser Cys Ala Leu Ser Leu
145                 150                 155                 160
Leu Ser Thr Gln Pro Trp Asp Thr Thr His Ser Ala Gly His Ser His
                165                 170                 175
Ala Gly Ser Met Pro Ala Thr Ala Gly Phe Asp Gly Asn Pro Val Ala
            180                 185                 190
Pro Ser Leu Met Ala Ser Ser Tyr Ile Ala Pro Ser Pro Trp Thr Asp
        195                 200                 205
Ser Arg Gly His Glu Gly Gly Arg Asn Val Pro Gln Leu Pro Pro Asp
210                 215                 220
Val Pro Leu Ser Glu Val His Ser Gly Ser Ser Ser His His Gly Gln
225                 230                 235                 240
Phe Ser Gly Glu Leu Glu Leu Ala Leu Gln Gly Asn Arg Pro Ala Pro
                245                 250                 255
Gly Ser Ala Pro Ala Pro Arg Asn Asp Gln Gly Ser Thr Gly Thr Phe
            260                 265                 270
Asp Gln Ser Gly Asn Thr Met Asp Trp Ser Leu
        275                 280

<210> SEQ ID NO 274
<211> LENGTH: 647
<212> TYPE: DNA
<213> ORGANISM: Festuca arundinacea

<400> SEQUENCE: 274
ggcacgaggg tggatctgag cggctccaag acctactact gccgccacaa ggtctgctcc     60
atgcactcca aggcgccccg cgtcgtcgtc gccggcctcg agcagcgctt ctgccagcag    120
tgcagcaggt tccaccagtt gcctgaattt gacaatggaa aacgcagctg ccgcagacgt    180
ctcgcaggtc acaatgaacg ccgtaggaag ccgcctcctg gccctctggc gtcacgctat    240
ggccgactcg ctgcatcctt tgaagaaccg gcaggtaca gaagctttct gttagatttc    300
tcctacccaa gggttccgag cagcgtgcgg gatgcttggc ctgcagttcg accaggctac    360
cgtatgccca gtgaaatcca gtggcaaggg aacctagacc tgcgtcctca cacgggttat    420
ggcccacatg catatggcag ccacggcttc cccggtccag agctccctcc aggcgggtgt    480
ctcacagggg tcgccaccga ctccagctgt gctctctctc ttctgtcaac tcagccatgg    540
gataccacca cccacggtgc cagccacgac catcggtctg cggccatgtc gcggccgcg    600
ggcttcgacg gcagccctgc ggcagtgtca ccctccatca tggcgag                  647

<210> SEQ ID NO 275
```

```
<211> LENGTH: 215
<212> TYPE: PRT
<213> ORGANISM: Festuca arundinacea

<400> SEQUENCE: 275

Gly Thr Arg Val Asp Leu Ser Gly Ser Lys Thr Tyr Tyr Cys Arg His
1               5                   10                  15

Lys Val Cys Ser Met His Ser Lys Ala Pro Arg Val Val Ala Gly
            20                  25                  30

Leu Glu Gln Arg Phe Cys Gln Cys Ser Arg Phe His Gln Leu Pro
            35                  40                  45

Glu Phe Asp Asn Gly Lys Arg Ser Cys Arg Arg Leu Ala Gly His
50                  55                  60

Asn Glu Arg Arg Arg Lys Pro Pro Gly Pro Leu Ala Ser Arg Tyr
65                  70                  75                  80

Gly Arg Leu Ala Ala Ser Phe Glu Glu Pro Gly Arg Tyr Arg Ser Phe
            85                  90                  95

Leu Leu Asp Phe Ser Tyr Pro Arg Val Pro Ser Ser Val Arg Asp Ala
                100                 105                 110

Trp Pro Ala Val Arg Pro Gly Tyr Arg Met Pro Ser Glu Ile Gln Trp
            115                 120                 125

Gln Gly Asn Leu Asp Leu Arg Pro His Thr Gly Tyr Gly Pro His Ala
130                 135                 140

Tyr Gly Ser His Gly Phe Pro Gly Pro Glu Leu Pro Pro Gly Gly Cys
145                 150                 155                 160

Leu Thr Gly Val Ala Thr Asp Ser Ser Cys Ala Leu Ser Leu Leu Ser
            165                 170                 175

Thr Gln Pro Trp Asp Thr Thr Thr His Gly Ala Ser His Asp His Arg
                180                 185                 190

Ser Ala Ala Met Ser Ala Ala Ala Gly Phe Asp Gly Ser Pro Ala Ala
            195                 200                 205

Val Ser Pro Ser Ile Met Ala
        210                 215

<210> SEQ ID NO 276
<211> LENGTH: 11
<212> TYPE: PRT
<213> ORGANISM: Artificial sequence
<220> FEATURE:
<223> OTHER INFORMATION: motif 1
<220> FEATURE:
<221> NAME/KEY: VARIANT
<222> LOCATION: (1)..(1)
<223> OTHER INFORMATION: Xaa is Gly or Thr
<220> FEATURE:
<221> NAME/KEY: VARIANT
<222> LOCATION: (3)..(3)
<223> OTHER INFORMATION: Xaa is Lys, Arg, Met, or Gln
<220> FEATURE:
<221> NAME/KEY: VARIANT
<222> LOCATION: (6)..(6)
<223> OTHER INFORMATION: Xaa is Lys, Gln, or Arg
<220> FEATURE:
<221> NAME/KEY: VARIANT
<222> LOCATION: (7)..(7)
<223> OTHER INFORMATION: Xaa is Lys, Arg, or Glu
<220> FEATURE:
<221> NAME/KEY: VARIANT
<222> LOCATION: (8)..(8)
<223> OTHER INFORMATION: Xaa is Ile or Val
<220> FEATURE:
<221> NAME/KEY: VARIANT
<222> LOCATION: (11)..(11)
<223> OTHER INFORMATION: Xaa is Glu or Gly
```

```
<400> SEQUENCE: 276

Xaa Leu Xaa Phe Gly Xaa Xaa Xaa Tyr Phe Xaa
1               5                   10

<210> SEQ ID NO 277
<211> LENGTH: 78
<212> TYPE: PRT
<213> ORGANISM: Artificial sequence
<220> FEATURE:
<223> OTHER INFORMATION: SPL DNA-binding domain (DBD) of Arath_SPL15
      transcription factor

<400> SEQUENCE: 277

Thr Ala Arg Cys Gln Val Glu Gly Cys Arg Met Asp Leu Ser Asn Val
1               5                   10                  15

Lys Ala Tyr Tyr Ser Arg His Lys Val Cys Cys Ile His Ser Lys Ser
            20                  25                  30

Ser Lys Val Ile Val Ser Gly Leu His Gln Arg Phe Cys Gln Gln Cys
        35                  40                  45

Ser Arg Phe His Gln Leu Ser Glu Phe Asp Leu Glu Lys Arg Ser Cys
    50                  55                  60

Arg Arg Arg Leu Ala Cys His Asn Glu Arg Arg Lys Pro
65                  70                  75

<210> SEQ ID NO 278
<211> LENGTH: 11
<212> TYPE: PRT
<213> ORGANISM: Artificial sequence
<220> FEATURE:
<223> OTHER INFORMATION: motif 2
<220> FEATURE:
<221> NAME/KEY: VARIANT
<222> LOCATION: (3)..(3)
<223> OTHER INFORMATION: Xaa is Ser, Asn, or Thr
<220> FEATURE:
<221> NAME/KEY: VARIANT
<222> LOCATION: (4)..(4)
<223> OTHER INFORMATION: Xaa is Cys, Gly, or Arg
<220> FEATURE:
<221> NAME/KEY: VARIANT
<222> LOCATION: (11)..(11)
<223> OTHER INFORMATION: Xaa is Asn or Thr

<400> SEQUENCE: 278

Asp Ser Xaa Xaa Ala Leu Ser Leu Leu Ser Xaa
1               5                   10

<210> SEQ ID NO 279
<211> LENGTH: 1130
<212> TYPE: DNA
<213> ORGANISM: Oryza sativa

<400> SEQUENCE: 279
catgcggcta atgtagatgc tcactgcgct agtagtaagg tactccagta cattatggaa      60
tatacaaagc tgtaatactc gtatcagcaa gagagaggca cacaagttgt agcagtagca     120
caggattaga aaacgggac gacaaatagt aatggaaaaa caaaaaaaaa caaggaaaca     180
catggcaata taatggaga atcacaaga ggaacagaat ccgggcaata cgctgcgaaa     240
gtactcgtac gtaaaaaaaa gaggcgcatt catgtgtgga cagcgtgcag cagaagcagg     300
gatttgaaac cactcaaatc caccactgca aaccttcaaa cgaggccatg gtttgaagca     360
tagaaagcac aggtaagaag cacaacgccc tcgctctcca ccctcccacc caatcgcgac     420
gcacctcgcg gatcggtgac gtggcctcgc cccccaaaaa tatcccgcgg cgtgaagctg     480
```

| | | |
|---|---|---|
| acaccccggg cccacccacc tgtcacgttg gcacatgttg gttatggttc ccggccgcac | 540 | |
| caaaatatca acgcggcgcg gcccaaaatt tccaaaatcc cgcccaagcc cctggcgcgt | 600 | |
| gccgctcttc cacccaggtc cctctcgtaa tccataatgg cgtgtgtacc ctcggctggt | 660 | |
| tgtacgtggg cggttaccc tggggtgtg ggtggatgac gggtgggccc ggaggaggtc | 720 | |
| cggcccgcg cgtcatcgcg gggcggggtg tagcgggtgc gaaaaggagg cgatcggtac | 780 | |
| gaaaattcaa attaggaggt gggggcgggg gcccttggag aataagcgga atcgcagata | 840 | |
| tgcccctgac ttggcttggc tcctcttctt cttatccctt gtcctcgcaa ccccgcttcc | 900 | |
| ttctctcctc tcctcttctc ttctcttctc tggtggtgtg ggtgtgtccc tgtctccct | 960 | |
| ctccttcctc ctctccttc ccctcctctc ttccccctc tcacaagaga gagagcgcca | 1020 | |
| gactctcccc aggtgaggtg agaccagtct ttttgctcga ttcgacgcgc ctttcacgcc | 1080 | |
| gcctcgcgcg gatctgaccg cttccctcgc ccttctcgca ggattcagcc | 1130 | |

<210> SEQ ID NO 280
<211> LENGTH: 56
<212> TYPE: DNA
<213> ORGANISM: Artificial sequence
<220> FEATURE:
<223> OTHER INFORMATION: primer: prm07277

<400> SEQUENCE: 280

| | | |
|---|---|---|
| ggggacaagt ttgtacaaaa aagcaggctt aaacaatgga gttgttaatg tgttcg | 56 | |

<210> SEQ ID NO 281
<211> LENGTH: 51
<212> TYPE: DNA
<213> ORGANISM: Artificial sequence
<220> FEATURE:
<223> OTHER INFORMATION: primer: prm07278

<400> SEQUENCE: 281

| | | |
|---|---|---|
| ggggaccact ttgtacaaga aagctgggtt gatgaagatc ttaaaaggtg a | 51 | |

<210> SEQ ID NO 282
<211> LENGTH: 1110
<212> TYPE: DNA
<213> ORGANISM: Brassica rapa

<400> SEQUENCE: 282

| | | |
|---|---|---|
| atggataggg gttccaactc gggtcttggt cttggtccag gccagacaga gtcgggtggt | 60 | |
| tcatccactg agtcatcctc tttaagtgga gggctcatgt ttggccagag gatctacttc | 120 | |
| gaggacgctg gaggtggaac cgggtcttct tcctccggcg ggtcaaacag aagggtacgt | 180 | |
| ggaagcgggt cggtccttc gggtcagata ccaaggtgtc aagtgaagg ttgtggaatg | 240 | |
| gatctaacca atgcaaaggg ttattacacg aggcatagag tttgtggaat gcactctaaa | 300 | |
| acaccaaaag tcattgtcgc tggtatagaa caaaggtttt gtcaacagtg cagcaggttt | 360 | |
| catcagcttc cggaatttga cctagagaaa aggagttgcc gtaggagact cgctggtcat | 420 | |
| aatgagagac gaaggaagcc acagcctgcg tctctatctg tgttgtcttc tcgttatggg | 480 | |
| aggatcactc cttctctata cggaaatggt gaaactacaa tgaatgggag ctttcttggt | 540 | |
| tcccaagaaa tgggttggaa tagtgcaaga acgttggata caagagtgat gagacggcca | 600 | |
| ccgtcgtggc agatcaatcc tatgaatgtg tttagtcatg gatcagtaag tggaggagga | 660 | |
| ggaggaggga taagcttctc atctccagag attatggaca ctaaaccaga gagctacaag | 720 | |
| ggaattggca gcgactcaaa ctgtgctctc tctcttctgt caaacccaca tcagccacat | 780 | |

```
gacaacaaca acagcaacaa cacatggaga acttcttcgg gttttggtcc gatgacggtt      840
acaatggctc agccaccacc tgcacctagc cagcagcatc agtatctgaa cccgccttgg      900
gtattcaagg acgatgataa tagctgtccg aatgatatgt ctcctgtttt gaatcttggt      960
cggttcaccg agacagagat aagcggtgga acgactttgg gtgagttcga gttatctgac     1020
catcatcatc agaataggag gcagtacatg gaaagtgaga acacaagggc ttatggctct     1080
tcttcacacc ataacaactg gtctctctga                                      1110
```

<210> SEQ ID NO 283
<211> LENGTH: 369
<212> TYPE: PRT
<213> ORGANISM: Brassica rapa

<400> SEQUENCE: 283

```
Met Asp Arg Gly Ser Asn Ser Gly Leu Gly Leu Pro Gly Gln Thr
1               5                   10                  15

Glu Ser Gly Gly Ser Ser Thr Glu Ser Ser Ser Leu Ser Gly Gly Leu
            20                  25                  30

Met Phe Gly Gln Arg Ile Tyr Phe Glu Asp Ala Gly Gly Thr Gly
        35                  40                  45

Ser Ser Ser Ser Gly Gly Ser Asn Arg Arg Val Arg Gly Ser Gly Ser
50                  55                  60

Gly Pro Ser Gly Gln Ile Pro Arg Cys Gln Val Glu Gly Cys Gly Met
65                  70                  75                  80

Asp Leu Thr Asn Ala Lys Gly Tyr Tyr Thr Arg His Arg Val Cys Gly
                85                  90                  95

Met His Ser Lys Thr Pro Lys Val Ile Val Ala Gly Ile Glu Gln Arg
            100                 105                 110

Phe Cys Gln Gln Cys Ser Arg Phe His Gln Leu Pro Glu Phe Asp Leu
        115                 120                 125

Glu Lys Arg Ser Cys Arg Arg Leu Ala Gly His Asn Glu Arg Arg
            130                 135                 140

Arg Lys Pro Gln Pro Ala Ser Leu Ser Val Leu Ser Ser Arg Tyr Gly
145                 150                 155                 160

Arg Ile Thr Pro Ser Leu Tyr Gly Asn Gly Glu Thr Thr Met Asn Gly
                165                 170                 175

Ser Phe Leu Gly Ser Gln Glu Met Gly Trp Asn Ser Ala Arg Thr Leu
            180                 185                 190

Asp Thr Arg Val Met Arg Arg Pro Ser Trp Gln Ile Asn Pro Met
        195                 200                 205

Asn Val Phe Ser His Gly Ser Val Ser Gly Gly Gly Gly Ile
            210                 215                 220

Ser Phe Ser Ser Pro Glu Ile Met Asp Thr Lys Pro Glu Ser Tyr Lys
225                 230                 235                 240

Gly Ile Gly Ser Asp Ser Asn Cys Ala Leu Ser Leu Leu Ser Asn Pro
                245                 250                 255

His Gln Pro His Asp Asn Asn Ser Asn Asn Thr Trp Arg Thr Ser
            260                 265                 270

Ser Gly Phe Gly Pro Met Thr Val Thr Met Ala Gln Pro Pro Ala
        275                 280                 285

Pro Ser Gln Gln His Gln Tyr Leu Asn Pro Pro Trp Val Phe Lys Asp
            290                 295                 300

Asp Asp Asn Ser Cys Pro Asn Asp Met Ser Pro Val Leu Asn Leu Gly
305                 310                 315                 320
```

```
Arg Phe Thr Glu Thr Glu Ile Ser Gly Gly Thr Thr Leu Gly Glu Phe
            325                 330                 335

Glu Leu Ser Asp His His His Gln Asn Arg Arg Gln Tyr Met Glu Ser
            340                 345                 350

Glu Asn Thr Arg Ala Tyr Gly Ser Ser His His Asn Asn Trp Ser
        355                 360                 365

Leu
```

<210> SEQ ID NO 284
<211> LENGTH: 1080
<212> TYPE: DNA
<213> ORGANISM: Glycine max

<400> SEQUENCE: 284

```
atggcttcag acgccaaact ctcctcttct gagtccctca acggtttgaa attcggccaa      60
aaaatctatt ttgaggatgt tggtcttgct actccagcca cctctcttac ttcttcttct    120
tcttcttctt ctgctgctac tgttacttct tcttcttctt caaggaaagg aagaggtggg    180
tctgttcaac cagctcaacc tcccaggtgt caagttgaag gtgcaaagt agatctgagt    240
gatgcaaaag cttactattc tagacacaag gtctgtggca tgcactctaa atccccttca    300
gtcattgttg ctggtcttca acaaaggttt tgtcaacagt gtagcaggtt tcatcagctt    360
cctgagtttg atcaaggaaa agaagttgc cgtaggcgac tagctggcca taatgaacgt    420
cggagaaagc ccccaacaag ctccctctta acctctcgct atgccagact tcttcgtct    480
gcttttgata atagtggcag aggtagcaac tttctgatgg aattgacttc atacccaaag    540
cttagtctga gaaattcact tccaactcct agatcatctg agctagctcc tggaaatcaa    600
acctccacac ttagctggaa tggcaactca gagacatcat ctgaccttt cttgcaaggt    660
tcggtgggtg ggacaagctt cgccagcccg ggacatcctc caggggaaag ttacattggg    720
gtcaccgaca cgagctgtgc tctctctctt ctgtcaaatc aaacatgggg ttctagaaac    780
acagcaccaa gtcttgggtt gagtaacatg ataaatttca acgggacacc cttgacacaa    840
cttgctgcat catctcatgg tgcatcaatc catcaacttc caaataccct cgtggttttt c    900
aagggcattg attctggtaa ctgttcgccc gaggtggtcc ctgatctagg tctcggtcag    960
atttcacagc ctctcaatag ccaacttcat ggtgagctgg acctgtccca acagggcagg   1020
aggcattata tggatctaga acagtccagg gcatatgaat ctgctcattg gtcactttaa   1080
```

<210> SEQ ID NO 285
<211> LENGTH: 359
<212> TYPE: PRT
<213> ORGANISM: Glycine max

<400> SEQUENCE: 285

```
Met Ala Ser Asp Ala Lys Leu Ser Ser Glu Ser Leu Asn Gly Leu
1               5                   10                  15

Lys Phe Gly Gln Lys Ile Tyr Phe Glu Asp Val Gly Leu Ala Thr Pro
            20                  25                  30

Ala Thr Ser Leu Thr Ser Ser Ser Ser Ser Ser Ala Ala Thr Val
            35                  40                  45

Thr Ser Ser Ser Ser Ser Arg Lys Gly Arg Gly Gly Ser Val Gln Pro
    50                  55                  60

Ala Gln Pro Pro Arg Cys Gln Val Glu Gly Cys Lys Val Asp Leu Ser
65                  70                  75                  80

Asp Ala Lys Ala Tyr Tyr Ser Arg His Lys Val Cys Gly Met His Ser
                85                  90                  95
```

```
Lys Ser Pro Ser Val Ile Val Ala Gly Leu Gln Gln Arg Phe Cys Gln
            100                 105                 110

Gln Cys Ser Arg Phe His Gln Leu Pro Glu Phe Asp Gln Gly Lys Arg
        115                 120                 125

Ser Cys Arg Arg Arg Leu Ala Gly His Asn Glu Arg Arg Lys Pro
    130                 135                 140

Pro Thr Ser Ser Leu Leu Thr Ser Arg Tyr Ala Arg Leu Ser Ser Ser
145                 150                 155                 160

Ala Phe Asp Asn Ser Gly Arg Gly Ser Asn Phe Leu Met Glu Leu Thr
                165                 170                 175

Ser Tyr Pro Lys Leu Ser Leu Arg Asn Ser Leu Pro Thr Pro Arg Ser
            180                 185                 190

Ser Glu Leu Ala Pro Gly Asn Gln Thr Ser Thr Leu Ser Trp Asn Gly
        195                 200                 205

Asn Ser Glu Thr Ser Ser Asp Leu Phe Leu Gln Gly Ser Val Gly Gly
    210                 215                 220

Thr Ser Phe Ala Ser Pro Gly His Pro Pro Gly Glu Ser Tyr Ile Gly
225                 230                 235                 240

Val Thr Asp Thr Ser Cys Ala Leu Ser Leu Leu Ser Asn Gln Thr Trp
                245                 250                 255

Gly Ser Arg Asn Thr Ala Pro Ser Leu Gly Leu Ser Asn Met Ile Asn
            260                 265                 270

Phe Asn Gly Thr Pro Leu Thr Gln Leu Ala Ala Ser Ser His Gly Ala
        275                 280                 285

Ser Ile His Gln Leu Pro Asn Thr Ser Trp Phe Phe Lys Gly Ile Asp
    290                 295                 300

Ser Gly Asn Cys Ser Pro Glu Val Val Pro Asp Leu Gly Leu Gly Gln
305                 310                 315                 320

Ile Ser Gln Pro Leu Asn Ser Gln Leu His Gly Glu Leu Asp Leu Ser
                325                 330                 335

Gln Gln Gly Arg Arg His Tyr Met Asp Leu Glu Gln Ser Arg Ala Tyr
            340                 345                 350

Glu Ser Ala His Trp Ser Leu
        355

<210> SEQ ID NO 286
<211> LENGTH: 1128
<212> TYPE: DNA
<213> ORGANISM: Populus tremuloides

<400> SEQUENCE: 286
atggaaatgg attcaggctc cctaaccgag tcagctactt ccaatgcaac ttctccgcca      60
gctgagtctg ttaatggatt gaaatttggt aagaagattt actttgagga tcacgtgggg    120
gtcggtgctc cggctaagag cggaactggg tcatcctcat ccggttccgg gtcagggtca    180
tctaggaagg ctcaaggtgg acagcaccag cagccaccaa ggtgtcaagt tgaagggtgc    240
aaagtagatc tgagtgatgc taagacttac tattcaaggc acaaagtttg tagtatgcac    300
tccaagtctc ctagagttat tgttgctggt ttggtgcaaa gattttgcca gcaatgtagc    360
agatttcatc tacttcctga atttgaccaa ggaaaacgaa gttgccgcag cgcctagct     420
ggccataatg agcgacggag gaagccacca tctggatcgg tgttgtccgc tcgccatggc    480
cgattctctc cctctttgtt tgataatagc agcagagctg gaggccttct gtggactttt    540
agtgcatatc caaggcatac tgggagagat ggatggcctg cagcaaggtc ttctgagctt    600
```

```
acccccggga atgatactgc tgccacagga aggtctatat ctcatatgtg gcagataagc      660
tcccagaatc ctccatccaa cctttgcttg caaggctcaa ctggcgggac tggccttttc      720
agttcaggaa ttcctccggg agaatgcttc acaggagttg ctgtttcaga ctcgagctgt      780
gctctctctc ttctgtcaaa tcaaccatgg ggctccacaa accgagcatc aagtcttgcg      840
gtgaatgact tgtttagtgc cgaagaggca cccgtggttc aatcaacagc tcaccatggt      900
gcggctgtca atcagtatcc aatcccttgg agcttcaaga gcaatgaagg aagtaacagt      960
tcacatgaga gtgtgccctga tctaggtctg ggtcaaattt caatgcctct caacagtcaa     1020
cttgctggtc agctcgagca gtctcaacag aataggaggc aatacatgga cctcgagcat     1080
tccagggctt atgactcttc aacccagcac atccactggt cactttaa                   1128
```

<210> SEQ ID NO 287
<211> LENGTH: 375
<212> TYPE: PRT
<213> ORGANISM: Populus tremuloides

<400> SEQUENCE: 287

```
Met Glu Met Asp Ser Gly Ser Leu Thr Glu Ser Ala Thr Ser Asn Ala
 1               5                  10                  15

Thr Ser Pro Pro Ala Glu Ser Val Asn Gly Leu Lys Phe Gly Lys Lys
            20                  25                  30

Ile Tyr Phe Glu Asp His Val Gly Val Gly Ala Pro Ala Lys Ser Gly
        35                  40                  45

Thr Gly Ser Ser Ser Gly Ser Gly Ser Ser Arg Lys Ala
    50                  55                  60

Gln Gly Gly Gln His Gln Gln Pro Pro Arg Cys Gln Val Glu Gly Cys
65                  70                  75                  80

Lys Val Asp Leu Ser Asp Ala Lys Thr Tyr Tyr Ser Arg His Lys Val
                85                  90                  95

Cys Ser Met His Ser Lys Ser Pro Arg Val Ile Val Ala Gly Leu Val
            100                 105                 110

Gln Arg Phe Cys Gln Gln Cys Ser Arg Phe His Leu Leu Pro Glu Phe
        115                 120                 125

Asp Gln Gly Lys Arg Ser Cys Arg Arg Leu Ala Gly His Asn Glu
    130                 135                 140

Arg Arg Arg Lys Pro Pro Gly Ser Val Leu Ser Ala Arg His Gly
145                 150                 155                 160

Arg Phe Ser Pro Ser Leu Phe Asp Asn Ser Arg Ala Gly Gly Leu
                165                 170                 175

Leu Val Asp Phe Ser Ala Tyr Pro Arg His Thr Gly Arg Asp Gly Trp
            180                 185                 190

Pro Ala Ala Arg Ser Ser Glu Leu Thr Pro Gly Asn Asp Thr Ala Ala
        195                 200                 205

Thr Gly Arg Ser Ile Ser His Met Trp Gln Ile Ser Gln Asn Pro
    210                 215                 220

Pro Ser Asn Leu Cys Leu Gln Gly Ser Thr Gly Gly Thr Gly Leu Phe
225                 230                 235                 240

Ser Ser Gly Ile Pro Pro Gly Glu Cys Phe Thr Gly Val Ala Val Ser
                245                 250                 255

Asp Ser Ser Cys Ala Leu Ser Leu Leu Ser Asn Gln Pro Trp Gly Ser
            260                 265                 270

Thr Asn Arg Ala Ser Ser Leu Ala Val Asn Asp Leu Phe Ser Ala Glu
        275                 280                 285
```

```
Glu Ala Pro Val Val Gln Ser Thr Ala His His Gly Ala Ala Val Asn
        290                 295                 300

Gln Tyr Pro Ile Pro Trp Ser Phe Lys Ser Asn Glu Gly Ser Asn Ser
305                 310                 315                 320

Ser His Glu Met Cys Pro Asp Leu Gly Leu Gly Gln Ile Ser Met Pro
                325                 330                 335

Leu Asn Ser Gln Leu Ala Gly Gln Leu Glu Gln Ser Gln Gln Asn Arg
            340                 345                 350

Arg Gln Tyr Met Asp Leu Glu His Ser Arg Ala Tyr Asp Ser Ser Thr
        355                 360                 365

Gln His Ile His Trp Ser Leu
        370                 375

<210> SEQ ID NO 288
<211> LENGTH: 1059
<212> TYPE: DNA
<213> ORGANISM: Citrus clementina

<400> SEQUENCE: 288
atggaactgg gttcagacta tttggctgaa tcaggtggtg gctccggctc cggctcaggc      60
tccggcttat catccgctga gccatcactt aatggtttga gtttggcaa aaaaatctat     120 tttgaggatg tcggtactgc cggagctcca tttccaggat ctgggtcatc atctgggtcc    180
gggtcagggt caggttcagg gtcagggagg aaggtgaggg gtgttggcgg tggtatggtt    240
actagtgggc agcagccacc aaggtgccaa gtggagggg t gtaaagttga tctgagtgat    300
gccaaagctt actattcaag gcacaaagtt tgtggcatgc attcaaagtc tcctgttgtc    360
actgttgccg gccttgagca gaggttttgc agcaatgta gcagatttca tcagcttccg    420
gagtttgacc aaggaaaacg aagttgccgc aggcgcctgg caggccataa tgagcgccgg    480
aggaagccaa cttctggacc attttttggc actcgttatg caggctctc ttcctctgtc     540 attgagaaca gcagccaagg tggaggattt ctgatcgact cagtgcata tcagatggtt    600 ggtgggaggg atggatggcc agtgacaagt gtctccaagc aggtatctgg aaatcaaacc   660
actgtcacag caaggcatct tcctcagcca ctatggcaaa accactctca ggatcctcca    720
cctgatcgtt accttcagtg ttcaacagct gggactggtt tctctggtcc tggaattcct    780
tgtggaggat gcttcacagg agttgctgac tcaaactgtg ctctctctct tctgtcaaat    840
caaccatggg gctctaagaa cccgacaccg ggtcatggag tgggtgactt aatgcatgcc    900
cataccaaat ccgtcactca accagtatcg ccccatggag cagctattaa tcaatatcca    960
aacatgtcat gggggggttca agggcaatgc aacctggtag cagttccaca ccaaatggcc   1020
ccccaaatgg ggtttgggtt caacattccg gcccattaa                          1059

<210> SEQ ID NO 289
<211> LENGTH: 352
<212> TYPE: PRT
<213> ORGANISM: Citrus clementina

<400> SEQUENCE: 289

Met Glu Leu Gly Ser Asp Tyr Leu Ala Glu Ser Gly Gly Gly Ser Gly
1               5                   10                  15

Ser Gly Ser Gly Ser Gly Leu Ser Ala Glu Pro Ser Leu Asn Gly
            20                  25                  30

Leu Lys Phe Gly Lys Lys Ile Tyr Phe Glu Asp Val Gly Thr Ala Gly
        35                  40                  45

Ala Pro Phe Pro Gly Ser Gly Ser Ser Ser Gly Ser Gly Ser Gly Ser
```

```
                50                  55                  60
Gly Ser Gly Ser Gly Arg Lys Val Arg Gly Val Gly Gly Met Val
 65                  70                  75                  80

Thr Ser Gly Gln Gln Pro Pro Arg Cys Gln Val Glu Gly Cys Lys Val
                 85                  90                  95

Asp Leu Ser Asp Ala Lys Ala Tyr Tyr Ser Arg His Lys Val Cys Gly
                100                 105                 110

Met His Ser Lys Ser Pro Val Val Thr Val Ala Gly Leu Glu Gln Arg
                115                 120                 125

Phe Cys Gln Gln Cys Ser Arg Phe His Gln Leu Pro Glu Phe Asp Gln
130                 135                 140

Gly Lys Arg Ser Cys Arg Arg Leu Ala Gly His Asn Glu Arg Arg
145                 150                 155                 160

Arg Lys Pro Thr Ser Gly Pro Phe Leu Gly Thr Arg Tyr Gly Arg Leu
                165                 170                 175

Ser Ser Ser Val Ile Glu Asn Ser Ser Gln Gly Gly Phe Leu Ile
                180                 185                 190

Asp Phe Ser Ala Tyr Gln Met Val Gly Gly Arg Asp Gly Trp Pro Val
                195                 200                 205

Thr Ser Val Ser Lys Gln Val Ser Gly Asn Gln Thr Thr Val Thr Ala
210                 215                 220

Arg His Leu Pro Gln Pro Leu Trp Gln Asn His Ser Gln Asp Pro Pro
225                 230                 235                 240

Pro Asp Arg Tyr Leu Gln Cys Ser Thr Ala Gly Thr Gly Phe Ser Gly
                245                 250                 255

Pro Gly Ile Pro Cys Gly Gly Cys Phe Thr Gly Val Ala Asp Ser Asn
                260                 265                 270

Cys Ala Leu Ser Leu Leu Ser Asn Gln Pro Trp Gly Ser Lys Asn Pro
                275                 280                 285

Thr Pro Gly His Gly Val Gly Asp Leu Met His Ala His Thr Lys Ser
                290                 295                 300

Val Thr Gln Pro Val Ser Pro His Gly Ala Ala Ile Asn Gln Tyr Pro
305                 310                 315                 320

Asn Met Ser Trp Gly Val Gln Gly Gln Cys Asn Leu Val Ala Val Pro
                325                 330                 335

His Gln Met Ala Pro Gln Met Gly Phe Gly Phe Asn Ile Pro Ala His
                340                 345                 350

<210> SEQ ID NO 290
<211> LENGTH: 565
<212> TYPE: DNA
<213> ORGANISM: Beta vulgaris

<400> SEQUENCE: 290
atggatacgg gttcaaatta tccgaccgtt aagggggtcat catcaacctc ttcatcatct      60
gggttgtcgg attcttttaaa tgggctgaaa tttgggcaaa aaatatactt tgaagatgtg     120
ggtggtgttg aacttccgg caagtcttcc gtcgccggaa gtggtggtgc tccggcgaaa      180
agggccggaa aagggggtggt gcaaagtggg caaccaccaa ggtgtcaagt agaagggtgt      240
aagatagatc ttagtgatgc taaaacttat tattctaggc ataaagtttg tggtatgcac      300
tctaaatctt ctgttgttat tgttgctggt cttgagcaac gttttttgcca gcagtgcagc      360 agatttcatc ggcttcctga gtttgaccaa gggaaacgaa gttgtcgcag acgccttgct      420
ggtcataatg agcgtcgaag aaaaccacca cctgggtctt tgttatcatc acgtttggga      480
```

-continued

```
cgtctctctt catcccttt tggtgataac accggcggaa gtggtggatt cttattggac      540
ttctcttcgt atccacggca ttctg                                          565
```

<210> SEQ ID NO 291
<211> LENGTH: 188
<212> TYPE: PRT
<213> ORGANISM: Beta vulgaris

<400> SEQUENCE: 291

```
Met Asp Thr Gly Ser Asn Tyr Pro Thr Val Lys Gly Ser Ser Thr
1               5                   10                  15

Ser Ser Ser Ser Gly Leu Ser Asp Ser Leu Asn Gly Leu Lys Phe Gly
            20                  25                  30

Gln Lys Ile Tyr Phe Glu Asp Val Gly Gly Val Gly Thr Ser Gly Lys
        35                  40                  45

Ser Ser Val Ala Gly Ser Gly Gly Ala Pro Ala Lys Arg Ala Gly Lys
    50                  55                  60

Gly Val Val Gln Ser Gly Gln Pro Pro Arg Cys Gln Val Glu Gly Cys
65                  70                  75                  80

Lys Ile Asp Leu Ser Asp Ala Lys Thr Tyr Tyr Ser Arg His Lys Val
                85                  90                  95

Cys Gly Met His Ser Lys Ser Ser Val Val Ile Val Ala Gly Leu Glu
            100                 105                 110

Gln Arg Phe Cys Gln Gln Cys Ser Arg Phe His Arg Leu Pro Glu Phe
        115                 120                 125

Asp Gln Gly Lys Arg Ser Cys Arg Arg Leu Ala Gly His Asn Glu
    130                 135                 140

Arg Arg Arg Lys Pro Pro Gly Ser Leu Leu Ser Ser Arg Leu Gly
145                 150                 155                 160

Arg Leu Ser Ser Ser Leu Phe Gly Asp Asn Thr Gly Ser Gly Gly
                165                 170                 175

Phe Leu Leu Asp Phe Ser Ser Tyr Pro Arg His Ser
            180                 185
```

<210> SEQ ID NO 292
<211> LENGTH: 536
<212> TYPE: DNA
<213> ORGANISM: Hevea brasiliensis

<400> SEQUENCE: 292

```
atggaaatgg ttcgggctc tttgacagag tcaggtacct ccaacgccac ttctccacct       60
gctgagtcaa taaatgggtt gaaatttggc caaaaatct attttgagaa tgcgggggct      120
aagactccgg ccaaatctgc acccgggtct tcatcttccg ggtccggggc cccgtccagg     180
aaggttcacg gtgggcagca gcagcagcca cccaggtgtc aagttgaggg atgtaaagtg     240
gatctgagtg atgctaaggc ttattattcg aggcacaaag tttgtggtat gcactctaag     300
tctcctaagg tcattgttgc tggtttggag caaagatttt gccagcagtg tagtagattt     360
catcagcttc ctgaatttga ccaaggaaaa cgaagttgcc gcagacgcct agctggtcat     420
aatgaacggc ggaggaagcc accaactgga tcagtgctgt catctcgcta taacagactt     480
ttttcaacaa tttttgataa cagcagccga gctgggggca ttcttgtgga tttcag        536
```

<210> SEQ ID NO 293
<211> LENGTH: 177
<212> TYPE: PRT
<213> ORGANISM: Hevea brasiliensis

<400> SEQUENCE: 293

```
Met Glu Met Gly Ser Gly Ser Leu Thr Glu Ser Gly Thr Ser Asn Ala
1               5                   10                  15

Thr Ser Pro Pro Ala Glu Ser Ile Asn Gly Leu Lys Phe Gly Gln Lys
            20                  25                  30

Ile Tyr Phe Glu Asn Ala Gly Ala Lys Thr Pro Ala Lys Ser Ala Pro
        35                  40                  45

Gly Ser Ser Ser Gly Ser Gly Ala Pro Ser Arg Lys Val His Gly
    50                  55                  60

Gly Gln Gln Gln Gln Pro Pro Arg Cys Gln Val Glu Gly Cys Lys Val
65              70                  75                  80

Asp Leu Ser Asp Ala Lys Ala Tyr Tyr Ser Arg His Lys Val Cys Gly
                85                  90                  95

Met His Ser Lys Ser Pro Lys Val Ile Val Ala Gly Leu Glu Gln Arg
            100                 105                 110

Phe Cys Gln Gln Cys Ser Arg Phe His Gln Leu Pro Glu Phe Asp Gln
        115                 120                 125

Gly Lys Arg Ser Cys Arg Arg Arg Leu Ala Gly His Asn Glu Arg Arg
    130                 135                 140

Arg Lys Pro Pro Thr Gly Ser Val Leu Ser Arg Tyr Asn Arg Leu
145             150                 155                 160

Phe Ser Thr Ile Phe Asp Asn Ser Ser Arg Ala Gly Gly Ile Leu Val
            165                 170                 175

Asp
```

<210> SEQ ID NO 294
<211> LENGTH: 1130
<212> TYPE: DNA
<213> ORGANISM: Oryza sativa

<400> SEQUENCE: 294

```
catgcggcta atgtagatgc tcactgcgct agtagtaagg tactccagta cattatggaa    60
tatacaaagc tgtaatactc gtatcagcaa gagagaggca cacaagttgt agcagtagca   120
caggattaga aaacgggac  gacaaatagt aatggaaaaa caaaaaaaaa caaggaaaca   180
catggcaata taaatggaga atcacaaga  ggaacagaat ccgggcaata cgctgcgaaa   240
gtactcgtac gtaaaaaaaa gaggcgcatt catgtgtgga cagcgtgcag cagaagcagg   300
gatttgaaac cactcaaatc caccactgca aaccttcaaa cgaggccatg gtttgaagca   360
tagaaagcac aggtaagaag cacaacgccc tcgctctcca ccctcccacc caatcgcgac   420
gcacctcgcg gatcggtgac gtggcctcgc cccccaaaaa tatcccgcgg cgtgaagctg   480
acaccccggg cccacccacc tgtcacgttg gcacatgttg gttatggttc ccggccgcac   540
caaaatatca acgcggcgcg gcccaaaatt tccaaaatcc cgcccaagcc cctggcgcgt   600
gccgctcttc cacccaggtc cctctcgtaa tccataatgg cgtgtgtacc ctcggctggt   660
tgtacgtggg cgggttaccc tgggggtgtg ggtggatgac gggtgggccc ggaggaggtc   720 cggcccgcg  cgtcatcgcg gggcggggtg tagcgggtgc gaaaggagg  cgatcggtac   780 gaaaattcaa attaggaggt gggggcggg  gcccttggag aataagcgga atcgcagata   840
tgcccctgac ttggcttggc tcctcttctt cttatccctt gtcctcgcaa cccgcttcc    900 ttctctcctc tcctcttctc ttctcttctc tggtggtgtg ggtgtgtccc tgtctcccct   960
ctccttcctc ctctccttc  ccctcctctc ttccccctc  tcacaagaga gagagcgcca  1020
```

```
gactctcccc aggtgaggtg agaccagtct ttttgctcga ttcgacgcgc ctttcacgcc    1080
gcctcgcgcg gatctgaccg cttccctcgg ccttctcgca ggattcagcc               1130

<210> SEQ ID NO 295
<211> LENGTH: 2194
<212> TYPE: DNA
<213> ORGANISM: Oryza sativa

<400> SEQUENCE: 295
aatccgaaaa gtttctgcac cgttttcacc ccctaactaa caatataggg aacgtgtgct      60
aaatataaaa tgagacctta tatatgtagc gctgataact agaactatgc aagaaaaact     120
catccaccta ctttagtggc aatcgggcta aataaaaaag agtcgctaca ctagtttcgt     180
tttccttagt aattaagtgg gaaaatgaaa tcattattgc ttagaatata cgttcacatc     240
tctgtcatga agttaaatta ttcgaggtag ccataattgt catcaaactc ttcttgaata     300
aaaaaatctt tctagctgaa ctcaatgggt aaagagagag atttttttta aaaaaataga     360
atgaagatat tctgaacgta ttggcaaaga tttaaacata taattatata attttatagt     420
ttgtgcattc gtcatatcgc acatcattaa ggacatgtct tactccatcc caattttttat     480 ttagtaatta aagacaattg acttattttt attatttatc ttttttcgat tagatgcaag     540
gtacttacgc acacctttg tgctcatgtg catgtgtgag tgcacctcct caatacacgt     600
tcaactagca acacatctct aatatcactc gcctatttaa tacatttagg tagcaatatc     660
tgaattcaag cactccacca tcaccagacc acttttaata atatctaaaa tacaaaaaat     720
aattttacag aatagcatga aaagtatgaa acgaactatt taggttttc acatacaaaa     780 aaaaaaagaa ttttgctcgt gcgcgagcgc caatctccca tattgggcac acaggcaaca     840
acagagtggc tgcccacaga acaacccaca aaaaacgatg atctaacgga ggacagcaag     900
tccgcaacaa ccttttaaca gcaggctttg cggccaggag agaggaggag aggcaaagaa     960
aaccaagcat cctccttctc ccatctataa attcctcccc ccttttcccc tctctatata    1020
ggaggcatcc aagccaagaa gagggagagc accaaggaca cgcgactagc agaagccgag    1080
cgaccgcctt ctcgatccat atcttccggt cgagttcttg gtcgatctct tccctcctcc    1140
acctcctcct cacagggtat gtgcctccct tcggttgttc ttggatttat tgttctaggt    1200
tgtgtagtac gggcgttgat gttaggaaag gggatctgta tctgtgatga ttcctgttct    1260
tggatttggg atagagggt tcttgatgtt gcatgttatc ggttcggttt gattagtagt    1320
atggttttca atcgtctgga gagctctatg gaaatgaaat ggtttaggga tcggaatctt    1380
gcgattttgt gagtaccttt tgtttgaggt aaaatcagag caccggtgat tttgcttggt    1440
gtaataaagt acggttgttt ggtcctcgat tctggtagtg atgcttctcg atttgacgaa    1500
gctatccttt gtttattccc tattgaacaa aaataatcca actttgaaga cggtcccgtt    1560
gatgagattg aatgattgat tcttaagcct gtccaaaatt tcgcagctgg cttgtttaga    1620
tacagtagtc cccatcacga aattcatgga aacagttata atcctcagga cagggggatt    1680
ccctgttctt ccgatttgct ttagtcccag aattttttt cccaaatatc ttaaaaagtc    1740
actttctggt tcagttcaat gaattgattg ctacaaataa tgcttttata gcgttatcct    1800
agctgtagtt cagttaatag gtaatacccc tatagtttag tcaggagaag aacttatccg    1860
atttctgatc tccattttta attatatgaa atgaactgta gcataagcag tattcatttg    1920
gattattttt tttattagct ctcaccccctt cattattctg agctgaaagt ctggcatgaa    1980
```

```
ctgtcctcaa ttttgttttc aaattcacat cgattatcta tgcattatcc tcttgtatct    2040
acctgtagaa gtttcttttt ggttattcct tgactgcttg attacagaaa gaaatttatg    2100
aagctgtaat cgggatagtt atactgcttg ttcttatgat tcatttcctt tgtgcagttc    2160
ttggtgtagc ttgccacttt caccagcaaa gttc                                2194
```

```
<210> SEQ ID NO 296
<211> LENGTH: 1149
<212> TYPE: DNA
<213> ORGANISM: Zea mays
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t
<220> FEATURE:
<221> NAME/KEY: misc_feature
<222> LOCATION: (954)..(954)
<223> OTHER INFORMATION: n is a, c, g, or t

<400> SEQUENCE: 296
```

```
atgcacaact gcaaagaaac cagcaagaat gcgccggcgg tttatagttc cccgctactg      60
caccgctctc tgctgcaggc tgcagctttg actaccaact catacagtac tagtactata    120
ctagagtact actacgccat tagcacggtg gttgcantag gccgtggtct ggaggtctct    180
ctcagctcag acgaggatcg tcggagcaag cagcagcgcg tgcagcctct gggagaccct    240
ggcggcgtcg acgccgatcc tggggctgag cgcctgcgag tggacggtgt agaatatctt    300
gtccccgatg acggagaagc tggcgctgac cacctcggcg ccctcctgct ccagcacggt    360
gatgacctcg tgcagcttga agggcctggc ggcctcgctg atgagcacca cgtccagcgt    420
cccgtcctgg caccgcacct cgatgaccgg catgcgcacg cctccgccgc cgccggtgga    480
cccggccgcc gccgttgcag cctccgtggc cgcgccgccg ccgttgcagc agcccgcctt    540
ccgctgcttc agcgcctcga tccgctcctt gagctgcttg atgtacgccg ccgcgctgtc    600
cagctggtcc agctgcgtca ccgcgtcctg cttgttgccg ggattggagg acaccgccgc    660
cgacgcggcg tcggagagga gggaggcgtg cgtggcggcg gcggcggcgg cgggagggat    720
gagggaggag agcttgaggc agaggccctt catgtgcagc ctccggttct tctccacgtc    780
cttcctctcc agcttgcacc ccccgccgct gctgtgcgcg ttcctctccc ccgcggcgca    840
ggcgcccgag ctgccccccgc tgctctgcct ccggctcttc atctcgatcg accngaccgg    900
tctgcagatc tctccttggc tgttctcgtc gctgctcctg ccgggcgtga agcngcgcag    960
cctttggttg ggacttggga gggacaagtt gcaacagcac ccacgggcca cggcacggag   1020
ggggcgaaag gcaaggaggc caggacaaga cgagagaaat acaggccggg ggagatggct   1080
ccgtggcgcg tacgtgtgtc tacctgcatg ttggttgatc cgattgcatc tgctgtaacc   1140
atatattaa                                                            1149
```

```
<210> SEQ ID NO 297
<211> LENGTH: 382
<212> TYPE: PRT
<213> ORGANISM: Zea mays
<220> FEATURE:
<221> NAME/KEY: UNSURE
<222> LOCATION: (53)..(53)
```

-continued

<223> OTHER INFORMATION: Xaa can be any naturally occurring amino acid

<400> SEQUENCE: 297

Met His Asn Cys Lys Glu Thr Ser Lys Asn Ala Pro Ala Val Tyr Ser
1               5                   10                  15

Ser Pro Leu Leu His Arg Ser Leu Leu Gln Ala Ala Leu Thr Thr
            20                  25                  30

Asn Ser Tyr Ser Thr Ser Thr Ile Leu Glu Tyr Tyr Ala Ile Ser
        35                  40                  45

Thr Val Val Ala Xaa Gly Arg Gly Leu Glu Val Ser Leu Ser Ser Asp
    50                  55                  60

Glu Asp Arg Arg Ser Lys Gln Gln Arg Val Gln Pro Leu Gly Asp Pro
65                  70                  75                  80

Gly Gly Val Asp Ala Asp Pro Gly Ala Glu Arg Leu Arg Val Asp Gly
                85                  90                  95

Val Glu Tyr Leu Val Pro Asp Asp Gly Glu Ala Gly Ala Asp His Leu
            100                 105                 110

Gly Ala Leu Leu Leu Gln His Gly Asp Asp Leu Val Gln Leu Glu Gly
        115                 120                 125

Pro Gly Gly Leu Ala Asp Glu His His Val Gln Arg Pro Val Leu Ala
130                 135                 140

Pro His Leu Asp Asp Arg His Ala His Ala Ser Ala Ala Ala Gly Gly
145                 150                 155                 160

Pro Gly Arg Arg Arg Cys Ser Leu Arg Gly Arg Ala Ala Val Ala
                165                 170                 175

Ala Ala Arg Leu Pro Leu Leu Gln Arg Leu Asp Pro Leu Leu Glu Leu
            180                 185                 190

Leu Asp Val Arg Arg Ala Val Gln Leu Val Gln Leu Arg His Arg
        195                 200                 205

Val Leu Leu Val Ala Gly Ile Gly Gly His Arg Arg Arg Gly Val
    210                 215                 220

Gly Glu Glu Gly Gly Val Arg Gly Gly Gly Gly Gly Arg Asp
225                 230                 235                 240

Glu Gly Gly Glu Leu Glu Ala Glu Ala Leu His Val Gln Pro Pro Val
                245                 250                 255

Leu Leu His Val Leu Pro Leu Gln Leu Ala Pro Pro Ala Ala Ala Val
            260                 265                 270

Arg Val Pro Leu Pro Arg Gly Ala Gly Ala Arg Ala Ala Pro Ala Ala
        275                 280                 285

Leu Pro Pro Ala Leu His Leu Asp Arg Pro Asp Arg Ser Ala Asp Leu
    290                 295                 300

Ser Leu Ala Val Leu Val Ala Ala Pro Ala Gly Arg Glu Ala Ala Gln
305                 310                 315                 320

Pro Leu Val Gly Thr Trp Glu Gly Gln Val Ala Thr Ala Pro Thr Gly
                325                 330                 335

His Gly Thr Glu Gly Ala Lys Gly Lys Glu Ala Arg Thr Arg Arg Glu
            340                 345                 350

Lys Tyr Arg Pro Gly Glu Met Ala Pro Trp Arg Val Arg Val Ser Thr
        355                 360                 365

Cys Met Leu Val Asp Pro Ile Ala Ser Ala Val Thr Ile Tyr
    370                 375                 380

<210> SEQ ID NO 298
<211> LENGTH: 660
<212> TYPE: DNA

<213> ORGANISM: Zea mays

<400> SEQUENCE: 298

```
atggagatga gagcgaagaa gagcagcaga agcagcacga gcaacaccag cggcagcacg    60
acgaccacgg cggtggagag gaaggagatc gagaggagga ggaggcagca gatgaagagc   120
ctctgcgcca agctcgcctc cctcatcccg aaagaacact actcctccaa ggatgctatg   180
acccagctgg gtagcctaga cgaggcagcc acgtacataa agagactcaa ggagagggtg   240
gaggagctgc ggcacaagag cgcctctgca cggctcttgg ccgctggcag tggcacgaga   300
cgaggcggag gaggaggagg cgcctccaca tcgtcggcag cgacgaccac ggcgagcggt   360
ggcgcaggat catctgaaga agccggccgg cgggaggacg acatgccgcc ggcggtggta   420
gaggttcggc agcacaatga cgggtcaagc ctggacgtgg tgctcatcag cagcgcggcg   480
cgacccttca agctgcacga ggtggtcacc gtgctggagg aagaaggcgc cgagaccgac   540
aacgccaacc tctccgtcgc cggcaccaaa atcttctaca ccatccactg caaggccttt   600
tgcccaagaa tcggtataga tgtttcaaga gtttctgaaa gattaagagc attgggatga   660
```

<210> SEQ ID NO 299
<211> LENGTH: 219
<212> TYPE: PRT
<213> ORGANISM: Zea mays

<400> SEQUENCE: 299

```
Met Glu Met Arg Ala Lys Lys Ser Ser Arg Ser Ser Thr Ser Asn Thr
 1               5                  10                  15
Ser Gly Ser Thr Thr Thr Thr Ala Val Glu Arg Lys Glu Ile Glu Arg
             20                  25                  30
Arg Arg Arg Gln Gln Met Lys Ser Leu Cys Ala Lys Leu Ala Ser Leu
         35                  40                  45
Ile Pro Lys Glu His Tyr Ser Ser Lys Asp Ala Met Thr Gln Leu Gly
     50                  55                  60
Ser Leu Asp Glu Ala Ala Thr Tyr Ile Lys Arg Leu Lys Glu Arg Val
 65                  70                  75                  80
Glu Glu Leu Arg His Lys Ser Ala Ser Ala Arg Leu Leu Ala Ala Gly
                 85                  90                  95
Ser Gly Thr Arg Arg Gly Gly Gly Gly Gly Ala Ser Thr Ser Ser
            100                 105                 110
Ala Ala Thr Thr Thr Ala Ser Gly Gly Ala Gly Ser Ser Glu Glu Ala
        115                 120                 125
Gly Arg Arg Glu Asp Asp Met Pro Pro Ala Val Val Glu Val Arg Gln
    130                 135                 140
His Asn Asp Gly Ser Ser Leu Asp Val Val Leu Ile Ser Ser Ala Ala
145                 150                 155                 160
Arg Pro Phe Lys Leu His Glu Val Val Thr Val Leu Glu Glu Gly
                165                 170                 175
Ala Glu Thr Asp Asn Ala Asn Leu Ser Val Ala Gly Thr Lys Ile Phe
            180                 185                 190
Tyr Thr Ile His Cys Lys Ala Phe Cys Pro Arg Ile Gly Ile Asp Val
        195                 200                 205
Ser Arg Val Ser Glu Arg Leu Arg Ala Leu Gly
    210                 215
```

<210> SEQ ID NO 300

```
<211> LENGTH: 669
<212> TYPE: DNA
<213> ORGANISM: Glycine max

<400> SEQUENCE: 300
atgggtcaac aacaacaggg aagtcaacct tctccaacca aagtcgaaag aaagattgta     60
gagaaaaaca ggagaagcca gatgaagaac ctctattccg aactcaactc tcttctccct    120
acccgtaatc ccaaggaagc gatgtcactg cctgatcaaa tagatgaagc aatcaactat    180
atcaaaagcc tagagacaaa agtgaagctg gagcaggaga agaaagaaag gttaaaggaa    240
aggaagagaa ctcgtggtgg ctgttcgagt tcttctgaag cacaaggaag cctgaaatcg    300
ccaaatatcc agattcacga aacgggaaat ttgcttgaag tcattctaac atgtggggtc    360
gatagccagt tcatgttctg tgaaattatt cgaattttgc atgaagagaa cgtcgaggtc    420
atcaatgcca attcttcaat ggtcggagat ttagtgattc atgttgtgca cggggaggtt    480
gagccatcta tctatcaatt cggagcgacc aaagtgagtg agaagctgaa atggtttatg    540
aacggatcct tcagtgatgt ggaaatggag cctgaattaa tgtggaattt taaaattgat    600
gctactgagc cgtgggggct tctagatgat cttacactgg acaatgtctt accaccaaat    660
actttgtaa                                                            669

<210> SEQ ID NO 301
<211> LENGTH: 222
<212> TYPE: PRT
<213> ORGANISM: Glycine max

<400> SEQUENCE: 301

Met Gly Gln Gln Gln Gln Gly Ser Gln Pro Ser Pro Thr Lys Val Glu
1               5                   10                  15

Arg Lys Ile Val Glu Lys Asn Arg Arg Ser Gln Met Lys Asn Leu Tyr
            20                  25                  30

Ser Glu Leu Asn Ser Leu Leu Pro Thr Arg Asn Pro Lys Glu Ala Met
        35                  40                  45

Ser Leu Pro Asp Gln Ile Asp Glu Ala Ile Asn Tyr Ile Lys Ser Leu
    50                  55                  60

Glu Thr Lys Val Lys Leu Glu Gln Glu Lys Lys Glu Arg Leu Lys Glu
65                  70                  75                  80

Arg Lys Arg Thr Arg Gly Gly Cys Ser Ser Ser Ser Glu Ala Gln Gly
                85                  90                  95

Ser Leu Lys Ser Pro Asn Ile Gln Ile His Glu Thr Gly Asn Leu Leu
            100                 105                 110

Glu Val Ile Leu Thr Cys Gly Val Asp Ser Gln Phe Met Phe Cys Glu
        115                 120                 125

Ile Ile Arg Ile Leu His Glu Glu Asn Val Glu Val Ile Asn Ala Asn
    130                 135                 140

Ser Ser Met Val Gly Asp Leu Val Ile His Val Val His Gly Glu Val
145                 150                 155                 160

Glu Pro Ser Ile Tyr Gln Phe Gly Ala Thr Lys Val Ser Glu Lys Leu
                165                 170                 175

Lys Trp Phe Met Asn Gly Ser Phe Ser Asp Val Glu Met Glu Pro Glu
            180                 185                 190

Leu Met Trp Asn Phe Lys Ile Asp Ala Thr Glu Pro Trp Gly Leu Leu
        195                 200                 205

Asp Asp Leu Thr Leu Asp Asn Val Leu Pro Pro Asn Thr Leu
    210                 215                 220
```